US011732251B2

(12) United States Patent
Fremaux et al.

(10) Patent No.: US 11,732,251 B2
(45) Date of Patent: Aug. 22, 2023

(54) ANTI-CRISPR POLYNUCLEOTIDES AND POLYPEPTIDES AND METHODS OF USE

(71) Applicants: DUPONT NUTRITION BIOSCIENCES APS, Copenhagen (DK); UNIVERSITE LAVAL (CANADA), Québec (CA)

(72) Inventors: Christophe Fremaux, Poitiers (FR); Philippe Horvath, Châtellerault (FR); Alexander Hynes, Québec City (CA); Marie-Laurence Lemay, Quebec City (CA); Sylvain Moineau, Quebec City (CA); Dennis A. Romero, Oregon, WI (US); Geneviève Rousseau, Québec City (CA); Joshua K Young, Johnston, IA (US)

(73) Assignees: DUPONT NUTRITION BIOSCIENCES APS, Kongens Lyngby (DK); UNIVERSITE LAVAL (CANADA), Quebec (CA)

( * ) Notice: Subject to any disclaimer, the term of this patent is extended or adjusted under 35 U.S.C. 154(b) by 371 days.

(21) Appl. No.: 16/607,849

(22) PCT Filed: Apr. 24, 2018

(86) PCT No.: PCT/EP2018/060510
§ 371 (c)(1),
(2) Date: Oct. 24, 2019

(87) PCT Pub. No.: WO2018/197520
PCT Pub. Date: Nov. 1, 2018

(65) Prior Publication Data
US 2020/0190492 A1 Jun. 18, 2020

Related U.S. Application Data

(60) Provisional application No. 62/488,969, filed on Apr. 24, 2017, provisional application No. 62/488,981, filed on Apr. 24, 2017, provisional application No. 62/510,896, filed on May 25, 2017, provisional application No. 62/510,914, filed on May 25, 2017.

(51) Int. Cl.
*C12N 9/22* (2006.01)
*C07K 14/005* (2006.01)
*C07K 14/315* (2006.01)
*C12N 15/63* (2006.01)

(52) U.S. Cl.
CPC .............. *C12N 9/22* (2013.01); *C07K 14/005* (2013.01); *C07K 14/315* (2013.01); *C12N 15/63* (2013.01); *C12N 2795/10322* (2013.01)

(58) Field of Classification Search
None
See application file for complete search history.

(56) References Cited

U.S. PATENT DOCUMENTS

| | | | |
|---|---|---|---|
| 4,873,192 | A | 10/1989 | Kunkel |
| 5,023,179 | A | 6/1991 | Lam et al. |
| 5,107,065 | A | 4/1992 | Shewmaker et al. |
| 5,110,732 | A | 5/1992 | Benfey et al. |
| 5,316,931 | A | 5/1994 | Donson et al. |
| 5,380,831 | A | 1/1995 | Adang et al. |
| 5,401,836 | A | 3/1995 | Baszczynski et al. |
| 5,436,391 | A | 7/1995 | Fujimoto et al. |
| 5,459,252 | A | 10/1995 | Conkling et al. |
| 5,589,367 | A | 12/1996 | Donson et al. |
| 5,605,793 | A | 2/1997 | Stemmer |
| 5,633,363 | A | 5/1997 | Colbert et al. |
| 5,659,026 | A | 8/1997 | Baszczynski et al. |
| 5,750,386 | A | 5/1998 | Conkling et al. |
| 5,789,156 | A | 8/1998 | Bujard et al. |
| 5,814,618 | A | 9/1998 | Bujard et al. |
| 5,837,458 | A | 11/1998 | Minshull et al. |
| 5,837,876 | A | 11/1998 | Conkling et al. |
| 5,866,785 | A | 2/1999 | Donson et al. |
| 5,889,190 | A | 3/1999 | Donson et al. |
| 5,889,191 | A | 3/1999 | Turpen |
| 6,225,529 | B1 | 5/2001 | Lappegard et al. |
| 2011/0035836 | A1 | 2/2011 | Eudes et al. |
| 2013/0312137 | A1 | 11/2013 | Cigan et al. |
| 2015/0045546 | A1 | 2/2015 | Siksnys et al. |
| 2015/0059010 | A1 | 2/2015 | Cigan et al. |
| 2015/0082478 | A1 | 3/2015 | Cigan et al. |

FOREIGN PATENT DOCUMENTS

| | | |
|---|---|---|
| EP | 2821486 B1 | 12/2018 |
| WO | 93/01294 | 1/1993 |
| WO | 00/11177 | 3/2000 |
| WO | 00/12733 A3 | 3/2000 |

(Continued)

OTHER PUBLICATIONS

Rauch et al., Cell, 168, pp. 150-158, Jan. 2017.*
Ngo et al. in The Protein Folding Problem and Tertiary Structure Prediction, 1994, Merz et al. (ed.), Birkhauser, Boston, MA, pp. 433 and 492-495.*
Singer et al., "Determination of the Amount of Homology Required for Recombination in Bacteriophage T4", Cell, vol. 31, 25-33, Nov. 1982.
Sinkunas et al., "In vitro reconstitution of Cascade-mediated CRISPR immunity in *Streptococcus thermophilus*", The EMBO Journal (2013) 32, 385-394.
Stemmer, "DNA shuffling by random fragmentation and reassembly: In vitro recombination for molecular evolution", Proc. Natl. Acad. Sci. USA, vol. 91, pp. 10747-10751, Oct. 1994.

(Continued)

*Primary Examiner* — Richard G Hutson

(57) ABSTRACT

Methods and compositions are provided for the use of anti-CRISPR (ACR) proteins in plants, including modulation of Cas endonuclease activity, improvement of frequency of homologous recombination, control of Cas endonuclease activity during various cell cycles, spatial and/or temporal regulation of Cas endonuclease activity in plants, usage in gene activation or repression, as well as reduction of off-target polynucleotide cleavage.

4 Claims, 23 Drawing Sheets

Figure 2A:
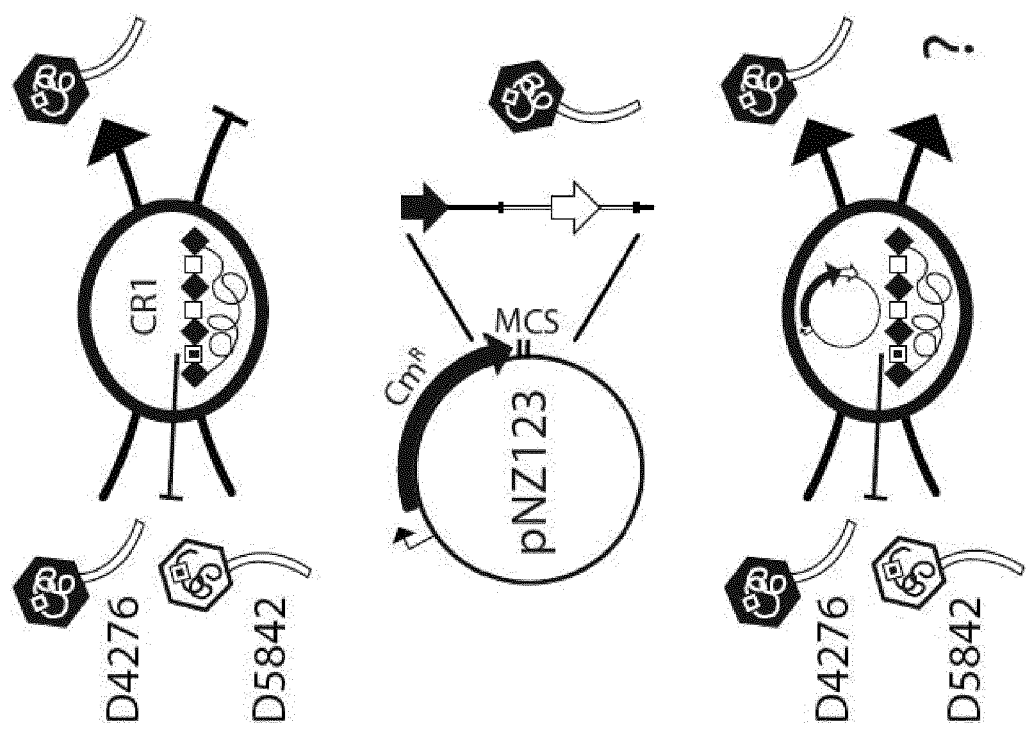

Specification includes a Sequence Listing.

(56) References Cited

FOREIGN PATENT DOCUMENTS

| WO | 2007/025097 A1 | 3/2007 |
|---|---|---|
| WO | 2013/103367 A1 | 7/2013 |
| WO | 2013/176772 A1 | 11/2013 |
| WO | 2014/093479 A1 | 6/2014 |
| WO | 2015/026886 A1 | 2/2015 |
| WO | 2016/007347 A1 | 1/2016 |
| WO | 2016/025131 A1 | 2/2016 |
| WO | 2016/186953 A1 | 11/2016 |
| WO | 2016/205613 A1 | 12/2016 |
| WO | 2017/062855 A1 | 4/2017 |
| WO | 2017/070029 A1 | 4/2017 |
| WO | 2017/070032 A1 | 4/2017 |
| WO | 2017/160689 | 9/2017 |
| WO | 2018/197495 A1 | 11/2018 |

OTHER PUBLICATIONS

Stemmer, "Rapid evolution of a protein in vitro by DNA shuffling", Nature, vol. 370, Aug. 4, 1994, 389-391.

Sugawara et al., "Characterization of Double-Strand Break-Induced Recombination: Homology Requirements and Single-Stranded DNA Formation", Molecular and Cellular Biology, vol. 12,. No 2, Feb. 1992, p. 563-575.

Szymczak et al., "Correction of multi-gene deficiency in vivo using a single 'self-cleaving' 2A peptide-based retroviral vector", Nature Biotechnology, vol. 22, No. 5, May 2004, pp. 589-594 and 760.

Teeri et al., "Gene fusions to lacZ reveal new expression patterns of chimeric genes in transgenic plants", The EMBO Journal, vol. 8, No. 2, pp. 343-350, 1989.

Thompson et al., "Structural Elements Regulating Zein Gene Expression", BioEssays, vol. 10, No. 4, Apr. 1989, pp. 108-113.

Timko et al., "Light regulation of plant gene expression by an upstream enhancer-like element", Nature, vol. 318, Dec. 12, 1985, pp. 579-582.

Turner et al., "The Potential Exploitation of Plant Viral Translational Enhancers in Biotechnology for Increased Gene Expression", Molecular Biotechnology, vol. 3, 1995, pp. 225-236.

Van Camp et al., "Tissue-Specific Activity of Two Manganese Superoxide Dismutase Promoters in Transgenic Tobacco", Plant Physiol. (1996) 112: 525-535.

Watt et al., "Homology requirements for recombination in *Escherichia coli*", Proc. Natl. Acad. Sci. USA, vol. 82, pp. 4768-4772, Jul. 1985.

Westra et al., "CRISPR Immunity Relies on the Consecutive Binding and Degradation of Negatively Supercoiled Invader DNA by Cascade and Cas3", Molecular Cell 46, 595-605, Jun. 8, 2012.

Yamamoto et al., "The Promoter of a Pine Photosynthetic Gene Allows Expression of a β-Glucuronidase Reporter Gene in Transgenic Rice Plants in a Light-Independent but Tissue-Specific Manner", Plant Cell Physiol. 35(5): 773-778, 1994.

Yamamoto et al., "Light-responsive elements of the tabacco PSI-D gene are located both upstream and within the transcribed region", The Plant Journal (1997) 12(2), 255-265.

Yamano et al., "Crystal Structure of Cpf1 in Complex with Guide RNA and Target DNA", Cell 165, 949-962, May 5, 2016.

Zetsche et al., "Cpf1 Is a Single RNA-Guided Endonuclease of a Class 2 CRISPR-Cas System", Cell 163, 759-771, Oct. 22, 2015.

Zhang et al., "Directed evolution of a fucosidase from a galactosidase by DNA shuffling and screening", Proc. Natl. Acad. Sci. USA, vol. 94, pp. 4504-4509, Apr. 1997.

Kasuga et al., "Improving plant drought, salt, and freezing tolerance by gene transfer of a single stress-inducible transcription factor", Nature Biotechnology, vol. 17, Mar. 1999, pp. 287-291.

Kawamata et al., "Temporal and Spatial Pattern of Expression of the Pea Phenylalanine Ammonia-Lyase Genel Promoter in Transgenic Tobacco", Plant Cell Physiol. 38(7): 792-803 (1997).

Keller et al., "Vascular-Specific Expression of the Bean GRP 1.8 Gene is Negatively Regulated", The Plant Cell, vol. 3, 1051-1061, Oct. 1991.

Kim et al., "Increasing the geonome-targeting scope and precision of base editing with engineered Cas9-cytidine deaminase fusions", Nature Biotechnology, vol. 35, No. 4, Apr. 2017, pp. 371-377.

Koonin et al., "Diversity, classification and evolution of CRISPR-Cas systems", Curr Opin Microbiol, Jun. 2017; 37, 37-78.

Kunkel, "Rapid and efficient site-specific mutagenesis without phenotypic selection", Proc. Natl. Acad. Sci. USA, vol. 32, pp. 488-492, Jan. 1985.

Kunkel et al., "Rapid and Efficient Site-Specific Mutagenesis without Phenotypic Selection", Methods in Enzymology, vol. 154, 1987, pp. 367-382.

Kuster et al., "The promoter of the Vicia faba L. VfENOD-GRP3 gene encoding a glycine-rich early nodnlin mediates a predominant gene expression in the interzone II-III region of transgenic Vicia hirsuta root nodules", Plant Molecular Biology 29: 759-772, 1995.

Kwon et al., Identification of a Light-Responsive Region of the Nuclear Gene Encoding the B Subunit of Chloroplast Glyceraldehyde 3-Phosphate Dehydrogenase f rotn *Arabidopsis thaliana*, Plant Physiol. (1994) 105: 357-367.

Lagos-Quintana et al., "Identification of Novel Genes Coding for Small Expressed RNAs", Science, vol. 294, Oct. 26, 2001, pp. 853-858.

Lagos-Quintana et al., "Identification of Tissue-Specific MicroRNAs from Mouse", Current Biology, vol. 12, 735-739, Apr. 30, 2002.

Lam, "Analysis of Tissue-Specific Elements in the CaMV 35S Promoter", Results and Problems in Cell Differentiation 20 L. Nover (Ed/) Plant Promoters and Transcription Factors, Springer-Verlag, Berlin Heidelberg, 1994, pp. 181-196.

Leach et al., "Promoter analysis of the highly expressed rolC and rolD root-inducing genes of Agrobacterium rhizogenes. enhancer and tissue-specific DNA determinants are dissociated", Plant Science, 79 (1991) 69-76.

Liskay et al., "Homology Requirement for Efficient Gene Conversion Between Duplicated Chromosomal Sequences in Mammalian Cells", Genetics 115: 161-167, Jan. 1987.

Lommel et al., "Identification of the Maize Chlorotic Mottle Virus Capsid Protein Cistron and Characterization of its Subgenomic Messenger RNA", Virology 181, 382-385, 1991.

Lu et al., "MicroRNA expression profiles classify human cancers", Nature, vol. 435, Jun. 9, 2005, pp. 834-838.

Macejak et al., "Internal initiation of translation mediated by the 5' leader of a cellular mRNA", Nature, vol. 353, Sep. 1991, pp. 90-94.

Makarova et al., "An updated evolutionary classification of CRISPR-Cas systems", Nature, vol. 13, Nov. 2015, pp. 722-736.

Mali et al., "Cas9 as a versatile tool for engineering biology", Nat Methods, Oct. 2013; 10(10): 957-963.

Matsuoka et al., "Tissue-specific light-regulated expression directed by the promoter of a C4 gene, maize pyruvate,orthophosphate dikinase, in a C3 plant, rice", Proc. Natl. Acad. Sci. USA, vol. 90, pp. 9586-9590, Oct. 1993.

McElroy et al., "Isolation of an Efficient Actin Promoter for Use in Rice Transformation", The Plant Cell, vol. 2, 163-171, Feb. 1990.

McNellis et al., "Glucocorticoid-inducible expression of a bacterial avirulence gene in transgenic *Arabidopsis* induces hypersensitive cell death", The Plant Journal (1998) 14(2), 247-257.

Miao et al., "Ammonia-Regulated Expression of a Soybean Gene Encoding Cytosolic Glutamine Synthetase in Transgenic Lotus corniculatus", The Plant Cell, vol. 3, Jan. 11-22, 1991.

Miki et al., "Selectable marker genes in transgenic plants: applications, alternatives and biosafety", Journal of Biotechnology 107 (2004) 193-232.

Mogen et al., "Upstream Sequences Other than AAUAAA Are Required for Efficient Messenger RNA 3'-End Formation in Plants", The Plant Cell, vol. 2, 1261-1272, Dec. 1990.

Moore et al., "Strategies for the in vitro Evolution of Protein Function: Enzyme Evolution by Random Recombination of Improved Sequences", J. Mol. Biol. (1997) 272, 336-347.

Munroe et al., "Tales of poly(A): a review", Gene, 91 (1990, 151-158.

Murai et al., "Phaseolin Gene from Bean Is Expressed After Transfer to Sunflower Via Tumor-Inducing Plasmid Vectors", Science, vol. 222, Issue 4623, Nov. 4, 1983, pp. 476-482.

(56) References Cited

OTHER PUBLICATIONS

Murray et al., "Codon usage in plant genes", Nucleic Acids Research, vol. 17, No. 2, 1989, pp. 477-498.
Needleman et al., "A General Method Applicable to the Search for Similarities in the Amino Acid Sequence of Two Proteins", J. Mol. Biol. (1970) 48, 443-453.
Nishitani et al., "The Cdt1 protein is required to license DNA for replication in fission yeast", Nature, vol. 404, Apr. 2000, pp. 625-628.
Nunez et al., "Chemical and Biophysical Modulation of Cas9 for Tunable Genome Engineering", ACS Chem. Biol., 2016, 11, 681-688.
Odell et al., "Identification of DNA sequences required for activity of the cauliflower mosaic virus 35S promoter", Nature, vol. 313, Feb. 28, 1985, pp. 810-812.
Ono et al., "Transient Assay System for the Analysis of PR-1a Gene Promoter in Tobacco BY-2 Cells", Biosci. Biotechnol. Biochem., 68(4), 803-807, 2004.
Orozco et al., "Localization of light-inducible and tissue-specific regions of the spinach ribulose bisphosphate carboxylase/oxygenase (rubisco) activase promoter in transgenic tobacco plants", Plant Molecular Biology 23: 1129-1138, 1993.
Pacher et al., "Two Unlinked Double-Strand Breaks Can Induce Reciprocal Exchanges in Plant Genomes via Homologous Recombination and Nonhomologous End Joining", Genetics 175: 21-29, Jan. 2007.
Pawluk et al., "Naturally Occurring Off-Switches for CRISPR-Cas9", Cell 167, 1829-1838, Dec. 15, 2016.
Proudfoot, "Poly(A) Signals", Cell, vol. 64, 671-674, Feb. 22, 1991.
Rauch et al., "Inhibition of CRISPR-Cas9 with Bacteriophage Proteins", Cell 168, 150-158, Jan. 12, 2017.
Rinehart et al., "Tissue-Specific and Developmental Regulation of Cotton Gene FbL2A", Plant Physiol. (1996) 112: 1331-1341.
Rubinitz et al., "The Minimum Amount of Homology Required for Homologous Recombination in Mammalian Cells", Molecular and Cellular Biology, vol. 4, No. 11, Nov. 1984, p. 2253-2258.
Russell et al., "Tissue-specific expression in transgenic maize of four endosperm promoters from maize and rice", Transgenic Research 6, 157-168, 1997.
Sanfacon et al., "A dissection of the cauliflower mosaic virus polyadenylation signal", Genes & Development 5: 141-149, 1991.
Sanger et al., "Characteristics of a strong promoter from figwort mosaic virus: comparison with the analogous 35S promoter from cauliflower mosaic virus and the regulated mannopine synthase promoter", Plant Molecular Biology 14: 433-443, 1990.
Schena et al. "A steroid-inducible gene expression system for plant cells", Proc. Natl. Acad. Sci. USA, vol. 88, 99. 10421-10425, Dec. 1991.
Sengupta-Gopalan et al., "Developmentally regulated expression of the bean f8-phaseolin gene in tobacco seed", Proc. Natl. Acad. Sci. USA, vol. 82, pp. 3320-3324, May 1985.
Shen et al., "Homologous Recombination in Escherzchza Coli: Dependence On Substrate Length and Homology", Genetics 112: 441-457, Mar. 1986.
Shmakov et al., "Discovery and Functional Characterization of Diverse Class 2 CRISPR-Cas Systems", Molecular Cell 60, 385-397, Nov. 5, 2015.
Siebert et al., "Efficient Repair of Genomic Double-Strand Breaks byHomologous Recombination between Directly Repeated Sequences in the Plant Genome", The Plant Cell, vol. 14, 1121-1131, May 2002.
Simpson et al., "Light-inducible and tissue-specific expression of a chimaeric gene under control of the 5'-flanking sequence of a pea chlorophyll a/bbinding protein gene", The EMBO Journal, vol. 4, No. 11, pp. 2723-2729, 1985.
Allison et al., "The Nucleotide Sequence of the Coding Region of Tobacco Etch Virus Genomic RNA: Evidence for the Synthesis of a Single Polyprotein",Virology 154, 9-20, (1986).
Ayares et al., "Sequence homology requirements for intermolecular recombination in mammalian cells", Proc. Natl. Acad. Sci. USA, vol. 83, pp. 5199-5203, Jul. 1986.
Ballas et al., "Efficient functioning of plant promoters and poly(A) sites in Xenopus oocytes", Nucleic Acids Research, vol. 17, No. 19, pp. 7891-7903, 1989.
Baskerville et al., "Microarray profiling of microRNAs reveals frequent coexpression with neighboring miRNAs and host genes", RNA, 2005, 11:241-247.
Bleuyard et al., "Recent advances in understanding of the DNA double-strand break repair machinery of plants", DNA Repairs 5, 2006, pp. 1-12.
Bogusz et al., "Nonlegume Expression Hemoglobin Genes Retain Organ-Specific in Heterologous Transgenic Plants", The Plant Cell, vol. 2, pp. 633-641, Jul. 1990.
Brown et al., "Endogenous microRNA regulation suppresses transgene expression in hematopoietic lineages and enables stable gene transfer", Nature Medicine, vol. 12, No. 5, May 2006, pp. 585-591.
Bruce et al., "Expression Profiling of the Maize Flavonoid Pathway Genes Controlled by Estradiol-Inducible Transcription Factors CRC and P", The Plant Cell, vol. 12, pp. 65-79, Jan. 2000.
Burstein et al., "New CRISPR-Cas systems from uncultivated microbes", Nature, vol. 542, Feb. 9, 2017, pp. 237-253.
Campbell et al., "Condon Usage in Higher Plants, Green Algae, and Cyanobacteria", Plant Physiol., (1990) 92, pp. 1-11.
Canevascini et al., "Tissue-Specific Expression and Promoter Analysis of the Tobacco Itp1 Gene", Plant Physiol. (1996) 112, pp. 513-524.
Capecchi, "Altering the Genome by Homologous Recombination", Science, vol. 244, Jun. 16, 1989, pp. 1288-1292.
Capone et al., "Expression in different populations of cells of the root meristem is controlled by different domains of the rolB promoter", Plant Molecular Biology 25, pp. 681-691, 1994.
Chen et al., "MicroRNAs Modulate Hematopoietic Lineage Differentiation", Science, vol. 303, Jan. 2, 2004, pp. 83-86.
Christensen et al., "Sequence analysis and transcriptional regulation by heat shock of polyubiquitin transcripts from maize", Plant Molecular Biology 12, pp. 619-632, 1989.
Chylinski et al., "Classification and evolution of type II CRISPR-Cas systems", Nucleic Acids Research, 2014, vol. 12, No. 10, pp. 6091-6105.
Crameri et al., "Molecular evolution of an arsenate detoxification pathway by DNA shuffling", Nature Biotechnology, vol. 15, May 1997, pp. 436-438.
Crameri et al., "DNA shuffling of a family of genes from diverse species accelerates directed evolution", Nature, vol. 391, Jan. 15, 1998, pp. 288-291.
Dayhoff et al., "A Model of Evolutionary Change in Proteins", Atlas of Protein Sequence and Structure, 1978, pp. 345-352.
De Almeida et al., "Transgenic expression of two marker genes under the control of an *Arabidopsis* rbcS promoter: Sequences encoding the Rubisco transit peptide increase expression levels", Mol Gen Genet (1989) 218: 78-86.
Della-Cioppa et al., "Protein Trafficking in Plant Cells", Plant Physiol. (1987) 84, 965-968.
De Veylder et al., "Herbicide Safener-lnducible Gene Expression in *Arabidopsis thaliana*", Plant Cell Physiol. 38 (5): 568-577 (1997).
Elroy-Stein et al., "Cap-independent translation of mRNA conferred by encephalomyocarditis virus 5' sequence improves the performance of the vaccinia virus/bacteriophage T7 hybrid expression system", Proc. Natl. Acad. Sci. USA, vol. 86. pp. 6126-6130, Aug. 1989.
Esvelt et al., "Orthogonal Cas9 Proteins for RNA-Guided Gene Regulation and Editing", Nat Methods, Nov. 2013; 10(11): 1116-1121.
Fonfara et al., "Phylogeny of Cas9 determines functional exchangeability of dual-RNA and Cas9 among orthologous type II CRISPR-Cas systems", Nucleic Acids Research, 2014, vol. 42, No. 4, 2577-2590.
Fu et al., "High-frequency off-target mutagenesis induced by CRISPR-Cas nucleases in human cells", Nature Biotechnology, vol. 31, No. 9, Sep. 2013, 822-827.

(56) References Cited

OTHER PUBLICATIONS

Gallie et al., "Eukaryotic viral 5'-leader sequences act as translational enhancers in eukaryotes and prokaryotes" in Molecular Biology of RNA, ed. Cech (Liss, New York), 1989, pp. 237-256.
Gallie et al., "The tobacco etch viral 5' leader and poly(A) tail are functionally synergistic regulators of translation", Gene 165(2):1995, 233-238.
Garcia et al., "Anti-CRISPR AcrllA5 Potently Inhibits All Cas9 Homologs Used for Genome Editing", Cell Reports, 29, 1739-1746, Nov. 12, 2019.
Gatz et al., "Regulation of a modified CaMV 35S promoter by the Tnl0-encoded Tet repressor in transgenic tobacco", Mol Gen Genet (1991) 227: 229-237.
Gotor et al., "Analysis of three tissue-specific elements from the wheat Cab-1 enhancer", The Plant Journal (1993) 3(4), 509-518.
Guerineau et al., "Effect of deletions in the cauliflower mosaic virus polyadenylation sequence on the choice of the polyadenylation sites in tobacco protoplasts", Mol Gen Genet (1991) 226: 141-144.
Guevara-Garcia et al., "Tissue Specific and wound inducible pattern of expression of the mannopine synthase promoter is determined by the interaction between positive and negative cis-regulatory elements", The Plant Journal (1993) 4(3), 495-505.
Haft et al., "A Guild of 45 CRISPR-Associated (Cas) Protein Families and Multiple CRISPR/Cas Subtypes Exist in Prokaryotic Genomes", PLoS Computational Biology, Nov. 2005, vol. 1, Issue 6, e60, 0474-0483.
Hansen et al., "Wound-inducible and organ-specific expression of ORF13 from Agrobacterium rhizogenes 8196 T-DNA in transgenic tobacco plants", Mol Gen Genet (1997) 254: 337-343.
Henikoff et al., "Amino acid substitution matrices from protein blocks", Proc. Natl. Acad. Sci. USA, vol. 89, pp. 10915-10919, Nov. 1992.
Heyer et al., "Regulation of Homologous Recombination in Eukaryotes", Annu. Rev. Genet. 2010 vol. 44: 113-39.
Higgins et al., "Fast and sensitive multiple sequence alignments on a microcomputer", Cabios Communications, vol. 5, No. 2, 1989, pp. 151-153.
Higgins et al., "CLUSTAL V: improved software for multiple sequence alignment", Cabios, vol. 8, No. 2, 1992, pp. 189-191.
Hirel et al., "Forcing expression of a soybean root glutamine synthetase gene in tobacco leaves induces a native gene encoding cytosolic enzyme", Plant Molecular Biology 20: 207-218, 1992.
Hirosawa et al., "Cell-type[specific genome editing wit ha microRNA-responsive CRISPR-Cas9 switch", Nucleic Acids Research, 2017, vol. 45, No. 13, e118, 11 pages.
Horvath et al., "CRISPR/Cas, the Immune System of Bacteria and Archaea", Science 327, 167, 2010, pp. 167-170.
Hsu et al., "Development and Applications of CRISPR-Cas9 for Genome Engineering", Cell 157, Jun. 5, 2014, pp. 1262-1278.
Hynes et al., "An anti-CRISPR from a virulent streptococcal phage inhibits *Streptococcus pyogenes* Cas9", Nature Microbiology, vol. 2, Oct. 2017, pp. 1374-1380.
Hynes et al., "Widespread anti-CRISPR proteins in virulent bacteriophages inhibit a range of Cas9 proteins", Nature Communications, 201, pp. 1-10.
Ingelbrecht et al., "Different 3' End Regions Strongly Influence the Level of Gene Expression in Plant Cells", The Plant Cell, vol. 1, 671-680, Jul. 1989.
Jobling et al., "Enhanced translation of chimaeric messenger RNAs containing a plant viral untranslated leader sequence", Nature, vol. 325, Feb. 12, 1987, pp. 622-625.
Jones et al., "High level expression of introduced chimaeric genes in regenerated transformed plants", The EMBO Journal, vol. 4, No. 10, pp. 2411-2418, 1985.
Jore et al., "Structural basis for CRISPR RNA-guided DNA recognition by Cascade", Nature Structural & Molecular Biology, vol. 18, No. 5, May 2011, pp. 529-537.
Joshi, "Putative polyadenylation signals in nuclear genes of higher plants: a compilation and analysis", Nucleic Acids Research, vol. 15, No. 23, 1987, 9627-9640.

\* cited by examiner

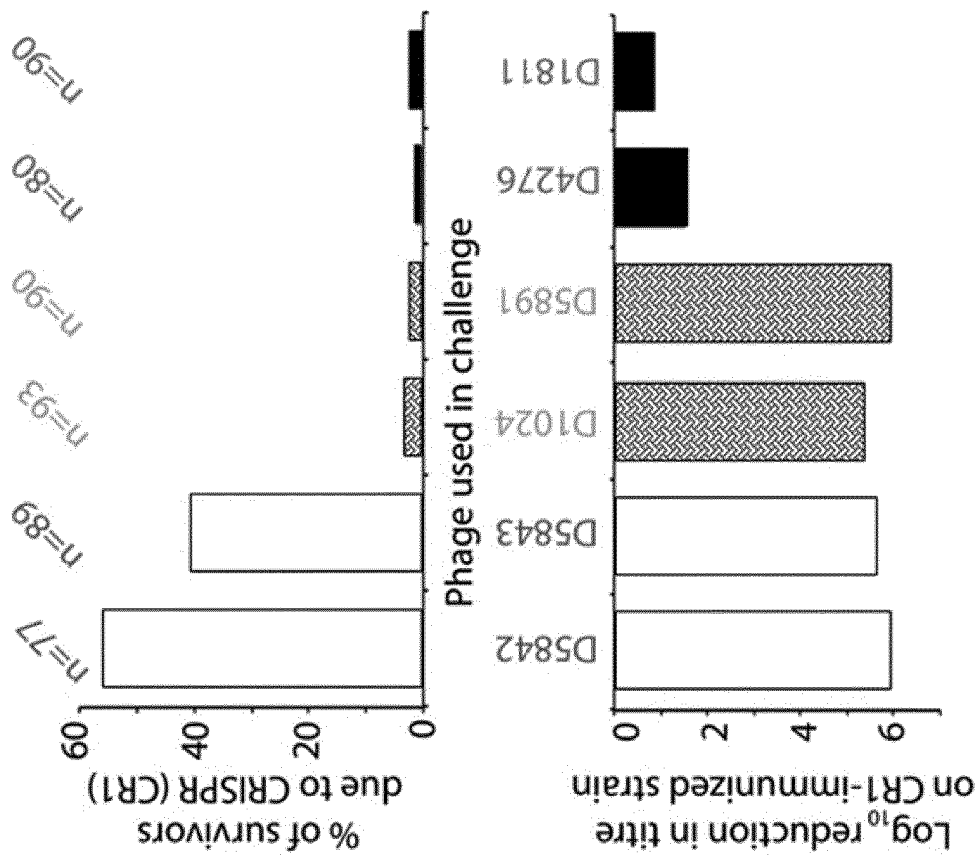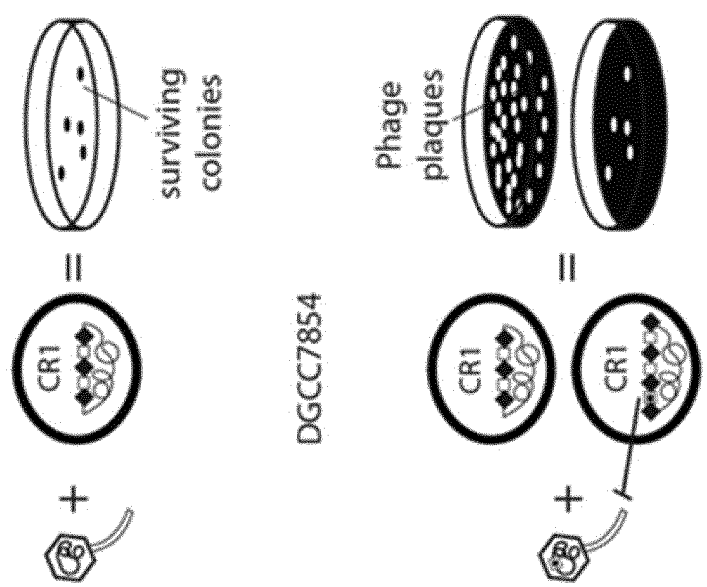
FIG. 1

```
                          HHHHHHHH
D4276    1MAYGKSRYNSYRKRSENRSNKQRREYAQ 28
Sf21                            I  DTK
TP778-L          F    N     P      D  K
S.species                          D  C
 01205                             D HHHHHHHHH         
D4276   29EMDRLEKAFENLDGWYLSSMKDSAYKDF 56
Sf21       EK      K
TP778-L  A  E      E  H          M
S.species   QT     K              N
 01205

EEEEE          EEEEEE
D4276   57GKYEIRLSNHSADNKYHDLENGRLIVNI 84
Sf21                                  V
TP778-L  E QV          Q     Y        V
S.species                             V
 01205

HHHHHHHHHHHH
D4276   85KASKLNFVDTIENKLDKTIEKIDKLDLD 112
Sf21                          T
TP778-L            K                L V
S.species                             
 01205        -------------------------

HHHH
D4276  113KYRFINATNLEHDIKCYYKGEKTKKEVI 140
Sf21          K  R            Y    D
TP778-L       RM              L Y  D
S.species     -----------------    D
 01205
```

FIG. 3B

FIG. 6A

>Bacteriophage O1205 Nucleic acid (SEQ ID NO: 1)
ATGGCATACGGAAAAAGCAGATACAACTCATATAGGAAACGCAGTTTCAATAGAAGCGATAAGCAACGTAGAGAATACGCACAAGAAATGGATAGATTAGAACAAACATTTGAA
AAACTTGATGGTTGGTTGTATCTATCTAGCATGGAAAAGATAGTGCGTATAAAGATTTCGGAAAATACGAAATTCGCTTATCAAATCATTCAGCAGACAACAAATATCGACCTAGAAAAA
TGGTCGTTTAATTGTTAATGTCAAAGCAAGTAAATTGAAATGTTACTATAAGGGATTAAGACAAAGAAGGATGTAATCTAA

FIG. 6B

> Bacteriophage O1205 Amino acid (SEQ ID NO: 2)
MAYGKSRYNSYRKRSFNRSDKQRREYAQEMDRLEQTFEKLDGWVLSSMKDSAYKDFGKYEIRLSNHSADNKYHDLENGRLIVNVKASKLKFVDIKCYYKGFKTKKDVI

FIG. 6C

> Bacteriophage Sfi21 Nucleic acid sequence (SEQ ID NO: 3)
ATGGCATACGGAAAAAGTAGATACTATATAAGCAACGTAGAGAATACGCACAAGAAATGGATAGATTAGAGGAAACGTTCGAA
AATCTTGACGGATGGTATCTATCTAGCATGAAGGATAGTGCGTACAAGGATTTCGGAAAAGATATGCTTATCAAATCATCAGCAGACAACAATATCATGACCTAGAAAAA
TGGTCGTTTAATTGTTAATGTCAAAGCAAGTAAATTGAACTTCGTTGATATCATCGAGAGAAATCATTGATAAATCATTGAGAAGATTGATACTCTTGATTAGATAAGTACAGATT
CATTAATGCTACTACTAAATTGCTACTATAAAGGCTATATAAGGCTATAAGAAGAAGGATGTAATCTAA

FIG. 6D

> Bacteriophage Sfi21 Amino acid sequence (SEQ ID NO: 4)
MAYGKSRYNSYRKRSFNRSNKQRREYAQEMDRLEKAFENLDGWYLSSMKDSAYKDFGKYEIRLSNHSADNKYHDLENGRLIVNVKASKLNFVDIIENKLDKIIEKIDTLDLDKYRFINATKLE
RDIKCYYKGYKTKDVI

FIG. 6E

> Bacteriophage TP-778L Nucleic acid sequence (SEQ ID NO: 5)
ATGGCATACGGAAAAAGCAGATACAACTCATATAGGAAACGCTAGTTTCAACATAGAAGTGACCAAGTAGGGAATATGCAAAAGAAAAGAAATTAGAAGAAGCATTTGAA
AAGCTAGATGGTTGGTATCTATCTAGCATGAAGGATATTTGGAAGGATATACAAGGATTTGGATACAAGGATATGCTTATCAAATCATTCAGCAGACAATAAATCATGACCTAGAAAA
TGGTCGTTTAATTGTTAATGTCAAAGCAAGTAAATTGAACTTCGTTGATATCATCGAAAAACAAACTTGATAAAATCATCGAGAAGATTGATAAAGCTTGATTAGATAAGTACAGATT
TATTAACGCTACTACTAGAATGGAGCATGACATTAAGTCTACTATAAAGCTACTATAAAGGATTTAAGACAAAGATAGATGTAATCTAA

FIG. 6F

> Bacteriophage TP-778L Amino acid sequence (SEQ ID NO: 6)

MAYGKSRYNSYRKRSFNISDTKRREYAKEMEKLEQAFEKLDGWYLSSMKDSAYKDFGKYEIRLSNHSADNKYHDLENGRLIVNVKASKLNFVDIIENKLDKIIEKIDKLDLDKYRFINATRMEH DIKCYKGFKTKKDVI

FIG. 6G

> Streptococcus sp. HMSC072D07 Nucleic acid sequence (SEQ ID NO: 7)

ATGGCATTTGGCAAGAACAGATACAATCCATACGGAACAGTAGTTTAATCGTAGTGATAAACAATGTCGAGAGTATGCTCAGGCAATGGACGAACTAGAACAAGCTTTGAGG AACTTGATGGATGGCACTTATCTAGTAGTGATAGTGCTTATAAAGAATTTTGAAAAGTACCAGGTTCGCCTATCAAATCATTCAGACAGACAACCAATATCATGACTTAGAAAATG GTTACTTGATTGTCAATGTTAAAGCAAGCATTAAATTGAACTTTGTCGATATTATCGAATAAGATTTTAGAGAAAGTAGACAAGCTTGATCTTGATAAGTATAGGTTTA TCAATGCGACCAATCTGGAACATGATATTAAATGTTATCTCAAAGGCTATAAGACGTGATTTAA

FIG. 6H

> Streptococcus sp. HMSC072D07 Amino acid sequence (SEQ ID NO: 8)

MAFGKNRYNPYRKRSFNRSDKQCREYAQAMDELEQAFEELDGWHLSMMDSAYKNFEKYQVRLSNHSADNQYHDLENGYLIVNVKASKLNFVDIIENKLDKILEKVDKLDLDKYRFINAT NLEHDIKCYLKGYKTKKDVI

FIG. 6I

> Bacteriophage D4276 Nucleic acid sequence (SEQ ID NO: 9)

ATGGCATACGGAAAAAGTAGATACAACTCATATCGTAGAAGCAGAATAAGAGAATGCGACAAGAAATGGATAGATTAGAGAAAGCTTTCGAA AATCTTGACGGATGGTATCTATCCAGCATGAAGGACAGTGTTACACAAGGATTTGGGAAATACGAAATTCGCTTATCAAATCATTCGGCAGACAACAATATCACGACTTAGAAAA CGGTTCGTTTAATTGTTAATATTAAAGCTAGTAAATTGAATTTCGTTGATATCATCGAGAATAAGCTTGATAAAATAATCGAGAAGATTGATAAGTACCGATT CATCAATGCGACCAACCTAGAGCATGATATCAAATGCTATTACAAGGGGTTTAAAACGAAAAAGGAGGTAATCTAA

FIG. 6J

> Bacteriophage D4276 Amino acid sequence (SEQ ID NO: 10)

MAYGKSRYNSYRKRSFNRSNKQRREYAQEMDRLEKAFENLDGWYLSSMKDSAYKDFGKYEIRLSNHSADNKYHDLENGRLIVNIKASKLNFVDIIENKLDKIIEKIDKLDLDKYRFINATNLE HDIKCYKGFKTKKEVI

> Bacteriophage D1126 Nucleic acid sequence (SEQ ID NO: 11)
ATGGCATACGGGAAAAAGCAGATACAATTCATATAGGAAGCGAATATGCTAAAAAAATGAAGGAGTTAGAACAAGCGTTTG
AAAACCTTGACGGATGGTATCTATCTAGCATGAAAGATAGTGCGTACAAAGATTTCGGAAAATACGAAATTCGCTTATCAAATCATTCAGCAGACAATAGATATCGACCTAG
AAAATGGTCGCTTAATGTTAAAGCTAGTAAATTGAACTTCGTTGATATCATCGAGATAAACTTGGTAAAATCATTGAGAAGATTGATACTCTTGATTTAGATAAGTA
CAGATTCATTAATGCTACTAAATTGGAACGTGATATCAAATGCTACTATAAAGGCTATAAGACAAAGAAGGATGTAATCTAA

FIG. 6K

> Bacteriophage D1126 Amino acid sequence (SEQ ID NO: 12)
MAYGKSRYNSYRKNFSISDNQRREYAKKMKELEQAFENLDGWYLSSMKDSAYKDFGKYEIRLSNHSADNRYHDLENGRLIVNVKASKLNFVDIIENKLGKIIEKIDTLDLDKYRFINATKL
ERDIKCYYKGYKTKKDVI

FIG. 6L

> Bacteriophage D4250 Nucleic acid sequence (SEQ ID NO: 13)
ATGGCATACGGGAAAAAGTAGATATAACTCATATAGAAAACGCAGTTTCAACAGAAGCGATAAACAGCGTAGAGAATACGCACAAGCAATGGAAGAATTAGAGCAAGCATTTG
AAAACTTTGATGATTGGTATCTATCAGCATGAAAGACAGCAGTGCTTACAAGGATTTTGGGAAATACGAAATTCGCTTATCAAATCATTCGGCAGACAACAAATATCACGACTTAG
AAAACGGTCGTTTAATTGTTAATATTAAAGCTAGTAAATTCGTTGATATCATCGAGAATAAGCTTGATAAATAATCGAGAAGATTGATAAGCTTGATTTAGATAAGTA
CCGATTCATCAATGCGACCAACCTAGAGCATGATATCAAATGCTATTACAAGGGGTTTAAAACGAAAAAGGAGGTAATCTAA

FIG. 6M

> Bacteriophage D4250 Amino acid sequence (SEQ ID NO: 14)
MAYGKSRYNSYRKRSFNRSDKQRREYAQAMEELEQAFENFDDWYLSSMKDSAYKDFGKYEIRLSNHSADNKYHDLENGRLIVNIKASKLNFVDIIENKLDKIIEKIDLDKYRFINATN
LEHDIKCYYKGFKTKKEVI

FIG. 6N

FIG. 6O

> Bacteriophage D4252 Nucleic acid sequence (SEQ ID NO: 15)
ATGGCATACGGAAAAAGCAGATACAAACTCATATAGAAAAGCGCAGTTTTAACAGAAGTGATAAGCAACGTAGAGAATACGCTAAAAAAATGAAGGAGTTAGAACAAGCGTTTGAAAAACTT
TGATGGTTGGTATCTATCGAGACGATGAATGACAGTGCTTATAAAAATTTTGGCAAATATGAAGTTCGATTGTCAAATCATTCGGCAGATAATAATATCACGACATAGAAAACGGTCGTTTAA
TTGTTAATGTTAAAGCTAGTAAATTGAATTTCGTTGATATCATCGAGAACAAGCTTGATAAATAATCGAGAAGATTGATAAGCTTGATTTAGATAAGTACCGATTCATCAACGCTACCAAT
CTAGAGCATAATATTAAATGCTATTACAAGGGATTTAAGACAAGAAGGATGTAATATAA

FIG. 6P

> Bacteriophage D4252 Amino acid sequence (SEQ ID NO: 16)
MAYGKSRYNSYRKRSFNRSDKQRREYAKKMKELEQAFENLDGWYLSSMNDSAYKNFGKYEVRLSNHSADNKYHDIENGRLIVNVKASKLNFVDIENKLDKIIEKIDKLDLDKYRFINATNLEHNIKCY
YKGFKTKKDVI

FIG. 6Q

> Bacteriophage D4598 Nucleic acid sequence (SEQ ID NO: 17)
ATGGCATACGGAAAAAGCAGATACAAACTCATATAGAAAAGCAGTTTCAACAGAAGTGATAAGCAATGGAAGAATACGACAAGCAATGGAAGAATTAGAGCAAGCATTTGAAAAACTT
TGATGATTGGTATCTATCAAGCATGAAAGATAGTGCTTACAAGGATTTCGGCAAATATGAAGTTCGGCAGACAATAAATATCATGACCTAGAAATGGTCGCTTA
ATCGTTAATGTTAAAGCTAGTAAATTGAACTTCGTCGATATCATCGAGAATAAAATCGATAAGATTGATAAGCTTGATTTAGATAAGTACCGATTCATCAACGCTACCAA
CCTAGAGCATGATATCAAATGTTATTACAAGGGATTTAAGACAAAAAAAGGATGTAATCTAA

FIG. 6R

> Bacteriophage D4598 Amino acid sequence (SEQ ID NO: 18)
MAYGKSRYNSYRKRSFNRSDKQRGEYAQAMEELEQAFENFDDWYLSSMKDSAYKDFGKYEIRLSNHSADNKYHDLENGRLIVNVKASKLNFVDIENKIDKIEKIDKLDLDKYRFINATNLEHDIKCY
YKGFKTKKDVI

FIG. 6S

>Streptococcus_mutans_NLML9 (SEQ ID NO: 19)
ATGGCATTTGGAAAAAGAAGAATATAACTCGTATCGTAAAGCGAGTTTTAATAGAAGTGATAAGCGAGTTTAATAGAAGTGATAAGCAACGTCGAGAATATGCACAAGCAATGGAAGAACTTGAACAAACATTGAAAATCTTGAAG
GTTGGAATTATCAAGCATGAAGATAGTGCTTATAAAGATTGAAGTTCGACTTCAAATCATTCAGCTGATAATCAATATCACAAGATGTAAATTAATCATCAATAT
CAAAGCTAGTAAAATGAATTTTGTTTGGATTATAGAAATAAACTTGATGCAATTCTTGAAAAAGTAAATAAGTTAGACCTTAGCAAATACAGATTTATTAATGCTACAAGTTAGATCATGATAT
CAAATGTTATTACAAAAATTATAAAACAAAGAAAAGATGTAATTTAA

FIG. 6T

>Streptococcus_mutans_NLML9 (SEQ ID NO: 20)
MAFGKKRYNSYRKRSFNRSDKQRREYAQAMEELEQTFENLEGWNLSSMKDSAYKDYDKYEVRLSNHSADNQYHNLQDGKLIINIKASKMNFVWIIENKLDAILEKVNKLDLSKYRFINATSLDHDIKCYYK
NYKTKKDVI

FIG. 6U

>Streptococcus_mutans_AD01 (SEQ ID NO: 21)
ATGGCATTTGGAACAAGAAGAATATAATTCATATCGTAAACGCAGTTTTAATAGAAGTGATAAGCAACGTCGAGAATATGCACAAGCAATGGAAGAACTTGAACAAACATTGAAAATCTTGAAG
ATTGGAATTTGTCGAGCATGAAATGTTGTTTATAAAGATTGAAGTTCGACTTCAAATCATTCAGCTGATAATCATCAGCTGATAATCATAACTTACAAGATGTAAATTAATCATCAATAT
CAAAGCTAGTAGAAATGAATTTTGTTTGGATTATAGAAATAAACTTGATGCAATTCTTGAAAAAGTAAATAAGTTAGACCTTAGACAGATACAGATTTATTAATGCTACAAATTTAGAACATGATAT
CAAATGTTATTACAAAAATTATAAAACAAAGAAAAGATGTAATTTAA

FIG. 6V

>Streptococcus_mutans_AD01 (SEQ ID NO: 22)
MAFGTRRYNSYRKRSFNRSDKQRREYAQAMEELEQTFENLEDWNLSSMKDSAYKDYDKYEVRLSNHSADNQYHNLQDGKLIINIKASKMNFVWIIENKLDAILEKVNKLDLSRYRFINATNLEHDIKCYYK
NYKTKKDVI

FIG. 6W

>Streptococcus_mutans_N66 (SEQ ID NO: 23)
ATGGCATTTGGAACAAGAAGAATATAATTCATATCGTAAACGCAGTTTTAATAGAAGTGATAAGCAACGTCGAGAATATGCACAAGCAATGGAAGAACTTGAACAAACATTTGAAAATC
TTGAAGATTGGAATTGTCGAGCATGTAAAGATAGTGCTTATAAAGATTATGAAATATGAAGTTAGACTTCAAATCATTCAGCTGTATAATCATATCATTACAAGATGGTAAAT
TAATCATCAATATCAAAGCTAGTAAAGCTGAATTTGTTTGGATTATAGAAAATAAACTTGATGTAATTCTTGAAAAAGTAAATAAGTTAGACCTTAGCAAATACAGATTTATTAATGCTAC
AAGTTTAGATCATGATATCAAATGTTATTACAAAAATTATAAAACAAAGAAAGATGTAATCTAA

FIG. 6X

>Streptococcus_mutans_N66 (SEQ ID NO: 24)
MAFGTRRYNSYRKRSPNRSDKQRREYAQAMEELEQTFENLEDWNLSSMKDSAYKDYDKYEVRLSNHSADNQYHNLQDGKLIINIKASKMNFVWIIENKLDVILEKVNKLDLSKYRFINATSLDH
DIKCYYKNYKTKKDVI

FIG. 6Y

>Streptococcus_mutans_24 (SEQ ID NO: 25)
ATGGCATTTGGAACAAGAAGAATATAATTCATATCGTAAACGCAATTTTAATGAAGTGATAAACAACGTCGAGAATATGCACAAGCAATGGAAGAACTTGAACAAACATTTGAAAATCT
TGAAGATTGGAATTGTCGAGCATGTAAAGATAGTGCTTATAAAGATTATGAAGTTCGACTTCAAATTCATTCAGCTGATAATCATATCAATTACAAGATGGTAAATT
AATCATCAATATCAAAGCTAGTAAAGCTAGTTTTGTTTGGATTATAGAAAATAAACTTGATGCAATTCTTGAAAAGTAAATAAGTTAGACCTTAGCAAATACAGATTATTATGCTAC
AAGTTTAGATCATGATATCAAATGTTATTACAAAAATTATAAAACAAAGAAAAAGATGTAATTTAA

FIG. 6Z

>Streptococcus_mutans_24 (SEQ ID NO: 26)
MAFGTRRYNSYRKRNFNRSDKQRREYAQAMEELEQTFENLEDWNLSSMKDSAYKDYDKFEVRLSNHSADNQYHNLQDGKLIINKASKMNFVWIIENKLDAILEKVNKLDLSKYRFINATSLDH
DIKCYYKNYKTKKDVI

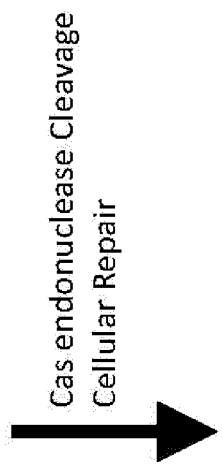
FIG. 9

SEQUENCE LISTING

```
<160> NUMBER OF SEQ ID NOS: 650

<210> SEQ ID NO 1
<211> LENGTH: 327
<212> TYPE: DNA
<213> ORGANISM: Bacteriophage O1205

<400> SEQUENCE: 1
atggcatacg gaaaaagcag atacaactca tataggaaac gcagtttcaa tagaagcgat      60
aagcaacgta gagaatacgc acaagaaatg gatagattag aacaaacatt tgaaaaactt     120
gatggttggt atctatctag catgaaagat agtgcgtata aagatttcgg aaaatacgaa     180
attcgcttat caaatcattc agcagacaac aaatatcatg acctagaaaa tggtcgttta     240
attgttaatg tcaaagcaag taaattgaaa ttcgttgata tcaaatgtta ctataaggga     300
tttaagacaa agaaggatgt aatctaa                                         327

<210> SEQ ID NO 2
<211> LENGTH: 108
<212> TYPE: PRT
<213> ORGANISM: Bacteriophage O1205

<400> SEQUENCE: 2

Met Ala Tyr Gly Lys Ser Arg Tyr Asn Ser Tyr Arg Lys Arg Ser Phe
1               5                   10                  15

Asn Arg Ser Asp Lys Gln Arg Arg Glu Tyr Ala Gln Glu Met Asp Arg
            20                  25                  30

Leu Glu Gln Thr Phe Glu Lys Leu Asp Gly Trp Tyr Leu Ser Ser Met
        35                  40                  45

Lys Asp Ser Ala Tyr Lys Asp Phe Gly Lys Tyr Glu Ile Arg Leu Ser
```

```
                50               55                60
Asn His Ser Ala Asp Asn Lys Tyr His Asp Leu Glu Asn Gly Arg Leu
 65                  70                  75                  80

Ile Val Asn Val Lys Ala Ser Lys Leu Lys Phe Val Asp Ile Lys Cys
                 85                  90                  95

Tyr Tyr Lys Gly Phe Lys Thr Lys Lys Asp Val Ile
            100                 105

<210> SEQ ID NO 3
<211> LENGTH: 423
<212> TYPE: DNA
<213> ORGANISM: Bacteriophage Sfi21

<400> SEQUENCE: 3
atggcatacg gaaaaagtag atataactca tatagaaagc gcagttttaa cagaagtaat    60
aagcaacgta gagaatacgc acaagaaatg gatagattag agaaagcttt cgaaaatctt   120
gacggatggt atctatctag catgaaagat agtgcgtaca agatttcgg aaaatacgaa    180 attcgcttat caaatcattc agcagacaac aaatatcatg acctagaaaa tggtcgttta   240
attgttaatg tcaaagcaag taaattgaac ttcgttgata tcatcgagaa caaacttgat   300
aaaatcattg agaagattga tactcttgat ttagataagt acagattcat taatgctact   360
aaattggaac gtgatatcaa atgctactat aaaggctata agacaaagaa ggatgtaatc   420
taa                                                                 423

<210> SEQ ID NO 4
<211> LENGTH: 140
<212> TYPE: PRT
<213> ORGANISM: Bacteriophage Sfi21

<400> SEQUENCE: 4

Met Ala Tyr Gly Lys Ser Arg Tyr Asn Ser Tyr Arg Lys Arg Ser Phe
 1               5                  10                  15

Asn Arg Ser Asn Lys Gln Arg Arg Glu Tyr Ala Gln Glu Met Asp Arg
                 20                  25                  30

Leu Glu Lys Ala Phe Glu Asn Leu Asp Gly Trp Tyr Leu Ser Ser Met
            35                  40                  45

Lys Asp Ser Ala Tyr Lys Asp Phe Gly Lys Tyr Glu Ile Arg Leu Ser
 50                  55                  60

Asn His Ser Ala Asp Asn Lys Tyr His Asp Leu Glu Asn Gly Arg Leu
 65                  70                  75                  80

Ile Val Asn Val Lys Ala Ser Lys Leu Asn Phe Val Asp Ile Ile Glu
                 85                  90                  95

Asn Lys Leu Asp Lys Ile Ile Glu Lys Ile Asp Thr Leu Asp Leu Asp
            100                 105                 110

Lys Tyr Arg Phe Ile Asn Ala Thr Lys Leu Glu Arg Asp Ile Lys Cys
        115                 120                 125

Tyr Tyr Lys Gly Tyr Lys Thr Lys Lys Asp Val Ile
    130                 135                 140

<210> SEQ ID NO 5
<211> LENGTH: 423
<212> TYPE: DNA
<213> ORGANISM: Bacteriophage TP-778L

<400> SEQUENCE: 5
atggcatacg gaaaaagcag atacaactca tatagaaaac gtagtttcaa cataagtgac    60
```

```
acaaagcgta gggaatatgc aaaagaaatg gagaaattag aacaagcatt tgaaaagcta      120
gatggttggt atctatctag catgaaggat agtgcataca aggattttgg aaaatacgaa      180
atccgcttat caaatcattc agcagacaat aaatatcatg acctagaaaa tggtcgttta      240
attgttaatg ttaaagcaag taaattgaac ttcgttgata tcatcgaaaa caaacttgat      300
aaaatcatcg agaagattga taagcttgat ttagataagt acagatttat aacgctact       360 agaatggagc atgacattaa atgctactat aaaggattta agacaaagaa agatgtaatc      420
taa                                                                    423
```

<210> SEQ ID NO 6
<211> LENGTH: 140
<212> TYPE: PRT
<213> ORGANISM: Bacteriophage TP-778L

<400> SEQUENCE: 6

```
Met Ala Tyr Gly Lys Ser Arg Tyr Asn Ser Tyr Arg Lys Arg Ser Phe
1               5                   10                  15

Asn Ile Ser Asp Thr Lys Arg Arg Glu Tyr Ala Lys Glu Met Glu Lys
            20                  25                  30

Leu Glu Gln Ala Phe Glu Lys Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Val Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Arg Met Glu His Asp Ile Lys Cys
        115                 120                 125

Tyr Tyr Lys Gly Phe Lys Thr Lys Lys Asp Val Ile
    130                 135                 140
```

<210> SEQ ID NO 7
<211> LENGTH: 423
<212> TYPE: DNA
<213> ORGANISM: Streptococcus sp. HMSC072D07

<400> SEQUENCE: 7

```
atggcatttg gcaagaacag atacaatcca tacaggaaac gtagttttaa tcgtagtgat       60
aaacaatgtc gagagtatgc tcaggcaatg gacgaactag aacaagcctt tgaggaactt      120
gatggatggc acttatctag tatgatggat agtgcttata gaattttga aaagtaccag       180 gttcgcctat caaatcattc agcagacaac aatatcatg acttagaaaa tggttacttg       240
attgtcaatg ttaaagcaag taaattgaac tttgtcgata ttatcgaaaa taaattggat      300
aagattttag agaaagtaga caagcttgat cttgataagt ataggtttat caatgcgacc      360
aatctggaac atgatattaa atgttatctc aaaggctata agacgaaaaa agacgtgatt      420
taa                                                                    423
```

<210> SEQ ID NO 8
<211> LENGTH: 140
<212> TYPE: PRT
<213> ORGANISM: Streptococcus sp. HMSC072D07

<400> SEQUENCE: 8

Met Ala Phe Gly Lys Asn Arg Tyr Asn Pro Tyr Arg Lys Arg Ser Phe
1               5                   10                  15

Asn Arg Ser Asp Lys Gln Cys Arg Glu Tyr Ala Gln Ala Met Asp Glu
            20                  25                  30

Leu Glu Gln Ala Phe Glu Glu Leu Asp Gly Trp His Leu Ser Ser Met
        35                  40                  45

Met Asp Ser Ala Tyr Lys Asn Phe Glu Lys Tyr Gln Val Arg Leu Ser
    50                  55                  60

Asn His Ser Ala Asp Asn Gln Tyr His Asp Leu Glu Asn Gly Tyr Leu
65                  70                  75                  80

Ile Val Asn Val Lys Ala Ser Lys Leu Asn Phe Val Asp Ile Ile Glu
                85                  90                  95

Asn Lys Leu Asp Lys Ile Leu Glu Lys Val Asp Lys Leu Asp Leu Asp
            100                 105                 110

Lys Tyr Arg Phe Ile Asn Ala Thr Asn Leu Glu His Ile Lys Cys
        115                 120                 125

Tyr Leu Lys Gly Tyr Lys Thr Lys Lys Asp Val Ile
    130                 135                 140

<210> SEQ ID NO 9
<211> LENGTH: 423
<212> TYPE: DNA
<213> ORGANISM: Bacteriophage D4276

<400> SEQUENCE: 9
atggcatacg gaaaagtag atataactca tatagaaagc gcagttttaa cagaagtaat     60
aagcaacgta gagaatacgc acaagaaatg gatagattag agaaagcttt cgaaaatctt    120
gacggatggt atctatctag catgaaagac agtgcttaca aggattttgg gaaatacgaa    180
attcgcttat caaatcattc ggcagacaac aaatatcacg acttagaaaa cggtcgttta    240
attgttaata ttaaagctag taaattgaat ttcgttgata tcatcgagaa taagcttgat    300
aaaataatcg agaagattga taagcttgat ttagataagt accgattcat caatgcgacc    360
aacctagagc atgatatcaa atgctattac aaggggttta aaacgaaaaa ggaggtaatc    420
taa                                                                  423

<210> SEQ ID NO 10
<211> LENGTH: 140
<212> TYPE: PRT
<213> ORGANISM: Bacteriophage D4276

<400> SEQUENCE: 10

Met Ala Tyr Gly Lys Ser Arg Tyr Asn Ser Tyr Arg Lys Arg Ser Phe
1               5                   10                  15

Asn Arg Ser Asn Lys Gln Arg Arg Glu Tyr Ala Gln Glu Met Asp Arg
            20                  25                  30

Leu Glu Lys Ala Phe Glu Asn Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Ile Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Asn Leu Glu His Asp Ile Lys Cys
        115                 120                 125

Tyr Tyr Lys Gly Phe Lys Thr Lys Lys Glu Val Ile
    130                 135                 140

<210> SEQ ID NO 11
<211> LENGTH: 423
<212> TYPE: DNA
<213> ORGANISM: Bacteriophage D1126

<400> SEQUENCE: 11
atggcatacg gaaaaagcag atacaattca tataggaagc gaaacttctc tataagcgac      60
aatcagcgta gggaatatgc taaaaaaatg aaggagttag aacaagcgtt tgaaaacctt     120
gacggatggt atctatctag catgaaagat agtgcgtaca agatttcgg aaaatacgaa      180 attcgcttat caaatcattc agcagacaat agatatcatg acctagaaaa tggtcgctta     240
atcgttaatg ttaaagctag taaattgaac ttcgttgata tcatcgagaa taaacttggt     300
aaaatcattg agaagattga tactcttgat ttagataagt acagattcat taatgctact     360
aaattggaac gtgatatcaa atgctactat aaaggctata agacaagaa ggatgtaatc      420 taa                                                                    423

<210> SEQ ID NO 12
<211> LENGTH: 140
<212> TYPE: PRT
<213> ORGANISM: Bacteriophage D1126

<400> SEQUENCE: 12

Met Ala Tyr Gly Lys Ser Arg Tyr Asn Ser Tyr Arg Lys Arg Asn Phe
1               5                   10                  15

Ser Ile Ser Asp Asn Gln Arg Arg Glu Tyr Ala Lys Lys Met Lys Glu
            20                  25                  30

Leu Glu Gln Ala Phe Glu Asn Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Arg Tyr His Asp Leu Glu Asn Gly Arg Leu
65                  70                  75                  80

Ile Val Asn Val Lys Ala Ser Lys Leu Asn Phe Val Asp Ile Ile Glu
                85                  90                  95

Asn Lys Leu Gly Lys Ile Ile Glu Lys Ile Asp Thr Leu Asp Leu Asp
            100                 105                 110

Lys Tyr Arg Phe Ile Asn Ala Thr Lys Leu Glu Arg Asp Ile Lys Cys
        115                 120                 125

Tyr Tyr Lys Gly Tyr Lys Thr Lys Lys Asp Val Ile
    130                 135                 140

<210> SEQ ID NO 13
<211> LENGTH: 423
<212> TYPE: DNA
<213> ORGANISM: Bacteriophage D4250

<400> SEQUENCE: 13
atggcatacg gaaaaagtag atataactca tatagaaaac gcagtttcaa cagaagcgat      60

```
aaacagcgta gagaatacgc acaagcaatg gaagaattag agcaagcatt tgaaaacttt    120
gatgattggt atctatcaag catgaaagac agtgcttaca aggattttgg gaaatacgaa    180
attcgcttat caaatcattc ggcagacaac aaatatcacg acttagaaaa cggtcgttta    240
attgttaata ttaaagctag taaattgaat ttcgttgata tcatcgagaa taagcttgat    300
aaaataatcg agaagattga taagcttgat ttagataagt accgattcat caatgcgacc    360
aacctagagc atgatatcaa atgctattac aaggggttta aacgaaaaa ggaggtaatc    420 taa                                                                  423
```

<210> SEQ ID NO 14
<211> LENGTH: 140
<212> TYPE: PRT
<213> ORGANISM: Bacteriophage D4250

<400> SEQUENCE: 14

```
Met Ala Tyr Gly Lys Ser Arg Tyr Asn Ser Tyr Arg Lys Arg Ser Phe
1               5                   10                  15

Asn Arg Ser Asp Lys Gln Arg Arg Glu Tyr Ala Gln Ala Met Glu Glu
            20                  25                  30

Leu Glu Gln Ala Phe Glu Asn Phe Asp Asp Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Ile Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Asn Leu Glu His Asp Ile Lys Cys
        115                 120                 125

Tyr Tyr Lys Gly Phe Lys Thr Lys Lys Glu Val Ile
    130                 135                 140
```

<210> SEQ ID NO 15
<211> LENGTH: 423
<212> TYPE: DNA
<213> ORGANISM: Bacteriophage D4252

<400> SEQUENCE: 15

```
atggcatacg gaaaaagcag atacaactca tatagaaagc gcagttttaa cagaagtgat     60
aagcaacgta gagaatacgc taaaaaaatg aaggagttag aacaagcgtt tgaaaacctt    120
gatggttggt atctatcgag catgaatgac agtgcttata aaaatttgg caaatatgaa    180 gttcgattgt caaatcattc ggcagataat aaatatcacg acatagaaaa cggtcgttta    240
attgttaatg ttaaagctag taaattgaat ttcgttgata tcatcgagaa caagcttgat    300
aaaataatcg agaagattga taagcttgat ttagataagt accgattcat caacgctacc    360
aatctagagc ataatattaa atgctattac aagggattta agacaaagaa ggatgtaata    420
taa                                                                  423
```

<210> SEQ ID NO 16
<211> LENGTH: 140
<212> TYPE: PRT
<213> ORGANISM: Bacteriophage D4252

<400> SEQUENCE: 16

Met Ala Tyr Gly Lys Ser Arg Tyr Asn Ser Tyr Arg Lys Arg Ser Phe
1               5                   10                  15

Asn Arg Ser Asp Lys Gln Arg Arg Glu Tyr Ala Lys Lys Met Lys Glu
            20                  25                  30

Leu Glu Gln Ala Phe Glu Asn Leu Asp Gly Trp Tyr Leu Ser Ser Met
        35                  40                  45

Asn Asp Ser Ala Tyr Lys Asn Phe Gly Lys Tyr Glu Val Arg Leu Ser
    50                  55                  60

Asn His Ser Ala Asp Asn Lys Tyr His Asp Ile Glu Asn Gly Arg Leu
65                  70                  75                  80

Ile Val Asn Val Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Asn Leu Glu His Asn Ile Lys Cys
        115                 120                 125

Tyr Tyr Lys Gly Phe Lys Thr Lys Lys Asp Val Ile
            130                 135                 140

<210> SEQ ID NO 17
<211> LENGTH: 423
<212> TYPE: DNA
<213> ORGANISM: Bacteriophage D4598

<400> SEQUENCE: 17
atggcatacg gaaaaagtag atataactca tatagaaaac gcagtttcaa cagaagcgat      60
aaacagcgtg gagaatacgc acaagcaatg gaagaattag agcaagcatt tgaaaacttt     120
gatgattggt atctatcaag catgaaagac agtgcttaca aggattttgg gaaatacgaa     180
attcgcttat caaatcattc ggcagacaat aaatatcatg acctagaaaa tggtcgctta     240
atcgttaatg ttaaagctag taaattgaac ttcgtcgata tcatcgagaa taaaatcgat     300
aaaatcattg agaagattga taagcttgat ttagataagt accgattcat caacgctacc     360
aacctagagc atgatatcaa atgttattac aagggattta agacaaaaaa ggatgtaatc     420
taa                                                                   423

<210> SEQ ID NO 18
<211> LENGTH: 140
<212> TYPE: PRT
<213> ORGANISM: Bacteriophage D4598

<400> SEQUENCE: 18

Met Ala Tyr Gly Lys Ser Arg Tyr Asn Ser Tyr Arg Lys Arg Ser Phe
1               5                   10                  15

Asn Arg Ser Asp Lys Gln Arg Gly Glu Tyr Ala Gln Ala Met Glu Glu
            20                  25                  30

Leu Glu Gln Ala Phe Glu Asn Phe Asp Asp Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Val Lys Ala Ser Lys Leu Asn Phe Val Asp Ile Ile Glu
                85                  90                  95

```
Asn Lys Ile Asp Lys Ile Ile Glu Lys Ile Asp Lys Leu Asp Leu Asp
            100                 105                 110

Lys Tyr Arg Phe Ile Asn Ala Thr Asn Leu Glu His Asp Ile Lys Cys
        115                 120                 125

Tyr Tyr Lys Gly Phe Lys Thr Lys Lys Asp Val Ile
        130                 135                 140

<210> SEQ ID NO 19
<211> LENGTH: 423
<212> TYPE: DNA
<213> ORGANISM: Streptococcus mutans

<400> SEQUENCE: 19
atggcatttg gaaaagaag atataactcg tatcgtaaac gcagttttaa tagaagtgat        60
aagcaacgtc gagaatatgc acaagcaatg gaagaacttg aacaaacatt tgaaaatctt      120
gaaggttgga atttatcaag catgaaagat agtgcttata agattatga taaatatgaa       180 gttcgacttt caaatcattc agctgataat caatatcata acttacaaga tggtaaatta      240
atcatcaata tcaaagctag taaatgaat tttgtttgga ttatagaaaa taaacttgat       300
gcaattcttg aaaagtaaa taagttagac cttagcaaat acagatttat taatgctaca      360
agtttagatc atgatatcaa atgttattac aaaaattata aacaaagaa agatgtaatt      420 taa                                                                    423

<210> SEQ ID NO 20
<211> LENGTH: 140
<212> TYPE: PRT
<213> ORGANISM: Streptococcus mutans

<400> SEQUENCE: 20

Met Ala Phe Gly Lys Arg Arg Tyr Asn Ser Tyr Arg Lys Arg Ser Phe
1               5                   10                  15

Asn Arg Ser Asp Lys Gln Arg Arg Glu Tyr Ala Gln Ala Met Glu Glu
            20                  25                  30

Leu Glu Gln Thr Phe Glu Asn Leu Glu Gly Trp Asn Leu Ser Ser Met
        35                  40                  45

Lys Asp Ser Ala Tyr Lys Asp Tyr Asp Lys Tyr Glu Val Arg Leu Ser
    50                  55                  60

Asn His Ser Ala Asp Asn Gln Tyr His Asn Leu Gln Asp Gly Lys Leu
65                  70                  75                  80

Ile Ile Asn Ile Lys Ala Ser Lys Met Asn Phe Val Trp Ile Ile Glu
                85                  90                  95

Asn Lys Leu Asp Ala Ile Leu Glu Lys Val Asn Lys Leu Asp Leu Ser
            100                 105                 110

Lys Tyr Arg Phe Ile Asn Ala Thr Ser Leu Asp His Asp Ile Lys Cys
        115                 120                 125

Tyr Tyr Lys Asn Tyr Lys Thr Lys Lys Asp Val Ile
        130                 135                 140

<210> SEQ ID NO 21
<211> LENGTH: 423
<212> TYPE: DNA
<213> ORGANISM: Streptococcus mutans

<400> SEQUENCE: 21
atggcatttg gaacaagaag atataattca tatcgtaaac gcagttttaa tagaagtgat        60
aagcaacgtc gagaatatgc acaagcaatg gaagaacttg aacaaacatt tgaaaatctt      120
```

```
gaagattgga atttgtcgag catgaaagat agtgcttata aagattatga taaatatgaa    180
gttcgacttt caaatcattc agctgataat caatatcata acttacaaga tggtaaatta    240
atcatcaata tcaaagctag taaaatgaat tttgtttgga ttatagaaaa taaacttgat    300
gcaattcttg aaaaagtaaa taagttagac cttagcagat acagatttat taatgctaca    360
aatttagaac atgatatcaa atgttattac aaaaattata aacaaagaa agatgtaatt    420 taa                                                                  423
```

<210> SEQ ID NO 22
<211> LENGTH: 140
<212> TYPE: PRT
<213> ORGANISM: Streptococcus mutans

<400> SEQUENCE: 22

```
Met Ala Phe Gly Thr Arg Arg Tyr Asn Ser Tyr Arg Lys Arg Ser Phe
1               5                   10                  15

Asn Arg Ser Asp Lys Gln Arg Glu Tyr Ala Gln Ala Met Glu Glu
            20                  25                  30

Leu Glu Gln Thr Phe Glu Asn Leu Glu Asp Trp Asn Leu Ser Ser Met
        35                  40                  45

Lys Asp Ser Ala Tyr Lys Asp Tyr Asp Lys Tyr Glu Val Arg Leu Ser
    50                  55                  60

Asn His Ser Ala Asp Asn Gln Tyr His Asn Leu Gln Asp Gly Lys Leu
65                  70                  75                  80

Ile Ile Asn Ile Lys Ala Ser Lys Met Asn Phe Val Trp Ile Ile Glu
                85                  90                  95

Asn Lys Leu Asp Ala Ile Leu Glu Lys Val Asn Lys Leu Asp Leu Ser
            100                 105                 110

Arg Tyr Arg Phe Ile Asn Ala Thr Asn Leu Glu His Asp Ile Lys Cys
        115                 120                 125

Tyr Tyr Lys Asn Tyr Lys Thr Lys Lys Asp Val Ile
    130                 135                 140
```

<210> SEQ ID NO 23
<211> LENGTH: 423
<212> TYPE: DNA
<213> ORGANISM: Streptococcus mutans

<400> SEQUENCE: 23

```
atggcatttg gaacaagaag atataattca tatcgtaaac gcagttttaa tagaagtgat     60
aagcaacgtc gagaatatgc acaagcaatg gaagaacttg aacaaacatt tgaaaatctt    120
gaagattgga atttgtcgag catgaaagat agtgcttata aagattatga taaatatgaa    180
gttagacttt caaatcattc agctgataat caatatcata acttacaaga tggtaaatta    240
atcatcaata tcaaagctag taaaatgaat tttgtttgga ttatagaaaa taaacttgat    300
gtaattcttg aaaaagtaaa taagttagac cttagcaaat acagatttat taatgctaca    360
agtttagatc atgatatcaa atgttattac aaaaattata aacaaagaa agatgtaatc    420 taa                                                                  423
```

<210> SEQ ID NO 24
<211> LENGTH: 140
<212> TYPE: PRT
<213> ORGANISM: Streptococcus mutans

<400> SEQUENCE: 24

Met Ala Phe Gly Thr Arg Arg Tyr Asn Ser Tyr Arg Lys Arg Ser Phe
1               5                   10                  15

Asn Arg Ser Asp Lys Gln Arg Arg Glu Tyr Ala Gln Ala Met Glu Glu
                20                  25                  30

Leu Glu Gln Thr Phe Glu Asn Leu Glu Asp Trp Asn Leu Ser Ser Met
            35                  40                  45

Lys Asp Ser Ala Tyr Lys Asp Tyr Asp Lys Tyr Glu Val Arg Leu Ser
        50                  55                  60

Asn His Ser Ala Asp Asn Gln Tyr His Asn Leu Gln Asp Gly Lys Leu
65                  70                  75                  80

Ile Ile Asn Ile Lys Ala Ser Lys Met Asn Phe Val Trp Ile Ile Glu
                85                  90                  95

Asn Lys Leu Asp Val Ile Leu Glu Lys Val Asn Lys Leu Asp Leu Ser
                100                 105                 110

Lys Tyr Arg Phe Ile Asn Ala Thr Ser Leu Asp His Asp Ile Lys Cys
            115                 120                 125

Tyr Tyr Lys Asn Tyr Lys Thr Lys Lys Asp Val Ile
        130                 135                 140

<210> SEQ ID NO 25
<211> LENGTH: 423
<212> TYPE: DNA
<213> ORGANISM: Streptococcus mutans

<400> SEQUENCE: 25

| | |
|---|---|
| atggcatttg gaacaagaag atataattca tatcgtaaac gcaattttaa tagaagtgat | 60 |
| aaacaacgtc gagaatatgc acaagcaatg gaagaacttg aacaaacatt tgaaaatctt | 120 |
| gaagattgga atttgtcgag catgaaagat agtgcttata agattatga taaatttgaa | 180 |
| gttcgacttt caaatcattc agctgataat caatatcata acttacaaga tggtaaatta | 240 |
| atcatcaata tcaaagctag taaatgaatt tttgtttgga ttatagaaaa taaacttgat | 300 |
| gcaattcttg aaaaggtaaa taagttagac cttagcaaat acagatttat taatgctaca | 360 |
| agtttagatc atgatatcaa atgttattac aaaaattata aaacaaaaaa agatgtaatt | 420 |
| taa | 423 |

<210> SEQ ID NO 26
<211> LENGTH: 140
<212> TYPE: PRT
<213> ORGANISM: Streptococcus mutans

<400> SEQUENCE: 26

Met Ala Phe Gly Thr Arg Arg Tyr Asn Ser Tyr Arg Lys Arg Asn Phe
1               5                   10                  15

Asn Arg Ser Asp Lys Gln Arg Arg Glu Tyr Ala Gln Ala Met Glu Glu
                20                  25                  30

Leu Glu Gln Thr Phe Glu Asn Leu Glu Asp Trp Asn Leu Ser Ser Met
            35                  40                  45

Lys Asp Ser Ala Tyr Lys Asp Tyr Asp Lys Phe Glu Val Arg Leu Ser
        50                  55                  60

Asn His Ser Ala Asp Asn Gln Tyr His Asn Leu Gln Asp Gly Lys Leu
65                  70                  75                  80

Ile Ile Asn Ile Lys Ala Ser Lys Met Asn Phe Val Trp Ile Ile Glu
                85                  90                  95

Asn Lys Leu Asp Ala Ile Leu Glu Lys Val Asn Lys Leu Asp Leu Ser

```
                100                 105                  110
Lys Tyr Arg Phe Ile Asn Ala Thr Ser Leu Asp His Asp Ile Lys Cys
        115                 120                 125

Tyr Tyr Lys Asn Tyr Lys Thr Lys Lys Asp Val Ile
        130                 135             140

<210> SEQ ID NO 27
<211> LENGTH: 552
<212> TYPE: DNA
<213> ORGANISM: Bacteriophage D1811

<400> SEQUENCE: 27
atgaaaataa atgacgacat caaagagtta attttagaat atatgagccg ttacttcaaa      60
ttcgagaacg acttttataa actgccaggc atcaagttca ctgatgcaaa ttggcagaag     120
ttcaaaaatg gaggcactga cattgagaag atggggggcgg cacgagtaaa cgccatgctc    180
gactgcctat tcgacgattt cgagcttgct atgattggca aggctcaaac taattattac    240
aatgataatt cactaaagat gaacatgcca ttttacactt actatgacat gttcaaaaag    300
cagcaacttc taaaatggct taaaaataac cgtgatgatg tcatcggcgg aactggtagg    360
atgtacacag caagtggtaa ttacattgct aacgcttatt tagaggtggc attagaatcg    420
agctcgcttg gtagtggctc ttacatgctt caaatgaggt ttaaagacta ttcaaaaggt    480
caagaaccta ttccgtcagg tcgtcagaat cgacttgaat ggattgaaaa caatctcgaa    540
aacattcgat aa                                                          552

<210> SEQ ID NO 28
<211> LENGTH: 183
<212> TYPE: PRT
<213> ORGANISM: Bacteriophage D1811

<400> SEQUENCE: 28

Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Gly Thr Asp Ile
            35                  40                  45

Glu Lys Met Gly Ala Ala Arg Val Asn Ala Met Leu Asp Cys Leu Phe
        50                  55                  60

Asp Asp Phe Glu Leu Ala Met Ile Gly Lys Ala Gln Thr Asn Tyr Tyr
65                  70                  75                  80

Asn Asp Asn Ser Leu Lys Met Asn Met Pro Phe Tyr Thr Tyr Tyr Asp
                85                  90                  95

Met Phe Lys Lys Gln Gln Leu Leu Lys Trp Leu Lys Asn Asn Arg Asp
                100                 105                 110

Asp Val Ile Gly Gly Thr Gly Arg Met Tyr Thr Ala Ser Gly Asn Tyr
            115                 120                 125

Ile Ala Asn Ala Tyr Leu Glu Val Ala Leu Glu Ser Ser Ser Leu Gly
        130                 135                 140

Ser Gly Ser Tyr Met Leu Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180
```

<210> SEQ ID NO 29
<211> LENGTH: 552
<212> TYPE: DNA
<213> ORGANISM: Bacteriophage D1024

<400> SEQUENCE: 29

```
atgaaaataa atgacgacat caaagagtta attttagaat atatgagccg ttacttcaaa    60
ttcgagaacg acttttataa actgccaggc atcaagttca ctgatgcaaa ttggcagaag   120
ttcaaaaatg gaggcactga cattgagaag atggggggcgg cacgagtaaa tgccatgctt   180
tcctgcctat tcgaggattt tgagcttgca atgattggca aggctcaaac taattattac   240
attgataact cacttaaatt gaacatgcca ttttacgctt actatgacat gttcaaaaag   300
caacttctta taaattggct taaaaataac cgtgatgatg tcatctgcgg aactggtagg   360
atgtacacag caagtggtaa ttacattgct aacgcttatt tagaggtggc attagaatct   420
agccgtctgg gtggtggtga gtacatgttg caaatgcgtt ttaaaaatta ttcaagaagt   480
caagaaccta ttccgtctgg tcgtcagaat cgacttgaat ggattgaaaa caatcttgaa   540
aacattcgat aa                                                       552
```

<210> SEQ ID NO 30
<211> LENGTH: 183
<212> TYPE: PRT
<213> ORGANISM: Bacteriophage D1024

<400> SEQUENCE: 30

```
Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Gly Thr Asp Ile
        35                  40                  45

Glu Lys Met Gly Ala Ala Arg Val Asn Ala Met Leu Ser Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Leu Leu Ile Asn Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ala Tyr Leu Glu Val Ala Leu Glu Ser Ser Arg Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180
```

<210> SEQ ID NO 31
<211> LENGTH: 552
<212> TYPE: DNA
<213> ORGANISM: Bacteriophage D4530

<400> SEQUENCE: 31

```
atgaaaatca ataatgacat caaagagcta attttggaat atgtaagtcg ctattttaaa      60
tttgaaaacg acttctacaa attgccaggc atcaaattca ctgatgcaaa ttggcaaaaa     120
ttcaagaatg gagatacttc catcgagaag atggggggcag cacgagtaaa tgccatgctt     180
gactgcctgt tcgaagattt tgagcttgca atgattggca aggctcaaac taattattac     240
aatgataatt cactaaagat gaacatgcca ttttacactt actatgacat gttcaaaaag     300
cagcaacttc taaaatggct aaaaataac cgtgatgatg tcatctgcgg aactggtagg      360
atgtacacag caagtggtaa ttacattgct aacgcttatt tagaaattgc gttagaatct     420
agccgtctgg gtagtggctc ttacatgctt caaatgagat tcaaagacta ttcaagaagt     480
caagaaccta ttccgtctgg tcgccaaaat agactagaat ggattgagag caacttggaa     540
aacattcgat aa                                                        552
```

<210> SEQ ID NO 32
<211> LENGTH: 183
<212> TYPE: PRT
<213> ORGANISM: Bacteriophage D4530

<400> SEQUENCE: 32

```
Met Lys Ile Asn Asn Asp Ile Lys Glu Leu Ile Leu Glu Tyr Val Ser
1               5                   10                  15
Arg Tyr Phe Lys Phe Glu Asn Asp Phe Tyr Lys Leu Pro Gly Ile Lys
                20                  25                  30
Phe Thr Asp Ala Asn Trp Gln Lys Phe Lys Asn Gly Asp Thr Ser Ile
            35                  40                  45
Glu Lys Met Gly Ala Ala Arg Val Asn Ala Met Leu Asp Cys Leu Phe
        50                  55                  60
Glu Asp Phe Glu Leu Ala Met Ile Gly Lys Ala Gln Thr Asn Tyr Tyr
65                  70                  75                  80
Asn Asp Asn Ser Leu Lys Met Asn Met Pro Phe Tyr Thr Tyr Tyr Asp
                85                  90                  95
Met Phe Lys Lys Gln Gln Leu Leu Lys Trp Leu Lys Asn Asn Arg Asp
            100                 105                 110
Asp Val Ile Cys Gly Thr Gly Arg Met Tyr Thr Ala Ser Gly Asn Tyr
        115                 120                 125
Ile Ala Asn Ala Tyr Leu Glu Ile Ala Leu Glu Ser Ser Arg Leu Gly
    130                 135                 140
Ser Gly Ser Tyr Met Leu Gln Met Arg Phe Lys Asp Tyr Ser Arg Ser
145                 150                 155                 160
Gln Glu Pro Ile Pro Ser Gly Arg Gln Asn Arg Leu Glu Trp Ile Glu
                165                 170                 175
Ser Asn Leu Glu Asn Ile Arg
            180
```

<210> SEQ ID NO 33
<211> LENGTH: 552
<212> TYPE: DNA
<213> ORGANISM: Bacteriophage D2759

<400> SEQUENCE: 33

```
atgaaaatca ataatgacat caaagagcta attttggaat atgtaagtcg ctattttaaa      60
tttgaaaacg acttctacaa attgccaggc atcaaattca ctgatgcaaa ttggcaaaaa     120
ttcaagaatg gagatacttc catcgagaag atggggggcag cacgagtaaa tgccatgctt     180
```

```
gactgcctat tcgacgattt tgagcttgct ttgattggca aggctcaaac taattattac    240
attgataact cacttaaatt gaacatgcca ttttacgctt actatgacat gttcaaaaag    300
cagcaacttc taaaatggct taaaaataac cgtgatgatg tcatctgcgg aactggtagg    360
atgtacacag caagtggtaa ttacattgct aactcttatt tagaggtagc gttagaatct    420
agccgtctgg gtagtggctc ttacatgctt caaatgagat caaagactta ttcaagaagt    480
caagaaccta ttccatctgg tcgccaaaat agactagaat ggattgagag caacttggaa    540
aacattcgat aa                                                        552
```

```
<210> SEQ ID NO 34
<211> LENGTH: 183
<212> TYPE: PRT
<213> ORGANISM: Bacteriophage D2759

<400> SEQUENCE: 34

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
        50                  55                  60

Asp Asp Phe Glu Leu Ala Leu Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ser Tyr Leu Glu Val Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 35
<211> LENGTH: 552
<212> TYPE: DNA
<213> ORGANISM: Bacteriophage D1297

<400> SEQUENCE: 35
atgaaaatca ataatgacat caaagagcta attttggaat atgtaagtcg ctattttaaa     60
tttgaaaacg acttctacaa attgcaaggc atcaaattca ctgatgcaaa ttggcaaaaa    120
ttcaagaatg gagatacttc catcgagaag atggggggcag cacgagtaaa tgccatgctt    180
gactgcctat tcgacgattt tgagcttgct ttgattggca aggctcaaca agaatactat    240
tcggataatt ccttgaaatt gaacatgcca ttttacgctt actatgacat gttcaaaaag    300
cagcaacttc taaaatggct taaaaataac cgtgatgatg tcatctgcgg aactggtagg    360
```

```
atgtacacag caagtggtaa ttacattgct aactcttatt tagaggtagc gttagaatct      420
agccgtctgg gtagtggctc ttacatgctt caaatgagat tcaaagacta ttcaagaagt      480
caagaaccta ttccgtcagg tcgcaaaaac cgacttgagt ggattgaaaa caatctggaa      540
aatattcgat aa                                                          552
```

```
<210> SEQ ID NO 36
<211> LENGTH: 183
<212> TYPE: PRT
<213> ORGANISM: Bacteriophage D1297

<400> SEQUENCE: 36

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Gln Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
        50                  55                  60

Asp Asp Phe Glu Leu Ala Leu Ile Gly Lys Ala Gln Gln Glu Tyr Tyr
65                  70                  75                  80

Ser Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ser Tyr Leu Glu Val Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180
```

```
<210> SEQ ID NO 37
<211> LENGTH: 552
<212> TYPE: DNA
<213> ORGANISM: Bacteriophage M5728

<400> SEQUENCE: 37
atgaaaatca ataatgacat caaagagcta tttttggaat atgtaagtcg ctattttaaa       60
tttgaaaacg acttctacaa attgccaggc atcaaattca ctgatgcaaa ttggcaaaaa      120
ttcaagaatg gagatacttc catcgagaag atgggggcag cacgagtaaa tgccatgctt      180
gactgcctat tcgacgattt tgagcttgct tttattggca aggctcaaca agaatactat      240
tcggataatt ccttgaaatt gaacatgcca ttttacgctt actatgacat gttcaaaaag      300
cagcaacttc taaatggct taaaaataac cgtgatgatg tcatctgcgg aactggtagg      360
atgtacacag caagtggtaa ttacattgct aactcttatt tagaggtagc gttagaatct      420
agccgtctgg gtagtggctc ttacatgctt caaatgagat tcaaagacta ttcaagaagt      480
caagaaccta ttccatctgg tcgcaaaat agactagaat ggattgaaaa caatcttgag      540
aatattcgat aa                                                          552
```

<210> SEQ ID NO 38
<211> LENGTH: 183
<212> TYPE: PRT
<213> ORGANISM: Bacteriophage M5728

<400> SEQUENCE: 38

```
Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Asp Asp Phe Glu Leu Ala Phe Ile Gly Lys Ala Gln Gln Glu Tyr Tyr
65                  70                  75                  80

Ser Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ser Tyr Leu Glu Val Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180
```

<210> SEQ ID NO 39
<211> LENGTH: 552
<212> TYPE: DNA
<213> ORGANISM: Bacteriophage D4419

<400> SEQUENCE: 39

| | | |
|---|---|---|
| atgaaaatca ataatgacat caaagagcta attttggaat atgtaagtcg ctattttaaa | 60 |
| tttgaaaacg acttctacaa attgccaggc atcaaattca ctgatgcaaa ttggcaaaaa | 120 |
| ttcaagaatg gagatacttc catcgagaag atggggcag cacgagtaaa tgccatgctt | 180 |
| gactgcctat tcgacgattt tgagcttgct ttgattggca aggctcaaca agaatactat | 240 |
| tcggataatt ccttgaaatt gaacatgcca ttttacgctt actatgacat gttcaaaaag | 300 |
| cagcaacttc taaatggct taaaaataac cgtgatgatg tcatctgcgg aactggtagg | 360 |
| atgtacacag caagtggtaa ttacattgct aactcttatt tagaggtagc gttagaatct | 420 |
| agccgtctgg gtagtggctc ttacatgctt caaatgagat tcaaagacta ttcaagaagt | 480 |
| caagaaccta ttccatctgg tcgccaaaat agactagaat ggattgagag caacttggaa | 540 |
| aacattcgat aa | 552 |

<210> SEQ ID NO 40
<211> LENGTH: 183
<212> TYPE: PRT
<213> ORGANISM: Bacteriophage D4419

<400> SEQUENCE: 40

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Asp Asp Phe Glu Leu Ala Leu Ile Gly Lys Ala Gln Gln Glu Tyr Tyr
65                  70                  75                  80

Ser Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ser Tyr Leu Glu Val Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 41
<211> LENGTH: 552
<212> TYPE: DNA
<213> ORGANISM: Bacteriophage D5891

<400> SEQUENCE: 41
atgaaaatca ataatgacat caaagagcta attttggaat atgtaagtcg ctattttaaa       60
tttgaaaacg acttctacaa attgccaggc atcaaattca ctgatgcaaa ttggcaaaaa      120
ttcaagaatg gagatacttc catcgagaag atgggggcag cacgagtaaa tgccatgctt      180
gactgcctat tcgacgattt tgagcttgct tttattggca aggctcaaca agaatactat      240
tcggataatt ccttgaaatt gaacatgcca ttttacgctt actatgacat gttcaaaaag      300
cagcaacttc taaaatggct taaaaataac cgtgatgatg tcatctgcgg aactggtagg      360
atgtacacag caagtggtaa ttacattgct aactcttatt tagaggtagc gttagaatct      420
agccgtctgg gtagtggctc ttacatgctt caaatgagat tcaaagacta ttcaagaagt      480
caagaaccta ttccatctgg tcgccaaaat agactagaat ggattgagag caacttggaa      540
aacattcgat aa                                                          552

<210> SEQ ID NO 42
<211> LENGTH: 183
<212> TYPE: PRT
<213> ORGANISM: Bacteriophage D5891

<400> SEQUENCE: 42

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
 50                  55                  60

Asp Asp Phe Glu Leu Ala Phe Ile Gly Lys Ala Gln Gln Glu Tyr Tyr
 65                  70                  75                  80

Ser Asp Asn Ser Leu Lys Leu Asn Met Pro Phe Tyr Ala Tyr Tyr Asp
            85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
            115                 120                 125

Ile Ala Asn Ser Tyr Leu Glu Val Ala Leu Glu Ser Ser Arg Leu Gly
130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
            165                 170                 175

Ser Asn Leu Glu Asn Ile Arg
            180

<210> SEQ ID NO 43
<211> LENGTH: 552
<212> TYPE: DNA
<213> ORGANISM: Bacteriophage ALQ13.2

<400> SEQUENCE: 43
atgaaaatca ataatgacat caaagagcta attttggaat atgtaagtcg ctattttaaa    60
tttgaaaacg acttctacaa attgccaggc atcaaattca ctgatgcaaa ttggcaaaaa   120
ttcaagaacg gagatacttc catcgagaag atgggggcag cacgagtaaa tgccatgctt   180
gactgcctat tcgacgattt tgagcttgct ttgattggca aggctcaaca agaatactat   240
tcggataatt ccttgaaatt gaacatgcca ttttacgctt actatgacat gttaaaaaag   300
cagcaacttc taaaatggct taaaaataac cgtgatgatg tcatctgcgg aactggtagg   360
atgtacacag caagtggtaa ttacattgct aactcttatt tagaggtagc gttagaatct   420
agccgtctgg gtagtggctc ttacatgctt caaatgagat tcaaagacta ttcaagaagt   480
caagaaccta ttccatctgg tcgccaaaat agactagaat ggattgagag caacttggaa   540
aacattcgat ga                                                       552

<210> SEQ ID NO 44
<211> LENGTH: 183
<212> TYPE: PRT
<213> ORGANISM: Bacteriophage ALQ13.2

<400> SEQUENCE: 44

Met Lys Ile Asn Asn Asp Ile Lys Glu Leu Ile Leu Glu Tyr Val Ser
 1               5                  10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
 50                  55                  60

Asp Asp Phe Glu Leu Ala Leu Ile Gly Lys Ala Gln Gln Glu Tyr Tyr
65                  70                  75                  80

Ser Asp Asn Ser Leu Lys Leu Asn Met Pro Phe Tyr Ala Tyr Tyr Asp
                85                  90                  95

Met Leu Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ser Tyr Leu Glu Val Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 45
<211> LENGTH: 552
<212> TYPE: DNA
<213> ORGANISM: Bacteriophage D802

<400> SEQUENCE: 45
atgaaaatca ataatgacat caaagagcta attttggaat atgtaagtcg ctattttaaa      60
ttcgagaacg acttttacag attgcctggc atcaaattca ctgatgccaa ctggcaaaaa     120
ttcaagaatg gaggcactgc cattgagaag atgggagcag cacgagttaa tgccatgctt     180
tcctgcctat tcgaggattt tgagcttgca atgattggca aggctcaata tgaatactat     240
tcggataatt ccttgaaatt gaacatgcca ttttacgctt actatgacat gttcaaaaag     300
cagcaacttc taaatggct taaaaataac cgtgatgatg tcatcggcgg aactggtaga     360
atgtacacgt caagcggtag ttacattgct aacgcttatt tagaaattgc gttagaatct     420
agccgtctgg gtagtggctc ttacatgctt caaatgagat tcaaagacta ttcaagaagt     480
caagaaccta ttccgtctgg tcgccaaaat agacttgaat ggattgagag caacttggaa     540
aacattcgat aa                                                         552

<210> SEQ ID NO 46
<211> LENGTH: 183
<212> TYPE: PRT
<213> ORGANISM: Bacteriophage D802

<400> SEQUENCE: 46

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Arg Leu Pro Gly Ile Lys
            20                  25                  30

Phe Thr Asp Ala Asn Trp Gln Lys Phe Lys Asn Gly Gly Thr Ala Ile
        35                  40                  45

Glu Lys Met Gly Ala Ala Arg Val Asn Ala Met Leu Ser Cys Leu Phe
    50                  55                  60

Glu Asp Phe Glu Leu Ala Met Ile Gly Lys Ala Gln Tyr Glu Tyr Tyr
65                  70                  75                  80

Ser Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp

```
                100              105              110
Asp Val Ile Gly Gly Thr Gly Arg Met Tyr Thr Ser Ser Gly Ser Tyr
            115              120              125

Ile Ala Asn Ala Tyr Leu Glu Ile Ala Leu Glu Ser Ser Arg Leu Gly
            130              135              140

Ser Gly Ser Tyr Met Leu Gln Met Arg Phe Lys Asp Tyr Ser Arg Ser
145              150              155              160

Gln Glu Pro Ile Pro Ser Gly Arg Gln Asn Arg Leu Glu Trp Ile Glu
            165              170              175

Ser Asn Leu Glu Asn Ile Arg
            180

<210> SEQ ID NO 47
<211> LENGTH: 552
<212> TYPE: DNA
<213> ORGANISM: Bacteriophage 73

<400> SEQUENCE: 47
atgaaaatca ataatgacat caaagagcta attttggaat atgtaagtcg ctattttaaa     60
tttgaaaacg acttctacaa attacctggc atcaaattca ctgatgccaa ctggcaaaaa    120
ttcaagaatg gagatacttc catcgagaag atgggggcag cacgagtaaa tgccatgctt    180
gactgcctat tcgaggattt tgagcttgca atgattggca aggctcaaac taattattac    240
attgataact cacttaaatt gaacatgcca ttttacgctt actatgacat gttcaaaaag    300
cagcaacttc taaaatggct taaaaataac cgtgatgatg tcatcggcgg aactggtagg    360
atgtacacag caagtggtaa ttacattgct aacgcttatt tagaggtggc attagaatcg    420
agctcgcttg gtagtggctc ttacatgctt caaatgaggt ttaaagacta ttcaaaaggt    480
caagaaccta ttccgtcagg tcgtcagaat cgacttgaat ggattgaaaa caatctcgaa    540
aacattcgat aa                                                         552

<210> SEQ ID NO 48
<211> LENGTH: 183
<212> TYPE: PRT
<213> ORGANISM: Bacteriophage 73

<400> SEQUENCE: 48

Met Lys Ile Asn Asn Asp Ile Lys Glu Leu Ile Leu Glu Tyr Val Ser
1               5               10              15

Arg Tyr Phe Lys Phe Glu Asn Asp Phe Tyr Lys Leu Pro Gly Ile Lys
            20              25              30

Phe Thr Asp Ala Asn Trp Gln Lys Phe Lys Asn Gly Asp Thr Ser Ile
        35              40              45

Glu Lys Met Gly Ala Ala Arg Val Asn Ala Met Leu Asp Cys Leu Phe
    50              55              60

Glu Asp Phe Glu Leu Ala Met Ile Gly Lys Ala Gln Thr Asn Tyr Tyr
65              70              75              80

Ile Asp Asn Ser Leu Lys Leu Asn Met Pro Phe Tyr Ala Tyr Tyr Asp
            85              90              95

Met Phe Lys Lys Gln Gln Leu Leu Lys Trp Leu Lys Asn Asn Arg Asp
            100             105             110

Asp Val Ile Gly Gly Thr Gly Arg Met Tyr Thr Ala Ser Gly Asn Tyr
            115             120             125

Ile Ala Asn Ala Tyr Leu Glu Val Ala Leu Glu Ser Ser Ser Leu Gly
        130             135             140
```

Ser Gly Ser Tyr Met Leu Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
            165                 170                 175

Asn Asn Leu Glu Asn Ile Arg
        180

<210> SEQ ID NO 49
<211> LENGTH: 552
<212> TYPE: DNA
<213> ORGANISM: Bacteriophage DT1

<400> SEQUENCE: 49

```
atgaaaatca ataatgacat caaagagcta attttggaat atgtaagtcg ctattttaaa      60
tttgaaaacg acttctacaa attacctggc atcaaattca ctgatgccaa ctggcaaaaa     120
ttcaagaatg gagaaacttc aatcgaaaaa atgggagcag cacgagttaa tgccatgctt     180
tcatgcctat tcgaggattt tgagcttgca atgattggca aggctcaaac taattattac     240
attgataact cacttaaatt gaacatgcca ttttacgctt actatgacat gttcaaaaag     300
caacttctta taaattggct taaaaataac cgtgatgatg tcatcggcgg aactggtagg     360
atgtacacag caagtggtaa ttacattgct aacgcttatt tagaggtggc attagaatca     420
agctcgcttg gtagtggctc ttacatgatc caaatgaggt ttaaagacta ttcaaaaggt     480
caagaaccta ttccgtcagg tcgcaaaaac cgacttgagt ggattgaaaa caatctggaa     540
aatattcgat aa                                                         552
```

<210> SEQ ID NO 50
<211> LENGTH: 183
<212> TYPE: PRT
<213> ORGANISM: Bacteriophage DT1

<400> SEQUENCE: 50

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Glu Thr Ser Ile
        35                  40                  45

Glu Lys Met Gly Ala Ala Arg Val Asn Ala Met Leu Ser Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Leu Leu Ile Asn Trp Leu Lys Asn Asn Arg Asp
            100                 105                 110

Asp Val Ile Gly Gly Thr Gly Arg Met Tyr Thr Ala Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Lys Asn Arg Leu Glu Trp Ile Glu
            165                 170                 175

Asn Asn Leu Glu Asn Ile Arg
            180

<210> SEQ ID NO 51
<211> LENGTH: 552
<212> TYPE: DNA
<213> ORGANISM: Bacteriophage D1427

<400> SEQUENCE: 51
atgaaaatca ataatgacat caaagagcta attttggaat atgtaagtcg ctattttaaa    60
tttgaaaacg acttctacaa attacctggc atcaaattca ctgatgccaa ctggcaaaaa   120
ttcaagaatg gagaaacttc aatcgaaaaa atgggagcag cacgagttaa tgccatgctt   180
tcatgcctat tcgaggattt tgagcttgca atgattggca aggctcaaac taattattac   240
attgataact cacttaaatt gaacatgcca ttttacgctt actatgacat gttcaaaaag   300
caacttctta taaattggct taaaaataac cgtgatgatg tcatcggcgg aactggtagg   360
atgtacacag caagtggtaa ttacattgct aacgcttatt tagaggtggc attagaatca   420
agctcgcttg gtagtggctc ttacatgatc caaatgaggt ttaaagacta ttcaaaaggt   480
caagaaccta ttccgtcagg tcgccaaaat agactagaat ggattgagag caacttggaa   540
aacattcgat aa                                                       552

<210> SEQ ID NO 52
<211> LENGTH: 183
<212> TYPE: PRT
<213> ORGANISM: Bacteriophage D1427

<400> SEQUENCE: 52

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Glu Thr Ser Ile
        35                  40                  45

Glu Lys Met Gly Ala Ala Arg Val Asn Ala Met Leu Ser Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Leu Leu Ile Asn Trp Leu Lys Asn Asn Arg Asp
            100                 105                 110

Asp Val Ile Gly Gly Thr Gly Arg Met Tyr Thr Ala Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 53
<211> LENGTH: 552
<212> TYPE: DNA

<213> ORGANISM: Bacteriophage N1162

<400> SEQUENCE: 53

| | | |
|---|---|---|
| atgaaaatca ataatgacat caaagagcta attttggaat atgtaagtcg ctattttaaa | 60 |
| tttgaaaacg acttctacaa attacctggc atcaaattca ctgatgccaa ctggcaaaaa | 120 |
| ttcaagaatg gagatacttc catcgagaag atgggggcag cacgagtaaa tgccatgctt | 180 |
| gactgcctat tcgaggattt tgagcttgca atgattggca aggctcaaac taattattac | 240 |
| attgataact cacttaaatt gaacatgcca ttttacgctt actatgacat gttcaaaaag | 300 |
| cagcaacttc taaaatggct aaaaataac cgtgatgatg tcatcggcgg aactggtagg | 360 |
| atgtacacat caaccggtaa ttacattgct aacgcttatt tagaaattgc gttagaatct | 420 |
| agccgtctgg gtagtggctc ttacatgatc caaatgaggt ttaaagacta ttcaaaaggt | 480 |
| caagaaccta ttccgtctgg tcgtcagaat cgacttgaat ggattgaaaa caatctggaa | 540 |
| aatattcgat aa | 552 |

<210> SEQ ID NO 54
<211> LENGTH: 183
<212> TYPE: PRT
<213> ORGANISM: Bacteriophage N1162

<400> SEQUENCE: 54

```
Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Gly Gly Thr Gly Arg Met Tyr Thr Ser Thr Gly Asn Tyr
        115                 120                 125

Ile Ala Asn Ala Tyr Leu Glu Ile Ala Leu Glu Ser Ser Arg Leu Gly
    130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180
```

<210> SEQ ID NO 55
<211> LENGTH: 552
<212> TYPE: DNA
<213> ORGANISM: Bacteriophage D1018

<400> SEQUENCE: 55

| | | |
|---|---|---|
| atgaaaatca ataatgatat caaagagcta attttggaat atgtaagtcg ctattttaaa | 60 |
| tttgaaaacg acttctacaa attgccagac atcaagttca cagatgctaa ttggcaaaaa | 120 |

```
tttaagaatg gagaaacttc aatcgaaaaa atgggagcag cacgagtaaa tgccatgctt      180
gactgcctat tcgaggattt tgagcttgca atgattggca aggctcaaac taattattac      240
attgataact cacttaaatt gaacatgcca ttttacgctt actatgacat gttcaaaaag      300
cagcaacttc taaaatggct taaaaataac cgtgatgatg tcatcggcgg aactggtagg      360
atgtacacat caaccggtaa ttacattgct aacgcttatt tagaaattgc gttagaatct      420
agccgtctgg gtagtggctc ttacatgatc caaatgaggt ttaaagacta ttcaaaaggt      480
caagaaccta ttccgtctgg tcgtcagaat cgacttgaat ggattgaaaa caatctggaa      540
aatattcgat aa                                                         552
```

```
<210> SEQ ID NO 56
<211> LENGTH: 183
<212> TYPE: PRT
<213> ORGANISM: Bacteriophage D1018

<400> SEQUENCE: 56
```

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Glu Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Gly Gly Thr Gly Arg Met Tyr Thr Ser Thr Gly Asn Tyr
        115                 120                 125

Ile Ala Asn Ala Tyr Leu Glu Ile Ala Leu Glu Ser Ser Arg Leu Gly
    130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

```
<210> SEQ ID NO 57
<211> LENGTH: 552
<212> TYPE: DNA
<213> ORGANISM: Bacteriophage D3577

<400> SEQUENCE: 57
```

```
atgaaaataa acaacgatat caaagagcta atttttggaat acgctaaacg ttatttcaag      60
tttgaaaacg acttctacaa actgccagac atcaaattca ctgatgccaa ctggcaaaaa     120
tttaagaatg gagaaacttc catcgaaaaa atgggagcag cacgagttaa tgccatgctt     180
tcctgcctgt tcgacgattt tgagcttgct atgattggca aggctcaaac taattattac     240
aatgataact cacttaaatt gaacatgcca ttttacgctt actatgacat gttcaaaaag     300
```

```
cagcaacttc taaaatggct taaaaataac cgtgatgata tcatctgcgg aactggtaga    360
atgtacactt caagaggtag ttacattgct aacgcttatt tagaggtagc gttagaatca    420
agcttgcttg gtagtggctc ttacatgctt caaatgaggt tcaaagacta ttcaaaaagt    480
caagaaccta ttccatctgg tcgtcagaat cgacttgaat ggattgagag caacttggaa    540
aatattcgat aa                                                        552
```

<210> SEQ ID NO 58
<211> LENGTH: 183
<212> TYPE: PRT
<213> ORGANISM: Bacteriophage D3577

<400> SEQUENCE: 58

```
Met Lys Ile Asn Asn Asp Ile Lys Glu Leu Ile Leu Glu Tyr Ala Lys
1               5                   10                  15

Arg Tyr Phe Lys Phe Glu Asn Asp Phe Tyr Lys Leu Pro Asp Ile Lys
                20                  25                  30

Phe Thr Asp Ala Asn Trp Gln Lys Phe Lys Asn Gly Glu Thr Ser Ile
            35                  40                  45

Glu Lys Met Gly Ala Ala Arg Val Asn Ala Met Leu Ser Cys Leu Phe
        50                  55                  60

Asp Asp Phe Glu Leu Ala Met Ile Gly Lys Ala Gln Thr Asn Tyr Tyr
65                  70                  75                  80

Asn Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Ile Ile Cys Gly Thr Gly Arg Met Tyr Thr Ser Arg Gly Ser Tyr
        115                 120                 125

Ile Ala Asn Ala Tyr Leu Glu Val Ala Leu Glu Ser Ser Leu Leu Gly
    130                 135                 140

Ser Gly Ser Tyr Met Leu Gln Met Arg Phe Lys Asp Tyr Ser Lys Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180
```

<210> SEQ ID NO 59
<211> LENGTH: 552
<212> TYPE: DNA
<213> ORGANISM: Bacteriophage CHPC577

<400> SEQUENCE: 59

```
atgaaaataa acaacgatat caaagagcta attttggaat atggaagtcg ctattttaaa     60
tttgaaaacg acttctacaa actgcctggc atcaagttca ctgatgctaa ttggcaaaaa    120
ttcaaaaatg gtgatacttt aatcgaaaaa atggggggcag cacgagtaaa tgccatgctt    180
gactgcctgt tcgacgattt tgagcttgct atgattggca aggctcaaac taattattac    240
aatgataatt ccttgaaatt gaacatgcca ttttacgctt actatgacat gttcaaaaag    300
caacagctta tacattggct caaaaacaac cgtgatgaca tcgtaggcgg aactggtaga    360
ctgtacactt caagcggtag ttacattgct aacgcttatt tagaaattgc attagaatcg    420
agctcgcttg gtagtggctc ttacatgctt caaatgagat tcaaaaacta ttcaaaaagt    480
caagaaccta ttccatctgg tcgccagaat cgacttgaat ggattgaaaa caatcttgag    540
```
aatattcgat aa                                                              552

<210> SEQ ID NO 60
<211> LENGTH: 183
<212> TYPE: PRT
<213> ORGANISM: Bacteriophage CHPC577

<400> SEQUENCE: 60

Met Lys Ile Asn Asn Asp Ile Lys Glu Leu Ile Leu Glu Tyr Gly Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Leu Ile
        35                  40                  45

Glu Lys Met Gly Ala Ala Arg Val Asn Ala Met Leu Asp Cys Leu Phe
    50                  55                  60

Asp Asp Phe Glu Leu Ala Met Ile Gly Lys Ala Gln Thr Asn Tyr Tyr
65                  70                  75                  80

Asn Asp Asn Ser Leu Lys Leu Asn Met Pro Phe Tyr Ala Tyr Tyr Asp
                85                  90                  95

Met Phe Lys Lys Gln Gln Leu Ile His Trp Leu Lys Asn Asn Arg Asp
            100                 105                 110

Asp Ile Val Gly Gly Thr Gly Arg Leu Tyr Thr Ser Ser Gly Ser Tyr
        115                 120                 125

Ile Ala Asn Ala Tyr Leu Glu Ile Ala Leu Glu Ser Ser Ser Leu Gly
    130                 135                 140

Ser Gly Ser Tyr Met Leu Gln Met Arg Phe Lys Asn Tyr Ser Lys Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 61
<211> LENGTH: 552
<212> TYPE: DNA
<213> ORGANISM: Bacteriophage D4237

<400> SEQUENCE: 61
atgaaaataa ataacgacat caaagaatta attttagaat atatgagccg ttacttcaaa    60
ttcgaaaacg acttctacaa attgccagac atcaagttca cagatgctaa ttggcaaaaa   120
tttaagaatg gagaaacttc aatcgaaaaa atgggagcag cacgagttaa tgccatgctc   180
aactgcctat tcgaagattt tgagcttgct atgattggca aggctcaaat taattattac   240
aatgataact cacttaaaat gaacatgcca ttttacgctt actatgatat gttcaaaaaa   300
caacagcttc taaatggct taagatcac catgatgaca tcatcggagg agctggcaga   360
atgtacacat caaccggtag ttacattgct aatgcttatt tagaggtagc gttagaatca   420
agctcgcttg gtgatggtga gtacatgttg caaatgcgtt ttaaaaatta ttcacgaagt   480
caagaaccta ttccgtcagg tcgcaaaaac cgacttgagt ggattgaaaa caatctggaa   540
aatattcgat aa                                                         552

<210> SEQ ID NO 62
<211> LENGTH: 183
<212> TYPE: PRT

<213> ORGANISM: Bacteriophage D4237

<400> SEQUENCE: 62

| Met | Lys | Ile | Asn | Asp | Ile | Lys | Glu | Leu | Ile | Leu | Glu | Tyr | Met | Ser |
|---|---|---|---|---|---|---|---|---|---|---|---|---|---|---|
| 1 |  |  |  | 5 |  |  |  |  | 10 |  |  |  |  | 15 |

Arg Tyr Phe Lys Phe Glu Asn Asp Phe Tyr Lys Leu Pro Asp Ile Lys
              20                  25                  30

Phe Thr Asp Ala Asn Trp Gln Lys Phe Lys Asn Gly Glu Thr Ser Ile
          35                  40                  45

Glu Lys Met Gly Ala Ala Arg Val Asn Ala Met Leu Asn Cys Leu Phe
50                  55                  60

Glu Asp Phe Glu Leu Ala Met Ile Gly Lys Ala Gln Ile Asn Tyr Tyr
65                  70                  75                  80

Asn Asp Asn Ser Leu Lys Met Asn Met Pro Phe Tyr Ala Tyr Tyr Asp
              85                  90                  95

Met Phe Lys Lys Gln Gln Leu Leu Lys Trp Leu Lys Asp His His Asp
              100                 105                 110

Asp Ile Ile Gly Gly Ala Gly Arg Met Tyr Thr Ser Thr Gly Ser Tyr
          115                 120                 125

Ile Ala Asn Ala Tyr Leu Glu Val Ala Leu Glu Ser Ser Ser Leu Gly
      130                 135                 140

Asp Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
              165                 170                 175

Asn Asn Leu Glu Asn Ile Arg
          180

<210> SEQ ID NO 63
<211> LENGTH: 552
<212> TYPE: DNA
<213> ORGANISM: Bacteriophage 9874

<400> SEQUENCE: 63
atgaaaataa atgacgacat caaagaatta attttagaat atatgagccg ttacttcaaa      60
ttcgagaacg acttctacaa attgcctgac atcaaattca ctgatgccaa ctggcaaaaa     120
ttcaaaaatg gagatacttc catcgagaag atggggcag cacgagtaaa tgccatgctt      180
gactgcctat tcgaagattt cgaacttgcc atgattggca aggctcaaca agaatactat     240
ttggataatt cactaaagat gaacatgcca ttttacgctt attatgatat gttcaagaaa     300
aaacagctcg tcaaatggct taaagatcac catgatgaca tcctaggcgg aactggtagg     360
atgtacactt cagacggtag ttacattgct aactcttatt tagaggtagc gttagaatct     420
agccgtctgg gtagtggctc ttacatgctt caaatgagat tcaaagacta ttcaagaagt     480
caagaaccca ttccgtcagg tcgcaaaaac cgacttgagt ggattgaaaa caatctggaa     540
aatattcgat aa                                                        552

<210> SEQ ID NO 64
<211> LENGTH: 183
<212> TYPE: PRT
<213> ORGANISM: Bacteriophage 9874

<400> SEQUENCE: 64

Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
 50                  55                  60

Glu Asp Phe Glu Leu Ala Met Ile Gly Lys Ala Gln Gln Glu Tyr Tyr
 65                  70                  75                  80

Leu Asp Asn Ser Leu Lys Met Asn Met Pro Phe Tyr Ala Tyr Tyr Asp
                85                  90                  95

Met Phe Lys Lys Lys Gln Leu Val Lys Trp Leu Lys Asp His His Asp
            100                 105                 110

Asp Ile Leu Gly Gly Thr Gly Arg Met Tyr Thr Ser Asp Gly Ser Tyr
            115                 120                 125

Ile Ala Asn Ser Tyr Leu Glu Val Ala Leu Glu Ser Ser Arg Leu Gly
        130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 65
<211> LENGTH: 552
<212> TYPE: DNA
<213> ORGANISM: Bacteriophage 5093

<400> SEQUENCE: 65
atggaaatca acaacgatat caaagagtta attttggaat acgtgaaaag atacttcaag      60
ttcgagaacg acttctacaa attgcctgac atcaaattca ctgatgccaa ctggcagaag     120
ttcaaaaatg gcgaaacagc cattgagaag atggggggcag cacgagtaaa cgcaatgctc    180
gactgcctat tcgaagattt tgagcttgcc atgattggca aggctcaaac taattattat    240
attgataact cgcttaaatt aaacatgcca ttttatgctt actatgatat gtttaagaaa    300
caacagctcg tcaaatggct tgaaactagt cgtgaagaca tcatcggagg ggctggcaga    360
atgtacactt cagacggtag ttacattgct aacgcttatt agaagtagc gttagaatca     420
agctcgcttg gtgatagtga atacatgttg caaatgcgtt ttaaaaatta ttcaaaaagt    480
caagaaccta ttccgtctgg tcgtcaaaat agactggaat ggattgaaaa caatcttaaa    540
aacattcgat aa                                                        552

<210> SEQ ID NO 66
<211> LENGTH: 183
<212> TYPE: PRT
<213> ORGANISM: Bacteriophage 5093

<400> SEQUENCE: 66

Met Glu Ile Asn Asn Asp Ile Lys Glu Leu Ile Leu Glu Tyr Val Lys
1                5                  10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Glu Thr Ala Ile
        35                  40                  45

Glu Lys Met Gly Ala Ala Arg Val Asn Ala Met Leu Asp Cys Leu Phe
 50                  55                  60

```
                50                  55                  60
Glu Asp Phe Glu Leu Ala Met Ile Gly Lys Ala Gln Thr Asn Tyr Tyr
 65                  70                  75                  80

Ile Asp Asn Ser Leu Lys Leu Asn Met Pro Phe Tyr Ala Tyr Tyr Asp
                 85                  90                  95

Met Phe Lys Lys Gln Gln Leu Val Lys Trp Leu Glu Thr Ser Arg Glu
                100                 105                 110

Asp Ile Ile Gly Gly Ala Gly Arg Met Tyr Thr Ser Asp Gly Ser Tyr
                115                 120                 125

Ile Ala Asn Ala Tyr Leu Glu Val Ala Leu Glu Ser Ser Ser Leu Gly
                130                 135                 140

Asp Ser Glu Tyr Met Leu Gln Met Arg Phe Lys Asn Tyr Ser Lys Ser
145                 150                 155                 160

Gln Glu Pro Ile Pro Ser Gly Arg Gln Asn Arg Leu Glu Trp Ile Glu
                165                 170                 175

Asn Asn Leu Lys Asn Ile Arg
                180
```

<210> SEQ ID NO 67
<211> LENGTH: 552
<212> TYPE: DNA
<213> ORGANISM: Bacteriophage D4154

<400> SEQUENCE: 67

```
atgctaataa ataacgacat caaagagttg attttggaat acgtcaaacg ctattttaaa     60
tatgaaaatg acttctacag attgccgggc atcaagttta ccgatgcaaa ttggcagaag    120
tttaaaaatg gcgacacttc catcgagaag atgggggcag cacgagtaaa cgccatgctc    180
gactgcctat cgaagatttt gagcttgcc atgattggta aggctcaaac caattattat     240
atcaataatt cattgaaaat gaatatgccg ttttacgctt actatgatat gttcaagaag    300
gaacagctta tgaaatggct tgaaaccagc cgtgaagaca tcataggcgg aactggcagg    360
atgtacactt cagacggtag ttacattgct aacgcttatt tggaaattgc attagaatcg    420
agctcgcttg gtagtggctc ttacatgctt caaatgcgtt ttaaagatta ttcaaaaggt    480
caagagccta tcccgtctgg tcgtcaaaac cgacttgagt ggattgaaaa caatcttgaa    540
aacattcgat aa                                                        552
```

<210> SEQ ID NO 68
<211> LENGTH: 183
<212> TYPE: PRT
<213> ORGANISM: Bacteriophage D4154

<400> SEQUENCE: 68

```
Met Leu Ile Asn Asn Asp Ile Lys Glu Leu Ile Leu Glu Tyr Val Lys
  1               5                  10                  15

Arg Tyr Phe Lys Tyr Glu Asn Asp Phe Tyr Arg Leu Pro Gly Ile Lys
                 20                  25                  30

Phe Thr Asp Ala Asn Trp Gln Lys Phe Lys Asn Gly Asp Thr Ser Ile
                 35                  40                  45

Glu Lys Met Gly Ala Ala Arg Val Asn Ala Met Leu Asp Cys Leu Phe
                 50                  55                  60

Glu Asp Phe Glu Leu Ala Met Ile Gly Lys Ala Gln Thr Asn Tyr Tyr
 65                  70                  75                  80

Ile Asn Asn Ser Leu Lys Met Asn Met Pro Phe Tyr Ala Tyr Tyr Asp
                 85                  90                  95
```

Met Phe Lys Lys Glu Gln Leu Met Lys Trp Leu Glu Thr Ser Arg Glu
            100                 105                 110

Asp Ile Ile Gly Gly Thr Gly Arg Met Tyr Thr Ser Asp Gly Ser Tyr
            115                 120                 125

Ile Ala Asn Ala Tyr Leu Glu Ile Ala Leu Gly Ser Ser Ser Leu Gly
            130                 135                 140

Ser Gly Ser Tyr Met Leu Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 69
<211> LENGTH: 552
<212> TYPE: DNA
<213> ORGANISM: Streptococcus thermophilus DGCC11758

<400> SEQUENCE: 69
atgctaataa ataacgacat caaagagttg attttggaat acgtcaaacg ctatttaaa       60 tttgaaaatg acttctacag attgccgggc atcaagttta ccgatgcaaa ttggcagaag     120
tttaaaaatg cgacactgc cattgagaag atggggcat cacgagtaaa ctctatgctt       180
gactgcctgt tcgaagattt tgagcttgct atgattggca aggctcaaga tgaatactat     240
ttggataatt cactaaagat gaacatgcca ttttacgctt attatgatat gttcaagaaa     300
aaacagctcg tcaaatggct taaagatcac catgatgaca tcctaggcgg aactggtagg     360
atgtatactt caagcggcaa ttacattgct aacgcttatt tagaggtagc gttagaatca     420
agctcgcttg gtagtggctc ttacatgatt caaatgcgtt ttaaaaatta ttcaaaaggt     480
caagagccta tcccgtctgg tcgtcaaaac cgacttgagt ggattgaaaa aaacttggag     540
aacattcgat aa                                                         552

<210> SEQ ID NO 70
<211> LENGTH: 183
<212> TYPE: PRT
<213> ORGANISM: Streptococcus thermophilus DGCC11758

<400> SEQUENCE: 70

Met Leu Ile Asn Asn Asp Ile Lys Glu Leu Ile Leu Glu Tyr Val Lys
1               5                   10                  15

Arg Tyr Phe Lys Phe Glu Asn Asp Phe Tyr Arg Leu Pro Gly Ile Lys
            20                  25                  30

Phe Thr Asp Ala Asn Trp Gln Lys Phe Lys Asn Gly Asp Thr Ala Ile
            35                  40                  45

Glu Lys Met Gly Ala Ser Arg Val Asn Ser Met Leu Asp Cys Leu Phe
            50                  55                  60

Glu Asp Phe Glu Leu Ala Met Ile Gly Lys Ala Gln Asp Glu Tyr Tyr
65                  70                  75                  80

Leu Asp Asn Ser Leu Lys Met Asn Met Pro Phe Tyr Ala Tyr Tyr Asp
                85                  90                  95

Met Phe Lys Lys Lys Gln Leu Val Lys Trp Leu Lys Asp His His Asp
            100                 105                 110

Asp Ile Leu Gly Gly Thr Gly Arg Met Tyr Thr Ser Ser Gly Asn Tyr
            115                 120                 125

```
Ile Ala Asn Ala Tyr Leu Glu Val Ala Leu Glu Ser Ser Leu Gly
            130                 135                 140

Ser Gly Ser Tyr Met Ile Gln Met Arg Phe Lys Asn Tyr Ser Lys Gly
145                 150                 155                 160

Gln Glu Pro Ile Pro Ser Gly Arg Gln Asn Arg Leu Glu Trp Ile Glu
                165                 170                 175

Lys Asn Leu Glu Asn Ile Arg
            180
```

<210> SEQ ID NO 71
<211> LENGTH: 552
<212> TYPE: DNA
<213> ORGANISM: Streptococcus thermophilus DSM 20617

<400> SEQUENCE: 71

```
atggaaatca acaacgatat taaacaactg atcttggaat acgctaaacg ttatttcaag      60
tttgagaacg acttttataa actgccaggc atcaagttca ctgatgcaaa ttggcagaag     120
ttcaaaaatg gaggcactgc cattgagaag atggggcag cacgagtaaa cgccatgctc      180
gactgcctat tcgaagattt cgagcttgca atgattggca aggctcaaca agaatactat     240
tcggataatt ccttgaaagt aaatatggca ttctatgctt attacgatca attcaaaaaa     300
caacagctta tgaaatggct taagataat cacgatgaca tcataggagg gactggtaga      360
atgtacacgt caagcggtag ttacattgct aacgcttatt tagaaattgc gttagaatct     420
agccgtctgg gtggtggttc ttacatgatc caaatgaggt ttaaagacta ttcaaaaggt     480
caagaaccta ttccgtctgg tcgtcagaat cgacttgaat ggattgagag caacttggaa     540
aacattcgat aa                                                         552
```

<210> SEQ ID NO 72
<211> LENGTH: 183
<212> TYPE: PRT
<213> ORGANISM: Streptococcus thermophilus DSM 20617

<400> SEQUENCE: 72

```
Met Glu Ile Asn Asn Asp Ile Lys Gln Leu Ile Leu Glu Tyr Ala Lys
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Gly Thr Ala Ile
            35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Gln Glu Tyr Tyr
65                  70                  75                  80

Ser Asp Asn Ser Leu Lys Val Asn Met Ala Phe Tyr Ala Tyr Tyr Asp
                85                  90                  95

Gln Phe Lys Lys Gln Gln Leu Met Lys Trp Leu Lys Asn His Asp
            100                 105                 110

Asp Ile Ile Gly Gly Thr Gly Arg Met Tyr Thr Ser Ser Gly Ser Tyr
            115                 120                 125

Ile Ala Asn Ala Tyr Leu Glu Ile Ala Leu Glu Ser Ser Arg Leu Gly
            130                 135                 140

Gly Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
```

```
                          165                 170                 175
Ser Asn Leu Glu Asn Ile Arg
            180

<210> SEQ ID NO 73
<211> LENGTH: 552
<212> TYPE: DNA
<213> ORGANISM: Bacteriophage Sfi19

<400> SEQUENCE: 73
atggaaatca acaacgacat taaacaactg atcttggaat acgtgggacg ctatttaaa        60 tttgaaaatg acttctacaa attgcccggc atcaaattca ctgatgccaa ttggcagaag      120
ttcaaaaatg gcgatacttc catcgaaaag atgggagcag cacgagtaaa cgcaatgctt      180
gactgcctgt tcgaagattt cgaacttgcc atgattggca aggctcaaac taattattat      240
attgataatt cccttaaatt aaacatgcca ttttacgctt attatgatat gttcaagaag      300
gaacagctta tgaaatggct taagatcac catgatgaca tcataggcgg aactggtagg      360
atgtacattt caagcggtag ctacattgct aacgcttatt tggaaattgc actagaatca      420
agtacgcttg gtggtggtga gtacatgttg caaatgcgct ttaaaaatta ttcacgaagc      480
caagaaccta ttccatcagg tcgcaaaaat agacttgaat ggattgaaaa caatcttgaa      540
aacattcgat aa                                                           552

<210> SEQ ID NO 74
<211> LENGTH: 183
<212> TYPE: PRT
<213> ORGANISM: Bacteriophage Sfi19

<400> SEQUENCE: 74

Met Glu Ile Asn Asn Asp Ile Lys Gln Leu Ile Leu Glu Tyr Val Gly
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Glu Gln Leu Met Lys Trp Leu Lys Asp His His Asp
            100                 105                 110

Asp Ile Ile Gly Gly Thr Gly Arg Met Tyr Ile Ser Ser Gly Ser Tyr
        115                 120                 125

Ile Ala Asn Ala Tyr Leu Glu Ile Ala Leu Glu Ser Ser Thr Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 75
```

<211> LENGTH: 552
<212> TYPE: DNA
<213> ORGANISM: Bacteriophage Sfi11

<400> SEQUENCE: 75

```
atggaaatca acaacgacat taaacaactg atcttggaat acgtgggacg ctattttaaa      60
tttgaaaatg acttctacaa attgcccggc atcaaattca ctgatgccaa ttggcagaag     120
ttcaaaaatg gcgatacttc catcgaaaag atgggagcag cacgagtaaa cgcaatgctt     180
gactgcctgt tcgaagattt cgaacttgcc atgattggca aggctcaaac taattattat     240
attgataatt cccttaaatt aaacatgcca ttttacgctt attatgatat gttcaagaag     300
gaacagctta tgaaatggct aaagatcac catgatgaca tcataggcgg aactggtagg     360
atgtacactt caagcggtag ctacattgct aacgcttatt tggaaattgc actagaatca     420
agtacgcttg gtggtggtga gtacatgttg caaatgcgct ttaaaaatta ttcacgaagc     480
caagaaccta ttccatcagg tcgcaaaaat agacttgaat ggattgaaaa caatcttgaa     540
aacattcgat aa                                                         552
```

<210> SEQ ID NO 76
<211> LENGTH: 183
<212> TYPE: PRT
<213> ORGANISM: Bacteriophage Sfi11

<400> SEQUENCE: 76

```
Met Glu Ile Asn Asn Asp Ile Lys Gln Leu Ile Leu Glu Tyr Val Gly
1               5                   10                  15
Arg Tyr Phe Lys Phe Glu Asn Asp Phe Tyr Lys Leu Pro Gly Ile Lys
            20                  25                  30
Phe Thr Asp Ala Asn Trp Gln Lys Phe Lys Asn Gly Asp Thr Ser Ile
        35                  40                  45
Glu Lys Met Gly Ala Ala Arg Val Asn Ala Met Leu Asp Cys Leu Phe
    50                  55                  60
Glu Asp Phe Glu Leu Ala Met Ile Gly Lys Ala Gln Thr Asn Tyr Tyr
65                  70                  75                  80
Ile Asp Asn Ser Leu Lys Leu Asn Met Pro Phe Tyr Ala Tyr Tyr Asp
                85                  90                  95
Met Phe Lys Lys Glu Gln Leu Met Lys Trp Leu Lys Asp His His Asp
            100                 105                 110
Asp Ile Ile Gly Gly Thr Gly Arg Met Tyr Thr Ser Ser Gly Ser Tyr
        115                 120                 125
Ile Ala Asn Ala Tyr Leu Glu Ile Ala Leu Glu Ser Ser Thr Leu Gly
    130                 135                 140
Gly Gly Glu Tyr Met Leu Gln Met Arg Phe Lys Asn Tyr Ser Arg Ser
145                 150                 155                 160
Gln Glu Pro Ile Pro Ser Gly Arg Lys Asn Arg Leu Glu Trp Ile Glu
                165                 170                 175
Asn Asn Leu Glu Asn Ile Arg
            180
```

<210> SEQ ID NO 77
<211> LENGTH: 552
<212> TYPE: DNA
<213> ORGANISM: Streptococcus thermophilus M17PTZA496

<400> SEQUENCE: 77

```
atggaaatca acaaagacat caaagagttg attttggaat acgtcaaacg ctattttaaa      60
```

```
tttgaaaatg atttctacag attgccgggc atcaagttta ccgatgccaa ctggcaaaaa      120
ttcaagaatg gagatacttc catcgagaag atggggcag cacgagtaaa cgccatgctt       180
gactgcctgt tcgaagattt cgaacttgct atgattggca aggctcaaga tgaatactat     240
ttggataatt cacttaagtt taatatggca ttccatactt attacgatca atttaaaaaa     300
caacagctta tgaaatggct tgaaactagc ctcgaagaca tcataggcgg aactggtagg     360
atgtacactt caagcggtag ttacattgct aacgcttatt tggaaattgc actagaatca     420
agctcgcttg gtggtggtga gtacatgttg caaatgcgtt ttaaaaatta ttcacgaagc     480
caagaaccta ttccgtcagg tcgcaaaaac cgacttgagt ggattgaaaa caatctggaa     540
aatatccgat aa                                                          552

<210> SEQ ID NO 78
<211> LENGTH: 183
<212> TYPE: PRT
<213> ORGANISM: Streptococcus thermophilus M17PTZA496

<400> SEQUENCE: 78

Met Glu Ile Asn Lys Asp Ile Lys Glu Leu Ile Leu Glu Tyr Val Lys
1               5                   10                  15

Arg Tyr Phe Lys Phe Glu Asn Asp Phe Tyr Arg Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
        50                  55                  60

Glu Asp Phe Glu Leu Ala Met Ile Gly Lys Ala Gln Asp Glu Tyr Tyr
65                  70                  75                  80

Leu Asp Asn Ser Leu Lys Phe Asn Met Ala Phe His Thr Tyr Tyr Asp
                85                  90                  95

Gln Phe Lys Lys Gln Gln Leu Met Lys Trp Leu Glu Thr Ser Leu Glu
            100                 105                 110

Asp Ile Ile Gly Gly Thr Gly Arg Met Tyr Thr Ser Ser Gly Ser Tyr
        115                 120                 125

Ile Ala Asn Ala Tyr Leu Glu Ile Ala Leu Glu Ser Ser Ser Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 79
<211> LENGTH: 552
<212> TYPE: DNA
<213> ORGANISM: Bacteriophage D4769

<400> SEQUENCE: 79
atgaaaatca ataatgacat caaagagcta attttggaat atgtaagtcg ctattttaaa      60
tttgaaaacg acttctacaa attacctggc atcaaattca ctgatgccaa ctggcaaaaa     120
ttcaagaatg gagatacttc catcgagaag atggggcag cacgagtaaa cgccatgctt      180
gactgcctgt tcgaagattt cgaacttgct atgattggca aggctcaaga tgaatactat     240
```

```
ttggataatt cacttaagtt taatatggca ttccatactt attacgatca atttaaaaaa    300
caacagctta tgaaatggct tgaaactagc ctcgaagaca tcataggcgg aactggtagg    360
atgtacactt caagcggtag ttacattgct aacgcttatt tggaaattgc actagaatca    420
agctcgcttg gtggtggtga gtacatgttg caaatgcgtt ttaaaaatta ttcacgaagc    480
caagaaccta ttccgtcagg tcgcaaaaac cgacttgagt ggattgaaaa caatctggaa    540
aatatccgat aa                                                        552

<210> SEQ ID NO 80
<211> LENGTH: 183
<212> TYPE: PRT
<213> ORGANISM: Bacteriophage D4769

<400> SEQUENCE: 80

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Asp Glu Tyr Tyr
65                  70                  75                  80

Leu Asp Asn Ser Leu Lys Phe Asn Met Ala Phe His Thr Tyr Tyr Asp
                85                  90                  95

Gln Phe Lys Lys Gln Gln Leu Met Lys Trp Leu Glu Thr Ser Leu Glu
            100                 105                 110

Asp Ile Ile Gly Gly Thr Gly Arg Met Tyr Thr Ser Ser Gly Ser Tyr
        115                 120                 125

Ile Ala Asn Ala Tyr Leu Glu Ile Ala Leu Glu Ser Ser Ser Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 81
<211> LENGTH: 552
<212> TYPE: DNA
<213> ORGANISM: Bacteriophage D5691

<400> SEQUENCE: 81
atgattataa atattgatat caaggaattg attttagagt atatgagtag atacttcaaa     60
tttgaaaatg atttctacaa actccccggc atcaaattca ctgatgccaa ttggcaaaaa    120
tttaagaatg gtgacacttc catcgaaaag atgggagcgg ctcgagtaaa tgccatgctc    180
gactgtctat tcgatgactt tgaacttgct atgattggca aggctcaaat taattattac    240
atagacaatt cccttaaatt gaacatgcca ttctatgctt attatgacat gttcaaaaaa    300
caacaactga tcaaatggat tgaaaccagc cgtgatgatg tcatcggagg aactggcagg    360
atgtatacag caagcggaag ctacatagct aacgcttatc tagaaatagc actagaatct    420
agctctctgg gtggtggctc ttatatgctt caaatgagat tcaaaaacta ctcacgaagc    480
```

```
caagagccaa taccatctgg tcggaaaaac cgacttgagt ggattgagag caacttggaa    540
aacattagat aa                                                        552

<210> SEQ ID NO 82
<211> LENGTH: 183
<212> TYPE: PRT
<213> ORGANISM: Bacteriophage D5691

<400> SEQUENCE: 82

Met Ile Ile Asn Ile Asp Ile Lys Glu Leu Ile Leu Glu Tyr Met Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Asp Asp Phe Glu Leu Ala Met Ile Gly Lys Ala Gln Ile Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Ile Lys Trp Ile Glu Thr Ser Arg Asp
            100                 105                 110

Asp Val Ile Gly Gly Thr Gly Arg Met Tyr Thr Ala Ser Gly Ser Tyr
        115                 120                 125

Ile Ala Asn Ala Tyr Leu Glu Ile Ala Leu Glu Ser Ser Leu Gly
    130                 135                 140

Gly Gly Ser Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Ser Asn Leu Glu Asn Ile Arg
            180

<210> SEQ ID NO 83
<211> LENGTH: 552
<212> TYPE: DNA
<213> ORGANISM: Streptococcus sp. HMSC10E12

<400> SEQUENCE: 83
atggaaatca acaatgacat caaagagtta atcttggaat acgtgggacg ctatttcaag    60
tttgaaaatg atttttacaa attgccgggc atcaaattta ccgatgcaaa ttggcaaaaa   120
ttcaaaaacg gtgatacatc catcgagaaa atggggggcgg cacgagtaaa cgcaatgctc   180
gactgcctat tcgatgattt cgagcttgct atgattggca aggctcaaac tgattattac   240
attgataact cacttaaatt gaacatgcca ttttatgctt attatgacat gttcaaaaaa   300
caacagcttc taaatggat tgagaatagt cgtgaagaca tcatcggagg ggctggcaga   360
atgtacacag cgggcggtaa ttggatttct agcgcttatt tagagatcgc attagaatct   420
agttccatcg gtggcggtgg ctatatgctt caaatgcggt tcaaaaacta ctcaagagac   480
cctagaccga ttccagcagg ccaccaaaat cgtctcgaat ggattgaaaa caacttggag   540
aatatccgat aa                                                       552

<210> SEQ ID NO 84
```

```
<211> LENGTH: 183
<212> TYPE: PRT
<213> ORGANISM: Streptococcus sp. HMSC10E12

<400> SEQUENCE: 84
```

Met Glu Ile Asn Asn Asp Ile Lys Glu Leu Ile Leu Glu Tyr Val Gly
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Asp Asp Phe Glu Leu Ala Met Ile Gly Lys Ala Gln Thr Asp Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Ile Glu Asn Ser Arg Glu
            100                 105                 110

Asp Ile Ile Gly Gly Ala Gly Arg Met Tyr Thr Ala Gly Gly Asn Trp
        115                 120                 125

Ile Ser Ser Ala Tyr Leu Glu Ile Ala Leu Glu Ser Ser Ser Ile Gly
130                 135                 140

Gly Gly Gly Tyr Met Leu Gln Met Arg Phe Lys Asn Tyr Ser Arg Asp
145                 150                 155                 160

Pro Arg Pro Ile Pro Ala Gly His Gln Asn Arg Leu Glu Trp Ile Glu
                165                 170                 175

Asn Asn Leu Glu Asn Ile Arg
            180

```
<210> SEQ ID NO 85
<211> LENGTH: 552
<212> TYPE: DNA
<213> ORGANISM: Streptococcus sp. HSISS2

<400> SEQUENCE: 85
```

| | | | | | |
|---|---|---|---|---|---|
| atggaaatca | acaatgacat | caaggaccta | attttagaat | acgtaggacg | atattttcga | 60 |
| tttgaaaacg | acttctacaa | acttcccaga | atcaagttta | ccgattccaa | ttggcaaaaa | 120 |
| ttcaagaacg | gtgacacttc | catcgaaaaa | atgggagctg | cagagtgaa | cgcaatgctc | 180 |
| gattgtctat | tgatgattt | tgagcttgct | atgattggta | aggctcaaac | cgattactac | 240 |
| atggacaatt | ctttaaagat | gaatatgcca | ttttatgcct | attatgacca | atttaagaaa | 300 |
| cagcaactat | tgaaatggat | cgagaatagt | agagaggata | tcataggcgg | tgctggcaga | 360 |
| atgtacacag | ctagtgggaa | ttggatttct | agtgcctatt | tagaaattgc | attggaatcc | 420 |
| agctcgttag | gtggtggtga | gtacatgttg | caaatgcgtt | tcaaagacta | ctcacgaagc | 480 |
| caagagccga | taccagcagg | ccgccagaat | cgacttgagt | ggattgagaa | taatttggag | 540 |
| aatattcgat | aa | | | | | 552 |

```
<210> SEQ ID NO 86
<211> LENGTH: 183
<212> TYPE: PRT
<213> ORGANISM: Streptococcus sp. HSISS2

<400> SEQUENCE: 86
```

Met Glu Ile Asn Asn Asp Ile Lys Asp Leu Ile Leu Glu Tyr Val Gly

```
  1               5                  10                 15
Arg Tyr Phe Arg Phe Glu Asn Asp Phe Tyr Lys Leu Pro Arg Ile Lys
                 20                 25                 30
Phe Thr Asp Ser Asn Trp Gln Lys Phe Lys Asn Gly Asp Thr Ser Ile
                 35                 40                 45
Glu Lys Met Gly Ala Gly Arg Val Asn Ala Met Leu Asp Cys Leu Phe
    50                  55                 60
Asp Asp Phe Glu Leu Ala Met Ile Gly Lys Ala Gln Thr Asp Tyr Tyr
65                  70                 75                 80
Met Asp Asn Ser Leu Lys Met Asn Met Pro Phe Tyr Ala Tyr Tyr Asp
                85                 90                 95
Gln Phe Lys Lys Gln Gln Leu Leu Lys Trp Ile Glu Asn Ser Arg Glu
                100                105                110
Asp Ile Ile Gly Gly Ala Gly Arg Met Tyr Thr Ala Ser Gly Asn Trp
                115                120                125
Ile Ser Ser Ala Tyr Leu Glu Ile Ala Leu Glu Ser Ser Ser Leu Gly
130                135                140
Gly Gly Glu Tyr Met Leu Gln Met Arg Phe Lys Asp Tyr Ser Arg Ser
145                150                155                160
Gln Glu Pro Ile Pro Ala Gly Arg Gln Asn Arg Leu Glu Trp Ile Glu
                165                170                175
Asn Asn Leu Glu Asn Ile Arg
                180
```

<210> SEQ ID NO 87
<211> LENGTH: 51
<212> TYPE: DNA
<213> ORGANISM: Artificial
<220> FEATURE:
<223> OTHER INFORMATION: primer/oligo

<400> SEQUENCE: 87
attacagctc cagatccagt actgaattct cgctgatggt gatagcattg g       51

<210> SEQ ID NO 88
<211> LENGTH: 50
<212> TYPE: DNA
<213> ORGANISM: Artificial
<220> FEATURE:
<223> OTHER INFORMATION: primer/oligo

<400> SEQUENCE: 88
gaaaatatgc actcgagaag cttgagctct tgctttcgca gtctcgaatt          50

<210> SEQ ID NO 89
<211> LENGTH: 20
<212> TYPE: DNA
<213> ORGANISM: Artificial
<220> FEATURE:
<223> OTHER INFORMATION: primer/oligo

<400> SEQUENCE: 89
aatgtcacta acctgccccg                                           20

<210> SEQ ID NO 90
<211> LENGTH: 20
<212> TYPE: DNA
<213> ORGANISM: Artificial
<220> FEATURE:
<223> OTHER INFORMATION: primer/oligo

<400> SEQUENCE: 90
cattgaacat gctgaagagc                                                    20

<210> SEQ ID NO 91
<211> LENGTH: 35
<212> TYPE: DNA
<213> ORGANISM: Artificial
<220> FEATURE:
<223> OTHER INFORMATION: primer/oligo

<400> SEQUENCE: 91
aaactccgtt acaattagaa caaaattctt gtttg                                   35

<210> SEQ ID NO 92
<211> LENGTH: 35
<212> TYPE: DNA
<213> ORGANISM: Artificial
<220> FEATURE:
<223> OTHER INFORMATION: primer/oligo

<400> SEQUENCE: 92
aaaacaaaca agaattttgt tctaattgta acgga                                   35

<210> SEQ ID NO 93
<211> LENGTH: 30
<212> TYPE: DNA
<213> ORGANISM: Artificial
<220> FEATURE:
<223> OTHER INFORMATION: primer/oligo

<400> SEQUENCE: 93
gttcttagtg catataacaa acatagagac                                         30

<210> SEQ ID NO 94
<211> LENGTH: 18
<212> TYPE: DNA
<213> ORGANISM: Artificial
<220> FEATURE:
<223> OTHER INFORMATION: primer/oligo

<400> SEQUENCE: 94
ccaagtagcg aagcgagc                                                      18

<210> SEQ ID NO 95
<211> LENGTH: 52
<212> TYPE: DNA
<213> ORGANISM: Artificial
<220> FEATURE:
<223> OTHER INFORMATION: primer/oligo

<400> SEQUENCE: 95
attacagctc cagatccagt actgaattct tcgctgaaaa agtttgggaa gt                 52

<210> SEQ ID NO 96
<211> LENGTH: 54
<212> TYPE: DNA
<213> ORGANISM: Artificial
<220> FEATURE:
<223> OTHER INFORMATION: primer/oligo

<400> SEQUENCE: 96
gaaaatatgc actcgagaag cttgagctct cctctctctt atgatagtct gcca              54

<210> SEQ ID NO 97
<211> LENGTH: 20

```
<212> TYPE: DNA
<213> ORGANISM: Artificial
<220> FEATURE:
<223> OTHER INFORMATION: primer/oligo

<400> SEQUENCE: 97
aatgtcacta acctgccccg                                               20

<210> SEQ ID NO 98
<211> LENGTH: 20
<212> TYPE: DNA
<213> ORGANISM: Artificial
<220> FEATURE:
<223> OTHER INFORMATION: primer/oligo

<400> SEQUENCE: 98
cattgaacat gctgaagagc                                               20

<210> SEQ ID NO 99
<211> LENGTH: 327
<212> TYPE: DNA
<213> ORGANISM: Bacteriophage O

<400> SEQUENCE: 99
atggcatacg gaaaaagcag atacaactca tataggaaac gcagtttcaa tagaagcgat    60
aagcaacgta gagaatacgc acaagaaatg gatagattag aacaaacatt tgaaaaactt   120
gatggttggt atctatctag catgaaagat agtgcgtata agatttcgg aaaatacgaa    180 attcgcttat caaatcattc agcagacaac aaatatcatg acctagaaaa tggtcgttta   240
attgttaatg tcaaagcaag taaattgaaa ttcgttgata tcaaatgtta ctataaggga   300
tttaagacaa agaaggatgt aatctaa                                      327

<210> SEQ ID NO 100
<211> LENGTH: 423
<212> TYPE: DNA
<213> ORGANISM: Bacteriophage Sfi

<400> SEQUENCE: 100
atggcatacg gaaaaagtag atataactca tatagaaagc gcagttttaa cagaagtaat    60
aagcaacgta gagaatacgc acaagaaatg gatagattag agaaagcttt cgaaaatctt   120
gacggatggt atctatctag catgaaagat agtgcgtaca agatttcgg aaaatacgaa    180 attcgcttat caaatcattc agcagacaac aaatatcatg acctagaaaa tggtcgttta   240
attgttaatg tcaaagcaag taaattgaac ttcgttgata tcatcgagaa caaacttgat   300
aaaatcattg agaagattga tactcttgat ttagataagt acagattcat taatgctact   360
aaattggaac gtgatatcaa atgctactat aaaggctata agacaaagaa ggatgtaatc   420
taa                                                                423

<210> SEQ ID NO 101
<211> LENGTH: 423
<212> TYPE: DNA
<213> ORGANISM: Bacteriophage TPL

<400> SEQUENCE: 101
atggcatacg gaaaaagcag atacaactca tatagaaaac gtagtttcaa cataagtgac    60
acaaagcgta gggaatatgc aaaagaaatg gagaaattag aacaagcatt tgaaaagcta   120
gatggttggt atctatctag catgaaggat agtgcataca aggattttgg aaaatacgaa   180
```

```
atccgcttat caaatcattc agcagacaat aaatatcatg acctagaaaa tggtcgttta    240
attgttaatg ttaaagcaag taaattgaac ttcgttgata tcatcgaaaa caaacttgat    300
aaaatcatcg agaagattga taagcttgat ttagataagt acagatttat taacgctact    360
agaatggagc atgacattaa atgctactat aaaggattta agacaaagaa agatgtaatc    420
taa                                                                 423
```

<210> SEQ ID NO 102
<211> LENGTH: 423
<212> TYPE: DNA
<213> ORGANISM: Streptococcus sp

<400> SEQUENCE: 102

```
atggcatttg gcaagaacag atacaatcca tacaggaaac gtagtttttaa tcgtagtgat    60 aaacaatgtc gagagtatgc tcaggcaatg gacgaactag aacaagcctt tgaggaactt   120
gatggatggc acttatctag tatgatggat agtgcttata gaattttgaa aaagtaccag   180
gttcgcctat caaatcattc agcagacaac caatatcatg acttagaaaa tggttacttg   240
attgtcaatg ttaaagcaag taaattgaac tttgtcgata ttatcgaaaa taaattggat   300
aagattttag agaagtaga caagcttgat cttgataagt ataggtttat caatgcgacc   360
aatctggaac atgatattaa atgttatctc aaaggctata agacgaaaaa agacgtgatt   420
taa                                                                 423
```

<210> SEQ ID NO 103
<211> LENGTH: 423
<212> TYPE: DNA
<213> ORGANISM: Bacteriophage D

<400> SEQUENCE: 103

```
atggcatacg gaaaaagtag atataactca tatagaaagc gcagtttttaa cagaagtaat    60 aagcaacgta gagaatacgc acaagaaatg gatagattag agaaagcttt cgaaaatctt   120
gacggatggt atctatctag catgaaagac agtgcttaca aggattttgg gaaatacgaa   180
attcgcttat caaatcattc ggcagacaac aaatatcacg acttagaaaa cggtcgttta   240
attgttaata ttaaagctag taaattgaat ttcgttgata tcatcgagaa taagcttgat   300
aaaataatcg agaagattga taagcttgat ttagataagt accgattcat caatgcgacc   360
aacctagagc atgatatcaa atgctattac aaggggttta aaacgaaaaa ggaggtaatc   420
taa                                                                 423
```

<210> SEQ ID NO 104
<211> LENGTH: 423
<212> TYPE: DNA
<213> ORGANISM: Bacteriophage D

<400> SEQUENCE: 104

```
atggcatacg gaaaaagcag atacaattca tataggaagc gaaacttctc tataagcgac    60
aatcagcgta gggaatatgc taaaaaaatg aaggagttag aacaagcgtt tgaaaacctt   120
gacggatggt atctatctag catgaaagat agtgcgtaca agatttcgg aaaatacgaa   180 attcgcttat caaatcattc agcagacaat agatatcatg acctagaaaa tggtcgctta   240
atcgttaatg ttaaagctag taaattgaac ttcgttgata tcatcgagaa taaacttggt   300
aaaatcattg agaagattga tactcttgat ttagataagt acagattcat taatgctact   360
aaattggaac gtgatatcaa atgctactat aaaggctata agacaaagaa ggatgtaatc   420
```

<210> SEQ ID NO 105
<211> LENGTH: 423
<212> TYPE: DNA
<213> ORGANISM: Bacteriophage D

<400> SEQUENCE: 105

```
atggcatacg gaaaaagtag atataactca tatagaaaac gcagtttcaa cagaagcgat      60
aaacagcgta gagaatacgc acaagcaatg gaagaattag agcaagcatt tgaaaacttt     120
gatgattggt atctatcaag catgaaagac agtgcttaca aggattttgg gaaatacgaa     180
attcgcttat caaatcattc ggcagacaac aaatatcacg acttagaaaa cggtcgttta     240
attgttaata ttaaagctag taaattgaat ttcgttgata tcatcgagaa taagcttgat     300
aaaataatcg agaagattga taagcttgat ttagataagt accgattcat caatgcgacc     360
aacctagagc atgatatcaa atgctattac aaggggttta aaacgaaaaa ggaggtaatc     420
taa                                                                    423
```

<210> SEQ ID NO 106
<211> LENGTH: 423
<212> TYPE: DNA
<213> ORGANISM: Bacteriophage D

<400> SEQUENCE: 106

```
atggcatacg gaaaaagcag atacaactca tatagaaagc gcagtttttaa cagaagtgat     60
aagcaacgta gagaatacgc taaaaaaatg aaggagttag aacaagcgtt tgaaaacctt     120
gatggttggt atctatcgag catgaatgac agtgcttata aaaattttgg caaatatgaa     180
gttcgattgt caaatcattc ggcagataat aaatatcacg acatagaaaa cggtcgttta     240
attgttaatg ttaaagctag taaattgaat ttcgttgata tcatcgagaa caagcttgat     300
aaaataatcg agaagattga taagcttgat ttagataagt accgattcat caacgctacc     360
aatctagagc ataatattaa atgctattac aagggattta agacaaagaa ggatgtaata     420
taa                                                                    423
```

<210> SEQ ID NO 107
<211> LENGTH: 423
<212> TYPE: DNA
<213> ORGANISM: Bacteriophage D

<400> SEQUENCE: 107

```
atggcatacg gaaaaagtag atataactca tatagaaaac gcagtttcaa cagaagcgat      60
aaacagcgtg gagaatacgc acaagcaatg gaagaattag agcaagcatt tgaaaacttt     120
gatgattggt atctatcaag catgaaagac agtgcttaca aggattttgg gaaatacgaa     180
attcgcttat caaatcattc ggcagacaat aaatatcatg acttagaaaa tggtcgctta     240
atcgttaatg ttaaagctag taaattgaac ttcgtcgata tcatcgagaa taaaatcgat     300
aaaatcattg agaagattga taagcttgat ttagataagt accgattcat caacgctacc     360
aacctagagc atgatatcaa atgttattac aagggattta agacaaaaaa ggatgtaatc     420
taa                                                                    423
```

<210> SEQ ID NO 108
<211> LENGTH: 423
<212> TYPE: DNA

<213> ORGANISM: Streptococcus mutans

<400> SEQUENCE: 108

| | |
|---|---|
| atggcatttg gaaaaagaag atataactcg tatcgtaaac gcagttttaa tagaagtgat | 60 |
| aagcaacgtc gagaatatgc acaagcaatg gaagaacttg aacaaacatt tgaaaatctt | 120 |
| gaaggttgga atttatcaag catgaaagat agtgcttata aagattatga taaatatgaa | 180 |
| gttcgacttt caaatcattc agctgataat caatatcata acttacaaga tggtaaatta | 240 |
| atcatcaata tcaaagctag taaatgaat tttgtttgga ttatagaaaa taaacttgat | 300 |
| gcaattcttg aaaaagtaaa taagttagac cttagcaaat acagatttat taatgctaca | 360 |
| agtttagatc atgatatcaa atgttattac aaaaattata aaacaaagaa agatgtaatt | 420 |
| taa | 423 |

<210> SEQ ID NO 109
<211> LENGTH: 423
<212> TYPE: DNA
<213> ORGANISM: Streptococcus mutans

<400> SEQUENCE: 109

| | |
|---|---|
| atggcatttg gaacaagaag atataattca tatcgtaaac gcagttttaa tagaagtgat | 60 |
| aagcaacgtc gagaatatgc acaagcaatg gaagaacttg aacaaacatt tgaaaatctt | 120 |
| gaagattgga atttgtcgag catgaaagat agtgcttata aagattatga taaatatgaa | 180 |
| gttcgacttt caaatcattc agctgataat caatatcata acttacaaga tggtaaatta | 240 |
| atcatcaata tcaaagctag taaatgaat tttgtttgga ttatagaaaa taaacttgat | 300 |
| gcaattcttg aaaaagtaaa taagttagac cttagcagat acagatttat taatgctaca | 360 |
| aatttagaac atgatatcaa atgttattac aaaaattata aaacaaagaa agatgtaatt | 420 |
| taa | 423 |

<210> SEQ ID NO 110
<211> LENGTH: 423
<212> TYPE: DNA
<213> ORGANISM: Streptococcus mutans

<400> SEQUENCE: 110

| | |
|---|---|
| atggcatttg gaacaagaag atataattca tatcgtaaac gcagttttaa tagaagtgat | 60 |
| aagcaacgtc gagaatatgc acaagcaatg gaagaacttg aacaaacatt tgaaaatctt | 120 |
| gaagattgga atttgtcgag catgaaagat agtgcttata aagattatga taaatatgaa | 180 |
| gttagacttt caaatcattc agctgataat caatatcata acttacaaga tggtaaatta | 240 |
| atcatcaata tcaaagctag taaatgaat tttgtttgga ttatagaaaa taaacttgat | 300 |
| gtaattcttg aaaaagtaaa taagttagac cttagcaaat acagatttat taatgctaca | 360 |
| agtttagatc atgatatcaa atgttattac aaaaattata aaacaaagaa agatgtaatc | 420 |
| taa | 423 |

<210> SEQ ID NO 111
<211> LENGTH: 423
<212> TYPE: DNA
<213> ORGANISM: Streptococcus mutans

<400> SEQUENCE: 111

| | |
|---|---|
| atggcatttg gaacaagaag atataattca tatcgtaaac gcaattttaa tagaagtgat | 60 |
| aaacaacgtc gagaatatgc acaagcaatg gaagaacttg aacaaacatt tgaaaatctt | 120 |

```
gaagattgga atttgtcgag catgaaagat agtgcttata aagattatga taaatttgaa      180
gttcgacttt caaatcattc agctgataat caatatcata acttacaaga tggtaaatta      240
atcatcaata tcaaagctag taaaatgaat tttgtttgga ttatagaaaa taaacttgat      300
gcaattcttg aaaaggtaaa taagttagac cttagcaaat acagatttat taatgctaca      360
agtttagatc atgatatcaa atgttattac aaaaattata aaacaaaaaa agatgtaatt      420
taa                                                                    423

<210> SEQ ID NO 112
<211> LENGTH: 552
<212> TYPE: DNA
<213> ORGANISM: Bacteriophage D

<400> SEQUENCE: 112
atgaaaataa atgacgacat caaagagtta attttagaat atatgagccg ttacttcaaa       60
ttcgagaacg acttttataa actgccaggc atcaagttca ctgatgcaaa ttggcagaag      120
ttcaaaaatg gaggcactga cattgagaag atggggggcgg cacgagtaaa cgccatgctc      180
gactgcctat tcgacgattt cgagcttgct atgattggca aggctcaaac taattattac      240
aatgataatt cactaaagat gaacatgcca ttttacactt actatgacat gttcaaaaag      300
cagcaacttc taaaatggct taaaaataac cgtgatgatg tcatcggcgg aactggtagg      360
atgtacacag caagtggtaa ttcattgct aacgcttatt tagaggtggc attagaatcg      420
agctcgcttg gtagtggctc ttacatgctt caaatgaggt ttaaagacta ttcaaaaggt      480
caagaaccta ttccgtcagg tcgtcagaat cgacttgaat ggattgaaaa caatctcgaa      540
aacattcgat aa                                                          552

<210> SEQ ID NO 113
<211> LENGTH: 552
<212> TYPE: DNA
<213> ORGANISM: Bacteriophage D

<400> SEQUENCE: 113
atgaaaataa atgacgacat caaagagtta attttagaat atatgagccg ttacttcaaa       60
ttcgagaacg acttttataa actgccaggc atcaagttca ctgatgcaaa ttggcagaag      120
ttcaaaaatg gaggcactga cattgagaag atggggggcgg cacgagtaaa tgccatgctt      180
tcctgcctat tcgaggattt tgagcttgca atgattggca aggctcaaac taattattac      240
attgataact cacttaaatt gaacatgcca ttttacgctt actatgacat gttcaaaaag      300
caacttctta taaattggct taaaaataac cgtgatgatg tcatctgcgg aactggtagg      360
atgtacacag caagtggtaa ttcattgct aacgcttatt tagaggtggc attagaatct      420
agccgtctgg gtggtggtga gtacatgttg caaatgcgtt ttaaaaatta ttcaagaagt      480
caagaaccta ttccgtctgg tcgtcagaat cgacttgaat ggattgaaaa caatcttgaa      540
aacattcgat aa                                                          552

<210> SEQ ID NO 114
<211> LENGTH: 552
<212> TYPE: DNA
<213> ORGANISM: Bacteriophage D

<400> SEQUENCE: 114
atgaaaatca ataatgacat caaagagcta attttggaat atgtaagtcg ctattttaaa       60
```

```
tttgaaaacg acttctacaa attgccaggc atcaaattca ctgatgcaaa ttggcaaaaa      120
ttcaagaatg gagatacttc catcgagaag atggggcag cacgagtaaa tgccatgctt       180
gactgcctgt tcgaagattt tgagcttgca atgattggca aggctcaaac taattattac      240
aatgataatt cactaaagat gaacatgcca ttttacactt actatgacat gttcaaaaag      300
cagcaacttc taaaatggct taaaaataac cgtgatgatg tcatctgcgg aactggtagg      360
atgtacacag caagtggtaa ttacattgct aacgcttatt tagaaattgc gttagaatct      420
agccgtctgg gtagtggctc ttacatgctt caaatgagat tcaaagacta ttcaagaagt      480
caagaaccta ttccgtctgg tcgccaaaat agactagaat ggattgagag caacttggaa      540
aacattcgat aa                                                          552

<210> SEQ ID NO 115
<211> LENGTH: 552
<212> TYPE: DNA
<213> ORGANISM: Bacteriophage D

<400> SEQUENCE: 115
atgaaaatca ataatgacat caaagagcta attttggaat atgtaagtcg ctattttaaa       60
tttgaaaacg acttctacaa attgccaggc atcaaattca ctgatgcaaa ttggcaaaaa      120
ttcaagaatg gagatacttc catcgagaag atggggcag cacgagtaaa tgccatgctt       180
gactgcctat tcgacgattt tgagcttgct ttgattggca aggctcaaac taattattac      240
attgataact cacttaaatt gaacatgcca ttttacgctt actatgacat gttcaaaaag      300
cagcaacttc taaaatggct taaaaataac cgtgatgatg tcatctgcgg aactggtagg      360
atgtacacag caagtggtaa ttacattgct aactcttatt tagaggtagc gttagaatct      420
agccgtctgg gtagtggctc ttacatgctt caaatgagat tcaaagacta ttcaagaagt      480
caagaaccta ttccatctgg tcgccaaaat agactagaat ggattgagag caacttggaa      540
aacattcgat aa                                                          552

<210> SEQ ID NO 116
<211> LENGTH: 552
<212> TYPE: DNA
<213> ORGANISM: Bacteriophage D

<400> SEQUENCE: 116
atgaaaatca ataatgacat caaagagcta attttggaat atgtaagtcg ctattttaaa       60
tttgaaaacg acttctacaa attgcaaggc atcaaattca ctgatgcaaa ttggcaaaaa      120
ttcaagaatg gagatacttc catcgagaag atggggcag cacgagtaaa tgccatgctt       180
gactgcctat tcgacgattt tgagcttgct ttgattggca aggctcaaca agaatactat      240
tcggataatt ccttgaaatt gaacatgcca ttttacgctt actatgacat gttcaaaaag      300
cagcaacttc taaaatggct taaaaataac cgtgatgatg tcatctgcgg aactggtagg      360
atgtacacag caagtggtaa ttacattgct aactcttatt tagaggtagc gttagaatct      420
agccgtctgg gtagtggctc ttacatgctt caaatgagat tcaaagacta ttcaagaagt      480
caagaaccta ttccgtcagg tcgcaaaaac cgacttgagt ggattgaaaa caatctggaa      540
aatattcgat aa                                                          552

<210> SEQ ID NO 117
<211> LENGTH: 552
<212> TYPE: DNA
<213> ORGANISM: Bacteriophage M
```

<400> SEQUENCE: 117

```
atgaaaatca ataatgacat caaagagcta attttggaat atgtaagtcg ctattttaaa      60
tttgaaaacg acttctacaa attgccaggc atcaaattca ctgatgcaaa ttggcaaaaa     120
ttcaagaatg gagatacttc catcgagaag atggggcag cacgagtaaa tgccatgctt      180
gactgcctat tcgacgattt tgagcttgct tttattggca aggctcaaca agaatactat     240
tcggataatt ccttgaaatt gaacatgcca ttttacgctt actatgacat gttcaaaaag     300
cagcaacttc taaaatggct taaaaataac cgtgatgatg tcatctgcgg aactggtagg     360
atgtacacag caagtggtaa ttacattgct aactcttatt tagaggtagc gttagaatct     420
agccgtctgg gtagtggctc ttacatgctt caaatgagat tcaaagacta ttcaagaagt     480
caagaaccta ttccatctgg tcgccaaaat agactagaat ggattgaaaa caatcttgag     540
aatattcgat aa                                                          552
```

<210> SEQ ID NO 118
<211> LENGTH: 552
<212> TYPE: DNA
<213> ORGANISM: Bacteriophage D

<400> SEQUENCE: 118

```
atgaaaatca ataatgacat caaagagcta attttggaat atgtaagtcg ctattttaaa      60
tttgaaaacg acttctacaa attgccaggc atcaaattca ctgatgcaaa ttggcaaaaa     120
ttcaagaatg gagatacttc catcgagaag atggggcag cacgagtaaa tgccatgctt      180
gactgcctat tcgacgattt tgagcttgct ttgattggca aggctcaaca agaatactat     240
tcggataatt ccttgaaatt gaacatgcca ttttacgctt actatgacat gttcaaaaag     300
cagcaacttc taaaatggct taaaaataac cgtgatgatg tcatctgcgg aactggtagg     360
atgtacacag caagtggtaa ttacattgct aactcttatt tagaggtagc gttagaatct     420
agccgtctgg gtagtggctc ttacatgctt caaatgagat tcaaagacta ttcaagaagt     480
caagaaccta ttccatctgg tcgccaaaat agactagaat ggattgagag caacttggaa     540
aacattcgat aa                                                          552
```

<210> SEQ ID NO 119
<211> LENGTH: 552
<212> TYPE: DNA
<213> ORGANISM: Bacteriophage D

<400> SEQUENCE: 119

```
atgaaaatca ataatgacat caaagagcta attttggaat atgtaagtcg ctattttaaa      60
tttgaaaacg acttctacaa attgccaggc atcaaattca ctgatgcaaa ttggcaaaaa     120
ttcaagaatg gagatacttc catcgagaag atggggcag cacgagtaaa tgccatgctt      180
gactgcctat tcgacgattt tgagcttgct tttattggca aggctcaaca agaatactat     240
tcggataatt ccttgaaatt gaacatgcca ttttacgctt actatgacat gttcaaaaag     300
cagcaacttc taaaatggct taaaaataac cgtgatgatg tcatctgcgg aactggtagg     360
atgtacacag caagtggtaa ttacattgct aactcttatt tagaggtagc gttagaatct     420
agccgtctgg gtagtggctc ttacatgctt caaatgagat tcaaagacta ttcaagaagt     480
caagaaccta ttccatctgg tcgccaaaat agactagaat ggattgagag caacttggaa     540
aacattcgat aa                                                          552
```

<210> SEQ ID NO 120
<211> LENGTH: 552
<212> TYPE: DNA
<213> ORGANISM: Bacteriophage ALQ

<400> SEQUENCE: 120

```
atgaaaatca ataatgacat caaagagcta attttggaat atgtaagtcg ctattttaaa    60
tttgaaaacg acttctacaa attgccaggc atcaaattca ctgatgcaaa ttggcaaaaa   120
ttcaagaacg agatacttc catcgagaag atggggcag cacgagtaaa tgccatgctt     180
gactgcctat cgacgatttt tgagcttgct ttgattggca aggctcaaca agaatactat   240
tcggataatt ccttgaaatt gaacatgcca ttttacgctt actatgacat gttaaaaaag   300
cagcaacttc taaatggct taaaaataac cgtgatgatg tcatctgcgg aactggtagg    360
atgtacacag caagtggtaa ttacattgct aactcttatt tagaggtagc gttagaatct   420
agccgtctgg gtagtggctc ttacatgctt caaatgagat tcaaagacta ttcaagaagt   480
caagaaccta ttccatctgg tcgccaaaat agactagaat ggattgagag caacttggaa   540
aacattcgat ga                                                       552
```

<210> SEQ ID NO 121
<211> LENGTH: 552
<212> TYPE: DNA
<213> ORGANISM: Bacteriophage D

<400> SEQUENCE: 121

```
atgaaaatca ataatgacat caaagagcta attttggaat atgtaagtcg ctattttaaa    60
ttcgagaacg acttttacag attgcctggc atcaaattca ctgatgccaa ctggcaaaaa   120
ttcaagaatg gaggcactgc cattgagaag atgggagcag cacgagttaa tgccatgctt   180
tcctgcctat cgaggatttt tgagcttgca atgattggca aggctcaata tgaatactat   240
tcggataatt ccttgaaatt gaacatgcca ttttacgctt actatgacat gttcaaaaag   300
cagcaacttc taaatggct taaaaataac cgtgatgatg tcatcggcgg aactggtaga    360
atgtacacgt caagcggtag ttacattgct aacgcttatt tagaaattgc gttagaatct   420
agccgtctgg gtagtggctc ttacatgctt caaatgagat tcaaagacta ttcaagaagt   480
caagaaccta ttccgtctgg tcgccaaaat agacttgaat ggattgagag caacttggaa   540
aacattcgat aa                                                       552
```

<210> SEQ ID NO 122
<211> LENGTH: 552
<212> TYPE: DNA
<213> ORGANISM: Bacteriophage

<400> SEQUENCE: 122

```
atgaaaatca ataatgacat caaagagcta attttggaat atgtaagtcg ctattttaaa    60
tttgaaaacg acttctacaa attacctggc atcaaattca ctgatgccaa ctggcaaaaa   120
ttcaagaatg gagatacttc catcgagaag atggggcag cacgagtaaa tgccatgctt    180
gactgcctat cgaggatttt tgagcttgca atgattggca aggctcaaac taattattac   240
attgataact cacttaaatt gaacatgcca ttttacgctt actatgacat gttcaaaaag   300
cagcaacttc taaatggct taaaaataac cgtgatgatg tcatcggcgg aactggtagg    360
atgtacacag caagtggtaa ttacattgct aacgcttatt tagaggtggc attagaatcg   420
agctcgcttg gtagtggctc ttacatgctt caaatgaggt ttaaagacta ttcaaaaggt   480
```

```
caagaaccta ttccgtcagg tcgtcagaat cgacttgaat ggattgaaaa caatctcgaa      540
aacattcgat aa                                                         552

<210> SEQ ID NO 123
<211> LENGTH: 552
<212> TYPE: DNA
<213> ORGANISM: Bacteriophage DT

<400> SEQUENCE: 123
atgaaaatca ataatgacat caaagagcta attttggaat atgtaagtcg ctattttaaa      60
tttgaaaacg acttctacaa attacctggc atcaaattca ctgatgccaa ctggcaaaaa     120
ttcaagaatg gagaaacttc aatcgaaaaa atgggagcag cacgagttaa tgccatgctt     180
tcatgcctat tcgaggattt tgagcttgca atgattggca aggctcaaac taattattac     240
attgataact cacttaaatt gaacatgcca ttttacgctt actatgacat gttcaaaaag     300
caacttctta taaattggct taaaaataac cgtgatgatg tcatcggcgg aactggtagg     360
atgtacacag caagtggtaa ttacattgct aacgcttatt tagaggtggc attagaatca     420
agctcgcttg gtagtggctc ttacatgatc caaatgaggt ttaaagacta ttcaaaaggt     480
caagaaccta ttccgtcagg tcgcaaaaac cgacttgagt ggattgaaaa caatctggaa     540
aatattcgat aa                                                         552

<210> SEQ ID NO 124
<211> LENGTH: 552
<212> TYPE: DNA
<213> ORGANISM: Bacteriophage D

<400> SEQUENCE: 124
atgaaaatca ataatgacat caaagagcta attttggaat atgtaagtcg ctattttaaa      60
tttgaaaacg acttctacaa attacctggc atcaaattca ctgatgccaa ctggcaaaaa     120
ttcaagaatg gagaaacttc aatcgaaaaa atgggagcag cacgagttaa tgccatgctt     180
tcatgcctat tcgaggattt tgagcttgca atgattggca aggctcaaac taattattac     240
attgataact cacttaaatt gaacatgcca ttttacgctt actatgacat gttcaaaaag     300
caacttctta taaattggct taaaaataac cgtgatgatg tcatcggcgg aactggtagg     360
atgtacacag caagtggtaa ttacattgct aacgcttatt tagaggtggc attagaatca     420
agctcgcttg gtagtggctc ttacatgatc caaatgaggt ttaaagacta ttcaaaaggt     480
caagaaccta ttccgtcagg tcgccaaaat agactagaat ggattgagag caacttggaa     540
aacattcgat aa                                                         552

<210> SEQ ID NO 125
<211> LENGTH: 552
<212> TYPE: DNA
<213> ORGANISM: Bacteriophage N

<400> SEQUENCE: 125
atgaaaatca ataatgacat caaagagcta attttggaat atgtaagtcg ctattttaaa      60
tttgaaaacg acttctacaa attacctggc atcaaattca ctgatgccaa ctggcaaaaa     120
ttcaagaatg gagatacttc catcgagaag atggggcag cacgagtaaa tgccatgctt     180
gactgcctat tcgaggattt tgagcttgca atgattggca aggctcaaac taattattac     240
attgataact cacttaaatt gaacatgcca ttttacgctt actatgacat gttcaaaaag     300
```

```
cagcaacttc taaaatggct taaaaataac cgtgatgatg tcatcggcgg aactggtagg    360
atgtacacat caaccggtaa ttacattgct aacgcttatt tagaaattgc gttagaatct    420
agccgtctgg gtagtggctc ttacatgatc caaatgaggt ttaaagacta ttcaaaaggt    480
caagaaccta ttccgtctgg tcgtcagaat cgacttgaat ggattgaaaa caatctggaa    540
aatattcgat aa                                                        552
```

<210> SEQ ID NO 126
<211> LENGTH: 552
<212> TYPE: DNA
<213> ORGANISM: Bacteriophage D

<400> SEQUENCE: 126

```
atgaaaatca ataatgatat caaagagcta attttggaat atgtaagtcg ctattttaaa     60
tttgaaaacg acttctacaa attgccagac atcaagttca cagatgctaa ttggcaaaaa    120
tttaagaatg gagaaacttc aatcgaaaaa atgggagcag cacgagtaaa tgccatgctt    180
gactgcctat tcgaggattt tgagcttgca atgattggca aggctcaaac taattattac    240
attgataact cacttaaatt gaacatgcca ttttacgctt actatgacat gttcaaaaag    300
cagcaacttc taaaatggct taaaaataac cgtgatgatg tcatcggcgg aactggtagg    360
atgtacacat caaccggtaa ttacattgct aacgcttatt tagaaattgc gttagaatct    420
agccgtctgg gtagtggctc ttacatgatc caaatgaggt ttaaagacta ttcaaaaggt    480
caagaaccta ttccgtctgg tcgtcagaat cgacttgaat ggattgaaaa caatctggaa    540
aatattcgat aa                                                        552
```

<210> SEQ ID NO 127
<211> LENGTH: 552
<212> TYPE: DNA
<213> ORGANISM: Bacteriophage D

<400> SEQUENCE: 127

```
atgaaaataa acaacgatat caaagagcta attttggaat acgctaaacg ttatttcaag     60
tttgaaaacg acttctacaa actgccagac atcaaattca ctgatgccaa ctggcaaaaa    120
tttaagaatg gagaaacttc catcgaaaaa atgggagcag cacgagttaa tgccatgctt    180
tcctgcctgt tcgacgattt tgagcttgct atgattggca aggctcaaac taattattac    240
aatgataact cacttaaatt gaacatgcca ttttacgctt actatgacat gttcaaaaag    300
cagcaacttc taaaatggct taaaaataac cgtgatgata tcatctgcgg aactggtaga    360
atgtacactt caagaggtag ttacattgct aacgcttatt tagaggtagc gttagaatca    420
agcttgcttg gtagtggctc ttacatgctt caaatgaggt tcaaagacta ttcaaaaagt    480
caagaaccta ttccatctgg tcgtcagaat cgacttgaat ggattgagag caacttggaa    540
aatattcgat aa                                                        552
```

<210> SEQ ID NO 128
<211> LENGTH: 552
<212> TYPE: DNA
<213> ORGANISM: Bacteriophage CHPC

<400> SEQUENCE: 128

```
atgaaaataa acaacgatat caaagagcta attttggaat atggaagtcg ctattttaaa     60
tttgaaaacg acttctacaa actgcctggc atcaagttca ctgatgctaa ttggcaaaaa    120
ttcaaaaatg gtgatacttt aatcgaaaaa atgggggcag cacgagtaaa tgccatgctt    180
```

```
gactgcctgt tcgacgattt tgagcttgct atgattggca aggctcaaac taattattac    240
aatgataatt ccttgaaatt gaacatgcca ttttacgctt actatgacat gttcaaaaag    300
caacagctta tacattggct caaaaacaac cgtgatgaca tcgtaggcgg aactggtaga    360
ctgtacactt caagcggtag ttacattgct aacgcttatt tagaaattgc attagaatcg    420
agctcgcttg gtagtggctc ttacatgctt caaatgagat tcaaaaacta ttcaaaaagt    480
caagaaccta ttccatctgg tcgccagaat cgacttgaat ggattgaaaa caatcttgag    540
aatattcgat aa                                                        552
```

<210> SEQ ID NO 129
<211> LENGTH: 552
<212> TYPE: DNA
<213> ORGANISM: Bacteriophage D

<400> SEQUENCE: 129

```
atgaaaataa ataacgacat caaagaatta attttagaat atatgagccg ttacttcaaa     60
ttcgaaaacg acttctacaa attgccagac atcaagttca cagatgctaa ttggcaaaaa    120
tttaagaatg gagaaacttc aatcgaaaaa atgggagcag cacgagttaa tgccatgctc    180
aactgcctat tcgaagattt tgagcttgct atgattggca aggctcaaat taattattac    240
aatgataact cacttaaaat gaacatgcca ttttacgctt actatgatat gttcaaaaaa    300
caacagcttc taaaatggct taaagatcac catgatgaca tcatcggagg agctggcaga    360
atgtacacat caaccggtag ttacattgct aatgcttatt tagaggtagc gttagaatca    420
agctcgcttg gtgatggtga gtacatgttg caaatgcgtt ttaaaaatta ttcacgaagt    480
caagaaccta ttccgtcagg tcgcaaaaac cgacttgagt ggattgaaaa caatctggaa    540
aatattcgat aa                                                        552
```

<210> SEQ ID NO 130
<211> LENGTH: 552
<212> TYPE: DNA
<213> ORGANISM: Bacteriophage

<400> SEQUENCE: 130

```
atgaaaataa atgacgacat caaagaatta attttagaat atatgagccg ttacttcaaa     60
ttcgagaacg acttctacaa attgcctgac atcaaattca ctgatgccaa ctggcaaaaa    120
ttcaaaaatg gagatacttc catcgagaag atgggggcag cacgagtaaa tgccatgctt    180
gactgcctat tcgaagattt cgaacttgcc atgattggca aggctcaaca agaatactat    240
ttggataatt cactaaagat gaacatgcca ttttacgctt attatgatat gttcaagaaa    300
aaacagctcg tcaaatggct taaagatcac catgatgaca tcctaggcgg aactggtagg    360
atgtacactt cagacggtag ttacattgct aactcttatt tagaggtagc gttagaatct    420
agccgtctgg gtagtggctc ttacatgctt caaatgagat tcaaagacta ttcaagaagt    480
caagaaccca ttccgtcagg tcgcaaaaac cgacttgagt ggattgaaaa caatctggaa    540
aatattcgat aa                                                        552
```

<210> SEQ ID NO 131
<211> LENGTH: 552
<212> TYPE: DNA
<213> ORGANISM: Bacteriophage

<400> SEQUENCE: 131

```
atggaaatca caacgatat caaagagtta attttggaat acgtgaaaag atacttcaag    60
ttcgagaacg acttctacaa attgcctgac atcaaattca ctgatgccaa ctggcagaag   120
ttcaaaaatg gcgaaacagc cattgagaag atgggggcag cacgagtaaa cgcaatgctc   180
gactgcctat tcgaagattt tgagcttgcc atgattggca aggctcaaac taattattat   240
attgataact cgcttaaatt aaacatgcca ttttatgctt actatgatat gtttaagaaa   300
caacagctcg tcaaatggct tgaaactagt cgtgaagaca tcatcggagg ggctggcaga   360
atgtacactt cagacggtag ttacattgct aacgcttatt agaagtagc gttagaatca    420
agctcgcttg gtgatagtga atacatgttg caaatgcgtt ttaaaaatta ttcaaaaagt   480
caagaaccta ttccgtctgg tcgtcaaaat agactggaat ggattgaaaa caatcttaaa   540
aacattcgat aa                                                       552
```

```
<210> SEQ ID NO 132
<211> LENGTH: 552
<212> TYPE: DNA
<213> ORGANISM: Bacteriophage D

<400> SEQUENCE: 132
```

```
atgctaataa ataacgacat caaagagttg attttggaat acgtcaaacg ctatttaaa    60
tatgaaaatg acttctacag attgccgggc atcaagttta ccgatgcaaa ttggcagaag   120
tttaaaaatg gcgacacttc catcgagaag atggggggcag cacgagtaaa cgccatgctc   180
gactgcctat tcgaagattt tgagcttgcc atgattggta aggctcaaac caattattat   240
atcaataatt cattgaaaat gaatatgccg ttttacgctt actatgatat gttcaagaag   300
gaacagctta tgaaatggct tgaaaccagc cgtgaagaca tcataggcgg aactggcagg   360
atgtacactt cagacggtag ttacattgct aacgcttatt tggaaattgc attagaatcg   420
agctcgcttg gtagtggctc ttacatgctt caaatgcgtt ttaaagatta ttcaaaaggt   480
caagagccta tcccgtctgg tcgtcaaaac cgacttgagt ggattgaaaa caatcttgaa   540
aacattcgat aa                                                       552
```

```
<210> SEQ ID NO 133
<211> LENGTH: 552
<212> TYPE: DNA
<213> ORGANISM: Streptococcus thermophilus

<400> SEQUENCE: 133
```

```
atgctaataa ataacgacat caaagagttg attttggaat acgtcaaacg ctatttaaa    60
tttgaaaatg acttctacag attgccgggc atcaagttta ccgatgcaaa ttggcagaag   120
tttaaaaatg gcgacactgc cattgagaag atgggggcat cacgagtaaa ctctatgctt   180
gactgcctgt tcgaagattt tgagcttgct atgattggca aggctcaaga tgaatactat   240
ttggataatt cactaaagat gaacatgcca ttttacgctt attatgatat gttcaagaaa   300
aaacagctcg tcaaatggct taaagatcac catgatgaca tcctaggcgg aactggtagg   360
atgtatactt caagcggcaa ttacattgct aacgcttatt agaggtagc gttagaatca    420
agctcgcttg gtagtggctc ttacatgatt caaatgcgtt ttaaaaatta ttcaaaaggt   480
caagagccta tcccgtctgg tcgtcaaaac cgacttgagt ggattgaaaa aaacttggag   540
aacattcgat aa                                                       552
```

```
<210> SEQ ID NO 134
<211> LENGTH: 552
```

```
<212> TYPE: DNA
<213> ORGANISM: Streptococcus thermophilus

<400> SEQUENCE: 134
atggaaatca acaacgatat taaacaactg atcttggaat acgctaaacg ttatttcaag      60
tttgagaacg acttttataa actgccaggc atcaagttca ctgatgcaaa ttggcagaag     120
ttcaaaaatg gaggcactgc cattgagaag atggggcag cacgagtaaa cgccatgctc      180
gactgcctat tcgaagattt cgagcttgca atgattggca aggctcaaca agaatactat     240
tcggataatt ccttgaaagt aaatatggca ttctatgctt attacgatca attcaaaaaa     300
caacagctta tgaaatggct aaagataat cacgatgaca tcataggagg gactggtaga      360
atgtacacgt caagcggtag ttacattgct aacgcttatt tagaaattgc gttagaatct     420
agccgtctgg gtggtggttc ttacatgatc caaatgaggt ttaaagacta ttcaaaaggt     480
caagaaccta ttccgtctgg tcgtcagaat cgacttgaat ggattgagag caacttggaa     540
aacattcgat aa                                                          552

<210> SEQ ID NO 135
<211> LENGTH: 552
<212> TYPE: DNA
<213> ORGANISM: Bacteriophage Sfi

<400> SEQUENCE: 135
atggaaatca acaacgacat taaacaactg atcttggaat acgtgggacg ctattttaaa     60
tttgaaaatg acttctacaa attgcccggc atcaaattca ctgatgccaa ttggcagaag    120
ttcaaaaatg gcgatacttc catcgaaaag atgggagcag cacgagtaaa cgcaatgctt    180
gactgcctgt tcgaagattt cgaacttgcc atgattggca aggctcaaac taattattat    240
attgataatt cccttaaatt aaacatgcca ttttacgctt attatgatat gttcaagaag    300
gaacagctta tgaaatggct aaagatcac catgatgaca tcataggcgg aactggtagg    360
atgtacattt caagcggtag ctacattgct aacgcttatt tggaaattgc actagaatca    420
agtacgcttg gtggtggtga gtacatgttg caaatgcgct ttaaaaatta ttcacgaagc    480
caagaaccta ttccatcagg tcgcaaaaat agacttgaat ggattgaaaa caatcttgaa    540
aacattcgat aa                                                         552

<210> SEQ ID NO 136
<211> LENGTH: 552
<212> TYPE: DNA
<213> ORGANISM: Bacteriophage Sfi

<400> SEQUENCE: 136
atggaaatca acaacgacat taaacaactg atcttggaat acgtgggacg ctattttaaa     60
tttgaaaatg acttctacaa attgcccggc atcaaattca ctgatgccaa ttggcagaag    120
ttcaaaaatg gcgatacttc catcgaaaag atgggagcag cacgagtaaa cgcaatgctt    180
gactgcctgt tcgaagattt cgaacttgcc atgattggca aggctcaaac taattattat    240
attgataatt cccttaaatt aaacatgcca ttttacgctt attatgatat gttcaagaag    300
gaacagctta tgaaatggct aaagatcac catgatgaca tcataggcgg aactggtagg    360
atgtacactt caagcggtag ctacattgct aacgcttatt tggaaattgc actagaatca    420
agtacgcttg gtggtggtga gtacatgttg caaatgcgct ttaaaaatta ttcacgaagc    480
caagaaccta ttccatcagg tcgcaaaaat agacttgaat ggattgaaaa caatcttgaa    540
```

```
aacattcgat aa                                                        552

<210> SEQ ID NO 137
<211> LENGTH: 552
<212> TYPE: DNA
<213> ORGANISM: Streptococcus thermophilus

<400> SEQUENCE: 137
atggaaatca acaaagacat caaagagttg attttggaat acgtcaaacg ctattttaaa    60
tttgaaaatg atttctacag attgccgggc atcaagttta ccgatgccaa ctggcaaaaa   120
ttcaagaatg gagatacttc catcgagaag atggggcag cacgagtaaa cgccatgctt    180
gactgcctgt tcgaagattt cgaacttgct atgattggca aggctcaaga tgaatactat   240
ttggataatt cacttaagtt taatatggca ttccatactt attacgatca atttaaaaaa   300
caacagctta tgaaatggct tgaaactagc ctcgaagaca tcataggcgg aactggtagg   360
atgtacactt caagcggtag ttacattgct aacgcttatt tggaaattgc actagaatca   420
agctcgcttg gtggtggtga gtacatgttg caaatgcgtt ttaaaaatta ttcacgaagc   480
caagaaccta ttccgtcagg tcgcaaaaac cgacttgagt ggattgaaaa caatctggaa   540
aatatccgat aa                                                        552

<210> SEQ ID NO 138
<211> LENGTH: 552
<212> TYPE: DNA
<213> ORGANISM: Bacteriophage D

<400> SEQUENCE: 138
atgaaaatca ataatgacat caaagagcta attttggaat atgtaagtcg ctattttaaa    60
tttgaaaacg acttctacaa attacctggc atcaaattca ctgatgccaa ctggcaaaaa   120
ttcaagaatg gagatacttc catcgagaag atggggcag cacgagtaaa cgccatgctt    180
gactgcctgt tcgaagattt cgaacttgct atgattggca aggctcaaga tgaatactat   240
ttggataatt cacttaagtt taatatggca ttccatactt attacgatca atttaaaaaa   300
caacagctta tgaaatggct tgaaactagc ctcgaagaca tcataggcgg aactggtagg   360
atgtacactt caagcggtag ttacattgct aacgcttatt tggaaattgc actagaatca   420
agctcgcttg gtggtggtga gtacatgttg caaatgcgtt ttaaaaatta ttcacgaagc   480
caagaaccta ttccgtcagg tcgcaaaaac cgacttgagt ggattgaaaa caatctggaa   540
aatatccgat aa                                                        552

<210> SEQ ID NO 139
<211> LENGTH: 552
<212> TYPE: DNA
<213> ORGANISM: Bacteriophage D

<400> SEQUENCE: 139
atgattataa atattgatat caaggaattg attttagagt atatgagtag atacttcaaa    60
tttgaaaatg atttctacaa actccccggc atcaaattca ctgatgccaa ttggcaaaaa   120
tttaagaatg gtgacacttc catcgaaaag atggagcgg ctcgagtaaa tgccatgctc    180
gactgtctat tcgatgactt tgaacttgct atgattggca aggctcaaat taattattac   240
atagacaatt cccttaaatt gaacatgcca ttctatgctt attatgacat gttcaaaaaa   300
caacaactga tcaatggat tgaaaccagc cgtgatgatg tcatcggagg aactggcagg   360
atgtatacag caagcggaag ctacatagct aacgcttatc tagaaatagc actagaatct   420
```

```
agctctctgg gtggtggctc ttatatgctt caaatgagat tcaaaaacta ctcacgaagc    480
caagagccaa taccatctgg tcggaaaaac cgacttgagt ggattgagag caacttggaa    540
aacattagat aa                                                        552

<210> SEQ ID NO 140
<211> LENGTH: 552
<212> TYPE: DNA
<213> ORGANISM: Streptococcus sp

<400> SEQUENCE: 140
atggaaatca acaatgacat caaagagtta atcttggaat acgtgggacg ctatttcaag     60
tttgaaaatg attttacaa attgccgggc atcaaattta ccgatgcaaa ttggcaaaaa    120
ttcaaaaacg gtgatacatc catcgagaaa atggggcgg cacgagtaaa cgcaatgctc    180
gactgcctat tcgatgattt cgagcttgct atgattggca aggctcaaac tgattattac    240
attgataact cacttaaatt gaacatgcca ttttatgctt attatgacat gttcaaaaaa    300
caacagcttc taaaatggat tgagaatagt cgtgaagaca tcatcggagg ggctggcaga    360
atgtacacag cggcggtaa ttggatttct agcgcttatt tagagatcgc attagaatct    420
agttccatcg gtggcggtgg ctatatgctt caaatgcggt tcaaaaacta ctcaagagac    480
cctagaccga ttccagcagg ccaccaaaat cgtctcgaat ggattgaaaa caacttggag    540
aatatccgat aa                                                        552

<210> SEQ ID NO 141
<211> LENGTH: 552
<212> TYPE: DNA
<213> ORGANISM: Streptococcus sp

<400> SEQUENCE: 141
atggaaatca acaatgacat caaggaccta attttagaat acgtaggacg atattttcga     60
tttgaaaacg acttctacaa acttcccaga atcaagttta ccgattccaa ttggcaaaaa    120
ttcaagaacg gtgacacttc catcgaaaaa atgggagctg gcagagtgaa cgcaatgctc    180
gattgtctat ttgatgattt tgagcttgct atgattggta aggctcaaac cgattactac    240
atggacaatt cttttaaagat gaatatgcca ttttatgcct attatgacca atttaagaaa    300
cagcaactat tgaaatggat cgagaatagt agagaggata tcataggcgg tgctggcaga    360
atgtacacag ctagtgggaa ttggatttct agtgcctatt tagaaattgc attggaatcc    420
agctcgttag gtggtggtga gtacatgttg caaatgcgtt tcaaagacta ctcacgaagc    480
caagagccga taccagcagg ccgccagaat cgacttgagt ggattgagaa taatttggag    540
aatattcgat aa                                                        552

<210> SEQ ID NO 142
<211> LENGTH: 315
<212> TYPE: DNA
<213> ORGANISM: Bacteriophage D

<400> SEQUENCE: 142
atgaaaaaag ctaaacaact actcaaagaa attaaaacca ataatgtatc atacgcaatt     60
atggacgagg ataatgaaat ttattgcaac aaggaaacta acaacatcat ggatatttat    120
gaatatgata tgaaaatgg ccatttctat ggtgtttata tgacgttgt tggtggtaaa    180 gttgatagta gatacttatc tgacgaatat attttgaaag ctatcgataa attgctaaat    240
```

```
ttaggcgatc ccgtgaaacg cactgaacta cctgcggacg ctgatttcaa acgcacattc      300 tttttttgaag aataa                                                      315

<210> SEQ ID NO 143
<211> LENGTH: 315
<212> TYPE: DNA
<213> ORGANISM: Bacteriophage D

<400> SEQUENCE: 143
atgaaaaaag ctcaacaact gctcaaagaa attaaaaaca ctaatgtatc atacgcaatt       60
atggacgagg ataatgaaat ttattgcaac aaggaaacta acaacatcat ggatatttat      120
ggatatgata atgaaaatgg ccatttctat ggtgtttata gtgacgttgt tggtggtaaa      180
gttgatagta gatacttatc tgacgaatat attttgaaag ctatcgataa attgctattc      240
ctaggcgacc ctataaaacg aacagatcta ccttcggacg ctgatttcaa acgcacattc      300 tttttttgaag aataa                                                      315

<210> SEQ ID NO 144
<211> LENGTH: 291
<212> TYPE: DNA
<213> ORGANISM: Bacteriophage P

<400> SEQUENCE: 144
atgaaaaaca gacttttggg ttctcgatat actgacgcga tcaaaaacga ttgcggaaca       60
gccaataaaa tgtcgaatat ttacaataaa ttgaacaaag atagtttgcg agaaatccat      120
agtgcactat atggcctatt aacagctgga tacgacatta gtaacatgcg aaacatcgaa      180
gatttagaaa aatatgtgaa tttaaaaaaa tcacgtggcc aactattaaa tgtttcgagc      240
gatgatatta agctatacca taaattattt gtcatcagat ttgaaaaata g              291

<210> SEQ ID NO 145
<211> LENGTH: 279
<212> TYPE: DNA
<213> ORGANISM: Bacteriophage CHPC

<400> SEQUENCE: 145
atgaaaaaca aactttatac tgacgcaatc aaaaacgatt ccagaacagc cagtaaaatg       60
gcgaacattt acaataaatt ggaaagcgat actatgcgag aaatccatag tgcactatct      120
ggcctattaa cggctggata cgacattagt aacatgcgaa acatcgaaga gttagaaaaa      180
tatgtgactt taaaaaaatc acgtggccaa ctattaaatg tctctagcga agacattaaa      240
ttgtaccata aattatttgt catcaggttt ggcaaatag                             279

<210> SEQ ID NO 146
<211> LENGTH: 297
<212> TYPE: DNA
<213> ORGANISM: Bacteriophage D

<400> SEQUENCE: 146
atgaaaaaca gacttttggg ttctcgatat actgacgcga tcaaaaacga ttgcggaaca       60
gccaataaaa tgtcgaatat ttacaataaa ttgaacaaag atagtttgcg agaaattcat      120
agtgcactat atggcctatt aacagctggt tacgacatta gtaacatgcg aaaaatagaa      180
gagttagaaa aatatgtgaa tttaaaaaaa tcacgtggcc aactattaaa tgtttctagc      240
aacgatatta agctatacca taaattattt gtcatcagat ttggaaaaga gaggtaa        297
```

```
<210> SEQ ID NO 147
<211> LENGTH: 285
<212> TYPE: DNA
<213> ORGANISM: Bacteriophage D

<400> SEQUENCE: 147
atgaaaaaca gactatatac tgacgcgatc aaaaacgatt gcggaacagc caataaaatg      60
tcgaatattt acaataaatt gaacaaagat agtttgcgag aaattcatag tgcactatat     120
ggcctattaa cagctggtta cgacattagt aacatgcgaa aaatagaaga gttagaaaaa     180
tatgtgaatt taaaaaaatc acgtggccaa ctattaaatg tttctagcaa cgatattaag     240
ctataccata aattatttgt catcagattt ggaaaagaga ggtaa                    285

<210> SEQ ID NO 148
<211> LENGTH: 279
<212> TYPE: DNA
<213> ORGANISM: Bacteriophage D

<400> SEQUENCE: 148
atgaaaaaca aactttatac tgacgcaatc aaaaacgatt ccgcaacagc caataaaatg      60
gcgaatattt atagcaagct aaacaaagat agtttgcgag aaatccatag tgcactatct     120
ggcctattaa cggctggata cgacattagt aacatgcaaa acatcgcaga gttacaaaaa     180
tatgtgattt taaaaaaatc acgggggcaa ctattaaatg tctctagcaa agacattgaa     240
ctgtatcata aattatttgt catcagattt ggaaaataa                           279

<210> SEQ ID NO 149
<211> LENGTH: 291
<212> TYPE: DNA
<213> ORGANISM: Bacteriophage D

<400> SEQUENCE: 149
atgaaaaaca gacttttggg ttctcgatat actgacgcga tcaaaaacga ttgcggaaca      60
gccaataaaa tgtcgaatat ttacaataaa ttgaacaaag atagtttgcg agaaattcat     120
agtgcactat atggcctatt aacagctggt tacgacatta gtaacatgcg aaaaatagaa     180
gagttagaaa aatatgtgaa tttaaaaaaa tcacgtggcc aactattaaa tgtttctagc     240
aacgatatta agctatacca taaattattt gtcatcagat ttggaaaata g             291

<210> SEQ ID NO 150
<211> LENGTH: 285
<212> TYPE: DNA
<213> ORGANISM: Bacteriophage D

<400> SEQUENCE: 150
atgaaaaaca gacttttggg ttctcgatat actgacgcga tcaaaaacga ttgcggaaca      60
gccaataaaa tgtcgaatat ttacaataaa ttgaacaaag atagtttgcg agaaattcat     120
agtgcactat atggcctatt aacagctggt tacgacatta gtaacatgcg aaaaatagaa     180
gagttagaaa aatatgtgaa tttatcacgt ggccaactat taaatgtttc tagcaacgat     240
attaagctat atcataaatt atttgtcatc agatttggaa aatag                    285

<210> SEQ ID NO 151
<211> LENGTH: 303
<212> TYPE: DNA
<213> ORGANISM: Bacteriophage D

<400> SEQUENCE: 151
```

```
atgaaaaaca gacttttggg ttctcgatat actgacgcaa tcaaaaacga ttccggaaca    60
gccaataaaa tgtctaatat ttacaattca gtcataaaca aggagggtt gcgaggaatc    120 catagtgcac tatatggcct attaacagct ggatacgaca ttagtaacat gcgaaaaata    180
gaagagttag aaaaatatgt gaatttaaaa aaatcacgtg gccaactatt aaatgtttct    240
agcagcgata ttaagctata ccataaatta tttgtcatca gatttggaaa aaagttaaaa    300
taa                                                                  303
```

<210> SEQ ID NO 152
<211> LENGTH: 297
<212> TYPE: DNA
<213> ORGANISM: Bacteriophage D

<400> SEQUENCE: 152

```
atgaaaaatg gtaacaaaat tttaggttat cgatacactg atgagattaa aaacgattct    60
gcaacagaga ataaaatgtc taatctttat aacaaattgg acaaagatag tttacgagag    120
atccatagtg cattatacgg tctattaaca gctggatata atatcagcaa catgcgaaat    180
gtcgaagaac ttgaaaaata cgtgaacgtt aaaaaatctc atggaaaatt attagatgtt    240
actaatagtg acattcagtt atatcataaa ttatttgttg ttcgatttgg gaagtag       297
```

<210> SEQ ID NO 153
<211> LENGTH: 291
<212> TYPE: DNA
<213> ORGANISM: Bacteriophage D

<400> SEQUENCE: 153

```
atgaaaaaca gacttttggg ttctcgatat actgacgcga tcaaaaacga ttgcggaaca    60
gccaataaaa tgtcgaatat ttacaataaa ttgaacaaag atagtttgcg agaaatccat    120
agtgcactat atggcctatt aacagctgga tacgacatta gtaacatgcg aaacatcgaa    180
gagttagaaa atatgtgaa tttaaaaaaa tcacgtggcc aactattaaa tgtttctagc    240
agcgatatta agctatacca taaattattt gtcatcagat ttggaaaata g            291
```

<210> SEQ ID NO 154
<211> LENGTH: 294
<212> TYPE: DNA
<213> ORGANISM: Bacteriophage N

<400> SEQUENCE: 154

```
atgaaaaaca gacttttggg ttctcgatat actgacgcaa tcaaaaacga ttccggaaca    60
gccaataaaa tgtctaatat ttacaattca gtcataaaca aggagggt gcgaggaatc     120 catagtgcac tatatggcct attaacagct ggatacgaca ttagtaacat gcgaaaaata    180
gaagagttag aaaaatatgt gaatttaaaa aaatcacgtg gccaactatt aaatgtttct    240
agcagcgata ttaagctata ccataaatta tttgtcatca gatttggaaa atag          294
```

<210> SEQ ID NO 155
<211> LENGTH: 294
<212> TYPE: DNA
<213> ORGANISM: Bacteriophage N

<400> SEQUENCE: 155

```
atgaaaaaca gacttttggg ttctcgatat actgacgcaa tcaaaaacga ttccggaaca    60
gccaataaaa tgtctaatat ttacaattca gtcataaaca aggagggtt gcgagaaatc    120 catagtgcac tatatggcct attaacagct ggttacgaca ttagtaacat gcgaaaaata    180
```

```
gaagagttag aaaaatatgt gaatttaaaa aaatcacgtg gccaactatt aaatgtgtct    240
agcaatgata ttaagctata ccataaatta tttgtcacca gatttggaaa ataa          294
```

<210> SEQ ID NO 156
<211> LENGTH: 291
<212> TYPE: DNA
<213> ORGANISM: Bacteriophage P

<400> SEQUENCE: 156

```
atgaaaaaca gacttttggg ttctcgatat actgacgcaa tcaaaaacga ttccggaaca    60
gccaataaaa tgtcgaatat ttacaataaa ttgaacaaag atagtttgcg agaaattcat   120
agtgcactat atggcctatt aacagctggt tacgacatta gtaacatgcg aaacatcgaa   180
gagttagaaa aatatgtgaa tttaaaaaaa tcacgtggcc aactattaaa tgttactagc   240
aatgatatta agctatacca taaattattt gtcatcagat ttggaaaata g            291
```

<210> SEQ ID NO 157
<211> LENGTH: 291
<212> TYPE: DNA
<213> ORGANISM: Bacteriophage P

<400> SEQUENCE: 157

```
atgaaaaaca gacttttggg ttctcgatat actgacgcga tcaaaaacga ttgcggaaca    60
gccaataaaa tgtcgaatat ttacaataaa ttgaacaaag atagtttgcg agagatccat   120
agtgcactat atggcctatt aacagctgga tacgacatta gtaacatgcg aaacatcgaa   180
gagttagaaa aatatgtgaa tttaaaaaaa tcacgtggcc aactattaaa tgtttcgagc   240
gatgatatta agctatacca taaattattt gtcatcagat ttggaaaata g            291
```

<210> SEQ ID NO 158
<211> LENGTH: 297
<212> TYPE: DNA
<213> ORGANISM: Bacteriophage V

<400> SEQUENCE: 158

```
atgaaaaatg gtaacaaaat tttaggttat cgatacactg atgagattaa aaacgattct    60
gcaacagaga ataaaatgtc taatctttat aacaaattgg acaaagatag tttacgagag   120
atccatagtg cattatacgg tctattaaca gctggatatg atatcagcaa catgcgaaat   180
gtcgaagaac ttgaaaaata cgtgaacgtt aaaaaatctc atggaaaatt attagatgtt   240
actaatagtg acattcagtt atatcataaa ttatttgttg ttcgatttgg gaggtaa      297
```

<210> SEQ ID NO 159
<211> LENGTH: 387
<212> TYPE: DNA
<213> ORGANISM: Bacteriophage D

<400> SEQUENCE: 159

```
atgacagaat ggaaaacaat aaactttaat gcacaaaaca ttgaatacga ggcggcaaaa    60
gcaatcctca ttaagatgcc aaacaattct gaatggcacg gttacacttt ctggcatccg   120
tcaaaatgtg tgcgtacatt aagcaagggt aatggttatt tcaaaacttt cagctataca   180
gaaaattggg agtttaccat tttcaaatca aataaaaaag gggaagaac cattgaacaa   240 gtacttacgg caagagatat ggaaaaagca tttagtgtgg tgaatgaaca aattgcaagt   300
aatgcttcaa cagaaagtta ccttgaaatt gaagaaccta aaaaggttga taaaacagtt   360
```

```
agtattaaca atgagttaaa acgttaa                                        387
```

<210> SEQ ID NO 160
<211> LENGTH: 387
<212> TYPE: DNA
<213> ORGANISM: Bacteriophage D

<400> SEQUENCE: 160

```
atgacagaat ggaaaacgat taattttaat aaacaaaaca ttgaacatga aacagcgaaa     60
gctgttctca ttaagatgcc aaataattct gaatggtacg gctataaatt ctggcatccg    120
tcaaaatgtg tgcgtacatt aagcaagggc aatggttatt tcaaaacttt cagctataca    180
gaaaattggg agtttaccat tttcaaatca ataaaaagg gggaaagaac cgctgaacaa     240
atacttacag cagaggatat ggaaatagct tttgatgttg ttaacgaaca aattagcgcg    300
aacgcttcaa cagaaagtta tcttgaaatt gaagaaccta aaaaggttga taaaacagtt    360
agtattaaca atgagttaaa acgttaa                                        387
```

<210> SEQ ID NO 161
<211> LENGTH: 387
<212> TYPE: DNA
<213> ORGANISM: Bacteriophage D

<400> SEQUENCE: 161

```
atgacagaat ggaaaacaat aaactttaat gcacaaaaca ttgaatacga ggcggcaaaa    60
gcaatcctca ttaagatgcc aaacaattct gaatggcacg gttacacttt ctggcatccg    120
tcaaaatgtg tgcgtacatt aagcaagggt aatggttatt tcaaaacttt cagctataca    180
gaaaattggg agtttaccat tttcaaatca ataaaaagg gggaaagaac cgctgaacaa     240
atacttacag cagaggatat ggaaatagct tttgatgttg ttaacgaaca aatcagtgta    300
gacgcttcga cagaaagtta ccttgaaatc gaagagccta aaaaggttga taaaacagtt    360
agtattaaca atgaattaaa acgttaa                                        387
```

<210> SEQ ID NO 162
<211> LENGTH: 381
<212> TYPE: DNA
<213> ORGANISM: Bacteriophage D

<400> SEQUENCE: 162

```
atgtggaaat caatcaattt taacgcacaa acatcgaac acgagacagc gaaagctgtt      60
ctcattaaga tgccaaataa ttctgaatgg agtggttata aattttggca cccatctaaa   120
tgcgtccgta ctctaagcaa gggcaaaggc tatttcaaaa ttttcagcta tacagaaaat   180
tgggagttta ccattttcaa atcaaataaa aagggggaaa gaaccgctga acaaatactt   240
acagcagagg atatggaaat agcttttgat gttgttaacg aacaaattag cgcgaacgct   300
tcaacagaaa gttatcttga aattgaagaa cctaaaaagg ttgataaaac agttagtatt   360
aacaatgagt taaaacgtta a                                              381
```

<210> SEQ ID NO 163
<211> LENGTH: 381
<212> TYPE: DNA
<213> ORGANISM: Bacteriophage D

<400> SEQUENCE: 163

```
atgtggaaat caatcaattt taacgcacaa acatcgaac acgagacagc gaaagctgtt      60
ctcattaaga tgccaaataa ttctgaatgg agtggttata aattttggca cccatctaaa   120
```

| | |
|---|---|
| ttcgtccgta ctctaagcaa gggcaaaggc tatttcaaaa ttttcagcta tacagaaaat | 180 |
| tgggagttta ccattttcaa atcaaataaa aagggggaaa gaaccgctga acaaatactt | 240 |
| acagcagagg atatggaaat agcttttgat gttgttaacg aacaaattag cgcgaacgct | 300 |
| tcaacagaaa gttatcttga aattgaagaa cctaaaaagg ttgataaaac agttagtatt | 360 |
| aacaatgagt taaaacgtta a | 381 |

<210> SEQ ID NO 164
<211> LENGTH: 381
<212> TYPE: DNA
<213> ORGANISM: Bacteriophage D

<400> SEQUENCE: 164

| | |
|---|---|
| atgtggaaat caatcaattt taacgcacaa aacatcgaac acgagacagc gaaagctgtt | 60 |
| ctcattaaga tgccaaataa ttctgaatgg agtggttata aattttggca ctcatctaaa | 120 |
| tgcgtccgta ctctaagcaa gggcaaaggc tatttccaaa gtttcagcta tacagaaaat | 180 |
| tgggagttta ccattttcaa atcaaataaa aagggggaaa gaaccgctga acaaatactt | 240 |
| acagcagagg atatggaaat agcttttgat gttgttaacg aacaaattag cgcgaacgct | 300 |
| tcaacagaaa gttatcttga aattgaagaa cctaaaaagg ttgataaaac agttagtatt | 360 |
| aacaatgagt taaaacgtta a | 381 |

<210> SEQ ID NO 165
<211> LENGTH: 387
<212> TYPE: DNA
<213> ORGANISM: Bacteriophage D

<400> SEQUENCE: 165

| | |
|---|---|
| atgacagaat ggaaaacgat taatttaat aaacaaaaca ttgaacatga aacagtgaaa | 60 |
| gctgttctca ttaagatgcc aaataattct gaatggtacg gctataaatt ctggcatccg | 120 |
| tcaaaatgtg tgcgtacatt aagcaagggc aatggttatt tcaaaacttt cagctataca | 180 |
| gaaaattggg agtttaccat tttcaaatca ataaaaagg gggaagaac cgctgaacaa | 240 |
| atacttacag cagaggatat ggaaatagct tttgatgttg ttaacgaaca aattagcgcg | 300 |
| aacgcttcaa cagaaagtta tcttgaaatt gaagaaccta aaaggttga taaaacagtt | 360 |
| agtattaaca atgagttaaa acgttaa | 387 |

<210> SEQ ID NO 166
<211> LENGTH: 372
<212> TYPE: DNA
<213> ORGANISM: Bacteriophage D

<400> SEQUENCE: 166

| | |
|---|---|
| atgtggaaat caatcaaatt taacgcacag aacataaaat ttgagactgc gaaagcagta | 60 |
| ttgattaaaa tgccgaataa gtctaggtat gctggatata tgttctggca tcctttaaaa | 120 |
| cttgtccgtg ttgaaggcgg aaaaggctac tttatgagtt ttagctatac agatgatttt | 180 |
| gagtttaagg tttttaaaca aggtaaaaat cgtcaaatca ccgctgaatc aatattatca | 240 |
| cacgaagaaa ttgaggaagc ttttgaaatt gtgaatgaac aattatctta tatggatgaa | 300 |
| tgctatctag aggttacaga acctactaaa attgataaag aggtagaggt caaagaagaa | 360 |
| ttgagaaagt aa | 372 |

<210> SEQ ID NO 167

```
<211> LENGTH: 372
<212> TYPE: DNA
<213> ORGANISM: Bacteriophage D

<400> SEQUENCE: 167
atgtggaaat caatcaaatt taatgcacaa aacatcaaat tcgagacagc aaaagcagtc    60
ttgattaaaa tgcccaataa atctaggtat gctgggtata tgttctggca tcctgcaaaa   120
ctagtccgag tggtaggtgg aaaaggttac tttatgagtt ttagctatac tgatgaattt   180
gagtttaaga tatttaaaca aggaaaaaat cgtcaaatta ctgttgaaaa aatcttatca   240
cccgaagaaa tagaagacgc ttttgaagtt gtgaacgaac aattatctga tatcgatgaa   300
tgctatttag aagtgacaga accaactaaa attaatgata aggtagaaat cagagcagaa   360
ttaagaaaat aa                                                       372

<210> SEQ ID NO 168
<211> LENGTH: 372
<212> TYPE: DNA
<213> ORGANISM: Bacteriophage D

<400> SEQUENCE: 168
atgtggaaat caatcaaatt taacgcacag aacataaaat tcgagactgc gaaagcagta    60
ttaattaaaa tgccaaataa atctaggtat gctggatata tgttctggca tccttcaaaa   120
cttgtccgtg ttgaaggcgg aaaaggctac tttatgagtt ttagctatac agatgatttt   180
gagtttaagg tttttaaaca aggtaaaaat cgtcaaatca ccgctgaatc aatattatca   240
cacgaagaaa ttgaggaagc ttttgaaatt gtgaatgaac aattatctta tatggatgaa   300
tgctatctag aggttacaga acctactaaa attgataaag aggtagaggt caaagaagaa   360
ttgagaaagt aa                                                       372

<210> SEQ ID NO 169
<211> LENGTH: 372
<212> TYPE: DNA
<213> ORGANISM: Bacteriophage D

<400> SEQUENCE: 169
atgtggaaat caataaaatt taatgcacaa aacgtaaaat tcgagactgc gaattcagtt    60
ttgattaaaa tgccgaataa atctagctat gctggatata tgttctggca ccctgcgaaa   120
ctagttcgtg tgttaggtgg caaaggttac ttttgagtt ttagctatac agatgaattt    180
gagtttaagg tttttaagca aggaaaaaat cgtcaaatca ccgctgaagc aatcttatca   240
cacgaagaaa tggaagacgc gttttgaaatt gtgaatgagc atttgtccta tacagatgaa  300
tgctatctag aagttgcaga acctactaaa atcgataaag aggtagagat cagagaagaa   360
ttgagaaagt aa                                                       372

<210> SEQ ID NO 170
<211> LENGTH: 180
<212> TYPE: DNA
<213> ORGANISM: Bacteriophage D

<400> SEQUENCE: 170
atgaaagttt attataatct agcagatagc ggactcttca aagaaatcaa gaaacaacta    60
gctctggacg atgcggaaaa cggcgattta attcatacaa cagaagacaa cgaggcttca   120
gatgggacaa aaatcgtcgc aatctggaac gcaaacagac aaaactattt tataaagtaa   180
```

```
<210> SEQ ID NO 171
<211> LENGTH: 438
<212> TYPE: DNA
<213> ORGANISM: Bacteriophage D

<400> SEQUENCE: 171
atgagaaacg attttattaa taaagtttat gatgaattaa atcagattat taatcattgg      60
gctaaacaaa aatatttaag tgataagatt tttgaatata ctaatacttt tagtattaag     120
aaggtttatg gactttattg ggaagttaag attttatgta agaatgatta tcgaattttg     180
ttgagatttt ataaaaatta tgagtggtat aacgattcta atattttaaa tgtatctgta     240
ttagcacctg cggtggaaag agttaaaaat gaagatggaa gcgttgatgt ttatccaagt     300
aaaataatta agataaaat tgaatttatt gaaggtgatt ttgatattga tggagatgat     360
tgggtagatg aagtgttgga atatataaat aaatgggtaa ataagataaa agctgatgtg     420
gaggtattag ataaatga                                                   438

<210> SEQ ID NO 172
<211> LENGTH: 438
<212> TYPE: DNA
<213> ORGANISM: Bacteriophage D

<400> SEQUENCE: 172
atgagaaacg attttattaa taaagtttat gatgaattaa atcagattat taatcattgg      60
gctaaacaaa aatatttaag tgataagatt tttgaatata ctaatacttt tagtattaag     120
aaggtttatg gactttattg ggaagttaag attttatgta agaatgatta tcgaattttg     180
ttgagatttt ataaaaatta tgagtggtat aacgattcta atattttaaa tgtatctgta     240
ttagcacctg cggtggaaag agttaaaaat gaagatggaa gcgttgatgt ttatccaagt     300
aaaaaaatta agataaaat tgaatttatt gaaggtgatt ttgatattga tggagatgat     360
tgggtagatg aagtgttgga atatataaat aaatgggtaa ataagataaa agctgatgtg     420
gaggtattag ataaatga                                                   438

<210> SEQ ID NO 173
<211> LENGTH: 438
<212> TYPE: DNA
<213> ORGANISM: Bacteriophage D

<400> SEQUENCE: 173
atgagaaacg attttattaa taaagtttat gatgaattaa atcagattat taatcattgg      60
gctaaacaaa aatatttaag tgataagatt tttgaatata ctaatacttt tagtattaag     120
aaggtttatg gactttattg ggaagttaag attttatgta agaatgatta tcgaattttg     180
ttgagatttt ataaaaatta tgagtggtat aacgattcta atattttaaa tgtatctgta     240
ttagcacctg cggtggaaag agttaaaaat gaagatggaa gcgttgatgt ttatccaagt     300
aaaaaaatta agataaaat tgaatttatt gaaggtaatt ttgatattga tggagatgat     360
tgggtagatg aagtgttgga atatataaat aaatgggtaa ataagataaa agctgatgtg     420
gaggtattag ataaatga                                                   438

<210> SEQ ID NO 174
<211> LENGTH: 366
<212> TYPE: DNA
<213> ORGANISM: Bacteriophage D

<400> SEQUENCE: 174
```

```
atgagaaacg attttattaa taaagtttat gatgaattaa atcagattat taatcattgg      60
gctaaacaaa aatatttaag tgataagatt tttgaatata ctaatacttt tagtattaag     120
aaggtttatg gactttattg ggaagttaag attttatgta agaatgatta tcgaattttg     180
ttgagatttt ataaaaatta tgagtggtat aacgattcta atattttaaa tgtatctgta     240
ttagcacctg cggtggaaag agttaaaaat gaagatggaa gcgttgatgt ttatccaagt     300
aaaaaattaa agataaaatt gaatttattg aaggtgattt tgatattgat ggagatgatt     360
gggtag                                                               366
```

<210> SEQ ID NO 175
<211> LENGTH: 438
<212> TYPE: DNA
<213> ORGANISM: Bacteriophage D

<400> SEQUENCE: 175

```
atgagaaacg attttattaa taaagtttat gatgaattaa atcagattat taatcattgg      60
gctaaacaaa aatatttaag tgataagatt tttgaatata ctaatacttt tagtattaag     120
aaggtttatg gactttattg ggaagttaag attttatgta agaatgatta tcgaattttg     180
ttgagatttt ataaaaatta tgagtggtat aacgattcta atattttaaa tgtatctgta     240
ttagcacctg cggtggaaag agttgaaaat gaagatggaa gcgttgatgt ttatccaagt     300
aaaataatta agataaaat tgaatttatt gaaggtgatt tgatatcga tggagatgat     360 tgggtagatg aagtgttgga atatataaat aaatgggtaa ataaagataa agctgatgtg     420
gaggtattag ataaatga                                                  438
```

<210> SEQ ID NO 176
<211> LENGTH: 438
<212> TYPE: DNA
<213> ORGANISM: Bacteriophage D

<400> SEQUENCE: 176

```
atgagaaacg attttattaa taaagtttat gatgaattaa atccgattat taatcattgg      60
gctaaacaaa aatatttaag tgataagatt tttgaatata ctaatacttt tagtattaag     120
aaggtttatg gactttattg ggaagttaag attttatgta agaatgatta tcgaattttg     180
ttgagatttt ataaaaatca tgagtggtat aatgattcta atattttaaa tgtatctgta     240
ttagcacctg cggtggaaag agttaaacat gaagatggaa gcgttgatgt ttatccaagt     300
aaaataatta agataaaat tgaatttatt gaaggtgatt tgatattga tggatatgat     360 tgggtagatg aagtgttgga atatataaat aaatgggtaa ataaagataa agatgatgtg     420
gaggtattag ataagtga                                                  438
```

<210> SEQ ID NO 177
<211> LENGTH: 438
<212> TYPE: DNA
<213> ORGANISM: Bacteriophage O

<400> SEQUENCE: 177

```
atgagaaacg attttattaa taaagtctat gatgaattaa atcagattat taatcattgg      60
gctaaacaaa aatatttaag tgataagatt tttgaatata ctaatacttt tagtattaag     120
aaggtttatg gactctattg ggaagttaag attttatgta agaatgatta tcgaattttg     180
ttgagatttt ataaaaatta tgagtggtat aatgattcta atattttaaa tgtatctgta     240
ttagcacctg cggtggaaag agttaaaaat gaagatggaa gcgttgatgt ttatccaagt     300
```

```
aaaataatta aagataaaat tgaatttatt gaaggtaatt ttgatattga tggagatgat    360
tgggtagatg aagtgttgga atatataaat aaatgggtaa ataagataaa agctgatgtg    420
gaggtattag ataaatga                                                  438
```

<210> SEQ ID NO 178
<211> LENGTH: 318
<212> TYPE: DNA
<213> ORGANISM: Bacteriophage D

<400> SEQUENCE: 178

```
atgaaaaatt tcaaaataag ctctacttat agagctgcac gaaaacagca gaaaactgct     60
aatcgtaaat cgttttataa cgatgagggc tacatgatca gcccaagtga atgggctgat    120
ggagtcatta aggggcttat aaaccctaaa aactcttggt caaatgacca tgtgaaaggg    180
tacctcccta gagtttcccc acgtagccat tggacaaaga atggttatag ggagtacctt    240
ggtattggta atcaaggga tatccctgaa aaagagcctg aagttatcga gatgatggat    300
ctcgagttag ttccttaa                                                  318
```

<210> SEQ ID NO 179
<211> LENGTH: 318
<212> TYPE: DNA
<213> ORGANISM: Bacteriophage P

<400> SEQUENCE: 179

```
atgaaaaatt tcaaaataag ctctacttat agagctgcac gaaaacagca gaaaactgct     60
aatcgtaaat cgttttataa cgatgagggc tacatgatca gcccaagtga atgggttgat    120
ggagtcatta aggggcttat aaaccctaaa aactcttggt caaatgacca tgtgaaaggg    180
tacctcccta gagtttcccc acgtagccat tggacaaaga atggttatag ggagtacctt    240
ggtattggta atcaaggga tatccctgaa aaagagcctg aagttatcga gatgatggat    300
ctcgagttag ttccttaa                                                  318
```

<210> SEQ ID NO 180
<211> LENGTH: 318
<212> TYPE: DNA
<213> ORGANISM: Bacteriophage Proph

<400> SEQUENCE: 180

```
atgaaaaatt tcaaaataag ctctacttat agagctgcac gaaaacagca gaaaactgct     60
aatcgtaaat cgttttataa cgatgagggc tacatgatca gcccaagtga atgggctgat    120
ggagtcatta aggggcttat aaaccctaaa aactcttggt caaatgacca tgtgaaaggg    180
tacctcccta gagtttcccc acgtagccat tggacaaaga atggttatag ggagtacctt    240
ggtattggta atcaaggga tatccctaaa aaagagcctg aagttatcga gatgatggat    300
ctcgagttag ttccttaa                                                  318
```

<210> SEQ ID NO 181
<211> LENGTH: 387
<212> TYPE: DNA
<213> ORGANISM: Bacteriophage D

<400> SEQUENCE: 181

```
atgaaatatg ataagtcagg aatcatgaaa gaagcttgga acttatttaa taatgatgac     60
atcacttttg cagactttga atatctcact cgtgaagaac gccaaggtaa aaaaacattt    120
```

```
actctttgct tgaaagaagc ttgggcacac gaaaaagaaa ttgttgacag catcaaaaaa      180
gaccacgctg atgctgaaca ttcagtggaa gcaaaagctt gggattgggc ttgtaaaaaa      240
ttaggtgtct ctattgaaat ggatgcttac acaaaattcg ttaacgttaa cgatatgaaa      300
aaagaagcat ggcctggaac aagcgtttgg tcattggcta tgcgtgcggt taaactacat      360
atcaaacttt ttggtcaagt agcttaa                                          387
```

<210> SEQ ID NO 182
<211> LENGTH: 522
<212> TYPE: DNA
<213> ORGANISM: Bacteriophage D

<400> SEQUENCE: 182

```
ttgaatggat taaaaacaat cttgaaaaca ttcgataaaa acatatattt tttaaccaaa       60
agtgttgaca tacgtcaaca taggagatat aatatatatg taaagttaag agaggaagta      120
aatgacatga aaaatcaac atacgacaaa tcaggaatta tgaaagaagc ttggaattta      180
tttaataacg atgacatcac tactgcagat tttgaatatc tcactcgtgg agaattgcaa      240
gaaggaaaaa catttgctat ttgcttaaaa gaagcttggg ctcacgaaaa agacattgtt      300
gaaagtttaa acgaagatta tgaaaatgct gaacattcag tacaagctaa agcttgggac      360
tgggcttgta aaaaattagg tgtctctatt gaagtagatg cttacacaaa attggttaac      420
gtcaacgaca tgcaaaaaga atcatggcct ggaacaagcg catggtcttt ggctatgcgt      480
gcagttaaac tacatatcaa acttttcggt caagcggctt aa                         522
```

<210> SEQ ID NO 183
<211> LENGTH: 522
<212> TYPE: DNA
<213> ORGANISM: Bacteriophage D

<400> SEQUENCE: 183

```
ttgaatggat taaaaacaat cttgaaaaca ttcgataaaa acatatattt tttaaccaaa       60
agtgttgaca tacgtcaaca caggagatat aatatatatg taaagttaag agaggaagta      120
aatgacatga aaaatcaac atacgacaaa tcaggaatta tgaaagaagc ttggaattta      180
tttaataacg atgacatcac tactgcagat tttgaatatc ttactcgtgg agaattgcaa      240
gaaggaaaaa catttgctat ttgcttaaaa gaagcttggg ctcacgaaaa agacattgtt      300
gaaagtttaa acgaagatta tgaaaatgct gaacattcag tacaagctaa agcttgggac      360
tgggcttgta aaaaattagg tgtctctatt gaagtagatg cttacacaaa attggttaac      420
gtcaacgaca tgcaaaaaga atcatggcct ggaacaagcg catggtcttt ggctatgcgt      480
gcagttaaac tacatatcaa acttttcggt caagcggctt aa                         522
```

<210> SEQ ID NO 184
<211> LENGTH: 336
<212> TYPE: DNA
<213> ORGANISM: Bacteriophage

<400> SEQUENCE: 184

```
atgaaaaaag aagttatgac aaacgcatgg aaaatcgcta agaagcagt taagaaattc        60 ggcggcaaag ctatcgaata catcgcagaa gcattgaaaa tggcttgggc tgccgcaaaa      120
ggcggaaacg ctagcctagc taaatttcaa gcagtagaat ctaaaatgcg taaagctggt      180
aaatactcaa tgattcaagt tttaaatttc gctaaggaag tgaaatttaa cgaagttatg      240
cacaaagttg gtgcttacta cggtatcgaa gtagtagctg acggagacag cattggtact      300
```

```
tactacatcg ctgaaaaagt ttgggatgca gcttaa                              336
```

<210> SEQ ID NO 185
<211> LENGTH: 336
<212> TYPE: DNA
<213> ORGANISM: Bacteriophage P

<400> SEQUENCE: 185

```
atgaaaaaag aaattatgac aaaagcatgg aaaatcgcta agaagcagt taaaactttt   60
ggtgggaaag ctatcgaata catcgctggg gctatgaaaa tggcttgggc tgctatcaaa  120
gataacggaa ctagccttgc taaattccaa gctgttgaag caaaaatgcg taaagctggt  180
aaatactcaa tgatccaagt tcttgatttt gctaaagaag tacgtttcaa tgaagtaatg  240
cacaaagttg gcgcttatta cggaatcgaa gtaattgctg atggtgatag cattggtact  300
tactacatcg ctgagaatgt tggaacgca gcataa                              336
```

<210> SEQ ID NO 186
<211> LENGTH: 336
<212> TYPE: DNA
<213> ORGANISM: Bacteriophage CHPC

<400> SEQUENCE: 186

```
atgaaaaaag aaattatgac aaaagcatgg aaaatcgcta aaaacgcaag tacaaaattc   60
ggtggcaaag ctatcgaata cattgctgga gctatgaaaa tggcttgggc tgctatcaaa  120
gaaaacggaa ctagccttgc taaattccaa gcagttgaag ctaaaatgcg caaagctggc  180
aaacactcaa tggtccaagt tttaaatttt gctaaggaag tgaaatttaa cgaagttatg  240
cataaagttg gtgcttacta cggaattgaa gtaattgctg atggtgatag cattggtact  300
tactacatcg ctgaaaaagt ttggaacgca gcataa                              336
```

<210> SEQ ID NO 187
<211> LENGTH: 336
<212> TYPE: DNA
<213> ORGANISM: Bacteriophage D

<400> SEQUENCE: 187

```
atgaaaaaag aaattatgac aaaagcatgg aaaatcgcta agaagcagt tgaaaaattc   60
ggtggcaaag ctatcgaata catcgctgga gctatgaaaa tggcttgggc tgctgctaaa  120
gctggaaaca ctagcgtcgc taaatttcaa gctgttgaag ataaaatgcg caaagctggt  180
aaatactcaa tgattcaagt tttaaatttc gctaatgaag tgaaatttaa cgaagttatg  240
cacaaagctg gtgcgtacta cggcatcgaa gtaattgctg atggtgatag cattggtact  300
tactacatcg ctgaaaaagt ttgggaagta gcataa                              336
```

<210> SEQ ID NO 188
<211> LENGTH: 327
<212> TYPE: DNA
<213> ORGANISM: Bacteriophage D

<400> SEQUENCE: 188

```
atgaaaaaag aagttatgac aaacgcgtgg gaaattgcta aaaacgcttc taaaaaattc   60
ggtggtaaag ctatcgaata catcgctgga gctatgaaaa tggcttgggc tgctgcaaaa  120
ggcggcttag ctaaattcca agcagtagaa tctaaaatgc gtaaagctgg aaaacattca  180
atggtgcaag tgttgaattt cgctaaggaa gtgaaattta cgaagttat gcacaaagct  240
```

```
ggtgcttact acggtatcga gtaatcgct gatggtgata gcattggtac ttactacatt      300
tctgaaaaag tttgggaagt agcttaa                                         327

<210> SEQ ID NO 189
<211> LENGTH: 336
<212> TYPE: DNA
<213> ORGANISM: Bacteriophage D

<400> SEQUENCE: 189
atgaaaaaag aaattatgac aaaagcatgg aaaatcgcta agaagcagt taaaactttc      60 ggtggtaaag ctatcgaata cattgctgga gctatgaaaa tggcttgggc tgctgctaaa    120
gctggaaaca ctagcttagc taaattccaa gcagtagaat ctaaaatgcg taaagctggt    180
aaatactcaa tgattcaagt tttaaatttc gctaaggaag tgaaatttaa cgaagttatg    240
cacaaagttg gcgcttatta cggtatcgaa gtaattgctg atggtgatag cattggtact    300
tactacatcg ctgaaagcgt ttgggaagta gcataa                              336

<210> SEQ ID NO 190
<211> LENGTH: 336
<212> TYPE: DNA
<213> ORGANISM: Bacteriophage D

<400> SEQUENCE: 190
atgaaaaaag aaattatgac aaaagcatgg aaaatcgcta agaagcagt tgaaaaattc      60 ggtggcaaag ctatcgaata catcgctgga gctatgaaaa tggcttgggc tgctgctaaa    120
gctggaaaca ctagcgtcgc taaatttcaa gctgttgaag ataaaatgcg caaagctggt    180
aaatactcaa tgattcaagt tttaaatttc gctaatgaag tgaaatttaa cgaagttatg    240
cacaaagctg gtgcgtacta cggaatcgaa gtaattgctg atggtgatag cattggtact    300
tactacatcg ctgaaaaagt tgggaagta gcataa                               336

<210> SEQ ID NO 191
<211> LENGTH: 318
<212> TYPE: DNA
<213> ORGANISM: Bacteriophage D

<400> SEQUENCE: 191
atgaaaaaag aaattatgac aaaagcatgg aaaatcgcta agaagcagt taaaactttc      60 ggtggaaaag ctatcgaata cattgcggaa gcaatgaaaa tggcttgggc tgctgctaaa    120
ggcggcttag ctaaattcca agcagtagaa tctaaaatgc gtaaagctgg aatgattcaa    180
gttttaaatt tcgctaagga agtgaaattt aacgaagtta tgcacaaagt tggcgcttat    240
tacggtatcg aagtaattgc tgatggtgat agcattggta cttactacat cgctgaaagc    300
gtttgggaag tagcataa                                                  318

<210> SEQ ID NO 192
<211> LENGTH: 336
<212> TYPE: DNA
<213> ORGANISM: Bacteriophage D

<400> SEQUENCE: 192
atgaaatcac aagtaatgag cctagcatgg aaaatcgcta aaacgcaag tacaaaattc      60 ggtggcaaag ctatcgaata cattgctaga gctatgaaaa tggcttggtc tgctatcaaa    120
gaaaacggaa ctagccttgc taaatttcaa gcaattgaag ctaaaattcg caaagctgga    180
aaacactcaa tggtccaagt tttaaaattc gctaaggaag tgaaatttaa cgaagttatg    240
```
cataaagttg gtgcttacta cggaattgaa gtaattgctg atggtgatag cattggtact    300
tactacatcg ctgaaaaagt ttgggatgca gcgtaa    336

<210> SEQ ID NO 193
<211> LENGTH: 336
<212> TYPE: DNA
<213> ORGANISM: Bacteriophage D

<400> SEQUENCE: 193
atgaaaaaag aaattatgaa aaagcatgg aaaatcgcta agaagcagt taagaaattc    60 ggtggtaaag ctatcgaata catcgcagaa gcattgaaaa tggcttgggc tgatgctaaa    120
ggtggtaaca ctagcttggc taaattccaa gctgttgagg aaaagatgcg taaagctggc    180
aaatactcaa tgattcaagt gctcaacttt gctaaagaag tgaaattcaa cgaagtaatg    240
cataaagttg gtgcttacta cggaattgaa gttattgctg acggagacaa aatcggtact    300
tactttatcg ctgaaaaagt ttgggatgca gcttaa    336

<210> SEQ ID NO 194
<211> LENGTH: 336
<212> TYPE: DNA
<213> ORGANISM: Bacteriophage D

<400> SEQUENCE: 194
atgaaaaaag aacttatgaa agacgcttgg gaaattgcta aaaacgcttc taaaaaattc    60
ggtggtaaag ctatcgaata cattgctgga gctatgaaaa tggcttgggc tgctgctaaa    120
gctggaaaca ctagcgtcgc taaattccaa gcggtagaag ctaaaatgcg caaagctggc    180
aaacactcaa tgattcaagt tctcgatttc gctaaagaag ttaagttcaa cgaagtgatg    240
cacaaagttg gtgcgtacta cggcatcgaa gtagtcgctg acggcgatag cattggtact    300
tactacatcg ctgaaaaagt ttgggatgta gcttaa    336

<210> SEQ ID NO 195
<211> LENGTH: 336
<212> TYPE: DNA
<213> ORGANISM: Bacteriophage D

<400> SEQUENCE: 195
atgaaaaaag aagttatgac aaacgcatgg aaaatcgcta agaagcagt taagaaattc    60 ggtggtaaag ctatcgaata catctctgaa gctatgaaaa tggcttgggc tgctgccaag    120
ggtgaaaaca ctagcttagc taaattccaa gctgttgagg aaaagatgcg taaagctggc    180
aaatactcaa tgattcaagt tcttgacttt gctaaagaag ttaaattcaa cgaagtaatg    240
cataaagttg gtgcttacta cggaattgaa gttattgctg acggagacaa cattggtact    300
tactacattg ctgaaaaagt ttgggaagta gcataa    336

<210> SEQ ID NO 196
<211> LENGTH: 321
<212> TYPE: DNA
<213> ORGANISM: Bacteriophage D

<400> SEQUENCE: 196
atgacaaacg catggaaaat cgctaaagaa gcagttaaga aattcggtgg taaagctatc    60
gaatacatct ctgaagctat gaaaattgct tgggctgacg ctaaagaagg aaacactagc    120
gtagctaaat tccaagctgt agaagctaaa atgcgtaaag ctggaaaaca ttcaatggtg    180

```
caagtgttga atttcgctaa agaagtgaaa ttcaacgaag taatgcacaa agttggtgct    240
tactacggta tcgaagtaat cgctgatggt gatagcattg gtacttacta catttctgaa    300
aaagtttggg aagtagctta a                                              321
```

<210> SEQ ID NO 197
<211> LENGTH: 336
<212> TYPE: DNA
<213> ORGANISM: Bacteriophage D

<400> SEQUENCE: 197

```
atgaaaaaag aaattatgac aaaagcatgg aaaatcgcta agaagcagt taaaactttc    60 ggtgaaaaag ctatcgaata cattgcggaa gcaatgaaaa tggcttgggc tgctgctaaa   120
ggcggaaacg ctagcttagc taaattccaa gcagtagaat ctaaaatgcg taaagctggt   180
aaatactcaa tgattcaagt tttaaatttc gctaaggaag tgaaatttaa cgaagttatg   240
cacaaagttg gcgcttatta cggtattgaa gtaattgctg atggtgatag cattggtact   300
tactacatcg ctgaaagcgt tgggaagta gcataa                              336
```

<210> SEQ ID NO 198
<211> LENGTH: 327
<212> TYPE: DNA
<213> ORGANISM: Bacteriophage D

<400> SEQUENCE: 198

```
atgaaaaaag aaattatgac aaaagcatgg aaaatcgcta agaagcagt taaaactttc    60 ggtgaaaaag ctatcgaata cattgcggaa gcaatgaaaa tggcttgggc tgctgctaaa   120
ggcggcttag ctaaattcca agcagtagaa tctaaaatgc gtaaagctgg taaatactca   180
atgattcaag ttttaaattt cgctaaggaa gtgaaattta acgaagttat gcacaaagtt   240
ggcgcttatt acggtatcga gtaattgct gatggtgata gcattggtac ttactacatc   300
gctgaaagcg tttgggaagt agcataa                                        327
```

<210> SEQ ID NO 199
<211> LENGTH: 336
<212> TYPE: DNA
<213> ORGANISM: Bacteriophage D

<400> SEQUENCE: 199

```
atgaagaaag agattatgaa aaaagcgtgg gaaatcgcta agaagcagt taaaaaattc    60 ggtggcaaag ctatcgaata catcgcgaaa gcattgaaaa tggcttggtc tgatgcaaag   120
ggtagtaata ctagcttagc taaattccaa gctgttgagg aaaagatgcg taaagctggc   180
aaatactcaa tgattcaagt tcttgactttt gctaaagaag ttaaattcaa tgaagtaatg   240
cacaaagaag gtgcttacta tggtatcgaa gtggtagctg acggagacag cattggtact   300
tattacattg ctgaaaaagt ttgggaagta gcataa                              336
```

<210> SEQ ID NO 200
<211> LENGTH: 336
<212> TYPE: DNA
<213> ORGANISM: Bacteriophage D

<400> SEQUENCE: 200

```
atgaaaaaag aaattatgac aaaagcatgg aaattgcta aaacgcttc taaaaaattc      60 ggtggtaaag ctatcgaata catcgctgga gctatgaaaa tggcttgggc tgctgctaaa   120
gctggaaaca ctagcgtcgc taaattccaa gcggtagaag ctaaaatgcg caaagctgga   180
```

```
aaacattcaa tggtccaagt tttgaatttt gcaaagaag ttaagttcaa cgaagtaatg      240
cacaaagttg gcacttatta cggcatcgaa gtagtagctg acggcgatag cattggtact      300
tactacatcg ctgaaaaagt ttgggatgca gcataa                                336
```

<210> SEQ ID NO 201
<211> LENGTH: 336
<212> TYPE: DNA
<213> ORGANISM: Bacteriophage D

<400> SEQUENCE: 201

```
atgaaaaaag aaattatgac aaaagcttgg gaaattgcta aaaacgcttc taaaaaattc      60
ggtggtaaag ctatcgaata catcgctgga gctatgaaaa tggcttgggc tgctgctaaa     120
gctggaaaaa ctagcgtcgc taaattccaa gcggtagaag ctaaaatgcg caaagctgga     180
aaacattcaa tggtccaagt tttgaatttt gctaaagaag tacgtttcaa cgaagtaatg     240
cacaaagctg gcgcttatta cggtatcgaa gtaattgctg atggtgatag cattggtact     300
tacttcattg ctgagaatgt ttggaacgca gcataa                                336
```

<210> SEQ ID NO 202
<211> LENGTH: 336
<212> TYPE: DNA
<213> ORGANISM: Bacteriophage D

<400> SEQUENCE: 202

```
atgaaaaaag aaattatgac aaaagcatgg aaaatcgcta agaagcagt taaaactttc       60 ggtggtaaag ctatcgaata catcgcagaa gcattgaaaa tggcttgggc tgctgccaag     120
ggtgaaaaca ctagcttagc taaaattcaa gctgttgagg aaaagatgcg taaatctggt     180
aaatactcaa tgatccaagt tcttgatttt gctaaagaag tgaaatttaa cgaagtaatg     240
cacaaagctg gtgcttacta cggtatcgaa gttattgctg atggcgatag cattggtact     300
tattacattg ctgaaaaagt ttgggaagta gcttaa                                336
```

<210> SEQ ID NO 203
<211> LENGTH: 336
<212> TYPE: DNA
<213> ORGANISM: Bacteriophage D

<400> SEQUENCE: 203

```
atgaaaaaag aaattatgac aaaagcatgg aaaatcgcta agaagcagt taaaactttc       60 ggtggaaaag ctatcgaata cattgcggaa gcaatgaaaa tggcttgggc tgctgctaaa     120
ggcggaaacg ctagcttagc taaattccaa gcagtagaat ctaaaatgcg taaagctggt     180
aaatactcaa tgattcaagt tttaaatttc gctaaggaag tgaaatttaa cgaagttatg     240
cacaaagttg gcgcttatta cggtatcgaa gtaattgctg atggtgatag cattggtact     300
tactacatcg ctgaaaacgt ttggaacgca gcataa                                336
```

<210> SEQ ID NO 204
<211> LENGTH: 336
<212> TYPE: DNA
<213> ORGANISM: Bacteriophage D

<400> SEQUENCE: 204

```
atgaaaaaag aaattatgac aaaagcatgg aaaatcgcta agaagcagt tgagaagttc       60 ggtggtaaat ctatcgaata cattgcggaa gcaatgaaaa tggcttgggc tgctgcaaaa     120
```

```
ggcggaaacg ctagcttagc taaatttcaa gcggtagaag ctaaaatgcg caaagctggt      180
aaatactcaa tgattcaagt tttaaatttc gctaaggaag tgaaatttaa cgaagttatg      240
cacaaagctg gtgcttacta tggaatcgaa gtggtagctg acggagacag cattggtact      300
tattacatcg ctgaaaaagt ttgggaagta gcataa                                336
```

<210> SEQ ID NO 205
<211> LENGTH: 336
<212> TYPE: DNA
<213> ORGANISM: Bacteriophage N

<400> SEQUENCE: 205

```
atgaaaaaag aaattatgac aaaagcttgg gaaattgcta aaaacgcttc taaaaaattc      60
ggtggtaaag ctatcgaata catcgctgga gctatgaaaa tggcttgggc tgctgctaaa     120
gctggaaaca ctagcgtcgc taaattccaa gcggtagaag ctaaaatgcg caaagctgga     180
aaacattcaa tggtccaagt tttgaatttt gcaaagaag ttaagttcaa cgaagtaatg      240
cacaaagttg gcacttatta cggcatcgaa gtagtagctg acggcgatag cattggtact     300
tactacatcg ctgaaaaagt ttgggatgca gcataa                                336
```

<210> SEQ ID NO 206
<211> LENGTH: 336
<212> TYPE: DNA
<213> ORGANISM: Bacteriophage O

<400> SEQUENCE: 206

```
atgaaatcac aagtaatgag ccaagcatgg aaaatcgcta agaagcagt taagaaattc       60 ggtggtaaag ctatcgaata catctctgaa gctatgaaaa tggcttgggc tgctgccaag    120
ggtgaaaaca ctagcttaac taaatttcaa gctgttgagg aaaagatgcg taaagctggc    180
aaatactcaa tgattcaagt tcttgacttt gctaaagaag tgaaattcaa cgaagtaatg    240
cataaagttg gtgcttacta cggaattgaa gttattgctg acggagacag cattggtact    300
tactttatcg ctgaaaaagt ttgggatgta gcttaa                                336
```

<210> SEQ ID NO 207
<211> LENGTH: 336
<212> TYPE: DNA
<213> ORGANISM: Bacteriophage P

<400> SEQUENCE: 207

```
atgaaaaaag aaattatgaa aaaagcatgg aaaatcgcta agaagcagt taagaagttc       60 ggcggcaaag ctatcgaata catcgcagaa gcattgaaaa tggcttggtc tgatgcaaag    120
ggtagtaata ctagcttagc taaattccaa gctgttgagg aaaagatgcg taaagctggc    180
aaatactcaa tgatccaagt tcttgatttt gctaaagaag tgaaatttaa cgaagtaatg    240
cacaaagctg gtgcttacta cggtatcgaa gttattgctg atggcgatag cattggtact    300
tattacattg ctgaaaaagt ttgggaagta gcttaa                                336
```

<210> SEQ ID NO 208
<211> LENGTH: 336
<212> TYPE: DNA
<213> ORGANISM: Bacteriophage P

<400> SEQUENCE: 208

```
atgaaaaaag aaattatgac aaaagcttgg gaaattgcta aaaacgcttc taaaaaattc      60
ggtggtaaag ctatcgaata catcgctgga gctatgaaaa tggcttgggc tgctgctaaa    120
```

```
gctggaaaca ctagcgtcgc taaattccaa gcggtagaag ctaaaatgcg caaagctgga        180
aaacattcaa tggtccaagt tttgaatttt gcaaaagaag ttaagttcaa cgaagtaatg        240
cacaaagttg gcgcttatta cggcatcgaa gtagtagctg acggcgatag cattggtact        300
tattacattg ctgaaaaagt ttgggaagta gcataa                                  336
```

<210> SEQ ID NO 209
<211> LENGTH: 336
<212> TYPE: DNA
<213> ORGANISM: Bacteriophage P

<400> SEQUENCE: 209

```
atgaaaaaag aaattatgac aaacgcgtgg gaaattgcta aaaacgcttc taaaaaattc        60
ggtggtaaag ctatcgaata catcgcagaa gcattgaaaa tggcttggtc tgatgcaaag        120
ggtagtaata ctagcttagc taaattccaa gctgttgagg aaaagatgcg taaagctggc        180
aaatactcaa tgattcaagt tttaaatttc gctaaagaag tgaaattcaa tgaagtaatg        240
cacaaagaag gtgcttacta tggtatcgaa gtagtagctg acggagacag cattggtact        300
tattacattg ctgaaaaagt ttgggatgca gcgtaa                                  336
```

<210> SEQ ID NO 210
<211> LENGTH: 336
<212> TYPE: DNA
<213> ORGANISM: Bacteriophage SFi

<400> SEQUENCE: 210

```
atgaaaaaag aagttatgac aaacgcatgg aaaatcgcta agaagcagt taagaaattc         60 ggtggtaaag ctatcgaata catctctgaa gctatgaaaa tggcttgggc tgctgccaag        120
ggtgaaaaca ctagcttagc taaattccaa gctgttgagg aaaagatgcg taaagctggc        180
aaatactcaa tgattcaagt tcttgacttt gctaaagaag ttaaaatcaa cgaagtaatg        240
cataaagttg gtgcttacta cggaattgaa gttattgctg acggagacaa cattggtact        300
tactacattg ctgaaaaagt ttgggaagta gcataa                                  336
```

<210> SEQ ID NO 211
<211> LENGTH: 336
<212> TYPE: DNA
<213> ORGANISM: Bacteriophage Sfi

<400> SEQUENCE: 211

```
atgaaaaaag aagttatgac aaacgcatgg aaaatcgcta agaagcagt taagaaattc         60 ggtggtaaag ctatcgaata catctctgaa ggctatgaaa tggcttgggc tgctgccaag        120
ggtgaaaaca ctagcttagc taaattccaa gctgttgagg aaaagatgcg taaagctggc        180
aaatactcaa tgattcaagt tcttgacttt gctaaagaag ttaaattcaa cgaagtaatg        240
cataaagttg gtgcttacta cggaattgaa gttattgctg acggagacaa cattggtact        300
tactacattg ctgaaaaagt ttgggaagta gcataa                                  336
```

<210> SEQ ID NO 212
<211> LENGTH: 336
<212> TYPE: DNA
<213> ORGANISM: Bacteriophage Sfi

<400> SEQUENCE: 212

```
atgaagaaag agattatgaa aaaagcgtgg gaaatcgcta agaagcagt taaaaaattc         60
```

```
ggtggcaaag ctatcgaata catcgcagaa gcattgaaaa tggcttggtc tgatgcaaag      120
ggtagtaata ctagcttagc taaattccaa gctgttgagg aaaagatgcg taaagctggc      180
aaatactcaa tgattcaagt tcttgacttt gctaaagaag ttaaattcaa tgaagtaatg      240
cacaaagaag gtgcttacta tggtatcgaa gtggtagctg acggagacag cattggtact      300
tactacattg ctgaaaaagt ttgggaagta gcataa                                336
```

<210> SEQ ID NO 213
<211> LENGTH: 333
<212> TYPE: DNA
<213> ORGANISM: Bacteriophage Sfi

<400> SEQUENCE: 213

```
atgaaaaaaa ttatgacaaa cgcatggaaa atcgctaaag aagcagttaa gaaattcggt       60
ggtaaagcta tcgaatacat ctctgaagct atgaaaattg cttgggctga tgctaaagaa      120
ggaaacacta gcgtagctaa attccaagct gtagaagcta aatgcgtaa agctggaaaa       180 cattcaatgg tgcaagtgtt gaatttcgct aaagaagtga aattcaacga agtaatgcac      240
aaagttggtg cttactacgg tatcgaagta atcgctgatg gtgatagcat tggtacttac      300
tacatttctg aaaagtttg ggaagtagct taa                                    333
```

<210> SEQ ID NO 214
<211> LENGTH: 336
<212> TYPE: DNA
<213> ORGANISM: Bacteriophage Proph

<400> SEQUENCE: 214

```
atgaaaaaag aaattatgaa aaagcatgg aaaatcgcta agaagcagt taagaagttc        60 ggcggcaaag ctatcgaata catcgcagaa gcattgaaaa tggcttggtc tgatgcaaag     120
ggtagtaata ctagcttagc taaattccaa gctgtagaag ataaaatgaa caaaaccgga     180
aaacactcaa tggtccaagt cttgaatttt gctaaagaag tgaatttcaa agaagtaatg     240
cataaagttg gtgcttacta cggtatcgaa gtagtagctg acggagacag cattggtact     300
tactacatcg ctgaaaaggt ttgggatgca gcttaa                                336
```

<210> SEQ ID NO 215
<211> LENGTH: 111
<212> TYPE: DNA
<213> ORGANISM: Bacteriophage D

<400> SEQUENCE: 215

```
atgaaaaaag aagttatgac aaacgcgtgg aaattgcta aaaacgcttc taaaaaattc        60
ggtggtaaag ctatcgaata catcgctgaa aacgtttgga acgcagcata a               111
```

<210> SEQ ID NO 216
<211> LENGTH: 345
<212> TYPE: DNA
<213> ORGANISM: Bacteriophage D

<400> SEQUENCE: 216

```
atgaaatcac aagtaatgag cctagcatgg aaaatcttca aaaacgaaaa aaacgacgta       60
actttttctg aagcattgaa gtttgcttgg aaagccgtta acgtcaaaa tatggcagat      120 gatttctact tcttccattc ttcaaatgtt aaatttcaag gtgttaagaa atggtttgct     180
gaaaaagagt tccgtggacg caacaaaaaa gacttggcgt tcatgtcagt aagtgcaatc     240
agtgttaaag ggttggtcga agaaactgat aaagcagtta aacttgaaat cgtgacacct     300
```

```
tatgggtttt ctgctaaatg gtacccaaaa agtgtaattg cttaa           345
```

<210> SEQ ID NO 217
<211> LENGTH: 345
<212> TYPE: DNA
<213> ORGANISM: Bacteriophage D

<400> SEQUENCE: 217

```
atgaaatcac aagtaatgag cctagcatgg aaaatcttca aaaacgaaaa aaacgatgta    60 acttttctg aagcgttgaa atttgcttgg aaagccgtta acgtcaaaa catggcggat    120 gattttact tcttccgttc ttcaaatgtt aaattccaag gtgttaagaa atggtttgct    180 gaaaagaat tcgtggacg caacaagaaa gacttggcgt ttatgtcagt aactgcaatc    240
agtgttaaag ggttgattga agaaactgat aaagcggtta agcttgaaat cgtaacacct    300
tatggagttt ctactaaatg gtatccaaag agtgtaattg cttaa                  345
```

<210> SEQ ID NO 218
<211> LENGTH: 345
<212> TYPE: DNA
<213> ORGANISM: Bacteriophage D

<400> SEQUENCE: 218

```
atgaaatcac aagtaatgag cctagcatgg aaaattttca aaaacgaaaa aaacgacgta    60 acttttctg aagcattgaa gtttgcttgg aaagccgtta acgtcaaaa catggcggat    120 gatttctact tcttccgttc ttcaaacgtt aaattccaag gtgttaagaa atggtttgct    180 gaaaagaat tcgtggacg caacaagaaa gacttggcgt ttatgtcagt aactgcaatc    240
agcattaaag ggttggttga agaaactgat aaagcggtta agcttgaaat cgtgacacct    300
tatggaattt ctactaaatg gtatccaaag agtgtaattg cttaa                  345
```

<210> SEQ ID NO 219
<211> LENGTH: 345
<212> TYPE: DNA
<213> ORGANISM: Bacteriophage Proph

<400> SEQUENCE: 219

```
atgaaatcac aagtaatgag cctagcatgg aaaatcttca aaaacgaaaa aaacgatgta    60 acttttctg aagcgttgaa atttgcttgg aaagccgtta acgtcaaaa catggcggat    120 gatttctact tcttccgttc ttcaaacgtt aaattccaag gtgttaagaa atggtttgct    180 gaaaagaat tcgtggacg caacaagaaa gacttggcgt ttatgtcagt aactgcaatc    240
agcgttaaag ggttgatcga agaaactgat aaagcggtta agcttgaaat cgtaacacct    300
tatggagttt ctactaaatg gtatccaaag agtgtaattg cttaa                  345
```

<210> SEQ ID NO 220
<211> LENGTH: 345
<212> TYPE: DNA
<213> ORGANISM: Bacteriophage Proph

<400> SEQUENCE: 220

```
atgaaatcac aagtaatgag cctagcatgg aaaatcttca aaaacgaaaa aaacgatgta    60 acttttctg aagcgttgaa atttgcttgg aaagccgtta acgtcaaaa catggcggat    120 gatttctact tcttccgttc ttcaaacgtt aaattccaag gtgttaagaa atggtttgct    180 gaaaagaat tcgtggacg caacaagaaa gacttggcgt ttatgtcagt aactgcaatc    240
```

```
agcattaaag ggttggttga agaaactgat aaagcggtta agcttgaaat cgtgacacct    300
tatggaattt ctactaaatg gtatccaaag agtgtaattg cttaa                    345
```

<210> SEQ ID NO 221
<211> LENGTH: 261
<212> TYPE: DNA
<213> ORGANISM: Bacteriophage

<400> SEQUENCE: 221

```
gtgaaaacaa tggatgcata taaagaacaa tttcaagaat tacaagaata cgcttttaac    60
gttttaagag aatatcctct agacaagaca gcagttaatg tgctttctgc actcgttaac   120
tcaaaaaaga aagatcgcat cgagttttt aaactaaaca aaggcgaaga tgccatgaaa    180
gtttattata atctagcaga tagcggaacg attgaaaaat atttagaaac atctgcattt   240
ttagattaca tcaatgaata a                                              261
```

<210> SEQ ID NO 222
<211> LENGTH: 252
<212> TYPE: DNA
<213> ORGANISM: Bacteriophage D

<400> SEQUENCE: 222

```
atggatacat ataaagaaca atttcaaaaa ttacaagaat acgcttttaa cgttttaaga    60
gaataccctc tagataagac agcagttaat gtactttctg cactcgttaa ctcaaaaaag   120
aaagatcgca tcgagttttt taaactaaac aaaggcgaag atgccatgaa agtttattat   180
aatctagcag atagcggaac gattgaaaaa tatttagaaa catctgcatt tttagaatac   240
ataaatgaat aa                                                        252
```

<210> SEQ ID NO 223
<211> LENGTH: 252
<212> TYPE: DNA
<213> ORGANISM: Bacteriophage D

<400> SEQUENCE: 223

```
atggatacat ataaagaaca atttcaagaa ttacaagaat acgcttttaa cgttttaaga    60
gaatatcctc tagacaagac agcagttaat gtactttctg cactcgttaa ctcaaaaaag   120
aaagatcgca tcgagttttt taaactaaac aaagacgaag atgccatgaa agtttattat   180
aatctagcag atagcggaac gattgaaaaa tatttagaaa catctgcatt tttagaatac   240
atcaatgaat aa                                                        252
```

<210> SEQ ID NO 224
<211> LENGTH: 252
<212> TYPE: DNA
<213> ORGANISM: Bacteriophage D

<400> SEQUENCE: 224

```
atggatacat ataaagaaca atttcaagaa ttacaagaat acgcttttaa cattttaaga    60
gaatatcctc tagacaagac agcagttaat gtactttctg cactcgttaa ctcaaaaaag   120
aaagatcgca tcgagttttt taaactaaac aaagacgaag atgccatgaa agtttattat   180
aatctagcag atagcggaac gattgaaaaa tatttagaaa catctgcatt tttagaatac   240
atcaatgaat aa                                                        252
```

<210> SEQ ID NO 225
<211> LENGTH: 252

```
<212> TYPE: DNA
<213> ORGANISM: Bacteriophage D

<400> SEQUENCE: 225
atggatacat acaaagaaca atttcaaaaa ttacaagaat acgcttttaa cgttttaaga      60
gaataccctc tagataagac agcagttaat gtactttctg cactcgttaa ctcaaaaaag    120
aaagatcgca tcgagttttt taaactaaac aaaggcgaag atgccatgaa agtttattat    180
aatctagcag atagcggaac gattgaaaaa tatttagaaa catctgcatt tttagaatac    240
acaaatgaat aa                                                        252

<210> SEQ ID NO 226
<211> LENGTH: 252
<212> TYPE: DNA
<213> ORGANISM: Bacteriophage Sfi

<400> SEQUENCE: 226
atggatacat ataaagaaca atttcaagaa ttacaagaat acgcttttaa cattttaaga      60
gaatatcctc tagacaagac agcagttaat gtactttctg cactcgttaa ctcaaaaaag    120
aaagatcgca tcgagttttt taaacttaac aaagacgaag atgccatgaa agtttattat    180
aatctagcag atagcggaac gattgaaaaa tatttagaaa catctgcatt tttagaatac    240
atcaatgaat aa                                                        252

<210> SEQ ID NO 227
<211> LENGTH: 252
<212> TYPE: DNA
<213> ORGANISM: Bacteriophage Proph

<400> SEQUENCE: 227
atggatacat acaaagaaca atttcaagaa ttacaagaat acgcttttaa cgttttaaga      60
gaataccctc tagataagac agcagttaat gtactttctg cactcgttaa ctcaaaaaag    120
aaagatcgca tcgagttttt taaactaaac aaaggcgaag acgccatgaa agtttattat    180
aatctagcag atagcggaac gattgaaaaa tatttagaaa catctgcatt cttagaatac    240
atcaatgaat aa                                                        252

<210> SEQ ID NO 228
<211> LENGTH: 252
<212> TYPE: DNA
<213> ORGANISM: Bacteriophage Proph

<400> SEQUENCE: 228
atggatacat ataaagaaca atttcaagaa ttacaagaat acgcttttaa cgttttaaga      60
gaatatcctc tagacaagac agcagttaat gtactttctg cactcgttaa ctcaaaaaag    120
aaagatcgca tcgagttttt taaactaaac aaaggcgaag atgccatgaa agtttattat    180
agtctagcag atagcggaac gattgagaga tacttggaag tctgtggatt tttagagtac    240
atcaacgaat aa                                                        252

<210> SEQ ID NO 229
<211> LENGTH: 282
<212> TYPE: DNA
<213> ORGANISM: Bacteriophage D

<400> SEQUENCE: 229
atgataacta agaacaatt aaaagaatac tacagcgaac acttggaaga gctcgtcgaa       60
```

```
tgggcagacg atataaataa aatatgccta tttgcctacc tagatgaaga tgataacttg    120
tattgtggga ttaatcaact gtcctacaca caattcagag ttccaattca agctgaggtg    180
acagtggatg atgattggaa ctacgatttc ttcaaaaatc cagctgccta tgatggatgg    240
gatgaaactt tggaagaaat gttggaagaa ttaaatgatt aa                      282

<210> SEQ ID NO 230
<211> LENGTH: 282
<212> TYPE: DNA
<213> ORGANISM: Bacteriophage D

<400> SEQUENCE: 230
atgataacta agaacaatt aaaagaatac tacagcgaac acttggaaga gctcgtcgaa    60
tgggcagacg atataaataa aatatgccta tttgcctacc tagatgaaga tgataacttg    120
tattgtggga ttaatcaact gtcctacaca caattcagag ttccaattca agctgaggtg    180
acagtggatg atgattggaa ctacgatttc ttcaaaaatc cagctgccta tgatggatgg    240
gatgaaactt tggaagaaat gttggaagaa ttaaatgatt aa                      282

<210> SEQ ID NO 231
<211> LENGTH: 282
<212> TYPE: DNA
<213> ORGANISM: Bacteriophage D

<400> SEQUENCE: 231
atgataacta agaacaatt aaaagaatac tacagcgaac acttggaaga gctcgtcgaa    60
tgggcagacg atataaataa aatatgccta tttgcctacc tagatgaaga tgataacttg    120
tattgtggga taatcaact gtcctacaca caattcagag ttccaattca agctgaggtg    180
acagtggatg atgattggaa ctacgatttc ttcaaaaatc cagctgccta tgatggatgg    240
gatgaaactt tggaagaaat gttggaagaa ttaaatgatt aa                      282

<210> SEQ ID NO 232
<211> LENGTH: 141
<212> TYPE: DNA
<213> ORGANISM: Bacteriophage D

<400> SEQUENCE: 232
gtgaaaacaa tggatacata taagaacaa ttttattatt tggatcctat ttatattagt    60
gtggatatta ataggaggac ttttatttta ggaaaaagag ggcaatcgct ctcttttttt    120
tattgtaata aaacaattta a                                              141

<210> SEQ ID NO 233
<211> LENGTH: 225
<212> TYPE: DNA
<213> ORGANISM: Bacteriophage O

<400> SEQUENCE: 233
atgacacaaa ttaaagatgg ttggcacatg gtttatgacg aaaaagtgta tgtagagagc    60
gggaaagttg tccgtggaat aactaaagac aataacaatt ctgaaatagc ttgctaccct    120
tacgaataca caaagacta tgattgctgg attaacattt ctgggaaagt aactctatca    180
gcttatagat caggtcgtaa aaaagggaca aaatgtatga agtga                    225

<210> SEQ ID NO 234
<211> LENGTH: 225
<212> TYPE: DNA
<213> ORGANISM: Bacteriophage Sfi
```

<400> SEQUENCE: 234

```
atgacacaaa ttaaagatgg ttggcacata gtttatgacg aaaaagtgta cgtagagagc      60
gggaaagttg tccgtggaat aactaaagac aataacaatt ctgaaatagc ttgctaccct     120
tacgaataca acgaagacta tgattgctgg attaacattt ctgggaaagt aactctatca     180
gcttatagat caggtcgtaa aaaagggaca aaatgtatga agtga                     225
```

<210> SEQ ID NO 235
<211> LENGTH: 153
<212> TYPE: DNA
<213> ORGANISM: Bacteriophage D

<400> SEQUENCE: 235

```
ttgtttgaat gcttggcatc gtttcggtta aattctcgaa ctgtaacctc gacttttgt      60 cggggttttc tttttttaca aaaaaatcta aattcctttta tcaaaagtgt tgacaaacta    120
tcatatatga tatataatgt atacataaga taa                                  153
```

<210> SEQ ID NO 236
<211> LENGTH: 192
<212> TYPE: DNA
<213> ORGANISM: Bacteriophage D

<400> SEQUENCE: 236

```
atgaatgaaa gtgaattgct tgagcagttc tgcgtttctc tttgtgaatt tagctctaga     60
cagtggccac gagatgggtt tttagaccct attaaccgtg tggtctacat caatagggat    120
ttaccaaccg aaagacgttt aaaggtccta ctgcacgaat tagggcactt agaacacgac    180
cctaaacact aa                                                        192
```

<210> SEQ ID NO 237
<211> LENGTH: 150
<212> TYPE: DNA
<213> ORGANISM: Bacteriophage D

<400> SEQUENCE: 237

```
ttgttggggg ctaagaccac cctttttgat ataatatacc tatatcaatg gcttcccacg     60
catacgcgca gatacgttct gagggaagtt ttttatttgc tttgttttga tagaaatgct    120
actatattaa tggatacagt taaaagctga                                     150
```

<210> SEQ ID NO 238
<211> LENGTH: 150
<212> TYPE: DNA
<213> ORGANISM: Bacteriophage D

<400> SEQUENCE: 238

```
ttgttggggg ttaagaccac cctttttgat ataatatacc tatatcaatg gcttcccacg     60
catacgcgca gatacgttct gagggaagtt ttttatttgc tttgttttga tagaaatgct    120
actatattaa tggatacagt taaaagctga                                     150
```

<210> SEQ ID NO 239
<211> LENGTH: 138
<212> TYPE: DNA
<213> ORGANISM: Bacteriophage

<400> SEQUENCE: 239

```
atgaggaggt gtcttttttt tggtttgctc aaaaaacgca acaatggtat aataattttt     60
```

```
gcaacgacaa accccctgca accacatgga cagatacgct ctgacgcagg gctttttta    120 tttgctttat ttttataa                                                 138

<210> SEQ ID NO 240
<211> LENGTH: 423
<212> TYPE: DNA
<213> ORGANISM: Bacteriophage

<400> SEQUENCE: 240
atgaaaatca atacgacaag agttaaaatg gtcttgaaga atgaggctat acctgctgat    60
tatttagaga gcgagattgg cattagtcgt tccgttgttg aaaaagtgag agaagatgag   120
agcgaattta aaaatttaac tcttgatttt gttgcgaaaa ttcaaaagtg gattgatgat   180
ggaaactaca ctttcagcta tgattacagc gacttgatag aagagttgga agaagatatt   240
gcagaaggtc taacggatga gtatatctat gttgtcagag gacaatacaa cgaaatttta   300
gagaaatgcc caataattga ctactactac acttctgaag agattgaaga aggagatctc   360
gcagagaaga ccctaacagc ttctgccttg tctgaaatga aacaggacaa cgaaatcttt   420
taa                                                                 423

<210> SEQ ID NO 241
<211> LENGTH: 423
<212> TYPE: DNA
<213> ORGANISM: Bacteriophage D

<400> SEQUENCE: 241
atgaaaatca atacgacaag agttaaaatg gtcttgaaga ataaggttat acctgctatt    60
tatttagaga atgagcttgg tatcagtcgt tctgttattg aaaaagtgag agatggcgag   120
cgaaaaatag agaatctaac gctcgaaaca attattaaag tccagaaatg gatagattcg   180
ggcaaatata ccttctctta tgattattcc gacttgatag aagagttgga agaagatatt   240
gcagaaggct tggtagatga gtatatctac gtagtcagag gtccgtataa tgaacttta   300 gataaatgcc caataattga ctactactac acttctgaag agattgaaga aggagatctc   360
gcagagaaga ccctaacagc ttctgtcttg gctgaaatga aaaggacaa cgaaatcttt   420 taa                                                                 423

<210> SEQ ID NO 242
<211> LENGTH: 423
<212> TYPE: DNA
<213> ORGANISM: Bacteriophage D

<400> SEQUENCE: 242
atgaaaatca atacgacaag aattaaaatg gtcttgaaga atgaggctat acctgctatt    60
tatttagaaa atgagcttgg tatcagtcgt tctgttattg aaaaagtgag agaagacgag   120
agcgaattta aaaatctaac tcttgatgtt gttgcgaaaa ttcaaaagtg gattgatgat   180
ggcaattaca cgtttagtta tgattacagt gaatttatcg aggaattaga agaagatctc   240
gctgagggtt aatagatga ttacctattc gttgttcgtg gagattatga cgaagcctta   300
ggaaaatgtc ccatcattga ctattactac acttccgaag aaattgaaga aggagatctc   360
gcagagaaga ccctaacagc ttctgtcttg gctgaaatga aaaggacaa cggaatcttt   420 taa                                                                 423

<210> SEQ ID NO 243
<211> LENGTH: 423
```

```
<212> TYPE: DNA
<213> ORGANISM: Bacteriophage D

<400> SEQUENCE: 243
atgaaaatca atacaacaag agtcaacatg gtcttgaaga acgaggctat acctgctgat      60
tatttagaga acgtgattgg tatcagtcgt tccgttattg aaagagtgag agaagatgag     120
agcggattta aaaatttaac tcttgatgtt attgcgaaaa ttcaaaagtg gatagatgaa     180
ggaaactaca cgtttagtta tgattacagc gacttgatag aagagttgga agaagatatt     240
gcagaaggct tggtagatga gtatatctac gtagtcagag gtccttataa tgagatttta     300
gagaaatgcc caatcattga ctactactac acttctgaag aaattgaaga aggagatctc     360
gcagagaaga ccctgacagc ctctgcctta gctgaaatga agttagacaa caaaatcttt     420
taa                                                                   423

<210> SEQ ID NO 244
<211> LENGTH: 423
<212> TYPE: DNA
<213> ORGANISM: Bacteriophage D

<400> SEQUENCE: 244
atgaaaatca atacgacaag agttaacatg gtcttgaaga acaaagctat accagctaat      60
tatttagaaa aggaactggg aataaaccgt tcgacaatta caagagtgcg gaacggtgag     120
agaaagcttg agaatctaac gctcgaaaca atcataaaag tccagaaatg gatagattcg     180
ggcaaatata cattctctta tgattattcc gacttgatag aagagttgga agaagatatt     240
gaagaaggcc taacagatga gtatatctat gttgtcagag gtccgtataa tgaacttta     300
gagaaatgcc caataattga ctactactac acttctgaag agattgaaga aggagatctc     360
acagagaaga ccctaacagc ttctgccttg gctgagatga acaggataa cgaaatcttt     420
taa                                                                   423

<210> SEQ ID NO 245
<211> LENGTH: 423
<212> TYPE: DNA
<213> ORGANISM: Bacteriophage O

<400> SEQUENCE: 245
atgataataa acactgcacg agttgaatta gttttaatga acaaagctat accagcaaat      60
tatttagaaa gcgaaatagg tattagtcgt tcagcaatta ctagggtaag aaatgatgag     120
cgaaaaatag agaatctgaa gctcgaaaca atcataaaag tccagaaatg gatagattcg     180
ggcaaataca cattctctta tgattattcc gacttgatag aagagttgga agaagatatt     240
gcaaaaggtc tggcaggtaa gtatatctac gttgtcagag gaccatacaa cgagatttta     300
gagaaatgtc caatcattga ctattactac acttccgaag agattgaaga aggagagctc     360
gcagagaaga ccttgacagc ttctgtcttg gctgaaatga agtcagacaa cgaaatcttt     420
taa                                                                   423

<210> SEQ ID NO 246
<211> LENGTH: 396
<212> TYPE: DNA
<213> ORGANISM: Bacteriophage Proph

<400> SEQUENCE: 246
atggtcttga agaacgaggc tatacctgct gattatttag agagcgagat tggcattagt      60
```

```
cgttccgttg ttgaaaaagt gagagaagat gagagcgaat ttaaaaattt aactcttgat      120
gttgttgcga aaattcaaaa gtggattgat gatggaaact acactttcag ctatgattac      180
agcgacctaa tcgaagaact ggaggaagat attgcagaag gcttggtaga tgagtatatc      240
tacgtagtca gaggtccgta taatgaactt ttagagaaat gcccaatcat tgactactac      300
tatacttctg aagaaattga agaaggggat cttgcagaga agaccttgat aacttctgtc      360
ttagctgaaa tgaagtcaga acaacaaaatc ttttaa                              396
```

<210> SEQ ID NO 247
<211> LENGTH: 423
<212> TYPE: DNA
<213> ORGANISM: Bacteriophage Sfi

<400> SEQUENCE: 247

```
atgataataa atgttgcacg agttgaaaca gttttaatga acaatgctat accagctaat       60
tatttagaaa gagaaatagg aattagtcgt tcagcaatta ctagggtaag aaacggtgag      120
cgaaaaatag agaatctgaa gctcgaaaca atcataaaag tccagaaatg gatagattcg      180
ggcaaatata cattctctta tgattattcc gacttgatag aagagttgga agaagatatt      240
gcagaaggac taacggatga gtatatctac gttgtcagag gagcatacaa cgagattta      300 gagaaatgcc aatcattga ctattactac acttccgaag agattgaaga aggagatctc      360
gcagagaaga ccctaacagc ttctgccttg tctgaaatga acaggacaa cgaaatcttt      420 taa                                                                   423
```

<210> SEQ ID NO 248
<211> LENGTH: 423
<212> TYPE: DNA
<213> ORGANISM: Bacteriophage TPL

<400> SEQUENCE: 248

```
atgataataa acactgcacg agttgaatta gttttaatga acaaagctat accagcaaat       60
tatttagaaa gagagatagg aattagtcgt tcagcaatta caagagttcg aacggtgag       120 agaaagcttg agaacctaac ccttgaaact attatgacta ttcaaaagtg gatagatgaa      180
ggaaactatc gctttagtta cgattatagt gagcttatcg aagaccttga ggaagatatt      240
gcagaaggcc taacagatga gtatatctat gttgtcagag gtccgtataa tgaactttta      300
gagaaatgtc caatcattga ctattactac acttccgaag agattgaaga aggaaatctc      360
gcagagaaga ccttgacagc ttctgtcttg gctgaaatga acaggacaa cgaaatatttt     420 taa                                                                   423
```

<210> SEQ ID NO 249
<211> LENGTH: 423
<212> TYPE: DNA
<213> ORGANISM: Bacteriophage TPJ

<400> SEQUENCE: 249

```
atgaaaatca atacgacaag aattaaaatg gtcttgaaga tgaggctat acctgctatt       60 tatttagaaa atgagcttgg tatcagtcgt tctattattg aaaaagtgag agatgatgag      120
agcgaattta aaatctaac tcttgaaact attataaaaa tacaaagttt gataaattcg      180
ggcaaatata cattctctta tgattattcc gacttgatag aagagttgga agaagatatt      240
gcagaaggac taacggatga gtatatctac gttgtcagag gaccatacaa cgagatttta      300
gagaaatgtc caatcattga ctattactac acttccgaag agattgaaga aggaaatctc      360
```

```
gcagagaaga ccttgacagc ttctgtcttg gctgaaatga acaggacaa cgaaatattt    420 taa                                                                 423

<210> SEQ ID NO 250
<211> LENGTH: 423
<212> TYPE: DNA
<213> ORGANISM: Bacteriophage Proph

<400> SEQUENCE: 250
atgaaaatca atacgacaag agttaaaatg gtcttgaaga atgaggttat acctgctatt    60
tatttagaga atgagcttgg tatcagtcgt tctgttattg aaaaagtgag agatggcgag    120
cgaaaaatag agaatctaac tcttgaaacg attataaaaa ttcaaaagtg gatcgatgat    180
ggaaactaca ctttcagcta cgactatagc gacctaatcg aagaactgga ggaagatatt    240
gcagaaggct tggtagatga gtatatctac gtagtcagag gtccgtataa tgaactttta    300
gagaaatgcc caatcattga ctactactat acttctgaag aaattgaaga gggggatctt    360
gcagagaaga ccttgataac ttctgtctta gctgaaatga agtcagacaa caaaatcttt    420
taa                                                                 423

<210> SEQ ID NO 251
<211> LENGTH: 183
<212> TYPE: DNA
<213> ORGANISM: Bacteriophage D

<400> SEQUENCE: 251
atggaccaag ttaaattagt tttaatgaac aaagctatac cagctaatta tttagaaaga    60
caaactggtg ttagtcgttc agcaattact agggttagaa atggcgagcg aaaaatagaa    120
aatctaacac ttgaaacaat tattaaaatt caaagttgga tagactctga aatacgata     180 tag                                                                 183

<210> SEQ ID NO 252
<211> LENGTH: 195
<212> TYPE: DNA
<213> ORGANISM: Bacteriophage D

<400> SEQUENCE: 252
atgataatta atgtggaccg agttaaagcg gttttaatgg ataaatctat accggcaaat    60
tatttagaaa tgcaaactgg cattagtcgt tcggcaatta ccagagtaag gaacggcgag    120
cgaaagatag aaaatctaac tatcggaaca attattaaaa ttcaaagttg gttggataga    180
aggatgatta gataa                                                    195

<210> SEQ ID NO 253
<211> LENGTH: 183
<212> TYPE: DNA
<213> ORGANISM: Bacteriophage D

<400> SEQUENCE: 253
atggaccgag ttaaattagt tttaatgaac aaagctatac cagcaaattt tttagaaaga    60
caaactggag ttagtcgttc agcaattact agggttagaa ataacgagcg aaaaatagaa    120
aatctaacac ttgaaacaat tattaaaatt caaagttgga tagattctga caatacgata    180
tag                                                                 183

<210> SEQ ID NO 254
```

```
<211> LENGTH: 228
<212> TYPE: DNA
<213> ORGANISM: Bacteriophage D

<400> SEQUENCE: 254
ttgggaagaa ggataaggat aaagataaag ataatgataa taaatatgga ccaagttaaa      60
ttagttttaa tgaacaaaga tataccagct aattttatag aaagacaaac tggtgttagt     120
cgttcagcaa ttactaaggt tagaaatggt gagcgaaaaa tagaaaatct aagacttgaa     180
acaattatta aaattcaaag ttggatagac tctgggaata cgatatag                  228

<210> SEQ ID NO 255
<211> LENGTH: 216
<212> TYPE: DNA
<213> ORGANISM: Bacteriophage D

<400> SEQUENCE: 255
ttgggaagta ggataaggat aatgataatt aatgtggacc gagttaaagc ggttttaatg      60
gataaatcta taccggcaaa ttatttagaa atgcaaactg gcattagtcg ttcggcaatt     120
accagagtaa ggaacggcga gcgaaagata gaaaatctaa ctatcggaac aattattaaa     180
attcaaagtt ggttggatag aaggatgatt agataa                               216

<210> SEQ ID NO 256
<211> LENGTH: 195
<212> TYPE: DNA
<213> ORGANISM: Bacteriophage D

<400> SEQUENCE: 256
atgataataa atatggaccg agttaaatta gttttaatga caaagatat accagctaat       60 tttttagaaa gacaaactgg tgttagtcgt tcagcaatta ctaaggttag aaatggtgag     120
cgaaaaatag aaaatctaac acttgaaaca attattaaaa ttcaaagttg gttagactct     180
gagaatacga tatag                                                      195

<210> SEQ ID NO 257
<211> LENGTH: 195
<212> TYPE: DNA
<213> ORGANISM: Bacteriophage D

<400> SEQUENCE: 257
atgataataa acactgcacg agttgaatta gttttaatga caaagctat accagctaat       60 tttttagaaa gacaaactgg tgttagtcgt tcagcaatta ctagggttag agatggtgag     120
cgaaagatag aaaatctaac acttgaaaca attattaaaa ttcaaagttg gatagactct     180
gacaataaga tatag                                                      195

<210> SEQ ID NO 258
<211> LENGTH: 216
<212> TYPE: DNA
<213> ORGANISM: Bacteriophage D

<400> SEQUENCE: 258
atgacaaaaa ggataaagac aatgataata aatatggacc gagttaaatt agttttaatg      60
aaaaaagata taccagctaa ttttttagaa agacaaactg gtgttagtcg ttcagcaatt     120
actagggtta gaaatggtga gcgaaaaata gaaaatctaa cacttgaaac aattattaaa     180
attcaaagtt ggatagactc tgagaatacg atatag                               216
```

```
<210> SEQ ID NO 259
<211> LENGTH: 195
<212> TYPE: DNA
<213> ORGANISM: Bacteriophage D

<400> SEQUENCE: 259
atgataataa acactgcacg agttgaatta gttttaatga acaaagctat accagcaaat      60
tatttagaaa gacaaactgg tgttagtcgt tcagcaatta ctagggtgag gaatggtgag     120
cgaaagatag aaaatctaac acttgaaaca attattaaaa ttcaaagttg gatagactct     180
gacaataaga tatag                                                      195

<210> SEQ ID NO 260
<211> LENGTH: 195
<212> TYPE: DNA
<213> ORGANISM: Bacteriophage P

<400> SEQUENCE: 260
atgataatta atgtggaccg agttaaagcg gttttaatgg ataaatctat atcagcaaat      60
tatttagaaa tagaaactgg cattagtcgt tcggcaatta ccagagtaag gaacggcgag     120
cgaaagatag aaaatctaac tatcggaaca attattaaaa ttcaaagttg gttggataga     180
aggatgatta gataa                                                      195

<210> SEQ ID NO 261
<211> LENGTH: 513
<212> TYPE: DNA
<213> ORGANISM: Bacteriophage D

<400> SEQUENCE: 261
atggtagtaa aaattaaaag aattgtttgg gttaaaaata tggttttga aatcagagaa       60 cgtgagctag attgttactt taaaaatgat ggaagttaca aaaagagttc tggagattgg     120
gaaagtcgtt gttatgaaca attcggagat gaatttcaac tcattagaga tagcaaagca     180
ttagaatctt atagtggttt gacaagagat tatcaaaaag acttaaaaat cttgcgtaag     240
tataaacata gagatatgac tatttcagag tatgaagcaa tgaaatatgt cgtggagaat     300
tggacaaaag aatggtctca gtcaccttac agttatagtt tttatagttc aaaaaacatt     360
gactggggtt acaaaccaga aggcagctta cgcatttctg accattggaa ttttggcgaa     420
aatggtgaac attgcccaac agctgaacca gttgatggct gggcagtatg taagtttgaa     480
aatggtaaat atcatttaat taaaaagttt taa                                  513

<210> SEQ ID NO 262
<211> LENGTH: 513
<212> TYPE: DNA
<213> ORGANISM: Bacteriophage D

<400> SEQUENCE: 262
atggtagtaa aaattaaaag aattgtttgg gttaaaaata tggttttga aatcagagaa       60 cgtgagctag attgttactt taaaaatgat ggaagttaca aaaaagagttc tggagattgg    120 gaaagtcgtt gttatgaaca attcggagat gaatttcaac tcattagaga tagcaaagca     180
ttagaatctt atagtggttt gacaagagat tatcaaaaag acttaaaaat cttgcgtaag     240
tataaacata gagatatgac tatttcagag tatgaagcaa tgaaatatgt cgtggagaat     300
tggacaaaag agtggtcaca atcaccatac agcaatagtt tctatagctc taaagatatt     360
gattggggct acaaaccaga aggtagctta agagtctcag accattggaa ttttggcgaa     420
```

```
aatggtgaac attgcccaac agctgaacca gttgatggct gggcagtatg taagtttgaa        480
aatggtaaat atcatttaat taaaaagttt taa                                     513

<210> SEQ ID NO 263
<211> LENGTH: 474
<212> TYPE: DNA
<213> ORGANISM: Bacteriophage D

<400> SEQUENCE: 263
atggtagtaa aaattaaaag aattgtttgg gttaaaaata atggttttga aatcagagaa         60
cgtgagctag attgttactt taaaaatgat ggaagttaca aaaagagttc tggagattgg        120
gaaagtcgtt gttatgaaca attcggtaat aaacttcaac ttattaaaga cagtaaaaaa        180
ttagaatcgt acaacggatt aacaaaagat tatcaaaaag atttaaaaat cttacgtaaa        240
tgtggacgtt cggaaatgaa tgcaacagag tacgaagcaa tgaaatatgt tgaagaaaac        300
tggacaaaag agtggtcaca atcaccatac agcaatagtt tctatagctc taaagatatt        360
gattggggct acaaaccaga aggtagctta agagtctcag accattggaa ttttggcgaa        420
aatggtgaac attgcccaac agctgaacca gttgatggct gggcagtatt ttga             474

<210> SEQ ID NO 264
<211> LENGTH: 513
<212> TYPE: DNA
<213> ORGANISM: Bacteriophage D

<400> SEQUENCE: 264
atggtagtaa aaattaaaag aattgtttgg gttaaaaata atggttttga aatcagagaa         60
cgtgagctag attgttactt taaaaatgat ggaagttaca aaaaagttc tggagattgg        120 gaaagtcgtt gttatgaaca attcggagat gaatttcagc tcattagaga tagcaaagca        180
ttagaatctt atagtggttt gacaagagat tatcaaaaag acttaaaaat cttgcgtaag        240
tataaacata gagatatgac tatttcagag tatgaagcaa tgaaatatgt cgtggagaat        300
tggacaaaag agtggtcaca atcaccatac agcaatagtt tctatagctc taaagatatt        360
gattggggct acaaaccaga aggtagctta agagtctcag accattggaa ttttggcgaa        420
aatggtgaac attgcccaac agctgaacca gttgatggct gggcagtatg taagtttgaa        480
aatggtaaat atcatttaat taaaaagttt taa                                     513

<210> SEQ ID NO 265
<211> LENGTH: 513
<212> TYPE: DNA
<213> ORGANISM: Bacteriophage D

<400> SEQUENCE: 265
atggtagtaa aaattaaaag aattgtttgg gttaaaaata atggttttga aatcagagaa         60
cgtgagctag attgttactt taaaaatgat ggaagttaca aaaaagttc tggagattgg         120 gaaagtcgtt gttatgaaca attcggagat gaatttcaac tcattagaga taacaaagca        180
ttagaatctt atagtggttt gacaagagat tatcaaaaag acttaaaaat cttgcgtaag        240
tataaacata gagatatgac tatttcagag tatgaagcaa tgaaatatgt cgtggagaat        300
tggacaaaag agtggtcaca atcaccatac agcaatagtt tctatagctc taaagatatt        360
gattggggct acaaaccaga aggtagctta agagtctcag accattggaa ttttggcgaa        420
aatggtgaac attgcccaac agctgaacca gttgatggct gggcagtatg taagtttgaa        480
aatggtaaat atcatttaat taaaaagttt taa                                     513
```

<210> SEQ ID NO 266
<211> LENGTH: 513
<212> TYPE: DNA
<213> ORGANISM: Bacteriophage D

<400> SEQUENCE: 266

| | | | | | |
|---|---|---|---|---|---|
| atggtagtaa | aaattaaaag | aattgtttgg | gttaaaaata | atggttttga | aatcagagaa | 60 |
| cgtgagctag | attgttactt | taaaaatgat | ggaagttaca | aaaaaagttc | tggagattgg | 120 |
| gaaagtcgtt | gttatgaaca | attcggagat | gaatttcaac | tcattagaga | taacaaagca | 180 |
| ttagaatctt | atagtggttt | gacaagagat | tatcaaaaag | acttaaaaat | cttgcgtaag | 240 |
| tataaacata | gagatatgac | tatttcagag | tatgaagcaa | tgaaatatgt | cgtggagaat | 300 |
| tggacaaaag | agtggtcaca | atcaccatac | agcaatagtt | tttatagctc | taagatatt | 360 |
| gattggggct | acaaaccaga | aggtagctta | agagtctcag | accattggaa | ttttggcgaa | 420 |
| aatggtgaac | attgcccaac | agctgaacca | gttgatggct | gggcagtatg | taagtttgaa | 480 |
| aatggtaaat | atcatttaat | taaaaagttt | taa | | | 513 |

<210> SEQ ID NO 267
<211> LENGTH: 225
<212> TYPE: DNA
<213> ORGANISM: Bacteriophage D

<400> SEQUENCE: 267

| | | | | | |
|---|---|---|---|---|---|
| atgattaaaa | cggaaatgat | tgacgatatt | ctcactttga | ttgaagaaat | tgaagctgtt | 60 |
| agcgataaga | ataaagaaaa | gtttattgaa | aaatttgacg | agttagaaac | caatttacaa | 120 |
| gcattgaata | aacaaaccac | tgatgatttg | gttgaaattt | tacaagaaga | ttattctgat | 180 |
| aattgggtag | caaagaggt | gattgaactt | gttactaaca | gctag | | 225 |

<210> SEQ ID NO 268
<211> LENGTH: 225
<212> TYPE: DNA
<213> ORGANISM: Bacteriophage D

<400> SEQUENCE: 268

| | | | | | |
|---|---|---|---|---|---|
| atgaataaaa | tagaaatgat | tgacgatatt | ctcactttga | ttgaagagat | tgacgccatt | 60 |
| agtgataaga | gtaaagaaac | gttttttgaa | aaaattgatg | agttggaaac | aaatttacaa | 120 |
| gcattgaaca | gacaaatcac | tgatgaattg | gttgaaattt | tacaagaaga | ttattctgat | 180 |
| aattgggtag | caaagaggt | gattgaactt | gttactaaca | gctag | | 225 |

<210> SEQ ID NO 269
<211> LENGTH: 225
<212> TYPE: DNA
<213> ORGANISM: Bacteriophage D

<400> SEQUENCE: 269

| | | | | | |
|---|---|---|---|---|---|
| atgattaaaa | cggaaatgat | tgacgatatt | ctcactttga | ttgaagaaat | tgaagctgtt | 60 |
| agcgataaga | ataaagaaaa | gtttattgaa | aaatttgacg | agttagaaac | caatttacaa | 120 |
| gcattgaata | aacaaaccac | tgatgatttg | gttgaaattt | tacaagaaga | ttattctgat | 180 |
| aattgggtag | caaagaggt | gattgaactt | gtcgatgact | actag | | 225 |

<210> SEQ ID NO 270
<211> LENGTH: 225
<212> TYPE: DNA

<213> ORGANISM: Bacteriophage D

<400> SEQUENCE: 270

| atgattaaaa cggaaatgat tgacgatatt ctcactttga ttgaagaaat tgaagctgtt | 60 |
| agcgataaga ataaagaaaa gtttattgaa aaatttgatg agttagaaac caatttacaa | 120 |
| gcattgaata acaaaccac tgatgatttg gttgaaattt acaagaaga ttattctgat | 180 |
| aattgggtag caaaagaggt gattgaactt gtcgatgact actag | 225 |

<210> SEQ ID NO 271
<211> LENGTH: 513
<212> TYPE: DNA
<213> ORGANISM: Bacteriophage D

<400> SEQUENCE: 271

| atgagttata caagcccagt ttataacatt aaacgagtac ccattgacaa aatccaagca | 60 |
| aacagttata atccaaatca tgtagcacct cccgaaatga aattgcttta taagtctatt | 120 |
| ttagaggacg gatacactat gccaatcgtt tgttattatc ttaaagacga ggataaatac | 180 |
| gagattgtag acggttttca ccgttacagc actatgctta accacaaaga tatttatgaa | 240 |
| cgtgagggtg gttgtttgcc agtatccgtt attgataagc caattagcga ccgcatggcg | 300 |
| tcaactatcc gacacaatcg agcgagaggg tcacatgata tcgacctaat gacaaacatt | 360 |
| gtcgctgacc ttgtagacag tggtatgtct gacgcttgga ttttaaaaaa tatcggaatg | 420 |
| gacgcagacg aattgttgcg tttgaaacaa ttaactggtt tagcgagttt gtttgcagac | 480 |
| aaagaattca gtaaatcatg ggatgtagaa taa | 513 |

<210> SEQ ID NO 272
<211> LENGTH: 513
<212> TYPE: DNA
<213> ORGANISM: Bacteriophage D

<400> SEQUENCE: 272

| atgagttata caagcccagt ttataacatt aaacgagtac ccattgacaa aatccaagca | 60 |
| aacagttata atccaaatca tgtagcacct cccgaaatga aattgcttta taagtctatt | 120 |
| ttagaggacg gatacactat gccaatcgtt tgttattatc ttaaagacga ggataaatac | 180 |
| gagattgtag acggttttca ccgttacagc actatgctta accacaaaga tatttatgaa | 240 |
| cgtgagggtg gttgtttgcc agtatccgtt attgataagc caattagcga ccgcatggcg | 300 |
| tcaactatcc gacacaatcg agcgagaggg tcacatgata tcgacctaat gacaaacatt | 360 |
| gtcgctgacc ttgtagacag tggtatgtct gacgcttgga ttttaaaaaa tatcggaatg | 420 |
| gacgcagacg aattgttgcg tttgaaacaa ttaactggct tgtcgagttt gtttgcagac | 480 |
| aaagaattca gtaaatcatg ggatgtagaa taa | 513 |

<210> SEQ ID NO 273
<211> LENGTH: 513
<212> TYPE: DNA
<213> ORGANISM: Bacteriophage D

<400> SEQUENCE: 273

| atgagttaca caagtccagt ttataacatt aaacgagtac ccattgacaa aattcaggca | 60 |
| aacagttata atccaaacca tgtagcacct cctgaaatga aactacttta caagtctatt | 120 |
| ttagaggatg gatacacaat gccaatcgtt tgttattatc ttaaagatga agataaatat | 180 |
| gagattgtag atggctttca ccgttatagc actatgctta accacaaaga tatttatgac | 240 |

```
cgtgagggcg gttgtttgcc agtatccgtt attaataagc caatcagtga ccgtatggca      300
tcaactatcc gacataatcg agcgagaggg tcacatgata ttgacctaat gacaaacatt      360
gtcgctgacc ttgtagacag tggtatgtct gacgcttgga ttttaaaaaa tatcggaatg      420
gacgcagacg aattgttgcg tttgaaacaa ttaactggct tggcaagttt gtttgcagac      480
aaagaattca gtaaatcatg ggatgtagaa taa                                   513
```

<210> SEQ ID NO 274
<211> LENGTH: 513
<212> TYPE: DNA
<213> ORGANISM: Bacteriophage D

<400> SEQUENCE: 274

```
atgagttata caagcccagt ttataacatt aaacgagtac ccattgacaa atccaagca       60 aatagttata atccaaatca tgtagcacct cccgaaatga aattgcttta taagtctatt      120
ttagaggacg gatacactat gccaatcgtt tgttattatc ttaaagacga ggataaaatac     180 gagattgtag acggttttca ccgttacagc actatgctta accacaaaga tatttatgaa     240
cgtgagggtg gttgtttgcc agtatccgtt attgataagc caattagcga ccgcatggcg      300
tcaactatcc gacacaatcg agcgagaggg tcacatgata tcgacctaat gacaaacatt      360
gtcgctgacc ttgtagacag tggtatgtct gacgcttgga ttttaaaaaa tatcggaatg      420
gacgcagacg aattgttgcg tttgaaacaa ttaactggct tggcaagttt gtttgcagac      480
aaagaattca gtaaatcatg ggatgtagaa taa                                   513
```

<210> SEQ ID NO 275
<211> LENGTH: 513
<212> TYPE: DNA
<213> ORGANISM: Bacteriophage D

<400> SEQUENCE: 275

```
atgagttaca caagtccagt ttataacatt aaacgagtac ctattgataa aattcaggca      60
aacagttata atccaaacca tgtagcacct cctgaaatga aactactttta caagtctatt     120 ttagaggatg ggtacacaat gccaatcgtt tgttattatc ttaaagatga agataaatat      180
gagattgtag atggctttca tcgctatagc actatgctta accacaaaga tatttatgac     240
cgtgagggcg gttgtttgcc agtatccgtt attaataaac cgattagtga ccgcatggcg      300
tcaactatcc gacacaaccg ggcgagaggg tcacatgata ttgacctaat gacaaacatt      360
gttgctgacc ttgtagatag tggcatgtct gacgcttgga ttttgaaaaa tatcggaatg      420
gacgcagacg aattgttgcg gttgaaacag ttaactggtt tagctagtct atttgcagac      480
aaagaattca gtaaatcgtg gatcgtagaa taa                                   513
```

<210> SEQ ID NO 276
<211> LENGTH: 513
<212> TYPE: DNA
<213> ORGANISM: Bacteriophage D

<400> SEQUENCE: 276

```
atgagttaca caagtccagt ttataacatt aaacgagtac ccattgacaa atccaagca       60 aacagttata atccaaatca tgtagcacct cccgaaatga aattgcttta taagtctatt      120
ttagaggacg gatacactat gccaatcgtt tgttattatc ttaaagacga ggataaaatac     180 gagattgtag acggttttca ccgttacagc actatgctta accacaaaga tatttatgaa     240
```

```
cgtgagggtg gttgtttgcc agtatccgtt attgataagc caattagcga ccgcatggcg      300
tcaactatcc gacacaatcg agcgagaggg tcacatgata tcgacctaat gacaaacatt      360
gtcgccgacc ttgtagacag tggtatgtct gacgcttgga ttttaaaaaa tatcggaatg      420
gacgcagacg aattgttgcg tttgaaacaa ttaactggct tggcaagttt gtttgcagac      480
aaagaattca gtaaatcatg ggatgtagaa taa                                   513

<210> SEQ ID NO 277
<211> LENGTH: 180
<212> TYPE: DNA
<213> ORGANISM: Bacteriophage D

<400> SEQUENCE: 277
atgcctaaag tttccgagag caaacggaaa gcaaatgaca aatgggacaa aaagaacaaa      60
gaacgcaagc agtatatcaa cagacgttct gtcgcaagga actttattaa gaatatggaa      120
ggcgaagata ttccagaatt taaaaaacta atagaagaaa gagcttccaa aatcaaataa      180

<210> SEQ ID NO 278
<211> LENGTH: 180
<212> TYPE: DNA
<213> ORGANISM: Bacteriophage D

<400> SEQUENCE: 278
atgcctaaag tttccgagag caaacggaaa gcaaatgaca aatgggacaa aaagaacaaa      60
gaacgcaagc agtatattaa cagacgttct gtcgcaagga actttattaa gaatatggaa      120
gacgaagata ttccagaatt taaaaaacta atggaagaaa gagcttccaa aatcaaataa      180

<210> SEQ ID NO 279
<211> LENGTH: 180
<212> TYPE: DNA
<213> ORGANISM: Bacteriophage D

<400> SEQUENCE: 279
atgcctaaag tttccgagag caaacggaaa gcaaatgaca aatgggacaa aaagaacaaa      60
gaacgcaagc agtatattaa cagacgttct gtcgcaagga actttattaa gaatatggaa      120
gacgaagata ttccagaatt taaaaaacta atggaagaaa gaacttccaa aatcaaataa      180

<210> SEQ ID NO 280
<211> LENGTH: 198
<212> TYPE: DNA
<213> ORGANISM: Bacteriophage D

<400> SEQUENCE: 280
atgcctaaag tctcagaaag caaacggaga gcgaataata aatgggataa aaaaaataaa      60
gaacgtaaac aatatataaa caaacgttcc gttgcaagaa actttattaa gaacatggaa      120
gatgaagatg ttccggaatt taaaaaacta atggaagaaa gagcttccaa aacaaataaa      180
acgtgtttta gttcatga                                                    198

<210> SEQ ID NO 281
<211> LENGTH: 180
<212> TYPE: DNA
<213> ORGANISM: Bacteriophage D

<400> SEQUENCE: 281
atgcctaaag tttccgagag caaacggaaa gcaaacgaca aatgggataa aaataacaaa      60
gaacgcaagc agtatattaa cagacgttct gtcgcaagga actttattaa gaatatggaa      120
```

```
gacgaagata ttccagaatt taaaaaacta atggaagaaa gaacttccaa atcaaataa      180
```

<210> SEQ ID NO 282
<211> LENGTH: 246
<212> TYPE: DNA
<213> ORGANISM: Bacteriophage D

<400> SEQUENCE: 282

```
atgaagttaa ctaatcaaca gaatcaagcc tttaagaaat tcaaaaattt gagagttgga       60
gctctattta tggagcaagg aacaggtaag acaagagtag cactagagtt aatcagaaaa      120
acagatgctg atttagcctt gttcttttgt ccgttttcaa ccaaaaacaa tcttttatct      180
gagattgaaa aatggggaat tgatattgaa tttatggtgt atggatatga aacgatttca      240
tcatag                                                                246
```

<210> SEQ ID NO 283
<211> LENGTH: 177
<212> TYPE: DNA
<213> ORGANISM: Bacteriophage D

<400> SEQUENCE: 283

```
gtggaaacag aaccaaattt tcaaataata tgttataata aaagtacctc gtttgaggta       60 ttttttatc ttacaactgc acccgaattt tttcaggtgt ttttttttcg cccaaaaatc      120
acccgaaaac tttgggaaaa gctagaaaaa ataaaaataa acgaggtaaa aacatag        177
```

<210> SEQ ID NO 284
<211> LENGTH: 204
<212> TYPE: DNA
<213> ORGANISM: Bacteriophage D

<400> SEQUENCE: 284

```
gtggaaacag aaccaaattt tcaaataata tgttataata aaagtacctc gtttgaggta       60 tttttttatct tacaactgca cccgaatttt ttcaggtgtt tttttgccc aaaaatcacc      120 caaaaacttt gggaaaagct agaaaaaata aaaataaac gaggtaaaaa catagtatgt      180
tttactaatt ttcaagctga ttaa                                            204
```

<210> SEQ ID NO 285
<211> LENGTH: 159
<212> TYPE: DNA
<213> ORGANISM: Bacteriophage D

<400> SEQUENCE: 285

```
atgggtttta cggttacatg ttgcaataac ctgcggtcac tgagtaacca taaccactac       60
tgctgctttc ttcgcctcgt tttcgtccca actaaaattg aaatcatacc aataatctgg      120
tttatcttta gggtgtctca cggatttcaa acggtgtga                            159
```

<210> SEQ ID NO 286
<211> LENGTH: 453
<212> TYPE: DNA
<213> ORGANISM: Bacteriophage D

<400> SEQUENCE: 286

```
ttggaatact tggcatcgtt tcggttaaat tctcgaactg taacctcgac ttttagtcga       60
ggttttcttt tttgcaaaa aaaactaaat tccttaataa ataaaaataa aaactataaa      120
aacttagtac agcttcattt attctcaaat tttatatatt ttcgttcaag aattgttctg      180
```

```
ttgttaaacc taaagcgcga gcgaaatcat cagctttatt cagcgggaac acccgactac    240
ctgaaagata tcttgtttga atcccagct ttatttgcat tgacatggaa ctgttgtcta     300
aatagctttt tattatcgtt gtttctcata tttaatagta taaacattat acaaaagttc   360
ccaaaaataa acaatatgtt cccaaaaata aactttttc atatttttt gattttagtg     420 ttgacaaatg ggaacgtgtt agatatacta taa                                 453

<210> SEQ ID NO 287
<211> LENGTH: 282
<212> TYPE: DNA
<213> ORGANISM: Bacteriophage D

<400> SEQUENCE: 287
atggaagttg aacaaagact agaacaacta agacaagatt ggttgaaaca cccaaattta    60
acagatactt aaaagaata tctaaacgaa tattttacg atgattattc ttattgtgag     120
aaatgtgata ggattgccag cgatagcgat tggttttggt atgaaggcga agactatacg   180 gatttttac acattgattg taataaagaa aaattttacg aagcaacaaa aaaaacctct    240
ggaaggagga gaccagagga aacataaaa ggagaaagtt ag                        282

<210> SEQ ID NO 288
<211> LENGTH: 228
<212> TYPE: DNA
<213> ORGANISM: Bacteriophage D

<400> SEQUENCE: 288
atgaaaacta agacacttgg gcgccgttta agacgtttaa gaaaaatcaa tggagaaaca    60 caaaggaat tgccgaaaa ttttggaaga cattatagaa ccgttcaaaa ttgggagcta    120
gattgttcaa taccagacgt tttcacagca atggcattgg cagaatatta taacatggac   180
gttgaagaat tggtgaatgg agaagatgac tatgacaaag aattttga                228

<210> SEQ ID NO 289
<211> LENGTH: 378
<212> TYPE: DNA
<213> ORGANISM: Bacteriophage D

<400> SEQUENCE: 289
atggagaaga tgactatgac aaagaattt gaaaatttta aaaaaggctg ggataatgtt     60
caacaagtag taaatgaata cagcaaaaaa ctcgttgaaa acagtcaaga aaatgtaacc   120
aaccgagata gtgaagagta tcagcaaatc aaaggtaaag ataacgtaat tagtccaaac   180
cactatgtaa ccgataaggg ttttgaagtg ttgacgtgc aagaagcttt tatccacgaa    240
ttaaaaggaa tggcagctag ttactggtgc aatgttgtga agtatatttt gagatttcaa   300 agaagaatg gagtggaaga cttaaaaaa gctaagtact acttggaaaa attaattgaa     360
aaagaggaag gtaaataa                                                 378

<210> SEQ ID NO 290
<211> LENGTH: 546
<212> TYPE: DNA
<213> ORGANISM: Bacteriophage D

<400> SEQUENCE: 290
atgaataaac aagaagcaat tgaactagta aaaaatactt catacagtgt accaattgat    60
agcccagtga acatcttac agaagataca gttatcaata ttatcaaaca gcttgatgaa   120
ccagagaaag ctacagtgcc agattttgta gcaaaataca ttgaagaaag cagagaattt   180
```

```
gacagaaaat taaatgacgc tttatcttac tcaaacacta ccgtcgcaat ggacgactgg      240
tttgaagaaa acgaagtaga caacacggaa atatttgcta aggcatggct tcacggctat      300
gaagtagaaa aagaaaaact ttacacagtt gaaattccag accctaatgc aagtggttac      360
ggtaagacat ttcttggcag agatgatgat ggaaaagtag tgctatctac ttggactggt      420
tttagttcca ttgaatttgc tgatgattgg aaacaatcag aacgtgcaca gttgacagaa      480
gatgaaatta aaaaggttt tacttgggct tggaatgaag ggtttgccga agaggtgaaa      540
gaatga                                                                546

<210> SEQ ID NO 291
<211> LENGTH: 162
<212> TYPE: DNA
<213> ORGANISM: Bacteriophage D

<400> SEQUENCE: 291
atgaaacgct tgtagtaac aggttacaaa gatggttggt ttgtcttctc atttcctta       60 aacgccataa actcttatta tgctatccaa tatgcaagcg aagatgaatt ggtagaaggt     120
atggagttcg ataagctggt tataaaagag gtgaaagaat ga                        162

<210> SEQ ID NO 292
<211> LENGTH: 147
<212> TYPE: DNA
<213> ORGANISM: Bacteriophage D

<400> SEQUENCE: 292
atgaacataa aagaggtgtt ctgtattgat tgctatgaat ggaaaaagaa agaagactta      60
acagggagca aatttccaa tgatatttta tattgcaaag aatgtggtta cgccttagtt     120
cgtacgtgtg accgtaataa caaatga                                         147

<210> SEQ ID NO 293
<211> LENGTH: 165
<212> TYPE: DNA
<213> ORGANISM: Bacteriophage D

<400> SEQUENCE: 293
atgacaaaca ttgttgctga ccttgtagat agtggcatgt ctgacgcttg gattttgaaa      60 acattggga tggatgctga cgaattgctg cgactaaagc aacttagcgg actggcttcc     120
ttgttcaaag ataaggaatt cactacagct tgggaagtag gataa                     165

<210> SEQ ID NO 294
<211> LENGTH: 273
<212> TYPE: DNA
<213> ORGANISM: Bacteriophage D

<400> SEQUENCE: 294
atggaaactt ataagaata caacaacaa cagaaagaag aacgtgaaag agtaagagcg       60
cttcgtagtg aagtatttc aggcaacgct gaaaagcttg cgacagatat tgtaaggatt     120
tcgagcggag atgtttataa aattatccca cgttttggga ctagatatga aaaaagtcca    180
atcatcaaat tagacccaga agaagtagaa cgccacatca agaagctcg tgaagtcaga    240 gaacttgcga aaattatggc aagcaaagaa tag                                 273

<210> SEQ ID NO 295
<211> LENGTH: 243
<212> TYPE: DNA
```

<213> ORGANISM: Bacteriophage D

<400> SEQUENCE: 295

| | |
|---|---|
| atggcagtag tggtcgaagc ctcagcatta tgctggggct ttttttgtta taatatacct | 60 |
| atatcaatgg cctcccacgc atacgcgcag atacgttctg atgggaggtt ttttttgttg | 120 |
| ccgttaaaac ggacaaaaaa atttaaaaag tttgatttta ttgttgataa tacacgcata | 180 |
| agcgtgtata atgtaattaa agataaggaa agcgaggaaa acaaaaatgg tagtaaaaat | 240 |
| taa | 243 |

<210> SEQ ID NO 296
<211> LENGTH: 471
<212> TYPE: DNA
<213> ORGANISM: Bacteriophage D

<400> SEQUENCE: 296

| | |
|---|---|
| ttgctggggc ttttttttgtg ttataataga ataaaaaaac aaatagatga ggtaagaaaa | 60 |
| acggctattg acctgtatcg tgaactggat atccaatcgt tggagcaaag attggaaaag | 120 |
| aacgaagaaa acactcaacg cttcctccaa caaacagcca aaagcttaaa ccaagacaag | 180 |
| actgaactat ctctccgaac tgaccagtta gggcgtagtg ttgaaaagat tgaaaacaaa | 240 |
| ctagacgaca tgtacgctaa gaacgaacta gacttgaaat tccagatgat ggatcaaaag | 300 |
| attgacgcta aatttgatac cttttggtca cgcatggaaa acatgttctt agcacaaacc | 360 |
| aataggcaac ttgaggaaca agccaagaat agaaagaat tcacatattg gtttatttgc | 420 |
| attcttgtag ctatcgctgt tattgctatt cctgtttggt tcggcaaata a | 471 |

<210> SEQ ID NO 297
<211> LENGTH: 204
<212> TYPE: DNA
<213> ORGANISM: Bacteriophage D

<400> SEQUENCE: 297

| | |
|---|---|
| atgtcatttt ttacgtcaac aaaaacggca acgtcaactt ttttcatagc aagtaataga | 60 |
| atacttgcat catttcgatt aaattctcga actgtacacc cgtctttttt aggtgggttt | 120 |
| tttgttttgc aaaaaaatct aaatttattt atcaaaagca ttgacaaact atcatgtatg | 180 |
| atatataata tacttataag ataa | 204 |

<210> SEQ ID NO 298
<211> LENGTH: 129
<212> TYPE: DNA
<213> ORGANISM: Bacteriophage D

<400> SEQUENCE: 298

| | |
|---|---|
| atgttactaa tagtgacatt cagttatatc ataaattatt tgttgttcga tttgggaagt | 60 |
| agcttaatta aaaaggaga agaaaatgc tactataaag gatttaagac aaagaaggat | 120 |
| gtaatctaa | 129 |

<210> SEQ ID NO 299
<211> LENGTH: 159
<212> TYPE: DNA
<213> ORGANISM: Bacteriophage D

<400> SEQUENCE: 299

| | |
|---|---|
| ttggagtgct tatatttag gaaaaagag ggcgcttgct ctcttttttt tatgtattca | 60 |
| ataaaaagta actttataa attttagagt tattttgtta aaaactcaaa aaaacttgaa | 120 |

```
aaaaaatcaa gaaaactgtt gacattgaat tttgtttaa                            159
```

<210> SEQ ID NO 300
<211> LENGTH: 690
<212> TYPE: DNA
<213> ORGANISM: Bacteriophage D

<400> SEQUENCE: 300

```
ttggatatttt acgtttatac tgatgaatca ggagtatttg ataaagaaca tgaaacaata    60
tatgtttatg gtggagtgat tttttttaact tctgaggaca agagaattc aggtagaaga   120
tatatatatg cggaaaaagc actaagaaaa agccatagta attataggaa aggggaactg   180
aaagcaagta ggcttaaaaa tagacataaa gccagtttgt ttaggtcgct taatagggaa   240
ataaaatttt ctatagtggt gagtattggc agggtgcatg ataggattt ttgtgagaaa    300
aaaagtaagc agcgttactt agattatgtt tacaaagttg gtttgaaaaa ggtgttacaa   360
cgtcttgtag cagattgtaa aatagagact accgaagtag atacgatcag tattttaca    420
gatgagcata gtactgcgac taatggaaaa tatgagttaa gagaggcgct gttaaacgag   480
tttaaatatg gcacgtttaa cccagactgg aatatttttt atcctccctt attcgaaaaa   540
ctatctagtt taactgttga atactgtaat tcagctaaaa agccacatat acgtatggca   600
gatataatag cgaatagagc atattatctt gcaaagaatg atctttttgg agagttggga   660
gagaaaacta tatcaatcca cttcccttag                                     690
```

<210> SEQ ID NO 301
<211> LENGTH: 135
<212> TYPE: DNA
<213> ORGANISM: Bacteriophage D

<400> SEQUENCE: 301

```
ttggagagtt gggagagaaa actatatcaa tccacttccc ttagttttag aaagaggcga    60
ggctgtaagc ctcttttttat tataatggtc aagtatgtgg gattttgctt aattctgttc   120
atgacattag ggtag                                                    135
```

<210> SEQ ID NO 302
<211> LENGTH: 150
<212> TYPE: DNA
<213> ORGANISM: Bacteriophage M

<400> SEQUENCE: 302

```
gtgcacaaaa agggaattca tataaaaaaa gtcggctatt ttagtcgact cttttttta    60
tgtcatgtaa acagcagtat agcgttttct attatgttat cgatgtcgtg tcgtttctct   120
aacttttttca aatgttggaa acttttctga                                   150
```

<210> SEQ ID NO 303
<211> LENGTH: 141
<212> TYPE: DNA
<213> ORGANISM: Bacteriophage M

<400> SEQUENCE: 303

```
ttgttggggg ggctaagacg ccccctttttt gatatatcaa cggcctccca cccgtctttt    60
ttaggtgggt ttttgttttt gcaaaaaatt tttttatcaa agtacggat acatacaaag    120
aatacgcttt taacgttttta a                                            141
```

<210> SEQ ID NO 304

```
<211> LENGTH: 438
<212> TYPE: DNA
<213> ORGANISM: Bacteriophage P

<400> SEQUENCE: 304
atgaacgaaa tagcattatc ggacaatctt gcacagattg aacttgaaat caatcatcat      60
aagcagattg caggtcagtc tatttgggaa atcggcaggc gtttaaatca tgttaaagag     120
cacgatttag cgcatgggca atttatggaa tgggttgaaa aacttggtat aaatcaacca     180
gaagccaatc gtatgatgag agttgctaaa gaactaccaa attcttcaac gttgagtaat     240
ttaggaagca cggctctcta cttaatcgcc actcttccag atgatgaaaa gcaagaacaa     300
attgaaaaga ttgagcaagg tgaatcacca acggtcagag aattgcaaga dataaagcgt     360
cgtctcaaac tcaaagacca agcactggaa gcggtcaagg gtgagttgga acgtgctata     420
cttggtatta aagtttaa                                                   438

<210> SEQ ID NO 305
<211> LENGTH: 438
<212> TYPE: DNA
<213> ORGANISM: Bacteriophage P

<400> SEQUENCE: 305
atgaacgaaa tagcattatc ggacaatctt gcacagattg aacttgaaat caatcatcat      60
aagcagattg caggtcagtc tatttgggaa atcggcaggc gtttaaatca tgttaaagag     120
cacgatttag cgcatgggca atttatggaa tgggttgaaa aacttggtat aaatcaacca     180
gaagccaatc gtatgatgag agttgctaaa gaactaccaa attcttcaac gttgagtaat     240
ttaggaagca cggctctcta cttaatcgcc actcttccag atgatgaaaa gcaagaacaa     300
attgaaaaga ttgagcaagg tgaatcacca acggtcagag aattgcaaga dataaagcgt     360
cgtctcaaac tcaaagacca agaactggaa gcggtcaagg gtgagttgga acgtgctata     420
cttggtatta aagtttaa                                                   438

<210> SEQ ID NO 306
<211> LENGTH: 336
<212> TYPE: DNA
<213> ORGANISM: Bacteriophage P

<400> SEQUENCE: 306
atggaagaat tagaacaagc gttttgaaaat cttgatgatt ggtatctatc aagcatgaaa      60
gacagtgctt acaaggattt tgggaaatac gaaattcgct tatcaaatca ttcggcagac     120
aataaatatc atgacctaga aaatggtcgc ttaatcgtta atgttaaagc tagtaaattg     180
aacttcgttg atatcatcga gaataaaatc tataaaatca ttgagaaaat tgaaactctc     240
gatttagaca agtacagatt tattaacgct actaaaatgg aaaacgatat caaatgttat     300
tacaagggat ttaagacaaa gaaggatgtg atctaa                                336

<210> SEQ ID NO 307
<211> LENGTH: 177
<212> TYPE: DNA
<213> ORGANISM: Bacteriophage P

<400> SEQUENCE: 307
atgacagatg cgcacaaaaa agctgttaag aagtggaata aaacaacag agaacataga      60
aattatctaa acaagcgttc atcagctcgt ggtttcatca gaataatgc gactgctgaa     120
gatttgagag agctagagga gcttattgca gaaagaagaa aaaagaattt taggtaa        177
```

<210> SEQ ID NO 308
<211> LENGTH: 294
<212> TYPE: DNA
<213> ORGANISM: Bacteriophage P

<400> SEQUENCE: 308

```
ttgttaaacc taaagcgcga gcgaaatcat cagctttatt cagcgggaac acccgactac      60
ctgaaagata tcttgtttga aatcccagct ttatttgcat tgacatggaa ctgttgtcta     120
aatagctttt tattatcgtt gtttctcata tttaatagta taaacattat acaaaagttc     180
ccaaaaaata aacaatatgt tcccaaaaat aaactttttt catattttttt tgattttagt     240
gttgacaaat gggaacgtgt tagatatact ataattgttc taaggaacaa gtaa           294
```

<210> SEQ ID NO 309
<211> LENGTH: 105
<212> TYPE: DNA
<213> ORGANISM: Bacteriophage P

<400> SEQUENCE: 309

```
ttgcaaaaaa aatatataat ttttataaa aacagttttcc gtctggtcgc aaaaatcgac      60
ttgaatggat tgaaaacaat cttgaaaaca ttcgataaaa aataa                     105
```

<210> SEQ ID NO 310
<211> LENGTH: 105
<212> TYPE: DNA
<213> ORGANISM: Bacteriophage P

<400> SEQUENCE: 310

```
ttgcgcacac acaagcataa gggaaaattt tgttgggggg ggctaagacg cccccttttt      60
gatataatat acctatatca acggcctccc acccgtcttt tttag                     105
```

<210> SEQ ID NO 311
<211> LENGTH: 132
<212> TYPE: DNA
<213> ORGANISM: Bacteriophage P

<400> SEQUENCE: 311

```
atgctggggc ttttttttaa tataaatgct actatattaa tggatacagt taaaagagaa      60
gcatccagat atgatggatt ttatggacct gatagattgg tatttagaaa atcgcaaacc     120
ataagatatt ga                                                        132
```

<210> SEQ ID NO 312
<211> LENGTH: 222
<212> TYPE: DNA
<213> ORGANISM: Bacteriophage TPL

<400> SEQUENCE: 312

```
atgtacgcta agaacgaact agatttgaaa ttccagatga tggatcaaaa gattgacgct      60
aaatttgata cctttggtca acgcatggaa acatgttct tagcacaaac caataggcaa     120
cttgaggaac aagccaagaa tagaaaagaa ttcacatatt ggtttatttg cattcttgta     180
gctatcgctg ttattgctat tcctgttttgg ttcggcaaat aa                       222
```

<210> SEQ ID NO 313
<211> LENGTH: 222
<212> TYPE: DNA
<213> ORGANISM: Bacteriophage TPJ

<400> SEQUENCE: 313

```
atgtacgcta agaacgaact agacttgaaa ttccagatga tggatcaaaa gattgacgct      60
aaatttgata cctttggtca acgcatggaa aacatgttct tagcacaaac caataggcaa     120
cttgaggaac aagccaagaa tagaaaagaa ttcacatatt ggtttatttg cattcttgta     180
gctatcgctg ttattgctat tcctgtttgg ttcggcaaat aa                         222
```

<210> SEQ ID NO 314
<211> LENGTH: 183
<212> TYPE: DNA
<213> ORGANISM: Bacteriophage D

<400> SEQUENCE: 314

```
atggatacat ataaagaaca attttattat ttggatccta tttatattag tgtggatatt      60
aataggagga cttttatttt aggaaaaaga gggcaatcgc tctcttttt tattgtaata      120
aaacaattta aaatataac taaaaaaact tcaaaaaaat cgaaaaaaaa tattgacaaa     180
taa                                                                   183
```

<210> SEQ ID NO 315
<211> LENGTH: 177
<212> TYPE: DNA
<213> ORGANISM: Bacteriophage P

<400> SEQUENCE: 315

```
atgctggggc ttttttttgtg ttataatatg aatgagatgt caatcccccc acatcctttt     60
atggacagat acgttctgag tgggggtttt tttgttttgc tattttttaa cctaacagcc    120
cgtaattccc ccacctctaa ggtggcggga tgtaagggct tcggtctagt gcagtga       177
```

<210> SEQ ID NO 316
<211> LENGTH: 195
<212> TYPE: DNA
<213> ORGANISM: Bacteriophage D

<400> SEQUENCE: 316

```
atgttcagcg accttgtgcg ttcgaaagtg tataagggaa cattttgttg tgggctaaga     60
ccccctttt ttgatataat atatctatat caatgtcctc ccacgcataa gcgcagatac   120
gttctgaggg aggttttta tttgttttat tttgataaaa atgctactat attaacggat   180
acagttaaaa gctga                                                     195
```

<210> SEQ ID NO 317
<211> LENGTH: 195
<212> TYPE: DNA
<213> ORGANISM: Bacteriophage D

<400> SEQUENCE: 317

```
atgttcagcg accttgtgcg ttcgcaagtg tataagggaa cattttgttg tgggctaaga     60
ccccctttt ttgatataat atatctatat caatgtcctc ccacgcataa gcgcagatac   120
gttctgaggg aggttttta tttgttttat tttgatataa atgctactat aataatggat   180
acagttaaaa gctga                                                     195
```

<210> SEQ ID NO 318
<211> LENGTH: 264
<212> TYPE: DNA
<213> ORGANISM: Bacteriophage P

<400> SEQUENCE: 318

```
atgaatagca tgaaaaagcc ccacactgcg gaaaacggcg atttaattca tacaacagaa    60
gacaacgagg cttcagatat atcaatcatt acaatttcgt tgttcgcaa aacgaacaag    120 caaatattga aaaattcgaa agtttgccta aaacgttaca agctcaagta tctaaaccat   180
ctgccaatcc agaggttaat caagcagtat tcgacggaga tatcaaagca aaagaaatt   240 atagctcttg aaaaaaatga gtga                                         264

<210> SEQ ID NO 319
<211> LENGTH: 243
<212> TYPE: DNA
<213> ORGANISM: Bacteriophage P

<400> SEQUENCE: 319
atgaatagca tgaaaaagcc ccacactgcg gaaaacggcg atttaattca tacaacagaa    60
gacaacgagg cttcagatat atcaatcatt acaatttcgt tgttcgcaa aacgaacaag    120 caaatattga aaaattcgaa agtttgccta aaacgttaca agctcaagta tctaaaccat   180
ctgccaatcc agaggttaat caagcagtat tcgacggaga tatcaaagca aaagaatat   240 tga                                                                243

<210> SEQ ID NO 320
<211> LENGTH: 81
<212> TYPE: DNA
<213> ORGANISM: Bacteriophage D

<400> SEQUENCE: 320
atgttcagcg accttgtgcg ttcgaaagtg tataagggaa cattttgttg tgggctaaga    60 ccccccttt ttttgatata a                                              81

<210> SEQ ID NO 321
<211> LENGTH: 153
<212> TYPE: DNA
<213> ORGANISM: Bacteriophage D

<400> SEQUENCE: 321
atggcagtag tggtcgaagc ctcagcattt ttgctggggc ttttttgtg ttataatatg    60 aaacatcatt ttatggacag atatttgctt tgttttgata aaaatgctac tatattaatg   120
gtcttcgata aactctctct cgccctgact tga                                153

<210> SEQ ID NO 322
<211> LENGTH: 276
<212> TYPE: DNA
<213> ORGANISM: Bacteriophage D

<400> SEQUENCE: 322
atgataacta agaacaatt aaaaggatac tacagcgaac acttggaaga gctcgtcgaa    60
tgggcagacg atataaataa atcgcttat gagatagatg ggaaaagtca tcaaactaag   120
ataggttggg tgaatgatag attaaaagac cattttatga aagaaaaagg ggttttagtt   180
attcattaca ccaatgagca agtcgaaaca gcctacaatg agtgggtaaa aattacagag   240
gaggcgttta atggattctt taataacaca atctaa                             276

<210> SEQ ID NO 323
<211> LENGTH: 138
<212> TYPE: DNA
<213> ORGANISM: Bacteriophage P
```

<400> SEQUENCE: 323
atggcagcag tggtcgaagc ctcagcattt tgctggggc ttttttttgtg ttataatatg     60 aatgagatgt caatcccccc acatcctttt atggacagat acgttctgat gggaagtttt    120
ttatttgctt tgttttga                                                  138

<210> SEQ ID NO 324
<211> LENGTH: 147
<212> TYPE: DNA
<213> ORGANISM: Bacteriophage D

<400> SEQUENCE: 324
atggcagtag tggtcgaagc ctcagcatta tgctggggct ttttttgtgt tataatatac     60
ctatatcaat ggcctcccac gcatacgcgc agatacgttc tgatgggagg ttttttttgtt   120 gccgttaaaa cggacaaaaa aatttaa                                        147

<210> SEQ ID NO 325
<211> LENGTH: 120
<212> TYPE: DNA
<213> ORGANISM: Bacteriophage D

<400> SEQUENCE: 325
gtggtcgaag cctcagcatt atgctggggc ttttttttgtg ttaataaca tatatcaatg     60 gcttcccacg catacgcgca gatacgttct gagggaagtt tttatttgc ttttttttga   120

<210> SEQ ID NO 326
<211> LENGTH: 126
<212> TYPE: DNA
<213> ORGANISM: Bacteriophage D

<400> SEQUENCE: 326
atggcagtag tggtcgaagc ctcagcattt tgctggggct ttttttgtgt tataatatac     60
atggaacgac aaaccccctg catccacatg gacagatacg ctctgacgca gggctttttt   120
atttga                                                               126

<210> SEQ ID NO 327
<211> LENGTH: 132
<212> TYPE: DNA
<213> ORGANISM: Bacteriophage P

<400> SEQUENCE: 327
atggcagcag tggtcgaagc ctcagcattt tgctggggc ttttttttgtg ttataatata    60 cctatatcaa tggcttccca cgcatacgcg cagatacgtt ctgagggagg ttttttgtttt  120 gctttatttt ga                                                        132

<210> SEQ ID NO 328
<211> LENGTH: 519
<212> TYPE: DNA
<213> ORGANISM: Bacteriophage D

<400> SEQUENCE: 328
atggaaaatt actctagtcc agtgtataat attaaaaaaa tcccgattga aaaaattcaa     60
gcgaatagct ataaccccaa ccatgtagcg acaccagaaa tgaagttgtt atatgaatcc   120
atcaaagcag acggatacac aatgcctatc gtttgttatt atcttaaaga tgaagacaaa   180
tacgagattg tagatggctt tcaccgttat acaactatgc ttaatcataa agatatttac   240
gaacgagaga atggctgttt acctgtatct gttattgata aaccattaga ggagcgcatg   300

```
gcttctacag tacgacacaa tcgagcaaga ggtagtcatg atattggctt aatggctaat      360
attgtaactg aattggttga tagcggaatg tctgatgcca agttatgaa aagtcttgga       420 atggacgcag acgagttatt aagattaaaa caggttagcg gtttagcaag tttgtttgca     480
aacaaggagt tcagtaaatc gtgggatata aaaaaatag                            519
```

<210> SEQ ID NO 329
<211> LENGTH: 516
<212> TYPE: DNA
<213> ORGANISM: Bacteriophage D

<400> SEQUENCE: 329

```
atgcaaacat actctagccc tgtatataat attaagcgcg tgcctattga gaaaattcaa      60
gcaaacagct acaatcctaa ccatgtagca agcccagaaa tgaagttgct ttaccaatcc     120
atcaaagaag atggttacac aatgccaatc gtatgttatt accttgagga tgaagataag    180
tatgaaattg tggacggttt ccatcggtat acaacgatga agaacacaa ggatatctat     240 gaaagagagg aggggtgtct accagtttct gttatagata aaccaatcag tgaccgaatg    300
gcatcaacta tcagacacaa tagagcaaga gggtcgcacg acatcggtct gatgactaat    360
atcatttctg acctagttga ttctgggatg tcagatgcgt ggattatgaa aaatattggt    420
atggatgctg atgaattact acgactaaaa caagttagcg gactggcttc cttgttcaaa   480
gataaggaat tcacgacagc ttgggaagaa ggataa                              516
```

<210> SEQ ID NO 330
<211> LENGTH: 516
<212> TYPE: DNA
<213> ORGANISM: Bacteriophage D

<400> SEQUENCE: 330

```
atgcaaacat actctagccc tgtatataat attaagcgcg tgcctattga taaaattcaa      60
gcaaacagct acaatcctaa ccatgtagca agcccagaaa tgaagttgct ttatcaatcc    120
atcaaagaag atggttacac aatgccaatc gtatgttatt accttgagga tgaagataag    180
tatgaaattg tggacggttt tcatcggtat acaacgatga agaacacaa ggatatctat     240 gaaagagagg aggggtgtct accagtgtct gtcatagata aaccaatcag tgaccgaatg    300
gcatcaacta tcagacacaa tagagcaaga ggttcgcacg acatcggtct gatgactaat    360
atcatttctg acctagttga ttctgggatg tcagatgcgt ggattatgaa aaatattggt    420
atggatgctg atgaattact acgactaaaa caagttagcg gactggcttc cttgttcaaa   480
gataaggaat tcacgacagc ttgggaagaa ggataa                              516
```

<210> SEQ ID NO 331
<211> LENGTH: 513
<212> TYPE: DNA
<213> ORGANISM: Bacteriophage D

<400> SEQUENCE: 331

```
atgcaaacat actatagccc tgtatataat attaagcgcg tgcctattga gaaaattcaa      60
gcaaacagct acaatcctaa ccatgtagca agcccagaaa tgaagttgct ttatcaatcc    120
atcaaagaag atggttacac aatgccaatc gtatgttatt accttgagga tgaagataag    180
tatgaaattg tggacggttt ccatcggtat acaacgatga agaacacaa ggatatctat     240 gaaagagagg aggggtgtct accagtttct gtcatagata aaccaatcag tgaccgaatg    300
```

```
gcatcgacta tcagacacaa tagagcaaga gggtcgcacg acatcggtct gatgactaat    360
atcatttctg acctagttga ttctgggatg tcagatgcgt ggattatgaa aaatattggt    420
atggatgctg atgaattact acgactaaaa caagttagcg gactggcttc cttgttcaaa    480
gataaggaat tcacgacagc ttgggaagaa tga                                 513
```

<210> SEQ ID NO 332
<211> LENGTH: 225
<212> TYPE: DNA
<213> ORGANISM: Bacteriophage D

<400> SEQUENCE: 332

```
atggcacaaa ttaaagatgg ttggcataaa gtttataacg aaaatgttta tgttgaaaac     60
gaaaaagtag tacgaggaac aaaaaaagat tataacggtt ctgaggtcac ttgttatcct    120
tacgaatacg ataaaaacca agattgttgg attaatattt ctgggaaagc aactcttttct   180 tcttatagag caggactcaa aaaaggcact aagtgtatga agtaa                    225
```

<210> SEQ ID NO 333
<211> LENGTH: 138
<212> TYPE: DNA
<213> ORGANISM: Bacteriophage D

<400> SEQUENCE: 333

```
atgttcagcg accttgtgcg ttcgaaagtg tataagggaa cattttgttg tgggctaaga     60 ccccctttttt ttgatataat atatctatat caatgtcctc ccacgcataa gcgcagatac   120
gtgctgagtc ttcgataa                                                  138
```

<210> SEQ ID NO 334
<211> LENGTH: 123
<212> TYPE: DNA
<213> ORGANISM: Bacteriophage D

<400> SEQUENCE: 334

```
atgctggggc ttttttttgtg ttataatatg aatgagatgt caatccccccc acatccttttt   60 atggacagat acgttctgag tgggggttttt tttgttttgc tattttttaa aaatgtggta   120
taa                                                                  123
```

<210> SEQ ID NO 335
<211> LENGTH: 141
<212> TYPE: DNA
<213> ORGANISM: Bacteriophage D

<400> SEQUENCE: 335

```
atgctggggc ttttttttgtg ttataatatg aatgagatgt caatccccccc acatccttttt   60 atggacagat acgttctgag tgggggttttt ttgttttgct attttttaaa aatgtggtat   120
aatataaata tccattcata a                                              141
```

<210> SEQ ID NO 336
<211> LENGTH: 258
<212> TYPE: DNA
<213> ORGANISM: Bacteriophage D

<400> SEQUENCE: 336

```
atgaagaaat tttggcatag cggtatgatt gacaagaagg ttattgaaaa acgtaaacaa     60
gatgattata tgaataaatt acacaggact attcttgagt tgagtataaa accacctgaa    120
cccgaacctt ggtacagaca tccagaaatg agagcattgt tggataggat tgattctatg    180
```

```
gacatgatag attggtattc aaaatatcta aaacatcgca aaccatacga taattatagt      240
ggagaattag agaaatga                                                    258

<210> SEQ ID NO 337
<211> LENGTH: 180
<212> TYPE: DNA
<213> ORGANISM: Bacteriophage

<400> SEQUENCE: 337
atgaagaaat tttggcgtag tggaatgatt gacaagaagg ttatcgaaaa acgacaacaa       60
gaagagtata ttaataagtt acataggact attcttgagt tgagtataaa accacctgaa      120
ccagaacctt ggtacagaca tccagaaatg agagcattgt tggatagaat tgatgattag      180

<210> SEQ ID NO 338
<211> LENGTH: 198
<212> TYPE: DNA
<213> ORGANISM: Bacteriophage D

<400> SEQUENCE: 338
atgaagaagt tttggcgtag tggaatgatt gacaagaaag ttattgaaaa acgacaacaa       60
gatgattata tgaataagtt acataggact attcttgagt tgagtataaa accacctgaa      120
cccgaacctt ggtacagaca tccagaaatg agagcatttt tggataggat ttatgattcg      180
agaagcaatt taaagtaa                                                    198

<210> SEQ ID NO 339
<211> LENGTH: 180
<212> TYPE: DNA
<213> ORGANISM: Bacteriophage D

<400> SEQUENCE: 339
atgaagaaat tttggcgtag tggaatgatt gacaagaaaa ttattgcgaa acgtgaacag       60
gatgagtatt tgaataaatt acacaggact attcttgagt tgagtagaaa accacctgaa      120
caagaacctt ggtacagaca tccagaaatg agagcattgt tggatagaat tgatgattag      180

<210> SEQ ID NO 340
<211> LENGTH: 180
<212> TYPE: DNA
<213> ORGANISM: Bacteriophage D

<400> SEQUENCE: 340
atgaaaaaat tttggcatag cggtatgatt gacaagaaag ttattgaaaa acgtaaacaa       60
gatgattata tgaataagtt acataggact attcttgagt tgagtataaa accacctgaa      120
ccagaacctt ggtacagaca tccagaaatg agagcattgt tggataggat tgatgattag      180

<210> SEQ ID NO 341
<211> LENGTH: 198
<212> TYPE: DNA
<213> ORGANISM: Bacteriophage D

<400> SEQUENCE: 341
atgaagaagt tttggcgtag tggaatgatt gacaagaaag ttattgaaaa acgacaacaa       60
gatgattata tgaataagtt acataggact attcttgagt tgagtataaa accacctgaa      120
cccgaacctt ggtacagaca tccagaaatg agagcattgt tggataggat ttatgattcg      180
agaagcaatt taaagtaa                                                    198
```

<210> SEQ ID NO 342
<211> LENGTH: 180
<212> TYPE: DNA
<213> ORGANISM: Bacteriophage TPJ

<400> SEQUENCE: 342

```
atgaagaaat tttggcgtag tggaatgatt gacaagaagg ttattgaaaa acgtaaacaa      60
gatgattata tgaataaatt acacaggact attcttgagt tgagtataaa accacctgaa     120
ccagaacctt ggtacagaca tccagaaatg agagcattgt tggatagaat tgatgattag     180
```

<210> SEQ ID NO 343
<211> LENGTH: 180
<212> TYPE: DNA
<213> ORGANISM: Bacteriophage Proph

<400> SEQUENCE: 343

```
atgaagaaat tttggcgtag tggcatgatt gacaagaagg ttattgaaaa acgtaaacaa      60
gatgattata tgaataaatt acacaggact attcttgagt tgagtataaa accacctgaa     120
cccgaacctt ggtacagaca tccagaaatg agagcattgt tggataggat tgatgattag     180
```

<210> SEQ ID NO 344
<211> LENGTH: 177
<212> TYPE: DNA
<213> ORGANISM: Bacteriophage D

<400> SEQUENCE: 344

```
atgaagaaat tttggcgtag tggcatgatt gacaagaagg ttattaaaaa acgtaaacag      60
gaagagtata tgaataagat gcataggact attcttgaat taaaaaatga aagcatcca     120 gatatgatgg attttatgga cctgatagat tggtatttag aaaatcgcaa accataa       177
```

<210> SEQ ID NO 345
<211> LENGTH: 189
<212> TYPE: DNA
<213> ORGANISM: Bacteriophage D

<400> SEQUENCE: 345

```
atgaagaaat tttggcatag cggtatgatc gacaagaaag ttattgaaaa acgtaaacag      60
gatgagtatt tgaataaatt acacaggact attcttgagt taaaaaatga aagcatcca     120 gatatgatgg attttatgga cctgatagat tggtatttag agaatcgcaa accacgagat    180
attgattag                                                             189
```

<210> SEQ ID NO 346
<211> LENGTH: 189
<212> TYPE: DNA
<213> ORGANISM: Bacteriophage D

<400> SEQUENCE: 346

```
atgaagaaat tttggcatag cggtatgatt gacaagaagg ttattgaaaa acgtaaacag      60
gaagaatgta ttaatgaact gcataggact attcttgagt tgaaaaatga aagcatcca     120 gatatgatgg attttatgga cctgatagat tggtatttag aaaatcgcaa accacgagat    180
atttattag                                                             189
```

<210> SEQ ID NO 347
<211> LENGTH: 183
<212> TYPE: DNA
<213> ORGANISM: Bacteriophage D

<400> SEQUENCE: 347

```
atgatcgaca agaaagttat tgaaaaacgt aaacaggatg agtatttgaa taaattacac      60
aggactattc ttgagttaaa aaatgagaag catccagata tgatagattt tatggacctg     120
atagatttta tggacctgat agattggtat ttagagaatc gcaaaccacg agatattgat     180
tag                                                                   183
```

<210> SEQ ID NO 348
<211> LENGTH: 189
<212> TYPE: DNA
<213> ORGANISM: Bacteriophage D

<400> SEQUENCE: 348

```
atgaataaat tttggcatag cggtatgatc gacaagaaag ttattgaaaa ccgtaaacag      60
gaagaatata ttaataaact gcatagcact attcttgaat tgaaaaatga gaagcatcca     120
gatatgatgg attttatgga cctgatagat tggtatttag aaaatcgcaa accacaagat     180
attgattag                                                             189
```

<210> SEQ ID NO 349
<211> LENGTH: 189
<212> TYPE: DNA
<213> ORGANISM: Bacteriophage P

<400> SEQUENCE: 349

```
atgaagaaat tttggcgtag tggcatgatt gacaataagg ttattgaaaa acgtaaacaa      60
gatgattata tgaataaatt acacaggact attcttgagt tgacccgtga aattgaattg     120
agacgtggcc cagatatgat ggatttcatg gatctgatag attggtattt aaacagccgc     180
aaaccgtag                                                             189
```

<210> SEQ ID NO 350
<211> LENGTH: 216
<212> TYPE: DNA
<213> ORGANISM: Bacteriophage D

<400> SEQUENCE: 350

```
atgaagaagt tttggcatag cggtatgatt gacaagaaag ttattgaaaa acgccaacat      60
gatgagtata taaataaaat acataagact attattgagt tgaggaaaga accacctgaa     120
cctaaacctt gctcttgtca caagatata gatattaatg ctttgattaa tgatattgag     180
tgggatgatt attatacatg gtttaaagat aaataa                               216
```

<210> SEQ ID NO 351
<211> LENGTH: 216
<212> TYPE: DNA
<213> ORGANISM: Bacteriophage D

<400> SEQUENCE: 351

```
atgaagaaat tttggcgtag tggaatgatt gacaagaagg ttattgaaaa acgtaaacaa      60
gatgattata tgaataaatt acacaggact attcttgagt tgagtataaa accacctgaa     120
cctaaacctt gctcttgtca caagatata gatattaatg ctttgattaa tgatattgag     180
tgggatgatt attatacatg gtttaaagat aaataa                               216
```

<210> SEQ ID NO 352
<211> LENGTH: 216
<212> TYPE: DNA

<213> ORGANISM: Bacteriophage D

<400> SEQUENCE: 352

| | |
|---|---|
| atgaagaaat tttggcgtag tggcatgatt gacaagaagg ttattgaaaa acgtaaacag | 60 |
| gaagagtata tgaataagat gcataggact attcttgagt tgagtataaa accacctgaa | 120 |
| cctaaacctt gctcttgtca caagatata gatattaatg ctttgattaa tgatattgag | 180 |
| tgggatgatt attatacatg gtttaaagat aaataa | 216 |

<210> SEQ ID NO 353
<211> LENGTH: 192
<212> TYPE: DNA
<213> ORGANISM: Bacteriophage D

<400> SEQUENCE: 353

| | |
|---|---|
| atgattgaca agaaggttat tgaaaaacgt aaacaagatg attatatgaa taaattacac | 60 |
| aggactattc ttgagttgag tataaaacca cctgaaccta aaccttgctc ttgtcacaaa | 120 |
| gatatagata ttaatgcttt gattaatgat attgagtggg atgattatta tacatggttt | 180 |
| aaagataaat aa | 192 |

<210> SEQ ID NO 354
<211> LENGTH: 216
<212> TYPE: DNA
<213> ORGANISM: Bacteriophage D

<400> SEQUENCE: 354

| | |
|---|---|
| atgaagaaat tttggcatag cggtatgatt gacaagaaag ttattaaaaa acgtaaacag | 60 |
| gaagaatata tgaataaact tcaaagaatt atccttgagt tgagtataaa accacctgaa | 120 |
| cctaaacctt gctcttgtca caagatata gatattaatg ctttgattaa tgatattgag | 180 |
| tgggatgatt attatacatg gtttaaagat aaataa | 216 |

<210> SEQ ID NO 355
<211> LENGTH: 213
<212> TYPE: DNA
<213> ORGANISM: Bacteriophage O

<400> SEQUENCE: 355

| | |
|---|---|
| atgaagaagt tttggcatag cggtatgatt gacaagaaaa ttattgaaaa acgtgaacat | 60 |
| gatgagtatt tgaataaatt acatatgact attattgagt tgagaaaaga accacctgaa | 120 |
| actaaacctt gctcttgtca caaaatgta gatattaatg aattaattaa ctatattgag | 180 |
| tggaatgatt attatacatg gtttaaagat taa | 213 |

<210> SEQ ID NO 356
<211> LENGTH: 183
<212> TYPE: DNA
<213> ORGANISM: Bacteriophage D

<400> SEQUENCE: 356

| | |
|---|---|
| atgaagaaat tttggcatag cggtatgatc gacaagaaag ttattgaaaa acgtaaacag | 60 |
| gatgagtatt tgaataaatt acacaggact attcttgaga tagactttcc aattcaacgt | 120 |
| gtttgtcacc ggtcactatc accgacaccc ataacggtgc ccacggaaac ccttgatata | 180 |
| taa | 183 |

<210> SEQ ID NO 357
<211> LENGTH: 135

```
<212> TYPE: DNA
<213> ORGANISM: Bacteriophage D

<400> SEQUENCE: 357
atgaagaaat tttggcatag cggtatgatt gacaagaaag ttattaaaaa acgtaaacag    60
gaagagtata tgaataagat gcataggact attcttgagt tgagtataaa accaatagaa   120
gaaatggttt tttaa                                                    135

<210> SEQ ID NO 358
<211> LENGTH: 267
<212> TYPE: DNA
<213> ORGANISM: Bacteriophage Sfi

<400> SEQUENCE: 358
atgaagaaat tttggcgtag tggaatgatt gacaagaagg ttattgaaaa acgtaaacaa    60
gatgattata tgaataaatt acacaggact attcttgagt tgagtataaa accacctgaa   120
cctaaacctt gctcttgtca caagatata gatattaatg ctttgattaa tgatattgag   180
tgggatgatt gggtagatga agtgttggaa tatataaata aatgggtaaa taagataaa    240 gctgatgtgg aggtattaga taaatga                                       267

<210> SEQ ID NO 359
<211> LENGTH: 633
<212> TYPE: DNA
<213> ORGANISM: Bacteriophage D

<400> SEQUENCE: 359
atgaccaccc cacaaaagtt tcttagtatc agggaattgc ttaaaccact ccctagcaac    60
ggtgttaagt ttcctaagtt ctctgcactc tatcacgaaa gccaagtggg agcgtggcag   120
aagaaaatga gtaagcgaag acaccaagca aaggtacaag tagctatgga taagaaccgt   180
ggtgaactag ttcctcgtga gttagaggac ttctctaact ggcaacgtgc tagacaaatg   240
aaagcacgct atcaagagaa ggtggctaac aagcgtaagg actacctaca caaactaacc   300
acttatcttg ttaagactta tgatgttatc gtgattgagg acttgaaagc taagaacttg   360
atgaagaacc attacttagc taaatcaatc gctaacgctt catggcatga gtttaagaga   420
ctgctagaat acaagtgttc gtggtatggc aaggaactta tgttgttcc ggctcaccat    480 actagtcaag agtgttctaa ctgtcaccac aattcaggta agaaaccgct ccatatccgt   540
gagtggatgt gtgataattg tggtactcac catgatagag acattaacgc aagtatcaat   600
atcttgcacc gtggacttgc cacgttaaat taa                                633

<210> SEQ ID NO 360
<211> LENGTH: 303
<212> TYPE: DNA
<213> ORGANISM: Bacteriophage D

<400> SEQUENCE: 360
atgtcaacag ttttcttgat ttttttttcaa gttttttga ttttattatt aaacatcttg    60
aaaattagta aaacatacta tatattgttc tttgtatgta tccattgttt ttacctcgtt   120
tttttatttt ttatcgaatg ttttccaagt tgctctcaat ccattctagt ctattttggc   180
gaccagacgg aaactgtttt tataaaaaaa tatatatttt tttgcaaaac aaaaaccctg   240
actaattcaa gtcagggcaa gagagagttt atcgaagact cagcttttaa ctgtatccat   300
taa                                                                 303
```

<210> SEQ ID NO 361
<211> LENGTH: 303
<212> TYPE: DNA
<213> ORGANISM: Bacteriophage D

<400> SEQUENCE: 361

```
atgtcaacag ttttcttgat ttttttcaa gttttcttga ttttttatt aaacatcttg      60
aaaattagta aaacatacta tatattgttc tttgtatgta tccattgttt ttacctcgtt     120
tttttatttt ttatcgaatg ttttccaagt tgctctcaat ccattctagt ctattttggt    180
gaccagacgg aaactgtttt tataaaaaaa tatatatttt tttgcaaaac aaaaaccctg    240
actaattcaa gtcagggtga gagagagttt atcgaagact cagcttttaa ctgtattcat    300
taa                                                                   303
```

<210> SEQ ID NO 362
<211> LENGTH: 303
<212> TYPE: DNA
<213> ORGANISM: Bacteriophage P

<400> SEQUENCE: 362

```
atgtcaacag ttttcttgat ttttttcaa gttttcttga ttttttatt aaacatcttg      60
aaaattagta aaacatacta tatattgttc tttgtatgta tccattgttt ttacctcgtt    120
tttttatttt ttatcgaatg ttttccaagt tgctctcaat ccattctagt ctattttggt   180
gaccagacgg aaactgtttt tataaaaaaa tatatatttt tttgcaaaac aaaaaccctg   240
actaattcaa gtcagggtga gagagagttt atcgaagata acagcttttta ctgtaaccat   300
taa                                                                   303
```

<210> SEQ ID NO 363
<211> LENGTH: 231
<212> TYPE: DNA
<213> ORGANISM: Bacteriophage P

<400> SEQUENCE: 363

```
ttgattttt ttaaagtttt tttgatttta ttattaaaca acttgaaaat tagtaaaaca     60
tactatatat tgttctttgt atgtatccat tgttttacc tcgtttttt atttttatc      120
gaatattttc cagattgttt tcaatccatt caagtcgatt tttgcgacca gacggaaact   180
gtttttataa aaaattatat attttttttg caaaacaaaa accctgacta a             231
```

<210> SEQ ID NO 364
<211> LENGTH: 246
<212> TYPE: DNA
<213> ORGANISM: Bacteriophage P

<400> SEQUENCE: 364

```
atgtcaatag ttttcttgat ttttttaaa gttttttga ttttattatt aaacaacttg      60
aaaattagta aaacatacta tatattgttc tttgtatgta tccattgttt ttacctcgtt    120
tttttatttt ttatcgaata ttttccagat tgttttcaat ccattcaagt cgattttgc    180
gaccagacgg aaactgtttt tataaaaaaa tatatatttt ttttgcaaaa caaaaaccct   240
gactaa                                                                246
```

<210> SEQ ID NO 365
<211> LENGTH: 234
<212> TYPE: DNA
<213> ORGANISM: Bacteriophage P

<400> SEQUENCE: 365

```
atgtcaacag tttcttgat ttttttcaa gttttttga ttttttata tatttacttt      60
aaaattagta aaacatacta tatattgttc tttgtatgta tccattgttt tttattttt    120
tatcgaatgt tttccaagtt gctctcaatc cattctagtc tattttggcg accagacgga   180
aactgttttt ataaaaaaat atatattttt ttgcaaaaca aaaccctga ctaa          234
```

<210> SEQ ID NO 366
<211> LENGTH: 219
<212> TYPE: DNA
<213> ORGANISM: Bacteriophage P

<400> SEQUENCE: 366

```
ttgattttt ttcaagtttt cttgattttt ttattaaaca tcttgaaaat tagtaaaaca    60
tactatatat tgttctttgt atgtatccat tgttttttat tttttatcga atgttttcca   120
agttgctctc aatccattct agtctatttt ggcgaccaga cggaaactgt ttttataaaa   180
aaaatatata ttttttgca aacaaaaac cctgactaa                            219
```

<210> SEQ ID NO 367
<211> LENGTH: 198
<212> TYPE: DNA
<213> ORGANISM: Bacteriophage D

<400> SEQUENCE: 367

```
ttgtttattt ttgggaactg ttgtataatg tttatactat atatatcatg tatgatagtt   60
tgtcaacagt tttacctaaa ttattttagt ttttttgca aaaaagaaa acctcgacta     120
aaagtcgagg ttacagttcg agaatttaac cgaaacgata ccaagtattc caacaattat   180
attaccactt ttctatga                                                 198
```

<210> SEQ ID NO 368
<211> LENGTH: 189
<212> TYPE: DNA
<213> ORGANISM: Bacteriophage D

<400> SEQUENCE: 368

```
gtgagttctg aacatagtat tcaaaatcaa attcgagtgg aattatccaa ggctggcaac   60
atggtattta gaattaacgt tggtaaagtc agaatggctg atggacgttg gtttgatact   120
ggagcaccaa aaggattttg tgacctgttt ggatttagac cagctactgt aatagcactt   180
atctattag                                                           189
```

<210> SEQ ID NO 369
<211> LENGTH: 141
<212> TYPE: DNA
<213> ORGANISM: Bacteriophage P

<400> SEQUENCE: 369

```
ttgccaatcc tctttattgt cggtaacgca cagggagcaa gtcactgcac tagaccgaag   60
cccttacatc ccgccacctt agaggtgggg gaattacggg ctgttaggtt aaaaaaagca   120
aacaaaaaag ccccagcata a                                             141
```

<210> SEQ ID NO 370
<211> LENGTH: 171
<212> TYPE: DNA
<213> ORGANISM: Bacteriophage P

<400> SEQUENCE: 370

```
atgtcaacag tttcttgat ttttttcaa gttttcttga ttttttttatt aaacatcttg      60 aaaattagta aaacatacta tatattgttc tttgtatgta tccattgttt ttttatttt     120 tatcgaatgt tttccaagtt gctctcaatc cattctagtc tattttggtg a             171
```

<210> SEQ ID NO 371
<211> LENGTH: 144
<212> TYPE: DNA
<213> ORGANISM: Bacteriophage P

<400> SEQUENCE: 371

```
ttgattttt ttcaagtttt cttgattttt ttattaaaca tcttgaaaat tagtaaaaca      60
tactatatat tgttctttgt atgtatccat tgttttttt attttttatc gaatgttttc    120
caagttgctc tcaatccatt ctag                                           144
```

<210> SEQ ID NO 372
<211> LENGTH: 171
<212> TYPE: DNA
<213> ORGANISM: Bacteriophage P

<400> SEQUENCE: 372

```
ttggtcttag cccccaacaa aacgttccct tatgcttgtg tgtgcgcaag caatagggcg     60
ctgaacctaa tcagtctttt acctttgca ctagataaat tgtatctagg ttatccaatt    120
acattttatc aaattatcat ttataagtca aataaaaaag ccccagcata a             171
```

<210> SEQ ID NO 373
<211> LENGTH: 198
<212> TYPE: DNA
<213> ORGANISM: Bacteriophage P

<400> SEQUENCE: 373

```
ttgagaataa atgaagctgt actaagtttt tatagttttt atttttattt attaaggaat     60
ttagtttttt tttgcaaaaa aagaaaacct cgactaaaag tcgaggttac agttcgagaa   120
tttaaccgaa acgatgccaa gtattccaac aattatatga aaatagcaaa caaaagagc    180 tacgagatta tctcatag                                                  198
```

<210> SEQ ID NO 374
<211> LENGTH: 195
<212> TYPE: DNA
<213> ORGANISM: Bacteriophage Sequence

<400> SEQUENCE: 374

```
ttgttctacc tattgactaa agcgagtttt tacctctctc tttatcttat gtatacatta     60
catatcatat atgatagtct gccaactgtt tttataaaaa aatatatatt ttttgcaaa    120 acaaaaaccc tgactaattc aagtcagggt gagagagagt ttatcgaaga ctcagctttt   180
aactgtattc attaa                                                    195
```

<210> SEQ ID NO 375
<211> LENGTH: 108
<212> TYPE: PRT
<213> ORGANISM: Bacteriophage O

<400> SEQUENCE: 375

```
Met Ala Tyr Gly Lys Ser Arg Tyr Asn Ser Tyr Arg Lys Arg Ser Phe
 1               5                  10                  15
```

```
Asn Arg Ser Asp Lys Gln Arg Glu Tyr Ala Gln Glu Met Asp Arg
             20                  25                  30

Leu Glu Gln Thr Phe Glu Lys Leu Asp Gly Trp Tyr Leu Ser Ser Met
         35                  40                  45

Lys Asp Ser Ala Tyr Lys Asp Phe Gly Lys Tyr Glu Ile Arg Leu Ser
 50                  55                  60

Asn His Ser Ala Asp Asn Lys Tyr His Asp Leu Glu Asn Gly Arg Leu
 65                  70                  75                  80

Ile Val Asn Val Lys Ala Ser Lys Leu Lys Phe Val Asp Ile Lys Cys
             85                  90                  95

Tyr Tyr Lys Gly Phe Lys Thr Lys Lys Asp Val Ile
            100                 105
```

<210> SEQ ID NO 376
<211> LENGTH: 140
<212> TYPE: PRT
<213> ORGANISM: Bacteriophage Sfi

<400> SEQUENCE: 376

```
Met Ala Tyr Gly Lys Ser Arg Tyr Asn Ser Tyr Arg Lys Arg Ser Phe
1               5                  10                  15

Asn Arg Ser Asn Lys Gln Arg Arg Glu Tyr Ala Gln Glu Met Asp Arg
             20                  25                  30

Leu Glu Lys Ala Phe Glu Asn Leu Asp Gly Trp Tyr Leu Ser Ser Met
         35                  40                  45

Lys Asp Ser Ala Tyr Lys Asp Phe Gly Lys Tyr Glu Ile Arg Leu Ser
 50                  55                  60

Asn His Ser Ala Asp Asn Lys Tyr His Asp Leu Glu Asn Gly Arg Leu
 65                  70                  75                  80

Ile Val Asn Val Lys Ala Ser Lys Leu Asn Phe Val Asp Ile Ile Glu
             85                  90                  95

Asn Lys Leu Asp Lys Ile Ile Glu Lys Ile Asp Thr Leu Asp Leu Asp
            100                 105                 110

Lys Tyr Arg Phe Ile Asn Ala Thr Lys Leu Glu Arg Asp Ile Lys Cys
            115                 120                 125

Tyr Tyr Lys Gly Tyr Lys Thr Lys Lys Asp Val Ile
            130                 135                 140
```

<210> SEQ ID NO 377
<211> LENGTH: 140
<212> TYPE: PRT
<213> ORGANISM: Bacteriophage TPL

<400> SEQUENCE: 377

```
Met Ala Tyr Gly Lys Ser Arg Tyr Asn Ser Tyr Arg Lys Arg Ser Phe
1               5                  10                  15

Asn Ile Ser Asp Thr Lys Arg Arg Glu Tyr Ala Lys Glu Met Glu Lys
             20                  25                  30

Leu Glu Gln Ala Phe Glu Lys Leu Asp Gly Trp Tyr Leu Ser Ser Met
         35                  40                  45

Lys Asp Ser Ala Tyr Lys Asp Phe Gly Lys Tyr Glu Ile Arg Leu Ser
 50                  55                  60

Asn His Ser Ala Asp Asn Lys Tyr His Asp Leu Glu Asn Gly Arg Leu
 65                  70                  75                  80

Ile Val Asn Val Lys Ala Ser Lys Leu Asn Phe Val Asp Ile Ile Glu
             85                  90                  95
```

Asn Lys Leu Asp Lys Ile Ile Glu Lys Ile Asp Lys Leu Asp Leu Asp
            100                 105                 110

Lys Tyr Arg Phe Ile Asn Ala Thr Arg Met Glu His Asp Ile Lys Cys
            115                 120                 125

Tyr Tyr Lys Gly Phe Lys Thr Lys Lys Asp Val Ile
            130                 135                 140

<210> SEQ ID NO 378
<211> LENGTH: 140
<212> TYPE: PRT
<213> ORGANISM: Streptococcus sp

<400> SEQUENCE: 378

Met Ala Phe Gly Lys Asn Arg Tyr Asn Pro Tyr Arg Lys Arg Ser Phe
1               5                   10                  15

Asn Arg Ser Asp Lys Gln Cys Arg Glu Tyr Ala Gln Ala Met Asp Glu
            20                  25                  30

Leu Glu Gln Ala Phe Glu Glu Leu Asp Gly Trp His Leu Ser Ser Met
            35                  40                  45

Met Asp Ser Ala Tyr Lys Asn Phe Glu Lys Tyr Gln Val Arg Leu Ser
50                  55                  60

Asn His Ser Ala Asp Asn Gln Tyr His Asp Leu Glu Asn Gly Tyr Leu
65                  70                  75                  80

Ile Val Asn Val Lys Ala Ser Lys Leu Asn Phe Val Asp Ile Ile Glu
            85                  90                  95

Asn Lys Leu Asp Lys Ile Leu Glu Lys Val Asp Lys Leu Asp Leu Asp
            100                 105                 110

Lys Tyr Arg Phe Ile Asn Ala Thr Asn Leu Glu His Asp Ile Lys Cys
            115                 120                 125

Tyr Leu Lys Gly Tyr Lys Thr Lys Lys Asp Val Ile
            130                 135                 140

<210> SEQ ID NO 379
<211> LENGTH: 140
<212> TYPE: PRT
<213> ORGANISM: Bacteriophage D

<400> SEQUENCE: 379

Met Ala Tyr Gly Lys Ser Arg Tyr Asn Ser Tyr Arg Lys Arg Ser Phe
1               5                   10                  15

Asn Arg Ser Asn Lys Gln Arg Arg Glu Tyr Ala Gln Glu Met Asp Arg
            20                  25                  30

Leu Glu Lys Ala Phe Glu Asn Leu Asp Gly Trp Tyr Leu Ser Ser Met
            35                  40                  45

Lys Asp Ser Ala Tyr Lys Asp Phe Gly Lys Tyr Glu Ile Arg Leu Ser
50                  55                  60

Asn His Ser Ala Asp Asn Lys Tyr His Asp Leu Glu Asn Gly Arg Leu
65                  70                  75                  80

Ile Val Asn Ile Lys Ala Ser Lys Leu Asn Phe Val Asp Ile Ile Glu
            85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Asn Leu Glu His Asp Ile Lys Cys
            115                 120                 125

Tyr Tyr Lys Gly Phe Lys Thr Lys Lys Glu Val Ile
            130                 135                 140

<210> SEQ ID NO 380
<211> LENGTH: 140
<212> TYPE: PRT
<213> ORGANISM: Bacteriophage D

<400> SEQUENCE: 380

Met Ala Tyr Gly Lys Ser Arg Tyr Asn Ser Tyr Arg Lys Arg Asn Phe
1               5                   10                  15

Ser Ile Ser Asp Asn Gln Arg Arg Glu Tyr Ala Lys Lys Met Lys Glu
            20                  25                  30

Leu Glu Gln Ala Phe Glu Asn Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Arg Tyr His Asp Leu Glu Asn Gly Arg Leu
65                  70                  75                  80

Ile Val Asn Val Lys Ala Ser Lys Leu Asn Phe Val Asp Ile Ile Glu
                85                  90                  95

Asn Lys Leu Gly Lys Ile Ile Glu Lys Ile Asp Thr Leu Asp Leu Asp
            100                 105                 110

Lys Tyr Arg Phe Ile Asn Ala Thr Lys Leu Glu Arg Asp Ile Lys Cys
        115                 120                 125

Tyr Tyr Lys Gly Tyr Lys Thr Lys Lys Asp Val Ile
    130                 135                 140

<210> SEQ ID NO 381
<211> LENGTH: 140
<212> TYPE: PRT
<213> ORGANISM: Bacteriophage D

<400> SEQUENCE: 381

Met Ala Tyr Gly Lys Ser Arg Tyr Asn Ser Tyr Arg Lys Arg Ser Phe
1               5                   10                  15

Asn Arg Ser Asp Lys Gln Arg Arg Glu Tyr Ala Gln Ala Met Glu Glu
            20                  25                  30

Leu Glu Gln Ala Phe Glu Asn Phe Asp Asp Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Ile Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Asn Leu Glu His Asp Ile Lys Cys
        115                 120                 125

Tyr Tyr Lys Gly Phe Lys Thr Lys Lys Glu Val Ile
    130                 135                 140

<210> SEQ ID NO 382
<211> LENGTH: 140
<212> TYPE: PRT
<213> ORGANISM: Bacteriophage D

<400> SEQUENCE: 382

Met Ala Tyr Gly Lys Ser Arg Tyr Asn Ser Tyr Arg Lys Arg Ser Phe

-continued

```
                1               5                      10                      15
Asn Arg Ser Asp Lys Gln Arg Arg Glu Tyr Ala Lys Lys Met Lys Glu
                20                      25                      30

Leu Glu Gln Ala Phe Glu Asn Leu Asp Gly Trp Tyr Leu Ser Ser Met
                35                      40                      45

Asn Asp Ser Ala Tyr Lys Asn Phe Gly Lys Tyr Glu Val Arg Leu Ser
        50                      55                      60

Asn His Ser Ala Asp Asn Lys Tyr His Asp Ile Glu Asn Gly Arg Leu
65                      70                      75                      80

Ile Val Asn Val Lys Ala Ser Lys Leu Asn Phe Val Asp Ile Ile Glu
                85                      90                      95

Asn Lys Leu Asp Lys Ile Ile Glu Lys Ile Asp Lys Leu Asp Leu Asp
                100                     105                     110

Lys Tyr Arg Phe Ile Asn Ala Thr Asn Leu Glu His Asn Ile Lys Cys
                115                     120                     125

Tyr Tyr Lys Gly Phe Lys Thr Lys Lys Asp Val Ile
        130                     135                     140
```

<210> SEQ ID NO 383
<211> LENGTH: 140
<212> TYPE: PRT
<213> ORGANISM: Bacteriophage D

<400> SEQUENCE: 383

```
Met Ala Tyr Gly Lys Ser Arg Tyr Asn Ser Tyr Arg Lys Arg Ser Phe
1               5                       10                      15

Asn Arg Ser Asp Lys Gln Arg Gly Glu Tyr Ala Gln Ala Met Glu Glu
                20                      25                      30

Leu Glu Gln Ala Phe Glu Asn Phe Asp Asp Trp Tyr Leu Ser Ser Met
                35                      40                      45

Lys Asp Ser Ala Tyr Lys Asp Phe Gly Lys Tyr Glu Ile Arg Leu Ser
        50                      55                      60

Asn His Ser Ala Asp Asn Lys Tyr His Asp Leu Glu Asn Gly Arg Leu
65                      70                      75                      80

Ile Val Asn Val Lys Ala Ser Lys Leu Asn Phe Val Asp Ile Ile Glu
                85                      90                      95

Asn Lys Ile Asp Lys Ile Ile Glu Lys Ile Asp Lys Leu Asp Leu Asp
                100                     105                     110

Lys Tyr Arg Phe Ile Asn Ala Thr Asn Leu Glu His Asp Ile Lys Cys
                115                     120                     125

Tyr Tyr Lys Gly Phe Lys Thr Lys Lys Asp Val Ile
        130                     135                     140
```

<210> SEQ ID NO 384
<211> LENGTH: 140
<212> TYPE: PRT
<213> ORGANISM: Streptococcus mutans

<400> SEQUENCE: 384

```
Met Ala Phe Gly Lys Arg Arg Tyr Asn Ser Tyr Arg Lys Arg Ser Phe
1               5                       10                      15

Asn Arg Ser Asp Lys Gln Arg Arg Glu Tyr Ala Gln Ala Met Glu Glu
                20                      25                      30

Leu Glu Gln Thr Phe Glu Asn Leu Glu Gly Trp Asn Leu Ser Ser Met
                35                      40                      45

Lys Asp Ser Ala Tyr Lys Asp Tyr Asp Lys Tyr Glu Val Arg Leu Ser
```

```
                50                  55                  60
Asn His Ser Ala Asp Asn Gln Tyr His Asn Leu Gln Asp Gly Lys Leu
 65                  70                  75                  80

Ile Ile Asn Ile Lys Ala Ser Lys Met Asn Phe Val Trp Ile Ile Glu
                 85                  90                  95

Asn Lys Leu Asp Ala Ile Leu Glu Lys Val Asn Lys Leu Asp Leu Ser
                100                 105                 110

Lys Tyr Arg Phe Ile Asn Ala Thr Ser Leu Asp His Asp Ile Lys Cys
            115                 120                 125

Tyr Tyr Lys Asn Tyr Lys Thr Lys Lys Asp Val Ile
        130                 135                 140

<210> SEQ ID NO 385
<211> LENGTH: 140
<212> TYPE: PRT
<213> ORGANISM: Streptococcus mutans

<400> SEQUENCE: 385

Met Ala Phe Gly Thr Arg Arg Tyr Asn Ser Tyr Arg Lys Arg Ser Phe
 1               5                  10                  15

Asn Arg Ser Asp Lys Gln Arg Arg Glu Tyr Ala Gln Ala Met Glu Glu
                 20                  25                  30

Leu Glu Gln Thr Phe Glu Asn Leu Glu Asp Trp Asn Leu Ser Ser Met
             35                  40                  45

Lys Asp Ser Ala Tyr Lys Asp Tyr Asp Lys Tyr Glu Val Arg Leu Ser
         50                  55                  60

Asn His Ser Ala Asp Asn Gln Tyr His Asn Leu Gln Asp Gly Lys Leu
 65                  70                  75                  80

Ile Ile Asn Ile Lys Ala Ser Lys Met Asn Phe Val Trp Ile Ile Glu
                 85                  90                  95

Asn Lys Leu Asp Ala Ile Leu Glu Lys Val Asn Lys Leu Asp Leu Ser
                100                 105                 110

Arg Tyr Arg Phe Ile Asn Ala Thr Asn Leu Glu His Asp Ile Lys Cys
            115                 120                 125

Tyr Tyr Lys Asn Tyr Lys Thr Lys Lys Asp Val Ile
        130                 135                 140

<210> SEQ ID NO 386
<211> LENGTH: 140
<212> TYPE: PRT
<213> ORGANISM: Streptococcus mutans

<400> SEQUENCE: 386

Met Ala Phe Gly Thr Arg Arg Tyr Asn Ser Tyr Arg Lys Arg Ser Phe
 1               5                  10                  15

Asn Arg Ser Asp Lys Gln Arg Arg Glu Tyr Ala Gln Ala Met Glu Glu
                 20                  25                  30

Leu Glu Gln Thr Phe Glu Asn Leu Glu Asp Trp Asn Leu Ser Ser Met
             35                  40                  45

Lys Asp Ser Ala Tyr Lys Asp Tyr Asp Lys Tyr Glu Val Arg Leu Ser
         50                  55                  60

Asn His Ser Ala Asp Asn Gln Tyr His Asn Leu Gln Asp Gly Lys Leu
 65                  70                  75                  80

Ile Ile Asn Ile Lys Ala Ser Lys Met Asn Phe Val Trp Ile Ile Glu
                 85                  90                  95

Asn Lys Leu Asp Val Ile Leu Glu Lys Val Asn Lys Leu Asp Leu Ser
```

```
                    100                 105                 110
Lys Tyr Arg Phe Ile Asn Ala Thr Ser Leu Asp His Asp Ile Lys Cys
            115                 120                 125

Tyr Tyr Lys Asn Tyr Lys Thr Lys Lys Asp Val Ile
            130                 135                 140

<210> SEQ ID NO 387
<211> LENGTH: 140
<212> TYPE: PRT
<213> ORGANISM: Streptococcus mutans

<400> SEQUENCE: 387

Met Ala Phe Gly Thr Arg Arg Tyr Asn Ser Tyr Arg Lys Arg Asn Phe
1               5                   10                  15

Asn Arg Ser Asp Lys Gln Arg Arg Glu Tyr Ala Gln Ala Met Glu Glu
            20                  25                  30

Leu Glu Gln Thr Phe Glu Asn Leu Glu Asp Trp Asn Leu Ser Ser Met
        35                  40                  45

Lys Asp Ser Ala Tyr Lys Asp Tyr Asp Lys Phe Glu Val Arg Leu Ser
    50                  55                  60

Asn His Ser Ala Asp Asn Gln Tyr His Asn Leu Gln Asp Gly Lys Leu
65                  70                  75                  80

Ile Ile Asn Ile Lys Ala Ser Lys Met Asn Phe Val Trp Ile Ile Glu
                85                  90                  95

Asn Lys Leu Asp Ala Ile Leu Glu Lys Val Asn Lys Leu Asp Leu Ser
            100                 105                 110

Lys Tyr Arg Phe Ile Asn Ala Thr Ser Leu Asp His Asp Ile Lys Cys
        115                 120                 125

Tyr Tyr Lys Asn Tyr Lys Thr Lys Lys Asp Val Ile
    130                 135                 140

<210> SEQ ID NO 388
<211> LENGTH: 183
<212> TYPE: PRT
<213> ORGANISM: Bacteriophage D

<400> SEQUENCE: 388

Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Gly Thr Asp Ile
        35                  40                  45

Glu Lys Met Gly Ala Ala Arg Val Asn Ala Met Leu Asp Cys Leu Phe
    50                  55                  60

Asp Asp Phe Glu Leu Ala Met Ile Gly Lys Ala Gln Thr Asn Tyr Tyr
65                  70                  75                  80

Asn Asp Asn Ser Leu Lys Met Asn Met Pro Phe Tyr Thr Tyr Tyr Asp
                85                  90                  95

Met Phe Lys Lys Gln Gln Leu Leu Lys Trp Leu Lys Asn Asn Arg Asp
            100                 105                 110

Asp Val Ile Gly Gly Thr Gly Arg Met Tyr Thr Ala Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Leu Gln Met Arg Phe Lys Asp Tyr Ser Lys Gly
```

```
                145                 150                 155                 160
Gln Glu Pro Ile Pro Ser Gly Arg Gln Asn Arg Leu Glu Trp Ile Glu
                    165                 170                 175
Asn Asn Leu Glu Asn Ile Arg
            180

<210> SEQ ID NO 389
<211> LENGTH: 183
<212> TYPE: PRT
<213> ORGANISM: Bacteriophage D

<400> SEQUENCE: 389

Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Gly Thr Asp Ile
            35                  40                  45

Glu Lys Met Gly Ala Ala Arg Val Asn Ala Met Leu Ser Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Leu Leu Ile Asn Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ala Tyr Leu Glu Val Ala Leu Glu Ser Ser Arg Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 390
<211> LENGTH: 183
<212> TYPE: PRT
<213> ORGANISM: Bacteriophage D

<400> SEQUENCE: 390

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Asn Asp Asn Ser Leu Lys Met Asn Met Pro Phe Tyr Thr Tyr Tyr Asp
                85                  90                  95

Met Phe Lys Lys Gln Gln Leu Leu Lys Trp Leu Lys Asn Asn Arg Asp
```

```
            100                 105                 110
Asp Val Ile Cys Gly Thr Gly Arg Met Tyr Thr Ala Ser Gly Asn Tyr
            115                 120                 125

Ile Ala Asn Ala Tyr Leu Glu Ile Ala Leu Glu Ser Ser Arg Leu Gly
            130                 135             140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 391
<211> LENGTH: 183
<212> TYPE: PRT
<213> ORGANISM: Bacteriophage D

<400> SEQUENCE: 391

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Asp Asp Phe Glu Leu Ala Leu Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
            115                 120                 125

Ile Ala Asn Ser Tyr Leu Glu Val Ala Leu Glu Ser Ser Arg Leu Gly
            130                 135             140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 392
<211> LENGTH: 183
<212> TYPE: PRT
<213> ORGANISM: Bacteriophage D

<400> SEQUENCE: 392

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Gln Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
```

```
                    50                  55                  60
Asp Asp Phe Glu Leu Ala Leu Ile Gly Lys Ala Gln Gln Glu Tyr Tyr
 65                  70                  75                  80

Ser Asp Asn Ser Leu Lys Leu Asn Met Pro Phe Tyr Ala Tyr Tyr Asp
                    85                  90                  95

Met Phe Lys Lys Gln Gln Leu Leu Lys Trp Leu Lys Asn Asn Arg Asp
                100                 105                 110

Asp Val Ile Cys Gly Thr Gly Arg Met Tyr Thr Ala Ser Gly Asn Tyr
                115                 120                 125

Ile Ala Asn Ser Tyr Leu Glu Val Ala Leu Glu Ser Ser Arg Leu Gly
            130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 393
<211> LENGTH: 183
<212> TYPE: PRT
<213> ORGANISM: Bacteriophage M

<400> SEQUENCE: 393

Met Lys Ile Asn Asn Asp Ile Lys Glu Leu Ile Leu Glu Tyr Val Ser
 1               5                  10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
 50                  55                  60

Asp Asp Phe Glu Leu Ala Phe Ile Gly Lys Ala Gln Gln Glu Tyr Tyr
 65                  70                  75                  80

Ser Asp Asn Ser Leu Lys Leu Asn Met Pro Phe Tyr Ala Tyr Tyr Asp
                    85                  90                  95

Met Phe Lys Lys Gln Gln Leu Leu Lys Trp Leu Lys Asn Asn Arg Asp
                100                 105                 110

Asp Val Ile Cys Gly Thr Gly Arg Met Tyr Thr Ala Ser Gly Asn Tyr
                115                 120                 125

Ile Ala Asn Ser Tyr Leu Glu Val Ala Leu Glu Ser Ser Arg Leu Gly
            130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 394
<211> LENGTH: 183
<212> TYPE: PRT
<213> ORGANISM: Bacteriophage D

<400> SEQUENCE: 394

Met Lys Ile Asn Asn Asp Ile Lys Glu Leu Ile Leu Glu Tyr Val Ser
```

```
               1               5                  10                 15
Arg Tyr Phe Lys Phe Glu Asn Asp Phe Tyr Lys Leu Pro Gly Ile Lys
                20                 25                 30

Phe Thr Asp Ala Asn Trp Gln Lys Phe Lys Asn Gly Asp Thr Ser Ile
                35                 40                 45

Glu Lys Met Gly Ala Ala Arg Val Asn Ala Met Leu Asp Cys Leu Phe
             50                 55                 60

Asp Asp Phe Glu Leu Ala Leu Ile Gly Lys Ala Gln Gln Glu Tyr Tyr
 65                 70                 75                 80

Ser Asp Asn Ser Leu Lys Leu Asn Met Pro Phe Tyr Ala Tyr Tyr Asp
                85                 90                 95

Met Phe Lys Lys Gln Gln Leu Leu Lys Trp Leu Lys Asn Asn Arg Asp
                100                105                110

Asp Val Ile Cys Gly Thr Gly Arg Met Tyr Thr Ala Ser Gly Asn Tyr
                115                120                125

Ile Ala Asn Ser Tyr Leu Glu Val Ala Leu Glu Ser Ser Arg Leu Gly
                130                135                140

Ser Gly Ser Tyr Met Leu Gln Met Arg Phe Lys Asp Tyr Ser Arg Ser
145                150                155                160

Gln Glu Pro Ile Pro Ser Gly Arg Gln Asn Arg Leu Glu Trp Ile Glu
                165                170                175

Ser Asn Leu Glu Asn Ile Arg
                180

<210> SEQ ID NO 395
<211> LENGTH: 183
<212> TYPE: PRT
<213> ORGANISM: Bacteriophage D

<400> SEQUENCE: 395

Met Lys Ile Asn Asn Asp Ile Lys Glu Leu Ile Leu Glu Tyr Val Ser
1               5                  10                 15

Arg Tyr Phe Lys Phe Glu Asn Asp Phe Tyr Lys Leu Pro Gly Ile Lys
                20                 25                 30

Phe Thr Asp Ala Asn Trp Gln Lys Phe Lys Asn Gly Asp Thr Ser Ile
                35                 40                 45

Glu Lys Met Gly Ala Ala Arg Val Asn Ala Met Leu Asp Cys Leu Phe
             50                 55                 60

Asp Asp Phe Glu Leu Ala Phe Ile Gly Lys Ala Gln Gln Glu Tyr Tyr
 65                 70                 75                 80

Ser Asp Asn Ser Leu Lys Leu Asn Met Pro Phe Tyr Ala Tyr Tyr Asp
                85                 90                 95

Met Phe Lys Lys Gln Gln Leu Leu Lys Trp Leu Lys Asn Asn Arg Asp
                100                105                110

Asp Val Ile Cys Gly Thr Gly Arg Met Tyr Thr Ala Ser Gly Asn Tyr
                115                120                125

Ile Ala Asn Ser Tyr Leu Glu Val Ala Leu Glu Ser Ser Arg Leu Gly
                130                135                140

Ser Gly Ser Tyr Met Leu Gln Met Arg Phe Lys Asp Tyr Ser Arg Ser
145                150                155                160

Gln Glu Pro Ile Pro Ser Gly Arg Gln Asn Arg Leu Glu Trp Ile Glu
                165                170                175

Ser Asn Leu Glu Asn Ile Arg
                180
```

<210> SEQ ID NO 396
<211> LENGTH: 183
<212> TYPE: PRT
<213> ORGANISM: Bacteriophage ALQ

<400> SEQUENCE: 396

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Asp Asp Phe Glu Leu Ala Leu Ile Gly Lys Ala Gln Gln Glu Tyr Tyr
65                  70                  75                  80

Ser Asp Asn Ser Leu Lys Leu Asn Met Pro Phe Tyr Ala Tyr Tyr Asp
                85                  90                  95

Met Leu Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ser Tyr Leu Glu Val Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 397
<211> LENGTH: 183
<212> TYPE: PRT
<213> ORGANISM: Bacteriophage D

<400> SEQUENCE: 397

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Arg Leu Pro Gly Ile Lys
            20                  25                  30

Phe Thr Asp Ala Asn Trp Gln Lys Phe Lys Asn Gly Thr Ala Ile
        35                  40                  45

Glu Lys Met Gly Ala Ala Arg Val Asn Ala Met Leu Ser Cys Leu Phe
50                  55                  60

Glu Asp Phe Glu Leu Ala Met Ile Gly Lys Ala Gln Tyr Glu Tyr Tyr
65                  70                  75                  80

Ser Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Gly Gly Thr Gly Arg Met Tyr Thr Ser Ser Gly Ser Tyr
        115                 120                 125

Ile Ala Asn Ala Tyr Leu Glu Ile Ala Leu Glu Ser Ser Arg Leu Gly
    130                 135                 140

```
Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
            165                 170                 175

Ser Asn Leu Glu Asn Ile Arg
            180

<210> SEQ ID NO 398
<211> LENGTH: 183
<212> TYPE: PRT
<213> ORGANISM: Bacteriophage

<400> SEQUENCE: 398

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Gly Gly Thr Gly Arg Met Tyr Thr Ala Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Leu Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
            165                 170                 175

Asn Asn Leu Glu Asn Ile Arg
            180

<210> SEQ ID NO 399
<211> LENGTH: 183
<212> TYPE: PRT
<213> ORGANISM: Bacteriophage DT

<400> SEQUENCE: 399

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Glu Thr Ser Ile
        35                  40                  45

Glu Lys Met Gly Ala Ala Arg Val Asn Ala Met Leu Ser Cys Leu Phe
50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95
```

```
Met Phe Lys Lys Gln Leu Leu Ile Asn Trp Leu Lys Asn Asn Arg Asp
            100                 105                 110

Asp Val Ile Gly Gly Thr Gly Arg Met Tyr Thr Ala Ser Gly Asn Tyr
            115                 120                 125

Ile Ala Asn Ala Tyr Leu Glu Val Ala Leu Glu Ser Ser Ser Leu Gly
130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 400
<211> LENGTH: 183
<212> TYPE: PRT
<213> ORGANISM: Bacteriophage D

<400> SEQUENCE: 400

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Glu Thr Ser Ile
            35                  40                  45

Glu Lys Met Gly Ala Ala Arg Val Asn Ala Met Leu Ser Cys Leu Phe
50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Leu Leu Ile Asn Trp Leu Lys Asn Asn Arg Asp
            100                 105                 110

Asp Val Ile Gly Gly Thr Gly Arg Met Tyr Thr Ala Ser Gly Asn Tyr
            115                 120                 125

Ile Ala Asn Ala Tyr Leu Glu Val Ala Leu Glu Ser Ser Ser Leu Gly
130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 401
<211> LENGTH: 183
<212> TYPE: PRT
<213> ORGANISM: Bacteriophage N

<400> SEQUENCE: 401

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45
```

Glu Lys Met Gly Ala Ala Arg Val Asn Ala Met Leu Asp Cys Leu Phe
     50                  55                  60

Glu Asp Phe Glu Leu Ala Met Ile Gly Lys Ala Gln Thr Asn Tyr Tyr
 65                  70                  75                  80

Ile Asp Asn Ser Leu Lys Leu Asn Met Pro Phe Tyr Ala Tyr Tyr Asp
                 85                  90                  95

Met Phe Lys Lys Gln Gln Leu Leu Lys Trp Leu Lys Asn Asn Arg Asp
                100                 105                 110

Asp Val Ile Gly Gly Thr Gly Arg Met Tyr Thr Ser Thr Gly Asn Tyr
            115                 120                 125

Ile Ala Asn Ala Tyr Leu Glu Ile Ala Leu Glu Ser Ser Arg Leu Gly
    130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 402
<211> LENGTH: 183
<212> TYPE: PRT
<213> ORGANISM: Bacteriophage D

<400> SEQUENCE: 402

Met Lys Ile Asn Asn Asp Ile Lys Glu Leu Ile Leu Glu Tyr Val Ser
 1               5                  10                  15

Arg Tyr Phe Lys Phe Glu Asn Asp Phe Tyr Lys Leu Pro Asp Ile Lys
                 20                  25                  30

Phe Thr Asp Ala Asn Trp Gln Lys Phe Lys Asn Gly Glu Thr Ser Ile
             35                  40                  45

Glu Lys Met Gly Ala Ala Arg Val Asn Ala Met Leu Asp Cys Leu Phe
     50                  55                  60

Glu Asp Phe Glu Leu Ala Met Ile Gly Lys Ala Gln Thr Asn Tyr Tyr
 65                  70                  75                  80

Ile Asp Asn Ser Leu Lys Leu Asn Met Pro Phe Tyr Ala Tyr Tyr Asp
                 85                  90                  95

Met Phe Lys Lys Gln Gln Leu Leu Lys Trp Leu Lys Asn Asn Arg Asp
                100                 105                 110

Asp Val Ile Gly Gly Thr Gly Arg Met Tyr Thr Ser Thr Gly Asn Tyr
            115                 120                 125

Ile Ala Asn Ala Tyr Leu Glu Ile Ala Leu Glu Ser Ser Arg Leu Gly
    130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 403
<211> LENGTH: 183
<212> TYPE: PRT
<213> ORGANISM: Bacteriophage D

<400> SEQUENCE: 403

Met Lys Ile Asn Asn Asp Ile Lys Glu Leu Ile Leu Glu Tyr Ala Lys
1               5                   10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Glu Thr Ser Ile
        35                  40                  45

Glu Lys Met Gly Ala Ala Arg Val Asn Ala Met Leu Ser Cys Leu Phe
50                  55                  60

Asp Asp Phe Glu Leu Ala Met Ile Gly Lys Ala Gln Thr Asn Tyr Tyr
65                  70                  75                  80

Asn Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Ile Ile Cys Gly Thr Gly Arg Met Tyr Thr Ser Arg Gly Ser Tyr
        115                 120                 125

Ile Ala Asn Ala Tyr Leu Glu Val Ala Leu Ser Ser Leu Leu Gly
        130                 135                 140

Ser Gly Ser Tyr Met Leu Gln Met Arg Phe Lys Asp Tyr Ser Lys Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 404
<211> LENGTH: 183
<212> TYPE: PRT
<213> ORGANISM: Bacteriophage CHPC

<400> SEQUENCE: 404

Met Lys Ile Asn Asn Asp Ile Lys Glu Leu Ile Leu Glu Tyr Gly Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Leu Ile
        35                  40                  45

Glu Lys Met Gly Ala Ala Arg Val Asn Ala Met Leu Asp Cys Leu Phe
50                  55                  60

Asp Asp Phe Glu Leu Ala Met Ile Gly Lys Ala Gln Thr Asn Tyr Tyr
65                  70                  75                  80

Asn Asp Asn Ser Leu Lys Leu Asn Met Pro Phe Tyr Ala Tyr Tyr Asp
                85                  90                  95

Met Phe Lys Lys Gln Gln Leu Ile His Trp Leu Lys Asn Asn Arg Asp
            100                 105                 110

Asp Ile Val Gly Gly Thr Gly Arg Leu Tyr Thr Ser Ser Gly Ser Tyr
        115                 120                 125

Ile Ala Asn Ala Tyr Leu Glu Ile Ala Leu Glu Ser Ser Leu Gly
        130                 135                 140

Ser Gly Ser Tyr Met Leu Gln Met Arg Phe Lys Asn Tyr Ser Lys Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 405
<211> LENGTH: 183
<212> TYPE: PRT
<213> ORGANISM: Bacteriophage D

<400> SEQUENCE: 405

Met Lys Ile Asn Asn Asp Ile Lys Glu Leu Ile Leu Glu Tyr Met Ser
1               5                   10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Glu Thr Ser Ile
        35                  40                  45

Glu Lys Met Gly Ala Ala Arg Val Asn Ala Met Leu Asn Cys Leu Phe
50                  55                  60

Glu Asp Phe Glu Leu Ala Met Ile Gly Lys Ala Gln Ile Asn Tyr Tyr
65                  70                  75                  80

Asn Asp Asn Ser Leu Lys Met Asn Met Pro Phe Tyr Ala Tyr Tyr Asp
                85                  90                  95

Met Phe Lys Lys Gln Gln Leu Leu Lys Trp Leu Lys Asp His His Asp
            100                 105                 110

Asp Ile Ile Gly Gly Ala Gly Arg Met Tyr Thr Ser Thr Gly Ser Tyr
        115                 120                 125

Ile Ala Asn Ala Tyr Leu Glu Val Ala Leu Glu Ser Ser Ser Leu Gly
    130                 135                 140

Asp Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 406
<211> LENGTH: 183
<212> TYPE: PRT
<213> ORGANISM: Bacteriophage

<400> SEQUENCE: 406

Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Gln Glu Tyr Tyr
65                  70                  75                  80

Leu Asp Asn Ser Leu Lys Met Asn Met Pro Phe Tyr Ala Tyr Tyr Asp
                85                  90                  95

Met Phe Lys Lys Lys Gln Leu Val Lys Trp Leu Lys Asp His His Asp
            100                 105                 110

Asp Ile Leu Gly Gly Thr Gly Arg Met Tyr Thr Ser Asp Gly Ser Tyr
        115                 120                 125

Ile Ala Asn Ser Tyr Leu Glu Val Ala Leu Glu Ser Ser Arg Leu Gly
    130                 135                 140

```
Ser Gly Ser Tyr Met Leu Gln Met Arg Phe Lys Asp Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 407
<211> LENGTH: 183
<212> TYPE: PRT
<213> ORGANISM: Bacteriophage

<400> SEQUENCE: 407

Met Glu Ile Asn Asn Asp Ile Lys Glu Leu Ile Leu Glu Tyr Val Lys
1               5                   10                  15

Arg Tyr Phe Lys Phe Glu Asn Asp Phe Tyr Lys Leu Pro Asp Ile Lys
                20                  25                  30

Phe Thr Asp Ala Asn Trp Gln Lys Phe Lys Asn Gly Glu Thr Ala Ile
            35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Val Lys Trp Leu Glu Thr Ser Arg Glu
            100                 105                 110

Asp Ile Ile Gly Gly Ala Gly Arg Met Tyr Thr Ser Asp Gly Ser Tyr
        115                 120                 125

Ile Ala Asn Ala Tyr Leu Glu Val Ala Leu Glu Ser Ser Ser Leu Gly
130                 135                 140

Asp Ser Glu Tyr Met Leu Gln Met Arg Phe Lys Asn Tyr Ser Lys Ser
145                 150                 155                 160

Gln Glu Pro Ile Pro Ser Gly Arg Gln Asn Arg Leu Glu Trp Ile Glu
                165                 170                 175

Asn Asn Leu Lys Asn Ile Arg
            180

<210> SEQ ID NO 408
<211> LENGTH: 183
<212> TYPE: PRT
<213> ORGANISM: Bacteriophage D

<400> SEQUENCE: 408

Met Leu Ile Asn Asn Asp Ile Lys Glu Leu Ile Leu Glu Tyr Val Lys
1               5                   10                  15

Arg Tyr Phe Lys Tyr Glu Asn Asp Phe Tyr Arg Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Thr Asn Tyr Tyr
65                  70                  75                  80

Ile Asn Asn Ser Leu Lys Met Asn Met Pro Phe Tyr Ala Tyr Tyr Asp
                85                  90                  95
```

-continued

Met Phe Lys Lys Glu Gln Leu Met Lys Trp Leu Glu Thr Ser Arg Glu
            100                 105                 110

Asp Ile Ile Gly Gly Thr Gly Arg Met Tyr Thr Ser Asp Gly Ser Tyr
        115                 120                 125

Ile Ala Asn Ala Tyr Leu Glu Ile Ala Leu Glu Ser Ser Ser Leu Gly
    130                 135                 140

Ser Gly Ser Tyr Met Leu Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 409
<211> LENGTH: 183
<212> TYPE: PRT
<213> ORGANISM: Streptococcus thermophilus

<400> SEQUENCE: 409

Met Leu Ile Asn Asn Asp Ile Lys Glu Leu Ile Leu Glu Tyr Val Lys
1               5                   10                  15

Arg Tyr Phe Lys Phe Glu Asn Asp Phe Tyr Arg Leu Pro Gly Ile Lys
            20                  25                  30

Phe Thr Asp Ala Asn Trp Gln Lys Phe Lys Asn Gly Asp Thr Ala Ile
        35                  40                  45

Glu Lys Met Gly Ala Ser Arg Val Asn Ser Met Leu Asp Cys Leu Phe
    50                  55                  60

Glu Asp Phe Glu Leu Ala Met Ile Gly Lys Ala Gln Asp Glu Tyr Tyr
65                  70                  75                  80

Leu Asp Asn Ser Leu Lys Met Asn Met Pro Phe Tyr Ala Tyr Tyr Asp
                85                  90                  95

Met Phe Lys Lys Lys Gln Leu Val Lys Trp Leu Lys Asp His His Asp
            100                 105                 110

Asp Ile Leu Gly Gly Thr Gly Arg Met Tyr Thr Ser Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Ile Gln Met Arg Phe Lys Asn Tyr Ser Lys Gly
145                 150                 155                 160

Gln Glu Pro Ile Pro Ser Gly Arg Gln Asn Arg Leu Glu Trp Ile Glu
                165                 170                 175

Lys Asn Leu Glu Asn Ile Arg
            180

<210> SEQ ID NO 410
<211> LENGTH: 183
<212> TYPE: PRT
<213> ORGANISM: Streptococcus thermophilus

<400> SEQUENCE: 410

Met Glu Ile Asn Asn Asp Ile Lys Gln Leu Ile Leu Glu Tyr Ala Lys
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Gly Thr Ala Ile
        35                  40                  45

```
Glu Lys Met Gly Ala Ala Arg Val Asn Ala Met Leu Asp Cys Leu Phe
         50                  55                  60

Glu Asp Phe Glu Leu Ala Met Ile Gly Lys Ala Gln Gln Glu Tyr Tyr
 65                  70                  75                  80

Ser Asp Asn Ser Leu Lys Val Asn Met Ala Phe Tyr Ala Tyr Tyr Asp
                 85                  90                  95

Gln Phe Lys Lys Gln Gln Leu Met Lys Trp Leu Lys Asp Asn His Asp
                100                 105                 110

Asp Ile Ile Gly Gly Thr Gly Arg Met Tyr Thr Ser Ser Gly Ser Tyr
                115                 120                 125

Ile Ala Asn Ala Tyr Leu Glu Ile Ala Leu Glu Ser Ser Arg Leu Gly
        130                 135                 140

Gly Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 411
<211> LENGTH: 183
<212> TYPE: PRT
<213> ORGANISM: Bacteriophage Sfi

<400> SEQUENCE: 411

Met Glu Ile Asn Asn Asp Ile Lys Gln Leu Ile Leu Glu Tyr Val Gly
 1               5                  10                  15

Arg Tyr Phe Lys Phe Glu Asn Asp Phe Tyr Lys Leu Pro Gly Ile Lys
                 20                  25                  30

Phe Thr Asp Ala Asn Trp Gln Lys Phe Lys Asn Gly Asp Thr Ser Ile
         35                  40                  45

Glu Lys Met Gly Ala Ala Arg Val Asn Ala Met Leu Asp Cys Leu Phe
         50                  55                  60

Glu Asp Phe Glu Leu Ala Met Ile Gly Lys Ala Gln Thr Asn Tyr Tyr
 65                  70                  75                  80

Ile Asp Asn Ser Leu Lys Leu Asn Met Pro Phe Tyr Ala Tyr Tyr Asp
                 85                  90                  95

Met Phe Lys Lys Glu Gln Leu Met Lys Trp Leu Lys Asp His His Asp
                100                 105                 110

Asp Ile Ile Gly Gly Thr Gly Arg Met Tyr Ile Ser Ser Gly Ser Tyr
                115                 120                 125

Ile Ala Asn Ala Tyr Leu Glu Ile Ala Leu Glu Ser Ser Thr Leu Gly
        130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 412
<211> LENGTH: 183
<212> TYPE: PRT
<213> ORGANISM: Bacteriophage Sfi

<400> SEQUENCE: 412
```

```
Met Glu Ile Asn Asn Asp Ile Lys Gln Leu Ile Leu Glu Tyr Val Gly
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Glu Gln Leu Met Lys Trp Leu Lys Asp His His Asp
            100                 105                 110

Asp Ile Ile Gly Gly Thr Gly Arg Met Tyr Thr Ser Ser Gly Ser Tyr
        115                 120                 125

Ile Ala Asn Ala Tyr Leu Glu Ile Ala Leu Glu Ser Ser Thr Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 413
<211> LENGTH: 183
<212> TYPE: PRT
<213> ORGANISM: Streptococcus thermophilus

<400> SEQUENCE: 413

Met Glu Ile Asn Lys Asp Ile Lys Glu Leu Ile Leu Glu Tyr Val Lys
1               5                   10                  15

Arg Tyr Phe Lys Phe Glu Asn Asp Phe Tyr Arg Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Asp Glu Tyr Tyr
65                  70                  75                  80

Leu Asp Asn Ser Leu Lys Phe Asn Met Ala Phe His Thr Tyr Tyr Asp
                85                  90                  95

Gln Phe Lys Lys Gln Gln Leu Met Lys Trp Leu Glu Thr Ser Leu Glu
            100                 105                 110

Asp Ile Ile Gly Gly Thr Gly Arg Met Tyr Thr Ser Ser Gly Ser Tyr
        115                 120                 125

Ile Ala Asn Ala Tyr Leu Glu Ile Ala Leu Glu Ser Ser Ser Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
```

<210> SEQ ID NO 414
<211> LENGTH: 183
<212> TYPE: PRT
<213> ORGANISM: Bacteriophage D

<400> SEQUENCE: 414

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Asp Glu Tyr Tyr
65                  70                  75                  80

Leu Asp Asn Ser Leu Lys Phe Asn Met Ala Phe His Thr Tyr Tyr Asp
                85                  90                  95

Gln Phe Lys Lys Gln Gln Leu Met Lys Trp Leu Glu Thr Ser Leu Glu
            100                 105                 110

Asp Ile Ile Gly Gly Thr Gly Arg Met Tyr Thr Ser Ser Gly Ser Tyr
        115                 120                 125

Ile Ala Asn Ala Tyr Leu Glu Ile Ala Leu Glu Ser Ser Ser Leu Gly
130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 415
<211> LENGTH: 183
<212> TYPE: PRT
<213> ORGANISM: Bacteriophage D

<400> SEQUENCE: 415

Met Ile Ile Asn Ile Asp Ile Lys Glu Leu Ile Leu Glu Tyr Met Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
50                  55                  60

Asp Asp Phe Glu Leu Ala Met Ile Gly Lys Ala Gln Ile Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Ile Lys Trp Ile Glu Thr Ser Arg Asp
            100                 105                 110

Asp Val Ile Gly Gly Thr Gly Arg Met Tyr Thr Ala Ser Gly Ser Tyr
        115                 120                 125

Ile Ala Asn Ala Tyr Leu Glu Ile Ala Leu Glu Ser Ser Ser Leu Gly

```
                130                 135                 140
Gly Gly Ser Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Ser Asn Leu Glu Asn Ile Arg
            180

<210> SEQ ID NO 416
<211> LENGTH: 183
<212> TYPE: PRT
<213> ORGANISM: Streptococcus sp

<400> SEQUENCE: 416

Met Glu Ile Asn Asn Asp Ile Lys Glu Leu Ile Leu Glu Tyr Val Gly
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
    50                  55                  60

Asp Asp Phe Glu Leu Ala Met Ile Gly Lys Ala Gln Thr Asp Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Ile Glu Asn Ser Arg Glu
                100                 105                 110

Asp Ile Ile Gly Gly Ala Gly Arg Met Tyr Thr Ala Gly Gly Asn Trp
            115                 120                 125

Ile Ser Ser Ala Tyr Leu Glu Ile Ala Leu Glu Ser Ser Ser Ile Gly
        130                 135                 140

Gly Gly Gly Tyr Met Leu Gln Met Arg Phe Lys Asn Tyr Ser Arg Asp
145                 150                 155                 160

Pro Arg Pro Ile Pro Ala Gly His Gln Asn Arg Leu Glu Trp Ile Glu
                165                 170                 175

Asn Asn Leu Glu Asn Ile Arg
            180

<210> SEQ ID NO 417
<211> LENGTH: 183
<212> TYPE: PRT
<213> ORGANISM: Streptococcus sp

<400> SEQUENCE: 417

Met Glu Ile Asn Asn Asp Ile Lys Asp Leu Ile Leu Glu Tyr Val Gly
1               5                   10                  15

Arg Tyr Phe Arg Phe Glu Asn Asp Phe Tyr Lys Leu Pro Arg Ile Lys
                20                  25                  30

Phe Thr Asp Ser Asn Trp Gln Lys Phe Lys Asn Gly Asp Thr Ser Ile
            35                  40                  45

Glu Lys Met Gly Ala Gly Arg Val Asn Ala Met Leu Asp Cys Leu Phe
    50                  55                  60

Asp Asp Phe Glu Leu Ala Met Ile Gly Lys Ala Gln Thr Asp Tyr Tyr
65                  70                  75                  80

Met Asp Asn Ser Leu Lys Met Asn Met Pro Phe Tyr Ala Tyr Tyr Asp
```

```
                    85                  90                  95

Gln Phe Lys Lys Gln Gln Leu Leu Lys Trp Ile Glu Asn Ser Arg Glu
                100                 105                 110

Asp Ile Ile Gly Gly Ala Gly Arg Met Tyr Thr Ala Ser Gly Asn Trp
                115                 120                 125

Ile Ser Ser Ala Tyr Leu Glu Ile Ala Leu Glu Ser Ser Ser Leu Gly
                130                 135                 140

Gly Gly Glu Tyr Met Leu Gln Met Arg Phe Lys Asp Tyr Ser Arg Ser
145                 150                 155                 160

Gln Glu Pro Ile Pro Ala Gly Arg Gln Asn Arg Leu Glu Trp Ile Glu
                165                 170                 175

Asn Asn Leu Glu Asn Ile Arg
                180

<210> SEQ ID NO 418
<211> LENGTH: 104
<212> TYPE: PRT
<213> ORGANISM: Bacteriophage D

<400> SEQUENCE: 418

Met Lys Lys Ala Lys Gln Leu Leu Lys Glu Ile Lys Thr Asn Asn Val
1               5                   10                  15

Ser Tyr Ala Ile Met Asp Glu Asp Asn Glu Ile Tyr Cys Asn Lys Glu
                20                  25                  30

Thr Asn Asn Ile Met Asp Ile Tyr Glu Tyr Asp Asn Glu Asn Gly His
                35                  40                  45

Phe Tyr Gly Val Tyr Ser Asp Val Val Gly Gly Lys Val Asp Ser Arg
50                  55                  60

Tyr Leu Ser Asp Glu Tyr Ile Leu Lys Ala Ile Asp Lys Leu Leu Asn
65                  70                  75                  80

Leu Gly Asp Pro Val Lys Arg Thr Glu Leu Pro Ala Asp Ala Asp Phe
                85                  90                  95

Lys Arg Thr Phe Phe Glu Glu
                100

<210> SEQ ID NO 419
<211> LENGTH: 104
<212> TYPE: PRT
<213> ORGANISM: Bacteriophage D

<400> SEQUENCE: 419

Met Lys Lys Ala Gln Gln Leu Leu Lys Glu Ile Lys Asn Thr Asn Val
1               5                   10                  15

Ser Tyr Ala Ile Met Asp Glu Asp Asn Glu Ile Tyr Cys Asn Lys Glu
                20                  25                  30

Thr Asn Asn Ile Met Asp Ile Tyr Gly Tyr Asp Asn Glu Asn Gly His
                35                  40                  45

Phe Tyr Gly Val Tyr Ser Asp Val Val Gly Gly Lys Val Asp Ser Arg
50                  55                  60

Tyr Leu Ser Asp Glu Tyr Ile Leu Lys Ala Ile Asp Lys Leu Leu Phe
65                  70                  75                  80

Leu Gly Asp Pro Ile Lys Arg Thr Asp Leu Pro Ser Asp Ala Asp Phe
                85                  90                  95

Lys Arg Thr Phe Phe Glu Glu
                100
```

```
<210> SEQ ID NO 420
<211> LENGTH: 96
<212> TYPE: PRT
<213> ORGANISM: Bacteriophage P

<400> SEQUENCE: 420

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
                20                  25                  30

Lys Asp Ser Leu Arg Glu Ile His Ser Ala Leu Tyr Gly Leu Leu Thr
            35                  40                  45

Ala Gly Tyr Asp Ile Ser Asn Met Arg Asn Ile Glu Asp Leu Glu Lys
        50                  55                  60

Tyr Val Asn Leu Lys Lys Ser Arg Gly Gln Leu Leu Asn Val Ser Ser
65                  70                  75                  80

Asp Asp Ile Lys Leu Tyr His Lys Leu Phe Val Ile Arg Phe Glu Lys
                85                  90                  95

<210> SEQ ID NO 421
<211> LENGTH: 92
<212> TYPE: PRT
<213> ORGANISM: Bacteriophage CHPC

<400> SEQUENCE: 421

Met Lys Asn Lys Leu Tyr Thr Asp Ala Ile Lys Asn Asp Ser Arg Thr
1               5                   10                  15

Ala Ser Lys Met Ala Asn Ile Tyr Asn Lys Leu Glu Ser Asp Thr Met
                20                  25                  30

Arg Glu Ile His Ser Ala Leu Ser Gly Leu Leu Thr Ala Gly Tyr Asp
            35                  40                  45

Ile Ser Asn Met Arg Asn Ile Glu Glu Leu Glu Lys Tyr Val Thr Leu
        50                  55                  60

Lys Lys Ser Arg Gly Gln Leu Leu Asn Val Ser Ser Glu Asp Ile Lys
65                  70                  75                  80

Leu Tyr His Lys Leu Phe Val Ile Arg Phe Gly Lys
                85                  90

<210> SEQ ID NO 422
<211> LENGTH: 98
<212> TYPE: PRT
<213> ORGANISM: Bacteriophage D

<400> SEQUENCE: 422

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
                20                  25                  30

Lys Asp Ser Leu Arg Glu Ile His Ser Ala Leu Tyr Gly Leu Leu Thr
            35                  40                  45

Ala Gly Tyr Asp Ile Ser Asn Met Arg Lys Ile Glu Glu Leu Glu Lys
        50                  55                  60

Tyr Val Asn Leu Lys Lys Ser Arg Gly Gln Leu Leu Asn Val Ser Ser
65                  70                  75                  80

Asn Asp Ile Lys Leu Tyr His Lys Leu Phe Val Ile Arg Phe Gly Lys
                85                  90                  95

Glu Arg
```

<210> SEQ ID NO 423
<211> LENGTH: 94
<212> TYPE: PRT
<213> ORGANISM: Bacteriophage D

<400> SEQUENCE: 423

Met Lys Asn Arg Leu Tyr Thr Asp Ala Ile Lys Asn Asp Cys Gly Thr
1               5                   10                  15

Ala Asn Lys Met Ser Asn Ile Tyr Asn Lys Leu Asn Lys Asp Ser Leu
            20                  25                  30

Arg Glu Ile His Ser Ala Leu Tyr Gly Leu Leu Thr Ala Gly Tyr Asp
        35                  40                  45

Ile Ser Asn Met Arg Lys Ile Glu Glu Leu Glu Lys Tyr Val Asn Leu
    50                  55                  60

Lys Lys Ser Arg Gly Gln Leu Leu Asn Val Ser Ser Asn Asp Ile Lys
65                  70                  75                  80

Leu Tyr His Lys Leu Phe Val Ile Arg Phe Gly Lys Glu Arg
                85                  90

<210> SEQ ID NO 424
<211> LENGTH: 92
<212> TYPE: PRT
<213> ORGANISM: Bacteriophage D

<400> SEQUENCE: 424

Met Lys Asn Lys Leu Tyr Thr Asp Ala Ile Lys Asn Asp Ser Ala Thr
1               5                   10                  15

Ala Asn Lys Met Ala Asn Ile Tyr Ser Lys Leu Asn Lys Asp Ser Leu
            20                  25                  30

Arg Glu Ile His Ser Ala Leu Ser Gly Leu Leu Thr Ala Gly Tyr Asp
        35                  40                  45

Ile Ser Asn Met Gln Asn Ile Ala Glu Leu Gln Lys Tyr Val Ile Leu
    50                  55                  60

Lys Lys Ser Arg Gly Gln Leu Leu Asn Val Ser Ser Lys Asp Ile Glu
65                  70                  75                  80

Leu Tyr His Lys Leu Phe Val Ile Arg Phe Gly Lys
                85                  90

<210> SEQ ID NO 425
<211> LENGTH: 96
<212> TYPE: PRT
<213> ORGANISM: Bacteriophage D

<400> SEQUENCE: 425

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
            20                  25                  30

Lys Asp Ser Leu Arg Glu Ile His Ser Ala Leu Tyr Gly Leu Leu Thr
        35                  40                  45

Ala Gly Tyr Asp Ile Ser Asn Met Arg Lys Ile Glu Glu Leu Glu Lys
    50                  55                  60

Tyr Val Asn Leu Lys Lys Ser Arg Gly Gln Leu Leu Asn Val Ser Ser
65                  70                  75                  80

Asn Asp Ile Lys Leu Tyr His Lys Leu Phe Val Ile Arg Phe Gly Lys
                85                  90                  95

<210> SEQ ID NO 426
<211> LENGTH: 94
<212> TYPE: PRT
<213> ORGANISM: Bacteriophage D

<400> SEQUENCE: 426

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
            20                  25                  30

Lys Asp Ser Leu Arg Glu Ile His Ser Ala Leu Tyr Gly Leu Leu Thr
        35                  40                  45

Ala Gly Tyr Asp Ile Ser Asn Met Arg Lys Ile Glu Glu Leu Glu Lys
    50                  55                  60

Tyr Val Asn Leu Ser Arg Gly Gln Leu Leu Asn Val Ser Ser Asn Asp
65                  70                  75                  80

Ile Lys Leu Tyr His Lys Leu Phe Val Ile Arg Phe Gly Lys
                85                  90

<210> SEQ ID NO 427
<211> LENGTH: 100
<212> TYPE: PRT
<213> ORGANISM: Bacteriophage D

<400> SEQUENCE: 427

Met Lys Asn Arg Leu Leu Gly Ser Arg Tyr Thr Asp Ala Ile Lys Asn
1               5                   10                  15

Asp Ser Gly Thr Ala Asn Lys Met Ser Asn Ile Tyr Asn Ser Val Ile
            20                  25                  30

Asn Lys Glu Gly Leu Arg Gly Ile His Ser Ala Leu Tyr Gly Leu Leu
        35                  40                  45

Thr Ala Gly Tyr Asp Ile Ser Asn Met Arg Lys Ile Glu Glu Leu Glu
    50                  55                  60

Lys Tyr Val Asn Leu Lys Lys Ser Arg Gly Gln Leu Leu Asn Val Ser
65                  70                  75                  80

Ser Ser Asp Ile Lys Leu Tyr His Lys Leu Phe Val Ile Arg Phe Gly
                85                  90                  95

Lys Lys Leu Lys
            100

<210> SEQ ID NO 428
<211> LENGTH: 98
<212> TYPE: PRT
<213> ORGANISM: Bacteriophage D

<400> SEQUENCE: 428

Met Lys Asn Gly Asn Lys Ile Leu Gly Tyr Arg Tyr Thr Asp Glu Ile
1               5                   10                  15

Lys Asn Asp Ser Ala Thr Glu Asn Lys Met Ser Asn Leu Tyr Asn Lys
            20                  25                  30

Leu Asp Lys Asp Ser Leu Arg Glu Ile His Ser Ala Leu Tyr Gly Leu
        35                  40                  45

Leu Thr Ala Gly Tyr Asp Ile Ser Asn Met Arg Asn Val Glu Glu Leu
    50                  55                  60

Glu Lys Tyr Val Asn Val Lys Lys Ser His Gly Lys Leu Leu Asp Val
65                  70                  75                  80

Thr Asn Ser Asp Ile Gln Leu Tyr His Lys Leu Phe Val Val Arg Phe
                85                  90                  95

Gly Lys

<210> SEQ ID NO 429
<211> LENGTH: 96
<212> TYPE: PRT
<213> ORGANISM: Bacteriophage D

<400> SEQUENCE: 429

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
            20                  25                  30

Lys Asp Ser Leu Arg Glu Ile His Ser Ala Leu Tyr Gly Leu Leu Thr
        35                  40                  45

Ala Gly Tyr Asp Ile Ser Asn Met Arg Asn Ile Glu Glu Leu Glu Lys
    50                  55                  60

Tyr Val Asn Leu Lys Lys Ser Arg Gly Gln Leu Leu Asn Val Ser Ser
65                  70                  75                  80

Ser Asp Ile Lys Leu Tyr His Lys Leu Phe Val Ile Arg Phe Gly Lys
                85                  90                  95

<210> SEQ ID NO 430
<211> LENGTH: 97
<212> TYPE: PRT
<213> ORGANISM: Bacteriophage N

<400> SEQUENCE: 430

Met Lys Asn Arg Leu Leu Gly Ser Arg Tyr Thr Asp Ala Ile Lys Asn
1               5                   10                  15

Asp Ser Gly Thr Ala Asn Lys Met Ser Asn Ile Tyr Asn Ser Val Ile
            20                  25                  30

Asn Lys Glu Gly Leu Arg Gly Ile His Ser Ala Leu Tyr Gly Leu Leu
        35                  40                  45

Thr Ala Gly Tyr Asp Ile Ser Asn Met Arg Lys Ile Glu Glu Leu Glu
    50                  55                  60

Lys Tyr Val Asn Leu Lys Lys Ser Arg Gly Gln Leu Leu Asn Val Ser
65                  70                  75                  80

Ser Ser Asp Ile Lys Leu Tyr His Lys Leu Phe Val Ile Arg Phe Gly
                85                  90                  95

Lys

<210> SEQ ID NO 431
<211> LENGTH: 97
<212> TYPE: PRT
<213> ORGANISM: Bacteriophage N

<400> SEQUENCE: 431

Met Lys Asn Arg Leu Leu Gly Ser Arg Tyr Thr Asp Ala Ile Lys Asn
1               5                   10                  15

Asp Ser Gly Thr Ala Asn Lys Met Ser Asn Ile Tyr Asn Ser Val Ile
            20                  25                  30

Asn Lys Glu Gly Leu Arg Glu Ile His Ser Ala Leu Tyr Gly Leu Leu
        35                  40                  45

Thr Ala Gly Tyr Asp Ile Ser Asn Met Arg Lys Ile Glu Glu Leu Glu
    50                  55                  60

Lys Tyr Val Asn Leu Lys Lys Ser Arg Gly Gln Leu Leu Asn Val Ser
65                  70                  75                  80

```
Ser Asn Asp Ile Lys Leu Tyr His Lys Leu Phe Val Thr Arg Phe Gly
                85                  90                  95

Lys

<210> SEQ ID NO 432
<211> LENGTH: 96
<212> TYPE: PRT
<213> ORGANISM: Bacteriophage P

<400> SEQUENCE: 432

Met Lys Asn Arg Leu Leu Gly Ser Arg Tyr Thr Asp Ala Ile Lys Asn
1               5                   10                  15

Asp Ser Gly Thr Ala Asn Lys Met Ser Asn Ile Tyr Asn Lys Leu Asn
                20                  25                  30

Lys Asp Ser Leu Arg Glu Ile His Ser Ala Leu Tyr Gly Leu Leu Thr
            35                  40                  45

Ala Gly Tyr Asp Ile Ser Asn Met Arg Asn Ile Glu Glu Leu Glu Lys
        50                  55                  60

Tyr Val Asn Leu Lys Lys Ser Arg Gly Gln Leu Leu Asn Val Thr Ser
65                  70                  75                  80

Asn Asp Ile Lys Leu Tyr His Lys Leu Phe Val Ile Arg Phe Gly Lys
                85                  90                  95

<210> SEQ ID NO 433
<211> LENGTH: 96
<212> TYPE: PRT
<213> ORGANISM: Bacteriophage P

<400> SEQUENCE: 433

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
                20                  25                  30

Lys Asp Ser Leu Arg Glu Ile His Ser Ala Leu Tyr Gly Leu Leu Thr
            35                  40                  45

Ala Gly Tyr Asp Ile Ser Asn Met Arg Asn Ile Glu Glu Leu Glu Lys
        50                  55                  60

Tyr Val Asn Leu Lys Lys Ser Arg Gly Gln Leu Leu Asn Val Ser Ser
65                  70                  75                  80

Asp Asp Ile Lys Leu Tyr His Lys Leu Phe Val Ile Arg Phe Gly Lys
                85                  90                  95

<210> SEQ ID NO 434
<211> LENGTH: 98
<212> TYPE: PRT
<213> ORGANISM: Bacteriophage V

<400> SEQUENCE: 434

Met Lys Asn Gly Asn Lys Ile Leu Gly Tyr Arg Tyr Thr Asp Glu Ile
1               5                   10                  15

Lys Asn Asp Ser Ala Thr Glu Asn Lys Met Ser Asn Leu Tyr Asn Lys
                20                  25                  30

Leu Asp Lys Asp Ser Leu Arg Glu Ile His Ser Ala Leu Tyr Gly Leu
            35                  40                  45

Leu Thr Ala Gly Tyr Asp Ile Ser Asn Met Arg Asn Val Glu Glu Leu
        50                  55                  60

Glu Lys Tyr Val Asn Val Lys Lys Ser His Gly Lys Leu Leu Asp Val
```

```
                65                   70                  75                  80
Thr Asn Ser Asp Ile Gln Leu Tyr His Lys Leu Phe Val Val Arg Phe
                    85                  90                  95

Gly Arg

<210> SEQ ID NO 435
<211> LENGTH: 128
<212> TYPE: PRT
<213> ORGANISM: Bacteriophage D

<400> SEQUENCE: 435

Met Thr Glu Trp Lys Thr Ile Asn Phe Asn Ala Gln Asn Ile Glu Tyr
1               5                   10                  15

Glu Ala Ala Lys Ala Ile Leu Ile Lys Met Pro Asn Asn Ser Glu Trp
                20                  25                  30

His Gly Tyr Thr Phe Trp His Pro Ser Lys Cys Val Arg Thr Leu Ser
            35                  40                  45

Lys Gly Asn Gly Tyr Phe Lys Thr Phe Ser Tyr Thr Glu Asn Trp Glu
        50                  55                  60

Phe Thr Ile Phe Lys Ser Asn Lys Lys Gly Glu Arg Thr Ile Glu Gln
65                  70                  75                  80

Val Leu Thr Ala Arg Asp Met Glu Lys Ala Phe Ser Val Val Asn Glu
                85                  90                  95

Gln Ile Ala Ser Asn Ala Ser Thr Glu Ser Tyr Leu Glu Ile Glu Glu
                100                 105                 110

Pro Lys Lys Val Asp Lys Thr Val Ser Ile Asn Asn Glu Leu Lys Arg
            115                 120                 125

<210> SEQ ID NO 436
<211> LENGTH: 128
<212> TYPE: PRT
<213> ORGANISM: Bacteriophage D

<400> SEQUENCE: 436

Met Thr Glu Trp Lys Thr Ile Asn Phe Asn Lys Gln Asn Ile Glu His
1               5                   10                  15

Glu Thr Ala Lys Ala Val Leu Ile Lys Met Pro Asn Asn Ser Glu Trp
                20                  25                  30

Tyr Gly Tyr Lys Phe Trp His Pro Ser Lys Cys Val Arg Thr Leu Ser
            35                  40                  45

Lys Gly Asn Gly Tyr Phe Lys Thr Phe Ser Tyr Thr Glu Asn Trp Glu
        50                  55                  60

Phe Thr Ile Phe Lys Ser Asn Lys Lys Gly Glu Arg Thr Ala Glu Gln
65                  70                  75                  80

Ile Leu Thr Ala Glu Asp Met Glu Ile Ala Phe Asp Val Val Asn Glu
                85                  90                  95

Gln Ile Ser Ala Asn Ala Ser Thr Glu Ser Tyr Leu Glu Ile Glu Glu
                100                 105                 110

Pro Lys Lys Val Asp Lys Thr Val Ser Ile Asn Asn Glu Leu Lys Arg
            115                 120                 125

<210> SEQ ID NO 437
<211> LENGTH: 128
<212> TYPE: PRT
<213> ORGANISM: Bacteriophage D

<400> SEQUENCE: 437
```

```
Met Thr Glu Trp Lys Thr Ile Asn Phe Asn Ala Gln Asn Ile Glu Tyr
1               5                   10                  15

Glu Ala Ala Lys Ala Ile Leu Ile Lys Met Pro Asn Asn Ser Glu Trp
                20                  25                  30

His Gly Tyr Thr Phe Trp His Pro Ser Lys Cys Val Arg Thr Leu Ser
            35                  40                  45

Lys Gly Asn Gly Tyr Phe Lys Thr Phe Ser Tyr Thr Glu Asn Trp Glu
        50                  55                  60

Phe Thr Ile Phe Lys Ser Asn Lys Lys Gly Glu Arg Thr Ala Glu Gln
65                  70                  75                  80

Ile Leu Thr Ala Glu Asp Met Glu Ile Ala Phe Asp Val Val Asn Glu
                85                  90                  95

Gln Ile Ser Val Asp Ala Ser Thr Glu Ser Tyr Leu Glu Ile Glu Glu
            100                 105                 110

Pro Lys Lys Val Asp Lys Thr Val Ser Ile Asn Asn Glu Leu Lys Arg
        115                 120                 125
```

<210> SEQ ID NO 438
<211> LENGTH: 126
<212> TYPE: PRT
<213> ORGANISM: Bacteriophage D

<400> SEQUENCE: 438

```
Met Trp Lys Ser Ile Asn Phe Asn Ala Gln Asn Ile Glu His Glu Thr
1               5                   10                  15

Ala Lys Ala Val Leu Ile Lys Met Pro Asn Asn Ser Glu Trp Ser Gly
                20                  25                  30

Tyr Lys Phe Trp His Pro Ser Lys Cys Val Arg Thr Leu Ser Lys Gly
            35                  40                  45

Lys Gly Tyr Phe Lys Ile Phe Ser Tyr Thr Glu Asn Trp Glu Phe Thr
        50                  55                  60

Ile Phe Lys Ser Asn Lys Lys Gly Glu Arg Thr Ala Glu Gln Ile Leu
65                  70                  75                  80

Thr Ala Glu Asp Met Glu Ile Ala Phe Asp Val Val Asn Glu Gln Ile
                85                  90                  95

Ser Ala Asn Ala Ser Thr Glu Ser Tyr Leu Glu Ile Glu Glu Pro Lys
            100                 105                 110

Lys Val Asp Lys Thr Val Ser Ile Asn Asn Glu Leu Lys Arg
        115                 120                 125
```

<210> SEQ ID NO 439
<211> LENGTH: 126
<212> TYPE: PRT
<213> ORGANISM: Bacteriophage D

<400> SEQUENCE: 439

```
Met Trp Lys Ser Ile Asn Phe Asn Ala Gln Asn Ile Glu His Glu Thr
1               5                   10                  15

Ala Lys Ala Val Leu Ile Lys Met Pro Asn Asn Ser Glu Trp Ser Gly
                20                  25                  30

Tyr Lys Phe Trp His Pro Ser Lys Phe Val Arg Thr Leu Ser Lys Gly
            35                  40                  45

Lys Gly Tyr Phe Lys Ile Phe Ser Tyr Thr Glu Asn Trp Glu Phe Thr
        50                  55                  60

Ile Phe Lys Ser Asn Lys Lys Gly Glu Arg Thr Ala Glu Gln Ile Leu
65                  70                  75                  80
```

```
Thr Ala Glu Asp Met Glu Ile Ala Phe Asp Val Val Asn Glu Gln Ile
                85                  90                  95

Ser Ala Asn Ala Ser Thr Glu Ser Tyr Leu Glu Ile Glu Glu Pro Lys
            100                 105                 110

Lys Val Asp Lys Thr Val Ser Ile Asn Asn Glu Leu Lys Arg
        115                 120                 125

<210> SEQ ID NO 440
<211> LENGTH: 126
<212> TYPE: PRT
<213> ORGANISM: Bacteriophage D

<400> SEQUENCE: 440

Met Trp Lys Ser Ile Asn Phe Asn Ala Gln Asn Ile Glu His Glu Thr
1               5                   10                  15

Ala Lys Ala Val Leu Ile Lys Met Pro Asn Asn Ser Glu Trp Ser Gly
            20                  25                  30

Tyr Lys Phe Trp His Ser Ser Lys Cys Val Arg Thr Leu Ser Lys Gly
        35                  40                  45

Lys Gly Tyr Phe Gln Ser Phe Ser Tyr Thr Glu Asn Trp Glu Phe Thr
    50                  55                  60

Ile Phe Lys Ser Asn Lys Lys Gly Glu Arg Thr Ala Glu Gln Ile Leu
65                  70                  75                  80

Thr Ala Glu Asp Met Glu Ile Ala Phe Asp Val Val Asn Glu Gln Ile
                85                  90                  95

Ser Ala Asn Ala Ser Thr Glu Ser Tyr Leu Glu Ile Glu Glu Pro Lys
            100                 105                 110

Lys Val Asp Lys Thr Val Ser Ile Asn Asn Glu Leu Lys Arg
        115                 120                 125

<210> SEQ ID NO 441
<211> LENGTH: 128
<212> TYPE: PRT
<213> ORGANISM: Bacteriophage D

<400> SEQUENCE: 441

Met Thr Glu Trp Lys Thr Ile Asn Phe Asn Lys Gln Asn Ile Glu His
1               5                   10                  15

Glu Thr Val Lys Ala Val Leu Ile Lys Met Pro Asn Asn Ser Glu Trp
            20                  25                  30

Tyr Gly Tyr Lys Phe Trp His Pro Ser Lys Cys Val Arg Thr Leu Ser
        35                  40                  45

Lys Gly Asn Gly Tyr Phe Lys Thr Phe Ser Tyr Thr Glu Asn Trp Glu
    50                  55                  60

Phe Thr Ile Phe Lys Ser Asn Lys Lys Gly Glu Arg Thr Ala Glu Gln
65                  70                  75                  80

Ile Leu Thr Ala Glu Asp Met Glu Ile Ala Phe Asp Val Val Asn Glu
                85                  90                  95

Gln Ile Ser Ala Asn Ala Ser Thr Glu Ser Tyr Leu Glu Ile Glu Glu
            100                 105                 110

Pro Lys Lys Val Asp Lys Thr Val Ser Ile Asn Asn Glu Leu Lys Arg
        115                 120                 125

<210> SEQ ID NO 442
<211> LENGTH: 123
<212> TYPE: PRT
<213> ORGANISM: Bacteriophage D
```

```
<400> SEQUENCE: 442

Met Trp Lys Ser Ile Lys Phe Asn Ala Gln Asn Ile Lys Phe Glu Thr
1               5                   10                  15

Ala Lys Ala Val Leu Ile Lys Met Pro Asn Lys Ser Arg Tyr Ala Gly
            20                  25                  30

Tyr Met Phe Trp His Pro Leu Lys Leu Val Arg Val Glu Gly Gly Lys
        35                  40                  45

Gly Tyr Phe Met Ser Phe Ser Tyr Thr Asp Asp Phe Glu Phe Lys Val
    50                  55                  60

Phe Lys Gln Gly Lys Asn Arg Gln Ile Thr Ala Glu Ser Ile Leu Ser
65                  70                  75                  80

His Glu Glu Ile Glu Glu Ala Phe Glu Ile Val Asn Glu Gln Leu Ser
                85                  90                  95

Tyr Met Asp Glu Cys Tyr Leu Glu Val Thr Glu Pro Thr Lys Ile Asp
            100                 105                 110

Lys Glu Val Glu Val Lys Glu Glu Leu Arg Lys
        115                 120

<210> SEQ ID NO 443
<211> LENGTH: 123
<212> TYPE: PRT
<213> ORGANISM: Bacteriophage D

<400> SEQUENCE: 443

Met Trp Lys Ser Ile Lys Phe Asn Ala Gln Asn Ile Lys Phe Glu Thr
1               5                   10                  15

Ala Lys Ala Val Leu Ile Lys Met Pro Asn Lys Ser Arg Tyr Ala Gly
            20                  25                  30

Tyr Met Phe Trp His Pro Ala Lys Leu Val Arg Val Val Gly Gly Lys
        35                  40                  45

Gly Tyr Phe Met Ser Phe Ser Tyr Thr Asp Glu Phe Glu Phe Lys Ile
    50                  55                  60

Phe Lys Gln Gly Lys Asn Arg Gln Ile Thr Val Glu Lys Ile Leu Ser
65                  70                  75                  80

Pro Glu Glu Ile Glu Asp Ala Phe Glu Val Val Asn Glu Gln Leu Ser
                85                  90                  95

Asp Ile Asp Glu Cys Tyr Leu Glu Val Thr Glu Pro Thr Lys Ile Asn
            100                 105                 110

Asp Lys Val Glu Ile Arg Ala Glu Leu Arg Lys
        115                 120

<210> SEQ ID NO 444
<211> LENGTH: 123
<212> TYPE: PRT
<213> ORGANISM: Bacteriophage D

<400> SEQUENCE: 444

Met Trp Lys Ser Ile Lys Phe Asn Ala Gln Asn Ile Lys Phe Glu Thr
1               5                   10                  15

Ala Lys Ala Val Leu Ile Lys Met Pro Asn Lys Ser Arg Tyr Ala Gly
            20                  25                  30

Tyr Met Phe Trp His Pro Ser Lys Leu Val Arg Val Glu Gly Gly Lys
        35                  40                  45

Gly Tyr Phe Met Ser Phe Ser Tyr Thr Asp Asp Phe Glu Phe Lys Val
    50                  55                  60

Phe Lys Gln Gly Lys Asn Arg Gln Ile Thr Ala Glu Ser Ile Leu Ser
```

```
                65                  70                  75                  80
His Glu Glu Ile Glu Glu Ala Phe Glu Ile Val Asn Glu Gln Leu Ser
                    85                  90                  95

Tyr Met Asp Glu Cys Tyr Leu Glu Val Thr Glu Pro Thr Lys Ile Asp
                100                 105                 110

Lys Glu Val Glu Val Lys Glu Leu Arg Lys
                115                 120

<210> SEQ ID NO 445
<211> LENGTH: 123
<212> TYPE: PRT
<213> ORGANISM: Bacteriophage D

<400> SEQUENCE: 445

Met Trp Lys Ser Ile Lys Phe Asn Ala Gln Asn Val Lys Phe Glu Thr
  1               5                  10                  15

Ala Asn Ser Val Leu Ile Lys Met Pro Asn Lys Ser Ser Tyr Ala Gly
                 20                  25                  30

Tyr Met Phe Trp His Pro Ala Lys Leu Val Arg Val Leu Gly Gly Lys
             35                  40                  45

Gly Tyr Phe Leu Ser Phe Ser Tyr Thr Asp Glu Phe Glu Phe Lys Val
         50                  55                  60

Phe Lys Gln Gly Lys Asn Arg Gln Ile Thr Ala Glu Ala Ile Leu Ser
 65                  70                  75                  80

His Glu Glu Met Glu Asp Ala Phe Glu Ile Val Asn Glu His Leu Ser
                    85                  90                  95

Tyr Thr Asp Glu Cys Tyr Leu Glu Val Ala Glu Pro Thr Lys Ile Asp
                100                 105                 110

Lys Glu Val Glu Ile Arg Glu Glu Leu Arg Lys
                115                 120

<210> SEQ ID NO 446
<211> LENGTH: 59
<212> TYPE: PRT
<213> ORGANISM: Bacteriophage D

<400> SEQUENCE: 446

Met Lys Val Tyr Tyr Asn Leu Ala Asp Ser Gly Leu Phe Lys Glu Ile
  1               5                  10                  15

Lys Lys Gln Leu Ala Leu Asp Asp Ala Glu Asn Gly Asp Leu Ile His
                 20                  25                  30

Thr Thr Glu Asp Asn Glu Ala Ser Asp Gly Thr Lys Ile Val Ala Ile
             35                  40                  45

Trp Asn Ala Asn Arg Gln Asn Tyr Phe Ile Lys
         50                  55

<210> SEQ ID NO 447
<211> LENGTH: 145
<212> TYPE: PRT
<213> ORGANISM: Bacteriophage D

<400> SEQUENCE: 447

Met Arg Asn Asp Phe Ile Asn Lys Val Tyr Asp Glu Leu Asn Gln Ile
  1               5                  10                  15

Ile Asn His Trp Ala Lys Gln Lys Tyr Leu Ser Asp Lys Ile Phe Glu
                 20                  25                  30

Tyr Thr Asn Thr Phe Ser Ile Lys Lys Val Tyr Gly Leu Tyr Trp Glu
             35                  40                  45
```

Val Lys Ile Leu Cys Lys Asn Asp Tyr Arg Ile Leu Leu Arg Phe Tyr
    50                  55                  60

Lys Asn Tyr Glu Trp Tyr Asn Asp Ser Asn Ile Leu Asn Val Ser Val
 65                  70                  75                  80

Leu Ala Pro Ala Val Glu Arg Val Lys Asn Glu Asp Gly Ser Val Asp
                85                  90                  95

Val Tyr Pro Ser Lys Ile Ile Lys Asp Lys Ile Glu Phe Ile Glu Gly
               100                 105                 110

Asp Phe Asp Ile Asp Gly Asp Asp Trp Val Asp Glu Val Leu Glu Tyr
               115                 120                 125

Ile Asn Lys Trp Val Asn Lys Asp Lys Ala Asp Val Glu Val Leu Asp
           130                 135                 140

Lys
145

<210> SEQ ID NO 448
<211> LENGTH: 145
<212> TYPE: PRT
<213> ORGANISM: Bacteriophage D

<400> SEQUENCE: 448

Met Arg Asn Asp Phe Ile Asn Lys Val Tyr Asp Glu Leu Asn Gln Ile
  1               5                  10                  15

Ile Asn His Trp Ala Lys Gln Lys Tyr Leu Ser Asp Lys Ile Phe Glu
                20                  25                  30

Tyr Thr Asn Thr Phe Ser Ile Lys Lys Val Tyr Gly Leu Tyr Trp Glu
            35                  40                  45

Val Lys Ile Leu Cys Lys Asn Asp Tyr Arg Ile Leu Leu Arg Phe Tyr
    50                  55                  60

Lys Asn Tyr Glu Trp Tyr Asn Asp Ser Asn Ile Leu Asn Val Ser Val
 65                  70                  75                  80

Leu Ala Pro Ala Val Glu Arg Val Lys Asn Glu Asp Gly Ser Val Asp
                85                  90                  95

Val Tyr Pro Ser Lys Lys Ile Lys Asp Lys Ile Glu Phe Ile Glu Gly
               100                 105                 110

Asp Phe Asp Ile Asp Gly Asp Asp Trp Val Asp Glu Val Leu Glu Tyr
               115                 120                 125

Ile Asn Lys Trp Val Asn Lys Asp Lys Ala Asp Val Glu Val Leu Asp
           130                 135                 140

Lys
145

<210> SEQ ID NO 449
<211> LENGTH: 145
<212> TYPE: PRT
<213> ORGANISM: Bacteriophage D

<400> SEQUENCE: 449

Met Arg Asn Asp Phe Ile Asn Lys Val Tyr Asp Glu Leu Asn Gln Ile
  1               5                  10                  15

Ile Asn His Trp Ala Lys Gln Lys Tyr Leu Ser Asp Lys Ile Phe Glu
                20                  25                  30

Tyr Thr Asn Thr Phe Ser Ile Lys Lys Val Tyr Gly Leu Tyr Trp Glu
            35                  40                  45

Val Lys Ile Leu Cys Lys Asn Asp Tyr Arg Ile Leu Leu Arg Phe Tyr
    50                  55                  60

```
Lys Asn Tyr Glu Trp Tyr Asn Asp Ser Asn Ile Leu Asn Val Ser Val
 65                  70                  75                  80

Leu Ala Pro Ala Val Glu Arg Val Lys Asn Glu Asp Gly Ser Val Asp
                 85                  90                  95

Val Tyr Pro Ser Lys Lys Ile Lys Asp Lys Ile Glu Phe Ile Glu Gly
            100                 105                 110

Asn Phe Asp Ile Asp Gly Asp Asp Trp Val Asp Glu Val Leu Glu Tyr
        115                 120                 125

Ile Asn Lys Trp Val Asn Lys Asp Lys Ala Asp Val Glu Val Leu Asp
    130                 135                 140

Lys
145

<210> SEQ ID NO 450
<211> LENGTH: 121
<212> TYPE: PRT
<213> ORGANISM: Bacteriophage D

<400> SEQUENCE: 450

Met Arg Asn Asp Phe Ile Asn Lys Val Tyr Asp Glu Leu Asn Gln Ile
  1               5                  10                  15

Ile Asn His Trp Ala Lys Gln Lys Tyr Leu Ser Asp Lys Ile Phe Glu
                 20                  25                  30

Tyr Thr Asn Thr Phe Ser Ile Lys Val Tyr Gly Leu Tyr Trp Glu
             35                  40                  45

Val Lys Ile Leu Cys Lys Asn Asp Tyr Arg Ile Leu Leu Arg Phe Tyr
     50                  55                  60

Lys Asn Tyr Glu Trp Tyr Asn Asp Ser Asn Ile Leu Asn Val Ser Val
 65                  70                  75                  80

Leu Ala Pro Ala Val Glu Arg Val Lys Asn Glu Asp Gly Ser Val Asp
                 85                  90                  95

Val Tyr Pro Ser Lys Lys Leu Lys Ile Lys Leu Asn Leu Leu Lys Val
            100                 105                 110

Ile Leu Ile Leu Met Glu Met Ile Gly
        115                 120

<210> SEQ ID NO 451
<211> LENGTH: 145
<212> TYPE: PRT
<213> ORGANISM: Bacteriophage D

<400> SEQUENCE: 451

Met Arg Asn Asp Phe Ile Asn Lys Val Tyr Asp Glu Leu Asn Gln Ile
  1               5                  10                  15

Ile Asn His Trp Ala Lys Gln Lys Tyr Leu Ser Asp Lys Ile Phe Glu
                 20                  25                  30

Tyr Thr Asn Thr Phe Ser Ile Lys Val Tyr Gly Leu Tyr Trp Glu
             35                  40                  45

Val Lys Ile Leu Cys Lys Asn Asp Tyr Arg Ile Leu Leu Arg Phe Tyr
     50                  55                  60

Lys Asn Tyr Glu Trp Tyr Asn Asp Ser Asn Ile Leu Asn Val Ser Val
 65                  70                  75                  80

Leu Ala Pro Ala Val Glu Arg Val Glu Asn Glu Asp Gly Ser Val Asp
                 85                  90                  95

Val Tyr Pro Ser Lys Ile Ile Lys Asp Lys Ile Glu Phe Ile Glu Gly
            100                 105                 110
```

```
Asp Phe Asp Ile Asp Gly Asp Asp Trp Val Asp Glu Val Leu Glu Tyr
        115                 120                 125

Ile Asn Lys Trp Val Asn Lys Asp Lys Ala Asp Val Glu Val Leu Asp
130                 135                 140

Lys
145

<210> SEQ ID NO 452
<211> LENGTH: 145
<212> TYPE: PRT
<213> ORGANISM: Bacteriophage D

<400> SEQUENCE: 452

Met Arg Asn Asp Phe Ile Asn Lys Val Tyr Asp Glu Leu Asn Pro Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Lys Val Tyr Gly Leu Tyr Trp Glu
        35                  40                  45

Val Lys Ile Leu Cys Lys Asn Asp Tyr Arg Ile Leu Leu Arg Phe Tyr
50                  55                  60

Lys Asn His Glu Trp Tyr Asn Asp Ser Asn Ile Leu Asn Val Ser Val
65                  70                  75                  80

Leu Ala Pro Ala Val Glu Arg Val Lys His Glu Asp Gly Ser Val Asp
                85                  90                  95

Val Tyr Pro Ser Lys Ile Ile Lys Asp Lys Ile Glu Phe Ile Glu Gly
            100                 105                 110

Asp Phe Asp Ile Asp Gly Tyr Asp Trp Val Asp Glu Val Leu Glu Tyr
        115                 120                 125

Ile Asn Lys Trp Val Asn Lys Asp Asp Asp Val Glu Val Leu Asp
130                 135                 140

Lys
145

<210> SEQ ID NO 453
<211> LENGTH: 145
<212> TYPE: PRT
<213> ORGANISM: Bacteriophage O

<400> SEQUENCE: 453

Met Arg Asn Asp Phe Ile Asn Lys Val Tyr Asp Glu Leu Asn Gln Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Lys Val Tyr Gly Leu Tyr Trp Glu
        35                  40                  45

Val Lys Ile Leu Cys Lys Asn Asp Tyr Arg Ile Leu Leu Arg Phe Tyr
50                  55                  60

Lys Asn Tyr Glu Trp Tyr Asn Asp Ser Asn Ile Leu Asn Val Ser Val
65                  70                  75                  80

Leu Ala Pro Ala Val Glu Arg Val Lys Asn Glu Asp Gly Ser Val Asp
                85                  90                  95

Val Tyr Pro Ser Lys Ile Ile Lys Asp Lys Ile Glu Phe Ile Glu Gly
            100                 105                 110

Asn Phe Asp Ile Asp Gly Asp Asp Trp Val Asp Glu Val Leu Glu Tyr
        115                 120                 125
```

Ile Asn Lys Trp Val Asn Lys Asp Lys Ala Asp Val Glu Val Leu Asp
            130                 135                 140

Lys
145

<210> SEQ ID NO 454
<211> LENGTH: 105
<212> TYPE: PRT
<213> ORGANISM: Bacteriophage D

<400> SEQUENCE: 454

Met Lys Asn Phe Lys Ile Ser Ser Thr Tyr Arg Ala Ala Arg Lys Gln
1               5                   10                  15

Gln Lys Thr Ala Asn Arg Lys Ser Phe Tyr Asn Asp Glu Gly Tyr Met
            20                  25                  30

Ile Ser Pro Ser Glu Trp Ala Asp Gly Val Ile Lys Gly Leu Ile Asn
        35                  40                  45

Pro Lys Asn Ser Trp Ser Asn Asp His Val Lys Gly Tyr Leu Pro Arg
    50                  55                  60

Val Ser Pro Arg Ser His Trp Thr Lys Asn Gly Tyr Arg Glu Tyr Leu
65                  70                  75                  80

Gly Ile Gly Lys Ser Arg Asp Ile Pro Glu Lys Glu Pro Glu Val Ile
                85                  90                  95

Glu Met Met Asp Leu Glu Leu Val Pro
            100                 105

<210> SEQ ID NO 455
<211> LENGTH: 105
<212> TYPE: PRT
<213> ORGANISM: Bacteriophage P

<400> SEQUENCE: 455

Met Lys Asn Phe Lys Ile Ser Ser Thr Tyr Arg Ala Ala Arg Lys Gln
1               5                   10                  15

Gln Lys Thr Ala Asn Arg Lys Ser Phe Tyr Asn Asp Glu Gly Tyr Met
            20                  25                  30

Ile Ser Pro Ser Glu Trp Val Asp Gly Val Ile Lys Gly Leu Ile Asn
        35                  40                  45

Pro Lys Asn Ser Trp Ser Asn Asp His Val Lys Gly Tyr Leu Pro Arg
    50                  55                  60

Val Ser Pro Arg Ser His Trp Thr Lys Asn Gly Tyr Arg Glu Tyr Leu
65                  70                  75                  80

Gly Ile Gly Lys Ser Arg Asp Ile Pro Glu Lys Glu Pro Glu Val Ile
                85                  90                  95

Glu Met Met Asp Leu Glu Leu Val Pro
            100                 105

<210> SEQ ID NO 456
<211> LENGTH: 105
<212> TYPE: PRT
<213> ORGANISM: Bacteriophage Proph

<400> SEQUENCE: 456

Met Lys Asn Phe Lys Ile Ser Ser Thr Tyr Arg Ala Ala Arg Lys Gln
1               5                   10                  15

Gln Lys Thr Ala Asn Arg Lys Ser Phe Tyr Asn Asp Glu Gly Tyr Met
            20                  25                  30

```
Ile Ser Pro Ser Glu Trp Ala Asp Gly Val Ile Lys Gly Leu Ile Asn
         35                  40                  45

Pro Lys Asn Ser Trp Ser Asn Asp His Val Lys Gly Tyr Leu Pro Arg
 50                  55                  60

Val Ser Pro Arg Ser His Trp Thr Lys Asn Gly Tyr Arg Glu Tyr Leu
 65                  70                  75                  80

Gly Ile Gly Lys Ser Arg Asp Ile Pro Lys Lys Glu Pro Glu Val Ile
                 85                  90                  95

Glu Met Met Asp Leu Glu Leu Val Pro
            100                 105
```

<210> SEQ ID NO 457
<211> LENGTH: 128
<212> TYPE: PRT
<213> ORGANISM: Bacteriophage D

<400> SEQUENCE: 457

```
Met Lys Tyr Asp Lys Ser Gly Ile Met Lys Glu Ala Trp Asn Leu Phe
 1               5                  10                  15

Asn Asn Asp Asp Ile Thr Phe Ala Asp Phe Glu Tyr Leu Thr Arg Glu
                 20                  25                  30

Glu Arg Gln Gly Lys Lys Thr Phe Thr Leu Cys Leu Lys Glu Ala Trp
             35                  40                  45

Ala His Glu Lys Glu Ile Val Asp Ser Ile Lys Lys Asp His Ala Asp
 50                  55                  60

Ala Glu His Ser Val Glu Ala Lys Ala Trp Asp Trp Ala Cys Lys Lys
 65                  70                  75                  80

Leu Gly Val Ser Ile Glu Met Asp Ala Tyr Thr Lys Phe Val Asn Val
                 85                  90                  95

Asn Asp Met Lys Lys Glu Ala Trp Pro Gly Thr Ser Val Trp Ser Leu
            100                 105                 110

Ala Met Arg Ala Val Lys Leu His Ile Lys Leu Phe Gly Gln Val Ala
            115                 120                 125
```

<210> SEQ ID NO 458
<211> LENGTH: 173
<212> TYPE: PRT
<213> ORGANISM: Bacteriophage D

<400> SEQUENCE: 458

```
Met Asn Gly Leu Lys Thr Ile Leu Lys Thr Phe Asp Lys Asn Ile Tyr
 1               5                  10                  15

Phe Leu Thr Lys Ser Val Asp Ile Arg Gln His Arg Arg Tyr Asn Ile
                 20                  25                  30

Tyr Val Lys Leu Arg Glu Glu Val Asn Asp Met Lys Lys Ser Thr Tyr
             35                  40                  45

Asp Lys Ser Gly Ile Met Lys Glu Ala Trp Asn Leu Phe Asn Asn Asp
 50                  55                  60

Asp Ile Thr Thr Ala Asp Phe Glu Tyr Leu Thr Arg Gly Glu Leu Gln
 65                  70                  75                  80

Glu Gly Lys Thr Phe Ala Ile Cys Leu Lys Glu Ala Trp Ala His Glu
                 85                  90                  95

Lys Asp Ile Val Glu Ser Leu Asn Glu Asp Tyr Glu Asn Ala Glu His
            100                 105                 110

Ser Val Gln Ala Lys Ala Trp Asp Trp Ala Cys Lys Lys Leu Gly Val
            115                 120                 125
```

Ser Ile Glu Val Asp Ala Tyr Thr Lys Leu Val Asn Val Asn Asp Met
        130                 135                 140

Gln Lys Glu Ser Trp Pro Gly Thr Ser Ala Trp Ser Leu Ala Met Arg
145                 150                 155                 160

Ala Val Lys Leu His Ile Lys Leu Phe Gly Gln Ala Ala
                165                 170

<210> SEQ ID NO 459
<211> LENGTH: 173
<212> TYPE: PRT
<213> ORGANISM: Bacteriophage D

<400> SEQUENCE: 459

Met Asn Gly Leu Lys Thr Ile Leu Lys Thr Phe Asp Lys Asn Ile Tyr
1               5                   10                  15

Phe Leu Thr Lys Ser Val Asp Ile Arg Gln His Arg Arg Tyr Asn Ile
            20                  25                  30

Tyr Val Lys Leu Arg Glu Glu Val Asn Asp Met Lys Lys Ser Thr Tyr
            35                  40                  45

Asp Lys Ser Gly Ile Met Lys Glu Ala Trp Asn Leu Phe Asn Asn Asp
        50                  55                  60

Asp Ile Thr Thr Ala Asp Phe Glu Tyr Leu Thr Arg Gly Glu Leu Gln
65                  70                  75                  80

Glu Gly Lys Thr Phe Ala Ile Cys Leu Lys Glu Ala Trp Ala His Glu
                85                  90                  95

Lys Asp Ile Val Glu Ser Leu Asn Glu Asp Tyr Glu Asn Ala Glu His
            100                 105                 110

Ser Val Gln Ala Lys Ala Trp Asp Trp Ala Cys Lys Lys Leu Gly Val
        115                 120                 125

Ser Ile Glu Val Asp Ala Tyr Thr Lys Leu Val Asn Val Asn Asp Met
        130                 135                 140

Gln Lys Glu Ser Trp Pro Gly Thr Ser Ala Trp Ser Leu Ala Met Arg
145                 150                 155                 160

Ala Val Lys Leu His Ile Lys Leu Phe Gly Gln Ala Ala
                165                 170

<210> SEQ ID NO 460
<211> LENGTH: 111
<212> TYPE: PRT
<213> ORGANISM: Bacteriophage

<400> SEQUENCE: 460

Met Lys Lys Glu Val Met Thr Asn Ala Trp Lys Ile Ala Lys Glu Ala
1               5                   10                  15

Val Lys Lys Phe Gly Gly Lys Ala Ile Glu Tyr Ile Ala Glu Ala Leu
            20                  25                  30

Lys Met Ala Trp Ala Ala Ala Lys Gly Gly Asn Ala Ser Leu Ala Lys
            35                  40                  45

Phe Gln Ala Val Glu Ser Lys Met Arg Lys Ala Gly Lys Tyr Ser Met
        50                  55                  60

Ile Gln Val Leu Asn Phe Ala Lys Glu Val Lys Phe Asn Glu Val Met
65                  70                  75                  80

His Lys Val Gly Ala Tyr Tyr Gly Ile Glu Val Val Ala Asp Gly Asp
                85                  90                  95

Ser Ile Gly Thr Tyr Tyr Ile Ala Glu Lys Val Trp Asp Ala Ala
            100                 105                 110

```
<210> SEQ ID NO 461
<211> LENGTH: 111
<212> TYPE: PRT
<213> ORGANISM: Bacteriophage P

<400> SEQUENCE: 461

Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Gly Ala Met
            20                  25                  30

Lys Met Ala Trp Ala Ala Ile Lys Asp Asn Gly Thr Ser Leu Ala Lys
        35                  40                  45

Phe Gln Ala Val Glu Ala Lys Met Arg Lys Ala Gly Lys Tyr Ser Met
    50                  55                  60

Ile Gln Val Leu Asp Phe Ala Lys Glu Val Arg Phe Asn Glu Val Met
65                  70                  75                  80

His Lys Val Gly Ala Tyr Tyr Gly Ile Glu Val Ile Ala Asp Gly Asp
                85                  90                  95

Ser Ile Gly Thr Tyr Tyr Ile Ala Glu Asn Val Trp Asn Ala Ala
            100                 105                 110

<210> SEQ ID NO 462
<211> LENGTH: 111
<212> TYPE: PRT
<213> ORGANISM: Bacteriophage CHPC

<400> SEQUENCE: 462

Met Lys Lys Glu Ile Met Thr Lys Ala Trp Lys Ile Ala Lys Asn Ala
1               5                   10                  15

Ser Thr Lys Phe Gly Gly Lys Ala Ile Glu Tyr Ile Ala Gly Ala Met
            20                  25                  30

Lys Met Ala Trp Ala Ala Ile Lys Glu Asn Gly Thr Ser Leu Ala Lys
        35                  40                  45

Phe Gln Ala Val Glu Ala Lys Met Arg Lys Ala Gly Lys His Ser Met
    50                  55                  60

Val Gln Val Leu Asn Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Ser Ile Gly Thr Tyr Tyr Ile Ala Glu Lys Val Trp Asn Ala Ala
            100                 105                 110

<210> SEQ ID NO 463
<211> LENGTH: 111
<212> TYPE: PRT
<213> ORGANISM: Bacteriophage D

<400> SEQUENCE: 463

Met Lys Lys Glu Ile Met Thr Lys Ala Trp Lys Ile Ala Lys Glu Ala
1               5                   10                  15

Val Glu Lys Phe Gly Gly Lys Ala Ile Glu Tyr Ile Ala Gly Ala Met
            20                  25                  30

Lys Met Ala Trp Ala Ala Ala Lys Ala Gly Asn Thr Ser Val Ala Lys
        35                  40                  45

Phe Gln Ala Val Glu Asp Lys Met Arg Lys Ala Gly Lys Tyr Ser Met
    50                  55                  60

Ile Gln Val Leu Asn Phe Ala Asn Glu Val Lys Phe Asn Glu Val Met
```

```
                65                  70                  75                  80
His Lys Ala Gly Ala Tyr Tyr Gly Ile Glu Val Ile Ala Asp Gly Asp
                    85                  90                  95

Ser Ile Gly Thr Tyr Tyr Ile Ala Glu Lys Val Trp Glu Val Ala
                100                 105                 110

<210> SEQ ID NO 464
<211> LENGTH: 108
<212> TYPE: PRT
<213> ORGANISM: Bacteriophage D

<400> SEQUENCE: 464

Met Lys Lys Glu Val Met Thr Asn Ala Trp Glu Ile Ala Lys Asn Ala
1               5                   10                  15

Ser Lys Lys Phe Gly Gly Lys Ala Ile Glu Tyr Ile Ala Gly Ala Met
                20                  25                  30

Lys Met Ala Trp Ala Ala Ala Lys Gly Gly Leu Ala Lys Phe Gln Ala
                35                  40                  45

Val Glu Ser Lys Met Arg Lys Ala Gly Lys His Ser Met Val Gln Val
                50                  55                  60

Leu Asn Phe Ala Lys Glu Val Lys Phe Asn Glu Val Met His Lys Ala
65                  70                  75                  80

Gly Ala Tyr Tyr Gly Ile Glu Val Ile Ala Asp Gly Asp Ser Ile Gly
                    85                  90                  95

Thr Tyr Tyr Ile Ser Glu Lys Val Trp Glu Val Ala
                100                 105

<210> SEQ ID NO 465
<211> LENGTH: 111
<212> TYPE: PRT
<213> ORGANISM: Bacteriophage D

<400> SEQUENCE: 465

Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Gly Ala Met
                20                  25                  30

Lys Met Ala Trp Ala Ala Ala Lys Ala Gly Asn Thr Ser Leu Ala Lys
                35                  40                  45

Phe Gln Ala Val Glu Ser Lys Met Arg Lys Ala Gly Lys Tyr Ser Met
                50                  55                  60

Ile Gln Val Leu Asn Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                    85                  90                  95

Ser Ile Gly Thr Tyr Tyr Ile Ala Glu Ser Val Trp Glu Val Ala
                100                 105                 110

<210> SEQ ID NO 466
<211> LENGTH: 111
<212> TYPE: PRT
<213> ORGANISM: Bacteriophage D

<400> SEQUENCE: 466

Met Lys Lys Glu Ile Met Thr Lys Ala Trp Lys Ile Ala Lys Glu Ala
1               5                   10                  15

Val Glu Lys Phe Gly Gly Lys Ala Ile Glu Tyr Ile Ala Gly Ala Met
                20                  25                  30
```

```
Lys Met Ala Trp Ala Ala Ala Lys Ala Gly Asn Thr Ser Val Ala Lys
            35                  40                  45

Phe Gln Ala Val Glu Asp Lys Met Arg Lys Ala Gly Lys Tyr Ser Met
        50                  55                  60

Ile Gln Val Leu Asn Phe Ala Asn Glu Val Lys Phe Asn Glu Val Met
65                  70                  75                  80

His Lys Ala Gly Ala Tyr Tyr Gly Ile Glu Val Ile Ala Asp Gly Asp
                85                  90                  95

Ser Ile Gly Thr Tyr Tyr Ile Ala Glu Lys Val Trp Glu Val Ala
            100                 105                 110

<210> SEQ ID NO 467
<211> LENGTH: 105
<212> TYPE: PRT
<213> ORGANISM: Bacteriophage D

<400> SEQUENCE: 467

Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Met
            20                  25                  30

Lys Met Ala Trp Ala Ala Ala Lys Gly Gly Leu Ala Lys Phe Gln Ala
            35                  40                  45

Val Glu Ser Lys Met Arg Lys Ala Gly Met Ile Gln Val Leu Asn Phe
        50                  55                  60

Ala Lys Glu Val Lys Phe Asn Glu Val Met His Lys Val Gly Ala Tyr
65                  70                  75                  80

Tyr Gly Ile Glu Val Ile Ala Asp Gly Asp Ser Ile Gly Thr Tyr Tyr
                85                  90                  95

Ile Ala Glu Ser Val Trp Glu Val Ala
            100                 105

<210> SEQ ID NO 468
<211> LENGTH: 111
<212> TYPE: PRT
<213> ORGANISM: Bacteriophage D

<400> SEQUENCE: 468

Met Lys Ser Gln Val Met Ser Leu Ala Trp Lys Ile Ala Lys Asn Ala
1               5                   10                  15

Ser Thr Lys Phe Gly Gly Lys Ala Ile Glu Tyr Ile Ala Arg Ala Met
            20                  25                  30

Lys Met Ala Trp Ser Ala Ile Lys Glu Asn Gly Thr Ser Leu Ala Lys
            35                  40                  45

Phe Gln Ala Ile Glu Ala Lys Ile Arg Lys Ala Gly Lys His Ser Met
        50                  55                  60

Val Gln Val Leu Lys Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Ser Ile Gly Thr Tyr Tyr Ile Ala Glu Lys Val Trp Asp Ala Ala
            100                 105                 110

<210> SEQ ID NO 469
<211> LENGTH: 111
<212> TYPE: PRT
<213> ORGANISM: Bacteriophage D
```

<400> SEQUENCE: 469

Met Lys Lys Glu Ile Met Lys Lys Ala Trp Lys Ile Ala Lys Glu Ala
1               5                   10                  15

Val Lys Lys Phe Gly Gly Lys Ala Ile Glu Tyr Ile Ala Glu Ala Leu
            20                  25                  30

Lys Met Ala Trp Ala Asp Ala Lys Gly Gly Asn Thr Ser Leu Ala Lys
        35                  40                  45

Phe Gln Ala Val Glu Glu Lys Met Arg Lys Ala Gly Lys Tyr Ser Met
    50                  55                  60

Ile Gln Val Leu Asn Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Lys Ile Gly Thr Tyr Phe Ile Ala Glu Lys Val Trp Asp Ala Ala
            100                 105                 110

<210> SEQ ID NO 470
<211> LENGTH: 111
<212> TYPE: PRT
<213> ORGANISM: Bacteriophage D

<400> SEQUENCE: 470

Met Lys Lys Glu Leu Met Lys Asp Ala Trp Glu Ile Ala Lys Asn Ala
1               5                   10                  15

Ser Lys Lys Phe Gly Gly Lys Ala Ile Glu Tyr Ile Ala Gly Ala Met
            20                  25                  30

Lys Met Ala Trp Ala Ala Ala Lys Ala Gly Asn Thr Ser Val Ala Lys
        35                  40                  45

Phe Gln Ala Val Glu Ala Lys Met Arg Lys Ala Gly Lys His Ser Met
    50                  55                  60

Ile Gln Val Leu Asp Phe Ala Lys Glu Val Lys Phe Asn Glu Val Met
65                  70                  75                  80

His Lys Val Gly Ala Tyr Tyr Gly Ile Glu Val Val Ala Asp Gly Asp
                85                  90                  95

Ser Ile Gly Thr Tyr Tyr Ile Ala Glu Lys Val Trp Asp Val Ala
            100                 105                 110

<210> SEQ ID NO 471
<211> LENGTH: 111
<212> TYPE: PRT
<213> ORGANISM: Bacteriophage D

<400> SEQUENCE: 471

Met Lys Lys Glu Val Met Thr Asn Ala Trp Lys Ile Ala Lys Glu Ala
1               5                   10                  15

Val Lys Lys Phe Gly Gly Lys Ala Ile Glu Tyr Ile Ser Glu Ala Met
            20                  25                  30

Lys Met Ala Trp Ala Ala Ala Lys Gly Glu Asn Thr Ser Leu Ala Lys
        35                  40                  45

Phe Gln Ala Val Glu Glu Lys Met Arg Lys Ala Gly Lys Tyr Ser Met
    50                  55                  60

Ile Gln Val Leu Asp Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

```
Asn Ile Gly Thr Tyr Tyr Ile Ala Glu Lys Val Trp Glu Val Ala
            100                 105                 110
```

<210> SEQ ID NO 472
<211> LENGTH: 106
<212> TYPE: PRT
<213> ORGANISM: Bacteriophage D

<400> SEQUENCE: 472

```
Met Thr Asn Ala Trp Lys Ile Ala Lys Glu Ala Val Lys Lys Phe Gly
1               5                   10                  15

Gly Lys Ala Ile Glu Tyr Ile Ser Glu Ala Met Lys Ile Ala Trp Ala
            20                  25                  30

Asp Ala Lys Glu Gly Asn Thr Ser Val Ala Lys Phe Gln Ala Val Glu
        35                  40                  45

Ala Lys Met Arg Lys Ala Gly Lys His Ser Met Val Gln Val Leu Asn
    50                  55                  60

Phe Ala Lys Glu Val Lys Phe Asn Glu Val Met His Lys Val Gly Ala
65                  70                  75                  80

Tyr Tyr Gly Ile Glu Val Ile Ala Asp Gly Asp Ser Ile Gly Thr Tyr
                85                  90                  95

Tyr Ile Ser Glu Lys Val Trp Glu Val Ala
            100                 105
```

<210> SEQ ID NO 473
<211> LENGTH: 111
<212> TYPE: PRT
<213> ORGANISM: Bacteriophage D

<400> SEQUENCE: 473

```
Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Met
            20                  25                  30

Lys Met Ala Trp Ala Ala Ala Lys Gly Gly Asn Ala Ser Leu Ala Lys
        35                  40                  45

Phe Gln Ala Val Glu Ser Lys Met Arg Lys Ala Gly Lys Tyr Ser Met
    50                  55                  60

Ile Gln Val Leu Asn Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Ser Ile Gly Thr Tyr Tyr Ile Ala Glu Ser Val Trp Glu Val Ala
            100                 105                 110
```

<210> SEQ ID NO 474
<211> LENGTH: 108
<212> TYPE: PRT
<213> ORGANISM: Bacteriophage D

<400> SEQUENCE: 474

```
Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Met
            20                  25                  30

Lys Met Ala Trp Ala Ala Ala Lys Gly Gly Leu Ala Lys Phe Gln Ala
        35                  40                  45

Val Glu Ser Lys Met Arg Lys Ala Gly Lys Tyr Ser Met Ile Gln Val
```

```
                    50                  55                  60

Leu Asn Phe Ala Lys Glu Val Lys Phe Asn Glu Val Met His Lys Val
 65                  70                  75                  80

Gly Ala Tyr Tyr Gly Ile Glu Val Ile Ala Asp Gly Asp Ser Ile Gly
                     85                  90                  95

Thr Tyr Tyr Ile Ala Glu Ser Val Trp Glu Val Ala
                100                 105
```

<210> SEQ ID NO 475
<211> LENGTH: 111
<212> TYPE: PRT
<213> ORGANISM: Bacteriophage D

<400> SEQUENCE: 475

```
Met Lys Lys Glu Ile Met Lys Lys Ala Trp Glu Ile Ala Lys Glu Ala
 1               5                  10                  15

Val Lys Lys Phe Gly Gly Lys Ala Ile Glu Tyr Ile Ala Glu Ala Leu
                20                  25                  30

Lys Met Ala Trp Ser Asp Ala Lys Gly Ser Asn Thr Ser Leu Ala Lys
                35                  40                  45

Phe Gln Ala Val Glu Glu Lys Met Arg Lys Ala Gly Lys Tyr Ser Met
    50                  55                  60

Ile Gln Val Leu Asp Phe Ala Lys Glu Val Lys Phe Asn Glu Val Met
 65                  70                  75                  80

His Lys Glu Gly Ala Tyr Tyr Gly Ile Glu Val Val Ala Asp Gly Asp
                 85                  90                  95

Ser Ile Gly Thr Tyr Tyr Ile Ala Glu Lys Val Trp Glu Val Ala
                100                 105                 110
```

<210> SEQ ID NO 476
<211> LENGTH: 111
<212> TYPE: PRT
<213> ORGANISM: Bacteriophage D

<400> SEQUENCE: 476

```
Met Lys Lys Glu Ile Met Thr Lys Ala Trp Glu Ile Ala Lys Asn Ala
 1               5                  10                  15

Ser Lys Lys Phe Gly Gly Lys Ala Ile Glu Tyr Ile Ala Gly Ala Met
                20                  25                  30

Lys Met Ala Trp Ala Ala Ala Lys Ala Gly Asn Thr Ser Val Ala Lys
                35                  40                  45

Phe Gln Ala Val Glu Ala Lys Met Arg Lys Ala Gly Lys His Ser Met
    50                  55                  60

Val Gln Val Leu Asn Phe Ala Lys Glu Val Lys Phe Asn Glu Val Met
 65                  70                  75                  80

His Lys Val Gly Thr Tyr Tyr Gly Ile Glu Val Val Ala Asp Gly Asp
                 85                  90                  95

Ser Ile Gly Thr Tyr Tyr Ile Ala Glu Lys Val Trp Asp Ala Ala
                100                 105                 110
```

<210> SEQ ID NO 477
<211> LENGTH: 111
<212> TYPE: PRT
<213> ORGANISM: Bacteriophage D

<400> SEQUENCE: 477

```
Met Lys Lys Glu Ile Met Thr Lys Ala Trp Glu Ile Ala Lys Asn Ala
 1               5                  10                  15
```

```
Ser Lys Lys Phe Gly Gly Lys Ala Ile Glu Tyr Ile Ala Gly Ala Met
            20                  25                  30

Lys Met Ala Trp Ala Ala Ala Lys Ala Gly Lys Thr Ser Val Ala Lys
        35                  40                  45

Phe Gln Ala Val Glu Ala Lys Met Arg Lys Ala Gly Lys His Ser Met
50                  55                  60

Val Gln Val Leu Asn Phe Ala Lys Glu Val Arg Phe Asn Glu Val Met
65                  70                  75                  80

His Lys Ala Gly Ala Tyr Tyr Gly Ile Glu Val Ile Ala Asp Gly Asp
            85                  90                  95

Ser Ile Gly Thr Tyr Phe Ile Ala Glu Asn Val Trp Asn Ala Ala
            100                 105                 110

<210> SEQ ID NO 478
<211> LENGTH: 111
<212> TYPE: PRT
<213> ORGANISM: Bacteriophage D

<400> SEQUENCE: 478

Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Leu
            20                  25                  30

Lys Met Ala Trp Ala Ala Ala Lys Gly Glu Asn Thr Ser Leu Ala Lys
        35                  40                  45

Ile Gln Ala Val Glu Glu Lys Met Arg Lys Ser Gly Lys Tyr Ser Met
50                  55                  60

Ile Gln Val Leu Asp Phe Ala Lys Glu Val Lys Phe Asn Glu Val Met
65                  70                  75                  80

His Lys Ala Gly Ala Tyr Tyr Gly Ile Glu Val Ile Ala Asp Gly Asp
            85                  90                  95

Ser Ile Gly Thr Tyr Tyr Ile Ala Glu Lys Val Trp Glu Val Ala
            100                 105                 110

<210> SEQ ID NO 479
<211> LENGTH: 111
<212> TYPE: PRT
<213> ORGANISM: Bacteriophage D

<400> SEQUENCE: 479

Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Met
            20                  25                  30

Lys Met Ala Trp Ala Ala Ala Lys Gly Gly Asn Ala Ser Leu Ala Lys
        35                  40                  45

Phe Gln Ala Val Glu Ser Lys Met Arg Lys Ala Gly Lys Tyr Ser Met
50                  55                  60

Ile Gln Val Leu Asn Phe Ala Lys Glu Val Lys Phe Asn Glu Val Met
65                  70                  75                  80

His Lys Val Gly Ala Tyr Tyr Gly Ile Glu Val Ile Ala Asp Gly Asp
            85                  90                  95

Ser Ile Gly Thr Tyr Tyr Ile Ala Glu Asn Val Trp Asn Ala Ala
            100                 105                 110

<210> SEQ ID NO 480
```

```
<211> LENGTH: 111
<212> TYPE: PRT
<213> ORGANISM: Bacteriophage D

<400> SEQUENCE: 480

Met Lys Lys Glu Ile Met Thr Lys Ala Trp Lys Ile Ala Lys Glu Ala
1               5                   10                  15

Val Glu Lys Phe Gly Gly Lys Ser Ile Glu Tyr Ile Ala Glu Ala Met
                20                  25                  30

Lys Met Ala Trp Ala Ala Ala Lys Gly Gly Asn Ala Ser Leu Ala Lys
            35                  40                  45

Phe Gln Ala Val Glu Ala Lys Met Arg Lys Ala Gly Lys Tyr Ser Met
    50                  55                  60

Ile Gln Val Leu Asn Phe Ala Lys Glu Val Lys Phe Asn Glu Val Met
65                  70                  75                  80

His Lys Ala Gly Ala Tyr Tyr Gly Ile Glu Val Val Ala Asp Gly Asp
                85                  90                  95

Ser Ile Gly Thr Tyr Tyr Ile Ala Glu Lys Val Trp Glu Val Ala
            100                 105                 110

<210> SEQ ID NO 481
<211> LENGTH: 111
<212> TYPE: PRT
<213> ORGANISM: Bacteriophage N

<400> SEQUENCE: 481

Met Lys Lys Glu Ile Met Thr Lys Ala Trp Glu Ile Ala Lys Asn Ala
1               5                   10                  15

Ser Lys Lys Phe Gly Gly Lys Ala Ile Glu Tyr Ile Ala Gly Ala Met
                20                  25                  30

Lys Met Ala Trp Ala Ala Ala Lys Ala Gly Asn Thr Ser Val Ala Lys
            35                  40                  45

Phe Gln Ala Val Glu Ala Lys Met Arg Lys Ala Gly Lys His Ser Met
    50                  55                  60

Val Gln Val Leu Asn Phe Ala Lys Glu Val Lys Phe Asn Glu Val Met
65                  70                  75                  80

His Lys Val Gly Thr Tyr Tyr Gly Ile Glu Val Val Ala Asp Gly Asp
                85                  90                  95

Ser Ile Gly Thr Tyr Tyr Ile Ala Glu Lys Val Trp Asp Ala Ala
            100                 105                 110

<210> SEQ ID NO 482
<211> LENGTH: 111
<212> TYPE: PRT
<213> ORGANISM: Bacteriophage O

<400> SEQUENCE: 482

Met Lys Ser Gln Val Met Ser Gln Ala Trp Lys Ile Ala Lys Glu Ala
1               5                   10                  15

Val Lys Lys Phe Gly Gly Lys Ala Ile Glu Tyr Ile Ser Glu Ala Met
                20                  25                  30

Lys Met Ala Trp Ala Ala Ala Lys Gly Glu Asn Thr Ser Leu Thr Lys
            35                  40                  45

Phe Gln Ala Val Glu Glu Lys Met Arg Lys Ala Gly Lys Tyr Ser Met
    50                  55                  60

Ile Gln Val Leu Asp Phe Ala Lys Glu Val Lys Phe Asn Glu Val Met
65                  70                  75                  80
```

```
His Lys Val Gly Ala Tyr Tyr Gly Ile Glu Val Ile Ala Asp Gly Asp
                85                  90                  95

Ser Ile Gly Thr Tyr Phe Ile Ala Glu Lys Val Trp Asp Val Ala
            100                 105                 110

<210> SEQ ID NO 483
<211> LENGTH: 111
<212> TYPE: PRT
<213> ORGANISM: Bacteriophage P

<400> SEQUENCE: 483

Met Lys Lys Glu Ile Met Lys Lys Ala Trp Lys Ile Ala Lys Glu Ala
1               5                   10                  15

Val Lys Lys Phe Gly Gly Lys Ala Ile Glu Tyr Ile Ala Glu Ala Leu
            20                  25                  30

Lys Met Ala Trp Ser Asp Ala Lys Gly Ser Asn Thr Ser Leu Ala Lys
            35                  40                  45

Phe Gln Ala Val Glu Glu Lys Met Arg Lys Ala Gly Lys Tyr Ser Met
        50                  55                  60

Ile Gln Val Leu Asp Phe Ala Lys Glu Val Lys Phe Asn Glu Val Met
65                  70                  75                  80

His Lys Ala Gly Ala Tyr Tyr Gly Ile Glu Val Ile Ala Asp Gly Asp
                85                  90                  95

Ser Ile Gly Thr Tyr Tyr Ile Glu Lys Val Trp Glu Val Ala
            100                 105                 110

<210> SEQ ID NO 484
<211> LENGTH: 111
<212> TYPE: PRT
<213> ORGANISM: Bacteriophage P

<400> SEQUENCE: 484

Met Lys Lys Glu Ile Met Thr Lys Ala Trp Glu Ile Ala Lys Asn Ala
1               5                   10                  15

Ser Lys Lys Phe Gly Gly Lys Ala Ile Glu Tyr Ile Ala Gly Ala Met
            20                  25                  30

Lys Met Ala Trp Ala Ala Ala Lys Ala Gly Asn Thr Ser Val Ala Lys
            35                  40                  45

Phe Gln Ala Val Glu Ala Lys Met Arg Lys Ala Gly Lys His Ser Met
        50                  55                  60

Val Gln Val Leu Asn Phe Ala Lys Glu Val Lys Phe Asn Glu Val Met
65                  70                  75                  80

His Lys Val Gly Ala Tyr Tyr Gly Ile Glu Val Val Ala Asp Gly Asp
                85                  90                  95

Ser Ile Gly Thr Tyr Tyr Ile Glu Lys Val Trp Glu Val Ala
            100                 105                 110

<210> SEQ ID NO 485
<211> LENGTH: 111
<212> TYPE: PRT
<213> ORGANISM: Bacteriophage P

<400> SEQUENCE: 485

Met Lys Lys Glu Ile Met Thr Asn Ala Trp Glu Ile Ala Lys Asn Ala
1               5                   10                  15

Ser Lys Lys Phe Gly Gly Lys Ala Ile Glu Tyr Ile Ala Glu Ala Leu
            20                  25                  30

Lys Met Ala Trp Ser Asp Ala Lys Gly Ser Asn Thr Ser Leu Ala Lys
```

```
            35                  40                  45
Phe Gln Ala Val Glu Glu Lys Met Arg Lys Ala Gly Lys Tyr Ser Met
 50                  55                  60
Ile Gln Val Leu Asn Phe Ala Lys Glu Val Lys Phe Asn Glu Val Met
 65                  70                  75                  80
His Lys Glu Gly Ala Tyr Tyr Gly Ile Glu Val Val Ala Asp Gly Asp
                 85                  90                  95
Ser Ile Gly Thr Tyr Tyr Ile Ala Glu Lys Val Trp Asp Ala Ala
                100                 105                 110

<210> SEQ ID NO 486
<211> LENGTH: 111
<212> TYPE: PRT
<213> ORGANISM: Bacteriophage SFi

<400> SEQUENCE: 486

Met Lys Lys Glu Val Met Thr Asn Ala Trp Lys Ile Ala Lys Glu Ala
 1               5                  10                  15
Val Lys Lys Phe Gly Gly Lys Ala Ile Glu Tyr Ile Ser Glu Ala Met
                20                  25                  30
Lys Met Ala Trp Ala Ala Ala Lys Gly Glu Asn Thr Ser Leu Ala Lys
             35                  40                  45
Phe Gln Ala Val Glu Glu Lys Met Arg Lys Ala Gly Lys Tyr Ser Met
 50                  55                  60
Ile Gln Val Leu Asp Phe Ala Lys Glu Val Lys Ile Asn Glu Val Met
 65                  70                  75                  80
His Lys Val Gly Ala Tyr Tyr Gly Ile Glu Val Ile Ala Asp Gly Asp
                 85                  90                  95
Asn Ile Gly Thr Tyr Tyr Ile Ala Glu Lys Val Trp Glu Val Ala
                100                 105                 110

<210> SEQ ID NO 487
<211> LENGTH: 111
<212> TYPE: PRT
<213> ORGANISM: Bacteriophage Sfi

<400> SEQUENCE: 487

Met Lys Lys Glu Val Met Thr Asn Ala Trp Lys Ile Ala Lys Glu Ala
 1               5                  10                  15
Val Lys Lys Phe Gly Gly Lys Ala Ile Glu Tyr Ile Ser Glu Gly Tyr
                20                  25                  30
Glu Met Ala Trp Ala Ala Ala Lys Gly Glu Asn Thr Ser Leu Ala Lys
             35                  40                  45
Phe Gln Ala Val Glu Glu Lys Met Arg Lys Ala Gly Lys Tyr Ser Met
 50                  55                  60
Ile Gln Val Leu Asp Phe Ala Lys Glu Val Lys Phe Asn Glu Val Met
 65                  70                  75                  80
His Lys Val Gly Ala Tyr Tyr Gly Ile Glu Val Ile Ala Asp Gly Asp
                 85                  90                  95
Asn Ile Gly Thr Tyr Tyr Ile Ala Glu Lys Val Trp Glu Val Ala
                100                 105                 110

<210> SEQ ID NO 488
<211> LENGTH: 111
<212> TYPE: PRT
<213> ORGANISM: Bacteriophage Sfi

<400> SEQUENCE: 488
```

-continued

Met Lys Lys Glu Ile Met Lys Ala Trp Glu Ile Ala Lys Glu Ala
1               5                   10                  15

Val Lys Lys Phe Gly Gly Lys Ala Ile Glu Tyr Ile Ala Glu Ala Leu
                20                  25                  30

Lys Met Ala Trp Ser Asp Ala Lys Gly Ser Asn Thr Ser Leu Ala Lys
            35                  40                  45

Phe Gln Ala Val Glu Glu Lys Met Arg Lys Ala Gly Lys Tyr Ser Met
        50                  55                  60

Ile Gln Val Leu Asp Phe Ala Lys Glu Val Lys Phe Asn Glu Val Met
65                  70                  75                  80

His Lys Glu Gly Ala Tyr Tyr Gly Ile Glu Val Val Ala Asp Gly Asp
                85                  90                  95

Ser Ile Gly Thr Tyr Tyr Ile Ala Glu Lys Val Trp Glu Val Ala
            100                 105                 110

<210> SEQ ID NO 489
<211> LENGTH: 110
<212> TYPE: PRT
<213> ORGANISM: Bacteriophage Sfi

<400> SEQUENCE: 489

Met Lys Lys Ile Met Thr Asn Ala Trp Lys Ile Ala Lys Glu Ala Val
1               5                   10                  15

Lys Lys Phe Gly Gly Lys Ala Ile Glu Tyr Ile Ser Glu Ala Met Lys
                20                  25                  30

Ile Ala Trp Ala Asp Ala Lys Glu Gly Asn Thr Ser Val Ala Lys Phe
            35                  40                  45

Gln Ala Val Glu Ala Lys Met Arg Lys Ala Gly Lys His Ser Met Val
        50                  55                  60

Gln Val Leu Asn Phe Ala Lys Glu Val Lys Phe Asn Glu Val Met His
65                  70                  75                  80

Lys Val Gly Ala Tyr Tyr Gly Ile Glu Val Ile Ala Asp Gly Asp Ser
                85                  90                  95

Ile Gly Thr Tyr Tyr Ile Ser Glu Lys Val Trp Glu Val Ala
            100                 105                 110

<210> SEQ ID NO 490
<211> LENGTH: 111
<212> TYPE: PRT
<213> ORGANISM: Bacteriophage Proph

<400> SEQUENCE: 490

Met Lys Lys Glu Ile Met Lys Lys Ala Trp Lys Ile Ala Lys Glu Ala
1               5                   10                  15

Val Lys Lys Phe Gly Gly Lys Ala Ile Glu Tyr Ile Ala Glu Ala Leu
                20                  25                  30

Lys Met Ala Trp Ser Asp Ala Lys Gly Ser Asn Thr Ser Leu Ala Lys
            35                  40                  45

Phe Gln Ala Val Glu Asp Lys Met Asn Lys Thr Gly Lys His Ser Met
        50                  55                  60

Val Gln Val Leu Asn Phe Ala Lys Glu Val Asn Phe Lys Glu Val Met
65                  70                  75                  80

His Lys Val Gly Ala Tyr Tyr Gly Ile Glu Val Val Ala Asp Gly Asp
                85                  90                  95

Ser Ile Gly Thr Tyr Tyr Ile Ala Glu Lys Val Trp Asp Ala Ala
            100                 105                 110

<210> SEQ ID NO 491
<211> LENGTH: 36
<212> TYPE: PRT
<213> ORGANISM: Bacteriophage D

<400> SEQUENCE: 491

Met Lys Lys Glu Val Met Thr Asn Ala Trp Glu Ile Ala Lys Asn Ala
1               5                   10                  15

Ser Lys Lys Phe Gly Gly Lys Ala Ile Glu Tyr Ile Ala Glu Asn Val
            20                  25                  30

Trp Asn Ala Ala
        35

<210> SEQ ID NO 492
<211> LENGTH: 114
<212> TYPE: PRT
<213> ORGANISM: Bacteriophage D

<400> SEQUENCE: 492

Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
            20                  25                  30

Val Lys Arg Gln Asn Met Ala Asp Asp Phe Tyr Phe Phe His Ser Ser
        35                  40                  45

Asn Val Lys Phe Gln Gly Val Lys Lys Trp Phe Ala Glu Lys Glu Phe
    50                  55                  60

Arg Gly Arg Asn Lys Lys Asp Leu Ala Phe Met Ser Val Ser Ala Ile
65                  70                  75                  80

Ser Val Lys Gly Leu Val Glu Glu Thr Asp Lys Ala Val Lys Leu Glu
                85                  90                  95

Ile Val Thr Pro Tyr Gly Val Ser Ala Lys Trp Tyr Pro Lys Ser Val
            100                 105                 110

Ile Ala

<210> SEQ ID NO 493
<211> LENGTH: 114
<212> TYPE: PRT
<213> ORGANISM: Bacteriophage D

<400> SEQUENCE: 493

Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
            20                  25                  30

Val Lys Arg Gln Asn Met Ala Asp Asp Phe Tyr Phe Phe Arg Ser Ser
        35                  40                  45

Asn Val Lys Phe Gln Gly Val Lys Lys Trp Phe Ala Glu Lys Glu Phe
    50                  55                  60

Arg Gly Arg Asn Lys Lys Asp Leu Ala Phe Met Ser Val Thr Ala Ile
65                  70                  75                  80

Ser Val Lys Gly Leu Ile Glu Glu Thr Asp Lys Ala Val Lys Leu Glu
                85                  90                  95

Ile Val Thr Pro Tyr Gly Val Ser Thr Lys Trp Tyr Pro Lys Ser Val
            100                 105                 110

Ile Ala

<210> SEQ ID NO 494
<211> LENGTH: 114
<212> TYPE: PRT
<213> ORGANISM: Bacteriophage D

<400> SEQUENCE: 494

Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
            20                  25                  30

Val Lys Arg Gln Asn Met Ala Asp Asp Phe Tyr Phe Phe Arg Ser Ser
        35                  40                  45

Asn Val Lys Phe Gln Gly Val Lys Lys Trp Phe Ala Glu Lys Glu Phe
    50                  55                  60

Arg Gly Arg Asn Lys Lys Asp Leu Ala Phe Met Ser Val Thr Ala Ile
65                  70                  75                  80

Ser Ile Lys Gly Leu Val Glu Glu Thr Asp Lys Ala Val Lys Leu Glu
                85                  90                  95

Ile Val Thr Pro Tyr Gly Ile Ser Thr Lys Trp Tyr Pro Lys Ser Val
            100                 105                 110

Ile Ala

<210> SEQ ID NO 495
<211> LENGTH: 114
<212> TYPE: PRT
<213> ORGANISM: Bacteriophage Proph

<400> SEQUENCE: 495

Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
            20                  25                  30

Val Lys Arg Gln Asn Met Ala Asp Asp Phe Tyr Phe Phe Arg Ser Ser
        35                  40                  45

Asn Val Lys Phe Gln Gly Val Lys Lys Trp Phe Ala Glu Lys Glu Phe
    50                  55                  60

Arg Gly Arg Asn Lys Lys Asp Leu Ala Phe Met Ser Val Thr Ala Ile
65                  70                  75                  80

Ser Val Lys Gly Leu Ile Glu Glu Thr Asp Lys Ala Val Lys Leu Glu
                85                  90                  95

Ile Val Thr Pro Tyr Gly Val Ser Thr Lys Trp Tyr Pro Lys Ser Val
            100                 105                 110

Ile Ala

<210> SEQ ID NO 496
<211> LENGTH: 114
<212> TYPE: PRT
<213> ORGANISM: Bacteriophage Proph

<400> SEQUENCE: 496

Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
            20                  25                  30

Val Lys Arg Gln Asn Met Ala Asp Asp Phe Tyr Phe Phe Arg Ser Ser
        35                  40                  45

```
Asn Val Lys Phe Gln Gly Val Lys Lys Trp Phe Ala Glu Lys Glu Phe
        50                  55                  60

Arg Gly Arg Asn Lys Lys Asp Leu Ala Phe Met Ser Val Thr Ala Ile
65                  70                  75                  80

Ser Ile Lys Gly Leu Val Glu Glu Thr Asp Lys Ala Val Lys Leu Glu
                85                  90                  95

Ile Val Thr Pro Tyr Gly Ile Ser Thr Lys Trp Tyr Pro Lys Ser Val
                100                 105                 110

Ile Ala

<210> SEQ ID NO 497
<211> LENGTH: 86
<212> TYPE: PRT
<213> ORGANISM: Bacteriophage

<400> SEQUENCE: 497

Met Lys Thr Met Asp Ala Tyr Lys Glu Gln Phe Gln Glu Leu Gln Glu
1               5                   10                  15

Tyr Ala Phe Asn Val Leu Arg Glu Tyr Pro Leu Asp Lys Thr Ala Val
                20                  25                  30

Asn Val Leu Ser Ala Leu Val Asn Ser Lys Lys Lys Asp Arg Ile Glu
                35                  40                  45

Phe Phe Lys Leu Asn Lys Gly Glu Asp Ala Met Lys Val Tyr Tyr Asn
        50                  55                  60

Leu Ala Asp Ser Gly Thr Ile Glu Lys Tyr Leu Glu Thr Ser Ala Phe
65                  70                  75                  80

Leu Asp Tyr Ile Asn Glu
                85

<210> SEQ ID NO 498
<211> LENGTH: 83
<212> TYPE: PRT
<213> ORGANISM: Bacteriophage D

<400> SEQUENCE: 498

Met Asp Thr Tyr Lys Glu Gln Phe Gln Lys Leu Gln Glu Tyr Ala Phe
1               5                   10                  15

Asn Val Leu Arg Glu Tyr Pro Leu Asp Lys Thr Ala Val Asn Val Leu
                20                  25                  30

Ser Ala Leu Val Asn Ser Lys Lys Lys Asp Arg Ile Glu Phe Phe Lys
                35                  40                  45

Leu Asn Lys Gly Glu Asp Ala Met Lys Val Tyr Tyr Asn Leu Ala Asp
        50                  55                  60

Ser Gly Thr Ile Glu Lys Tyr Leu Glu Thr Ser Ala Phe Leu Asp Tyr
65                  70                  75                  80

Ile Asn Glu

<210> SEQ ID NO 499
<211> LENGTH: 83
<212> TYPE: PRT
<213> ORGANISM: Bacteriophage D

<400> SEQUENCE: 499

Met Asp Thr Tyr Lys Glu Gln Phe Gln Glu Leu Gln Glu Tyr Ala Phe
1               5                   10                  15

Asn Val Leu Arg Glu Tyr Pro Leu Asp Lys Thr Ala Val Asn Val Leu
                20                  25                  30
```

Ser Ala Leu Val Asn Ser Lys Lys Lys Asp Arg Ile Glu Phe Phe Lys
        35                  40                  45

Leu Asn Lys Asp Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
65                  70                  75                  80

Ile Asn Glu

<210> SEQ ID NO 500
<211> LENGTH: 83
<212> TYPE: PRT
<213> ORGANISM: Bacteriophage D

<400> SEQUENCE: 500

Met Asp Thr Tyr Lys Glu Gln Phe Gln Glu Leu Gln Glu Tyr Ala Phe
1               5                   10                  15

Asn Ile Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

Leu Asn Lys Asp Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
65                  70                  75                  80

Ile Asn Glu

<210> SEQ ID NO 501
<211> LENGTH: 83
<212> TYPE: PRT
<213> ORGANISM: Bacteriophage D

<400> SEQUENCE: 501

Met Asp Thr Tyr Lys Glu Gln Phe Gln Lys Leu Gln Glu Tyr Ala Phe
1               5                   10                  15

Asn Val Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

Leu Asn Lys Gly Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
65                  70                  75                  80

Thr Asn Glu

<210> SEQ ID NO 502
<211> LENGTH: 83
<212> TYPE: PRT
<213> ORGANISM: Bacteriophage Sfi

<400> SEQUENCE: 502

Met Asp Thr Tyr Lys Glu Gln Phe Gln Glu Leu Gln Glu Tyr Ala Phe
1               5                   10                  15

Asn Ile Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

```
Leu Asn Lys Asp Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
 65                  70                  75                  80

Ile Asn Glu
```

<210> SEQ ID NO 503
<211> LENGTH: 83
<212> TYPE: PRT
<213> ORGANISM: Bacteriophage Proph

<400> SEQUENCE: 503

```
Met Asp Thr Tyr Lys Glu Gln Phe Gln Glu Leu Gln Glu Tyr Ala Phe
 1               5                  10                  15

Asn Val Leu Arg Glu Tyr Pro Leu Asp Lys Thr Ala Val Asn Val Leu
                20                  25                  30

Ser Ala Leu Val Asn Ser Lys Lys Lys Asp Arg Ile Glu Phe Phe Lys
            35                  40                  45

Leu Asn Lys Gly Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
 65                  70                  75                  80

Ile Asn Glu
```

<210> SEQ ID NO 504
<211> LENGTH: 83
<212> TYPE: PRT
<213> ORGANISM: Bacteriophage Proph

<400> SEQUENCE: 504

```
Met Asp Thr Tyr Lys Glu Gln Phe Gln Glu Leu Gln Glu Tyr Ala Phe
 1               5                  10                  15

Asn Val Leu Arg Glu Tyr Pro Leu Asp Lys Thr Ala Val Asn Val Leu
                20                  25                  30

Ser Ala Leu Val Asn Ser Lys Lys Lys Asp Arg Ile Glu Phe Phe Lys
            35                  40                  45

Leu Asn Lys Gly Glu Asp Ala Met Lys Val Tyr Tyr Ser Leu Ala Asp
    50                  55                  60

Ser Gly Thr Ile Glu Arg Tyr Leu Glu Val Cys Gly Phe Leu Glu Tyr
 65                  70                  75                  80

Ile Asn Glu
```

<210> SEQ ID NO 505
<211> LENGTH: 93
<212> TYPE: PRT
<213> ORGANISM: Bacteriophage D

<400> SEQUENCE: 505

```
Met Ile Thr Lys Glu Gln Leu Lys Glu Tyr Tyr Ser Glu His Leu Glu
 1               5                  10                  15

Glu Leu Val Glu Trp Ala Asp Asp Ile Asn Lys Ile Cys Leu Phe Ala
                20                  25                  30

Tyr Leu Asp Glu Asp Asn Leu Tyr Cys Gly Ile Asn Gln Leu Ser
            35                  40                  45

Tyr Thr Gln Phe Arg Val Pro Ile Gln Ala Glu Val Thr Val Asp Asp
    50                  55                  60

Asp Trp Asn Tyr Asp Phe Phe Lys Asn Pro Ala Ala Tyr Asp Gly Trp
```

```
                65                  70                  75                  80

Asp Glu Thr Leu Glu Glu Met Leu Glu Glu Leu Asn Asp
                85                  90

<210> SEQ ID NO 506
<211> LENGTH: 93
<212> TYPE: PRT
<213> ORGANISM: Bacteriophage D

<400> SEQUENCE: 506

Met Ile Thr Lys Glu Gln Leu Lys Glu Tyr Tyr Ser Glu His Leu Glu
1               5                   10                  15

Glu Leu Val Glu Trp Ala Asp Asp Ile Asn Lys Ile Cys Leu Phe Ala
                20                  25                  30

Tyr Leu Asp Glu Asp Asp Asn Leu Tyr Cys Gly Ile Asn Gln Leu Ser
            35                  40                  45

Tyr Thr Gln Phe Arg Val Pro Ile Gln Ala Glu Val Thr Val Asp Asp
        50                  55                  60

Asp Trp Asn Tyr Asp Phe Phe Lys Asn Pro Ala Ala Tyr Asp Gly Trp
65                  70                  75                  80

Asp Glu Thr Leu Glu Glu Met Leu Glu Glu Leu Asn Asp
                85                  90

<210> SEQ ID NO 507
<211> LENGTH: 93
<212> TYPE: PRT
<213> ORGANISM: Bacteriophage D

<400> SEQUENCE: 507

Met Ile Thr Lys Glu Gln Leu Lys Glu Tyr Tyr Ser Glu His Leu Glu
1               5                   10                  15

Glu Leu Val Glu Trp Ala Asp Asp Ile Asn Lys Ile Cys Leu Phe Ala
                20                  25                  30

Tyr Leu Asp Glu Asp Asp Asn Leu Tyr Cys Gly Ile Asn Gln Leu Ser
            35                  40                  45

Tyr Thr Gln Phe Arg Val Pro Ile Gln Ala Glu Val Thr Val Asp Asp
        50                  55                  60

Asp Trp Asn Tyr Asp Phe Phe Asn Asn Pro Ala Ser Tyr Asp Gly Trp
65                  70                  75                  80

Asp Glu Thr Leu Glu Glu Met Leu Glu Glu Leu Asn Asp
                85                  90

<210> SEQ ID NO 508
<211> LENGTH: 46
<212> TYPE: PRT
<213> ORGANISM: Bacteriophage D

<400> SEQUENCE: 508

Met Lys Thr Met Asp Thr Tyr Lys Glu Gln Phe Tyr Tyr Leu Asp Pro
1               5                   10                  15

Ile Tyr Ile Ser Val Asp Ile Asn Arg Arg Thr Phe Ile Leu Gly Lys
                20                  25                  30

Arg Gly Gln Ser Leu Ser Phe Phe Tyr Cys Asn Lys Thr Ile
            35                  40                  45

<210> SEQ ID NO 509
<211> LENGTH: 74
<212> TYPE: PRT
<213> ORGANISM: Bacteriophage O
```

<400> SEQUENCE: 509

Met Thr Gln Ile Lys Asp Gly Trp His Met Val Tyr Asp Glu Lys Val
1               5                   10                  15

Tyr Val Glu Ser Gly Lys Val Val Arg Gly Ile Thr Lys Asp Asn Asn
            20                  25                  30

Asn Ser Glu Ile Ala Cys Tyr Pro Tyr Glu Tyr Asn Lys Asp Tyr Asp
        35                  40                  45

Cys Trp Ile Asn Ile Ser Gly Lys Val Thr Leu Ser Ala Tyr Arg Ser
    50                  55                  60

Gly Arg Lys Lys Gly Thr Lys Cys Met Lys
65                  70

<210> SEQ ID NO 510
<211> LENGTH: 74
<212> TYPE: PRT
<213> ORGANISM: Bacteriophage Sfi

<400> SEQUENCE: 510

Met Thr Gln Ile Lys Asp Gly Trp His Ile Val Tyr Asp Glu Lys Val
1               5                   10                  15

Tyr Val Glu Ser Gly Lys Val Val Arg Gly Ile Thr Lys Asp Asn Asn
            20                  25                  30

Asn Ser Glu Ile Ala Cys Tyr Pro Tyr Glu Tyr Asn Glu Asp Tyr Asp
        35                  40                  45

Cys Trp Ile Asn Ile Ser Gly Lys Val Thr Leu Ser Ala Tyr Arg Ser
    50                  55                  60

Gly Arg Lys Lys Gly Thr Lys Cys Met Lys
65                  70

<210> SEQ ID NO 511
<211> LENGTH: 50
<212> TYPE: PRT
<213> ORGANISM: Bacteriophage D

<400> SEQUENCE: 511

Met Phe Glu Cys Leu Ala Ser Phe Arg Leu Asn Ser Arg Thr Val Thr
1               5                   10                  15

Ser Thr Phe Cys Arg Gly Phe Leu Phe Leu Gln Lys Asn Leu Asn Ser
            20                  25                  30

Phe Ile Lys Ser Val Asp Lys Leu Ser Tyr Met Ile Tyr Asn Val Tyr
        35                  40                  45

Ile Arg
    50

<210> SEQ ID NO 512
<211> LENGTH: 63
<212> TYPE: PRT
<213> ORGANISM: Bacteriophage D

<400> SEQUENCE: 512

Met Asn Glu Ser Glu Leu Leu Glu Gln Phe Cys Val Ser Leu Cys Glu
1               5                   10                  15

Phe Ser Ser Arg Gln Trp Pro Arg Asp Gly Phe Leu Asp Pro Ile Asn
            20                  25                  30

Arg Val Val Tyr Ile Asn Arg Asp Leu Pro Thr Glu Arg Arg Leu Lys
        35                  40                  45

Val Leu Leu His Glu Leu Gly His Leu Glu His Asp Pro Lys His

```
                50                  55                  60
```

<210> SEQ ID NO 513
<211> LENGTH: 49
<212> TYPE: PRT
<213> ORGANISM: Bacteriophage D

<400> SEQUENCE: 513

Met Leu Gly Ala Lys Thr Thr Leu Phe Asp Ile Ile Tyr Leu Tyr Gln
1               5                   10                  15

Trp Leu Pro Thr His Thr Arg Arg Tyr Val Leu Arg Glu Val Phe Tyr
            20                  25                  30

Leu Leu Cys Phe Asp Arg Asn Ala Thr Ile Leu Met Asp Thr Val Lys
        35                  40                  45

Ser

<210> SEQ ID NO 514
<211> LENGTH: 49
<212> TYPE: PRT
<213> ORGANISM: Bacteriophage D

<400> SEQUENCE: 514

Met Leu Gly Val Lys Thr Thr Leu Phe Asp Ile Ile Tyr Leu Tyr Gln
1               5                   10                  15

Trp Leu Pro Thr His Thr Arg Arg Tyr Val Leu Arg Glu Val Phe Tyr
            20                  25                  30

Leu Leu Cys Phe Asp Arg Asn Ala Thr Ile Leu Met Asp Thr Val Lys
        35                  40                  45

Ser

<210> SEQ ID NO 515
<211> LENGTH: 45
<212> TYPE: PRT
<213> ORGANISM: Bacteriophage

<400> SEQUENCE: 515

Met Arg Arg Cys Leu Phe Phe Gly Leu Leu Lys Lys Arg Asn Asn Gly
1               5                   10                  15

Ile Ile Ile Phe Ala Thr Thr Asn Pro Leu Gln Pro His Gly Gln Ile
            20                  25                  30

Arg Ser Asp Ala Gly Leu Phe Leu Phe Ala Leu Phe Leu
        35                  40                  45

<210> SEQ ID NO 516
<211> LENGTH: 140
<212> TYPE: PRT
<213> ORGANISM: Bacteriophage

<400> SEQUENCE: 516

Met Lys Ile Asn Thr Thr Arg Val Lys Met Val Leu Lys Asn Glu Ala
1               5                   10                  15

Ile Pro Ala Asp Tyr Leu Glu Ser Glu Ile Gly Ile Ser Arg Ser Val
            20                  25                  30

Val Glu Lys Val Arg Glu Asp Glu Ser Glu Phe Lys Asn Leu Thr Leu
        35                  40                  45

Asp Phe Val Ala Lys Ile Gln Lys Trp Ile Asp Asp Gly Asn Tyr Thr
    50                  55                  60

Phe Ser Tyr Asp Tyr Ser Asp Leu Ile Glu Glu Leu Glu Glu Asp Ile
65                  70                  75                  80

```
Ala Glu Gly Leu Thr Asp Glu Tyr Ile Tyr Val Val Arg Gly Gln Tyr
                85                  90                  95

Asn Glu Ile Leu Glu Lys Cys Pro Ile Ile Asp Tyr Tyr Tyr Thr Ser
                100                 105                 110

Glu Glu Ile Glu Glu Gly Asp Leu Ala Glu Lys Thr Leu Thr Ala Ser
            115                 120                 125

Ala Leu Ser Glu Met Lys Gln Asp Asn Glu Ile Phe
            130                 135                 140

<210> SEQ ID NO 517
<211> LENGTH: 140
<212> TYPE: PRT
<213> ORGANISM: Bacteriophage D

<400> SEQUENCE: 517

Met Lys Ile Asn Thr Thr Arg Val Lys Met Val Leu Lys Asn Lys Val
1               5                   10                  15

Ile Pro Ala Ile Tyr Leu Glu Asn Glu Leu Gly Ile Ser Arg Ser Val
                20                  25                  30

Ile Glu Lys Val Arg Asp Gly Glu Arg Lys Ile Glu Asn Leu Thr Leu
            35                  40                  45

Glu Thr Ile Ile Lys Val Gln Lys Trp Ile Asp Ser Gly Lys Tyr Thr
50                  55                  60

Phe Ser Tyr Asp Tyr Ser Asp Leu Ile Glu Glu Leu Glu Glu Asp Ile
65                  70                  75                  80

Ala Glu Gly Leu Val Asp Glu Tyr Ile Tyr Val Val Arg Gly Pro Tyr
                85                  90                  95

Asn Glu Leu Leu Asp Lys Cys Pro Ile Ile Asp Tyr Tyr Tyr Thr Ser
                100                 105                 110

Glu Glu Ile Glu Glu Gly Asp Leu Ala Glu Lys Thr Leu Thr Ala Ser
            115                 120                 125

Val Leu Ala Glu Met Lys Lys Asp Asn Glu Ile Phe
            130                 135                 140

<210> SEQ ID NO 518
<211> LENGTH: 140
<212> TYPE: PRT
<213> ORGANISM: Bacteriophage D

<400> SEQUENCE: 518

Met Lys Ile Asn Thr Thr Arg Ile Lys Met Val Leu Lys Asn Glu Ala
1               5                   10                  15

Ile Pro Ala Ile Tyr Leu Glu Asn Glu Leu Gly Ile Ser Arg Ser Val
                20                  25                  30

Ile Glu Lys Val Arg Glu Asp Ser Glu Phe Lys Asn Leu Thr Leu
            35                  40                  45

Asp Val Val Ala Lys Ile Gln Lys Trp Ile Asp Asp Gly Asn Tyr Thr
50                  55                  60

Phe Ser Tyr Asp Tyr Ser Glu Phe Ile Glu Glu Leu Glu Glu Asp Leu
65                  70                  75                  80

Ala Glu Gly Leu Ile Asp Asp Tyr Leu Phe Val Val Arg Gly Asp Tyr
                85                  90                  95

Asp Glu Ala Leu Gly Lys Cys Pro Ile Ile Asp Tyr Tyr Tyr Thr Ser
                100                 105                 110

Glu Glu Ile Glu Glu Gly Asp Leu Ala Glu Lys Thr Leu Thr Ala Ser
            115                 120                 125
```

Val Leu Ala Glu Met Lys Lys Asp Asn Gly Ile Phe
    130                 135                 140

<210> SEQ ID NO 519
<211> LENGTH: 140
<212> TYPE: PRT
<213> ORGANISM: Bacteriophage D

<400> SEQUENCE: 519

Met Lys Ile Asn Thr Thr Arg Val Asn Met Val Leu Lys Asn Glu Ala
1               5                   10                  15

Ile Pro Ala Asp Tyr Leu Glu Asn Val Ile Gly Ile Ser Arg Ser Val
            20                  25                  30

Ile Glu Arg Val Arg Glu Asp Glu Ser Gly Phe Lys Asn Leu Thr Leu
        35                  40                  45

Asp Val Ile Ala Lys Ile Gln Lys Trp Ile Asp Glu Gly Asn Tyr Thr
    50                  55                  60

Phe Ser Tyr Asp Tyr Ser Asp Leu Ile Glu Glu Leu Glu Glu Asp Ile
65                  70                  75                  80

Ala Glu Gly Leu Val Asp Glu Tyr Ile Tyr Val Val Arg Gly Pro Tyr
                85                  90                  95

Asn Glu Ile Leu Glu Lys Cys Pro Ile Ile Asp Tyr Tyr Tyr Thr Ser
            100                 105                 110

Glu Glu Ile Glu Glu Gly Asp Leu Ala Glu Lys Thr Leu Thr Ala Ser
        115                 120                 125

Ala Leu Ala Glu Met Lys Leu Asp Asn Lys Ile Phe
    130                 135                 140

<210> SEQ ID NO 520
<211> LENGTH: 140
<212> TYPE: PRT
<213> ORGANISM: Bacteriophage D

<400> SEQUENCE: 520

Met Lys Ile Asn Thr Thr Arg Val Asn Met Val Leu Lys Asn Lys Ala
1               5                   10                  15

Ile Pro Ala Asn Tyr Leu Glu Lys Glu Leu Gly Ile Asn Arg Ser Thr
            20                  25                  30

Ile Thr Arg Val Arg Asn Gly Glu Arg Lys Leu Glu Asn Leu Thr Leu
        35                  40                  45

Glu Thr Ile Ile Lys Val Gln Lys Trp Ile Asp Ser Gly Lys Tyr Thr
    50                  55                  60

Phe Ser Tyr Asp Tyr Ser Asp Leu Ile Glu Glu Leu Glu Glu Asp Ile
65                  70                  75                  80

Glu Glu Gly Leu Thr Asp Glu Tyr Ile Tyr Val Val Arg Gly Pro Tyr
                85                  90                  95

Asn Glu Leu Leu Glu Lys Cys Pro Ile Ile Asp Tyr Tyr Tyr Thr Ser
            100                 105                 110

Glu Glu Ile Glu Glu Gly Asp Leu Thr Glu Lys Thr Leu Thr Ala Ser
        115                 120                 125

Ala Leu Ala Glu Met Lys Gln Asp Asn Glu Ile Phe
    130                 135                 140

<210> SEQ ID NO 521
<211> LENGTH: 140
<212> TYPE: PRT
<213> ORGANISM: Bacteriophage O -continued

```
<400> SEQUENCE: 521

Met Ile Ile Asn Thr Ala Arg Val Glu Leu Val Leu Met Asn Lys Ala
1               5                   10                  15

Ile Pro Ala Asn Tyr Leu Glu Ser Glu Ile Gly Ile Ser Arg Ser Ala
            20                  25                  30

Ile Thr Arg Val Arg Asn Asp Glu Arg Lys Ile Glu Asn Leu Lys Leu
        35                  40                  45

Glu Thr Ile Ile Lys Val Gln Lys Trp Ile Asp Ser Gly Lys Tyr Thr
    50                  55                  60

Phe Ser Tyr Asp Tyr Ser Asp Leu Ile Glu Glu Leu Glu Glu Asp Ile
65                  70                  75                  80

Ala Lys Gly Leu Ala Gly Lys Tyr Ile Tyr Val Val Arg Gly Pro Tyr
                85                  90                  95

Asn Glu Ile Leu Glu Lys Cys Pro Ile Ile Asp Tyr Tyr Tyr Thr Ser
            100                 105                 110

Glu Glu Ile Glu Glu Gly Glu Leu Ala Glu Lys Thr Leu Thr Ala Ser
        115                 120                 125

Val Leu Ala Glu Met Lys Ser Asp Asn Glu Ile Phe
    130                 135                 140

<210> SEQ ID NO 522
<211> LENGTH: 131
<212> TYPE: PRT
<213> ORGANISM: Bacteriophage Proph

<400> SEQUENCE: 522

Met Val Leu Lys Asn Glu Ala Ile Pro Ala Asp Tyr Leu Glu Ser Glu
1               5                   10                  15

Ile Gly Ile Ser Arg Ser Val Val Glu Lys Val Arg Glu Asp Glu Ser
            20                  25                  30

Glu Phe Lys Asn Leu Thr Leu Asp Val Val Ala Lys Ile Gln Lys Trp
        35                  40                  45

Ile Asp Asp Gly Asn Tyr Thr Phe Ser Tyr Asp Tyr Ser Asp Leu Ile
    50                  55                  60

Glu Glu Leu Glu Glu Asp Ile Ala Glu Gly Leu Val Asp Glu Tyr Ile
65                  70                  75                  80

Tyr Val Val Arg Gly Pro Tyr Asn Glu Leu Leu Glu Lys Cys Pro Ile
                85                  90                  95

Ile Asp Tyr Tyr Tyr Thr Ser Glu Glu Ile Glu Glu Gly Asp Leu Ala
            100                 105                 110

Glu Lys Thr Leu Ile Thr Ser Val Leu Ala Glu Met Lys Ser Asp Asn
        115                 120                 125

Lys Ile Phe
    130

<210> SEQ ID NO 523
<211> LENGTH: 140
<212> TYPE: PRT
<213> ORGANISM: Bacteriophage Sfi

<400> SEQUENCE: 523

Met Ile Ile Asn Val Ala Arg Val Glu Thr Val Leu Met Asn Asn Ala
1               5                   10                  15

Ile Pro Ala Asn Tyr Leu Glu Arg Glu Ile Gly Ile Ser Arg Ser Ala
            20                  25                  30
```

-continued

Ile Thr Arg Val Arg Asn Gly Glu Arg Lys Ile Glu Asn Leu Lys Leu
        35                  40                  45

Glu Thr Ile Ile Lys Val Gln Lys Trp Ile Asp Ser Gly Lys Tyr Thr
 50                  55                  60

Phe Ser Tyr Asp Tyr Ser Asp Leu Ile Glu Glu Leu Glu Glu Asp Ile
 65                  70                  75                  80

Ala Glu Gly Leu Thr Asp Glu Tyr Ile Tyr Val Val Arg Gly Ala Tyr
                 85                  90                  95

Asn Glu Ile Leu Glu Lys Cys Pro Ile Ile Asp Tyr Tyr Tyr Thr Ser
            100                 105                 110

Glu Glu Ile Glu Glu Gly Asp Leu Ala Glu Lys Thr Leu Thr Ala Ser
        115                 120                 125

Ala Leu Ser Glu Met Lys Gln Asp Asn Glu Ile Phe
    130                 135                 140

<210> SEQ ID NO 524
<211> LENGTH: 140
<212> TYPE: PRT
<213> ORGANISM: Bacteriophage TPL

<400> SEQUENCE: 524

Met Ile Ile Asn Thr Ala Arg Val Glu Leu Val Leu Met Asn Lys Ala
 1               5                  10                  15

Ile Pro Ala Asn Tyr Leu Glu Arg Glu Ile Gly Ile Ser Arg Ser Ala
            20                  25                  30

Ile Thr Arg Val Arg Asn Gly Glu Arg Lys Leu Glu Asn Leu Thr Leu
        35                  40                  45

Glu Thr Ile Met Thr Ile Gln Lys Trp Ile Asp Glu Gly Asn Tyr Arg
 50                  55                  60

Phe Ser Tyr Asp Tyr Ser Glu Leu Ile Glu Asp Leu Glu Glu Asp Ile
 65                  70                  75                  80

Ala Glu Gly Leu Thr Asp Glu Tyr Ile Tyr Val Val Arg Gly Pro Tyr
                 85                  90                  95

Asn Glu Leu Leu Glu Lys Cys Pro Ile Ile Asp Tyr Tyr Tyr Thr Ser
            100                 105                 110

Glu Glu Ile Glu Glu Gly Asn Leu Ala Glu Lys Thr Leu Thr Ala Ser
        115                 120                 125

Val Leu Ala Glu Met Lys Gln Asp Asn Glu Ile Phe
    130                 135                 140

<210> SEQ ID NO 525
<211> LENGTH: 140
<212> TYPE: PRT
<213> ORGANISM: Bacteriophage TPJ

<400> SEQUENCE: 525

Met Lys Ile Asn Thr Thr Arg Ile Lys Met Val Leu Lys Asn Glu Ala
 1               5                  10                  15

Ile Pro Ala Ile Tyr Leu Glu Asn Glu Leu Gly Ile Ser Arg Ser Ile
            20                  25                  30

Ile Glu Lys Val Arg Asp Asp Glu Ser Glu Phe Lys Asn Leu Thr Leu
        35                  40                  45

Glu Thr Ile Ile Lys Ile Gln Ser Leu Ile Asn Ser Gly Lys Tyr Thr
 50                  55                  60

Phe Ser Tyr Asp Tyr Ser Asp Leu Ile Glu Glu Leu Glu Glu Asp Ile
 65                  70                  75                  80

```
Ala Glu Gly Leu Thr Asp Glu Tyr Ile Tyr Val Val Arg Gly Pro Tyr
            85                  90                  95

Asn Glu Ile Leu Glu Lys Cys Pro Ile Ile Asp Tyr Tyr Tyr Thr Ser
            100                 105                 110

Glu Glu Ile Glu Glu Gly Asn Leu Ala Glu Lys Thr Leu Thr Ala Ser
            115                 120                 125

Val Leu Ala Glu Met Lys Gln Asp Asn Glu Ile Phe
            130                 135                 140

<210> SEQ ID NO 526
<211> LENGTH: 140
<212> TYPE: PRT
<213> ORGANISM: Bacteriophage Proph

<400> SEQUENCE: 526

Met Lys Ile Asn Thr Thr Arg Val Lys Met Val Leu Lys Asn Glu Val
1               5                   10                  15

Ile Pro Ala Ile Tyr Leu Glu Asn Glu Leu Gly Ile Ser Arg Ser Val
            20                  25                  30

Ile Glu Lys Val Arg Asp Gly Glu Arg Lys Ile Glu Asn Leu Thr Leu
            35                  40                  45

Glu Thr Ile Ile Lys Ile Gln Lys Trp Ile Asp Asp Gly Asn Tyr Thr
            50                  55                  60

Phe Ser Tyr Asp Tyr Ser Asp Leu Ile Glu Glu Leu Glu Glu Asp Ile
65              70                  75                  80

Ala Glu Gly Leu Val Asp Glu Tyr Ile Tyr Val Val Arg Gly Pro Tyr
            85                  90                  95

Asn Glu Leu Leu Glu Lys Cys Pro Ile Ile Asp Tyr Tyr Tyr Thr Ser
            100                 105                 110

Glu Glu Ile Glu Glu Gly Asp Leu Ala Glu Lys Thr Leu Ile Thr Ser
            115                 120                 125

Val Leu Ala Glu Met Lys Ser Asp Asn Lys Ile Phe
            130                 135                 140

<210> SEQ ID NO 527
<211> LENGTH: 60
<212> TYPE: PRT
<213> ORGANISM: Bacteriophage D

<400> SEQUENCE: 527

Met Asp Gln Val Lys Leu Val Leu Met Asn Lys Ala Ile Pro Ala Asn
1               5                   10                  15

Tyr Leu Glu Arg Gln Thr Gly Val Ser Arg Ser Ala Ile Thr Arg Val
            20                  25                  30

Arg Asn Gly Glu Arg Lys Ile Glu Asn Leu Thr Leu Glu Thr Ile Ile
            35                  40                  45

Lys Ile Gln Ser Trp Ile Asp Ser Glu Asn Thr Ile
            50                  55                  60

<210> SEQ ID NO 528
<211> LENGTH: 64
<212> TYPE: PRT
<213> ORGANISM: Bacteriophage D

<400> SEQUENCE: 528

Met Ile Ile Asn Val Asp Arg Val Lys Ala Val Leu Met Asp Lys Ser
1               5                   10                  15

Ile Pro Ala Asn Tyr Leu Glu Met Gln Thr Gly Ile Ser Arg Ser Ala
```

```
                20                  25                  30

Ile Thr Arg Val Arg Asn Gly Glu Arg Lys Ile Glu Asn Leu Thr Ile
            35                  40                  45

Gly Thr Ile Ile Lys Ile Gln Ser Trp Leu Asp Arg Arg Met Ile Arg
        50                  55                  60

<210> SEQ ID NO 529
<211> LENGTH: 60
<212> TYPE: PRT
<213> ORGANISM: Bacteriophage D

<400> SEQUENCE: 529

Met Asp Arg Val Lys Leu Val Leu Met Asn Lys Ala Ile Pro Ala Asn
1               5                   10                  15

Phe Leu Glu Arg Gln Thr Gly Val Ser Arg Ser Ala Ile Thr Arg Val
            20                  25                  30

Arg Asn Asn Glu Arg Lys Ile Glu Asn Leu Thr Leu Glu Thr Ile Ile
        35                  40                  45

Lys Ile Gln Ser Trp Ile Asp Ser Asp Asn Thr Ile
    50                  55                  60

<210> SEQ ID NO 530
<211> LENGTH: 75
<212> TYPE: PRT
<213> ORGANISM: Bacteriophage D

<400> SEQUENCE: 530

Met Gly Arg Arg Ile Arg Ile Lys Ile Lys Met Ile Ile Asn Met
1               5                   10                  15

Asp Gln Val Lys Leu Val Leu Met Asn Lys Asp Ile Pro Ala Asn Phe
            20                  25                  30

Ile Glu Arg Gln Thr Gly Val Ser Arg Ser Ala Ile Thr Lys Val Arg
        35                  40                  45

Asn Gly Glu Arg Lys Ile Glu Asn Leu Arg Leu Glu Thr Ile Ile Lys
    50                  55                  60

Ile Gln Ser Trp Ile Asp Ser Gly Asn Thr Ile
65                  70                  75

<210> SEQ ID NO 531
<211> LENGTH: 71
<212> TYPE: PRT
<213> ORGANISM: Bacteriophage D

<400> SEQUENCE: 531

Met Gly Ser Arg Ile Arg Ile Met Ile Ile Asn Val Asp Arg Val Lys
1               5                   10                  15

Ala Val Leu Met Asp Lys Ser Ile Pro Ala Asn Tyr Leu Glu Met Gln
            20                  25                  30

Thr Gly Ile Ser Arg Ser Ala Ile Thr Arg Val Arg Asn Gly Glu Arg
        35                  40                  45

Lys Ile Glu Asn Leu Thr Ile Gly Thr Ile Ile Lys Ile Gln Ser Trp
    50                  55                  60

Leu Asp Arg Arg Met Ile Arg
65                  70

<210> SEQ ID NO 532
<211> LENGTH: 64
<212> TYPE: PRT
<213> ORGANISM: Bacteriophage D
```

<400> SEQUENCE: 532

Met Ile Ile Asn Met Asp Arg Val Lys Leu Val Leu Met Asn Lys Asp
1               5                   10                  15

Ile Pro Ala Asn Phe Leu Glu Arg Gln Thr Gly Val Ser Arg Ser Ala
            20                  25                  30

Ile Thr Lys Val Arg Asn Gly Glu Arg Lys Ile Glu Asn Leu Thr Leu
        35                  40                  45

Glu Thr Ile Ile Lys Ile Gln Ser Trp Leu Asp Ser Glu Asn Thr Ile
50                  55                  60

<210> SEQ ID NO 533
<211> LENGTH: 64
<212> TYPE: PRT
<213> ORGANISM: Bacteriophage D

<400> SEQUENCE: 533

Met Ile Ile Asn Thr Ala Arg Val Glu Leu Val Leu Met Asn Lys Ala
1               5                   10                  15

Ile Pro Ala Asn Phe Leu Glu Arg Gln Thr Gly Val Ser Arg Ser Ala
            20                  25                  30

Ile Thr Arg Val Arg Asp Gly Glu Arg Lys Ile Glu Asn Leu Thr Leu
        35                  40                  45

Glu Thr Ile Ile Lys Ile Gln Ser Trp Ile Asp Ser Asp Asn Lys Ile
50                  55                  60

<210> SEQ ID NO 534
<211> LENGTH: 71
<212> TYPE: PRT
<213> ORGANISM: Bacteriophage D

<400> SEQUENCE: 534

Met Thr Lys Arg Ile Lys Thr Met Ile Ile Asn Met Asp Arg Val Lys
1               5                   10                  15

Leu Val Leu Met Lys Lys Asp Ile Pro Ala Asn Phe Leu Glu Arg Gln
            20                  25                  30

Thr Gly Val Ser Arg Ser Ala Ile Thr Arg Val Arg Asn Gly Glu Arg
        35                  40                  45

Lys Ile Glu Asn Leu Thr Leu Glu Thr Ile Ile Lys Ile Gln Ser Trp
50                  55                  60

Ile Asp Ser Glu Asn Thr Ile
65                  70

<210> SEQ ID NO 535
<211> LENGTH: 64
<212> TYPE: PRT
<213> ORGANISM: Bacteriophage D

<400> SEQUENCE: 535

Met Ile Ile Asn Thr Ala Arg Val Glu Leu Val Leu Met Asn Lys Ala
1               5                   10                  15

Ile Pro Ala Asn Tyr Leu Glu Arg Gln Thr Gly Val Ser Arg Ser Ala
            20                  25                  30

Ile Thr Arg Val Arg Asn Gly Glu Arg Lys Ile Glu Asn Leu Thr Leu
        35                  40                  45

Glu Thr Ile Ile Lys Ile Gln Ser Trp Ile Asp Ser Asp Asn Lys Ile
50                  55                  60

```
<210> SEQ ID NO 536
<211> LENGTH: 64
<212> TYPE: PRT
<213> ORGANISM: Bacteriophage P

<400> SEQUENCE: 536

Met Ile Ile Asn Val Asp Arg Val Lys Ala Val Leu Met Asp Lys Ser
1               5                   10                  15

Ile Ser Ala Asn Tyr Leu Glu Ile Glu Thr Gly Ile Ser Arg Ser Ala
            20                  25                  30

Ile Thr Arg Val Arg Asn Gly Glu Arg Lys Ile Glu Asn Leu Thr Ile
        35                  40                  45

Gly Thr Ile Ile Lys Ile Gln Ser Trp Leu Asp Arg Arg Met Ile Arg
50                  55                  60

<210> SEQ ID NO 537
<211> LENGTH: 170
<212> TYPE: PRT
<213> ORGANISM: Bacteriophage D

<400> SEQUENCE: 537

Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asp Glu Phe Gln Leu Ile Arg Asp Ser Lys Ala Leu Glu Ser Tyr
50                  55                  60

Ser Gly Leu Thr Arg Asp Tyr Gln Lys Asp Leu Lys Ile Leu Arg Lys
65                  70                  75                  80

Tyr Lys His Arg Asp Met Thr Ile Ser Glu Tyr Ala Met Lys Tyr
                85                  90                  95

Val Val Glu Asn Trp Thr Lys Glu Trp Ser Gln Ser Pro Tyr Ser Tyr
            100                 105                 110

Ser Phe Tyr Ser Ser Lys Asn Ile Asp Trp Gly Tyr Lys Pro Glu Gly
        115                 120                 125

Ser Leu Arg Ile Ser Asp His Trp Asn Phe Gly Glu Asn Gly Glu His
130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170

<210> SEQ ID NO 538
<211> LENGTH: 170
<212> TYPE: PRT
<213> ORGANISM: Bacteriophage D

<400> SEQUENCE: 538

Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asp Glu Phe Gln Leu Ile Arg Asp Ser Lys Ala Leu Glu Ser Tyr
50                  55                  60
```

Ser Gly Leu Thr Arg Asp Tyr Gln Lys Asp Leu Lys Ile Leu Arg Lys
65                  70                  75                  80

Tyr Lys His Arg Asp Met Thr Ile Ser Glu Tyr Glu Ala Met Lys Tyr
                85                  90                  95

Val Val Glu Asn Trp Thr Lys Glu Trp Ser Gln Ser Pro Tyr Ser Asn
            100                 105                 110

Ser Phe Tyr Ser Ser Lys Asp Ile Asp Trp Gly Tyr Lys Pro Glu Gly
        115                 120                 125

Ser Leu Arg Val Ser Asp His Trp Asn Phe Gly Glu Asn Gly Glu His
    130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170

<210> SEQ ID NO 539
<211> LENGTH: 157
<212> TYPE: PRT
<213> ORGANISM: Bacteriophage D

<400> SEQUENCE: 539

Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asn Lys Leu Gln Leu Ile Lys Asp Ser Lys Lys Leu Glu Ser Tyr
    50                  55                  60

Asn Gly Leu Thr Lys Asp Tyr Gln Lys Asp Leu Lys Ile Leu Arg Lys
65                  70                  75                  80

Cys Gly Arg Ser Glu Met Asn Ala Thr Glu Tyr Glu Ala Met Lys Tyr
                85                  90                  95

Val Glu Glu Asn Trp Thr Lys Glu Trp Ser Gln Ser Pro Tyr Ser Asn
            100                 105                 110

Ser Phe Tyr Ser Ser Lys Asp Ile Asp Trp Gly Tyr Lys Pro Glu Gly
        115                 120                 125

Ser Leu Arg Val Ser Asp His Trp Asn Phe Gly Glu Asn Gly Glu His
    130                 135                 140

Cys Pro Thr Ala Glu Pro Val Asp Gly Trp Ala Val Phe
145                 150                 155

<210> SEQ ID NO 540
<211> LENGTH: 170
<212> TYPE: PRT
<213> ORGANISM: Bacteriophage D

<400> SEQUENCE: 540

Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asp Glu Phe Gln Leu Ile Arg Asp Ser Lys Ala Leu Glu Ser Tyr
    50                  55                  60

```
Ser Gly Leu Thr Arg Asp Tyr Gln Lys Asp Leu Lys Ile Leu Arg Lys
 65                  70                  75                  80

Tyr Lys His Arg Asp Met Thr Ile Ser Glu Tyr Glu Ala Met Lys Tyr
                 85                  90                  95

Val Val Glu Asn Trp Thr Lys Glu Trp Ser Gln Ser Pro Tyr Ser Asn
            100                 105                 110

Ser Phe Tyr Ser Ser Lys Asp Ile Asp Trp Gly Tyr Lys Pro Glu Gly
        115                 120                 125

Ser Leu Arg Val Ser Asp His Trp Asn Phe Gly Glu Asn Gly Glu His
    130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170

<210> SEQ ID NO 541
<211> LENGTH: 170
<212> TYPE: PRT
<213> ORGANISM: Bacteriophage D

<400> SEQUENCE: 541

Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asp Glu Phe Gln Leu Ile Arg Asp Asn Lys Ala Leu Glu Ser Tyr
    50                  55                  60

Ser Gly Leu Thr Arg Asp Tyr Gln Lys Asp Leu Lys Ile Leu Arg Lys
 65                  70                  75                  80

Tyr Lys His Arg Asp Met Thr Ile Ser Glu Tyr Glu Ala Met Lys Tyr
                 85                  90                  95

Val Val Glu Asn Trp Thr Lys Glu Trp Ser Gln Ser Pro Tyr Ser Asn
            100                 105                 110

Ser Phe Tyr Ser Ser Lys Asp Ile Asp Trp Gly Tyr Lys Pro Glu Gly
        115                 120                 125

Ser Leu Arg Val Ser Asp His Trp Asn Phe Gly Glu Asn Gly Glu His
    130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170

<210> SEQ ID NO 542
<211> LENGTH: 170
<212> TYPE: PRT
<213> ORGANISM: Bacteriophage D

<400> SEQUENCE: 542

Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45
```

```
Gly Asp Glu Phe Gln Leu Ile Arg Asp Asn Lys Ala Leu Glu Ser Tyr
     50                  55                  60

Ser Gly Leu Thr Arg Asp Tyr Gln Lys Asp Leu Lys Ile Leu Arg Lys
 65                  70                  75                  80

Tyr Lys His Arg Asp Met Thr Ile Ser Glu Tyr Glu Ala Met Lys Tyr
                 85                  90                  95

Val Val Glu Asn Trp Thr Lys Glu Trp Ser Gln Ser Pro Tyr Ser Asn
            100                 105                 110

Ser Phe Tyr Ser Ser Lys Asp Ile Asp Trp Gly Tyr Lys Pro Glu Gly
        115                 120                 125

Ser Leu Arg Val Ser Asp His Trp Asn Phe Gly Glu Asn Gly Glu His
    130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170

<210> SEQ ID NO 543
<211> LENGTH: 74
<212> TYPE: PRT
<213> ORGANISM: Bacteriophage D

<400> SEQUENCE: 543

Met Ile Lys Thr Glu Met Ile Asp Asp Ile Leu Thr Leu Ile Glu Glu
  1               5                  10                  15

Ile Glu Ala Val Ser Asp Lys Asn Lys Glu Lys Phe Ile Glu Lys Phe
             20                  25                  30

Asp Glu Leu Glu Thr Asn Leu Gln Ala Leu Asn Lys Gln Thr Thr Asp
         35                  40                  45

Asp Leu Val Glu Ile Leu Gln Glu Asp Tyr Ser Asp Asn Trp Val Ala
     50                  55                  60

Lys Glu Val Ile Glu Leu Val Thr Asn Ser
 65                  70

<210> SEQ ID NO 544
<211> LENGTH: 74
<212> TYPE: PRT
<213> ORGANISM: Bacteriophage D

<400> SEQUENCE: 544

Met Asn Lys Ile Glu Met Ile Asp Asp Ile Leu Thr Leu Ile Glu Glu
  1               5                  10                  15

Ile Asp Ala Ile Ser Asp Lys Ser Lys Glu Thr Phe Phe Glu Lys Ile
             20                  25                  30

Asp Glu Leu Glu Thr Asn Leu Gln Ala Leu Asn Arg Gln Ile Thr Asp
         35                  40                  45

Glu Leu Val Glu Ile Leu Gln Glu Asp Tyr Ser Asp Asn Trp Val Ala
     50                  55                  60

Lys Glu Val Ile Glu Leu Val Thr Asn Ser
 65                  70

<210> SEQ ID NO 545
<211> LENGTH: 74
<212> TYPE: PRT
<213> ORGANISM: Bacteriophage D

<400> SEQUENCE: 545
```

Met Ile Lys Thr Glu Met Ile Asp Asp Ile Leu Thr Leu Ile Glu Glu
1               5                   10                  15

Ile Glu Ala Val Ser Asp Lys Asn Lys Glu Lys Phe Ile Glu Lys Phe
                20                  25                  30

Asp Glu Leu Glu Thr Asn Leu Gln Ala Leu Asn Lys Gln Thr Thr Asp
            35                  40                  45

Asp Leu Val Glu Ile Leu Gln Glu Asp Tyr Ser Asp Asn Trp Val Ala
        50                  55                  60

Lys Glu Val Ile Glu Leu Val Asp Asp Tyr
65                  70

<210> SEQ ID NO 546
<211> LENGTH: 74
<212> TYPE: PRT
<213> ORGANISM: Bacteriophage D

<400> SEQUENCE: 546

Met Ile Lys Thr Glu Met Ile Asp Asp Ile Leu Thr Leu Ile Glu Glu
1               5                   10                  15

Ile Glu Ala Val Ser Asp Lys Asn Lys Glu Lys Phe Ile Glu Lys Phe
                20                  25                  30

Asp Glu Leu Glu Thr Asn Leu Gln Ala Leu Asn Lys Gln Thr Thr Asp
            35                  40                  45

Asp Leu Val Glu Ile Leu Gln Glu Asp Tyr Ser Asp Asn Trp Val Ala
        50                  55                  60

Lys Glu Val Ile Glu Leu Val Asp Asp Tyr
65                  70

<210> SEQ ID NO 547
<211> LENGTH: 170
<212> TYPE: PRT
<213> ORGANISM: Bacteriophage D

<400> SEQUENCE: 547

Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
                20                  25                  30

Met Lys Leu Leu Tyr Lys Ser Ile Leu Glu Asp Gly Tyr Thr Met Pro
            35                  40                  45

Ile Val Cys Tyr Tyr Leu Lys Asp Glu Asp Lys Tyr Glu Ile Val Asp
        50                  55                  60

Gly Phe His Arg Tyr Ser Thr Met Leu Asn His Lys Asp Ile Tyr Glu
65                  70                  75                  80

Arg Glu Gly Gly Cys Leu Pro Val Ser Val Ile Asp Lys Pro Ile Ser
                85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
130                 135                 140

Leu Leu Arg Leu Lys Gln Leu Thr Gly Leu Ala Ser Leu Phe Ala Asp
145                 150                 155                 160

Lys Glu Phe Ser Lys Ser Trp Asp Val Glu
                165                 170

<210> SEQ ID NO 548
<211> LENGTH: 170
<212> TYPE: PRT
<213> ORGANISM: Bacteriophage D

<400> SEQUENCE: 548

Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
            20                  25                  30

Met Lys Leu Leu Tyr Lys Ser Ile Leu Glu Asp Gly Tyr Thr Met Pro
        35                  40                  45

Ile Val Cys Tyr Tyr Leu Lys Asp Glu Asp Lys Tyr Glu Ile Val Asp
    50                  55                  60

Gly Phe His Arg Tyr Ser Thr Met Leu Asn His Lys Asp Ile Tyr Glu
65                  70                  75                  80

Arg Glu Gly Gly Cys Leu Pro Val Ser Val Ile Asp Lys Pro Ile Ser
                85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
    130                 135                 140

Leu Leu Arg Leu Lys Gln Leu Thr Gly Leu Ser Ser Leu Phe Ala Asp
145                 150                 155                 160

Lys Glu Phe Ser Lys Ser Trp Asp Val Glu
                165                 170

<210> SEQ ID NO 549
<211> LENGTH: 170
<212> TYPE: PRT
<213> ORGANISM: Bacteriophage D

<400> SEQUENCE: 549

Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
            20                  25                  30

Met Lys Leu Leu Tyr Lys Ser Ile Leu Glu Asp Gly Tyr Thr Met Pro
        35                  40                  45

Ile Val Cys Tyr Tyr Leu Lys Asp Glu Asp Lys Tyr Glu Ile Val Asp
    50                  55                  60

Gly Phe His Arg Tyr Ser Thr Met Leu Asn His Lys Asp Ile Tyr Asp
65                  70                  75                  80

Arg Glu Gly Gly Cys Leu Pro Val Ser Val Ile Asn Lys Pro Ile Ser
                85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
    130                 135                 140

Leu Leu Arg Leu Lys Gln Leu Thr Gly Leu Ala Ser Leu Phe Ala Asp
145                 150                 155                 160

```
Lys Glu Phe Ser Lys Ser Trp Asp Val Glu
                165                 170

<210> SEQ ID NO 550
<211> LENGTH: 170
<212> TYPE: PRT
<213> ORGANISM: Bacteriophage D

<400> SEQUENCE: 550

Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
                20                  25                  30

Met Lys Leu Leu Tyr Lys Ser Ile Leu Glu Asp Gly Tyr Thr Met Pro
            35                  40                  45

Ile Val Cys Tyr Tyr Leu Lys Asp Glu Asp Lys Tyr Glu Ile Val Asp
50                  55                  60

Gly Phe His Arg Tyr Ser Thr Met Leu Asn His Lys Asp Ile Tyr Glu
65                  70                  75                  80

Arg Glu Gly Gly Cys Leu Pro Val Ser Val Ile Asp Lys Pro Ile Ser
                85                  90                  95

Asp Arg Met Ala Ser Thr Ile Arg His Asn Arg Ala Arg Gly Ser His
                100                 105                 110

Asp Ile Asp Leu Met Thr Asn Ile Val Ala Asp Leu Val Asp Ser Gly
            115                 120                 125

Met Ser Asp Ala Trp Ile Leu Lys Asn Ile Gly Met Asp Ala Asp Glu
    130                 135                 140

Leu Leu Arg Leu Lys Gln Leu Thr Gly Leu Ala Ser Leu Phe Ala Asp
145                 150                 155                 160

Lys Glu Phe Ser Lys Ser Trp Asp Val Glu
                165                 170

<210> SEQ ID NO 551
<211> LENGTH: 170
<212> TYPE: PRT
<213> ORGANISM: Bacteriophage D

<400> SEQUENCE: 551

Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
                20                  25                  30

Met Lys Leu Leu Tyr Lys Ser Ile Leu Glu Asp Gly Tyr Thr Met Pro
            35                  40                  45

Ile Val Cys Tyr Tyr Leu Lys Asp Glu Asp Lys Tyr Glu Ile Val Asp
50                  55                  60

Gly Phe His Arg Tyr Ser Thr Met Leu Asn His Lys Asp Ile Tyr Asp
65                  70                  75                  80

Arg Glu Gly Gly Cys Leu Pro Val Ser Val Ile Asn Lys Pro Ile Ser
                85                  90                  95

Asp Arg Met Ala Ser Thr Ile Arg His Asn Arg Ala Arg Gly Ser His
                100                 105                 110

Asp Ile Asp Leu Met Thr Asn Ile Val Ala Asp Leu Val Asp Ser Gly
            115                 120                 125

Met Ser Asp Ala Trp Ile Leu Lys Asn Ile Gly Met Asp Ala Asp Glu
    130                 135                 140
```

```
Leu Leu Arg Leu Lys Gln Leu Thr Gly Leu Ala Ser Leu Phe Ala Asp
145                 150                 155                 160

Lys Glu Phe Ser Lys Ser Trp Ile Val Glu
                165                 170

<210> SEQ ID NO 552
<211> LENGTH: 170
<212> TYPE: PRT
<213> ORGANISM: Bacteriophage D

<400> SEQUENCE: 552

Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
                20                  25                  30

Met Lys Leu Leu Tyr Lys Ser Ile Leu Glu Asp Gly Tyr Thr Met Pro
            35                  40                  45

Ile Val Cys Tyr Tyr Leu Lys Asp Glu Asp Lys Tyr Glu Ile Val Asp
        50                  55                  60

Gly Phe His Arg Tyr Ser Thr Met Leu Asn His Lys Asp Ile Tyr Glu
65                  70                  75                  80

Arg Glu Gly Gly Cys Leu Pro Val Ser Val Ile Asp Lys Pro Ile Ser
                85                  90                  95

Asp Arg Met Ala Ser Thr Ile Arg His Asn Arg Ala Arg Gly Ser His
                100                 105                 110

Asp Ile Asp Leu Met Thr Asn Ile Val Ala Asp Leu Val Asp Ser Gly
            115                 120                 125

Met Ser Asp Ala Trp Ile Leu Lys Asn Ile Gly Met Asp Ala Asp Glu
130                 135                 140

Leu Leu Arg Leu Lys Gln Leu Thr Gly Leu Ala Ser Leu Phe Ala Asp
145                 150                 155                 160

Lys Glu Phe Ser Lys Ser Trp Asp Val Glu
                165                 170

<210> SEQ ID NO 553
<211> LENGTH: 59
<212> TYPE: PRT
<213> ORGANISM: Bacteriophage D

<400> SEQUENCE: 553

Met Pro Lys Val Ser Glu Ser Lys Arg Lys Ala Asn Asp Lys Trp Asp
1               5                   10                  15

Lys Lys Asn Lys Glu Arg Lys Gln Tyr Ile Asn Arg Arg Ser Val Ala
                20                  25                  30

Arg Asn Phe Ile Lys Asn Met Glu Gly Glu Asp Ile Pro Glu Phe Lys
            35                  40                  45

Lys Leu Ile Glu Glu Arg Ala Ser Lys Ile Lys
        50                  55

<210> SEQ ID NO 554
<211> LENGTH: 59
<212> TYPE: PRT
<213> ORGANISM: Bacteriophage D

<400> SEQUENCE: 554

Met Pro Lys Val Ser Glu Ser Lys Arg Lys Ala Asn Asp Lys Trp Asp
1               5                   10                  15

Lys Lys Asn Lys Glu Arg Lys Gln Tyr Ile Asn Arg Arg Ser Val Ala
```

```
                    20                  25                  30

Arg Asn Phe Ile Lys Asn Met Glu Asp Glu Asp Ile Pro Glu Phe Lys
            35                  40                  45

Lys Leu Met Glu Glu Arg Ala Ser Lys Ile Lys
    50                  55

<210> SEQ ID NO 555
<211> LENGTH: 59
<212> TYPE: PRT
<213> ORGANISM: Bacteriophage D

<400> SEQUENCE: 555

Met Pro Lys Val Ser Glu Ser Lys Arg Lys Ala Asn Asp Lys Trp Asp
1               5                   10                  15

Lys Lys Asn Lys Glu Arg Lys Gln Tyr Ile Asn Arg Arg Ser Val Ala
            20                  25                  30

Arg Asn Phe Ile Lys Asn Met Glu Asp Glu Asp Ile Pro Glu Phe Lys
            35                  40                  45

Lys Leu Met Glu Glu Arg Thr Ser Lys Ile Lys
    50                  55

<210> SEQ ID NO 556
<211> LENGTH: 65
<212> TYPE: PRT
<213> ORGANISM: Bacteriophage D

<400> SEQUENCE: 556

Met Pro Lys Val Ser Glu Ser Lys Arg Arg Ala Asn Asn Lys Trp Asp
1               5                   10                  15

Lys Lys Asn Lys Glu Arg Lys Gln Tyr Ile Asn Lys Arg Ser Val Ala
            20                  25                  30

Arg Asn Phe Ile Lys Asn Met Glu Asp Glu Asp Val Pro Glu Phe Lys
            35                  40                  45

Lys Leu Met Glu Glu Arg Ala Ser Lys Thr Asn Lys Thr Cys Phe Ser
    50                  55                  60

Ser
65

<210> SEQ ID NO 557
<211> LENGTH: 59
<212> TYPE: PRT
<213> ORGANISM: Bacteriophage D

<400> SEQUENCE: 557

Met Pro Lys Val Ser Glu Ser Lys Arg Lys Ala Asn Asp Lys Trp Asp
1               5                   10                  15

Lys Asn Asn Lys Glu Arg Lys Gln Tyr Ile Asn Arg Arg Ser Val Ala
            20                  25                  30

Arg Asn Phe Ile Lys Asn Met Glu Asp Glu Asp Ile Pro Glu Phe Lys
            35                  40                  45

Lys Leu Met Glu Glu Arg Thr Ser Lys Ile Lys
    50                  55

<210> SEQ ID NO 558
<211> LENGTH: 81
<212> TYPE: PRT
<213> ORGANISM: Bacteriophage D

<400> SEQUENCE: 558
```

```
Met Lys Leu Thr Asn Gln Gln Asn Gln Ala Phe Lys Lys Phe Lys Asn
1               5                   10                  15

Leu Arg Val Gly Ala Leu Phe Met Glu Gln Gly Thr Gly Lys Thr Arg
            20                  25                  30

Val Ala Leu Glu Leu Ile Arg Lys Thr Asp Ala Asp Leu Ala Leu Phe
            35                  40                  45

Phe Cys Pro Phe Ser Thr Lys Asn Asn Leu Leu Ser Glu Ile Glu Lys
50                  55                  60

Trp Gly Ile Asp Ile Glu Phe Met Val Tyr Gly Tyr Glu Thr Ile Ser
65                  70                  75                  80

Ser
```

<210> SEQ ID NO 559
<211> LENGTH: 58
<212> TYPE: PRT
<213> ORGANISM: Bacteriophage D

<400> SEQUENCE: 559

```
Met Glu Thr Glu Pro Asn Phe Gln Ile Ile Cys Tyr Asn Lys Ser Thr
1               5                   10                  15

Ser Phe Glu Val Phe Phe Tyr Leu Thr Thr Ala Pro Glu Phe Phe Gln
            20                  25                  30

Val Phe Phe Phe Arg Pro Lys Ile Thr Arg Lys Leu Trp Glu Lys Leu
            35                  40                  45

Glu Lys Ile Lys Ile Asn Glu Val Lys Thr
50                  55
```

<210> SEQ ID NO 560
<211> LENGTH: 67
<212> TYPE: PRT
<213> ORGANISM: Bacteriophage D

<400> SEQUENCE: 560

```
Met Glu Thr Glu Pro Asn Phe Gln Ile Ile Cys Tyr Asn Lys Ser Thr
1               5                   10                  15

Ser Phe Glu Val Phe Phe Ile Leu Gln Leu His Pro Asn Phe Phe Arg
            20                  25                  30

Cys Phe Phe Cys Pro Lys Ile Thr Gln Lys Leu Trp Glu Lys Leu Glu
            35                  40                  45

Lys Ile Lys Asn Lys Arg Gly Lys Asn Ile Val Cys Phe Thr Asn Phe
50                  55                  60

Gln Ala Asp
65
```

<210> SEQ ID NO 561
<211> LENGTH: 52
<212> TYPE: PRT
<213> ORGANISM: Bacteriophage D

<400> SEQUENCE: 561

```
Met Gly Phe Thr Val Thr Cys Cys Asn Asn Leu Arg Ser Leu Ser Asn
1               5                   10                  15

His Asn His Tyr Cys Cys Phe Leu Arg Leu Val Phe Pro Thr Lys
            20                  25                  30

Ile Glu Ile Ile Pro Ile Ile Trp Phe Ile Phe Arg Val Ser His Gly
            35                  40                  45

Phe Gln Thr Val
50
```

<210> SEQ ID NO 562
<211> LENGTH: 150
<212> TYPE: PRT
<213> ORGANISM: Bacteriophage D

<400> SEQUENCE: 562

Met Glu Tyr Leu Ala Ser Phe Arg Leu Asn Ser Arg Thr Val Thr Ser
1               5                   10                  15
Thr Phe Ser Arg Gly Phe Leu Phe Leu Gln Lys Lys Leu Asn Ser Leu
            20                  25                  30
Ile Asn Lys Asn Lys Asn Tyr Lys Asn Leu Val Gln Leu His Leu Phe
        35                  40                  45
Ser Asn Phe Ile Tyr Phe Arg Ser Arg Ile Val Leu Leu Leu Asn Leu
    50                  55                  60
Lys Arg Glu Arg Asn His Gln Leu Tyr Ser Ala Gly Thr Pro Asp Tyr
65                  70                  75                  80
Leu Lys Asp Ile Leu Phe Glu Ile Pro Ala Leu Phe Ala Leu Thr Trp
                85                  90                  95
Asn Cys Cys Leu Asn Ser Phe Leu Leu Ser Leu Phe Leu Ile Phe Asn
            100                 105                 110
Ser Ile Asn Ile Ile Gln Lys Phe Pro Lys Ile Asn Asn Met Phe Pro
        115                 120                 125
Lys Ile Asn Phe Phe His Ile Phe Leu Ile Leu Val Leu Thr Asn Gly
    130                 135                 140
Asn Val Leu Asp Ile Leu
145                 150

<210> SEQ ID NO 563
<211> LENGTH: 93
<212> TYPE: PRT
<213> ORGANISM: Bacteriophage D

<400> SEQUENCE: 563

Met Glu Val Glu Gln Arg Leu Glu Gln Leu Arg Gln Asp Trp Leu Lys
1               5                   10                  15
His Pro Asn Leu Thr Asp Thr Leu Lys Glu Tyr Leu Asn Glu Tyr Phe
            20                  25                  30
Tyr Asp Asp Tyr Ser Tyr Cys Glu Lys Cys Asp Arg Ile Ala Ser Asp
        35                  40                  45
Ser Asp Trp Phe Trp Tyr Glu Gly Asp Tyr Thr Asp Phe Leu His
    50                  55                  60
Ile Asp Cys Asn Lys Glu Lys Phe Tyr Glu Ala Thr Lys Lys Thr Ser
65                  70                  75                  80
Gly Arg Arg Arg Pro Glu Glu Asn Ile Lys Gly Glu Ser
                85                  90

<210> SEQ ID NO 564
<211> LENGTH: 75
<212> TYPE: PRT
<213> ORGANISM: Bacteriophage D

<400> SEQUENCE: 564

Met Lys Thr Lys Thr Leu Gly Arg Arg Leu Arg Arg Leu Arg Lys Ile
1               5                   10                  15
Asn Gly Glu Thr Gln Lys Glu Phe Ala Glu Asn Phe Gly Arg His Tyr
            20                  25                  30

Arg Thr Val Gln Asn Trp Glu Leu Asp Cys Ser Ile Pro Asp Val Phe
            35                  40                  45

Thr Ala Met Ala Leu Ala Glu Tyr Tyr Asn Met Asp Val Glu Glu Leu
 50                  55                  60

Val Asn Gly Glu Asp Asp Tyr Asp Lys Glu Phe
 65                  70                  75

<210> SEQ ID NO 565
<211> LENGTH: 125
<212> TYPE: PRT
<213> ORGANISM: Bacteriophage D

<400> SEQUENCE: 565

Met Glu Lys Met Thr Met Thr Lys Asn Phe Glu Asn Phe Lys Lys Gly
 1               5                  10                  15

Trp Asp Asn Val Gln Gln Val Val Asn Glu Tyr Ser Lys Lys Leu Val
                20                  25                  30

Glu Asn Ser Gln Glu Asn Val Thr Asn Arg Asp Ser Glu Glu Tyr Gln
            35                  40                  45

Gln Ile Lys Gly Lys Asp Asn Val Ile Ser Pro Asn His Tyr Val Thr
 50                  55                  60

Asp Lys Gly Phe Glu Val Phe Asp Val Gln Glu Ala Phe Ile His Glu
 65                  70                  75                  80

Leu Lys Gly Met Ala Ala Ser Tyr Trp Cys Asn Val Val Lys Tyr Ile
                85                  90                  95

Leu Arg Phe Gln Arg Lys Asn Gly Val Glu Asp Leu Lys Lys Ala Lys
            100                 105                 110

Tyr Tyr Leu Glu Lys Leu Ile Glu Lys Glu Gly Lys
        115                 120                 125

<210> SEQ ID NO 566
<211> LENGTH: 181
<212> TYPE: PRT
<213> ORGANISM: Bacteriophage D

<400> SEQUENCE: 566

Met Asn Lys Gln Glu Ala Ile Glu Leu Val Lys Asn Thr Ser Tyr Ser
 1               5                  10                  15

Val Pro Ile Asp Ser Pro Val Lys His Leu Thr Glu Asp Thr Val Ile
                20                  25                  30

Asn Ile Ile Lys Gln Leu Asp Glu Pro Glu Lys Ala Thr Val Pro Asp
            35                  40                  45

Phe Val Ala Lys Tyr Ile Glu Glu Ser Arg Glu Phe Asp Arg Lys Leu
 50                  55                  60

Asn Asp Ala Leu Ser Tyr Ser Asn Thr Thr Val Ala Met Asp Asp Trp
 65                  70                  75                  80

Phe Glu Glu Asn Glu Val Asp Asn Thr Glu Ile Phe Ala Lys Ala Trp
                85                  90                  95

Leu His Gly Tyr Glu Val Glu Lys Glu Lys Leu Tyr Thr Val Glu Ile
            100                 105                 110

Pro Asp Pro Asn Ala Ser Gly Tyr Gly Lys Thr Phe Leu Gly Arg Asp
        115                 120                 125

Asp Asp Gly Lys Val Val Leu Ser Thr Trp Thr Gly Phe Ser Ser Ile
 130                 135                 140

Glu Phe Ala Asp Asp Trp Lys Gln Ser Glu Arg Ala Gln Leu Thr Glu
 145                 150                 155                 160

```
Asp Glu Ile Lys Lys Gly Phe Thr Trp Ala Trp Asn Glu Gly Phe Ala
                165                 170                 175
Glu Glu Val Lys Glu
        180
```

<210> SEQ ID NO 567
<211> LENGTH: 53
<212> TYPE: PRT
<213> ORGANISM: Bacteriophage D

<400> SEQUENCE: 567

```
Met Lys Arg Phe Val Val Thr Gly Tyr Lys Asp Gly Trp Phe Val Phe
1               5                   10                  15
Ser Phe Pro Leu Asn Ala Ile Asn Ser Tyr Tyr Ala Ile Gln Tyr Ala
                20                  25                  30
Ser Glu Asp Glu Leu Val Glu Gly Met Glu Phe Asp Lys Leu Val Ile
            35                  40                  45
Lys Glu Val Lys Glu
    50
```

<210> SEQ ID NO 568
<211> LENGTH: 48
<212> TYPE: PRT
<213> ORGANISM: Bacteriophage D

<400> SEQUENCE: 568

```
Met Asn Ile Lys Glu Val Phe Cys Ile Asp Cys Tyr Glu Trp Lys Lys
1               5                   10                  15
Lys Glu Asp Leu Thr Gly Ser Lys Phe Ser Asn Asp Ile Leu Tyr Cys
                20                  25                  30
Lys Glu Cys Gly Tyr Ala Leu Val Arg Thr Cys Asp Arg Asn Asn Lys
            35                  40                  45
```

<210> SEQ ID NO 569
<211> LENGTH: 54
<212> TYPE: PRT
<213> ORGANISM: Bacteriophage D

<400> SEQUENCE: 569

```
Met Thr Asn Ile Val Ala Asp Leu Val Asp Ser Gly Met Ser Asp Ala
1               5                   10                  15
Trp Ile Leu Lys Asn Ile Gly Met Asp Ala Asp Glu Leu Leu Arg Leu
                20                  25                  30
Lys Gln Leu Ser Gly Leu Ala Ser Leu Phe Lys Asp Lys Glu Phe Thr
            35                  40                  45
Thr Ala Trp Glu Val Gly
    50
```

<210> SEQ ID NO 570
<211> LENGTH: 90
<212> TYPE: PRT
<213> ORGANISM: Bacteriophage D

<400> SEQUENCE: 570

```
Met Glu Thr Tyr Lys Glu Tyr Lys Gln Gln Gln Lys Glu Glu Arg Glu
1               5                   10                  15
Arg Val Arg Ala Leu Arg Ser Glu Val Phe Ser Gly Asn Ala Glu Lys
                20                  25                  30
Leu Ala Thr Asp Ile Val Arg Ile Ser Ser Gly Asp Val Tyr Lys Ile
            35                  40                  45
```

Ile Pro Arg Phe Gly Thr Arg Tyr Glu Lys Ser Pro Ile Ile Lys Leu
    50                  55                  60

Asp Pro Glu Glu Val Glu Arg His Ile Lys Glu Ala Arg Glu Val Arg
65                  70                  75                  80

Glu Leu Ala Lys Ile Met Ala Ser Lys Glu
                85                  90

<210> SEQ ID NO 571
<211> LENGTH: 80
<212> TYPE: PRT
<213> ORGANISM: Bacteriophage D

<400> SEQUENCE: 571

Met Ala Val Val Val Glu Ala Ser Ala Leu Cys Trp Gly Phe Phe Cys
1               5                   10                  15

Tyr Asn Ile Pro Ile Ser Met Ala Ser His Ala Tyr Ala Gln Ile Arg
                20                  25                  30

Ser Asp Gly Arg Phe Phe Leu Leu Pro Leu Lys Arg Thr Lys Lys Phe
            35                  40                  45

Lys Lys Phe Asp Phe Ile Val Asp Asn Thr Arg Ile Ser Val Tyr Asn
    50                  55                  60

Val Ile Lys Asp Lys Glu Ser Glu Glu Asn Lys Asn Gly Ser Lys Asn
65                  70                  75                  80

<210> SEQ ID NO 572
<211> LENGTH: 156
<212> TYPE: PRT
<213> ORGANISM: Bacteriophage D

<400> SEQUENCE: 572

Met Leu Gly Leu Phe Leu Cys Tyr Asn Arg Ile Lys Lys Gln Ile Asp
1               5                   10                  15

Glu Val Arg Lys Thr Ala Ile Asp Leu Tyr Arg Glu Leu Asp Ile Gln
                20                  25                  30

Ser Leu Glu Gln Arg Leu Glu Lys Asn Glu Glu Asn Thr Gln Arg Phe
            35                  40                  45

Leu Gln Gln Thr Ala Lys Ser Leu Asn Gln Asp Lys Thr Glu Leu Ser
    50                  55                  60

Leu Arg Thr Asp Gln Leu Gly Arg Ser Val Glu Lys Ile Glu Asn Lys
65                  70                  75                  80

Leu Asp Asp Met Tyr Ala Lys Asn Glu Leu Asp Leu Lys Phe Gln Met
                85                  90                  95

Met Asp Gln Lys Ile Asp Ala Lys Phe Asp Thr Phe Gly Gln Arg Met
            100                 105                 110

Glu Asn Met Phe Leu Ala Gln Thr Asn Arg Gln Leu Glu Glu Gln Ala
        115                 120                 125

Lys Asn Arg Lys Glu Phe Thr Tyr Trp Phe Ile Cys Ile Leu Val Ala
    130                 135                 140

Ile Ala Val Ile Ala Ile Pro Val Trp Phe Gly Lys
145                 150                 155

<210> SEQ ID NO 573
<211> LENGTH: 67
<212> TYPE: PRT
<213> ORGANISM: Bacteriophage D

<400> SEQUENCE: 573

```
Met Ser Phe Phe Thr Ser Thr Lys Thr Ala Thr Ser Thr Phe Phe Ile
1               5                   10                  15

Ala Ser Asn Arg Ile Leu Ala Ser Phe Arg Leu Asn Ser Arg Thr Val
            20                  25                  30

His Pro Ser Phe Leu Gly Gly Phe Val Leu Gln Lys Asn Leu Asn
        35                  40                  45

Leu Phe Ile Lys Ser Ile Asp Lys Leu Ser Cys Met Ile Tyr Asn Ile
50                  55                  60

Leu Ile Arg
65
```

<210> SEQ ID NO 574
<211> LENGTH: 42
<212> TYPE: PRT
<213> ORGANISM: Bacteriophage D

<400> SEQUENCE: 574

```
Met Leu Leu Ile Val Thr Phe Ser Tyr Ile Ile Asn Tyr Leu Leu Phe
1               5                   10                  15

Asp Leu Gly Ser Ser Leu Ile Lys Lys Gly Glu Arg Lys Cys Tyr Tyr
            20                  25                  30

Lys Gly Phe Lys Thr Lys Lys Asp Val Ile
        35                  40
```

<210> SEQ ID NO 575
<211> LENGTH: 28
<212> TYPE: PRT
<213> ORGANISM: Bacteriophage D

<400> SEQUENCE: 575

```
Met Glu Cys Leu Tyr Phe Arg Lys Lys Glu Gly Ala Cys Ser Leu Phe
1               5                   10                  15

Phe Met Tyr Ser Ile Lys Ser Ile Leu Tyr Lys Phe
            20                  25
```

<210> SEQ ID NO 576
<211> LENGTH: 229
<212> TYPE: PRT
<213> ORGANISM: Bacteriophage D

<400> SEQUENCE: 576

```
Met Asp Ile Tyr Val Tyr Thr Asp Glu Ser Gly Val Phe Asp Lys Glu
1               5                   10                  15

His Glu Thr Ile Tyr Val Tyr Gly Gly Val Ile Phe Leu Thr Ser Glu
            20                  25                  30

Asp Lys Glu Asn Ser Gly Arg Arg Tyr Ile Tyr Ala Glu Lys Ala Leu
            35                  40                  45

Arg Lys Ser His Ser Asn Tyr Arg Lys Gly Glu Leu Lys Ala Ser Arg
50                  55                  60

Leu Lys Asn Arg His Lys Ala Ser Leu Phe Arg Ser Leu Asn Arg Glu
65                  70                  75                  80

Ile Lys Phe Ser Ile Val Val Ser Ile Gly Arg Val His Asp Arg Ile
                85                  90                  95

Phe Cys Glu Lys Lys Ser Lys Gln Arg Tyr Leu Asp Tyr Val Tyr Lys
                100                 105                 110

Val Gly Leu Lys Lys Val Leu Gln Arg Leu Val Ala Asp Cys Lys Ile
                115                 120                 125

Glu Thr Thr Glu Val Asp Thr Ile Ser Ile Phe Thr Asp Glu His Ser
```

```
                  130                 135                 140
Thr Ala Thr Asn Gly Lys Tyr Glu Leu Arg Glu Ala Leu Leu Asn Glu
145                 150                 155                 160

Phe Lys Tyr Gly Thr Phe Asn Pro Asp Trp Asn Ile Phe Tyr Pro Pro
                165                 170                 175

Leu Phe Glu Lys Leu Ser Ser Leu Thr Val Glu Tyr Cys Asn Ser Ala
            180                 185                 190

Lys Lys Pro His Ile Arg Met Ala Asp Ile Ile Ala Asn Arg Ala Tyr
        195                 200                 205

Tyr Leu Ala Lys Asn Asp Leu Phe Gly Glu Leu Gly Glu Lys Thr Ile
    210                 215                 220

Ser Ile His Phe Pro
225

<210> SEQ ID NO 577
<211> LENGTH: 44
<212> TYPE: PRT
<213> ORGANISM: Bacteriophage D

<400> SEQUENCE: 577

Met Glu Ser Trp Glu Arg Lys Leu Tyr Gln Ser Thr Ser Leu Ser Phe
1               5                   10                  15

Arg Lys Arg Arg Gly Cys Lys Pro Leu Phe Ile Ile Met Val Lys Tyr
            20                  25                  30

Val Gly Phe Cys Leu Ile Leu Phe Met Thr Leu Gly
        35                  40

<210> SEQ ID NO 578
<211> LENGTH: 49
<212> TYPE: PRT
<213> ORGANISM: Bacteriophage M

<400> SEQUENCE: 578

Met His Lys Lys Gly Ile His Ile Lys Lys Val Gly Tyr Phe Ser Arg
1               5                   10                  15

Leu Phe Phe Leu Cys His Val Asn Ser Ser Ile Ala Phe Ser Ile Met
            20                  25                  30

Leu Ser Met Ser Cys Arg Phe Ser Asn Phe Phe Lys Cys Trp Lys Leu
        35                  40                  45

Phe

<210> SEQ ID NO 579
<211> LENGTH: 46
<212> TYPE: PRT
<213> ORGANISM: Bacteriophage M

<400> SEQUENCE: 579

Met Leu Gly Gly Leu Arg Arg Pro Leu Phe Asp Ile Ser Thr Ala Ser
1               5                   10                  15

His Pro Ser Phe Leu Gly Gly Phe Phe Val Leu Gln Lys Ile Phe Leu
            20                  25                  30

Ser Lys Val Arg Ile His Thr Lys Asn Thr Leu Leu Thr Phe
        35                  40                  45

<210> SEQ ID NO 580
<211> LENGTH: 145
<212> TYPE: PRT
<213> ORGANISM: Bacteriophage P
```

-continued

```
<400> SEQUENCE: 580

Met Asn Glu Ile Ala Leu Ser Asp Asn Leu Ala Gln Ile Glu Leu Glu
1               5                   10                  15

Ile Asn His His Lys Gln Ile Ala Gly Gln Ser Ile Trp Glu Ile Gly
            20                  25                  30

Arg Arg Leu Asn His Val Lys Glu His Asp Leu Ala His Gly Gln Phe
        35                  40                  45

Met Glu Trp Val Glu Lys Leu Gly Ile Asn Gln Pro Glu Ala Asn Arg
    50                  55                  60

Met Met Arg Val Ala Lys Glu Leu Pro Asn Ser Ser Thr Leu Ser Asn
65                  70                  75                  80

Leu Gly Ser Thr Ala Leu Tyr Leu Ile Ala Thr Leu Pro Asp Asp Glu
                85                  90                  95

Lys Gln Glu Gln Ile Glu Lys Ile Glu Gln Gly Glu Ser Pro Thr Val
            100                 105                 110

Arg Glu Leu Gln Glu Ile Lys Arg Arg Leu Lys Leu Lys Asp Gln Ala
        115                 120                 125

Leu Glu Ala Val Lys Gly Glu Leu Glu Arg Ala Ile Leu Gly Ile Lys
    130                 135                 140

Val
145

<210> SEQ ID NO 581
<211> LENGTH: 145
<212> TYPE: PRT
<213> ORGANISM: Bacteriophage P

<400> SEQUENCE: 581

Met Asn Glu Ile Ala Leu Ser Asp Asn Leu Ala Gln Ile Glu Leu Glu
1               5                   10                  15

Ile Asn His His Lys Gln Ile Ala Gly Gln Ser Ile Trp Glu Ile Gly
            20                  25                  30

Arg Arg Leu Asn His Val Lys Glu His Asp Leu Ala His Gly Gln Phe
        35                  40                  45

Met Glu Trp Val Glu Lys Leu Gly Ile Asn Gln Pro Glu Ala Asn Arg
    50                  55                  60

Met Met Arg Val Ala Lys Glu Leu Pro Asn Ser Ser Thr Leu Ser Asn
65                  70                  75                  80

Leu Gly Ser Thr Ala Leu Tyr Leu Ile Ala Thr Leu Pro Asp Asp Glu
                85                  90                  95

Lys Gln Glu Gln Ile Glu Lys Ile Glu Gln Gly Glu Ser Pro Thr Val
            100                 105                 110

Arg Glu Leu Gln Glu Ile Lys Arg Arg Leu Lys Leu Lys Asp Gln Glu
        115                 120                 125

Leu Glu Ala Val Lys Gly Glu Leu Glu Arg Ala Ile Leu Gly Ile Lys
    130                 135                 140

Val
145

<210> SEQ ID NO 582
<211> LENGTH: 111
<212> TYPE: PRT
<213> ORGANISM: Bacteriophage P

<400> SEQUENCE: 582

Met Glu Glu Leu Glu Gln Ala Phe Glu Asn Leu Asp Asp Trp Tyr Leu
```

```
                1               5                  10                  15
          Ser Ser Met Lys Asp Ser Ala Tyr Lys Asp Phe Gly Lys Tyr Glu Ile
                         20                  25                  30

Arg Leu Ser Asn His Ser Ala Asp Asn Lys Tyr His Asp Leu Glu Asn
                         35                  40                  45

Gly Arg Leu Ile Val Asn Val Lys Ala Ser Lys Leu Asn Phe Val Asp
                   50                  55                  60

Ile Ile Glu Asn Lys Ile Tyr Lys Ile Glu Lys Ile Glu Thr Leu
          65                  70                  75                  80

Asp Leu Asp Lys Tyr Arg Phe Ile Asn Ala Thr Lys Met Glu Asn Asp
                              85                  90                  95

Ile Lys Cys Tyr Tyr Lys Gly Phe Lys Thr Lys Lys Asp Val Ile
                         100                 105                 110
```

<210> SEQ ID NO 583
<211> LENGTH: 58
<212> TYPE: PRT
<213> ORGANISM: Bacteriophage P

<400> SEQUENCE: 583

```
          Met Thr Asp Ala His Lys Lys Ala Val Lys Lys Trp Asn Lys Asn Asn
          1               5                  10                  15

Arg Glu His Arg Asn Tyr Leu Asn Lys Arg Ser Ser Ala Arg Gly Phe
                         20                  25                  30

Ile Arg Asn Asn Ala Thr Ala Glu Asp Leu Arg Glu Leu Glu Glu Leu
                         35                  40                  45

Ile Ala Glu Arg Arg Lys Lys Asn Phe Arg
                   50                  55
```

<210> SEQ ID NO 584
<211> LENGTH: 97
<212> TYPE: PRT
<213> ORGANISM: Bacteriophage P

<400> SEQUENCE: 584

```
          Met Leu Asn Leu Lys Arg Glu Arg Asn His Gln Leu Tyr Ser Ala Gly
          1               5                  10                  15

Thr Pro Asp Tyr Leu Lys Asp Ile Leu Phe Glu Ile Pro Ala Leu Phe
                         20                  25                  30

Ala Leu Thr Trp Asn Cys Cys Leu Asn Ser Phe Leu Ser Leu Phe
                         35                  40                  45

Leu Ile Phe Asn Ser Ile Asn Ile Ile Gln Lys Phe Pro Lys Asn Lys
                   50                  55                  60

Gln Tyr Val Pro Lys Asn Lys Leu Phe Ser Tyr Phe Asp Phe Ser
          65                  70                  75                  80

Val Asp Lys Trp Glu Arg Val Arg Tyr Thr Ile Ile Val Leu Arg Asn
                              85                  90                  95

Lys
```

<210> SEQ ID NO 585
<211> LENGTH: 34
<212> TYPE: PRT
<213> ORGANISM: Bacteriophage P

<400> SEQUENCE: 585

```
          Met Gln Lys Lys Tyr Ile Ile Phe Tyr Lys Asn Ser Phe Arg Leu Val
          1               5                  10                  15
```

```
Ala Lys Ile Asp Leu Asn Gly Leu Lys Thr Ile Leu Lys Thr Phe Asp
            20                  25                  30

Lys Lys

<210> SEQ ID NO 586
<211> LENGTH: 34
<212> TYPE: PRT
<213> ORGANISM: Bacteriophage P

<400> SEQUENCE: 586

Met Arg Thr His Lys His Lys Gly Lys Phe Cys Trp Gly Gly Leu Arg
1               5                   10                  15

Arg Pro Leu Phe Asp Ile Ile Tyr Leu Tyr Gln Arg Pro Pro Thr Arg
            20                  25                  30

Leu Phe

<210> SEQ ID NO 587
<211> LENGTH: 43
<212> TYPE: PRT
<213> ORGANISM: Bacteriophage P

<400> SEQUENCE: 587

Met Leu Gly Leu Phe Phe Asn Ile Asn Ala Thr Ile Leu Met Asp Thr
1               5                   10                  15

Val Lys Arg Glu Ala Ser Arg Tyr Asp Gly Phe Tyr Gly Pro Asp Arg
            20                  25                  30

Leu Val Phe Arg Lys Ser Gln Thr Ile Arg Tyr
        35                  40

<210> SEQ ID NO 588
<211> LENGTH: 73
<212> TYPE: PRT
<213> ORGANISM: Bacteriophage TPL

<400> SEQUENCE: 588

Met Tyr Ala Lys Asn Glu Leu Asp Leu Lys Phe Gln Met Met Asp Gln
1               5                   10                  15

Lys Ile Asp Ala Lys Phe Asp Thr Phe Gly Gln Arg Met Glu Asn Met
            20                  25                  30

Phe Leu Ala Gln Thr Asn Arg Gln Leu Glu Glu Gln Ala Lys Asn Arg
        35                  40                  45

Lys Glu Phe Thr Tyr Trp Phe Ile Cys Ile Leu Val Ala Ile Ala Val
    50                  55                  60

Ile Ala Ile Pro Val Trp Phe Gly Lys
65                  70

<210> SEQ ID NO 589
<211> LENGTH: 73
<212> TYPE: PRT
<213> ORGANISM: Bacteriophage TPJ

<400> SEQUENCE: 589

Met Tyr Ala Lys Asn Glu Leu Asp Leu Lys Phe Gln Met Met Asp Gln
1               5                   10                  15

Lys Ile Asp Ala Lys Phe Asp Thr Phe Gly Gln Arg Met Glu Asn Met
            20                  25                  30

Phe Leu Ala Gln Thr Asn Arg Gln Leu Glu Glu Gln Ala Lys Asn Arg
        35                  40                  45

Lys Glu Phe Thr Tyr Trp Phe Ile Cys Ile Leu Val Ala Ile Ala Val
```

```
                50                  55                  60
Ile Ala Ile Pro Val Trp Phe Gly Lys
65                  70

<210> SEQ ID NO 590
<211> LENGTH: 60
<212> TYPE: PRT
<213> ORGANISM: Bacteriophage D

<400> SEQUENCE: 590

Met Asp Thr Tyr Lys Glu Gln Phe Tyr Tyr Leu Asp Pro Ile Tyr Ile
1               5                   10                  15

Ser Val Asp Ile Asn Arg Arg Thr Phe Ile Leu Gly Lys Arg Gly Gln
            20                  25                  30

Ser Leu Ser Phe Phe Ile Val Ile Lys Gln Phe Lys Asn Ile Thr Lys
        35                  40                  45

Lys Thr Ser Lys Lys Ser Lys Lys Asn Ile Asp Lys
    50                  55                  60

<210> SEQ ID NO 591
<211> LENGTH: 58
<212> TYPE: PRT
<213> ORGANISM: Bacteriophage P

<400> SEQUENCE: 591

Met Leu Gly Leu Phe Leu Cys Tyr Asn Met Asn Glu Met Ser Ile Pro
1               5                   10                  15

Pro His Pro Phe Met Asp Arg Tyr Val Leu Ser Gly Gly Phe Phe Val
            20                  25                  30

Leu Leu Phe Phe Asn Leu Thr Ala Arg Asn Ser Pro Thr Ser Lys Val
        35                  40                  45

Ala Gly Cys Lys Gly Phe Gly Leu Val Gln
    50                  55

<210> SEQ ID NO 592
<211> LENGTH: 64
<212> TYPE: PRT
<213> ORGANISM: Bacteriophage D

<400> SEQUENCE: 592

Met Phe Ser Asp Leu Val Arg Ser Lys Val Tyr Lys Gly Thr Phe Cys
1               5                   10                  15

Cys Gly Leu Arg Pro Pro Phe Phe Asp Ile Ile Tyr Leu Tyr Gln Cys
            20                  25                  30

Pro Pro Thr His Lys Arg Arg Tyr Val Leu Arg Glu Val Phe Tyr Leu
        35                  40                  45

Phe Tyr Phe Asp Lys Asn Ala Thr Ile Leu Thr Asp Thr Val Lys Ser
    50                  55                  60

<210> SEQ ID NO 593
<211> LENGTH: 64
<212> TYPE: PRT
<213> ORGANISM: Bacteriophage D

<400> SEQUENCE: 593

Met Phe Ser Asp Leu Val Arg Ser Gln Val Tyr Lys Gly Thr Phe Cys
1               5                   10                  15

Cys Gly Leu Arg Pro Pro Phe Phe Asp Ile Ile Tyr Leu Tyr Gln Cys
            20                  25                  30
```

```
Pro Pro Thr His Lys Arg Arg Tyr Val Leu Arg Glu Val Phe Tyr Leu
        35                  40                  45

Phe Tyr Phe Asp Ile Asn Ala Thr Ile Ile Met Asp Thr Val Lys Ser
 50                  55                  60
```

<210> SEQ ID NO 594
<211> LENGTH: 87
<212> TYPE: PRT
<213> ORGANISM: Bacteriophage P

<400> SEQUENCE: 594

```
Met Asn Ser Met Lys Lys Pro His Thr Ala Glu Asn Gly Asp Leu Ile
 1               5                  10                  15

His Thr Thr Glu Asp Asn Glu Ala Ser Asp Ile Ser Ile Ile Thr Ile
             20                  25                  30

Ser Phe Val Arg Lys Thr Asn Lys Gln Ile Leu Lys Asn Ser Lys Val
        35                  40                  45

Cys Leu Lys Arg Tyr Lys Leu Lys Tyr Leu Asn His Leu Pro Ile Gln
 50                  55                  60

Arg Leu Ile Lys Gln Tyr Ser Thr Glu Ile Ser Lys Gln Lys Glu Ile
65                  70                  75                  80

Ile Ala Leu Glu Lys Asn Glu
                85
```

<210> SEQ ID NO 595
<211> LENGTH: 80
<212> TYPE: PRT
<213> ORGANISM: Bacteriophage P

<400> SEQUENCE: 595

```
Met Asn Ser Met Lys Lys Pro His Thr Ala Glu Asn Gly Asp Leu Ile
 1               5                  10                  15

His Thr Thr Glu Asp Asn Glu Ala Ser Asp Ile Ser Ile Ile Thr Ile
             20                  25                  30

Ser Phe Val Arg Lys Thr Asn Lys Gln Ile Leu Lys Asn Ser Lys Val
        35                  40                  45

Cys Leu Lys Arg Tyr Lys Leu Lys Tyr Leu Asn His Leu Pro Ile Gln
 50                  55                  60

Arg Leu Ile Lys Gln Tyr Ser Thr Glu Ile Ser Lys Gln Lys Glu Tyr
65                  70                  75                  80
```

<210> SEQ ID NO 596
<211> LENGTH: 26
<212> TYPE: PRT
<213> ORGANISM: Bacteriophage D

<400> SEQUENCE: 596

```
Met Phe Ser Asp Leu Val Arg Ser Lys Val Tyr Lys Gly Thr Phe Cys
 1               5                  10                  15

Cys Gly Leu Arg Pro Pro Phe Phe Leu Ile
             20                  25
```

<210> SEQ ID NO 597
<211> LENGTH: 50
<212> TYPE: PRT
<213> ORGANISM: Bacteriophage D

<400> SEQUENCE: 597

```
Met Ala Val Val Val Glu Ala Ser Ala Phe Leu Leu Gly Leu Phe Leu
 1               5                  10                  15
```

Cys Tyr Asn Met Lys His His Phe Met Asp Arg Tyr Leu Leu Cys Phe
            20                  25                  30

Asp Lys Asn Ala Thr Ile Leu Met Val Phe Asp Lys Leu Ser Leu Ala
            35                  40                  45

Leu Thr
    50

<210> SEQ ID NO 598
<211> LENGTH: 91
<212> TYPE: PRT
<213> ORGANISM: Bacteriophage D

<400> SEQUENCE: 598

Met Ile Thr Lys Glu Gln Leu Lys Gly Tyr Tyr Ser Glu His Leu Glu
1               5                   10                  15

Glu Leu Val Glu Trp Ala Asp Asp Ile Asn Lys Ile Ala Tyr Glu Ile
            20                  25                  30

Asp Gly Lys Ser His Gln Thr Lys Ile Gly Trp Val Asn Asp Arg Leu
            35                  40                  45

Lys Asp His Phe Met Lys Glu Lys Gly Val Leu Val Ile His Tyr Thr
50                  55                  60

Asn Glu Gln Val Glu Thr Ala Tyr Asn Glu Trp Val Lys Ile Thr Glu
65                  70                  75                  80

Glu Ala Phe Asn Gly Phe Phe Asn Asn Thr Ile
            85                  90

<210> SEQ ID NO 599
<211> LENGTH: 45
<212> TYPE: PRT
<213> ORGANISM: Bacteriophage P

<400> SEQUENCE: 599

Met Ala Ala Val Val Glu Ala Ser Ala Phe Leu Leu Gly Leu Phe Leu
1               5                   10                  15

Cys Tyr Asn Met Asn Glu Met Ser Ile Pro Pro His Pro Phe Met Asp
            20                  25                  30

Arg Tyr Val Leu Met Gly Ser Phe Leu Phe Ala Leu Phe
            35                  40                  45

<210> SEQ ID NO 600
<211> LENGTH: 48
<212> TYPE: PRT
<213> ORGANISM: Bacteriophage D

<400> SEQUENCE: 600

Met Ala Val Val Val Glu Ala Ser Ala Leu Cys Trp Gly Phe Phe Cys
1               5                   10                  15

Val Ile Ile Tyr Leu Tyr Gln Trp Pro Pro Thr His Thr Arg Arg Tyr
            20                  25                  30

Val Leu Met Gly Gly Phe Phe Val Ala Val Lys Thr Asp Lys Lys Ile
            35                  40                  45

<210> SEQ ID NO 601
<211> LENGTH: 39
<212> TYPE: PRT
<213> ORGANISM: Bacteriophage D

<400> SEQUENCE: 601

Met Val Glu Ala Ser Ala Leu Cys Trp Gly Phe Phe Cys Val Ile Ile

```
                1               5                   10                  15
            His Ile Ser Met Ala Ser His Ala Tyr Ala Gln Ile Arg Ser Glu Gly
                            20                  25                  30
            Ser Phe Leu Phe Ala Phe Phe
                            35

<210> SEQ ID NO 602
<211> LENGTH: 41
<212> TYPE: PRT
<213> ORGANISM: Bacteriophage D

<400> SEQUENCE: 602

Met Ala Val Val Val Glu Ala Ser Ala Phe Cys Trp Gly Phe Phe Cys
1               5                   10                  15

Val Ile Ile Tyr Met Glu Arg Gln Thr Pro Cys Ile His Met Asp Arg
                20                  25                  30

Tyr Ala Leu Thr Gln Gly Phe Phe Ile
                35                  40

<210> SEQ ID NO 603
<211> LENGTH: 43
<212> TYPE: PRT
<213> ORGANISM: Bacteriophage P

<400> SEQUENCE: 603

Met Ala Ala Val Val Glu Ala Ser Ala Phe Leu Leu Gly Leu Phe Leu
1               5                   10                  15

Cys Tyr Asn Ile Pro Ile Ser Met Ala Ser His Ala Tyr Ala Gln Ile
                20                  25                  30

Arg Ser Glu Gly Gly Phe Leu Phe Ala Leu Phe
                35                  40

<210> SEQ ID NO 604
<211> LENGTH: 172
<212> TYPE: PRT
<213> ORGANISM: Bacteriophage D

<400> SEQUENCE: 604

Met Glu Asn Tyr Ser Ser Pro Val Tyr Asn Ile Lys Lys Ile Pro Ile
1               5                   10                  15

Glu Lys Ile Gln Ala Asn Ser Tyr Asn Pro Asn His Val Ala Thr Pro
                20                  25                  30

Glu Met Lys Leu Leu Tyr Glu Ser Ile Lys Ala Asp Gly Tyr Thr Met
                35                  40                  45

Pro Ile Val Cys Tyr Tyr Leu Lys Asp Glu Asp Lys Tyr Glu Ile Val
        50                  55                  60

Asp Gly Phe His Arg Tyr Thr Thr Met Leu Asn His Lys Asp Ile Tyr
65                  70                  75                  80

Glu Arg Glu Asn Gly Cys Leu Pro Val Ser Val Ile Asp Lys Pro Leu
                85                  90                  95

Glu Glu Arg Met Ala Ser Thr Val Arg His Asn Arg Ala Arg Gly Ser
                100                 105                 110

His Asp Ile Gly Leu Met Ala Asn Ile Val Thr Glu Leu Val Asp Ser
                115                 120                 125

Gly Met Ser Asp Ala Lys Val Met Lys Ser Leu Gly Met Asp Ala Asp
            130                 135                 140

Glu Leu Leu Arg Leu Lys Gln Val Ser Gly Leu Ala Ser Leu Phe Ala
145                 150                 155                 160
```

```
Asn Lys Glu Phe Ser Lys Ser Trp Asp Ile Lys Lys
            165                 170
```

<210> SEQ ID NO 605
<211> LENGTH: 171
<212> TYPE: PRT
<213> ORGANISM: Bacteriophage D

<400> SEQUENCE: 605

```
Met Gln Thr Tyr Ser Ser Pro Val Tyr Asn Ile Lys Arg Val Pro Ile
1               5                   10                  15

Glu Lys Ile Gln Ala Asn Ser Tyr Asn Pro Asn His Val Ala Ser Pro
            20                  25                  30

Glu Met Lys Leu Leu Tyr Gln Ser Ile Lys Glu Asp Gly Tyr Thr Met
        35                  40                  45

Pro Ile Val Cys Tyr Tyr Leu Glu Asp Glu Asp Lys Tyr Glu Ile Val
    50                  55                  60

Asp Gly Phe His Arg Tyr Thr Thr Met Lys Glu His Lys Asp Ile Tyr
65                  70                  75                  80

Glu Arg Glu Glu Gly Cys Leu Pro Val Ser Val Ile Asp Lys Pro Ile
                85                  90                  95

Ser Asp Arg Met Ala Ser Thr Ile Arg His Asn Arg Ala Arg Gly Ser
            100                 105                 110

His Asp Ile Gly Leu Met Thr Asn Ile Ile Ser Asp Leu Val Asp Ser
        115                 120                 125

Gly Met Ser Asp Ala Trp Ile Met Lys Asn Ile Gly Met Asp Ala Asp
    130                 135                 140

Glu Leu Leu Arg Leu Lys Gln Val Ser Gly Leu Ala Ser Leu Phe Lys
145                 150                 155                 160

Asp Lys Glu Phe Thr Thr Ala Trp Glu Glu Gly
            165                 170
```

<210> SEQ ID NO 606
<211> LENGTH: 171
<212> TYPE: PRT
<213> ORGANISM: Bacteriophage D

<400> SEQUENCE: 606

```
Met Gln Thr Tyr Ser Ser Pro Val Tyr Asn Ile Lys Arg Val Pro Ile
1               5                   10                  15

Asp Lys Ile Gln Ala Asn Ser Tyr Asn Pro Asn His Val Ala Ser Pro
            20                  25                  30

Glu Met Lys Leu Leu Tyr Gln Ser Ile Lys Glu Asp Gly Tyr Thr Met
        35                  40                  45

Pro Ile Val Cys Tyr Tyr Leu Glu Asp Glu Asp Lys Tyr Glu Ile Val
    50                  55                  60

Asp Gly Phe His Arg Tyr Thr Thr Met Lys Glu His Lys Asp Ile Tyr
65                  70                  75                  80

Glu Arg Glu Glu Gly Cys Leu Pro Val Ser Val Ile Asp Lys Pro Ile
                85                  90                  95

Ser Asp Arg Met Ala Ser Thr Ile Arg His Asn Arg Ala Arg Gly Ser
            100                 105                 110

His Asp Ile Gly Leu Met Thr Asn Ile Ile Ser Asp Leu Val Asp Ser
        115                 120                 125

Gly Met Ser Asp Ala Trp Ile Met Lys Asn Ile Gly Met Asp Ala Asp
    130                 135                 140
```

Glu Leu Leu Arg Leu Lys Gln Val Ser Gly Leu Ala Ser Leu Phe Lys
145                 150                 155                 160

Asp Lys Glu Phe Thr Thr Ala Trp Glu Glu Gly
                165                 170

<210> SEQ ID NO 607
<211> LENGTH: 170
<212> TYPE: PRT
<213> ORGANISM: Bacteriophage D

<400> SEQUENCE: 607

Met Gln Thr Tyr Tyr Ser Pro Val Tyr Asn Ile Lys Arg Val Pro Ile
1               5                   10                  15

Glu Lys Ile Gln Ala Asn Ser Tyr Asn Pro Asn His Val Ala Ser Pro
                20                  25                  30

Glu Met Lys Leu Leu Tyr Gln Ser Ile Lys Glu Asp Gly Tyr Thr Met
            35                  40                  45

Pro Ile Val Cys Tyr Tyr Leu Glu Asp Glu Asp Lys Tyr Glu Ile Val
    50                  55                  60

Asp Gly Phe His Arg Tyr Thr Thr Met Lys Glu His Lys Asp Ile Tyr
65                  70                  75                  80

Glu Arg Glu Glu Gly Cys Leu Pro Val Ser Val Ile Asp Lys Pro Ile
                85                  90                  95

Ser Asp Arg Met Ala Ser Thr Ile Arg His Asn Arg Ala Arg Gly Ser
                100                 105                 110

His Asp Ile Gly Leu Met Thr Asn Ile Ile Ser Asp Leu Val Asp Ser
            115                 120                 125

Gly Met Ser Asp Ala Trp Ile Met Lys Asn Ile Gly Met Asp Ala Asp
    130                 135                 140

Glu Leu Leu Arg Leu Lys Gln Val Ser Gly Leu Ala Ser Leu Phe Lys
145                 150                 155                 160

Asp Lys Glu Phe Thr Thr Ala Trp Glu Glu
                165                 170

<210> SEQ ID NO 608
<211> LENGTH: 74
<212> TYPE: PRT
<213> ORGANISM: Bacteriophage D

<400> SEQUENCE: 608

Met Ala Gln Ile Lys Asp Gly Trp His Lys Val Tyr Asn Glu Asn Val
1               5                   10                  15

Tyr Val Glu Asn Glu Lys Val Val Arg Gly Thr Lys Lys Asp Tyr Asn
                20                  25                  30

Gly Ser Glu Val Thr Cys Tyr Pro Tyr Glu Tyr Asp Lys Asn Gln Asp
            35                  40                  45

Cys Trp Ile Asn Ile Ser Gly Lys Ala Thr Leu Ser Ser Tyr Arg Ala
    50                  55                  60

Gly Leu Lys Lys Gly Thr Lys Cys Met Lys
65                  70

<210> SEQ ID NO 609
<211> LENGTH: 45
<212> TYPE: PRT
<213> ORGANISM: Bacteriophage D

<400> SEQUENCE: 609

```
Met Phe Ser Asp Leu Val Arg Ser Lys Val Tyr Lys Gly Thr Phe Cys
1               5                   10                  15

Cys Gly Leu Arg Pro Pro Phe Phe Asp Ile Ile Tyr Leu Tyr Gln Cys
                20                  25                  30

Pro Pro Thr His Lys Arg Arg Tyr Val Leu Ser Leu Arg
            35                  40                  45
```

<210> SEQ ID NO 610
<211> LENGTH: 40
<212> TYPE: PRT
<213> ORGANISM: Bacteriophage D

<400> SEQUENCE: 610

```
Met Leu Gly Leu Phe Leu Cys Tyr Asn Met Asn Glu Met Ser Ile Pro
1               5                   10                  15

Pro His Pro Phe Met Asp Arg Tyr Val Leu Ser Gly Gly Phe Phe Val
                20                  25                  30

Leu Leu Phe Phe Lys Asn Val Val
            35                  40
```

<210> SEQ ID NO 611
<211> LENGTH: 46
<212> TYPE: PRT
<213> ORGANISM: Bacteriophage D

<400> SEQUENCE: 611

```
Met Leu Gly Leu Phe Leu Cys Tyr Asn Met Asn Glu Met Ser Ile Pro
1               5                   10                  15

Pro His Pro Phe Met Asp Arg Tyr Val Leu Ser Gly Gly Phe Leu Phe
                20                  25                  30

Cys Tyr Phe Leu Lys Met Trp Tyr Asn Ile Asn Ile His Ser
            35                  40                  45
```

<210> SEQ ID NO 612
<211> LENGTH: 85
<212> TYPE: PRT
<213> ORGANISM: Bacteriophage D

<400> SEQUENCE: 612

```
Met Lys Lys Phe Trp His Ser Gly Met Ile Asp Lys Lys Val Ile Glu
1               5                   10                  15

Lys Arg Lys Gln Asp Asp Tyr Met Asn Lys Leu His Arg Thr Ile Leu
                20                  25                  30

Glu Leu Ser Ile Lys Pro Pro Glu Pro Glu Pro Trp Tyr Arg His Pro
            35                  40                  45

Glu Met Arg Ala Leu Leu Asp Arg Ile Asp Ser Met Asp Met Ile Asp
        50                  55                  60

Trp Tyr Ser Lys Tyr Leu Lys His Arg Lys Pro Tyr Asp Asn Tyr Ser
65                  70                  75                  80

Gly Glu Leu Glu Lys
                85
```

<210> SEQ ID NO 613
<211> LENGTH: 59
<212> TYPE: PRT
<213> ORGANISM: Bacteriophage

<400> SEQUENCE: 613

```
Met Lys Lys Phe Trp Arg Ser Gly Met Ile Asp Lys Lys Val Ile Glu
1               5                   10                  15
```

Lys Arg Gln Gln Glu Glu Tyr Ile Asn Lys Leu His Arg Thr Ile Leu
            20                  25                  30

Glu Leu Ser Ile Lys Pro Pro Glu Pro Trp Tyr Arg His Pro
        35                  40                  45

Glu Met Arg Ala Leu Leu Asp Arg Ile Asp Asp
    50                  55

<210> SEQ ID NO 614
<211> LENGTH: 65
<212> TYPE: PRT
<213> ORGANISM: Bacteriophage D

<400> SEQUENCE: 614

Met Lys Lys Phe Trp Arg Ser Gly Met Ile Asp Lys Lys Val Ile Glu
1               5                   10                  15

Lys Arg Gln Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Phe Leu Asp Arg Ile Tyr Asp Ser Arg Ser Asn Leu
    50                  55                  60

Lys
65

<210> SEQ ID NO 615
<211> LENGTH: 59
<212> TYPE: PRT
<213> ORGANISM: Bacteriophage D

<400> SEQUENCE: 615

Met Lys Lys Phe Trp Arg Ser Gly Met Ile Asp Lys Lys Ile Ile Ala
1               5                   10                  15

Lys Arg Glu Gln Asp Glu Tyr Leu Asn Lys Leu His Arg Thr Ile Leu
            20                  25                  30

Glu Leu Ser Arg Lys Pro Pro Glu Gln Glu Pro Trp Tyr Arg His Pro
        35                  40                  45

Glu Met Arg Ala Leu Leu Asp Arg Ile Asp Asp
    50                  55

<210> SEQ ID NO 616
<211> LENGTH: 59
<212> TYPE: PRT
<213> ORGANISM: Bacteriophage D

<400> SEQUENCE: 616

Met Lys Lys Phe Trp His Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Asp Asp
    50                  55

<210> SEQ ID NO 617
<211> LENGTH: 65
<212> TYPE: PRT
<213> ORGANISM: Bacteriophage D

```
<400> SEQUENCE: 617

Met Lys Lys Phe Trp Arg Ser Gly Met Ile Asp Lys Lys Val Ile Glu
1               5                   10                  15

Lys Arg Gln Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Tyr Asp Ser Arg Ser Asn Leu
    50                  55                  60

Lys
65

<210> SEQ ID NO 618
<211> LENGTH: 59
<212> TYPE: PRT
<213> ORGANISM: Bacteriophage TPJ

<400> SEQUENCE: 618

Met Lys Lys Phe Trp Arg Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Asp Asp
    50                  55

<210> SEQ ID NO 619
<211> LENGTH: 59
<212> TYPE: PRT
<213> ORGANISM: Bacteriophage Proph

<400> SEQUENCE: 619

Met Lys Lys Phe Trp Arg Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Asp Asp
    50                  55

<210> SEQ ID NO 620
<211> LENGTH: 58
<212> TYPE: PRT
<213> ORGANISM: Bacteriophage D

<400> SEQUENCE: 620

Met Lys Lys Phe Trp Arg Ser Gly Met Ile Asp Lys Lys Val Ile Lys
1               5                   10                  15

Lys Arg Lys Gln Glu Glu Tyr Met Asn Lys Met His Arg Thr Ile Leu
            20                  25                  30

Glu Leu Lys Asn Glu Lys His Pro Asp Met Met Asp Phe Met Asp Leu
        35                  40                  45

Ile Asp Trp Tyr Leu Glu Asn Arg Lys Pro
    50                  55

<210> SEQ ID NO 621
```

```
<211> LENGTH: 62
<212> TYPE: PRT
<213> ORGANISM: Bacteriophage D

<400> SEQUENCE: 621

Met Lys Lys Phe Trp His Ser Gly Met Ile Asp Lys Lys Val Ile Glu
1               5                   10                  15

Lys Arg Lys Gln Asp Glu Tyr Leu Asn Lys Leu His Arg Thr Ile Leu
            20                  25                  30

Glu Leu Lys Asn Glu Lys His Pro Asp Met Met Asp Phe Met Asp Leu
        35                  40                  45

Ile Asp Trp Tyr Leu Glu Asn Arg Lys Pro Arg Asp Ile Asp
    50                  55                  60

<210> SEQ ID NO 622
<211> LENGTH: 62
<212> TYPE: PRT
<213> ORGANISM: Bacteriophage D

<400> SEQUENCE: 622

Met Lys Lys Phe Trp His Ser Gly Met Ile Asp Lys Lys Val Ile Glu
1               5                   10                  15

Lys Arg Lys Gln Glu Glu Cys Ile Asn Glu Leu His Arg Thr Ile Leu
            20                  25                  30

Glu Leu Lys Asn Glu Lys His Pro Asp Met Met Asp Phe Met Asp Leu
        35                  40                  45

Ile Asp Trp Tyr Leu Glu Asn Arg Lys Pro Arg Asp Ile Tyr
    50                  55                  60

<210> SEQ ID NO 623
<211> LENGTH: 60
<212> TYPE: PRT
<213> ORGANISM: Bacteriophage D

<400> SEQUENCE: 623

Met Ile Asp Lys Lys Val Ile Glu Lys Arg Lys Gln Asp Glu Tyr Leu
1               5                   10                  15

Asn Lys Leu His Arg Thr Ile Leu Glu Leu Lys Asn Glu Lys His Pro
            20                  25                  30

Asp Met Ile Asp Phe Met Asp Leu Ile Asp Phe Met Asp Leu Ile Asp
        35                  40                  45

Trp Tyr Leu Glu Asn Arg Lys Pro Arg Asp Ile Asp
    50                  55                  60

<210> SEQ ID NO 624
<211> LENGTH: 62
<212> TYPE: PRT
<213> ORGANISM: Bacteriophage D

<400> SEQUENCE: 624

Met Asn Lys Phe Trp His Ser Gly Met Ile Asp Lys Lys Val Ile Glu
1               5                   10                  15

Asn Arg Lys Gln Glu Glu Tyr Ile Asn Lys Leu His Ser Thr Ile Leu
            20                  25                  30

Glu Leu Lys Asn Glu Lys His Pro Asp Met Met Asp Phe Met Asp Leu
        35                  40                  45

Ile Asp Trp Tyr Leu Glu Asn Arg Lys Pro Gln Asp Ile Asp
    50                  55                  60
```

<210> SEQ ID NO 625
<211> LENGTH: 62
<212> TYPE: PRT
<213> ORGANISM: Bacteriophage P

<400> SEQUENCE: 625

Met Lys Lys Phe Trp Arg Ser Gly Met Ile Asp Asn Lys Val Ile Glu
1               5                   10                  15

Lys Arg Lys Gln Asp Asp Tyr Met Asn Lys Leu His Arg Thr Ile Leu
            20                  25                  30

Glu Leu Thr Arg Glu Ile Glu Leu Arg Arg Gly Pro Asp Met Met Asp
        35                  40                  45

Phe Met Asp Leu Ile Asp Trp Tyr Leu Asn Ser Arg Lys Pro
    50                  55                  60

<210> SEQ ID NO 626
<211> LENGTH: 71
<212> TYPE: PRT
<213> ORGANISM: Bacteriophage D

<400> SEQUENCE: 626

Met Lys Lys Phe Trp His Ser Gly Met Ile Asp Lys Lys Val Ile Glu
1               5                   10                  15

Lys Arg Gln His Asp Glu Tyr Ile Asn Lys Ile His Lys Thr Ile Ile
            20                  25                  30

Glu Leu Arg Lys Glu Pro Pro Glu Pro Lys Pro Cys Ser Cys His Lys
        35                  40                  45

Asp Ile Asp Ile Asn Ala Leu Ile Asn Asp Ile Glu Trp Asp Asp Tyr
    50                  55                  60

Tyr Thr Trp Phe Lys Asp Lys
65                  70

<210> SEQ ID NO 627
<211> LENGTH: 71
<212> TYPE: PRT
<213> ORGANISM: Bacteriophage D

<400> SEQUENCE: 627

Met Lys Lys Phe Trp Arg Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30

Glu Leu Ser Ile Lys Pro Pro Glu Pro Lys Pro Cys Ser Cys His Lys
        35                  40                  45

Asp Ile Asp Ile Asn Ala Leu Ile Asn Asp Ile Glu Trp Asp Asp Tyr
    50                  55                  60

Tyr Thr Trp Phe Lys Asp Lys
65                  70

<210> SEQ ID NO 628
<211> LENGTH: 71
<212> TYPE: PRT
<213> ORGANISM: Bacteriophage D

<400> SEQUENCE: 628

Met Lys Lys Phe Trp Arg Ser Gly Met Ile Asp Lys Lys Val Ile Glu
1               5                   10                  15

Lys Arg Lys Gln Glu Glu Tyr Met Asn Lys Met His Arg Thr Ile Leu
            20                  25                  30

```
Glu Leu Ser Ile Lys Pro Pro Glu Pro Lys Pro Cys Ser Cys His Lys
            35                  40                  45

Asp Ile Asp Ile Asn Ala Leu Ile Asn Asp Ile Glu Trp Asp Asp Tyr
 50                  55                  60

Tyr Thr Trp Phe Lys Asp Lys
 65                  70

<210> SEQ ID NO 629
<211> LENGTH: 63
<212> TYPE: PRT
<213> ORGANISM: Bacteriophage D

<400> SEQUENCE: 629

Met Ile Asp Lys Lys Val Ile Glu Lys Arg Lys Gln Asp Asp Tyr Met
 1               5                  10                  15

Asn Lys Leu His Arg Thr Ile Leu Glu Leu Ser Ile Lys Pro Pro Glu
            20                  25                  30

Pro Lys Pro Cys Ser Cys His Lys Asp Ile Asp Ile Asn Ala Leu Ile
        35                  40                  45

Asn Asp Ile Glu Trp Asp Asp Tyr Tyr Thr Trp Phe Lys Asp Lys
 50                  55                  60

<210> SEQ ID NO 630
<211> LENGTH: 71
<212> TYPE: PRT
<213> ORGANISM: Bacteriophage D

<400> SEQUENCE: 630

Met Lys Lys Phe Trp His Ser Gly Met Ile Asp Lys Lys Val Ile Lys
 1               5                  10                  15

Lys Arg Lys Gln Glu Glu Tyr Met Asn Lys Leu Gln Arg Ile Ile Leu
            20                  25                  30

Glu Leu Ser Ile Lys Pro Pro Glu Pro Lys Pro Cys Ser Cys His Lys
            35                  40                  45

Asp Ile Asp Ile Asn Ala Leu Ile Asn Asp Ile Glu Trp Asp Asp Tyr
 50                  55                  60

Tyr Thr Trp Phe Lys Asp Lys
 65                  70

<210> SEQ ID NO 631
<211> LENGTH: 70
<212> TYPE: PRT
<213> ORGANISM: Bacteriophage O

<400> SEQUENCE: 631

Met Lys Lys Phe Trp His Ser Gly Met Ile Asp Lys Lys Ile Ile Glu
 1               5                  10                  15

Lys Arg Glu His Asp Glu Tyr Leu Asn Lys Leu His Met Thr Ile Ile
            20                  25                  30

Glu Leu Arg Lys Glu Pro Pro Gly Thr Lys Pro Cys Ser Cys His Lys
            35                  40                  45

Asn Val Asp Ile Asn Glu Leu Ile Asn Tyr Ile Glu Trp Asn Asp Tyr
 50                  55                  60

Tyr Thr Trp Phe Lys Asp
 65                  70

<210> SEQ ID NO 632
<211> LENGTH: 60
<212> TYPE: PRT
```

<213> ORGANISM: Bacteriophage D

<400> SEQUENCE: 632

Met Lys Lys Phe Trp His Ser Gly Met Ile Asp Lys Lys Val Ile Glu
1               5                   10                  15
Lys Arg Lys Gln Asp Glu Tyr Leu Asn Lys Leu His Arg Thr Ile Leu
            20                  25                  30
Glu Ile Asp Phe Pro Ile Gln Arg Val Cys His Arg Ser Leu Ser Pro
        35                  40                  45
Thr Pro Ile Thr Val Pro Thr Glu Thr Leu Asp Ile
    50                  55                  60

<210> SEQ ID NO 633
<211> LENGTH: 44
<212> TYPE: PRT
<213> ORGANISM: Bacteriophage D

<400> SEQUENCE: 633

Met Lys Lys Phe Trp His Ser Gly Met Ile Asp Lys Lys Val Ile Lys
1               5                   10                  15
Lys Arg Lys Gln Glu Glu Tyr Met Asn Lys Met His Arg Thr Ile Leu
            20                  25                  30
Glu Leu Ser Ile Lys Pro Ile Glu Glu Met Val Phe
        35                  40

<210> SEQ ID NO 634
<211> LENGTH: 88
<212> TYPE: PRT
<213> ORGANISM: Bacteriophage Sfi

<400> SEQUENCE: 634

Met Lys Lys Phe Trp Arg Ser Gly Met Ile Asp Lys Lys Val Ile Glu
1               5                   10                  15
Lys Arg Lys Gln Asp Asp Tyr Met Asn Lys Leu His Arg Thr Ile Leu
            20                  25                  30
Glu Leu Ser Ile Lys Pro Pro Glu Pro Lys Pro Cys Ser Cys His Lys
        35                  40                  45
Asp Ile Asp Ile Asn Ala Leu Ile Asn Asp Ile Glu Trp Asp Asp Trp
    50                  55                  60
Val Asp Glu Val Leu Gly Tyr Ile Asn Lys Trp Val Asn Lys Asp Lys
65                  70                  75                  80
Ala Asp Val Glu Val Leu Asp Lys
                85

<210> SEQ ID NO 635
<211> LENGTH: 210
<212> TYPE: PRT
<213> ORGANISM: Bacteriophage D

<400> SEQUENCE: 635

Met Thr Thr Pro Gln Lys Phe Leu Ser Ile Arg Glu Leu Leu Lys Pro
1               5                   10                  15
Leu Pro Ser Asn Gly Val Lys Phe Pro Lys Phe Ser Ala Leu Tyr His
            20                  25                  30
Glu Ser Gln Val Gly Ala Trp Gln Lys Lys Met Ser Lys Arg Arg His
        35                  40                  45
Gln Ala Lys Val Gln Val Ala Met Asp Lys Asn Arg Gly Glu Leu Val
    50                  55                  60

```
Pro Arg Glu Leu Glu Asp Phe Ser Asn Trp Gln Ala Arg Gln Met
 65                  70                  75                  80

Lys Ala Arg Tyr Gln Glu Lys Val Ala Asn Lys Arg Lys Asp Tyr Leu
                 85                  90                  95

His Lys Leu Thr Thr Tyr Leu Val Lys Thr Tyr Asp Val Ile Val Ile
            100                 105                 110

Glu Asp Leu Lys Ala Lys Asn Leu Met Lys Asn His Tyr Leu Ala Lys
        115                 120                 125

Ser Ile Ala Asn Ala Ser Trp His Glu Phe Lys Arg Leu Leu Glu Tyr
130                 135                 140

Lys Cys Ser Trp Tyr Gly Lys Glu Leu Ile Val Val Pro Ala His His
145                 150                 155                 160

Thr Ser Gln Glu Cys Ser Asn Cys His His Asn Ser Gly Lys Lys Pro
                165                 170                 175

Leu His Ile Arg Glu Trp Met Cys Asp Asn Cys Gly Thr His His Asp
            180                 185                 190

Arg Asp Ile Asn Ala Ser Ile Asn Ile Leu His Arg Gly Leu Ala Thr
        195                 200                 205

Leu Asn
    210

<210> SEQ ID NO 636
<211> LENGTH: 100
<212> TYPE: PRT
<213> ORGANISM: Bacteriophage D

<400> SEQUENCE: 636

Met Ser Thr Val Phe Leu Ile Phe Phe Gln Val Phe Leu Ile Leu Leu
  1               5                  10                  15

Leu Asn Ile Leu Lys Ile Ser Lys Thr Tyr Tyr Ile Leu Phe Phe Val
                 20                  25                  30

Cys Ile His Cys Phe Tyr Leu Val Phe Leu Phe Phe Ile Glu Cys Phe
             35                  40                  45

Pro Ser Cys Ser Gln Ser Ile Leu Val Tyr Phe Gly Asp Gln Thr Glu
         50                  55                  60

Thr Val Phe Ile Lys Lys Tyr Ile Phe Phe Cys Lys Thr Lys Thr Leu
 65                  70                  75                  80

Thr Asn Ser Ser Gln Gly Lys Arg Glu Phe Ile Glu Asp Ser Ala Phe
                 85                  90                  95

Asn Cys Ile His
            100

<210> SEQ ID NO 637
<211> LENGTH: 100
<212> TYPE: PRT
<213> ORGANISM: Bacteriophage D

<400> SEQUENCE: 637

Met Ser Thr Val Phe Leu Ile Phe Phe Gln Val Phe Leu Ile Phe Leu
  1               5                  10                  15

Leu Asn Ile Leu Lys Ile Ser Lys Thr Tyr Tyr Ile Leu Phe Phe Val
                 20                  25                  30

Cys Ile His Cys Phe Tyr Leu Val Phe Leu Phe Phe Ile Glu Cys Phe
             35                  40                  45

Pro Ser Cys Ser Gln Ser Ile Leu Val Tyr Phe Gly Asp Gln Thr Glu
         50                  55                  60
```

```
Thr Val Phe Ile Lys Lys Tyr Ile Phe Phe Cys Lys Thr Lys Thr Leu
65                  70                  75                  80

Thr Asn Ser Ser Gln Gly Glu Arg Glu Phe Ile Glu Asp Ser Ala Phe
                85                  90                  95

Asn Cys Ile His
            100

<210> SEQ ID NO 638
<211> LENGTH: 100
<212> TYPE: PRT
<213> ORGANISM: Bacteriophage P

<400> SEQUENCE: 638

Met Ser Thr Val Phe Leu Ile Phe Phe Gln Val Phe Leu Ile Phe Leu
1               5                   10                  15

Leu Asn Ile Leu Lys Ile Ser Lys Thr Tyr Tyr Ile Leu Phe Phe Val
                20                  25                  30

Cys Ile His Cys Phe Tyr Leu Val Phe Leu Phe Phe Ile Glu Cys Phe
            35                  40                  45

Pro Ser Cys Ser Gln Ser Ile Leu Val Tyr Phe Gly Asp Gln Thr Glu
50                  55                  60

Thr Val Phe Ile Lys Lys Tyr Ile Phe Phe Cys Lys Thr Lys Thr Leu
65                  70                  75                  80

Thr Asn Ser Ser Gln Gly Glu Arg Glu Phe Ile Glu Asp Asn Ser Phe
                85                  90                  95

Tyr Cys Asn His
            100

<210> SEQ ID NO 639
<211> LENGTH: 76
<212> TYPE: PRT
<213> ORGANISM: Bacteriophage P

<400> SEQUENCE: 639

Met Ile Phe Phe Lys Val Phe Leu Ile Leu Leu Asn Asn Leu Lys
1               5                   10                  15

Ile Ser Lys Thr Tyr Tyr Ile Leu Phe Phe Val Cys Ile His Cys Phe
                20                  25                  30

Tyr Leu Val Phe Leu Phe Phe Ile Glu Tyr Phe Pro Asp Cys Phe Gln
            35                  40                  45

Ser Ile Gln Val Asp Phe Cys Asp Gln Thr Glu Thr Val Phe Ile Lys
50                  55                  60

Asn Tyr Ile Phe Phe Leu Gln Asn Lys Asn Pro Asp
65                  70                  75

<210> SEQ ID NO 640
<211> LENGTH: 81
<212> TYPE: PRT
<213> ORGANISM: Bacteriophage P

<400> SEQUENCE: 640

Met Ser Ile Val Phe Leu Ile Phe Phe Lys Val Phe Leu Ile Leu Leu
1               5                   10                  15

Leu Asn Asn Leu Lys Ile Ser Lys Thr Tyr Tyr Ile Leu Phe Phe Val
                20                  25                  30

Cys Ile His Cys Phe Tyr Leu Val Phe Leu Phe Phe Ile Glu Tyr Phe
            35                  40                  45

Pro Asp Cys Phe Gln Ser Ile Gln Val Asp Phe Cys Asp Gln Thr Glu
```

```
                50                  55                  60
Thr Val Phe Ile Lys Lys Tyr Ile Phe Phe Leu Gln Asn Lys Asn Pro
 65                  70                  75                  80

Asp

<210> SEQ ID NO 641
<211> LENGTH: 77
<212> TYPE: PRT
<213> ORGANISM: Bacteriophage P

<400> SEQUENCE: 641

Met Ser Thr Val Phe Leu Ile Phe Phe Gln Val Phe Leu Ile Phe Leu
  1               5                  10                  15

Tyr Ile Tyr Phe Lys Ile Ser Lys Thr Tyr Tyr Ile Leu Phe Phe Val
                 20                  25                  30

Cys Ile His Cys Phe Phe Ile Phe Tyr Arg Met Phe Ser Lys Leu Leu
             35                  40                  45

Ser Ile His Ser Ser Leu Phe Trp Arg Pro Asp Gly Asn Cys Phe Tyr
         50                  55                  60

Lys Lys Ile Tyr Ile Phe Leu Gln Asn Lys Asn Pro Asp
 65                  70                  75

<210> SEQ ID NO 642
<211> LENGTH: 72
<212> TYPE: PRT
<213> ORGANISM: Bacteriophage P

<400> SEQUENCE: 642

Met Ile Phe Phe Gln Val Phe Leu Ile Phe Leu Leu Asn Ile Leu Lys
  1               5                  10                  15

Ile Ser Lys Thr Tyr Tyr Ile Leu Phe Phe Val Cys Ile His Cys Phe
                 20                  25                  30

Leu Phe Phe Ile Glu Cys Phe Pro Ser Cys Ser Gln Ser Ile Leu Val
             35                  40                  45

Tyr Phe Gly Asp Gln Thr Glu Thr Val Phe Ile Lys Lys Ile Tyr Ile
         50                  55                  60

Phe Leu Gln Asn Lys Asn Pro Asp
 65                  70

<210> SEQ ID NO 643
<211> LENGTH: 65
<212> TYPE: PRT
<213> ORGANISM: Bacteriophage D

<400> SEQUENCE: 643

Met Phe Ile Phe Gly Asn Cys Cys Ile Met Phe Ile Leu Tyr Ile Ser
  1               5                  10                  15

Cys Met Ile Val Cys Gln Gln Phe Tyr Leu Asn Tyr Phe Ser Phe Phe
                 20                  25                  30

Cys Lys Lys Arg Lys Pro Arg Leu Lys Val Glu Val Thr Val Arg Glu
             35                  40                  45

Phe Asn Arg Asn Asp Thr Lys Tyr Ser Asn Asn Tyr Ile Thr Thr Phe
         50                  55                  60

Leu
 65

<210> SEQ ID NO 644
<211> LENGTH: 62
```

```
<212> TYPE: PRT
<213> ORGANISM: Bacteriophage D

<400> SEQUENCE: 644

Met Ser Ser Glu His Ser Ile Gln Asn Gln Ile Arg Val Glu Leu Ser
1               5                   10                  15

Lys Ala Gly Asn Met Val Phe Arg Ile Asn Val Gly Lys Val Arg Met
                20                  25                  30

Ala Asp Gly Arg Trp Phe Asp Thr Gly Ala Pro Lys Gly Phe Cys Asp
            35                  40                  45

Leu Phe Gly Phe Arg Pro Ala Thr Val Ile Ala Leu Ile Tyr
50                  55                  60

<210> SEQ ID NO 645
<211> LENGTH: 46
<212> TYPE: PRT
<213> ORGANISM: Bacteriophage P

<400> SEQUENCE: 645

Met Pro Ile Leu Phe Ile Val Gly Asn Ala Gln Gly Ala Ser His Cys
1               5                   10                  15

Thr Arg Pro Lys Pro Leu His Pro Ala Thr Leu Glu Val Gly Glu Leu
                20                  25                  30

Arg Ala Val Arg Leu Lys Lys Ala Asn Lys Lys Ala Pro Ala
            35                  40                  45

<210> SEQ ID NO 646
<211> LENGTH: 56
<212> TYPE: PRT
<213> ORGANISM: Bacteriophage P

<400> SEQUENCE: 646

Met Ser Thr Val Phe Leu Ile Phe Phe Gln Val Phe Leu Ile Phe Leu
1               5                   10                  15

Leu Asn Ile Leu Lys Ile Ser Lys Thr Tyr Tyr Ile Leu Phe Phe Val
                20                  25                  30

Cys Ile His Cys Phe Phe Ile Phe Tyr Arg Met Phe Ser Lys Leu Leu
            35                  40                  45

Ser Ile His Ser Ser Leu Phe Trp
50                  55

<210> SEQ ID NO 647
<211> LENGTH: 47
<212> TYPE: PRT
<213> ORGANISM: Bacteriophage P

<400> SEQUENCE: 647

Met Ile Phe Phe Gln Val Phe Leu Ile Phe Leu Leu Asn Ile Leu Lys
1               5                   10                  15

Ile Ser Lys Thr Tyr Tyr Ile Leu Phe Phe Val Cys Ile His Cys Phe
                20                  25                  30

Phe Tyr Phe Leu Ser Asn Val Phe Gln Val Ala Leu Asn Pro Phe
            35                  40                  45

<210> SEQ ID NO 648
<211> LENGTH: 56
<212> TYPE: PRT
<213> ORGANISM: Bacteriophage P

<400> SEQUENCE: 648
```

-continued

```
Met Val Leu Ala Pro Asn Lys Thr Phe Pro Tyr Ala Cys Val Cys Ala
1               5                   10                  15

Ser Asn Arg Ala Leu Asn Leu Ile Ser Leu Leu Pro Phe Ala Leu Asp
            20                  25                  30

Lys Leu Tyr Leu Gly Tyr Pro Ile Thr Phe Tyr Gln Ile Ile Ile Tyr
            35                  40                  45

Lys Ser Asn Lys Lys Ala Pro Ala
            50                  55

<210> SEQ ID NO 649
<211> LENGTH: 65
<212> TYPE: PRT
<213> ORGANISM: Bacteriophage P

<400> SEQUENCE: 649

Met Arg Ile Asn Glu Ala Val Leu Ser Phe Tyr Ser Phe Tyr Phe Tyr
1               5                   10                  15

Leu Leu Arg Asn Leu Val Phe Phe Cys Lys Lys Arg Lys Pro Arg Leu
            20                  25                  30

Lys Val Glu Val Thr Val Arg Glu Phe Asn Arg Asn Asp Ala Lys Tyr
            35                  40                  45

Ser Asn Asn Tyr Met Lys Ile Ala Asn Lys Lys Ser Tyr Glu Ile Ile
            50                  55                  60

Ser
65

<210> SEQ ID NO 650
<211> LENGTH: 64
<212> TYPE: PRT
<213> ORGANISM: Bacteriophage Sequence

<400> SEQUENCE: 650

Met Phe Tyr Leu Leu Thr Lys Ala Ser Phe Tyr Leu Ser Leu Tyr Leu
1               5                   10                  15

Met Tyr Thr Leu His Ile Ile Tyr Asp Ser Leu Pro Thr Val Phe Ile
            20                  25                  30

Lys Lys Tyr Ile Phe Phe Cys Lys Thr Lys Thr Leu Thr Asn Ser Ser
            35                  40                  45

Gln Gly Glu Arg Glu Phe Ile Glu Asp Ser Ala Phe Asn Cys Ile His
            50                  55                  60
```

US 11,732,251 B2

ANTI-CRISPR POLYNUCLEOTIDES AND POLYPEPTIDES AND METHODS OF USE

This application claims the benefit of U.S. Provisional Application No. 62/488,981 filed on 24 Apr. 2017, U.S. Provisional Application No. 62/510,914 filed on 25 May 2017, U.S. Provisional Patent Application No. 62/488,969 filed on 24 Apr. 2017, and U.S. Provisional Application No. 62/510,896 filed on 25 May 2017, all of which are incorporated herein in their entirety by reference.

REFERENCE TO SEQUENCE LISTING SUBMITTED ELECTRONICALLY

The official copy of the sequence listing is submitted electronically via EFS-Web as an ASCII formatted sequence listing with a file named 20191022_NB41268USPCT_SeqLst.txt created on Oct. 22, 2019 and having a size of 525,150 bytes and is filed concurrently with the specification. The sequence listing comprised in this ASCII formatted document is part of the specification and is herein incorporated by reference in its entirety.

FIELD OF THE INVENTION

The disclosure relates to the field of molecular biology, in particular, to compositions and methods relating to anti-CRISPR (ACR) proteins compositions and methods of use in plants.

BACKGROUND

Recombinant DNA technology has made it possible to modify (edit) specific endogenous chromosomal sequences and/or insert DNA sequences at targeted genomic locations, thus altering the organism's phenotype. Site-specific integration techniques, which employ site-specific recombination systems, as well as other types of recombination technologies, have been used to generate targeted insertions of genes of interest in a variety of organism. Genome-editing techniques such as designer zinc finger nucleases (ZFNs) or transcription activator-like effector nucleases (TALENs), or homing meganucleases, are available for producing targeted genome perturbations, but these systems tends to have a low specificity and employ designed nucleases that need to be redesigned for each target site, which renders them costly and time-consuming to prepare. Recently, genome-editing tools have been developed from bacterial and archaeal CRISPR systems that offer improved programmability to address a wider array of target sequences as well as improved specificity and efficiency in some applications.

Although CRISPR-derived systems offer many benefits over previous gene-editing tools, compositions and methods are still needed that can further improve these benefits.

SUMMARY OF INVENTION

As described herein, methods and compositions are provided for the identification, characterization, and utilization of anti-CRISPR (ACR) proteins in plants, including modulation of Cas endonuclease activity, improvement of frequency of homologous recombination, control of Cas endonuclease activity during various cell cycles, spatial and/or temporal regulation of Cas endonuclease activity in plants, usage in gene activation or repression, as well as reduction of off-target polynucleotide cleavage.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide capable of reducing the activity of said Cas endonuclease in said plant cell.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide capable of reducing the activity of said Cas endonuclease in said plant cell, wherein the activity selected from the group consisting of: target polynucleotide binding, target polynucleotide nicking, target polynucleotide double-strand-break creation, and target polynucleotide modification.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide capable of reducing the activity of said Cas endonuclease in said plant cell, wherein the activity selected from the group consisting of: target polynucleotide binding, target polynucleotide nicking, target polynucleotide double-strand-break creation, and target polynucleotide modification, wherein said target polynucleotide modification is selected from the group consisting of: insertion of at least one nucleotide, deletion of at least one nucleotide, substitution of at least one nucleotide, and chemical alteration of at least one nucleotide.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide capable of reducing the activity of said Cas endonuclease in said plant cell, wherein the Cas endonuclease lacks the ability to nick or cleave a target polynucleotide.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide capable of reducing the activity of said Cas endonuclease in said plant cell, wherein said activity is decreased as compared to an isoline plant cell comprising said Cas endonuclease and guide RNA but not comprising said anti-CRISPR polypeptide.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide, wherein the activity of said Cas endonuclease in said plant cell is abolished during at least one timepoint, in at least one tissue or cell type, or during at least one phase of the cell or plant life cycle.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide capable of reducing the activity of said Cas endonuclease in said plant cell, wherein the Cas endonuclease is a Type II-A Cas endonuclease.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide capable of reducing the activity of said Cas endonuclease in said plant cell, wherein the Cas endonuclease is Cas9.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR polypeptide capable of reducing the activity of said Cas endonuclease in said plant cell, wherein the Cas endonuclease is Cpf1.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR (ACR) polypeptide capable of reducing the activity of said Cas endonuclease in said plant cell, wherein the ACR has an amino acid sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 125, at least 125, between 125 and 150, at least 150, between 150 and 175, at least 175, between 175 and 200, or at least 200 contiguous amino acids of a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650.

In one aspect, a method for modulating the activity of a Cas endonuclease with a target polynucleotide in a plant cell is provided, comprising providing to said cell a Cas endonuclease, a guide RNA capable of binding to the target polynucleotide in the plant cell, and an anti-CRISPR (ACR) polynucleotide capable of reducing the activity of said Cas endonuclease in said plant cell, wherein the ACR has a polynucleotide sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 250, between 250 and 500, at least 500, between 500 and 600, or at least 600 contiguous nucleotides of a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide.

In one aspect, a method is provided for increasing the ratio of on-target polynucleotide cleavage activity to off-target polynucleotide cleavage activity of a Cas endonuclease and guide polynucleotide complex in a plant cell, comprising introducing together a Cas endonuclease, a guide polynucleotide, and an anti-CRISPR (ACR) polypeptide.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the specificity is increased by at least 5%, at least 6%, at least 7%, at least 8%, at least 9%, at least 10%, or even greater than 10%, greater than 15%, greater than 20%, or greater than 25% compared to the cleavage ratio of the Cas endonuclease in a sample lacking said ACR polypeptide.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein said method is performed during a specific cell cycle.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein said method is performed during meiosis.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein said method is performed during mitosis.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein said method is performed during a specific stage of the plant's development.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein said method is performed during a specific stage of the plant's development, wherein said stage is selected from the group consisting of: growth, reproductive, vegetative, and senescence.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein said method is performed during a specific time point.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein said method is performed in a specific tissue or cell type of the plant, in some embodiments selected from the group consisting of: whole plant, seedling, meristematic tissue, ground tissue, vascular tissue, dermal tissue, seed, leaf, root, shoot, stem, flower, fruit, stolon, bulb, tuber, corm, keiki, shoot, bud, tumor tissue, single cells, protoplasts, embryos, and callus tissue.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the Cas endonuclease and the guide RNA are both provided as polynucleotides.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the guide RNA does not solely comprise ribonucleic acids.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the Cas endonuclease is provided as a protein and the guide polynucleotide is provided as an RNA molecule.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the ACR is provided as a polynucleotide encoding a polypeptide.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the ACR is provided as a polypeptide.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the ACR is provided concurrently with either the Cas endonuclease or the guide polynucleotide.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the ACR is provided prior to the introduction of the Cas endonuclease or the guide polynucleotide.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the ACR is provided after the introduction of the Cas endonuclease or the guide polynucleotide.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein a polynucleotide encoding the ACR is pre-integrated into the genome of the cell or organism.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein a polynucleotide encoding the Cas endonuclease is pre-integrated into the genome of the cell or organism.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the expression or activity of the ACR is inducible.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the expression or activity of the ACR is inducible, wherein induction is in response to a condition selected from the group consisting of: temperature, presence or absence of an exogenously-applied molecule, activation or inhibition of an endogenous gene, light, cell cycle, organism phase, tissue or cell type, and environmental stress.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the ACR protein comprises a coiled-coil motif.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the ACR protein comprises a heptad repeat pattern of amino acids in the pattern of "hxxhcxc", wherein h=a hydrophobic amino acid, c=a charged amino acid, and x=any amino acid.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the ACR has an amino acid sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 125, at least 125, between 125 and 150, at least 150, between 150 and 175, at least 175, between 175 and 200, or at least 200 contiguous amino acids of a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polynucleotide, wherein the ACR has a polynucleotide sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 250, between 250 and 500, at least 500, between 500 and 600, or at least 600 contiguous nucleotides of a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the Cas endonuclease is a Type II-A Cas endonuclease.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the Cas endonuclease is Cas9.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the Cas endonuclease is Cpf1.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the Cas endonuclease lacks the ability to nick or cleave a target polynucleotide.

In one aspect, a method is provided for increasing the efficiency of homologous recombination of a target polynucleotide in a plant cell, comprising introducing to the target polynucleotide a Cas endonuclease, a guide polynucleotide, and an anti-CRISPR (ACR) polypeptide.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the specificity is increased by at least 5%, at least 6%, at least 7%, at least 8%, at least 9%, at least 10%, or even greater than 10%, greater than 15%, greater than 20%, or greater than 25% compared to the cleavage ratio of the Cas endonuclease in a sample lacking said ACR polypeptide.

In one aspect, a method is provided increasing the efficiency of homologous recombination of a target polynucleotide in a plant cell, comprising introducing together a Cas endonuclease, a guide polynucleotide, and an anti-CRISPR (ACR) polypeptide, wherein said method is performed during a specific cell cycle.

In one aspect, a method is provided increasing the efficiency of homologous recombination of a target polynucleotide in a plant cell, comprising introducing together a Cas endonuclease, a guide polynucleotide, and an anti-CRISPR (ACR) polypeptide, wherein said method is performed during meiosis.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein said method is performed during mitosis.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein said method is performed during a specific stage of the plant's development.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein said method is performed during a specific stage of the plant's development, wherein said stage is selected from the group consisting of: growth, reproductive, vegetative, and senescence.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein said method is performed during a specific time point.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein said method is performed in a specific tissue or cell type of the plant, in some embodiments selected from the group consisting of: whole plant, seedling, meristematic tissue, ground tissue, vascular tissue, dermal tissue, seed, leaf, root, shoot, stem, flower, fruit, stolon, bulb, tuber, corm, keiki, shoot, bud, tumor tissue, single cells, protoplasts, embryos, and callus tissue.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the Cas endonuclease and the guide RNA are both provided as polynucleotides.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the guide RNA does not solely comprise ribonucleic acids.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the Cas endonuclease is provided as a protein and the guide polynucleotide is provided as an RNA molecule.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the ACR is provided as a polynucleotide encoding a polypeptide.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the ACR is provided as a polypeptide.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the ACR is provided concurrently with either the Cas endonuclease or the guide polynucleotide.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the ACR is provided prior to the introduction of the Cas endonuclease or the guide polynucleotide.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the ACR is provided after the introduction of the Cas endonuclease or the guide polynucleotide.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein a polynucleotide encoding the ACR is pre-integrated into the genome of the cell or organism.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein a polynucleotide encoding the Cas endonuclease is pre-integrated into the genome of the cell or organism.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the expression or activity of the ACR is inducible.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the expression or activity of the ACR is inducible, wherein induction is in response to a condition selected from the group consisting of: temperature, presence or absence of an exogenously-applied molecule, activation or inhibition of an endogenous gene, light, cell cycle, organism phase, tissue or cell type, and environmental stress.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the ACR protein comprises a coiled-coil motif.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the ACR protein comprises a heptad repeat pattern of amino acids in the pattern of "hxxhcxc", wherein h=a hydrophobic amino acid, c=a charged amino acid, and x=any amino acid.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the ACR has an amino acid sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 125, at least 125, between 125 and 150, at least 150, between 150 and 175, at least 175, between 175 and 200, or at least 200 contiguous amino acids of a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650.

In one aspect, a method is provided for increasing the efficiency of homologous recombination of a target polynucleotide in a plant cell, comprising introducing together a Cas endonuclease, a guide polynucleotide, and an anti-CRISPR (ACR) polynucleotide, wherein the ACR has a polynucleotide sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 250, between 250 and 500, at least 500, between 500 and 600, or at least 600 contiguous nucleotides of a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the Cas endonuclease is a Type II-A Cas endonuclease.

In one aspect, a method is provided for increasing the specificity of a Cas endonuclease and guide polynucleotide complex in a plant cell, comprising introducing together a Cas endonuclease, a guide polynucleotide, and an anti-CRISPR (ACR) polypeptide, wherein the Cas endonuclease is Cas9.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the Cas endonuclease is Cpf1.

In one aspect, a method is provided for increasing the efficiency of homologous recombination of a target polynucleotide in a plant cell, comprising introducing together a Cas endonuclease, a guide polynucleotide, and an anti-CRISPR (ACR) polypeptide, wherein the Cas endonuclease lacks the ability to nick or cleave a target polynucleotide.

In one aspect, a plant cell comprising a Cas endonuclease and an ACR molecule is provided.

In one aspect, a plant cell comprising a Cas endonuclease and an ACR molecule is provided, wherein said ACR molecule is provided as a polynucleotide by a phage or virus.

In one aspect, a plant cell comprising a Cas endonuclease, a guide RNA, and an ACR molecule is provided.

In one aspect, a plant cell comprising a heterologous Cas endonuclease, a guide RNA, and an ACR protein is provided, wherein the guide RNA is capable of binding to a target polynucleotide in the plant's genome.

In one aspect, a plant cell comprising a Cas endonuclease and an ACR molecule is provided, wherein the plant cell is obtained or derived from a plant selected from the group consisting of: maize, rice, sorghum, rye, barley, wheat, millet, oats, sugarcane, turfgrass, switchgrass, soybean, canola, alfalfa, sunflower, cotton, tobacco, peanut, potato, tobacco, Arabidopsis, vegetable, and safflower.

In one aspect, a plant cell comprising a Cas endonuclease and an ACR molecule is provided, wherein the ACR has an amino acid sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 125, at least 125, between 125 and 150, at least 150, between 150 and 175, at least 175, between 175 and 200, or at least 200 contiguous amino acids of a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650.

In one aspect, a plant cell comprising a Cas endonuclease and an ACR molecule is provided, wherein the ACR has a polynucleotide sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 250, between 250 and 500, at least 500, between 500 and 600, or at least 600 contiguous nucleotides of a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374.

In one aspect, plant cell comprising a recombinant construct comprising a polynucleotide sequence encoding an ACR protein, operably linked to a heterologous regulatory expression element is provided.

In one aspect, plant cell comprising a recombinant construct comprising a polynucleotide sequence encoding an ACR protein, operably linked to a heterologous regulatory expression element is provided.

In one aspect, plant cell comprising a recombinant construct comprising a polynucleotide sequence encoding an ACR protein, operably linked to a heterologous regulatory expression element is provided, wherein said plant cell is selected from the group consisting of: maize, rice, sorghum, rye, barley, wheat, millet, oats, sugarcane, turfgrass, switchgrass, soybean, canola, alfalfa, sunflower, cotton, tobacco, peanut, potato, tobacco, Arabidopsis, vegetable, and safflower In one aspect, plant cell comprising a recombinant construct comprising a polynucleotide sequence encoding an ACR protein, operably linked to a heterologous regulatory expression element is provided, wherein the heterologous regulatory expression element is inducible in response to a condition selected from the group consisting of: temperature, presence or absence of an exogenously-applied molecule, activation or inhibition of an endogenous gene, light, cell cycle, organism phase, tissue or cell type, and environmental stress.

In one aspect, plant cell comprising a recombinant construct comprising a polynucleotide sequence encoding an ACR protein, operably linked to a heterologous regulatory expression element is provided, wherein the ACR protein comprises a coiled-coil motif.

In one aspect, plant cell comprising a recombinant construct comprising a polynucleotide sequence encoding an ACR protein, operably linked to a heterologous regulatory expression element is provided, wherein the ACR protein comprises a heptad repeat pattern of amino acids in the pattern of "hxxhcxc", wherein h=a hydrophobic amino acid, c=a charged amino acid, and x=any amino acid.

In one aspect, plant cell comprising a recombinant construct comprising a polynucleotide sequence encoding an ACR protein, operably linked to a heterologous regulatory expression element is provided, wherein the ACR protein comprises an amino acid sequence at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 125, at least 125, between 125 and 150, at least 150, between 150 and 175, at least 175, between 175 and 200, or at least 200 contiguous amino acids of a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650.

In one aspect, plant cell comprising a recombinant construct comprising a polynucleotide sequence encoding an ACR protein, operably linked to a heterologous regulatory expression element is provided, wherein the polynucleotide sequence encoding the ACR protein shares at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 250, between 250 and 500, at least 500, between 500 and 600, or at least 600 contiguous nucleotides of a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374.

In one aspect, a method is provided for characterizing the activity of an anti-CRISPR protein, comprising: (a) obtaining a bacterial host cell comprising a recombinant construct having a CRISPR system having a targeting sequence capable of targeting a genomic target sequence in a virulent phage; (b) introducing a construct comprising a promoter functional in the bacterial host cell operably linked to a polynucleotide encoding a polypeptide to be assayed for anti-CRISPR activity; (c) challenging the bacterial host with the virulent phage; and (d) identifying one or more bacterial colonies having a phage titre substantially similar to a bacterial cell lacking the recombinant construct encoding the CRISPR system having the targeting sequence capable of targeting a genomic target sequence in the virulent phage challenged with the virulent phage.

In one aspect, a method is provided for identifying an anti-CRISPR protein, comprising: (a) obtaining a first bacterial host cell comprising a recombinant construct having a Type II-A CRISPR system having a targeting sequence capable of targeting a genomic target sequence in a first virulent phage; (b) challenging the first bacterial host with the virulent phage; (c) obtaining a second bacterial host cell comprising a recombinant construct having a Type II-A CRISPR system having a targeting sequence capable of targeting a genomic target sequence in a second virulent phage; (d) challenging the second bacterial host with the second virulent phage; (e) identifying one or more bacterial colonies of the first bacterial host cell having a phage titre substantially similar to a bacterial cell lacking the recombinant construct encoding the CRISPR system having the targeting sequence capable of targeting a genomic target sequence in the first virulent phage challenged with the first virulent phage; (f) identifying one more bacterial colonies of the second bacterial host cell having a phage titre substantially different than a bacterial cell lacking the recombinant construct encoding the CRISPR system having the targeting sequence capable of targeting a genomic target sequence in the second virulent phage challenged with the second virulent phage; (g) sequencing the genomes of the first and second virulent phages; (h) identifying one or more gene(s) that is(are) present in the first virulent phage but not the second virulent phage; (i) obtaining a third bacterial host cell comprising a recombinant construct having a CRISPR system having a targeting sequence capable of targeting a genomic target sequence in the first virulent phage; (j) introducing a construct comprising a promoter functional in the third bacterial host cell operably linked to a polynucleotide identical to the gene of (h); (k) challenging the bacterial host with the first virulent phage; and (l) identifying one or more bacterial colonies of the third bacterial host cell having a phage titre substantially similar to a bacterial cell lacking the recombinant construct encoding the CRISPR system having the targeting sequence capable of targeting a genomic target sequence in the first virulent phage challenged with the first virulent phage.

In one aspect, a method is provided for identifying an anti-CRISPR protein, comprising: (a) obtaining a phage that displays virulence against a bacterium comprising a CRISPR; (b) sequencing the genome of the phage; and (c) identifying at least one contiguous polynucleotide of at least 100 bases that shares at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with a sequence selected from the group consisting of: SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374.

In one aspect, a method is provided for modulating the activity of a Cas endonuclease with a target polynucleotide in a cell, comprising providing an anti-CRISPR polypeptide to the cell, wherein the anti-CRISPR polypeptide modulates the activity of the Cas endonuclease in the cell, wherein the concentration ratio of Cas endonuclease to anti-CRISPR polypeptide is in the range of 1:1000 to 1:100, 1:100 to 1:10, 1:10 to 1:1, 1:1 to 10:1, 10:1 to 100:1, 100:1 to 1000:1, or any concentration ratio between 1:1000 and 1000:1.

In one aspect, a method is provided for increasing the specificity of a Cas endonuclease and guide polynucleotide complex in a cell, comprising introducing an anti-CRISPR (ACR) polypeptide to the cell, wherein the ACR polypeptide interacts with the Cas endonuclease, wherein the anti-CRISPR polypeptide modulates the activity of the Cas endonuclease in the cell, wherein the concentration ratio of Cas endonuclease to anti-CRISPR polypeptide is in the range of 1:1000 to 1:100, 1:100 to 1:10, 1:10 to 1:1, 1:1 to 10:1, 10:1 to 100:1, 100:1 to 1000:1, or any concentration ratio between 1:1000 and 1000:1.

In one aspect, a method is provided for increasing site-specific homologous recombination frequency of a donor polynucleotide in a cell, comprising introducing to the cell an anti-CRISPR (ACR) polypeptide to increase the homologous recombination of the donor polynucleotide by a polynucleotide-guided Cas endonuclease, wherein the anti-CRISPR polypeptide modulates the activity of the Cas endonuclease in the cell, wherein the concentration ratio of Cas endonuclease to anti-CRISPR polypeptide is in the range of 1:1000 to 1:100, 1:100 to 1:10, 1:10 to 1:1, 1:1 to 10:1, 10:1 to 100:1, 100:1 to 1000:1, or any concentration ratio between 1:1000 and 1000:1.

In one aspect, a cell is provided, wherein the cell comprises a Cas endonuclease and an ACR protein, wherein the concentration ratio of Cas endonuclease to anti-CRISPR polypeptide is in the range of 1:1000 to 1:100, 1:100 to 1:10, 1:10 to 1:1, 1:1 to 10:1, 10:1 to 100:1, 100:1 to 1000:1, or any concentration ratio between 1:1000 and 1000:1; wherein the cell optionally further comprises a heterologous polynucleotide.

In any of the methods or compositions described herein, the Cas endonuclease may be heterologous to the cell. In any of the methods or compositions described herein, the ACR may be heterologous to the cell. In any of the methods or compositions described herein, the Cas endonuclease and the ACR may be heterologous to the cell and/or to each other.

In any aspect, the specificity of the Cas endonuclease that is modulated by the ACR may be selected from the group consisting of: cleavage specificity, nicking specificity, binding specificity, or target recognition specificity.

Any of methods and compositions herein may comprise any of the sequences, motifs, or other features of an ACR described in PCT Application No. PCT/EP2018/060481, herein incorporated by reference in its entirety.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821 and 1.825. The sequence descriptions in the sequence listing comprise the three letter codes for amino acids as defined in 37 C.F.R. §§ 1.821 and 1.825, which are incorporated herein by reference.

FIG. 1 provides one embodiment of a schematic for the discovery of virulent phages impeding CRISPR-based immunity. (Top) When a virulent phage is used to challenge a bacterium, phage-resistant survivors can be isolated. Six virulent phages infecting *Streptococcus thermophilus* DGCC7854 generated differing frequencies of CRISPR-immune survivors. (Bottom) When comparing these same phages plated on the phage-sensitive wild-type strain DGCC7854 and a CRISPR-immunized mutant targeting a sequence conserved in all six phages, a large reduction in phage titre was expected. Phage D4276 and D1811 suffered a much smaller reduction in titre than the other four related phages. Phage names and associated data are divided according to CRISPR-interacting phenotypes; permissive (white, D5842 and D5843), impeded adaptation (fractal pattern, D1024 and D5891), and restrictive (black, D4276).

Figure 2B:
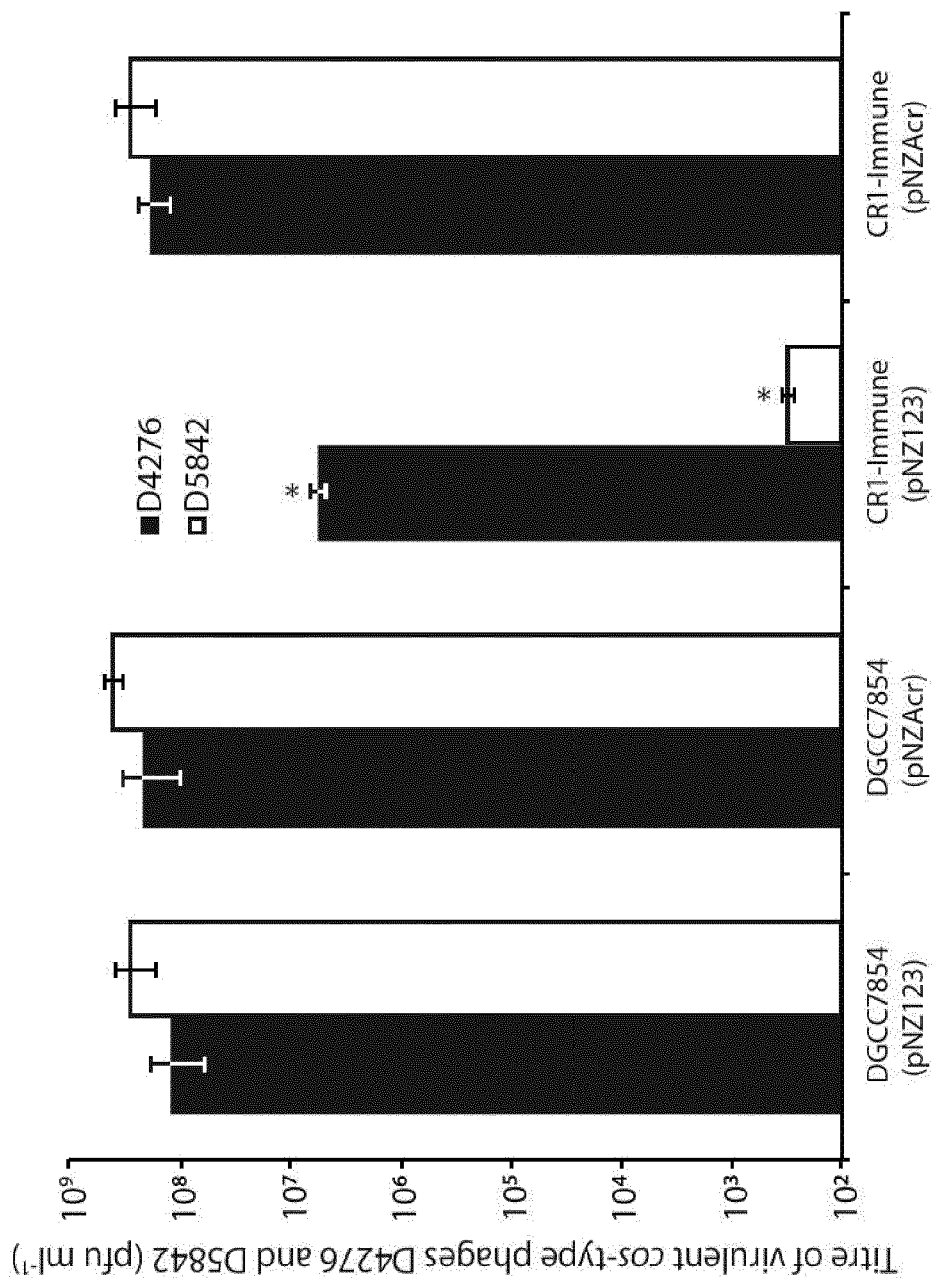
Figure 2C:
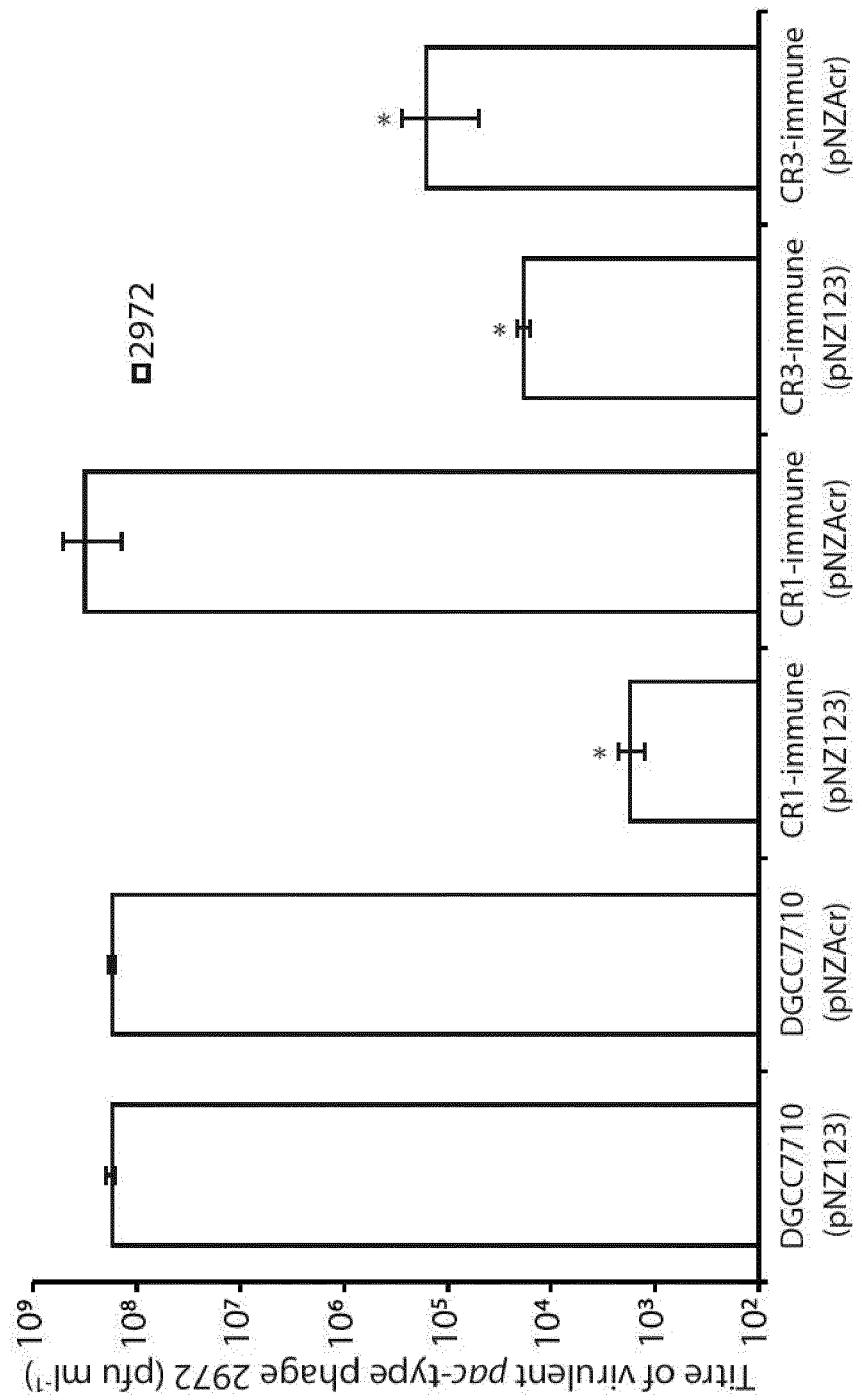
Figure 2D:
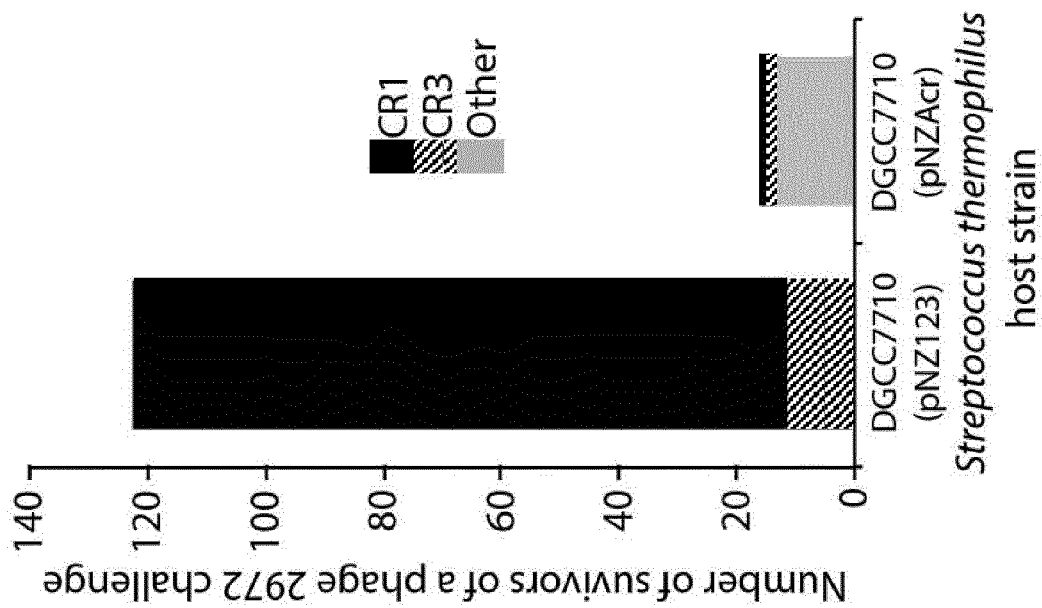

FIGS. 2A-2D provide a representative anti-CRISPR activity of StAcrIIA in *Streptococcus thermophilus*. FIG. 2A: Genes cloned from the CRISPR restrictive (black capsid) phage D4276 were expressed in the DGCC7854-derived immunized strain, and the resulting transformants were assayed for increased sensitivity to the permissive (white capsid) phage D5842. FIG. 2B: Titre of the restrictive (black) cos-type phage D4276 and permissive (white) cos-type phage D5842 on the naïve DGCC7854 or its CR1-immune derivative, carrying either the empty vector pNZ123 or the vector expressing StAcrIIA (pNZAcr). Each column depicts the average of three biological replicates, each of three technical replicates. FIG. 2C: Titre of the permissive (white) pac-type phage 2972 on the naïve DGCC7710, a CR1-immune mutant or a CR3-immune mutant carrying either the empty vector pNZ123 or the vector expressing StAcrIIA (pNZAcr). Each column depicts the average of three biological replicates, each of three technical replicates. In FIG. 2B and FIG. 2C, error bars represent the standard deviation, and an asterisk denotes a difference ($p<0.001$) from all other data, while no other strain differed from any other ($p>0.5$) as determined by one-way ANOVA and Tukey HSD test. FIG. 2D: Number and characterization of survivors following a phage 2972 challenge of DGCC7710, carrying either the empty vector pNZ123 or the vector expressing StAcrIIA (pNZAcr). The single CR1 acquisition detected in the presence of the ACR targeted the plasmid and not the phage. CR3 acquisitions targeted the phage, as expected. All cells maintained an intact stAcrIIA.

Figure 3A:
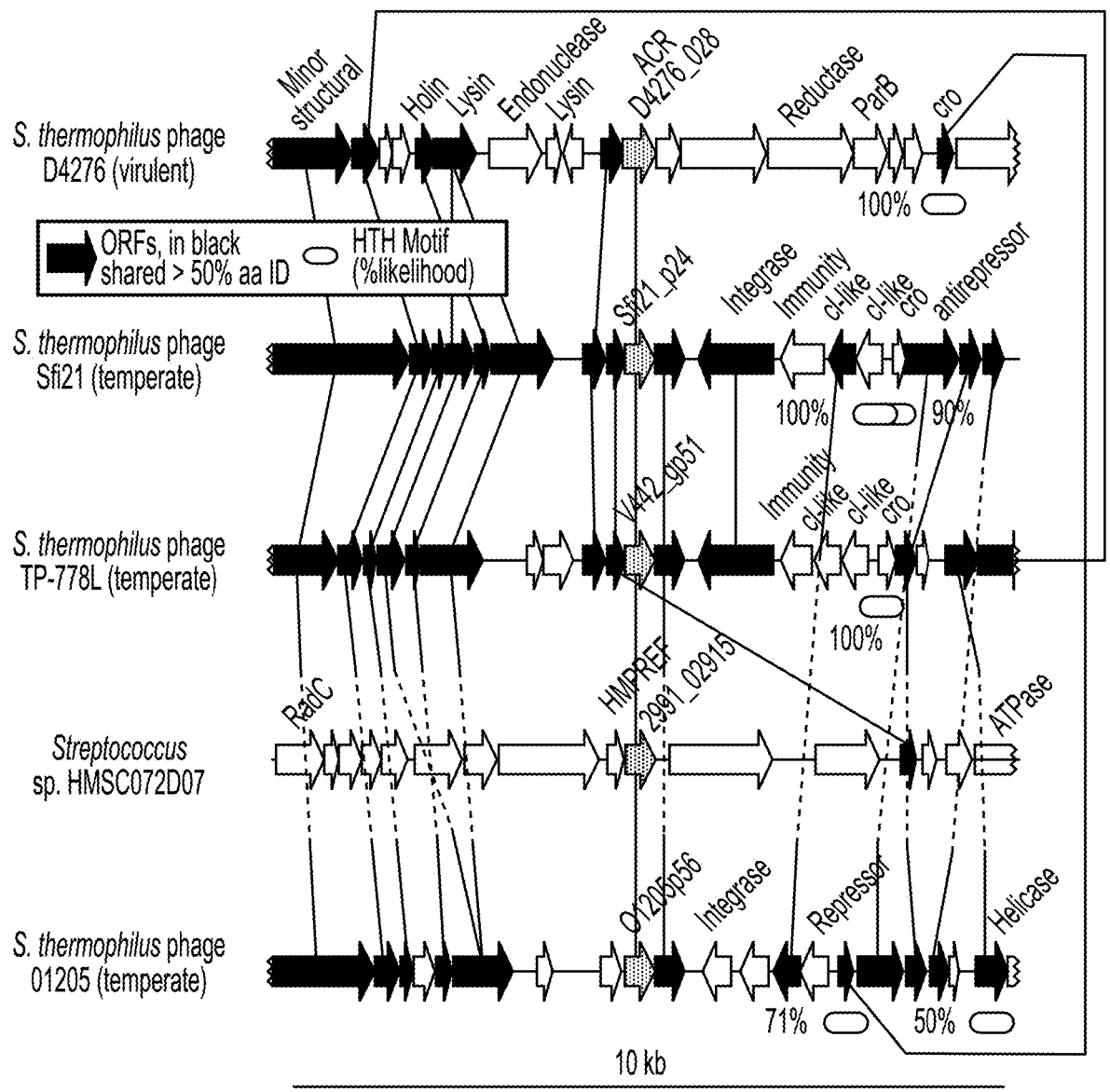

FIGS. 3A-3B provide one embodiment of an anti-CRISPR gene and protein. FIG. 3A: Genomic context of the gene encoding the ACR in all phage homologues, as well as the closest non-phage homologue (using blastP). The ACR homologue is centered (filled with dots and labelled as ACR D4276_028; Sfi21_p24; V442_gp51; HMPREF 2991_02915; and 01205p56, respectively), and identified by a locus tag. Gene function, where known, is annotated. ORFs are dark if their predicted protein product shares 50% amino acid identity with another in the dataset consisting of the full phage genomes, and white if they do not. A solid line connects these similar protein products, and the line is dotted where it passes through a protein that does not meet the similarity criterion. HTH annotations and likelihood were obtained from Helix-Turn-Helix motif prediction, and are displayed only if they have at least 50% likelihood. FIG. 3B: Protein alignment of all phage ACR homologues, as well as the closest non-phage homologue (using blastP), highlighting only differences. A dash (-) indicates the residue is absent from the protein. Bold residues (KQRRE-YAQEMDRLEKAFENLD and ENKLDKIIEKIDKL) are predicted coiled-coil motifs (pCoils, >90% confidence) from the consensus, while an "E" (extended) and "H" (helical) indicator above the residue are the consensus predictions obtained from jnet, jhmm and jpssm.

Figure 4A:
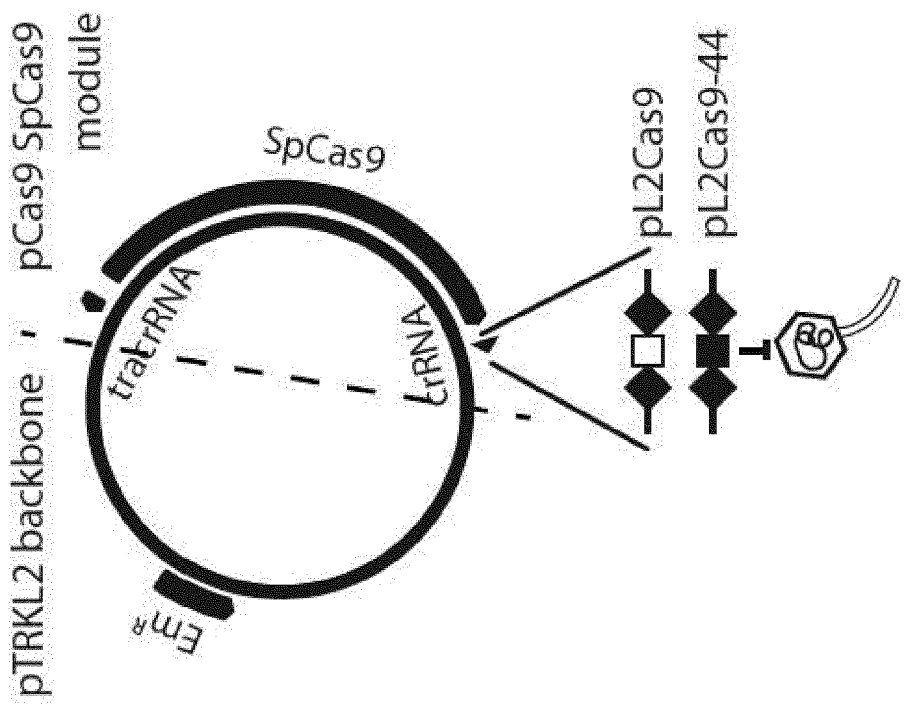
Figure 4B:
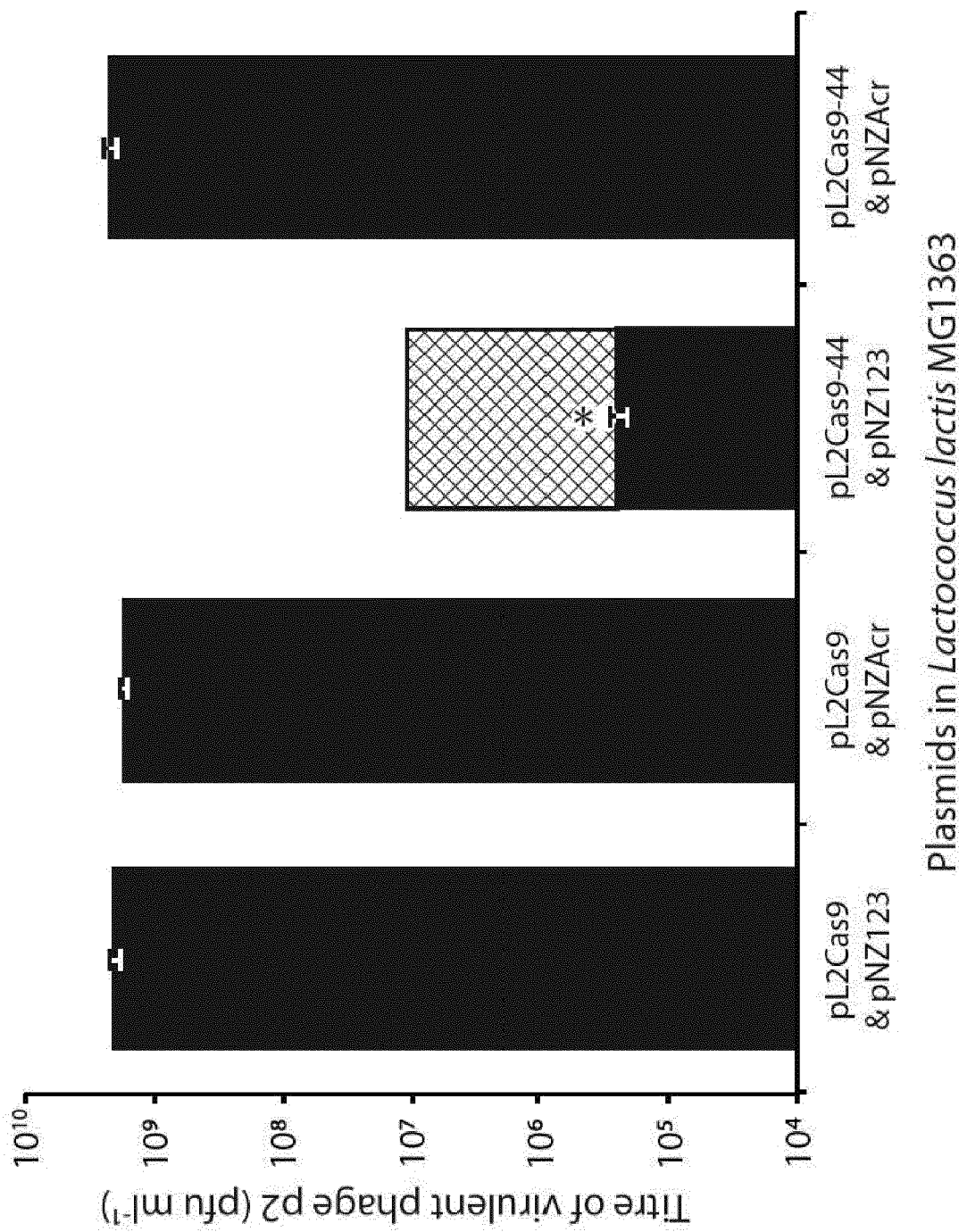

FIGS. 4A-4B provide schematic representation of one example of anti-CRISPR activity against SpCas9. FIG. 4A: Generating an immunized *Lactococcus lactis* MG1363 strain. pL2Cas9 contains the SpCas9 module from pCas9 on a pTRKL2 vector backbone. A spacer targeting orf44 of *L. lactis* virulent phage p2 was cloned-in to create a phage-targeting SpCas9. FIG. 4B: The titre of virulent phage p2 on its host *L. lactis* MG1363 carrying either pL2Cas9 or pL2Cas9 targeting the phage (pL2Cas9-44), and either the empty vector pNZ123 or the vector expressing StAcrIIA (pNZAcr). The titre was assayed by spot test, and each bar represents an average of three biological replicates, each of three technical replicates. Only plaques with typical morphology were counted, although a secondary morphology of tiny plaques occasionally appeared when plated on pL2Cas9-44 with pNZ123. While these plaques were not reliably countable, the maximum threshold at which they appeared is depicted by a patterned box. Error bars represent the standard deviation, and an asterisk denotes a difference ($p<0.001$) from all other data, while no other strain differed from any other ($p>0.5$) as determined by one-way ANOVA and Tukey HSD test.

Figure 5A:
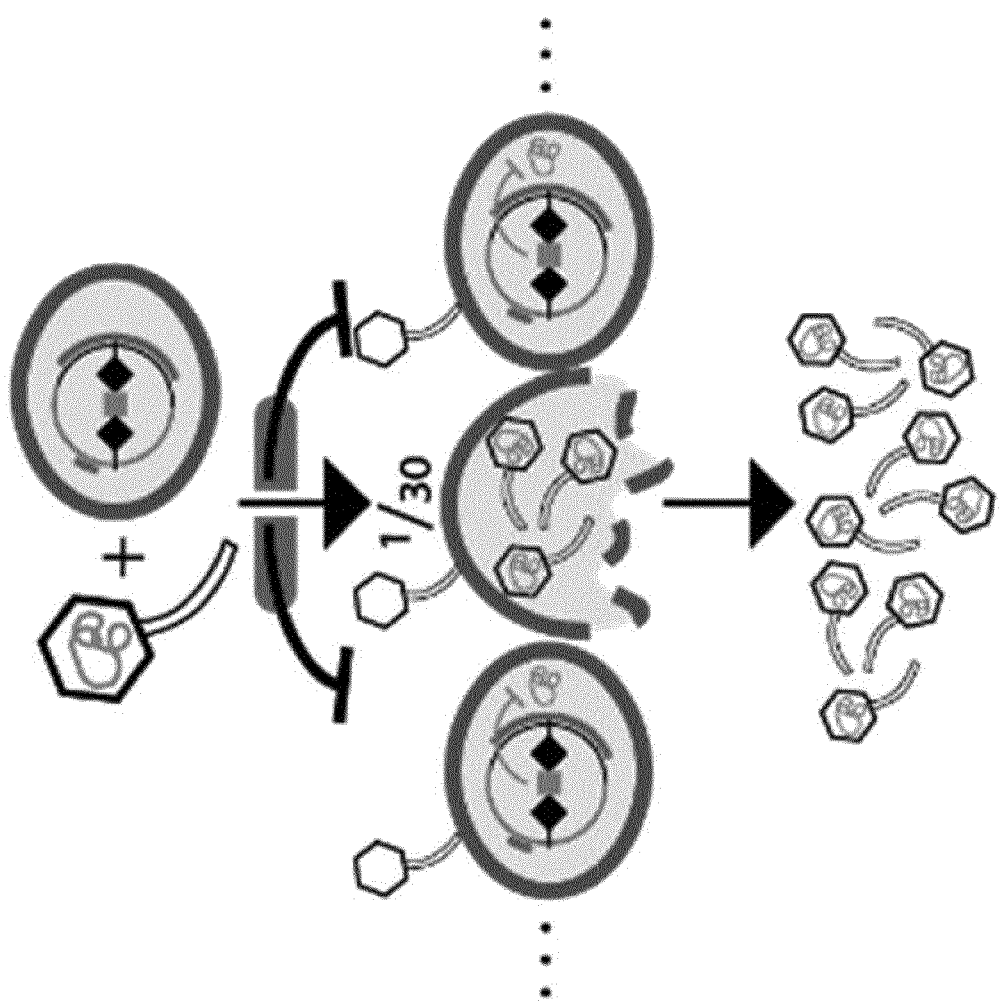
Figure 5B:
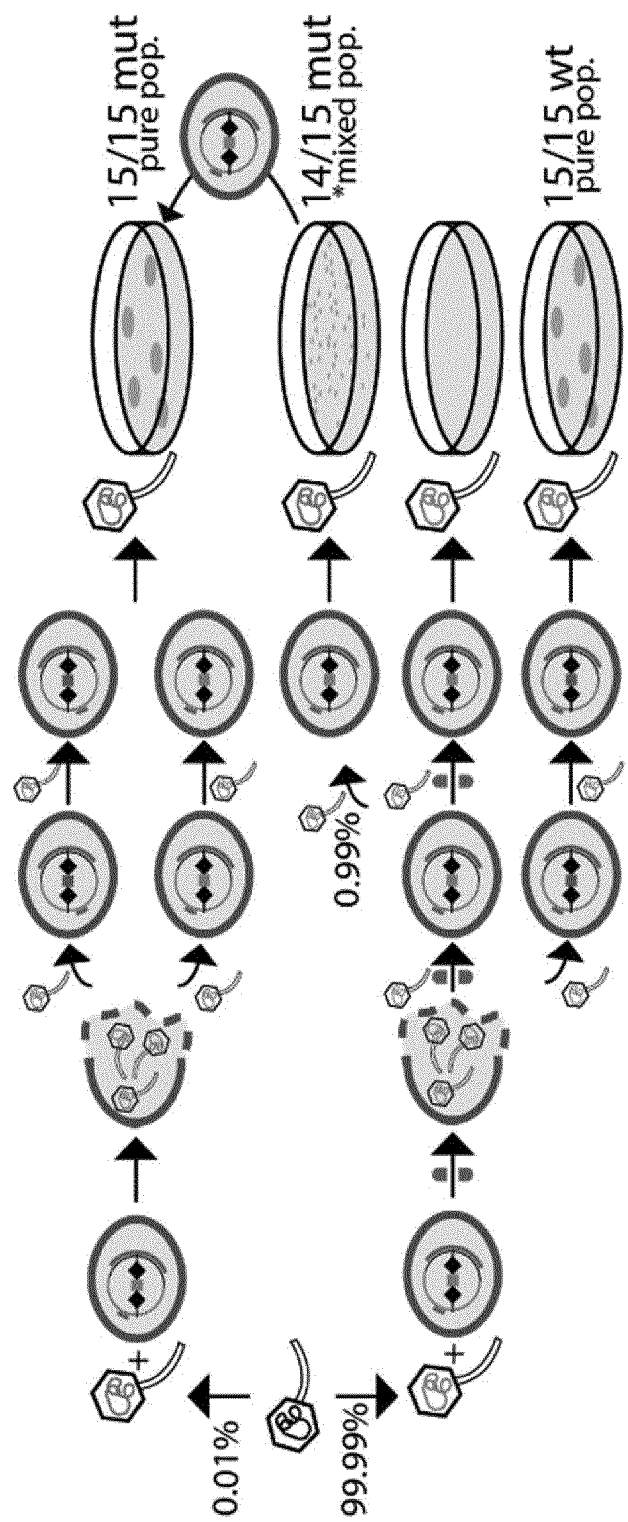

FIGS. 5A-5B provide a characterization of the "tiny-plaque" phenotype. When phage p2 is plated on its host carrying pL2Cas9-44, its titre is greatly reduced and a tiny plaque phenotype emerges (see FIG. 1). FIG. 5A: By ECOI assays (also depicted by following every downward-pointing arrow in FIG. 5B), where the phage is passaged on the restrictive host carrying pL2Cas9-44 then plated on a permissive host, we determined that $\frac{1}{30}^{th}$ of phage particles were still able to infect the restrictive host and release wild type (orange) progeny. The pL2Cas9-44 system was determined, in this way, to be "leaky". FIG. 5B: (Top 2 rows) A phage population is mixed, containing some pre-existing mutants in orf44 able to bypass the CRISPR-Cas system (top phage depicted on left). We attributed all of the large plaques (0.01% of the population) in FIG. 1 to pre-existing mutants able to replicate effectively on the restrictive host. When sequenced, all of these plaques contained pure populations mutated in the region targeted by pL2Cas9-44. (Bottom 2 rows) In contrast, the vast majority of phages are wild type, and will be replicating by occasionally 'leaking' through the restrictive strain; a typical burst of ~100 phages would result in only 3 productive infections. This phage replication, due to the leaky system, does not result in visible plaques as the effective burst size (burst size*ECOI) is too low. If plated on an indicator strain, however, it is clear that wild type phage (bottom phage depicted on left) plaques exist, they are simply not visible on the restrictive host. (middle row) The small plaques observed in FIG. 1 were found to also be mutated in the orf44 region (14/15 tested were clearly mutated, although all 15 plaques tested yielded signal consistent with a mixed population containing wild-type phages), and those mutations were indistinguishable from those observed in the large plaques. In fact, when a tiny plaque was passaged again on the restrictive strain, it resulted in large plaques containing pure populations of mutant phages. We attribute the tiny-plaque phenotype to mutations arising in the 'invisible' wild-plaques after several rounds of replication through the leaky pL2Cas9-44 system. Once a mutant emerges, it can replicate efficiently and begins to form a visible plaque—but the delay in generating that mutant constrains the plaque size. This is consistent with the mixed populations observed in the sequence data.

FIGS. 6A-6Z show representative anti-CRISPR gene sequences and anti-CRISPR protein sequences isolated from Bacteriophage O1205 (FIGS. 6A-6B), Bacteriophage Sfi21 (FIGS. 6C-6D), Bacteriophage TP-778L (FIGS. 6E-6F), *Streptococcus* sp. HMSC072D07 (FIGS. 6G-6H), Bacteriophage D4276 (FIGS. 6I-6J), Bacteriophage D1126 (FIGS. 6K-6L), Bacteriophage D4250 (FIGS. 6M-6N), Bacteriophage D4252 (FIGS. 6O-6P), Bacteriophage D4598 (FIGS. 6Q-6R), *Streptococcus mutans* NLML9 (FIGS. 6S-6T), *Streptococcus mutans* AD01 (FIGS. 6U-6V), *Streptococcus mutans* N66 (FIGS. 6W-6X), and *Streptococcus mutans* 24 (FIGS. 6Y-6Z).

Figure 7:
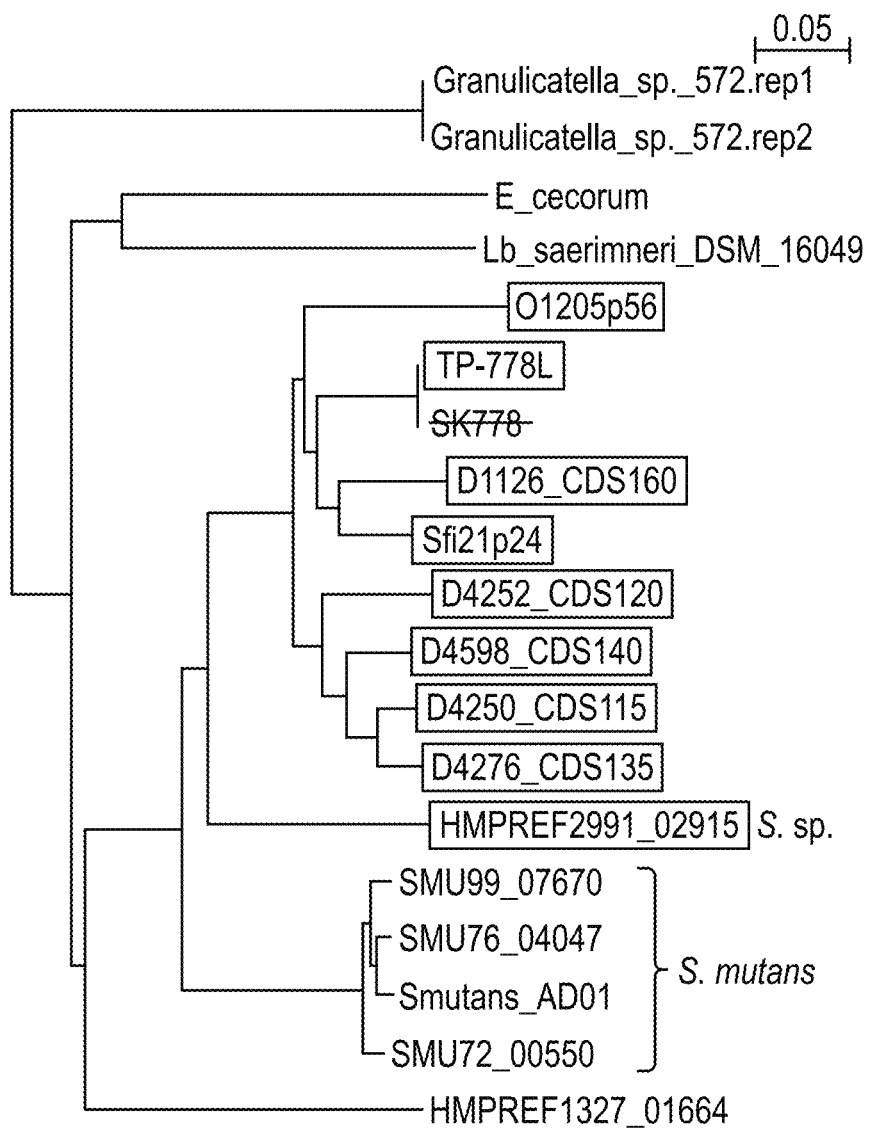

FIG. 7 provides a dendrogram of additional, more distant ACR orthologs identified in genomes from *Enterococcus faecalis, Enterococcus cecorum, Lactobacillus saerimneri,* and *Granulicatella* sp.

Figure 8A:
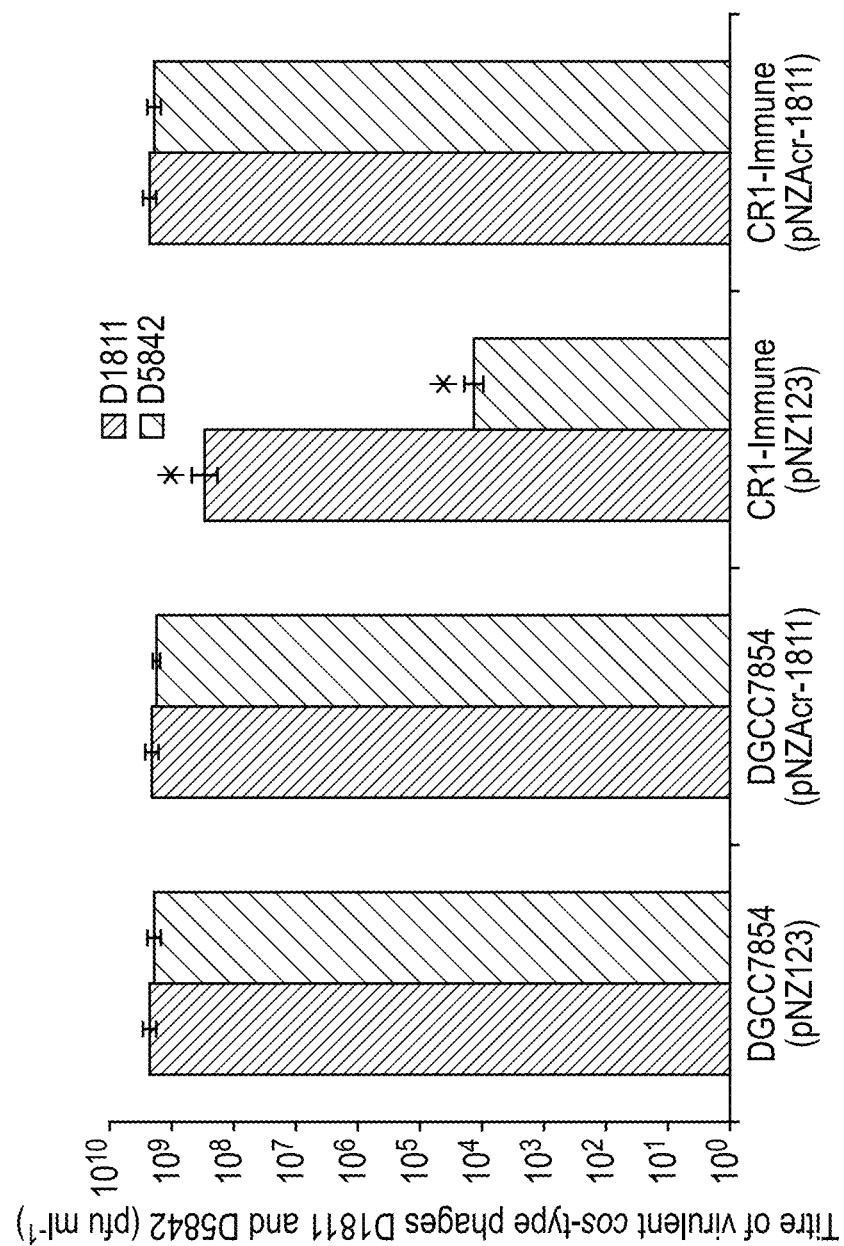
Figure 8B:
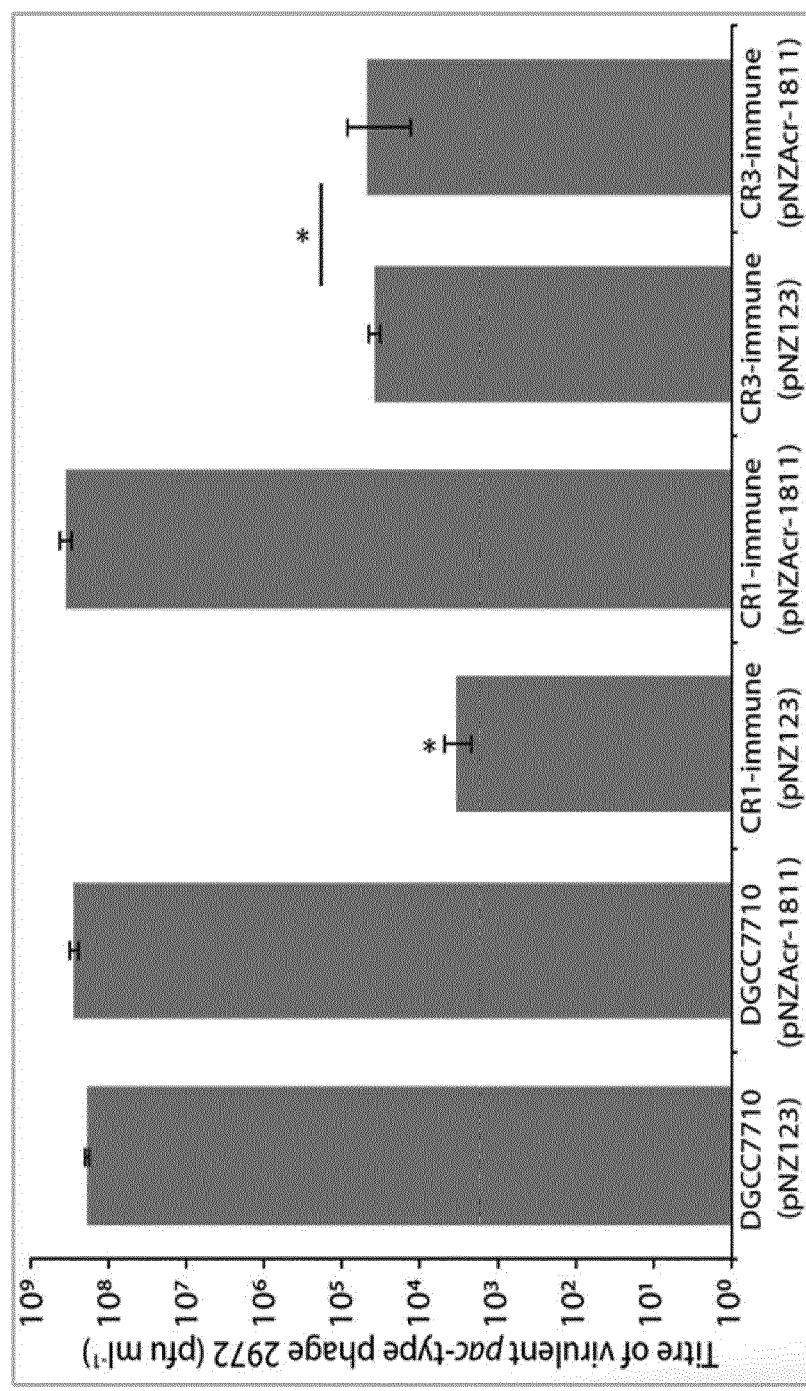

FIGS. 8A and 8B provide a representative anti-CRISPR activity of the Acr2 protein (SEQ ID NO:28) in *Streptococcus thermophilus*. FIG. 8A Titer of the restrictive cos-type phage D1811 and permissive cos-type phage D5842 on the naïve DGCC7854 or its CR1-immune derivative, carrying either the empty vector pNZ123 or the vector expressing the acr2 gene (SEQ ID NO:27) (pNZAcr). Each column depicts the average of three biological replicates, each of three technical replicates. FIG. 8B Titer of the permissive pac-type phage 2972 on the naïve DGCC7710, a CRISPR1-immune mutant or a CRISPR3-immune mutant carrying either the empty vector pNZ123 or the vector expressing the acr2 gene (pNZAcr). Each column depicts the average of three biological replicates, each of three technical replicates. In (A) and (B), error bars represent the standard deviation, and an asterisk denotes a difference (p<0.001) from all other data, while no other strain differed from any other (p>0.5) as determined by one-way ANOVA and Tukey HSD test.

FIG. 9 depicts one non-limiting depiction for using a Cas endonuclease to restore function, or abolish function in an ACR gene. In one embodiment, an ACR recombinant gene expression cassette is designed to be non-functional, then following Cas endonuclease expression and RNA guided cleavage or after a sufficient time has passed for site-specific cleavage, converted into a functional expression cassette.

Figure 10:
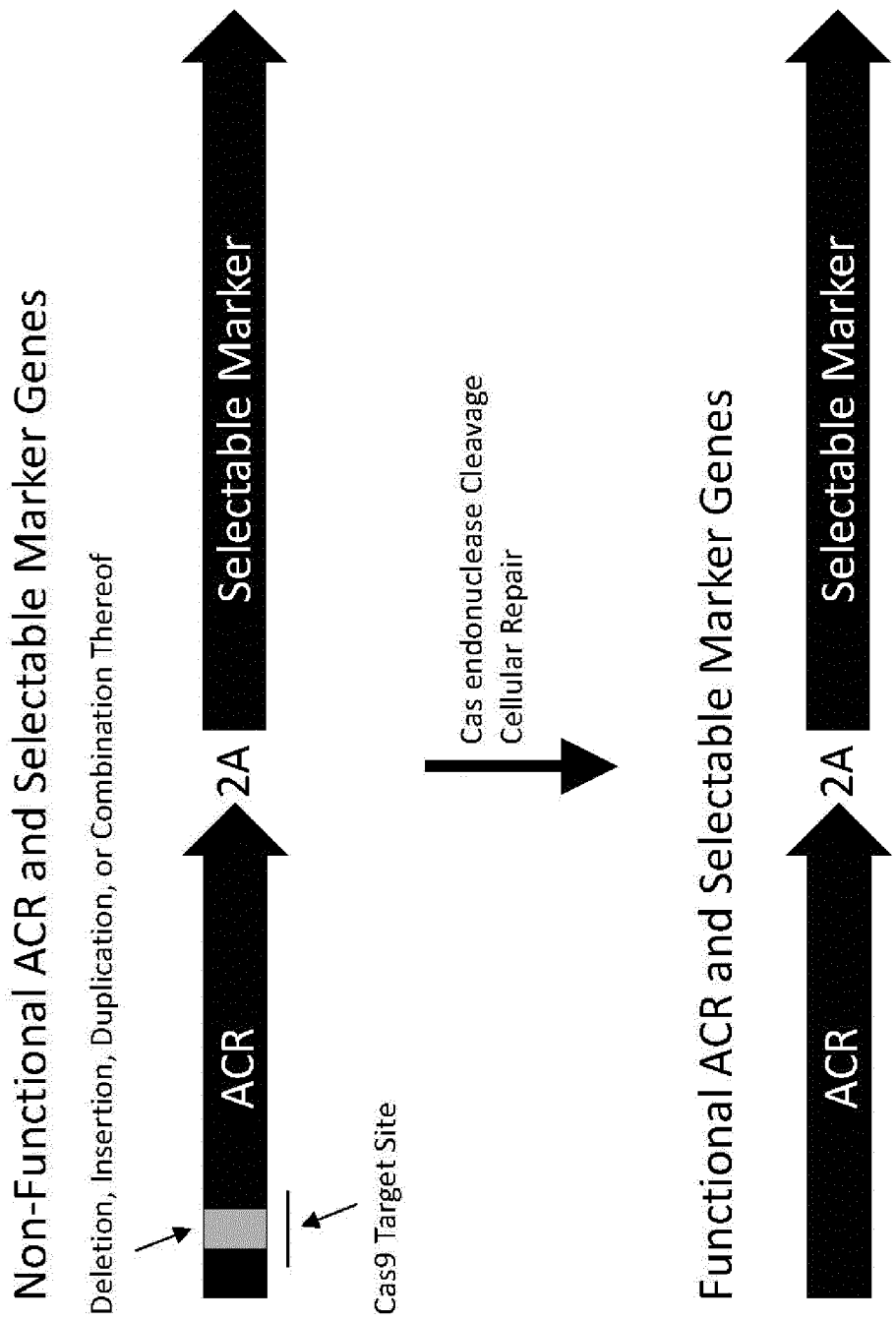

FIG. 10 provides one non-limiting depiction for using a Cas endonuclease with an ACR protein and another coding region. In one embodiment, the gene encoding an out-of-frame ACR protein may be combined with other genes (such as, but not limited to, a selectable marker) in a polycistron separated by sequences encoding 'self-cleaving' 2A peptides. Then, following restoration of the ACR ORF, the other genes in the multicistronic expression cassette can also be converted into a functional state.

Figure 11:
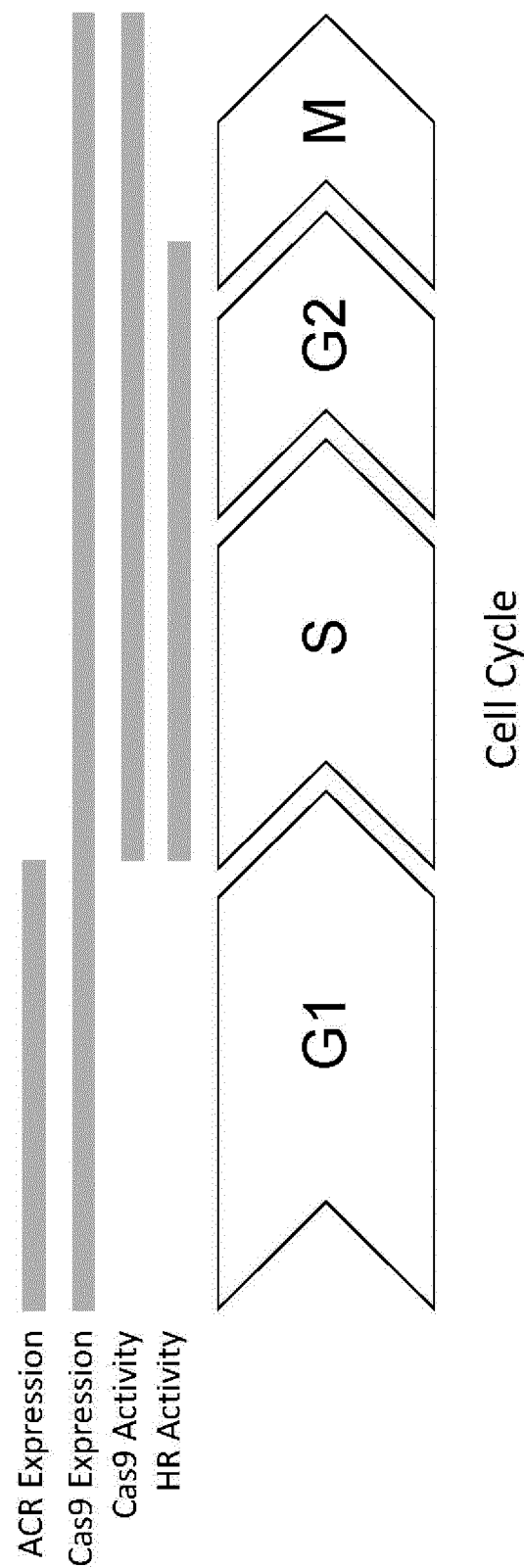

FIG. 11 provides one non-limiting depiction of modulating Cas endonuclease activity in a cell during particular cell cycle(s). In one embodiment, inactivating Cas9 during G1 when HR repair is inactive and permitting Cas9 re-activation during S and G2 when HR repair machinery is expressed and active may increase the frequency of homologous recombination in a cell.

The following anti-CRISPR gene sequences and anti-CRISPR protein sequences are disclosed as representative, but not limiting, examples in this application:

```
SEQ ID NO: 1/anti-CRISPR gene isolated from
bacteriophage O1205
ATGGCATACGGAAAAAGCAGATACAACTCATATAGGAAACGCAGTTTCA

ATAGAAGCGATAAGCAACGTAGAGAATACGCACAAGAAATGGATAGATT

AGAACAAACATTTGAAAAACTTGATGGTTGGTATCTATCTAGCATGAAA

GATAGTGCGTATAAAGATTTCGGAAAATACGAAATTCGCTTATCAAATC

ATTCAGCAGACAACAAATATCATGACCTAGAAAATGGTCGTTTAATTGT

TAATGTCAAAGCAAGTAAATTGAAATTCGTTGATATCAAATGTTACTAT

AAGGGATTTAAGACAAAGAAGGATGTAATCTAA

SEQ ID NO: 2/anti-CRISPR protein encoded by
SEQ ID NO: 1
MAYGKSRYNSYRKRSFNRSDKQRREYAQEMDRLEQTFEKLDGWYLSSMK

DSAYKDFGKYEIRLSNHSADNKYHDLENGRLIVNVKASKLKFVDIKCYY

KGFKTKKDVI

SEQ ID NO: 3/anti-CRISPR gene isolated from
Bacteriophage Sfi21
ATGGCATACGGAAAAAGTAGATATAACTCATATAGAAAGCGCAGTTTTA

ACAGAAGTAATAAGCAACGTAGAGAATACGCACAAGAAATGGATAGATT

AGAGAAAGCTTTCGAAAATCTTGACGGATGGTATCTATCTAGCATGAAA

GATAGTGCGTACAAAGATTTCGGAAAATACGAAATTCGCTTATCAAATC

ATTCAGCAGACAACAAATATCATGACCTAGAAAATGGTCGTTTAATTGT

TAATGTCAAAGCAAGTAAATTGAACTTCGTTGATATCATCGAGAACAAA

CTTGATAAAATCATTGAGAAGATTGATACTCTTGATTTAGATAAGTACA

GATTCATTAATGCTACTAAATTGGAACGTGATATCAAATGCTACTATAA

AGGCTATAAGACAAAGAAGGATGTAATCTAA

SEQ ID NO: 4/anti-CRISPR protein encoded by
SEQ ID NO: 3
MAYGKSRYNSYRKRSFNRSNKQRREYAQEMDRLEKAFENLDGWYLSSMK

DSAYKDFGKYEIRLSNHSADNKYHDLENGRLIVNVKASKLNFVDIIENK

LDKIIEKIDTLDLDKYRFINATKLERDIKCYYKGYKTKKDVI

SEQ ID NO: 5/anti-CRISPR gene isolated from
Bacteriophage TP-778L
ATGGCATACGGAAAAAGCAGATACAACTCATATAGAAAACGTAGTTTCA

ACATAAGTGACACAAAGCGTAGGGAATATGCAAAAGAAATGGAGAAATT

AGAACAAGCATTTGAAAAGCTAGATGGTTGGTATCTATCTAGCATGAAG

GATAGTGCATACAAGGATTTTGGAAAATACGAAATCCGCTTATCAAATC

ATTCAGCAGACAATAAATATCATGACCTAGAAAATGGTCGTTTAATTGT

TAATGTTAAAGCAAGTAAATTGAACTTCGTTGATATCATCGAAAACAAA

CTTGATAAAATCATCGAGAAGATTGATAAGCTTGATTTAGATAAGTACA
```

GATTTATTAACGCTACTAGAATGGAGCATGACATTAAATGCTACTATAA

AGGATTTAAGACAAAGAAAGATGTAATCTAA

SEQ ID NO: 6/anti-CRISPR protein encoded by
SEQ ID NO: 5
MAYGKSRYNSYRKRSFNISDTKRREYAKEMEKLEQAFEKLDGWYLSSMK

DSAYKDFGKYEIRLSNHSADNKYHDLENGRLIVNVKASKLNFVDIIENK

LDKIIEKIDKLDLDKYRFINATRMEHDIKCYYKGFKTKKDVI

SEQ ID NO: 7/anti-CRISPR gene isolated from the
genome of Streptococcus sp. HMSC072D07
ATGGCATTTGGCAAGAACAGATACAATCCATACAGGAAACGTAGTTTTA

ATCGTAGTGATAAACAATGTCGAGAGTATGCTCAGGCAATGGACGAACT

AGAACAAGCCTTTGAGGAACTTGATGGATGGCACTTATCTAGTATGATG

GATAGTGCTTATAAGAATTTTGAAAAGTACCAGGTTCGCCTATCAAATC

ATTCAGCAGACAACCAATATCATGACTTAGAAAATGGTTACTTGATTGT

CAATGTTAAAGCAAGTAAATTGAACTTTGTCGATATTATCGAAAATAAA

TTGGATAAGATTTTAGAGAAAGTAGACAAGCTTGATCTTGATAAGTATA

GGTTTATCAATGCGACCAATCTGGAACATGATATTAAATGTTATCTCAA

AGGCTATAAGACGAAAAAGACGTGATTTAA

SEQ ID NO: 8/anti-CRISPR protein encoded by
SEQ ID NO: 7
MAFGKNRYNPYRKRSFNRSDKQCREYAQAMDELEQAFEELDGWHLSSMM

DSAYKNFEKYQVRLSNHSADNQYHDLENGYLIVNVKASKLNFVDIIENK

LDKILEKVDKLDLDKYRFINATNLEHDIKCYLKGYKTKKDVI

SEQ ID NO: 9/anti-CRISPR gene isolated from
Bacteriophage D4276
ATGGCATACGGAAAAAGTAGATATAACTCATATAGAAAGCGCAGTTTTA

ACAGAAGTAATAAGCAACGTAGAGAATACGCACAAGAAATGGATAGATT

AGAGAAAGCTTTCGAAAATCTTGACGGATGGTATCTATCTAGCATGAAA

GACAGTGCTTACAAGGATTTTGGGAAATACGAAATTCGCTTATCAAATC

ATTCGGCAGACAACAAATATCACGACTTAGAAAACGGTCGTTTAATTGT

TAATATTAAAGCTAGTAAATTGAATTTCGTTGATATCATCGAGAATAAG

CTTGATAAAATAATCGAGAAGATTGATAAGCTTGATTTAGATAAGTACC

GATTCATCAATGCGACCAACCTAGAGCATGATATCAAATGCTATTACAA

GGGGTTTAAAACGAAAAGGAGGTAATCTAA

SEQ ID NO: 10/anti-CRISPR protein encoded by
SEQ ID NO: 9
MAYGKSRYNSYRKRSFNRSNKQRREYAQEMDRLEKAFENLDGWYLSSMK

DSAYKDFGKYEIRLSNHSADNKYHDLENGRLIVNIKASKLNFVDIIENK

LDKIIEKIDKLDLDKYRFINATNLEHDIKCYYKGFKTKKEVI

SEQ ID NO: 11/anti-CRISPR gene isolated from
Bacteriophage D1126
ATGGCATACGGAAAAGCAGATACAATTCATATAGGAAGCGAAACTTCT

CTATAAGCGACAATCAGCGTAGGGAATATGCTAAAAAAATGAAGGAGTT

AGAACAAGCGTTTGAAAACCTTGACGGATGGTATCTATCTAGCATGAAA

GATAGTGCTACAAAGATTTCGGAAAATACGAAATTCGCTTATCAAATC

ATTCAGCAGACAATAGATATCATGACCTAGAAAATGGTCGCTTAATCGT

TAATGTTAAAGCTAGTAAATTGAACTTCGTTGATATCATCGAGAATAAA

CTTGGTAAAATCATTGAGAAGATTGATACTCTTGATTTAGATAAGTACA

GATTCATTAATGCTACTAAATTGGAACGTGATATCAAATGCTACTATAA

AGGCTATAAGACAAAGAAGGATGTAATCTAA

SEQ ID NO: 12/anti-CRISPR protein encoded by
SEQ ID NO: 11
MAYGKSRYNSYRKRNFSISDNQRREYAKKMKELEQAFENLDGWYLSSMK

DSAYKDFGKYEIRLSNHSADNRYHDLENGRLIVNVKASKLNFVDIIENK

LGKIIEKIDTLDLDKYRFINATKLERDIKCYYKGYKTKKDVI

SEQ ID NO: 13/anti-CRISPR gene isolated from
Bacteriophage D4250
ATGGCATACGGAAAAGTAGATATAACTCATATAGAAAACGCAGTTTCA

ACAGAAGCGATAAACAGCGTAGAGAATACGCACAAGCAATGGAAGAATT

AGAGCAAGCATTTGAAAACTTTGATGATTGGTATCTATCAAGCATGAAA

GACAGTGCTTACAAGGATTTTGGGAAATACGAAATTCGCTTATCAAATC

ATTCGGCAGACAACAAATATCACGACTTAGAAAACGGTCGTTTAATTGT

TAATATTAAAGCTAGTAAATTGAATTTCGTTGATATCATCGAGAATAAG

CTTGATAAAATAATCGAGAAGATTGATAAGCTTGATTTAGATAAGTACC

GATTCATCAATGCGACCAACCTAGAGCATGATATCAAATGCTATTACAA

GGGGTTTAAAACGAAAAAGGAGGTAATCTAA

SEQ ID NO: 14/anti-CRISPR protein encoded by
SEQ ID NO: 13
MAYGKSRYNSYRKRSFNRSDKQRREYAQAMEELEQAFENFDDWYLSSMK

DSAYKDFGKYEIRLSNHSADNKYHDLENGRLIVNIKASKLNFVDIIENK

LDKIIEKIDKLDLDKYRFINATNLEHDIKCYYKGFKTKKEVI

SEQ ID NO: 15/anti-CRISPR gene isolated from
Bacteriophage D4252
ATGGCATACGGAAAAAGCAGATACAACTCATATAGAAAGCGCAGTTTTA

ACAGAAGTGATAAGCAACGTAGAGAATACGCTAAAAAAATGAAGGAGTT

AGAACAAGCGTTTGAAAACCTTGATGGTTGGTATCTATCGAGCATGAAT

GACAGTGCTTATAAAAATTTTGGCAAATATGAAGTTCGATTGTCAAATC

ATTCGGCAGATAATAAATATCACGACATAGAAAACGGTCGTTTAATTGT

TAATGTTAAAGCTAGTAAATTGAATTTCGTTGATATCATCGAGAACAAG

CTTGATAAAATAATCGAGAAGATTGATAAGCTTGATTTAGATAAGTACC

GATTCATCAACGCTACCAATCTAGAGCATAATATTAAATGCTATTACAA

GGGATTTAAGACAAAGAAGGATGTAATATAA

SEQ ID NO: 16/anti-CRISPR protein encoded by
SEQ ID NO: 15
MAYGKSRYNSYRKRSFNRSDKQRREYAKKMELEQAFENLDGWYLSSMN

DSAYKNFGKYEVRLSNHSADNKYHDIENGRLIVNVKASKLNFVDIIENK

LDKIIEKIDKLDLDKYRFINATNLEHNIKCYYKGFKTKKDVI

SEQ ID NO: 17/anti-CRISPR gene isolated from
Bacteriophage D4598
ATGGCATACGGAAAAGTAGATATAACTCATATAGAAAACGCAGTTTCA

ACAGAAGCGATAAACAGCGTGGAGAATACGCACAAGCAATGGAAGAATT

AGAGCAAGCATTTGAAAACTTTGATGATTGGTATCTATCAAGCATGAAA

GACAGTGCTTACAAGGATTTTGGGAAATACGAAATTCGCTTATCAAATC

ATTCGGCAGACAATAAATATCATGACCTAGAAAATGGTCGCTTAATCGT

TAATGTTAAAGCTAGTAAATTGAACTTCGTCGATATCATCGAGAATAAA

ATCGATAAAATCATTGAGAAGATTGATAAGCTTGATTTAGATAAGTACC

GATTCATCAACGCTACCAACCTAGAGCATGATATCAAATGTTATTACAA

GGGATTTAAGACAAAAAAGGATGTAATCTAA

SEQ ID NO: 18/anti-CRISPR protein encoded by
SEQ ID NO: 17
MAYGKSRYNSYRKRSFNRSDKQRGEYAQAMEELEQAFENFDDWYLSSMK

DSAYKDFGKYEIRLSNHSADNKYHDLENGRLIVNVKASKLNFVDIIENK

IDKIIEKIDKLDLDKYRFINATNLEHDIKCYYKGFKTKKDVI

SEQ ID NO: 19/anti-CRISPR gene isolated from the
genome of a Streptococcus mutans strain
ATGGCATTTGGAAAAAGAAGATATAACTCGTATCGTAAACGCAGTTTTA

ATAGAAGTGATAAGCAACGTCGAGAATATGCACAAGCAATGGAAGAACT

TGAACAAACATTTGAAAATCTTGAAGGTTGGAATTTATCAAGCATGAAA

GATAGTGCTTATAAAGATTATGATAAATATGAAGTTCGACTTTCAAATC

ATTCAGCTGATAATCAATATCATAACTTACAAGATGGTAAATTAATCAT

CAATATCAAAGCTAGTAAAATGAATTTTGTTTGGATTATAGAAAATAAA

CTTGATGCAATTCTTGAAAAAGTAAATAAGTTAGACCTTAGCAAATACA

GATTTATTAATGCTACAAGTTTAGATCATGATATCAAATGTTATTACAA

AAATTATAAAACAAAGAAAGATGTAATTTAA

SEQ ID NO: 20/anti-CRISPR protein encoded by
SEQ ID NO: 19
MAFGKRRYNSYRKRSFNRSDKQRREYAQAMEELEQTFENLEGWNLSSMK

DSAYKDYDKYEVRLSNHSADNQYHNLQDGKLIINIKASKMNFVWIIENK

LDAILEKVNKLDLSKYRFINATSLDHDIKCYYKNYKTKKDVI

SEQ ID NO: 21/anti-CRISPR gene isolated from the
genome of a Streptococcus mutans strain
ATGGCATTTGGAACAAGAAGATATAATTCATATCGTAAACGCAGTTTTA

ATAGAAGTGATAAGCAACGTCGAGAATATGCACAAGCAATGGAAGAACT

TGAACAAACATTTGAAAATCTTGAAGATTGGAATTTGTCGAGCATGAAA

GATAGTGCTTATAAAGATTATGATAAATATGAAGTTCGACTTTCAAATC

ATTCAGCTGATAATCAATATCATAACTTACAAGATGGTAAATTAATCAT

CAATATCAAAGCTAGTAAAATGAATTTTGTTTGGATTATAGAAAATAAA

CTTGATGCAATTCTTGAAAAGTAAATAAGTTAGACCTTAGCAGATACA

GATTTATTAATGCTACAAATTTAGAACATGATATCAAATGTTATTACAA

AAATTATAAAACAAAGAAAGATGTAATTTAA

SEQ ID NO: 22/anti-CRISPR protein encoded by
SEQ ID NO: 21
MAFGTRRYNSYRKRSFNRSDKQRREYAQAMEELEQTFENLEDWNLSSMK

DSAYKDYDKYEVRLSNHSADNQYHNLQDGKLIINIKASKMNFVWIIENK

LDAILEKVNKLDLSRYRFINATNLEHDIKCYYKNYKTKKDVI

SEQ ID NO: 23/anti-CRISPR gene isolated from the
genome of a Streptococcus mutans strain
ATGGCATTTGGAACAAGAAGATATAATTCATATCGTAAACGCAGTTTTA

ATAGAAGTGATAAGCAACGTCGAGAATATGCACAAGCAATGGAAGAACT

TGAACAAACATTTGAAAATCTTGAAGATTGGAATTTGTCGAGCATGAAA

GATAGTGCTTATAAAGATTATGATAAATATGAAGTTAGACTTTCAAATC

ATTCAGCTGATAATCAATATCATAACTTACAAGATGGTAAATTAATCAT

CAATATCAAAGCTAGTAAAATGAATTTTGTTTGGATTATAGAAAATAAA

CTTGATGTAATTCTTGAAAAAGTAAATAAGTTAGACCTTAGCAAATACA

GATTTATTAATGCTACAAGTTTAGATCATGATATCAAATGTTATTACAA

AAATTATAAAACAAAGAAAGATGTAATCTAA

SEQ ID NO: 24/anti-CRISPR protein encoded by
SEQ ID NO: 23
MAFGTRRYNSYRKRSFNRSDKQRREYAQAMEELEQTFENLEDWNLSSMK

DSAYKDYDKYEVRLSNHSADNQYHNLQDGKLIINIKASKMNFVWIIENK

LDVILEKVNKLDLSKYRFINATSLDHDIKCYYKNYKTKKDVI

SEQ ID NO: 25/anti-CRISPR gene isolated from the
genome of a Streptococcus mutans strain
ATGGCATTTGGAACAAGAAGATATAATTCATATCGTAAACGCAATTTTA

ATAGAAGTGATAAACAACGTCGAGAATATGCACAAGCAATGGAAGAACT

TGAACAAACATTTGAAAATCTTGAAGATTGGAATTTGTCGAGCATGAAA

GATAGTGCTTATAAAGATTATGATAAATTTGAAGTTCGACTTTCAAATC

ATTCAGCTGATAATCAATATCATAACTTACAAGATGGTAAATTAATCAT

CAATATCAAAGCTAGTAAAATGAATTTTGTTTGGATTATAGAAAATAAA

CTTGATGCAATTCTTGAAAAGGTAAATAAGTTAGACCTTAGCAAATACA

GATTTATTAATGCTACAAGTTTAGATCATGATATCAAATGTTATTACAA

AAATTATAAAACAAAAAAGATGTAATTTAA

SEQ ID NO: 26/anti-CRISPR protein encoded by
SEQ ID NO: 25
MAFGTRRYNSYRKRNFNRSDKQRREYAQAMEELEQTFENLEDWNLSSMK

DSAYKDYDKFEVRLSNHSADNQYHNLQDGKLIINIKASKMNFVWIIENK

LDAILEKVNKLDLSKYRFINATSLDHDIKCYYKNYKTKKDVI

SEQ ID NO: 27/anti-CRISPR gene isolated from
Bacteriophage D1811
ATGAAAATAAATGACGACATCAAAGAGTTAATTTTAGAATATATGAGCC

GTTACTTCAAATTCGAGAACGACTTTTATAAACTGCCAGGCATCAAGTT

CACTGATGCAAATTGGCAGAAGTTCAAAAATGGAGGCACTGACATTGAG

AAGATGGGGCGGCACGAGTAAACGCCATGCTCGACTGCCTATTCGACG

ATTTCGAGCTTGCTATGATTGGCAAGGCTCAAACTAATTATTACAATGA

TAATTCACTAAAGATGAACATGCCATTTTACACTTACTATGACATGTTC

AAAAAGCAGCAACTTCTAAATGGCTTAAAAATAACCGTGATGATGTCA

TCGGCGGAACTGGTAGGATGTACACAGCAAGTGGTAATTACATTGCTAA

CGCTTATTTAGAGGTGGCATTAGAATCGAGCTCGCTTGGTAGTGGCTCT

TACATGCTTCAAATGAGGTTTAAAGACTATTCAAAAGGTCAAGAACCTA

TTCCGTCAGGTCGTCAGAATCGACTTGAATGGATTGAAAACAATCTCGA

AAACATTCGATAA

SEQ ID NO: 28/anti-CRISPR protein encoded by
SEQ ID NO: 27
MKINDDIKELILEYMSRYFKFENDFYKLPGIKFTDANWQKFKNGGTDIE

KMGAARVNAMLDCLFDDFELAMIGKAQTNYYNDNSLKMNMPFYTYYDMF

KKQQLLKWLKNNRDDVIGGTGRMYTASGNYIANAYLEVALESSSLGSGS

YMLQMRFKDYSKGQEPIPSGRQNRLEWIENNLENIR

SEQ ID NO: 29/anti-CRISPR gene isolated from
Bacteriophage D1024
ATGAAAATAAATGACGACATCAAAGAGTTAATTTTAGAATATATGAGCC

GTTACTTCAAATTCGAGAACGACTTTTATAAACTGCCAGGCATCAAGTT

CACTGATGCAAATTGGCAGAAGTTCAAAAATGGAGGCACTGACATTGAG

AAGATGGGGCGGCACGAGTAAATGCCATGCTTTCCTGCCTATTCGAGG

ATTTTGAGCTTGCAATGATTGGCAAGGCTCAAACTAATTATTACATTGA

TAACTCACTTAAATTGAACATGCCATTTTACGCTTACTATGACATGTTC

AAAAAGCAACTTCTTATAAATTGGCTTAAAAATAACCGTGATGATGTCA

TCTGCGGAACTGGTAGGATGTACACAGCAAGTGGTAATTACATTGCTAA

CGCTTATTTAGAGGTGGCATTAGAATCTAGCCGTCTGGGTGGTGGTGAG

TACATGTTGCAAATGCGTTTTAAAAATTATTCAAGAAGTCAAGAACCTA

TTCCGTCTGGTCGTCAGAATCGACTTGAATGGATTGAAAACAATCTTGA

AAACATTCGATAA

SEQ ID NO: 30/anti-CRISPR protein encoded by
SEQ ID NO: 29
MKINDDIKELILEYMSRYFKFENDFYKLPGIKFTDANWQKFKNGGTDIE

KMGAARVNAMLSCLFEDFELAMIGKAQTNYYIDNSLKLNMPFYAYYDMF

KKQLLINWLKNNRDDVICGTGRMYTASGNYIANAYLEVALESSRLGGGE

YMLQMRFKNYSRSQEPIPSGRQNRLEWIENNLENIR

SEQ ID NO: 31/anti-CRISPR gene isolated from
Bacteriophage D4530
ATGAAAATCAATAATGACATCAAAGAGCTAATTTTGGAATATGTAAGTC

GCTATTTTAAATTTGAAAACGACTTCTACAAATTGCCAGGCATCAAATT

CACTGATGCAAATTGGCAAAAATTCAAGAATGGAGATACTTCCATCGAG

AAGATGGGGGCAGCACGAGTAAATGCCATGCTTGACTGCCTGTTCGAAG

ATTTTGAGCTTGCAATGATTGGCAAGGCTCAAACTAATTATTACAATGA

TAATTCACTAAAGATGAACATGCCATTTTACACTTACTATGACATGTTC

AAAAAGCAGCAACTTCTAAAATGGCTTAAAAATAACCGTGATGATGTCA

TCTGCGGAACTGGTAGGATGTACACAGCAAGTGGTAATTACATTGCTAA

CGCTTATTTAGAAATTGCGTTAGAATCTAGCCGTCTGGGTAGTGGCTCT

TACATGCTTCAAATGAGATTCAAAGACTATTCAAGAAGTCAAGAACCTA

TTCCGTCTGGTCGCCAAAATAGACTAGAATGGATTGAGAGCAACTTGGA

AAACATTCGATAA

SEQ ID NO: 32/anti-CRISPR protein encoded by
SEQ ID NO: 31
MKINNDIKELILEYVSRYFKFENDFYKLPGIKFTDANWQKFKNGDTSIE

KMGAARVNAMLDCLFEDFELAMIGKAQTNYYNDNSLKMNMPFYTYYDNI

FKKQQLLKWLKNNRDDVICGTGRMYTASGNYIANAYLEIALESSRLGSG

SYMLQMRFKDYSRSQEPIPSGRQNRLEWIESNLENIR

SEQ ID NO: 33/anti-CRISPR gene isolated from
Bacteriophage D2759
ATGAAAATCAATAATGACATCAAAGAGCTAATTTTGGAATATGTAAGTC

GCTATTTTAAATTTGAAAACGACTTCTACAAATTGCCAGGCATCAAATT

CACTGATGCAAATTGGCAAAAATTCAAGAATGGAGATACTTCCATCGAG

AAGATGGGGGCAGCACGAGTAAATGCCATGCTTGACTGCCTATTCGACG

ATTTTGAGCTTGCTTTGATTGGCAAGGCTCAAACTAATTATTACATTGA

TAACTCACTTAAATTGAACATGCCATTTTACGCTTACTATGACATGTTC

AAAAAGCAGCAACTTCTAAAATGGCTTAAAAATAACCGTGATGATGTCA

TCTGCGGAACTGGTAGGATGTACACAGCAAGTGGTAATTACATTGCTAA

CTCTTATTTAGAGGTAGCGTTAGAATCTAGCCGTCTGGGTAGTGGCTCT

TACATGCTTCAAATGAGATTCAAAGACTATTCAAGAAGTCAAGAACCTA

TTCCATCTGGTCGCCAAAATAGACTAGAATGGATTGAGAGCAACTTGGA

AAACATTCGATAA

SEQ ID NO: 34/anti-CRISPR protein encoded by
SEQ ID NO: 33
MKINNDIKELILEYVSRYFKFENDFYKLPGIKFTDANWQKFKNGDTSIE

KMGAARVNAMLDCLFDDFELALIGKAQTNYYIDNSLKLNMPFYAYYDNI

FKKQQLLKWLKNNRDDVICGTGRMYTASGNYIANSYLEVALESSRLGSG

SYMLQMRFKDYSRSQEPIPSGRQNRLEWIESNLENIR

SEQ ID NO: 35/anti-CRISPR gene isolated from
Bacteriophage D1297
ATGAAAATCAATAATGACATCAAAGAGCTAATTTTGGAATATGTAAGTC

GCTATTTTAAATTTGAAAACGACTTCTACAAATTGCAAGGCATCAAATT

CACTGATGCAAATTGGCAAAAATTCAAGAATGGAGATACTTCCATCGAG

AAGATGGGGGCAGCACGAGTAAATGCCATGCTTGACTGCCTATTCGACG

ATTTTGAGCTTGCTTTGATTGGCAAGGCTCAACAAGAATACTATTCGGA

TAATTCCTTGAAATTGAACATGCCATTTTACGCTTACTATGACATGTTC

AAAAAGCAGCAACTTCTAAAATGGCTTAAAAATAACCGTGATGATGTCA

TCTGCGGAACTGGTAGGATGTACACAGCAAGTGGTAATTACATTGCTAA

CTCTTATTTAGAGGTAGCGTTAGAATCTAGCCGTCTGGGTAGTGGCTCT

TACATGCTTCAAATGAGATTCAAAGACTATTCAAGAAGTCAAGAACCTA

TTCCGTCAGGTCGCAAAAACCGACTTGAGTGGATTGAAAACAATCTGGA

AAATATTCGATAA

SEQ ID NO: 36/anti-CRISPR protein encoded by
SEQ ID NO: 35
MKINNDIKELILEYVSRYFKFENDFYKLQGIKFTDANWQKFKNGDTSIE

KMGAARVNAMLDCLFDDFELALIGKAQQEYYSDNSLKLNMPFYAYYDMF

KKQQLLKWLKNNRDDVICGTGRMYTASGNYIANSYLEVALESSRLGSGS

YMLQMRFKDYSRSQEPIPSGRKNRLEWIENNLENIR

SEQ ID NO: 37/anti-CRISPR gene isolated from
Bacteriophage M5728
ATGAAAATCAATAATGACATCAAAGAGCTAATTTTGGAATATGTAAGTC

GCTATTTTAAATTTGAAAACGACTTCTACAAATTGCCAGGCATCAAATT

CACTGATGCAAATTGGCAAAAATTCAAGAATGGAGATACTTCCATCGAG

```
AAGATGGGGGCAGCACGAGTAAATGCCATGCTTGACTGCCTATTCGACG
ATTTTGAGCTTGCTTTTATTGGCAAGGCTCAACAAGAATACTATTCGGA
TAATTCCTTGAAATTGAACATGCCATTTTACGCTTACTATGACATGTTC
AAAAAGCAGCAACTTCTAAAATGGCTTAAAAATAACCGTGATGATGTCA
TCTGCGGAACTGGTAGGATGTACACAGCAAGTGGTAATTACATTGCTAA
CTCTTATTTAGAGGTAGCGTTAGAATCTAGCCGTCTGGGTAGTGGCTCT
TACATGCTTCAAATGAGATTCAAAGACTATTCAAGAAGTCAAGAACCTA
TTCCATCTGGTCGCCAAAATAGACTAGAATGGATTGAAAACAATCTTGA
GAATATTCGATAA
```

SEQ ID NO: 38/anti-CRISPR protein encoded by
SEQ ID NO: 37
MKINNDIKELILEYVSRYFKFENDFYKLPGIKFTDANWQKFKNGDTSIE
KMGAARVNAMLDCLFDDFELAFIGKAQQEYYSDNSLKLNMPFYAYYDMF
KKQQLLKWLKNNRDDVICGTGRMYTASGNYIANSYLEVALESSRLGSGS
YMLQMRFKDYSRSQEPIPSGRQNRLEWIENNLENIR SEQ ID NO: 39/anti-CRISPR gene isolated from
Bacteriophage D4419
```
ATGAAAATCAATAATGACATCAAAGAGCTAATTTTGGAATATGTAAGTC
GCTATTTTAAATTTGAAAACGACTTCTACAAATTGCCAGGCATCAAATT
CACTGATGCAAATTGGCAAAAATTCAAGAATGGAGATACTTCCATCGAG
AAGATGGGGGCAGCACGAGTAAATGCCATGCTTGACTGCCTATTCGACG
ATTTTGAGCTTGCTTTGATTGGCAAGGCTCAACAAGAATACTATTCGGA
TAATTCCTTGAAATTGAACATGCCATTTTACGCTTACTATGACATGTTC
AAAAAGCAGCAACTTCTAAAATGGCTTAAAAATAACCGTGATGATGTCA
TCTGCGGAACTGGTAGGATGTACACAGCAAGTGGTAATTACATTGCTAA
CTCTTATTTAGAGGTAGCGTTAGAATCTAGCCGTCTGGGTAGTGGCTCT
TACATGCTTCAAATGAGATTCAAAGACTATTCAAGAAGTCAAGAACCTA
TTCCATCTGGTCGCCAAAATAGACTAGAATGGATTGAGAGCAACTTGGA
AAACATTCGATAA
```

SEQ ID NO: 40/anti-CRISPR protein encoded by
SEQ ID NO: 39
MKINNDIKELILEYVSRYFKFENDFYKLPGIKFTDANWQKFKNGDTSIE
KMGAARVNAMLDCLFDDFELALIGKAQQEYYSDNSLKLNMPFYAYYDMF
KKQQLLKWLKNNRDDVICGTGRMYTASGNYIANSYLEVALESSRLGSGS
YMLQMRFKDYSRSQEPIPSGRQNRLEWIESNLENIR SEQ ID NO: 41/anti-CRISPR gene isolated from
Bacteriophage D5891
```
ATGAAAATCAATAATGACATCAAAGAGCTAATTTTGGAATATGTAAGTC
GCTATTTTAAATTTGAAAACGACTTCTACAAATTGCCAGGCATCAAATT
CACTGATGCAAATTGGCAAAAATTCAAGAATGGAGATACTTCCATCGAG
AAGATGGGGGCAGCACGAGTAAATGCCATGCTTGACTGCCTATTCGACG
ATTTTGAGCTTGCTTTTATTGGCAAGGCTCAACAAGAATACTATTCGGA
TAATTCCTTGAAATTGAACATGCCATTTTACGCTTACTATGACATGTTC
AAAAAGCAGCAACTTCTAAAATGGCTTAAAAATAACCGTGATGATGTCA
TCTGCGGAACTGGTAGGATGTACACAGCAAGTGGTAATTACATTGCTAA
CTCTTATTTAGAGGTAGCGTTAGAATCTAGCCGTCTGGGTAGTGGCTCT
TACATGCTTCAAATGAGATTCAAAGACTATTCAAGAAGTCAAGAACCTA
TTCCATCTGGTCGCCAAAATAGACTAGAATGGATTGAGAGCAACTTGGA
AAACATTCGATAA
```

SEQ ID NO: 42/anti-CRISPR protein encoded by
SEQ ID NO: 41
MKINNDIKELILEYVSRYFKFENDFYKLPGIKFTDANWQKFKNGDTSIE
KMGAARVNAMLDCLFDDFELAFIGKAQQEYYSDNSLKLNMPFYAYYDMF
KKQQLLKWLKNNRDDVICGTGRMYTASGNYIANSYLEVALESSRLGSGS
YMLQMRFKDYSRSQEPIPSGRQNRLEWIESNLENIR SEQ ID NO: 43/anti-CRISPR gene isolated from
Bacteriophage ALQ13.2
```
ATGAAAATCAATAATGACATCAAAGAGCTAATTTTGGAATATGTAAGTC
GCTATTTTAAATTTGAAAACGACTTCTACAAATTGCCAGGCATCAAATT
CACTGATGCAAATTGGCAAAAATTCAAGAACGGAGATACTTCCATCGAG
AAGATGGGGGCAGCACGAGTAAATGCCATGCTTGACTGCCTATTCGACG
ATTTTGAGCTTGCTTTGATTGGCAAGGCTCAACAAGAATACTATTCGGA
TAATTCCTTGAAATTGAACATGCCATTTTACGCTTACTATGACATGTTA
AAAAGCAGCAACTTCTAAAATGGCTTAAAAATAACCGTGATGATGTCA
TCTGCGGAACTGGTAGGATGTACACAGCAAGTGGTAATTACATTGCTAA
CTCTTATTTAGAGGTAGCGTTAGAATCTAGCCGTCTGGGTAGTGGCTCT
TACATGCTTCAAATGAGATTCAAAGACTATTCAAGAAGTCAAGAACCTA
TTCCATCTGGTCGCCAAAATAGACTAGAATGGATTGAGAGCAACTTGGA
AAACATTCGATGA
```

SEQ ID NO: 44/anti-CRISPR protein encoded by
SEQ ID NO: 43
MKINNDIKELILEYVSRYFKFENDFYKLPGIKFTDANWQKFKNGDTSIE
KMGAARVNAMLDCLFDDFELALIGKAQQEYYSDNSLKLNMPFYAYYDML
KKQQLLKWLKNNRDDVICGTGRMYTASGNYIANSYLEVALESSRLGSGS
YMLQMRFKDYSRSQEPIPSGRQNRLEWIESNLENIR SEQ ID NO: 45/anti-CRISPR gene isolated from
Bacteriophage D802
```
ATGAAAATCAATAATGACATCAAAGAGCTAATTTTGGAATATGTAAGTC
GCTATTTTAAATTCGAGAACGACTTTTACAGATTGCCTGGCATCAAATT
CACTGATGCCAACTGGCAAAAATTCAAGAATGGAGGCACTGCCATTGAG
AAGATGGGAGCAGCACGAGTTAATGCCATGCTTTCCTGCCTATTCGAGG
ATTTTGAGCTTGCAATGATTGGCAAGGCTCAATATGAATACTATTCGGA
TAATTCCTTGAAATTGAACATGCCATTTTACGCTTACTATGACATGTTC
AAAAAGCAGCAACTTCTAAAATGGCTTAAAAATAACCGTGATGATGTCA
TCGGCGGAACTGGTAGAATGTACACGTCAAGCGGTAGTTACATTGCTAA
CGCTTATTTAGAAATTGCGTTAGAATCTAGCCGTCTGGGTAGTGGCTCT
TACATGCTTCAAATGAGATTCAAAGACTATTCAAGAAGTCAAGAACCTA
TTCCGTCTGGTCGCCAAAATAGACTTGAATGGATTGAGAGCAACTTGGA
AAACATTCGATAA
```

SEQ ID NO: 46/anti-CRISPR protein encoded by
SEQ ID NO: 45
MKINNDIKELILEYVSRYFKFENDFYRLPGIKFTDANWQKFKNGGTAIE

KMGAARVNAMLSCLFEDFELAMIGKAQYEYYSDNSLKLNMPFYAYYDMF

KKQQLLKWLKNNRDDVIGGTGRMYTSSGSYIANAYLEIALESSRLGSGS

YMLQMRFKDYSRSQEPIPSGRQNRLEWIESNLENIR

SEQ ID NO: 47/anti-CRISPR gene isolated from
Bacteriophage 73
ATGAAAATCAATAATGACATCAAAGAGCTAATTTTGGAATATGTAAGTC

GCTATTTTAAATTTGAAAACGACTTCTACAAATTACCTGGCATCAAATT

CACTGATGCCAACTGGCAAAAATTCAAGAATGGAGATACTTCCATCGAG

AAGATGGGGCAGCACGAGTAAATGCCATGCTTGACTGCCTATTCGAGG

ATTTTGAGCTTGCAATGATTGGCAAGGCTCAAACTAATTATTACATTGA

TAACTCACTTAAATTGAACATGCCATTTTACGCTTACTATGACATGTTC

AAAAAGCAGCAACTTCTAAAATGGCTTAAAAATAACCGTGATGATGTCA

TCGGCGGAACTGGTAGGATGTACACAGCAAGTGGTAATTACATTGCTAA

CGCTTATTTAGAGGTGGCATTAGAATCGAGCTCGCTTGGTAGTGGCTCT

TACATGCTTCAAATGAGGTTTAAAGACTATTCAAAAGGTCAAGAACCTA

TTCCGTCAGGTCGTCAGAATCGACTTGAATGGATTGAAAACAATCTCGA

AAACATTCGATAA

SEQ ID NO: 48/anti-CRISPR protein encoded by
SEQ ID NO: 47
MKINNDIKELILEYVSRYFKFENDFYKLPGIKFTDANWQKFKNGDTSIE

KMGAARVNAMLDCLFEDFELAMIGKAQTNYYIDNSLKLNMPFYAYYDMF

KKQQLLKWLKNNRDDVIGGTGRMYTASGNYIANAYLEVALESSSLGSGS

YMLQMRFKDYSKGQEPIPSGRQNRLEWIENNLENIR

SEQ ID NO: 49/anti-CRISPR gene isolated from
Bacteriophage DT1
ATGAAAATCAATAATGACATCAAAGAGCTAATTTTGGAATATGTAAGTC

GCTATTTTAAATTTGAAAACGACTTCTACAAATTACCTGGCATCAAATT

CACTGATGCCAACTGGCAAAAATTCAAGAATGGAGAAACTTCAATCGAA

AAAATGGGAGCAGCACGAGTTAATGCCATGCTTTCATGCCTATTCGAGG

ATTTTGAGCTTGCAATGATTGGCAAGGCTCAAACTAATTATTACATTGA

TAACTCACTTAAATTGAACATGCCATTTTACGCTTACTATGACATGTTC

AAAAAGCAACTTCTTATAAATTGGCTTAAAAATAACCGTGATGATGTCA

TCGGCGGAACTGGTAGGATGTACACAGCAAGTGGTAATTACATTGCTAA

CGCTTATTTAGAGGTGGCATTAGAATCAAGCTCGCTTGGTAGTGGCTCT

TACATGATCCAAATGAGGTTTAAAGACTATTCAAAAGGTCAAGAACCTA

TTCCGTCAGGTCGCAAAACCGACTTGAGTGGATTGAAAACAATCTGGA

AAATATTCGATAA

SEQ ID NO: 50/anti-CRISPR protein encoded by
SEQ ID NO: 49
MKINNDIKELILEYVSRYFKFENDFYKLPGIKFTDANWQKFKNGETSIE

KMGAARVNAMLSCLFEDFELAMIGKAQTNYYIDNSLKLNMPFYAYYDMF

KKQLLINWLKNNRDDVIGGTGRMYTASGNYIANAYLEVALESSSLGSGS

YMIQMRFKDYSKGQEPIPSGRKNRLEWIENNLENIR

SEQ ID NO: 51/anti-CRISPR gene isolated from
Bacteriophage D1427
ATGAAAATCAATAATGACATCAAAGAGCTAATTTTGGAATATGTAAGTC

GCTATTTTAAATTTGAAAACGACTTCTACAAATTACCTGGCATCAAATT

CACTGATGCCAACTGGCAAAAATTCAAGAATGGAGAAACTTCAATCGAA

AAAATGGGAGCAGCACGAGTTAATGCCATGCTTTCATGCCTATTCGAGG

ATTTTGAGCTTGCAATGATTGGCAAGGCTCAAACTAATTATTACATTGA

TAACTCACTTAAATTGAACATGCCATTTTACGCTTACTATGACATGTTC

AAAAAGCAACTTCTTATAAATTGGCTTAAAAATAACCGTGATGATGTCA

TCGGCGGAACTGGTAGGATGTACACAGCAAGTGGTAATTACATTGCTAA

CGCTTATTTAGAGGTGGCATTAGAATCAAGCTCGCTTGGTAGTGGCTCT

TACATGATCCAAATGAGGTTTAAAGACTATTCAAAAGGTCAAGAACCTA

TTCCGTCAGGTCGCCAAAATAGACTAGAATGGATTGAGAGCAACTTGGA

AAACATTCGATAA

SEQ ID NO: 52/anti-CRISPR protein encoded by
SEQ ID NO: 51
MKINNDIKELILEYVSRYFKFENDFYKLPGIKFTDANWQKFKNGETSIE

KMGAARVNAMLSCLFEDFELAMIGKAQTNYYIDNSLKLNMPFYAYYDMF

KKQLLINWLKNNRDDVIGGTGRMYTASGNYIANAYLEVALESSSLGSGS

YMIQMRFKDYSKGQEPIPSGRQNRLEWIESNLENIR

SEQ ID NO: 53/anti-CRISPR gene isolated from
Bacteriophage N1162
ATGAAAATCAATAATGACATCAAAGAGCTAATTTTGGAATATGTAAGTC

GCTATTTTAAATTTGAAAACGACTTCTACAAATTACCTGGCATCAAATT

CACTGATGCCAACTGGCAAAAATTCAAGAATGGAGATACTTCCATCGAG

AAGATGGGGCAGCACGAGTAAATGCCATGCTTGACTGCCTATTCGAGG

ATTTTGAGCTTGCAATGATTGGCAAGGCTCAAACTAATTATTACATTGA

TAACTCACTTAAATTGAACATGCCATTTTACGCTTACTATGACATGTTC

AAAAAGCAGCAACTTCTAAAATGGCTTAAAAATAACCGTGATGATGTCA

TCGGCGGAACTGGTAGGATGTACACATCAACCGGTAATTACATTGCTAA

CGCTTATTTAGAAATTGCGTTAGAATCTAGCCGTCTGGGTAGTGGCTCT

TACATGATCCAAATGAGGTTTAAAGACTATTCAAAAGGTCAAGAACCTA

TTCCGTCTGGTCGTCAGAATCGACTTGAATGGATTGAAAACAATCTGGA

AAATATTCGATAA

SEQ ID NO: 54/anti-CRISPR protein encoded by
SEQ ID NO: 53
MKINNDIKELILEYVSRYFKFENDFYKLPGIKFTDANWQKFKNGDTSIE

KMGAARVNAMLDCLFEDFELAMIGKAQTNYYIDNSLKLNMPFYAYYDMF

KKQQLLKWLKNNRDDVIGGTGRMYTSTGNYIANAYLEIALESSRLGSGS

YMIQMRFKDYSKGQEPIPSGRQNRLEWIENNLENIR

SEQ ID NO: 55/anti-CRISPR gene isolated from
Bacteriophage D1018
ATGAAAATCAATAATGATATCAAAGAGCTAATTTTGGAATATGTAAGTC

GCTATTTTAAATTTGAAAACGACTTCTACAAATTGCCAGACATCAAGTT

CACAGATGCTAATTGGCAAAAATTTAAGAATGGAGAAACTTCAATCGAA

```
AAAATGGGAGCAGCACGAGTAAATGCCATGCTTGACTGCCTATTCGAGG

ATTTTGAGCTTGCAATGATTGGCAAGGCTCAAACTAATTATTACATTGA

TAACTCACTTAAATTGAACATGCCATTTTACGCTTACTATGACATGTTC

AAAAAGCAGCAACTTCTAAAATGGCTTAAAAATAACCGTGATGATGTCA

TCGGCGGAACTGGTAGGATGTACACATCAACCGGTAATTACATTGCTAA

CGCTTATTTAGAAATTGCGTTAGAATCTAGCCGTCTGGGTAGTGGCTCT

TACATGATCCAAATGAGGTTTAAAGACTATTCAAAAGGTCAAGAACCTA

TTCCGTCTGGTCGTCAGAATCGACTTGAATGGATTGAAAACAATCTGGA

AAATATTCGATAA

SEQ ID NO: 56/anti-CRISPR protein encoded by
SEQ ID NO: 55
MKINNDIKELILEYVSRYFKFENDFYKLPDIKFTDANWQKFKNGETSIE

KMGAARVNAMLDCLFEDFELAMIGKAQTNYYIDNSLKLNMPFYAYYDMF

KKQQLLKWLKNNRDDVIGGTGRMYTSTGNYIANAYLEIALESSRLGSGS

YMIQMRFKDYSKGQEPIPSGRQNRLEWIENNLENIR

SEQ ID NO: 57/anti-CRISPR gene isolated from
Bacteriophage D3577
ATGAAAATAAACAACGATATCAAAGAGCTAATTTTGGAATACGCTAAAC

GTTATTTCAAGTTTGAAAACGACTTCTACAAACTGCCAGACATCAAATT

CACTGATGCCAACTGGCAAAAATTTAAGAATGGAGAAACTTCCATCGAA

AAAATGGGAGCAGCACGAGTTAATGCCATGCTTTCCTGCCTGTTCGACG

ATTTTGAGCTTGCTATGATTGGCAAGGCTCAAACTAATTATTACAATGA

TAACTCACTTAAATTGAACATGCCATTTTACGCTTACTATGACATGTTC

AAAAAGCAGCAACTTCTAAAATGGCTTAAAAATAACCGTGATGATATCA

TCTGCGAACTGGTAGAATGTACACTTCAAGAGGTAGTTACATTGCTAA

CGCTTATTTAGAGGTAGCGTTAGAATCAAGCTTGCTTGGTAGTGGCTCT

TACATGCTTCAAATGAGGTTCAAAGACTATTCAAAAAGTCAAGAACCTA

TTCCATCTGGTCGTCAGAATCGACTTGAATGGATTGAGAGCAACTTGGA

AAATATTCGATAA

SEQ ID NO: 58/anti-CRISPR protein encoded by
SEQ ID NO: 57
MKINNDIKELILEYAKRYFKFENDFYKLPDIKFTDANWQKFKNGETSIE

KMGAARVNAMLSCLFDDFELAMIGKAQTNYYNDNSLKLNMPFYAYYDMF

KKQQLLKWLKNNRDDIICGTGRMYTSRGSYIANAYLEVALESSLLGSGS

YMLQMRFKDYSKSQEPIPSGRQNRLEWIESNLENIR

SEQ ID NO: 59/anti-CRISPR gene isolated from
Bacteriophage CHPC577
ATGAAAATAAACAACGATATCAAAGAGCTAATTTTGGAATATGGAAGTC

GCTATTTTAAATTTGAAAACGACTTCTACAAACTGCCTGGCATCAAGTT

CACTGATGCTAATTGGCAAAAATTCAAAAATGGTGATACTTTAATCGAA

AAAATGGGGGCAGCACGAGTAAATGCCATGCTTGACTGCCTGTTCGACG

ATTTTGAGCTTGCTATGATTGGCAAGGCTCAAACTAATTATTACAATGA

TAATTCCTTGAAATTGAACATGCCATTTTACGCTTACTATGACATGTTC

AAAAAGCAACAGCTTATACATTGGCTCAAAAACAACCGTGATGACATCG

TAGGCGGAACTGGTAGACTGTACACTTCAAGCGGTAGTTACATTGCTAA

CGCTTATTTAGAAATTGCATTAGAATCGAGCTCGCTTGGTAGTGGCTCT

TACATGCTTCAAATGAGATTCAAAAACTATTCAAAAAGTCAAGAACCTA

TTCCATCTGGTCGCCAGAATCGACTTGAATGGATTGAAAACAATCTTGA

GAATATTCGATAA

SEQ ID NO: 60/anti-CRISPR protein encoded by
SEQ ID NO: 59
MKINNDIKELILEYGSRYFKFENDFYKLPGIKFTDANWQKFKNGDTLIE

KMGAARVNAMLDCLFDDFELAMIGKAQTNYYNDNSLKLNMPFYAYYDNI

FKKQQLIHWLKNNRDDIVGGTGRLYTSSGSYIANAYLEIALESSSLGSG

SYMLQMRFKNYSKSQEPIPSGRQNRLEWIENNLENIR

SEQ ID NO: 61/anti-CRISPR gene isolated from
Bacteriophage D4237
ATGAAAATAAATAACGACATCAAAGAATTAATTTTAGAATATATGAGCC

GTTACTTCAAATTCGAAAACGACTTCTACAAATTGCCAGACATCAAGTT

CACAGATGCTAATTGGCAAAAATTTAAGAATGGAGAAACTTCAATCGAA

AAAATGGGAGCAGCACGAGTTAATGCCATGCTCAACTGCCTATTCGAAG

ATTTTGAGCTTGCTATGATTGGCAAGGCTCAAATTAATTATTACAATGA

TAACTCACTTAAAATGAACATGCCATTTTACGCTTACTATGATATGTTC

AAAAAACAACAGCTTCTAAAATGGCTTAAAGATCACCATGATGACATCA

TCGGAGGAGCTGGCAGAATGTACACATCAACCGGTAGTTACATTGCTAA

TGCTTATTTAGAGGTAGCGTTAGAATCAAGCTCGCTTGGTGATGGTGAG

TACATGTTGCAAATGCGTTTTAAAAATTATTCACGAAGTCAAGAACCTA

TTCCGTCAGGTCGCAAAAACCGACTTGAGTGGATTGAAAACAATCTGGA

AAATATTCGATAA

SEQ ID NO: 62/anti-CRISPR protein encoded by
SEQ ID NO: 61
MKINNDIKELILEYMSRYFKFENDFYKLPDIKFTDANWQKFKNGETSIE

KMGAARVNAMLNCLFEDFELAMIGKAQINYYNDNSLKMNMPFYAYYDMF

KKQQLLKWLKDHHDDIIGGAGRMYTSTGSYIANAYLEVALESSSLGDGE

YMLQMRFKNYSRSQEPIPSGRKNRLEWIENNLENIR

SEQ ID NO: 63/anti-CRISPR gene isolated from
Bacteriophage 9874
ATGAAAATAAATGACGACATCAAAGAATTAATTTTAGAATATATGAGCC

GTTACTTCAAATTCGAGAACGACTTCTACAAATTGCCTGACATCAAATT

CACTGATGCCAACTGGCAAAAATTCAAAAATGGAGATACTTCCATCGAG

AAGATGGGGGCAGCACGAGTAAATGCCATGCTTGACTGCCTATTCGAAG

ATTTCGAACTTGCCATGATTGGCAAGGCTCAACAAGAATACTATTTGGA

TAATTCACTAAAGATGAACATGCCATTTTACGCTTATTATGATATGTTC

AAGAAAAAACAGCTCGTCAAATGGCTTAAAGATCACCATGATGACATCC

TAGGCGGAACTGGTAGGATGTACACTTCAGACGGTAGTTACATTGCTAA

CTCTTATTTAGAGGTAGCGTTAGAATCTAGCCGTCTGGGTAGTGGCTCT

TACATGCTTCAAATGAGATTCAAAGACTATTCAAGAAGTCAAGAACCCA

TTCCGTCAGGTCGCAAAAACCGACTTGAGTGGATTGAAAACAATCTGGA

AAATATTCGATAA
```

SEQ ID NO: 64/anti-CRISPR protein encoded by
SEQ ID NO: 63
MKINDDIKELILEYMSRYFKFENDFYKLPDIKFTDANWQKFKNGDTSIE

KMGAARVNAMLDCLFEDFELAMIGKAQQEYYLDNSLKMNMPFYAYYDMF

KKKQLVKWLKDHHDDILGGTGRMYTSDGSYIANSYLEVALESSRLGSGS

YMLQMRFKDYSRSQEPIPSGRKNRLEWIENNLENIR

SEQ ID NO: 65/anti-CRISPR gene isolated from
Bacteriophage 5093
ATGGAAATCAACAACGATATCAAAGAGTTAATTTTGGAATACGTGAAAA

GATACTTCAAGTTCGAGAACGACTTCTACAAATTGCCTGACATCAAATT

CACTGATGCCAACTGGCAGAAGTTCAAAAATGGCGAAACAGCCATTGAG

AAGATGGGGGCAGCACGAGTAAACGCAATGCTCGACTGCCTATTCGAAG

ATTTTGAGCTTGCCATGATTGGCAAGGCTCAAACTAATTATTATATTGA

TAACTCGCTTAAATTAAACATGCCATTTTATGCTTACTATGATATGTTT

AAGAAACAACAGCTCGTCAAATGGCTTGAAACTAGTCGTGAAGACATCA

TCGGAGGGGCTGGCAGAATGTACACTTCAGACGGTAGTTACATTGCTAA

CGCTTATTTAGAAGTAGCGTTAGAATCAAGCTCGCTTGGTGATAGTGAA

TACATGTTGCAAATGCGTTTTAAAAATTATTCAAAAAGTCAAGAACCTA

TTCCGTCTGGTCGTCAAAATAGACTGGAATGGATTGAAAACAATCTTAA

AAACATTCGATAA

SEQ ID NO: 66/anti-CRISPR protein encoded by
SEQ ID NO: 65
MEINNDIKELILEYVKRYFKFENDFYKLPDIKFTDANWQKFKNGETAIE

KMGAARVNAMLDCLFEDFELAMIGKAQTNYYIDNSLKLNMPFYAYYDMF

KKQQLVKWLETSREDIIGGAGRMYTSDGSYIANAYLEVALESSSLGDSE

YMLQMRFKNYSKSQEPIPSGRQNRLEWIENNLKNIR

SEQ ID NO: 67/anti-CRISPR gene isolated from
Bacteriophage D4154
ATGCTAATAAATAACGACATCAAAGAGTTGATTTTGGAATACGTCAAAC

GCTATTTTAAATATGAAAATGACTTCTACAGATTGCCGGGCATCAAGTT

TACCGATGCAAATTGGCAGAAGTTTAAAAATGGCGACACTTCCATCGAG

AAGATGGGGGCAGCACGAGTAAACGCCATGCTCGACTGCCTATTCGAAG

ATTTTGAGCTTGCCATGATTGGTAAGGCTCAAACCAATTATTATATCAA

TAATTCATTGAAAATGAATATGCCGTTTTACGCTTACTATGATATGTTC

AAGAAGGAACAGCTTATGAAATGGCTTGAAACCAGCCGTGAAGACATCA

TAGGCGGAACTGGCAGGATGTACACTTCAGACGGTAGTTACATTGCTAA

CGCTTATTTGGAAATTGCATTAGAATCGAGCTCGCTTGGTAGTGGCTCT

TACATGCTTCAAATGCGTTTTAAAGATTATTCAAAAGGTCAAGAGCCTA

TCCCGTCTGGTCGTCAAAACCGACTTGAGTGGATTGAAAACAATCTTGA

AAACATTCGATAA

SEQ ID NO: 68/anti-CRISPR protein encoded by
SEQ ID NO: 67
MLINNDIKELILEYVKRYFKYENDFYRLPGIKFTDANWQKFKNGDTSIE

KMGAARVNAMLDCLFEDFELAMIGKAQTNYYINNSLKMNMPFYAYYDMF

KKEQLMKWLETSREDIIGGTGRMYTSDGSYIANAYLEIALESSSLGSGS

YMLQMRFKDYSKGQEPIPSGRQNRLEWIENNLENIR

SEQ ID NO: 69/anti-CRISPR gene isolated from the
genome of Streptococcus thermophilus DGCC11758
ATGCTAATAAATAACGACATCAAAGAGTTGATTTTGGAATACGTCAAAC

GCTATTTTAAATTTGAAAATGACTTCTACAGATTGCCGGGCATCAAGTT

TACCGATGCAAATTGGCAGAAGTTTAAAAATGGCGACACTGCCATTGAG

AAGATGGGGCATCACGAGTAAACTCTATGCTTGACTGCCTGTTCGAAG

ATTTTGAGCTTGCTATGATTGGCAAGGCTCAAGATGAATACTATTTGGA

TAATTCACTAAAGATGAACATGCCATTTTACGCTTATTATGATATGTTC

AAGAAAAAACAGCTCGTCAAATGGCTTAAAGATCACCATGATGACATCC

TAGGCGGAACTGGTAGGATGTATACTTCAAGCGGCAATTACATTGCTAA

CGCTTATTTAGAGGTAGCGTTAGAATCAAGCTCGCTTGGTAGTGGCTCT

TACATGATTCAAATGCGTTTTAAAAATTATTCAAAAGGTCAAGAGCCTA

TCCCGTCTGGTCGTCAAAACCGACTTGAGTGGATTGAAAAAAACTTGGA

GAACATTCGATAA

SEQ ID NO: 70/anti-CRISPR protein encoded by
SEQ ID NO: 69
MLINNDIKELILEYVKRYFKFENDFYRLPGIKFTDANWQKFKNGDTAIE

KMGASRVNSMLDCLFEDFELAMIGKAQDEYYLDNSLKMNMPFYAYYDMF

KKKQLVKWLKDHHDDILGGTGRMYTSSGNYIANAYLEVALESSSLGSGS

YMIQMRFKNYSKGQEPIPSGRQNRLEWIEKNLENIR

SEQ ID NO: 71/anti-CRISPR gene isolated from the
genome of Streptococcus thermophilus DSM 20617
ATGGAAATCAACAACGATATTAAACAACTGATCTTGGAATACGCTAAAC

GTTATTTCAAGTTTGAGAACGACTTTTATAAACTGCCAGGCATCAAGTT

CACTGATGCAAATTGGCAGAAGTTCAAAAATGGAGGCACTGCCATTGAG

AAGATGGGGGCAGCACGAGTAAACGCCATGCTCGACTGCCTATTCGAAG

ATTTCGAGCTTGCAATGATTGGCAAGGCTCAACAAGAATACTATTCGGA

TAATTCCTTGAAAGTAAATATGGCATTCTATGCTTATTACGATCAATTC

AAAAAACAACAGCTTATGAAATGGCTTAAAGATAATCACGATGACATCA

TAGGAGGGACTGGTAGAATGTACACGTCAAGCGGTAGTTACATTGCTAA

CGCTTATTTAGAAATTGCGTTAGAATCTAGCCGTCTGGGTGGTGGTTCT

TACATGATCCAAATGAGGTTTAAAGACTATTCAAAAGGTCAAGAACCTA

TTCCGTCTGGTCGTCAGAATCGACTTAATGGATTGAGAGCAACTTGGA

AAACATTCGATAA

SEQ ID NO: 72/anti-CRISPR protein encoded by
SEQ ID NO: 71
MEINNDIKQLILEYAKRYFKFENDFYKLPGIKFTDANWQKFKNGGTAIE

KMGAARVNAMLDCLFEDFELAMIGKAQQEYYSDNSLKVNMAFYAYYDQF

KKQQLMKWLKDNHDDIIGGTGRMYTSSGSYIANAYLEIALESSRLGGGS

YMIQMRFKDYSKGQEPIPSGRQNRLEWIESNLENIR

SEQ ID NO: 73/anti-CRISPR gene isolated from
Bacteriophage Sfi19
ATGGAAATCAACAACGACATTAAACAACTGATCTTGGAATACGTGGGAC

GCTATTTTAAATTTGAAAATGACTTCTACACAAATTGCCCGGCATCAAATT

CACTGATGCCAATTGGCAGAAGTTCAAAAATGGCGATACTTCCATCGAA

```
AAGATGGGAGCAGCACGAGTAAACGCAATGCTTGACTGCCTGTTCGAAG

ATTTCGAACTTGCCATGATTGGCAAGGCTCAAACTAATTATTATATTGA

TAATTCCCTTAAATTAAACATGCCATTTTACGCTTATTATGATATGTTC

AAGAAGGAACAGCTTATGAAATGGCTTAAAGATCACCATGATGACATCA

TAGGCGGAACTGGTAGGATGTACATTTCAAGCGGTAGCTACATTGCTAA

CGCTTATTTGGAAATTGCACTAGAATCAAGTACGCTTGGTGGTGGTGAG

TACATGTTGCAAATGCGCTTTAAAAATTATTCACGAAGCCAAGAACCTA

TTCCATCAGGTCGCAAAAATAGACTTGATGGATTGAAAACAATCTTGA

AAACATTCGATAA
```

SEQ ID NO: 74/anti-CRISPR protein encoded by
SEQ ID NO: 73
MEINNDIKQLILEYVGRYFKFENDFYKLPGIKFTDANWQKFKNGDTSIE

KMGAARVNAMLDCLFEDFELAMIGKAQTNYYIDNSLKLNMPFYAYYDMF

KKEQLMKWLKDHHDDIIGGTGRMYISSGSYIANAYLEIALESSTLGGGE

YMLQMRFKNYSRSQEPIPSGRKNRLEWIENNLENIR

SEQ ID NO: 75/anti-CRISPR gene isolated from
Bacteriophage Sfi11
```
ATGGAAATCAACAACGACATTAAACAACTGATCTTGGAATACGTGGGAC

GCTATTTTAAATTTGAAATGACTTCTACAAATTGCCCGGCATCAAATT

CACTGATGCCAATTGGCAGAAGTTCAAAAATGGCGATACTTCCATCGAA

AAGATGGGAGCAGCACGAGTAAACGCAATGCTTGACTGCCTGTTCGAAG

ATTTCGAACTTGCCATGATTGGCAAGGCTCAAACTAATTATTATATTGA

TAATTCCCTTAAATTAAACATGCCATTTTACGCTTATTATGATATGTTC

AAGAAGGAACAGCTTATGAAATGGCTTAAAGATCACCATGATGACATCA

TAGGCGGAACTGGTAGGATGTACACTTCAAGCGGTAGCTACATTGCTAA

CGCTTATTTGGAAATTGCACTAGAATCAAGTACGCTTGGTGGTGGTGAG

TACATGTTGCAAATGCGCTTTAAAAATTATTCACGAAGCCAAGAACCTA

TTCCATCAGGTCGCAAAAATAGACTTGATGGATTGAAAACAATCTTGA

AAACATTCGATAA
```

SEQ ID NO: 76/anti-CRISPR protein encoded by
SEQ ID NO: 75
MEINNDIKQLILEYVGRYFKFENDFYKLPGIKFTDANWQKFKNGDTSIE

KMGAARVNAMLDCLFEDFELAMIGKAQTNYYIDNSLKLNMPFYAYYDMF

KKEQLMKWLKDHHDDIIGGTGRMYTSSGSYIANAYLEIALESSTLGGGE

YMLQMRFKNYSRSQEPIPSGRKNRLEWIENNLENIR

SEQ ID NO: 77/anti-CRISPR gene isolated from the
genome of Streptococcus thermophilus M17PTZA496
```
ATGGAAATCAACAAAGACATCAAAGAGTTGATTTGGAATACGTCAAAC

GCTATTTTAAATTTGAAAATGATTTCTACAGATTGCCGGGCATCAAGTT

TACCGATGCCAACTGGCAAAAATTCAAGAATGGAGATACTTCCATCGAG

AAGATGGGGGCAGCACGAGTAAACGCCATGCTTGACTGCCTGTTCGAAG

ATTTCGAACTTGCTATGATTGGCAAGGCTCAAGATGAATACTATTTGGA

TAATTCACTTAAGTTTAATATGGCATTCCATACTTATTACGATCAATTT

AAAAAACAACAGCTTATGAAATGGCTTGAAACTAGCCTCGAAGACATCA

TAGGCGGAACTGGTAGGATGTACACTTCAAGCGGTAGTTACATTGCTAA
```

```
CGCTTATTTGGAAATTGCACTAGAATCAAGCTCGCTTGGTGGTGGTGAG

TACATGTTGCAAATGCGTTTTAAAAATTATTCACGAAGCCAAGAACCTA

TTCCGTCAGGTCGCAAAAACCGACTTGAGTGGATTGAAAACAATCTGGA

AAATATCCGATAA
```

SEQ ID NO: 78/anti-CRISPR protein encoded by
SEQ ID NO: 77
MEINKDIKELILEYVKRYFKFENDFYRLPGIKFTDANWQKFKNGDTSIE

KMGAARVNAMLDCLFEDFELAMIGKAQDEYYLDNSLKFNMAFHTYYDQF

KKQQLMKWLETSLEDIIGGTGRMYTSSGSYIANAYLEIALESSSLGGGE

YMLQMRFKNYSRSQEPIPSGRKNRLEWIENNLENIR

SEQ ID NO: 79/anti-CRISPR gene isolated from
Bacteriophage D4769
```
ATGAAAATCAATAATGACATCAAAGAGCTAATTTTGGAATATGTAAGTC

GCTATTTTAAATTTGAAAACGACTTCTACAAATTACCTGGCATCAAATT

CACTGATGCCAACTGGCAAAAATTCAAGAATGGAGATACTTCCATCGAG

AAGATGGGGGCAGCACGAGTAAACGCCATGCTTGACTGCCTGTTCGAAG

ATTTCGAACTTGCTATGATTGGCAAGGCTCAAGATGAATACTATTTGGA

TAATTCACTTAAGTTTAATATGGCATTCCATACTTATTACGATCAATTT

AAAAAACAACAGCTTATGAAATGGCTTGAAACTAGCCTCGAAGACATCA

TAGGCGGAACTGGTAGGATGTACACTTCAAGCGGTAGTTACATTGCTAA

CGCTTATTTGGAAATTGCACTAGAATCAAGCTCGCTTGGTGGTGGTGAG

TACATGTTGCAAATGCGTTTTAAAAATTATTCACGAAGCCAAGAACCTA

TTCCGTCAGGTCGCAAAAACCGACTTGAGTGGATTGAAAACAATCTGGA

AAATATCCGATAA
```

SEQ ID NO: 80/anti-CRISPR protein encoded by
SEQ ID NO: 79
MKINNDIKELILEYVSRYFKFENDFYKLPGIKFTDANWQKFKNGDTSIE

KMGAARVNAMLDCLFEDFELAMIGKAQDEYYLDNSLKFNMAFHTYYDQF

KKQQLMKWLETSLEDIIGGTGRMYTSSGSYIANAYLEIALESSSLGGGE

YMLQMRFKNYSRSQEPIPSGRKNRLEWIENNLENIR

SEQ ID NO: 81/anti-CRISPR gene isolated from
Bacteriophage D5691
```
ATGATTATAAATATTGATATCAAGGAATTGATTTTAGAGTATATGAGTA

GATACTTCAAATTTGAAAATGATTTCTACAAACTCCCCGGCATCAAATT

CACTGATGCCAATTGGCAAAAATTTAAGAATGGTGACACTTCCATCGAA

AAGATGGGAGCGGCTCGAGTAAATGCCATGCTCGACTGTCTATTCGATG

ACTTTGAACTTGCTATGATTGGCAAGGCTCAAATTAATTATTACATAGA

CAATTCCCTTAAATTGAACATGCCATTCTATGCTTATTATGACATGTTC

AAAAAACAACAACTGATCAAATGGATTGAAACCAGCCGTGATGATGTCA

TCGGAGGAACTGGCAGGATGTATACAGCAAGCGGAAGCTACATAGCTAA

CGCTTATCTAGAAATAGCACTAGAATCTAGCTCTCTGGGTGGTGGCTCT

TATATGCTTCAAATGAGATTCAAAAACTACTCACGAAGCCAAGAGCCAA

TACCATCTGGTCGGAAAAACCGACTTGAGTGGATTGAGAGCAACTTGGA

AAACATTAGATAA
```

-continued

SEQ ID NO: 82/anti-CRISPR protein encoded by
SEQ ID NO: 81
MIINIDIKELILEYMSRYFKFENDFYKLPGIKFTDANWQKFKNGDTSIE

KMGAARVNAMLDCLFDDFELAMIGKAQINYYIDNSLKLNMPFYAYYDMF

KKQQLIKWIETSRDDVIGGTGRMYTASGSYIANAYLEIALESSSLGGGS

YMLQMRFKNYSRSQEPIPSGRKNRLEWIESNLENIR

SEQ ID NO: 83/anti-CRISPR gene isolated from the
genome of Streptococcus sp. HMSC10E12
ATGGAAATCAACAATGACATCAAAGAGTTAATCTTGGAATACGTGGGAC

GCTATTTCAAGTTTGAAAATGATTTTTACAAATTGCCGGGCATCAAATT

TACCGATGCAAATTGGCAAAAATTCAAAAACGGTGATACATCCATCGAG

AAAATGGGGGCGGCACGAGTAAACGCAATGCTCGACTGCCTATTCGATG

ATTTCGAGCTTGCTATGATTGGCAAGGCTCAAACTGATTATTACATTGA

TAACTCACTTAAATTGAACATGCCATTTTATGCTTATTATGACATGTTC

AAAAAACAACAGCTTCTAAAATGGATTGAGAATAGTCGTGAAGACATCA

TCGGAGGGGCTGGCAGAATGTACACAGCGGGCGGTAATTGGATTTCTAG

CGCTTATTTAGAGATCGCATTAGAATCTAGTTCCATCGGTGGCGGTGGC

TATATGCTTCAAATGCGGTTCAAAAACTACTCAAGAGACCCTAGACCGA

TTCCAGCAGGCCACCAAAATCGTCTCGAATGGATTGAAAACAACTTGGA

GAATATCCGATAA

SEQ ID NO: 84/anti-CRISPR protein encoded by
SEQ ID NO: 83
MEINNDIKELILEYVGRYFKFENDFYKLPGIKFTDANWQKFKNGDTSIE

KMGAARVNAMLDCLFDDFELAMIGKAQTDYYIDNSLKLNMPFYAYYDMF

KKQQLLKWIENSREDIIGGAGRMYTAGGNWISSAYLEIALESSSIGGGG

YMLQMRFKNYSRDPRPIPAGHQNRLEWIENNLENIR

SEQ ID NO: 85/anti-CRISPR gene isolated from the
genome of Streptococcus sp. HSISS2
ATGGAAATCAACAATGACATCAAGGACCTAATTTTAGAATACGTAGGAC

GATATTTTCGATTTGAAAACGACTTCTACAAACTTCCCAGAATCAAGTT

TACCGATTCCAATTGGCAAAAATTCAAGAACGGTGACACTTCCATCGAA

AAAATGGGAGCTGGCAGAGTGAACGCAATGCTCGATTGTCTATTTGATG

ATTTTGAGCTTGCTATGATTGGTAAGGCTCAAACCGATTACTACATGGA

CAATTCTTTAAAGATGAATATGCCATTTTATGCCTATTATGACCAATTT

AAGAAACAGCAACTATTGAAATGGATCGAGAATAGTAGAGAGGATATCA

TAGGCGGTGCTGGCAGAATGTACACAGCTAGTGGGAATTGGATTTCTAG

TGCCTATTTAGAAATTGCATTGGAATCCAGCTCGTTAGGTGGTGGTGAG

TACATGTTGCAAATGCGTTTCAAAGACTACTCACGAAGCCAAGAGCCGA

TACCAGCAGGCCGCCAGAATCGACTTGAGTGGATTGAGAATAATTTGGA

GAATATTCGATAA

SEQ ID NO: 86/anti-CRISPR protein encoded by
SEQ ID NO: 85
MEINNDIKDLILEYVGRYFRFENDFYKLPRIKFTDSNWQKFKNGDTSIE

KMGAGRVNAMLDCLFDDFELAMIGKAQTDYYMDNSLKMNMPFYAYYDQF

KKQQLLKWIENSREDIIGGAGRMYTASGNWISSAYLEIALESSSLGGGE

YMLQMRFKDYSRSQEPIPAGRQNRLEWIENNLENIR

DETAILED DESCRIPTION

Compositions and methods are provided for novel anti-CRISPR ("ACR") polynucleotides and polypeptides as well as methods of use of such polynucleotides and polypeptides. The abbreviation "ACR" as used herein may be used as an alternative notation for "ACR polypeptide", "ACR protein", or "ACR polynucleotide", consistent with context. The disclosed methods include methods for inhibiting the activity of CRISPR-Cas complexes from modifying target DNA molecules. Accordingly, the disclosed compositions and methods find a wide range of uses in genome editing applications, particularly in plants.

The CRISPR-Cas system bases its utility as a genome-editing tool on its native function as an immune system in prokaryotes. The very first demonstration of its activity against bacterial viruses (phages) was also the first record of phages evading that immunity. This evasion can be due to point mutations, DNA modifications, or specific phage-encoded proteins that interfere with the CRISPR-Cas system, known as anti-CRISPRs (ACRs). The latter category is of considerable biotechnological interest, as these ACRs can serve as off-switches for CRISPR-based genome-editing. Every ACR characterized to date has originated from temperate phages, genomic islands, or prophages—and they have all been identified due to properties shared with the first ACR discovered, such as an association with helix-turn-helix motifs. Here, with a phage-oriented approach, we provide entirely novel ACRs in a virulent phage of *Streptococcus thermophilus*. In challenging an *S. thermophilus* strain CRISPR-immunized against a set of related virulent phages, we found one phage that evaded the CRISPR-Cas system at greater than 40000 times the rate of the others. We then identified an ACR solely responsible for the abolished immunity. We extended our findings by demonstrating anti-CRISPR activity in another *S. thermophilus* strain, against unrelated phages, and in another bacterial genus immunized using the heterologous *Streptococcus pyogenes* Cas9 (SpCas9) system commonly used in genome-editing. This ACR has the largest effect on SpCas9 activity demonstrated to date. Our phage-oriented approach is likely to serve to uncover many more ACRs. We also identified a second ACR also having anti-CRISPR activity against the *S. thermophilus* strain.

Disclosed herein are methods of identifying an ACR, methods of using an ACR to modulate the activity of a Cas endonuclease, particularly in a cell, particularly in a plant cell, and exemplary but not limiting compositions of ACR polypeptides, and polynucleotides encoding the same.

Definitions

Terms used in the claims and specification are defined as set forth below unless otherwise specified. It must be noted that, as used in the specification and the appended claims, the singular forms "a," "an" and "the" include plural referents unless the context clearly dictates otherwise.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA and/or RNA-DNA that is single- or double-stranded, optionally comprising synthetic, non-naturally occurring, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

"Open reading frame" is abbreviated ORF.

The term "selectively hybridizes" or "selective hybridization" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a polynucleotide/probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the polynucleotide/probe (homologous probing). Alternatively, stringency conditions can be adjusted to allow some mismatching in sequences so that lower degrees of similarity are detected (heterologous probing). Generally, a polynucleotide/probe is fewer than about 1000 nucleotides in length, fewer than 500 nucleotides, fewer than 100 nucleotides, fewer than 90 nucleotides, fewer than 80 nucleotides, fewer than 70 nucleotides, fewer than 60 nucleotides, fewer than 50 nucleotides, fewer than 40 nucleotides, fewer than 30 nucleotides, fewer than 20 nucleotides, 10 nucleotides, or even fewer than 10 nucleotides. Typically, stringent conditions will be those in which the salt concentration is less than about 1.5 M Na ion, typically about 0.01 to 1.0 M Na ion concentration (or other salt(s)) at pH 7.0 to 8.3, and at least 30° C. for short polynucleotides/probes (e.g., 10 to 50 nucleotides) and at least 60° C. for long polynucleotides/probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient similarity to undergo homologous recombination with the corresponding genomic region. "Sufficient similarity" indicates that two polynucleotide sequences have sufficient structural equivalency to act as substrates for a homologous recombination reaction. The structural equivalency includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

As used herein, a "genomic region" is a segment of a chromosome in the genome of a cell that is present on either side of a target site or, alternatively, also comprises a portion of a target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient similarity to undergo homologous recombination with the corresponding region of homology.

As used herein, "homologous recombination" (HR) includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) *Proc. Natl. Acad. Sci. USA* 82:4768-72, Sugawara and Haber, (1992) *Mol Cell Biol* 12:563-75, Rubnitz and Subramani, (1984) *Mol Cell Biol* 4:2253-8; Ayares et al., (1986) *Proc. Natl. Acad. Sci. USA* 83:5199-203; Liskay et al., (1987) *Genetics* 115:161-7.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, 95%, 96%, 97%, 98%, 99%, 100%, or any incremental or fractional percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program. Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases. "BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence. It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90%, 95%, 96%, 97%, 98%, 99%, 100%, or any incremental or fractional percentage from 50% to 100%. Indeed, any amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid sequences wherein changes in one or more amino acids or nucleotide bases do not affect the function of the molecule, such as the ability to mediate gene expression or to produce a certain phenotype. These terms also refer to modification(s) of nucleic acid sequences that do not substantially alter the functional properties of the resulting nucleic acid relative to the initial, unmodified nucleic acid. These modifications include deletion, substitution, and/or insertion of one or more nucleotides in the nucleic acid fragment, the association of an atom or a molecule to an existing nucleotide in a polynucleotide (for example but not limited to: a covalent addition of a methyl group, or an ionic interaction with a metal ion), the chemical alteration of at least one nucleotide, or any combination of the preceding. Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

A "centimorgan" (cM) or "map unit" is the distance between two polynucleotide sequences, linked genes, markers, target sites, loci, or any pair thereof, wherein 1% of the products of meiosis are recombinant. Thus, a centimorgan is equivalent to a distance equal to a 1% average recombination frequency between the two linked genes, markers, target sites, loci, or any pair thereof.

An "isolated" or "purified" nucleic acid molecule, polynucleotide, polypeptide, or protein, or biologically active portion thereof, is substantially or essentially free from components that normally accompany or interact with the polynucleotide or protein as found in its naturally occurring environment. Thus, an isolated or purified polynucleotide or polypeptide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. Isolated polynucleotides may be purified from a cell in which they naturally occur. Conventional nucleic acid purification methods known to skilled artisans may be used to obtain isolated polynucleotides. The term also embraces recombinant polynucleotides and chemically synthesized polynucleotides.

The term "fragment" refers to a contiguous set of polynucleotides or polypeptides. In one embodiment, a fragment is 2, 3, 4, 5, 6, 7 8, 9, 10, 11, 12, 13, 14, 15, 16, 17, 18, 19, 20, or greater than 20 contiguous polynucleotides. In one embodiment, a fragment is 2, 3, 4, 5, 6, 7 8, 9, 10, 11, 12, 13, 14, 15, 16, 17, 18, 19, 20, or greater than 20 contiguous polypeptides. A fragment may or may not exhibit the function of a sequence sharing some percent identity over the length of said fragment.

The terms "fragment that is functionally equivalent" and "functionally equivalent fragment" are used interchangeably herein. These terms refer to a portion or subsequence of an isolated nucleic acid fragment or polypeptide that displays the same activity or function as the longer sequence from which it derives. In one example, the fragment retains the ability to alter gene expression or produce a certain phenotype whether or not the fragment encodes an active protein. For example, the fragment can be used in the design of genes to produce the desired phenotype in a modified plant. Genes can be designed for use in suppression by linking a nucleic acid fragment, whether or not it encodes an active enzyme, in the sense or antisense orientation relative to a promoter sequence.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of a polypeptide disclosed herein. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis, and which may encode a polypeptide. Generally, variants of a particular polynucleotide disclosed herein will have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to that particular polynucleotide (e.g., to the ACR sequences of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374) as determined by sequence alignment programs and parameters described elsewhere herein or known in the art.

"Variant" protein is intended to mean a protein derived from the native protein by deletion or addition of one or more amino acids at one or more sites in the native protein and/or substitution of one or more amino acids at one or more sites in the native protein. In some embodiments, a variant proteins disclosed herein include those that are biologically active, that is they continue to possess biological activity of the native protein. Such variants are referred to as "functional variants", "biologically active variant" or "active variant" interchangeably herein, and may result from, for example, genetic polymorphism or human manipulation.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in its natural endogenous location with its own regulatory sequences.

By the term "endogenous" it is meant a sequence or other molecule that naturally occurs in a cell or organism. In one aspect, an endogenous polynucleotide is normally found in the genome of the cell from which it is obtained; that is, not heterologous.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence that may be transcribed into an RNA molecule and optionally further translated into a polypeptide. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, promoters, translation leader sequences, 5' untranslated sequences, 3' untranslated sequences, introns, polyadenylation target sequences, RNA processing sites, effector binding sites, and stem-loop structures.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, a "targeted mutation" is a mutation in a gene (referred to as the target gene), including a native gene, that was made by altering a target sequence within the target gene using any method known to one skilled in the art, including a method involving a guided Cas endonuclease system as disclosed herein.

The terms "knock-out", "gene knock-out" and "genetic knock-out" are used interchangeably herein. A knock-out represents a DNA sequence of a cell that has been rendered partially or completely inoperative by targeting with a Cas protein; for example, a DNA sequence prior to knock-out could have encoded an amino acid sequence, or could have had a regulatory function (e.g., promoter).

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (for example by homologous recombination (HR), wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

By "domain" it is meant a contiguous stretch of nucleotides (that can be RNA, DNA, and/or RNA-DNA-combination sequence) or amino acids.

The term "conserved domain" or "motif" means a set of polynucleotides or amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

A "codon-modified gene" or "codon-preferred gene" or "codon-optimized gene" is a gene having its frequency of codon usage designed to mimic the frequency of preferred codon usage of the host cell.

An "optimized" polynucleotide is a sequence that has been optimized for improved expression or function in a particular heterologous host cell.

A "plant-optimized nucleotide sequence" is a nucleotide sequence that has been optimized for expression or function in plants, particularly for increased expression in plants. A plant-optimized nucleotide sequence includes a codon-optimized gene. A plant-optimized nucleotide sequence can be synthesized by modifying a nucleotide sequence encoding a protein such as, for example, a Cas endonuclease as disclosed herein, using one or more plant-preferred codons for improved expression. See, for example, Campbell and Gowri (1990) *Plant Physiol.* 92:1-11 for a discussion of host-preferred codon usage.

A "promoter" is a region of DNA involved in recognition and binding of RNA polymerase and other proteins to initiate transcription. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

Promoters that cause a gene to be expressed in most cell types at most times are commonly referred to as "constitutive promoters". The term "inducible promoter" refers to a promoter that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre-mRNA. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated yet has an effect on cellular processes. The terms "complement" and "reverse complement" are used interchangeably herein with respect to mRNA transcripts, and are meant to define the antisense RNA of the message.

The term "genome" refers to the entire complement of genetic material (genes and non-coding sequences) that is present in each cell of an organism, or virus or organelle; and/or a complete set of chromosomes inherited as a (haploid) unit from one parent.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

"Introducing" is intended to mean presenting to the organism, such as a cell or organism, the polynucleotide or polypeptide or a polynucleotide-protein complex (e.g. an engineered CRISPR-Cas complex), in such a manner that the component(s) gains access to the interior of a cell of the organism or to the cell itself. The methods and compositions do not depend on a particular method for introducing a sequence into an organism or cell, only that the polynucleotide or polypeptide gains access to the interior of at least one cell of the organism. Introducing includes reference to the incorporation of a nucleic acid into a eukaryotic or prokaryotic cell where the nucleic acid may be incorporated into the genome of the cell, and includes reference to the transient (direct) provision of a polynucleotide or polypeptide to the cell.

Generally, "host" refers to an organism or cell into which a heterologous component (polynucleotide, polypeptide, other molecule, cell) has been introduced. As used herein, a "host cell" refers to an in vivo or in vitro eukaryotic cell, prokaryotic cell (e.g., bacterial or archaeal cell), or cell from a multicellular organism (e.g., a cell line) cultured as a unicellular entity, into which a heterologous polynucleotide or polypeptide has been introduced. In some embodiments, the cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, an insect cell, a mammalian cell, a pig cell, a cow cell, a goat cell, a sheep cell, a rodent cell, a rat cell, a mouse cell, a non-human primate cell, and a human cell. In some cases, the cell is in vitro. In some cases, the cell is in vivo.

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to a linear or circular extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector comprising a gene and having elements in addition to the gene that facilitates transformation of a particular host cell. "Expression cassette" refers to a specific vector comprising a gene and having elements in addition to the gene that allow for expression of that gene in a host.

The terms "recombinant DNA molecule", "recombinant DNA construct", "expression construct", "construct", and "recombinant construct" are used interchangeably herein. A recombinant DNA construct comprises an artificial combination of nucleic acid sequences, e.g., regulatory and coding sequences that are not all found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to introduce the vector into the host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "heterologous" refers to the difference between the original environment, location, or composition of a particular polynucleotide or polypeptide sequence and its current environment, location, or composition. Non-limiting examples include differences in taxonomic derivation (e.g., a polynucleotide sequence obtained from *Zea mays* would be heterologous if inserted into the genome of an *Oryza sativa* plant, or of a different variety or cultivar of *Zea mays*; or a polynucleotide obtained from a bacterium was introduced into a cell of a plant), or sequence (e.g., a polynucleotide sequence obtained from *Zea mays*, isolated, modified, and re-introduced into a maize plant). As used herein, "heterologous" in reference to a sequence can refer to a sequence that originates from a different species, variety, foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, one or more regulatory region(s) and/or a polynucleotide provided herein may be entirely synthetic.

The term "expression", as used herein, refers to the production of a functional end-product (e.g., an mRNA, guide RNA, or a protein) in either precursor or mature form.

A "mature" protein refers to a post-translationally processed polypeptide (i.e., one from which any pre- or propeptides present in the primary translation product have been removed).

"Precursor" protein refers to the primary product of translation of mRNA (i.e., with pre- and propeptides still present). Pre- and propeptides may be but are not limited to intracellular localization signals.

"CRISPR" (Clustered Regularly Interspaced Short Palindromic Repeats) loci refers to certain genetic loci encoding components of DNA cleavage systems, for example, used by bacterial and archaeal cells to destroy foreign DNA (Horvath and Barrangou, 2010, *Science* 327:167-170; WO2007025097, published 1 Mar. 2007). A CRISPR locus can consist of a CRISPR array, comprising short direct repeats (CRISPR repeats) separated by short variable DNA sequences (called spacers), which can be flanked by diverse Cas (CRISPR-associated) genes.

As used herein, an "effector" or "effector protein" is a protein that encompasses an activity including recognizing, binding to, and/or cleaving or nicking a polynucleotide target. The "effector complex" of a CRISPR system includes Cas proteins involved in crRNA and target recognition and binding. Some of the component Cas proteins may additionally comprise domains involved in target polynucleotide cleavage.

The term "Cas protein" refers to a polypeptide encoded by a Cas (CRISPR-associated) gene. A Cas protein includes but is not limited to: the novel Cas9 orthologs disclosed herein, a Cas9 protein, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease", that when in complex with a suitable polynucleotide component, is capable of recognizing, binding to, and optionally nicking or cleaving all or part of a specific polynucleotide target sequence. A Cas endonuclease described herein comprises one or more nuclease domains. A Cas protein is further defined as a functional fragment or functional variant of a native Cas protein, or a protein that shares at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% 85, and 99-374%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 150, at least 150, between 150 and 200, at least 200, between 200 and 250, at least 250, between 250 and 300, at least 300, between 300 and 350, at least 350, between 350 and 400, at least 400, between 400 and 450, at least 500, or greater than 500 contiguous amino acids of a native Cas protein, and retains at least partial activity.

A "functional fragment", "fragment that is functionally equivalent" and "functionally equivalent fragment" of a Cas endonuclease are used interchangeably herein, and refer to a portion or subsequence of the Cas endonuclease of the present disclosure in which the ability to recognize, bind to, and optionally unwind, nick or cleave (introduce a single or double-strand break in) the target site is retained. The portion or subsequence of the Cas endonuclease can comprise a complete or partial (functional) peptide of any one of its domains such as for example, but not limiting to a complete or functional part of a HD domain, a complete or functional part of a helicase domain, a complete or functional part of an endonuclease domain, a complete or functional part of a PAM-interacting domain, a complete or functional part of a Wedge domain, a complete or functional part of an RuvC domain, a complete or functional part of a zinc-finger domain, or a complete or functional part of a Cas protein (such as but not limiting to a Cas9, Cpf1, Cas5, Cas5d, Cas7, Cas8b1, Cas1, Cas2, Cas4, or Cas9 ortholog).

The terms "functional variant", "variant that is functionally equivalent" and "functionally equivalent variant" of a Cas endonuclease or Cas endonuclease, including Cas9 ortholog described herein, are used interchangeably herein, and refer to a variant of the Cas endonuclease disclosed herein in which the ability to recognize, bind to, and optionally unwind, nick or cleave all or part of a target sequence is retained.

In some aspects, a functional fragment or functional variant retains about the same level and type (e.g., target polynucleotide recognition, binding, and cleavage) of activity as the parental molecule from which it was derived. In some aspects, a functional fragment or functional variant displays improved activity of the same type (e.g., increased specificity of target polynucleotide recognition) as the parental molecule from which it was derived. In some aspects, a functional fragment or functional variant displays reduced activity of the same type (e.g., lower target polynucleotide binding affinity) as the parental molecule from which it was derived. In some aspects, a functional fragment or functional variant displays partial activity (e.g. polynucleotide recognition and binding, but not cleavage) as the parental molecule from which it was derived. In some aspects, a functional fragment or functional variant displays a different type of activity (e.g., creation of a single-strand nick on a target polynucleotide vs. a double strand break) than the parental molecule from which it was derived. Any similarity or difference in type or level of activity may be chosen as a desired outcome, according to the needs of the practitioner.

A Cas endonuclease may also include a multifunctional Cas endonuclease. The term "multifunctional Cas endonuclease" and "multifunctional Cas endonuclease polypeptide" are used interchangeably herein and includes reference to a single polypeptide that has Cas endonuclease functionality (comprising at least one protein domain that can act as a Cas endonuclease) and at least one other functionality, such as but not limited to, the functionality to form a cascade (comprises at least a second protein domain that can form a cascade with other proteins). In one aspect, the multifunctional Cas endonuclease comprises at least one additional protein domain relative (either internally, upstream (5'), downstream (3'), or both internally 5' and 3', or any combination thereof) to those domains typical of a Cas endonuclease.

As used herein, the term "guide polynucleotide", relates to a polynucleotide sequence that can form a complex with a Cas endonuclease, including the Cas endonuclease described herein, and enables the Cas endonuclease to recognize, optionally bind to, and optionally cleave a DNA target site. The guide polynucleotide sequence can be a RNA sequence, a DNA sequence, or a combination thereof (a RNA-DNA combination sequence).

The terms "functional fragment", "fragment that is functionally equivalent" and "functionally equivalent fragment" of a guide RNA, crRNA or tracrRNA are used interchangeably herein, and refer to a portion or subsequence of the guide RNA, crRNA or tracrRNA, respectively, of the present disclosure in which the ability to function as a guide RNA, crRNA or tracrRNA, respectively, is retained.

The terms "functional variant", "variant that is functionally equivalent" and "functionally equivalent variant" of a guide RNA, crRNA or tracrRNA (respectively) are used interchangeably herein, and refer to a variant of the guide RNA, crRNA or tracrRNA, respectively, of the present disclosure in which the ability to function as a guide RNA, crRNA or tracrRNA, respectively, is retained.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (transactivating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, optionally bind to, and optionally nick or cleave (introduce a single or double-strand break) the DNA target site.

The term "variable targeting domain" or "VT domain" is used interchangeably herein and includes a nucleotide sequence that can hybridize (is complementary) to one strand (nucleotide sequence) of a double strand DNA target site. The percent complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a (trans-acting) tracrNucleotide mate sequence followed by a tracrNucleotide sequence. The CER domain can be composed of a DNA sequence, a RNA sequence, a modified DNA sequence, a modified RNA sequence (see for example US20150059010A1, published 26 Feb. 2015), or any combination thereof.

As used herein, the terms "guide polynucleotide/Cas endonuclease complex", "guide polynucleotide/Cas endonuclease system", "guide polynucleotide/Cas complex", "guide polynucleotide/Cas system" and "guided Cas system" "polynucleotide-guided endonuclease", and "PGEN" are used interchangeably herein and refer to at least one guide polynucleotide and at least one Cas endonuclease, that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double-strand break) the DNA target site. A guide polynucleotide/Cas endonuclease complex herein can comprise Cas protein(s) and suitable polynucleotide component(s) of any of the known CRISPR systems (Horvath and Barrangou, 2010, *Science* 327:167-170; Makarova et al. 2015, *Nature Reviews Microbiology* Vol. 13:1-15; Zetsche et al., 2015, *Cell* 163, 1-13; Shmakov et al., 2015, *Molecular Cell* 60, 1-13).

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", and "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site. In some aspects, the components are provided as a ribonucleoprotein complex ("RNP") of a Cas endonuclease protein and a guide RNA.

The terms "target site", "target sequence", "target polynucleotide", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, a locus, or any other DNA molecule in the genome (including chromosomal, chloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

A "protospacer adjacent motif" (PAM) herein refers to a short nucleotide sequence adjacent to a target sequence (protospacer) that is recognized (targeted) by a guide polynucleotide/Cas endonuclease system described herein. In some aspects, the Cas endonuclease may not successfully recognize a target DNA sequence if the target DNA sequence is not adjacent to, or near, a PAM sequence. In some aspects, the PAM precedes the target sequence (e.g. Cas12a). In some aspects, the PAM follows the target sequence (e.g. *S. pyogenes* Cas9). The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: modifications include deletion, substitution, and/or insertion of one or more nucleotides in the nucleic acid fragment, the association of an atom or a molecule to an existing nucleotide in a polynucleotide (for example but not limited to: a covalent addition of a methyl group, or an ionic interaction with a metal ion), the chemical alteration of at least one nucleotide, or any combination of the preceding.

A "modified nucleotide" or "edited nucleotide" refers to a nucleotide sequence of interest that comprises at least one alteration when compared to its non-modified nucleotide sequence. Such "alterations" include, for example: modifications include deletion, substitution, and/or insertion of one or more nucleotides in the nucleic acid fragment, the association of an atom or a molecule to an existing nucleotide in a polynucleotide (for example but not limited to: a covalent addition of a methyl group, or an ionic interaction with a metal ion), the chemical alteration of at least one nucleotide, or any combination of the preceding.

Methods for "modifying a target site" and "altering a target site" are used interchangeably herein and refer to methods for producing an altered target site.

As used herein, "donor DNA" is a DNA construct that comprises a polynucleotide of interest to be inserted into the target site of a Cas endonuclease.

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

Eukaryotic cells include, but are not limited to, human, non-human, animal, mammalian, bacterial, fungal, insect, yeast, and plant cells as well as plants and seeds produced by the methods described herein.

The term "plant-optimized Cas endonuclease" herein refers to a Cas protein, including a multifunctional Cas protein, encoded by a nucleotide sequence that has been optimized for expression in a plant cell or plant.

A "plant-optimized nucleotide sequence encoding a Cas endonuclease", "plant-optimized construct encoding a Cas endonuclease" and a "plant-optimized polynucleotide encoding a Cas endonuclease" are used interchangeably herein and refer to a nucleotide sequence encoding a Cas protein, or a variant or functional fragment thereof, that has been optimized for expression in a plant cell or plant. A plant comprising a plant-optimized Cas endonuclease includes a plant comprising the nucleotide sequence encoding for the Cas sequence and/or a plant comprising the Cas endonuclease protein. In one aspect, the plant-optimized Cas endonuclease nucleotide sequence is a maize-optimized, rice-optimized, wheat-optimized, soybean-optimized, cotton-optimized, or canola-optimized Cas endonuclease.

The term "plant" generically includes whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. A "plant element" is intended to reference either a whole plant or a plant component, which may comprise differentiated and/or undifferentiated tissues, for example but not limited to plant tissues, parts, and cell types. In one embodiment, a plant element is one of the following: whole plant, seedling, meristematic tissue, ground tissue, vascular tissue, dermal tissue, seed, leaf, root, shoot, stem, flower, fruit, stolon, bulb, tuber, corm, keiki, shoot, bud, tumor tissue, and various forms of cells and culture (e.g., single cells, protoplasts, embryos, callus tissue). The term "plant organ" refers to plant tissue or a group of tissues that constitute a morphologically and functionally distinct part of a plant. As used herein, a "plant element" is synonymous to a "portion" of a plant, and refers to any part of the plant, and can include distinct tissues and/or organs, and may be used interchangeably with the term "tissue" throughout. Similarly, a "plant reproductive element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keiki, or bud. The plant element may be in plant or in a plant organ, tissue culture, or cell culture.

"Progeny" comprises any subsequent generation of a plant.

As used herein, the term "plant part" refers to plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The term "monocotyledonous" or "monocot" refers to the subclass of angiosperm plants also known as "monocotyledoneae", whose seeds typically comprise only one embryonic leaf, or cotyledon. The term includes references to whole plants, plant elements, plant organs (e.g., leaves, stems, roots, etc.), seeds, plant cells, and progeny of the same.

The term "dicotyledonous" or "dicot" refers to the subclass of angiosperm plants also knows as "dicotyledoneae", whose seeds typically comprise two embryonic leaves, or cotyledons. The term includes references to whole plants, plant elements, plant organs (e.g., leaves, stems, roots, etc.), seeds, plant cells, and progeny of the same.

The term "isoline" is a comparative term, and references organisms that are genetically identical, but differ in treatment. In one example, two genetically identical maize plant embryos may be separated into two different groups, one receiving a treatment (such as the introduction of a CRISPR-Cas effector endonuclease) and one control that does not receive such treatment. In some aspects, "isoline" refers to two cells or organisms that are genetically identical except for the presence of a heterologous polynucleotide or polypeptide that has been introduced as part of an experiment. Any phenotypic differences between the two groups may thus be attributed solely to the treatment or presence of the heterologous molecule, and not to any inherent property of the organism's endogenous genetic makeup.

"Introducing" is intended to mean presenting to a target, such as a cell or organism, a polynucleotide or polypeptide or polynucleotide-protein complex, in such a manner that the component(s) gains access to the interior of a cell of the organism or to the cell itself.

A "polynucleotide of interest" includes any nucleotide sequence encoding a protein or polypeptide that improves desirability of crops. Polynucleotides of interest: include, but are not limited to, polynucleotides encoding important traits for agronomics, herbicide-resistance, insecticidal resistance, disease resistance, nematode resistance, herbicide resistance, microbial resistance, fungal resistance, viral resistance, fertility or sterility, grain characteristics, commercial products, phenotypic marker, or any other trait of agronomic or commercial importance. A polynucleotide of interest may additionally be utilized in either the sense or anti-sense orientation. Further, more than one polynucleotide of interest may be utilized together, or "stacked", to provide additional benefit.

An "isolated" or "purified" nucleic acid molecule, polynucleotide, polypeptide, or protein, or biologically active portion thereof, is substantially or essentially free from components that normally accompany or interact with the polynucleotide or protein as found in its naturally occurring environment. Thus, an isolated or purified polynucleotide or polypeptide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

A protein that is substantially free of cellular material includes preparations of protein having less than about 30%, 20%, 10%, 5%, or 1% (by dry weight) of contaminating protein. When the polypeptides disclosed herein or biologically active portion thereof is recombinantly produced, optimally culture medium represents less than about 30%, 20%, 10%, 5%, or 1% (by dry weight) of chemical precursors or non-protein-of-interest chemicals.

The compositions and methods herein may provide for an improved "agronomic trait" or "trait of agronomic importance" or "trait of agronomic interest" to a plant, which may include, but not be limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein.

"Agronomic trait potential" is intended to mean a capability of a plant element for exhibiting a phenotype, preferably an improved agronomic trait, at some point during its life cycle, or conveying said phenotype to another plant element with which it is associated in the same plant.

The terms "decreased," "fewer," "slower" and "increased" "faster" "enhanced" "greater" as used herein refers to a decrease or increase in a characteristic of the modified plant element or resulting plant compared to an unmodified plant element or resulting plant. For example, a decrease in a characteristic may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least 60%, between 60% and 70%, between 70% and 80%, at least 75%, at least 80%, between 80% and 90%, at least 90%, between 90% and 100%, at least 100%, between 100% and 200%, at least 200%, at least 300%, at least 400%) or more lower than the untreated control and an increase may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least 60%, between 60% and 70%, between 70% and 80%, at least 75%, at least 80%, between 80% and 90%, at least 90%, between 90% and 100%, at least 100%, between 100% and 200%, at least 200%, at least 300%), at least 400% or more higher than the untreated control.

As used herein, the term "before", in reference to a sequence position, refers to an occurrence of one sequence upstream, or 5', to another sequence.

The meaning of abbreviations is as follows: "sec" means second(s), "min" means minute(s), "h" means hour(s), "d" means day(s), "µL" or "uL" or "ul" means microliter(s), "mL" means milliliter(s), "L" means liter(s), "µM" means micromolar, "mM" means millimolar, "M" means molar, "mmol" means millimole(s), "µmole" or "umole" mean micromole(s), "g" means gram(s), "µg" or "ug" means microgram(s), "ng" means nanogram(s), "U" means unit(s), "bp" means base pair(s) and "kb" means kilobase(s).

CRISPR-Cas Systems

In general, a CRISPR system is characterized by elements that promote the formation of a CRISPR complex (comprising a Cas protein (e.g. a Cas9 protein), a tracr and a crRNA (having a repeat sequence and a spacer, or guide, sequence)) at the site of a target sequence (also referred to as a protospacer in the context of an endogenous CRISPR system). In an engineered CRISPR-Cas9 complex, the natural spacer sequence has been replaced with a sequence designed to be complementary to a target sequence, for example, a target sequence in a eukaryotic cell. In the context of formation of a CRISPR complex, "target sequence" refers to a sequence to which a guide sequence is designed to have complementarity. A target sequence can be any polynucleotide, such as DNA or RNA polynucleotides. In some embodiments, a target sequence is located in the nucleus or cytoplasm of a cell.

CRISPR-Cas systems have been classified according to sequence and structural analysis of components. Multiple CRISPR/Cas systems have been described including Class 1 systems, with multisubunit effector complexes (comprising type I, type III, and type IV), and Class 2 systems, with single protein effectors (comprising type II, type V, and type VI) (Makarova et al. 2015, *Nature Reviews Microbiology* Vol. 13:1-15; Zetsche et al., 2015, *Cell* 163, 1-13; Shmakov et al., 2015, *Molecular Cell* 60, 1-13; Haft et al., 2005, *Computational Biology, PLoS Comput Biol* 1(6): e60; and Koonin et al. 2017, *Curr Opinion Microbiology* 37:67-78).

A CRISPR-Cas system comprises, at a minimum, a CRISPR RNA (crRNA) molecule and at least one CRISPR-associated (Cas) protein to form crRNA ribonucleoprotein (crRNP) effector complexes. CRISPR-Cas loci comprise an array of identical repeats interspersed with DNA-targeting spacers that encode the crRNA components and an operon-like unit of cas genes encoding the Cas protein components. The resulting ribonucleoprotein complex is called a Cascade, that recognizes a polynucleotide in a sequence-specific manner (Jore et al., *Nature Structural & Molecular Biology* 18, 529-536 (2011)). The crRNA serves as a guide RNA for sequence specific binding of the effector (protein or complex) to double strand DNA sequences, by forming base pairs with the complementary DNA strand while displacing the noncomplementary strand to form a so-called R-loop. (Jore et al., 2011. *Nature Structural & Molecular Biology* 18, 529-536).

The Cas endonuclease is guided by a single CRISPR RNA (crRNA) through direct RNA-DNA base-pairing to recognize a DNA target site that is in close vicinity to a protospacer adjacent motif (PAM) (Jore, M. M. et al., 2011, *Nat. Struct. Mol. Biol.* 18:529-536, Westra, E. R. et al., 2012, *Molecular Cell* 46:595-605, and Sinkunas, T. et al., 2013, *EMBO J.* 32:385-394). Class 1 CRISPR-Cas systems comprise Types I, III, and IV. A characteristic feature of Class I systems is the presence of an effector endonuclease complex instead of a single protein. Class 2 CRISPR-Cas systems comprise Types II, V, and VI. A characteristic feature of Class 2 systems is the presence of a single Cas protein instead of an effector module endonuclease complex. Types II and V Cas proteins comprise an RuvC-like endonuclease domain that adopts the RNase H fold.

Class 2 Type II CRISPR/Cas systems employ a crRNA and tracrRNA (trans-activating CRISPR RNA) to guide the Cas endonuclease to its DNA target. The crRNA comprises a spacer region complementary to one strand of the double strand DNA target and a region that base pairs with the tracrRNA (trans-activating CRISPR RNA) forming a RNA duplex that directs the Cas endonuclease to cleave the DNA target. For the *S. pyogenes* Cas9 endonuclease, the cleavage leaves a blunt end. Type II CRISR-Cas loci can encode a tracrRNA, which is partially complementary to the repeats within the respective CRISPR array, and can comprise other proteins.

Cas endonucleases can be used for targeted genome editing (via simplex and multiplex double-strand breaks and nicks) and targeted genome regulation (via tethering of epigenetic effector domains to either the Cas protein or gRNA. A Cas endonuclease can also be engineered to function as an RNA-guided recombinase, and via RNA tethers could serve as a scaffold for the assembly of multi-protein and nucleic acid complexes (Mali et al., 2013, *Nature Methods* Vol. 10: 957-963).

CRISPR-Cas System Compositions

Methods and compositions are provided for genome editing with a CRISPR Associated (Cas) endonuclease. Class I Cas endonucleases comprise multisubunit effector complexes (Types I, III, and IV), while Class 2 systems comprise single protein effectors (Types II, V, and VI) (Makarova et al. 2015, *Nature Reviews Microbiology* Vol. 13:1-15; Zetsche et al., 2015, *Cell* 163, 1-13; Shmakov et al., 2015, *Molecular Cell* 60, 1-13; Haft et al., 2005, *Computational Biology, PLoS Comput Biol* 1(6): e60; and Koonin et al. 2017, *Curr Opinion Microbiology* 37:67-78). In Class 2 Type II systems, the Cas endonuclease acts in complex with a guide RNA (gRNA) that directs the Cas endonuclease to cleave the DNA target to enable target recognition, binding, and cleavage by the Cas endonuclease. The gRNA comprises a Cas endonuclease recognition (CER) domain that interacts with the Cas endonuclease, and a Variable Targeting (VT) domain that hybridizes to a nucleotide sequence in a target DNA. In some aspects, the gRNA comprises a CRISPR RNA (crRNA) and a trans-activating CRISPR RNA (tracrRNA) to guide the Cas endonuclease to its DNA target. The crRNA comprises a spacer region complementary to one strand of the double strand DNA target and a region that base pairs with the tracrRNA, forming an RNA duplex. In some aspects, the gRNA is a "single guide RNA" (sgRNA) that comprises a synthetic fusion of crRNA and tracrRNA. In many systems, the Cas endonuclease-guide polynucleotide complex recognizes a short nucleotide sequence adjacent to the target sequence (protospacer), called a "protospacer adjacent motif" (PAM).

Examples of a Cas endonuclease include but are not limited to Cas9 and Cpf1. Cas9 (formerly referred to as Cas5, Csn1, or Csx12) is a Class 2 Type II Cas endonuclease (Makarova et al. 2015, *Nature Reviews Microbiology* Vol. 13:1-15). A Cas9-gRNA complex recognizes a 3' PAM sequence (NGG for the *S. pyogenes* Cas9) at the target site, permitting the spacer of the guide RNA to invade the double-stranded DNA target, and, if sufficient homology between the spacer and protospacer exists, generate a double-strand break cleavage. Cas9 endonucleases comprise RuvC and HNH domains that together produce double strand breaks, and separately can produce single strand breaks. For the *S. pyogenes* Cas9 endonuclease, the double-strand break leaves a blunt end. Cpf1 is a Class 2 Type V Cas endonuclease, and comprises nuclease RuvC domain but lacks an HNH domain (Yamane et al., 2016, *Cell* 165:949-962). Cpf1 endonucleases create "sticky" overhang ends.

A large number of Cas9 orthologs are known in the art as well as their associated tracrRNA and crRNA components (see, e.g., "Supplementary Table S2. List of bacterial strains with identified Cas9 orthologs," Fonfara, Ines, et al., "Phylogeny of Cas9 Determines Functional Exchangeability of Dual-RNA and Cas9 among Orthologous Type II CRISPR/Cas Systems," Nucleic Acids Research 42.4 (2014): 2577-2590, including all Supplemental Data; Chylinski K., et al., "Classification and evolution of type II CRISPR-Cas systems," Nucleic Acids Research, 2014; 42(10):6091-6105, including all Supplemental Data; Kevin M Esvelt, K. M., et al., (2013) "Orthogonal Cas9 proteins for RNA-guided gene regulation and editing," Nature Methods 10, 1116-1121, a number of orthogonal Cas9 proteins identified including a Cas9 protein from *Neisseria meningitidis*). A representative list of Type-II CRISPR systems that find use with the compositions and methods disclosed herein, includes those described in Makarova et al. 2015, Nature Reviews Microbiology|AOP, published online 28 Sep. 2015; doi:10.1038/nrmicro3569; and in Burstein, D. et al. New CRISPR-Cas systems from uncultivated microbes. Nature http://dx-.doi.org/10.1038/nature21059 (2016) and in WO 2017 062 855. In some embodiments, the Cas endonuclease is identified from a Type II-A CRISPR complex, such as those derived from *Streptococcus thermophilus*, or *Streptococcus pyogenes*.

In some aspects, a "polynucleotide modification template" is provided that comprises at least one nucleotide modification when compared to the nucleotide sequence to be edited. A nucleotide modification can be at least one nucleotide substitution, addition, deletion, or chemical alteration. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In some aspects, a polynucleotide of interest is inserted at a target site and provided as part of a "donor DNA" molecule. As used herein, "donor DNA" is a DNA construct that comprises a polynucleotide of interest to be inserted into the target site of a Cas endonuclease. The donor DNA construct further comprises a first and a second region of homology that flank the polynucleotide of interest. The first and second regions of homology of the donor DNA share homology to a first and a second genomic region, respectively, present in or flanking the target site of the cell or organism genome. The donor DNA can be tethered to the guide polynucleotide. Tethered donor DNAs can allow for co-localizing target and donor DNA, useful in genome editing, gene insertion, and targeted genome regulation, and can also be useful in targeting post-mitotic cells where function of endogenous HR machinery is expected to be highly diminished (Mali et al., 2013, *Nature Methods* Vol. 10: 957-963). The amount of homology or sequence identity shared by a target and a donor polynucleotide can vary and includes total lengths and/or regions.

To facilitate optimal expression and nuclear localization for eukaryotic cells, the gene comprising the Cas endonuclease may be optimized as described in WO2016186953 published 24 Nov. 2016, and then delivered into cells as DNA expression cassettes by methods known in the art.

In some aspects, the Cas endonuclease is provided as a polypeptide. In some aspects, the Cas endonuclease is provided as a polynucleotide encoding a polypeptide. In some aspects, the guide RNA is provided as a DNA molecule encoding one or more RNA molecules. In some aspects, the guide RNA is provide as RNA or chemically-modified RNA. In some aspects, the Cas endonuclease protein and guide RNA are provided as a ribonucleoprotein complex (RNP).

Also of use with the ACR compositions and methods provided herein are Cas endonuclease variants that have a reduced activity towards off-target sequences. Such Cas endonuclease variants include those disclosed, for example, in WO2016 205 613. Such combinations may provide for an even greater reduction in off-target activity.

CRISPR-Cas Mediated Genome Editing

As used herein, CRISPR-Cas-mediated genome editing composition (or, an engineered CRISPR-Cas complex) refers to the elements of a CRISPR system needed to carry out CRISPR-Cas-mediated genome editing in a host cell, such as a eukaryotic cell. Engineered CRISPR-Cas complex compositions typically include one or more nucleic acids comprising a crRNA, a tracrRNA (or chimeric thereof also referred to a guide RNA or single guide RNA) and a Cas enzyme, for example, Cas9. The crRNA and tracrRNAs of engineered-Cas complex compositions can also be provided to the system indirectly by nucleic acids encoding the crRNA, tracrRNA and/or guide RNA. The CRISPR/Cas-mediated genome editing composition can optionally include a donor polynucleotide that can be recombined into the target cell's genome at or adjacent to the target site (e.g., the site of single or double stand break induced by the Cas9). Examples of engineered CRISPR-Cas complexes include those disclosed in U.S. Publication No. 2015/0045546 and International Application publication number WO 2013/176772.

Some uses for Cas9-gRNA systems at a genomic target site include but are not limited to insertions, deletions, substitutions, or modifications of one or more nucleotides at the target site; modifying or replacing nucleotide sequences of interest (such as a regulatory elements); insertion of polynucleotides of interest; gene knock-out; gene-knock in; modification of splicing sites and/or introducing alternate splicing sites; modifications of nucleotide sequences encoding a protein of interest; amino acid and/or protein fusions; and gene silencing by expressing an inverted repeat into a gene of interest.

The process for editing a genomic sequence at a Cas9-gRNA double-strand-break site with a modification template generally comprises: providing a host cell with a Cas9-gRNA complex that recognizes a target sequence in the genome of the host cell and is able to induce a double-strand-break in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the double-strand break. Genome editing using double-strand-break-inducing agents, such as Cas9-gRNA complexes, has been described, for example in US20150082478 published on 19 Mar. 2015, WO2015026886 published on 26 Feb. 2015, WO2016007347 published 14 Jan. 2016, and WO2016025131 published on 18 Feb. 2016.

To facilitate optimal expression and nuclear localization for eukaryotic cells, the gene comprising the Cas endonuclease may be optimized as described in WO2016186953 published 24 Nov. 2016, and then delivered into cells as DNA expression cassettes by methods known in the art. In some aspects, the Cas endonuclease is provided as a polypeptide. In some aspects, the Cas endonuclease is provided as a polynucleotide encoding a polypeptide. In some aspects, the guide RNA is provided as a DNA molecule encoding one or more RNA molecules. In some aspects, the guide RNA is provide as RNA or chemically-modified RNA. In some aspects, the Cas endonuclease protein and guide RNA are provided as a ribonucleoprotein complex (RNP).

Anti-CRISPR (ACR) Proteins

Compositions disclosed herein include isolated polynucleotides and polypeptides encoding anti-CRISPR ("ACR") proteins. In some embodiments, the disclosed ACR polypeptides are capable of reducing or inhibiting the ability of Cas endonuclease, for example but not limited to a Cas9 protein, to recognize, bind, and optionally modify, nick, or cleave a target polynucleotide.

In one embodiment polynucleotides and polynucleotide encoding polypeptides are provided which reduce and/or inhibit Cas9 activity against a target DNA molecule. In certain embodiments, polypeptides that reduce and/or inhibit the activity of Type II-A Cas9 proteins are provided.

isolated or identified from a bacteriophage or bacterium

In one embodiment, isolated or recombinant polynucleotides are provided which comprise a nucleotide sequence set forth in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374), or functional fragments or variants thereof. Also provided are recombinant polynucleotides that encode the polypeptides having a sequence set forth in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650, or functional fragments or variants thereof. Further provided are isolated or recombinant polypeptides which comprise an amino acid sequence set forth in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650), or functional fragments or variants thereof.

The ACR polynucleotides and polypeptides disclosed herein include both the naturally occurring sequences as well as nucleic acid variants. Likewise, the polypeptides and proteins encompass both naturally occurring polypeptides as well as variations and modified forms thereof. Such polynucleotide and polypeptide variants may continue to possess the desired activity, in which case the mutations that will be made in the DNA encoding the variant will not place the sequence out of reading frame.

Functional variants of a protein disclosed herein will have at least about 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the amino acid sequence for the native protein (e.g. the polypeptides provided in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650). Functional variants of a protein disclosed herein may also have at least about 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the amino acid sequence for the native protein (e.g. the polypeptides provided in SEQ ID NOs: 2, 4, 6, 8, 10, 12, 14, 16, 18, 20, 22, 24, and 26) and have a coiled-coil motif. A functional variant of a protein disclosed herein may differ from that protein by as few as 1-15 amino acid residues, as few as 1-10, such as 6-10, as few as 5, as few as 4, 3, 2, or even 1 amino acid residue.

In some embodiments, the ACR polypeptides include those that contain a coiled coil motif. In some embodiments, coiled coil motifs of the ACR proteins include those polypeptide sequences that contain a repeated pattern of amino acids, hxxhcxc, of hydrophobic (h) and charged (c) amino acids, also sometimes referred to as a heptad repeat. In some embodiments, the coiled coil motif includes the polypeptide sequences KQRREYAQEMDRLEKAFENLD and/or ENKLDKIIEKIDKL and those that contain 70%, 75%, 80%, 85%, 90%, 90%, 95%, 96%, 97%, 98%, and 99% sequence identity to SEQ ID NOs: 2, 4, 6, 8, 10, 12, 14, 16, 18, 20, 22, 24, and 26. and retain the coiled coil structure.

The proteins disclosed herein may be altered in various ways including amino acid substitutions, deletions, truncations, and insertions. Methods for such manipulations are generally known in the art. For example, amino acid sequence variants and fragments of polypeptides can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.). Conservative substitutions, such as exchanging one amino acid with another having similar properties, may be optimal.

An "active" polypeptide, or fragments thereof, retains a biological activity of the native or naturally-occurring counterpart of the active polypeptide. Biological activity refers to a function mediated by the native or naturally-occurring counterpart of the active polypeptide. For example, binding or protein-protein interaction constitutes a biological activity.

In some embodiments, certain deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect may be evaluated by screening assays, such as those described herein.

Variant functional polynucleotides and proteins also encompass sequences and proteins derived from a mutagenic and recombinogenic procedure such as DNA shuffling. With such a procedure, one or more different sequences can be manipulated to create a new polypeptide possessing desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the polynucleotides disclosed herein and other known polynucleotides to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Fragments and variants of the disclosed polynucleotides and proteins encoded thereby are also provided. By "fragment" is intended a portion of the polynucleotide or a portion of the amino acid sequence and hence protein encoded thereby. Fragments of a polynucleotide may encode protein fragments that retain the biological activity of the native protein, or fragments of a polynucleotide, may retain the biological activity of the full size polynucleotide; these fragments are referred to herein as "functional fragments". The terms "functional fragment", "active fragment", "fragment that is functionally equivalent" and "functionally equivalent fragment" are used interchangeably herein.

A functional fragment of a polynucleotide that encodes a biologically active portion of an ACR polypeptide will encode at least 15, 25, 30, 50, 100, or 125 contiguous amino acids, or up to the total number of amino acids present in a full-length ACR polypeptide (e.g. the polypeptides provided in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 375-650). Such functional fragments of SEQ ID NOs: 2, 4, 6, 8, 10, 12, 14, 16, 18, 20, 22, 24, and 26 may optionally include a coiled-coil motif.

Functional fragments of ACR proteins of the present disclosure include fragments comprising 50-130, 60-120, 70-110, 80-100 amino acids of an ACR protein and retain activity. Functional fragments of ACR proteins of the present disclosure can also include fragments comprising 50-130, 60-120, 70-110, 80-100 amino acids of an ACR protein and have a coiled-coil motif.

A biologically active portion of a polypeptide can be prepared by isolating a portion of one of the polynucleotides disclosed herein, expressing the encoded portion of the protein (e.g., by recombinant expression in vitro), and assessing the activity of the encoded portion of the polypeptide. Polynucleotides that are functional fragments of a polynucleotide encoding an ACR protein comprise at least 50, 75, 100, 150, 200, 250, 300, 350, or 400 nucleotides, or up to the number of nucleotides present in a full-length polynucleotide disclosed herein.

Recombinant Constructs

The ACR compositions provided herein, as well as any of the CRISPR-Cas compositions, may be provided as part of a recombinant construct. The recombinant construct may be part of an expression cassette for use in transforming a heterologous host cell with said compositions. Standard recombinant DNA and molecular cloning techniques used herein are well known in the art and are described more fully in Sambrook et al., *Molecular Cloning: A Laboratory Manual*; Cold Spring Harbor Laboratory: Cold Spring Harbor, N.Y. (1989).

A recombinant DNA construct may comprise regulatory sequences and coding sequences that are derived from different sources. Such a construct may be used by itself or may be used in conjunction with a vector. If a vector is used, then the choice of vector is dependent upon the method that will be used to introduce the vector into the host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

In one aspect, the recombinant DNA construct includes heterologous 5' and 3' regulatory sequences operably linked to an ACR polynucleotide as disclosed herein. These regulatory sequences include but are not limited to a transcriptional and translational initiation region (i.e., a promoter), a nuclear localization signal, and a transcriptional and translational termination region (i.e., termination region) functional in the host cell (such as eukaryotic cell).

In one aspect, the recombinant DNA construct comprises a DNA encoding an ACR protein described herein, wherein the ACR protein is operably linked to or comprises a heterologous regulatory element such as a nuclear localization sequence (NLS).

In some embodiments, the ACR vectors can be combined with expression cassettes for the expression of one more components of an engineered CRISPR-Cas complex. In one example, one or more constructs are provided that comprise an expression cassette having a promoter functional in a eukaryotic cell operably linked to a polynucleotide encoding an ACR protein as disclosed herein, a second cassette having a promoter functional in a eukaryotic cell operably linked to a single-guide sequence and a third cassette comprising a promoter functional in a eukaryotic cell operably linked to a Cas9 protein, where the guide and the Cas9 are capable of forming a complex that can modify a target DNA molecule. The cassettes may be provided on a single recombinant construct or on multiple recombinant constructs, which can be used for introduction into host cells either simultaneously or sequentially.

Expression Cassettes

The ACR polynucleotides disclosed herein can be provided in an expression cassette (also referred to as DNA construct) for expression of the ACR polypeptides in a host cell. The cassette can include 5' and 3' regulatory sequences operably linked to a polynucleotide as disclosed herein. "Operably linked" is intended to mean a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame.

Where appropriate, the ACR polynucleotides may be optimized for increased expression in the transformed or targeted host cell. For example, the polynucleotides can be synthesized or altered to use mammalian-preferred or plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498.

The expression cassettes disclosed herein may include in the 5'-3' direction of transcription, a transcriptional and translational initiation region (i.e., a promoter), an ACR polynucleotide, and a transcriptional and translational termination region (i.e., termination region) functional in the host cell (e.g., a eukaryotic cell). Expression cassettes are also provided with a plurality of restriction sites and/or recombination sites for insertion of the polynucleotide to be under the transcriptional regulation of the regulatory regions described elsewhere herein. The regulatory regions (i.e., promoters, transcriptional regulatory regions, and translational termination regions) and/or the polynucleotide of interest may be native/analogous to the host cell or to each other. Alternatively, the regulatory regions and/or the polynucleotide of interest may be heterologous to the host cell or to each other. As used herein, "heterologous" in reference to a polynucleotide or polypeptide sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, unless otherwise specified, a chimeric polynucleotide comprises a coding sequence operably linked to a transcription initiation region that is heterologous to the coding sequence.

In some embodiments, a nucleotide sequence encoding an ACR protein is operably linked to a control element, e.g., a transcriptional control element, such as a promoter. The transcriptional control element may be functional in either a eukaryotic cell, e.g., a plant or mammalian cell; or a prokaryotic cell (e.g., bacterial or archaeal cell). In some embodiments, an ACR nucleotide sequence encoding an ACR protein is operably linked to multiple control elements that allow expression of the nucleotide sequence encoding an ACR protein in both prokaryotic and eukaryotic cells.
Expression Elements The recombinant construct, or expression cassette, may further comprise a non-coding regulatory element for use in expressing the ACR and/or CRISPR components in a heterologous cell, particularly a plant cell.

In one embodiment, expression cassettes are provided that comprise a promoter functional in a eukaryotic cell operably linked to a polynucleotide encoding an ACR protein, variant or fragment thereof as disclosed herein.

The expression cassettes may comprise a promoter operably linked to an ACR polynucleotide, along with a corresponding termination region. The termination region may be native to the transcriptional initiation region, may be native to the operably linked polynucleotide of interest or to the promoter sequences, may be native to the host cell, or may be derived from another source (i.e., foreign or heterologous). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. The expression vector may also contain a ribosome binding site for translation initiation and a transcription terminator. The expression vector may also contain one or more nuclear localization sequences (NLS sequences) to direct the ACR protein to the nucleus in a eukaryotic cell. The expression vector may also include appropriate sequences for amplifying expression. The expression vector may also include nucleotide sequences encoding protein tags (e.g., 6×His tag, hemagglutinin tag, green fluorescent protein, etc.) that are fused to the ACR protein, thus resulting in a chimeric polypeptide.

In embodiments where plant cells are employed, plant promoters will find use in the constructs. It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters".

A plant promoter includes a promoter capable of initiating transcription in a plant cell. For a review of plant promoters, see, Potenza et al., 2004, In Vitro Cell Dev Biol 40:1-22; Porto et al., 2014, Molecular Biotechnology (2014), 56(1), 38-49.

Constitutive promoters include, for example, the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; ALS promoter (U.S. Pat. No. 5,659,026) and the like.

Tissue-preferred promoters can be utilized to target enhanced expression within a particular plant tissue. Tissue-preferred promoters include, for example, WO2013/103367 published on 11 Jul. 2013, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

The term "inducible promoter" refers to a promoter that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

Chemical inducible (regulated) promoters can be used to modulate the expression of a gene in a prokaryotic and eukaryotic cell or organism through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Pathogen inducible promoters induced following infection by a pathogen include, but are not limited to those regulating expression of PR proteins, SAR proteins, beta-1, 3-glucanase, chitinase, etc.

A stress-inducible promoter includes the RD29A promoter (Kasuga et al. (1999) *Nature Biotechnol.* 17:287-91). One of ordinary skill in the art is familiar with protocols for simulating stress conditions such as drought, osmotic stress, salt stress and temperature stress and for evaluating stress tolerance of plants that have been subjected to simulated or naturally-occurring stress conditions.

Another example of an inducible promoter useful in plant cells, is the ZmCAS1 promoter, described in US patent application, US 2013-0312137A1, published on Nov. 21, 2013, incorporated by reference herein.

New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, N.Y.: Academic Press), pp. 1-82.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Johnson et al. (1986) *Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA, ed. Cech* (*Liss*, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

Optimized and Modified Sequences

Where appropriate, the ACR polynucleotides may be optimized for increased expression in the transformed or targeted host cell. For example, the polynucleotides can be synthesized or altered to use mammalian-preferred or plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Cells

The polynucleotides, polypeptides or expression cassettes disclosed herein can be introduced into a host cell using any method available.

Methods for introducing polynucleotides or polypeptides into a cell or organism, include, but are not limited to, microinjection, electroporation, stable transformation methods, transient transformation methods, ballistic particle acceleration (particle bombardment), whiskers mediated transformation, *Agrobacterium*-mediated transformation, direct gene transfer, viral-mediated introduction, transfection, transduction, cell-penetrating peptides, mesoporous silica nanoparticle (MSN)-mediated direct protein delivery, topical applications, sexual crossing, sexual breeding, and any combination thereof. Stable transformation is intended to mean that the nucleotide construct introduced into host cell integrates into a genome of the organism and is capable of being inherited by the progeny thereof. Transient transformation is intended to mean that a polynucleotide is introduced into the cell and does not integrate into a genome of the organism or a polypeptide is introduced into an organism. Transient transformation indicates that the introduced composition is only temporarily expressed or present in the organism.

An ACR protein can be introduced into a cell by directly introducing the ACR protein itself or an mRNA encoding the ACR protein. The ACR protein can also be introduced into a cell indirectly by introducing a recombinant DNA molecule that encodes the ACR protein. The ACR protein can be introduced into a cell transiently or can be incorporated into the genome of the host cell. Uptake of the ACR protein into the cell can be facilitated with a Cell Penetrating Peptide (CPP). Any promoter capable of expressing the ACR protein in a cell can be used and includes a heat shock/heat inducible promoter operably linked to a nucleotide sequence encoding the ACR protein.

Direct delivery of any one of the ACR polynucleotides or polypeptides, or CRISPR-Cas complex components can be accompanied by direct delivery (co-delivery) of other mRNAs that can promote the enrichment and/or visualization of cells receiving the components. For example, direct co-delivery of the ACR compositions or CRISPR-Cas complex components together with mRNA encoding phenotypic markers (such as but not limiting to transcriptional activators such as CRC (Bruce et al. 2000 The Plant Cell 12:65-79) can enable the selection and enrichment of cells without the use of an exogenous selectable marker by restoring function to a non-functional gene product as described in PCT/US16/57272 filed Oct. 17, 2016 and PCT/US16/57279, filed Oct. 17, 2016.

Alternatively, polynucleotides may be introduced into cells by contacting cells or organisms with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931.

The polynucleotide or recombinant DNA construct can be provided to or introduced into a prokaryotic and eukaryotic cell or organism using a variety of transient transformation methods. Such transient transformation methods include, but are not limited to, the introduction of the polynucleotide construct directly into the plant.

Nucleic acids and proteins can be provided to a cell by any method including methods using molecules to facilitate the uptake of anyone or all components of a, such as cell-penetrating peptides and nanocarriers. See also US20110035836 Nanocarrier-based plant transfection and transduction, and EP 2821486 A1 Method of introducing nucleic acid into plant cells.

Other methods of introducing polynucleotides into a prokaryotic and eukaryotic cell or organism or animal or plant part can be used, including transformation methods, and the methods for introducing polynucleotides into tissues, for example in plants from seedlings or mature seeds.

Animals

The presently disclosed polynucleotides and polypeptides can be introduced into a cell, such as a prokaryotic and eukaryotic cells, such as animal cells, in particular mammalian cells.

Numerous mammalian cell lines have been utilized for expression of gene products including HEK 293 (Human embryonic kidney) and CHO (Chinese Hamster Ovary). These cell lines can be transfected by standard methods (e.g., using calcium phosphate or polyethyleneimine (PEI), or electroporation). Other typical mammalian cell lines include, but are not limited to: HeLa, U2OS, 549, HT1080, CAD, P19, NIH 3T3, L929, N2a, Human embryonic kidney 293 cells, MCF-7, Y79, SO-Rb50, Hep G2, DUKX-X11, J558L, and Baby hamster kidney (BHK) cells.

The terms "therapeutic composition," "pharmaceutical composition," "therapeutic preparation," and "pharmaceutical preparation" are used interchangeably herein and encompass compositions of the present invention suitable for application or administration to a subject, typically a human. In general such compositions are safe, sterile, and preferably free of contaminants that are capable of eliciting undesirable responses in the subject (i.e., the compound(s) comprising the composition are pharmaceutically acceptable). Compositions can be formulated for application or administration to a subject in need thereof by a number of different routes of administration including oral (i.e., administered by mouth or alimentary canal) or parenteral (e.g., buccal, rectal, transdermal, transmucosal, subcutaneous, intravenous, intraperitoneal, intradermal, intratracheal, intrathecal, pulmonary, and the like).

The term "subject" as used herein refers to any member of the subphylum chordata, including, without limitation, humans and other primates, including non-human primates such as rhesus macaque, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese; and the like. The term does not denote a particular age. Thus, adult, young, and newborn individuals are intended to be covered.

Plants

The presently disclosed polynucleotides and polypeptides can be introduced into a cell, such as a prokaryotic and eukaryotic cells.

Numerous plant cells also find use with the compositions and methods provided herein. Plants are further provided comprising an expression cassette comprising a polynucleotide disclosed herein operably linked to a promoter that is active in the plant.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, by "grain" is intended the mature seed produced by commercial growers for purposes other than growing or reproducing the species. Progeny, variants, and mutants of the regenerated plants are also included within the scope of the disclosure, provided that these parts comprise genomic modifications of the regenerated plant such as those resulting from transformation or genome editing.

Any plant or plant part can be used, including monocot and dicot plants or plant parts.

Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum* species, *Triticum aestivum, Triticum monococcum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses.

The term "dicotyledonous" or "dicot" refers to the subclass of angiosperm plants also knows as "dicotyledoneae" and includes reference to whole plants, plant organs (e.g., leaves, stems, roots, etc.), seeds, plant cells, and progeny of the same. Examples of dicot plants that can be used include, but are not limited to, soybean (*Glycine max*), Brassica species (Canola) (*Brassica napus, B. campestris, Brassica rapa, Brassica. juncea*), alfalfa (*Medicago sativa*,), alfalfa (*Medicago sativa*), tobacco (*Nicotiana tabacum*), Arabidopsis (*Arabidopsis thaliana*), sunflower (*Helianthus annuus*), cotton (*Gossypium arboreum, Gossypium barbadense*), and peanut (*Arachis hypogaea*), tomato (*Solanum lycopersicum*), potato (*Solanum tuberosum*).

Plant that can be used include safflower (*Carthamus tinctorius*), sweet potato (*Ipomoea batatus*), cassava (*Manihot esculenta*), coffee (*Coffea* spp.), coconut (*Cocos nucifera*), citrus trees (*Citrus* spp.), cocoa (*Theobroma cacao*), tea (*Camellia sinensis*), banana (*Musa* spp.), avocado (*Persea americana*), fig (*Ficus* casica), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus* caryophyllus), poinsettia (*Euphorbia pulcherrima*), and *chrysanthemum*.

Conifers include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*).

The term "plant" includes whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

As used herein, the term "plant part" refers to plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a fertile plant is a plant that produces viable male and female gametes and is self-fertile.

ACR Protein Activity

The ACR polypeptides, variants and fragments described herein can be expressed and/or purified and their biological activity can be confirmed by any method, including those methods disclosed herein. For example, the biological activity of ACR polypeptides, variants, and fragments thereof can assayed by co-expressing an ACR polynucleotide expressing an ACR polypeptide, variant or fragment thereof in a bacterial cell containing and expressing a CRISPR-Cas9 of a *Streptococcus thermophilus* or *Streptococcus pyogenes* CRISPR system targeting a target sequence of a virulent phage strain and assaying for a reduction in viral titre between bacteria expressing the ACR polypeptide, variant or fragment compared to bacteria lacking the ACR polypeptide, variant or fragment.

Analysis of Cas Inhibitory Activity of ACR Proteins

In one aspect, the biological activity of the ACR protein of the present disclosure (including the polypeptides encoded by the polynucleotides of the present disclosure), and functional fragment and variants thereof, is an ability to inhibit the cleavage activity of a Cas protein, for example, a Type II Cas9 protein. Methods to determine inhibitory activity by an ACR protein are disclosed herein.

The disclosure thus provides methods for identifying anti-CRISPR proteins, where the method comprises obtaining a bacterial host cell comprising a recombinant construct capable of expressing a Type II-A CRISPR system having a targeting sequence (also referred to as spacer sequence) capable of targeting a genomic target sequence in a virulent phage, then introducing a construct comprising a promoter functional in the bacterial host cell operably linked to a polynucleotide encoding a polypeptide to be assayed for anti-CRISPR activity, challenging the bacterial host with the virulent phage, and identifying one or more bacterial colonies having a phage titre substantially similar to a bacterial cell lacking the recombinant construct encoding the Type II-A CRISPR system having the targeting sequence capable of targeting a genomic target sequence in the virulent phage challenged with the virulent phage.

In some embodiments, the anti-CRISPR activity assayed is the ability of a polypeptide to substantially restore the phage titre levels in a bacterial culture having a Type IIA CRISPR system challenged with a virulent phage. In some embodiments, the anti-CRISPR activity assayed results in a bacterial culture having a given Type II CRISPR system a substantially similar susceptibility to a given phage in the presence of the ACR protein as that of the same bacterial strain lacking the Type II CRISPR system being challenged with the same phage.

Modification of CRISPR system activity and/or genome modification activity by CRISPR systems, such as but not limiting to Type II-A CRISPR-Cas9 complexes, can also be measured as disclosed in described in Rauch et al., 2017, cell 168:150-158.

Methods of Use for ACR proteins

The compositions and methods provided herein find use in a wide variety of host cells, for example but not limited to those embodiments described herein. As used herein, a "host cell," refers to an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell or plant cell), by virtue of introduction into a suitable eukaryotic host cell of an exogenous nucleic acid.

In some embodiments, the cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, an insect cell, a yeast cell, a mammalian cell, a pig cell, a cow cell, a goat cell, a sheep cell, a rodent cell, a rat cell, a mouse cell, a non-human primate cell, and a human cell. In some cases, the cell is in vitro. In some cases, the cell is in vivo. For example, where the cell is a human cell, the human cell can be either in tissue culture or in vivo.

The methods provided herein can be used with any CRISPR-Cas system. In one embodiment, the methods and compositions provided herein can be used in combination with CRISPR-Cas systems (e.g. engineered CRISPR-Cas complexes derived from bacterial CRISPR systems) belonging to the Type II CRISPR-Cas systems. Such systems include engineered Type II-A CRISPR-Cas9 complexes.

In one embodiment, methods are provided for the immunization of eukaryotic cells against CRISPR-Cas9-mediated DNA modification, for example, to reduce or prevent the cleavage of DNA in a eukaryotic cell by a Cas9 protein complex. Such methods include introducing an ACR polypeptide (or a polynucleotide encoding an ACR polypeptide) into a cell containing a CRISPR-Cas9 complex capable of directing the cleavage of a target DNA in the cell. Such methods can be used in prokaryotic cells. The ACR polypeptide can be introduced simultaneously with the engineered CRISPR-Cas9 complex, or components of the CRISPR-Cas9 complex or sequentially to the CRISPR-Cas9 complex or components thereof. Where the introduction is sequentially, the ACR polypeptide can be introduced prior to the CRISPR-Cas9 complex or after the CRISPR-Cas9 complex. In other embodiments, the ACR polypeptide can be introduced via an expression cassette that provides for an inducible expression of the ACR or a temporal expression of the ACR polypeptide.

Where activity of an engineered CRISPR-Cas complex is reduced, the reduction in activity can be compared to the activity of the engineered CRISPR-Cas complex in the absence of the anti-CRISPR protein. The reduction in activity can be any measurably amount of reduction when compared to the activity of the engineered CRISPR-Cas complex in the absence of the ACR protein, and includes a reduction of about 5%, 10%, 15%, 20%, 25%, 30%, 40%, 50%, 60%, 65%, 70%, 75%, 80%, 85%, 90%, 95% or more in activity. The activity measured can be assayed using a viral titre assay in a bacterial host as described herein, or can be measured as the cleavage activity of the engineered CRISPR-Cas complex itself.

In some embodiments, the methods include methods for reducing the activity of CRISPR-Cas complexes in a host cell. In some embodiments, such methods include introducing into a host cell a recombinant construct comprising a promoter operably linked to a polynucleotide encoding an ACR protein, variant, or fragment thereof, where the host cell also comprises a CRISPR-Cas complex capable of modifying a target DNA molecule.

Also provided, are methods for providing an inducible expression of an ACR polypeptide in a cell. Such methods include introducing into a cell an expression cassette comprising an ACR polynucleotide encoding an ACR polypeptide under the operable linkage of an inducible promoter. Examples of inducible promoters for use in methods where an inducible expression of the ACR polypeptide is desired include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g., Tet-ON, Tet-OFF, etc.), Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; and the like.

Also provided are methods for controlling the cleavage (e.g. single or double-stranded cleavage) of a target DNA by a Type-II CRISPR complex in a eukaryotic cell. Such methods involve the expression or introduction of an ACR polypeptide disclosed herein into a cell containing or expressing a Type-II CRISPR complex capable of cleaving a target DNA molecule. In some embodiments, the methods involve the inducible expression of an ACR polypeptide disclosed herein to allow for the control of the timing of the expression of the ACR polypeptide.

Also provided are methods for reducing off-target DNA cleavage by a Type-II CRISPR complex in a eukaryotic cell. Such methods involve the expression or introduction of an ACR polypeptide disclosed herein into a cell containing or expressing a Type-II CRISPR complex capable of cleaving a target DNA molecule.

Such off-target DNA cleavage may be reduced by 5%, 10%, 15%, 20%, 25%, 30%, 35%, 40%, 45%, 50%, 60%, 65%, 70%, 75%, 80%, 85%, 90%, or more compared to the cleavage by the Type-II CRISPR complex in a cell in the absence of the ACR polypeptide.

Also provided are methods for immunizing a population of cells in which genome editing by a CRISPR-Cas9 complex is desired, but complete penetration is not desired. The methods general comprise expressing or introducing an ACR polypeptide disclosed herein into a population of cells containing a CRISPR-Cas9 complex that is capable of cleaving a target DNA molecule. Such methods may also further involve the identification or selection of a cell having a modification of the target DNA molecule.

Also provided are methods for protecting cells, e.g. eukaryotic cells, from DNA damage from the activity of an engineered CRISPR-Cas9 complex. Such methods include introducing into a cell a recombinant construct for the expression of an ACR polypeptide as provided herein.

Also provided are methods for modulating the activity of a Cas endonuclease via the usage of an ACR, by controlling the expression or activity of the Cas endonuclease or the ACR protein during one more cell cycles. In some aspects, the cell cycle is selected from a meiotic phase. In some aspects, the cell cycle is selected from the mitotic phase.

Also provided are methods for increasing the frequency of homologous recombination during genome editing, and/or reducing the frequency of non-homologous end joining during genome editing.

The ACR polynucleotides, polypeptides, and methods disclosed herein find use in combination with a wide variety of CRISPR complexes, for example, to inhibit the activity of CRISPR complexes against target DNA molecules. The CRISPR complexes of particular interest include those from Type II CRISPR systems, including those derived from Type II-A CRISPR systems. In some embodiments, the Type II-A CRISPR complexes are those derived from *Streptococcus thermophilus, Streptococcus pyogenes,* and *S. aureus.* In other embodiments, the Type II-A CRISPR complexes are those derived from *Streptococcus thermophilus.* In other embodiments, the Type II-A CRISPR complexes are those derived from *Streptococcus thermophilus,* CRISPR1 locus.

In *Streptococcus thermophilus,* although CRISPR1 and CRISPR3 belong to class 2 type II-A systems, they are different in terms of sequence including Cas9 sequence. For the distinction of CRISPR1 and CRISPR3, reference is made herein to the publication of Chylinski et al. 2014, where the CRISPR1-Cas system is represented by the Cas9 sequence of LMD-9 116628213, and the CRISPR3-Cas system is represented by the Cas9 sequence of LMD-9 116627542.

In some embodiments, an engineered CRISPR-Cas endonuclease (e.g. an engineered Type II-A CRISPR-Cas9) can (or is capable of) recognize, bind to a DNA target sequence and introduce a single strand (nick) or double-strand break. Once a single or double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements (such as chromosomal translocations) are possible (Siebert and Puchta, 2002, Plant Cell 14:1121-31; Pacher et al., 2007, *Genetics* 175: 21-9).

While the invention has been particularly shown and described with reference to a preferred embodiment and various alternate embodiments, it will be understood by persons skilled in the relevant art that various changes in form and details can be made therein without departing from the spirit and scope of the invention. For instance, while the particular examples below may illustrate the methods and embodiments described herein using a specific plant, the principles in these examples may be applied to any plant. Therefore, it will be appreciated that the scope of this invention is encompassed by the embodiments of the inventions recited herein and in the specification rather than the specific examples that are exemplified below. All cited patents and publications referred to in this application are herein incorporated by reference in their entirety, for all purposes, to the same extent as if each were individually and specifically incorporated by reference.

EXAMPLES

The following are examples of specific embodiments of some aspects of the invention. The examples are offered for illustrative purposes only, and are not intended to limit the scope of the invention in any way. Efforts have been made to ensure accuracy with respect to numbers used (e.g., amounts, temperatures, etc.), but some experimental error and deviation should, of course, be allowed for.

The meaning of abbreviations is as follows: "sec" means second(s), "min" means minute(s), "h" means hour(s), "d" means day(s), "μL" or "uL" or "ul" means microliter(s), "mL" means milliliter(s), "L" means liter(s), "μM" means micromolar, "mM" means millimolar, "M" means molar, "mmol" means millimole(s), "μmole" or "umole" mean micromole(s), "g" means gram(s), "μg" or "ug" means microgram(s), "ng" means nanogram(s), "U" means unit(s), "bp" means base pair(s) and "kb" means kilobase(s).

Anti-CRISPR (ACR) proteins may be identified, characterized, and utilized according to a number of techniques, some of which are described herein.

Example 1

Genomic sequences are obtained for a phage that displays virulence against a bacterium comprising a CRISPR-Cas system, wherein the CRISPR-Cas system comprises a targeting sequence that is substantially complementary to a sequence in the phage genome. The sequences are analyzed, and compared to the polynucleotide sequence of at least one known anti-CRISPR protein. In some aspects, at least one polynucleotide of the phage genome shares at least 70% sequence identity with at least 100 bases of a sequence selected from the group consisting of: SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, and 99-374.

Example 2

A first bacterial host cell comprising a recombinant construct having a Type II-A CRISPR system having a targeting sequence capable of targeting a genomic target sequence in a first virulent phage is obtained. The first bacterial host is challenged with the virulent phage. A second bacterial host cell, preferably of the same strain and genetic composition (isoline) as the first bacterial host cell, comprising a recombinant construct having a Type II-A CRISPR system having a targeting sequence capable of targeting a genomic target sequence in a second virulent phage is obtained. The second bacterial host is challenged with the second virulent phage. One or more bacterial colonies of the first bacterial host cell is/are identified having a phage titre substantially similar to an otherwise isoline bacterial cell lacking the recombinant construct encoding the CRISPR system having the targeting sequence capable of targeting a genomic target sequence in the first virulent phage challenged with the first virulent phage. One or more bacterial colonies of the second bacterial host cell are identified having a phage titre substantially different than a bacterial cell lacking the recombinant construct encoding the CRISPR system having the targeting sequence capable of targeting a genomic target sequence in the second virulent phage challenged with the second virulent phage. The genomes of the first and second virulent phages are sequenced. One ore more gene(s) is/are present in the first virulent phage but not the second virulent phage. A third bacterial host cell is obtained, preferably of the same strain and genetic composition (isoline) as the first bacterial host cell, comprising a recombinant construct having a CRISPR system having a targeting sequence capable of targeting a genomic target sequence in the first virulent phage. A construct is introduced into the third bacterial host cell, wherein the construct comprises a promoter functional in the third bacterial host cell operably linked to a polynucleotide identical to the gene identified as present in the first virulent phage but not the second virulent phage. The third bacterial host is challenged with the first virulent phage. One or more bacterial colonies of the third bacterial host cell is/are identified, having a phage titre substantially similar to a bacterial cell lacking the recombinant construct encoding the CRISPR system having the targeting sequence capable of targeting a genomic target sequence in the first virulent phage challenged with the first virulent phage.

Example 3

A bacterial host cell comprising a recombinant construct having a CRISPR system having a targeting sequence capable of targeting a genomic target sequence in a virulent phage was obtained. A construct comprising a promoter functional in the bacterial host cell operably linked to a polynucleotide encoding a polypeptide to be assayed for anti-CRISPR activity was introduced into the bacterial host cell. The bacterial host was challenged with the virulent phage. One or more bacterial colonies were identified, that displayed a phage titre substantially similar to a bacterial cell lacking the recombinant construct encoding the CRISPR system having the targeting sequence capable of targeting a genomic target sequence in the virulent phage challenged with the virulent phage.

Example 4

As *Streptococcus thermophilus* is a model for the study of CRISPR adaptation, a detailed step-by-step protocol for many of the methods used here is available elsewhere.
Strain Culturing
*S. thermophilus* cultures were grown in M17 medium (Oxoid, Ontario, Canada) supplemented with 0.5% w/v lactose (LM17). Chloramphenicol, when necessary, was added at 5 ug/ml. When used to generate an overnight culture for use the following day, cultures were grown at 37° C. without shaking. In all other cases, they were grown at 42° C. without shaking. If phages were to be added, the media was further supplemented with 10 mM $CaCl_2$.
*Lactococcus lactis* cultures were grown in M17 medium (Oxoid, Ontario, Canada) supplemented with 0.5% w/v glucose monohydrate (GM17). Chloramphenicol or erythromycin, when necessary, were added at 5 ug/ml. Cultures were grown at 30° C. without shaking, except when the activity of an SpCas9-containing construct was assayed, in which case incubations took place at 33° C. If phages were to be added, the media was further supplemented with 10 mM $CaCl_2$.

*Escherichia coli* cultures were grown in LB medium. Chloramphenicol, when necessary, was provided at 20 ug/ml. Cultures were grown at 37° C. with shaking.
Phage Amplification
A scraping from a phage lysate preserved at −80° C. with 15% glycerol was co-inoculated with its host strain, in media supplemented with 10 mM $CaCl_2$, and grown until complete lysis was observed. This first amplification lysate was then filtered through a 0.45 um PES filter, and 100 ul used to inoculate its host strain grown to an $OD_{600}$ of 0.1 in media supplemented with 10 mM $CaCl_2$. This second amplification lysate was also filtered through a 0.45 um PES filter, then stored at 4° C.
Phage Titering
As depicted in FIG. 1, phages were serially diluted in phage buffer (50 mM Tris-HCl, pH 7.5, 100 mM NaCl, 8 mM $MgSO_4$). Three ml of molten 0.75% agar medium at 55° C., supplemented with 10 mM $CaCl_2$, was inoculated with 300 ul of an overnight culture of the host strain, then rapidly poured over a pre-set plate of the same medium with 1% agar. The plate was allowed to set and dry. Phage dilutions, 3 ul from each, were spotted onto the dry overlay and allowed to dry for 20 min. The plates were then incubated overnight, and plaques counted at the lowest dilution at which they were visible.
As depicted in FIG. 2, phages were serially diluted in phage buffer. Three ml of molten 0.75% agar medium at 55° C., supplemented with 10 mM $CaCl_2$, is co-inoculated with 300 ul of an $OD_{600}$ 0.6 culture of the host strain and 100 ul of diluted phage. The plates were then incubated overnight, and plaques counted from plates with between 30-300 plaques.
Immunizing Assays for BIM (Bacteriophage Insensitive Mutants)
Phages were diluted in phage buffer in order to obtain a final multiplicity of infection (MOI) of 0.1 plaque forming units per colony forming units (pfu/cfu). Three ml of molten 0.75% agar medium at 55° C., supplemented with 10 mM $CaCl_2$ was co-inoculated with 300 ul of a culture at an $OD_{600}$ of 0.6 (~$1.2 \times 10^8$ cfu/ml) of the host strain and 100 ul of the appropriate phage dilution. The plates were then incubated overnight, and surviving colonies counted.
Characterization of Surviving Colonies
Random surviving bacterial colonies were screened by PCR for acquisition of new spacers at the CRISPR1 & CRISPR3 loci (*S. thermophilus* strain DGCC7710) or CRISPR1 locus (*S. thermophilus* strain DGCC7854). An increase in the size of the PCR product relative to the wild type was indicative of CRISPR immunization. The resulting PCR products were sequenced to confirm the identity of the newly acquired spacer. For assays in FIG. 2, presence of the insert in pNZAcr was confirmed by sequencing in cells that had acquired spacers.
Plasmid Programming
A plasmid was designed to contain a protospacer (CRISPR-acquirable sequence) targeting the five phages used in the challenges. Two oligos consisting of a conserved protospacer in the gene encoding the tape measure protein, as well as overhangs suited for cloning, were annealed together by mixing them in equal parts, heating them to 98° C., then cooling them slowly to 50° C. This annealed construct was then ligated directly into an EcoRI/XhoI double-digested pNZ123, transformed into commercial NEB5α, and selected for with chloramphenicol. The constructed plasmid was then isolated using Qiaprep Spin Miniprep kit (Qiagen, Ontario, Canada) according to the manufacturer's recommendations. *S. thermophilus*

DGCC7854 was transformed with this plasmid, pNZ5phage, then grown in the absence of selection for 7 generations and subjected to an immunizing assay (see above) with virulent phage D5842. The surviving colonies had naturally acquired the desired spacer from the plasmid, immunizing them to the phages. The spacer sequence was confirmed as described in "characterization of surviving colonies" above.

Phage Genome Sequencing & Annotation

DNA from the phage D4276 was purified using a PureLink Viral RNA/DNA kit (Invitrogen, MA, USA). The purified DNA was sequenced on a MiSeq system using a MiSeq reagent kit v2 after preparation using the Nextera XT DNA library preparation kit (Illumina, British Columbia, Canada). The resulting reads assembled using Ray version 2.2.0 (32). The genome was annotated using NCBI ORF finder and GeneMark.hmm prokaryotic, and those annotations then manually curated based on comparisons to related phages.

Phage Gene Cloning and pNZAcr Construction

Primers were designed to systematically clone all of phage D4276 into pNZ123 oriented so as to drive transcription from the promoter upstream of the chloramphenicol resistance gene, cat. Initially, inserts were designed to contain several genes, but if cloning failed the inserts were redesigned as smaller, single-gene constructs. The gene of greatest interest, D4276_028, exemplifies this cloning technique. Primers were designed to amplify the gene and append 30 nt extensions overlapping the pNZ123 MCS (SEQ ID NO:87 and SEQ ID NO:88). The amplified gene was then cloned by Gibson reaction into XhoI digested pNZ123. The resulting plasmid, pNZAcr, was transformed into commercial NEB5a, isolated using a Qiaprep Spin Miniprep kit, and then transformed into the relevant *S. thermophilus* and *L. lactis* strains. The sequence of the insert was confirmed by sequencing using primers (SEQ ID NO:89 and SEQ ID NO:90).

Plasmid Loss Assays

Cultures carrying pNZAcr were serially grown in the absence of selection, inoculating fresh 10 ml of LM17 broth media with 100 ul of a culture grown to saturation. This was repeated 5 times. Dilutions of the resulting culture were spread upon plates in order to obtain isolated colonies, and 120 such colonies were then patch-plated on LM17 with and without chloramphenicol. Colonies, which grew on LM17 (all 120) but failed to grow on LM17 Cm (two), were screened by PCR to confirm plasmid loss using pNZinsF and pNZinsR, and their CRISPR1 locus was amplified to confirm the presence of the immunizing spacer. Colonies were then used to titer the phages D4276 and D5842, and confirm that they had regained resistance to the phages from losing the plasmid.

pL2Cas9-44 Construction pL2Cas9 (Lemay et al. 2017) is a derivative of the lactococcal vector pTRKL2 (O'Sullivan et al. 1993) with the SpCas9 module of pCas9 (Jiang et al. 2013). A pair of oligos comprising a spacer sequence targeting orf44 of phage p2 and overhangs for ligation into pL2cas9 were designed (SEQ ID NO:90 and SEQ ID NO:91). They were annealed together by mixing them in equal parts, heating them to 98° C., then cooling them slowly to 50° C. This annealed construct was then ligated directly into digested pL2Cas9 and transformed directly into *L. lactis*. The resulting transformants were screened by PCR amplification and sequencing to confirm the presence of the desired spacer, using primers (SEQ ID NO:93 and SEQ ID NO:94).

Efficiency of Centers of Infection (ECOI)

Cultures of all four strains depicted in FIG. 3B were grown at 33° C. to an $OD_{600}$ of 0.8 (~$1.9*10^8$ cfu/ml), 2 ml spun down and resuspended 1 ml in fresh GM17 media with 10 mM $CaCl_2$. Then, phage p2 was added to an MOI of 0.2, mixed by inversion, and given 5 min to allow adsorption to the cells at 33° C. The phage-cell mix was then spun down and resuspended in fresh media thrice in order to wash away unbound phages, then serially diluted. 100 ul of the resulting dilutions were then added to 300 ul of indicator strain (MG1363 pNZ123 pL2Cas9), embedded in a soft agar overlay (see phage titering), and incubated at 33° C. overnight.

Results

*Streptococcus thermophilus* has become a model for acquisition of new CRISPR immunities, shares its genus with the source of SpCas9, and its active CRISPR-Cas systems are also of type II-A. A set of five virulent phages infecting *S. thermophilus* strain DGCC7854 proved ideal for identifying phages that were less likely to lead to the acquisition of new spacers (phage-derived sequences in the CRISPR array, conferring immunity); while two of the phages readily gave rise to CRISPR-immune colonies, three did not (FIG. 1, Top). The dearth of spacer acquisition from these three phages did not necessarily confirm the presence of anti-CRISPRs. Those phages could simply be more sensitive to non-CRISPR forms of resistance, be quicker to take over the host cell, or produce fewer immunogenic defective particles. It was necessary to establish whether the CRISPR-Cas system was impeded during the adaptation ('memorization' of new targets) or interference (cleavage of that target) process. Using plasmid-programming, a strain targeting a protospacer conserved in all five phage genomes was generated. Then, in plaquing each phage upon this strain, it was observed that four of the five phages suffered a drastic reduction (~6 Log) in titer, consistent with CRISPR interference, but one phage, D4276, did not (FIG. 1, bottom). These phages were categorized according to these CRISPR-interacting phenotypes; permissive (white) phages D5842 and D5843, impeded adaptation (fractal pattern) phages D1024 and D5891, and restrictive (black) phage D4276—a candidate to harbor an anti-CRISPR.

Genes from the restrictive phage D4276 were cloned into a vector where they could be expressed in the immunized strain (FIG. 2A). A phage gene encoding an anti-CRISPR protein should inactivate the pre-existing immunity and thereby restore the titer of a sensitive (permissive) phage plated upon the strain. A new anti-CRISPR gene (acr gene, described herein as SEQ ID NO:9 encoding an anti-CRISPR protein as described in SEQ ID NO:10) was obtained, which completely restored the immunized strain's sensitivity to the permissive phage D5842 (~6 Log increase), as well as increased sensitivity to the restrictive phage D4276 back to wild-type levels (FIG. 2B). We attribute this increase in titer for even the anti-CRISPR-containing phage D4276 to high anti-CRISPR production before phage exposure, which would otherwise be a time-sensitive process whereby production must outrace CRISPR activity. In order to ensure the gain-of-sensitivity phenotypes were due only to this anti-CRISPR, we allowed loss of the anti-CRISPR-bearing plasmid and confirmed a return-of-resistance phenotype (data not shown).

As all five phages infecting *S. thermophilus* DGCC7854 are related cos-type phages, we could not rule out that the anti-CRISPR might be dependent upon interaction with partner proteins present in these phages. Furthermore, strain DGCC7854 contains only a single active CRISPR-Cas system (CRISPR1), as opposed to the two systems (CRISPR1

& CRISPR3) commonly active in *S. thermophilus* strains. We ported our anti-CRISPR vector over to the well-characterized model strain, *S. thermophilus* DGCC7710, which is sensitive to an unrelated virulentpac-type phage, 2972—and for which we have strains immunized at either the CRISPR1 or CRISPR3 locus (FIG. 2C). In this system, the anti-CRISPR activity was maintained, completely restoring phage sensitivity to a CRISPR1-immunized strain, and partially restoring sensitivity for a CRISPR3-immunized strain. When we attempted immunizing assays on DGCC7710 bearing the acr gene, the number of surviving colonies fell sharply (FIG. 2D). Moreover, the nature of those survivors changed drastically. The number of CRISPR3-immune colonies dropped, a number of previously undetectable non-CRISPR mutants were observed, and whereas CRISPR1 immunizations normally compose upwards of 90% of surviving colonies, only a single colony with a CRISPR1 spacer acquisition was recovered (FIG. 2D). Of note, the CRISPR1 spacer in question targeted the plasmid (still present and carrying an intact acr gene), rather than the phage genome. This indicates that the ACR protein likely impedes Cas9-mediated cleavage, but not Cas9's role in spacer acquisition.

The ACR protein (SEQ ID NO:10) is 140 amino acids long and is predicted to contain a distinctive coiled-coil motif, which might act in a nucleic acid binding role, similar to HTH and AP2 motifs associated with other anti-CRISPR proteins. We have found several new anti-CRISPR genes both in phage genome (SEQ ID NO: 1, 3, 5, 11, 13, 15 and 17 encoding respectively anti-CRISPR protein as defined in SEQ ID NO: 2, 4, 6, 12 14, 16 and 18) as well as in the genome of *Streptococcus* strains (SEQ ID NO:5, 7, 19, 21, 23 and 25 encoding respectively anti-CRISPR protein as defined in SEQ ID NO: 6, 8, 20, 22, 24 and 26).

Finally, despite the fact that the genome-editing tool SpCas9 (Cas9 from *S. pyogenes*) is more closely related to the Cas9 of the CRISPR3 system of *S. thermophilus*, we were keen to determine whether the ACR protein would have any effectiveness against SpCas9. We initially attempted to assay the effectiveness of ACR (pNZAcr) on SpCas9 (pCas9) in *Escherichia coli*, but despite the ability to clone each separately, the two systems were not able to co-exist. Some aspects of the ACR-Cas9 interaction may be pernicious to *E. coli*. Instead, we used a pCas9 derivative adjusted for use in *Lactococcus lactis*, with demonstrated efficacy in the genome-editing of virulent phages (FIG. 3A). The pL2Cas9-44 construct, targeting orf44 of the virulent phage p2, resulted in a 4 Log decrease in measurable phage titer (FIG. 3B), which was completely restored by the presence of the acr gene. This is the strongest reported anti-CRISPR activity against SpCas9 to date.

The 4 Log reduction associated with pL2Cas9-44 was also accompanied by a 'tiny plaque' phenotype that proved difficult to quantify, as they were only observable on some technical replicates. The maximum number of tiny plaques observed is displayed in pale orange (FIG. 3B). We characterized the phenotype and genotype of these smaller plaques, establishing that they were CRISPR-bypassing mutants genetically indistinguishable from those in the larger plaques, but arising only after several rounds of replication on the 'leaky' targeting strain. Notably, however, the expression of the ACR completely rescued both the titer and the tiny-plaque phenotype.

The ACR protein (SEQ ID NO:10) is the first anti-CRISPR protein with demonstrated activity from a virulent phage, is structurally distinct from previously characterized anti-CRISPRs, and displays the strongest in vivo activity against SpCas9 to date.

Example 5

Strain culturing, phage amplification, phage titering, immunizing assays, characterization of surviving colonies and transformation were done the same way as in Example 1.

Phage Genome Sequencing and Annotation

DNA from the phage D1811 was purified using a PureLink Viral RNA/DNA kit (Invitrogen, MA, USA). The purified DNA was sequenced on a MiSeq system using a MiSeq reagent kit v2 after preparation using the Nextera XT DNA library preparation kit (Illumina, British Columbia, Canada). The resulting reads assembled using Ray version 2.2.0 (32). The genome was annotated using NCBI ORF finder and GeneMark.hmm prokaryotic, and those annotations then manually curated based on comparisons to related phages.

Phage Gene Cloning and pNZAcr Construction

Primers were designed to amplify a gene of interest, D1811_026, and append 30 nt extensions overlapping the pNZ123 MCS (SEQ ID NO:95 and SEQ ID NO:96). The amplified gene was then cloned by Gibson reaction into XhoI digested pNZ123. The resulting plasmid, pNZAcr-1811, was transformed into commercial NEB5a, isolated using a Qiaprep Spin Miniprep kit, and then transformed into the relevant *S. thermophilus*. The sequence of the insert was confirmed by sequencing using primers (SEQ ID NO:97 and SEQ ID NO:98).

Plasmid Loss Assays

Cultures carrying pNZAcr were serially grown in the absence of selection, inoculating fresh 10 ml of LM17 broth media with 100 ul of a culture grown to saturation. This was repeated 14 times. Dilutions of the resulting culture were spread upon plates in order to obtain isolated colonies, and 160 such colonies were then patch-plated on LM17 with and without chloramphenicol. Colonies, which grew on LM17 (all 120) but failed to grow on LM17 Cm (two), were screened by PCR to confirm plasmid loss using pNZinsF and pNZinsR, and their CRISPR1 locus was amplified to confirm the presence of the immunizing spacer. Colonies were then used to titer the phages D1811 and D5842, and confirm that they had regained resistance to the phages from losing the plasmid.

Results

In plaquing an additional phage (D1811) upon the DGCC7854 strain, it was observed that this phage suffers a much smaller reduction in titer than 4 other related phages (FIG. 1, bottom). This phage was categorized as restrictive (black) phage.

We found a second new anti-CRISPR gene (acr2 gene, defined herein as SEQ ID NO:27 encoding an anti-CRISPR protein as defined in SEQ ID NO:28), which completely restored the immunized strain's sensitivity to the permissive phage D5842 (~5 Log increase), as well as increased sensitivity to the restrictive phage D1811 back to wild-type levels (FIG. 4A). We attribute this increase in titer for even the anti-CRISPR-containing phage D1811 to high anti-CRISPR production before phage exposure, which would otherwise be a time-sensitive process whereby production must outrace CRISPR activity. In order to ensure the gain-of-sensitivity phenotypes were due only to this anti- CRISPR, we allowed loss of the anti-CRISPR-bearing plasmid and confirmed a return-of-resistance phenotype (data not shown).

Since D1811 is related to the five other phages disclosed in example 1, we could not rule out that the anti-CRISPR might be dependent upon interaction with partner proteins present in these phages. We ported our anti-CRISPR vector over to the well-characterized model strain, S. thermophilus DGCC7710, which is sensitive to an unrelated virulent pac-type phage, 2972—and for which we have strains immunized at either the CRISPR1 or CRISPR3 locus (FIG. 4B). In this system, the anti-CRISPR activity was maintained, completely restoring phage sensitivity to a CRISPR1-immunized strain.

The Acr2 protein (SEQ ID NO:28) is 183 amino acids long. We have found several new anti-CRISPR genes both in phage genome (SEQ ID NO: 29, 31, 33, 35, 37, 39, 41, 43, 45, 47, 49, 51, 53, 55, 57, 59, 61, 63, 65, 67, 69, 71, 73, 75, 77, 79 and 81 encoding respectively anti-CRISPR protein as defined in SEQ ID NO: 30, 32, 34, 36, 38, 40, 42, 44, 46, 48, 50, 52, 54, 56, 58, 60, 62, 64, 66, 68, 70, 80 and 82,) as well as in the genome of Streptococcus strains (SEQ ID NO: 83 85, and 99-374 encoding respectively anti-CRISPR protein as defined in SEQ ID NO: 84 86, and 375-650).

Example 6

In this example, methods to reduce "off-target" chromosomal DNA cleavage by the RNA guided endonuclease are described. In some aspects, any Cas endonuclease may be used to generate double-strand breaks. In some aspects, a Type II Cas endonuclease may be used to generate double-strand breaks. In some aspects, a Cas9 endonuclease from any organism may be used to generate double-strand breaks. In some aspects, the Cas9 endonuclease is from S. pyogenes or S. thermophilus.

In one example, a Cas endonuclease, for example but not limited to S. pyogenes Cas9 (SpCas9), can be directed by guide RNAs (gRNAs) to cleave DNA targets and introduce double-strand breaks (DSBs) at high efficiencies in multiple organisms including plants (Hsu, P. D. et al. (2014) Cell. 157:1262-1278). The cellular repair of the DSB(s) is then used to introduce genetic modifications. This may include small insertion or deletion (indel) mutations, large deletions (if more than one DNA site is targeted), purposeful edits (for example alteration of a codon in a gene), and insertion of DNA within or near the DNA target sequence. Depending on the nature of the experimental system used, SpCas9 may generate DSBs and chromosomal alterations in other locations in the genome besides those intended (Fu, Y. et al. (2013) Nat. Biotechnol. 31:822-826). To reduce these potential "off-target" effects, an anti-CRISPR (ACR) can be utilized. The method relies on the recombinant expression of an ACR that inhibits SpCas9 or other Cas9s or any other Cas endonuclease from binding, nicking, or cleaving DNA. In this case, the timing of ACR expression is relevant. If it is expressed before the Cas endonuclease has cleaved the intended on-target sequence, then the intended target site may have no or reduced DSB activity. Alternatively, if it is expressed too late, continued activity of the Cas endonuclease protein may not be affected by ACR expression, resulting in less specific activity. To ensure proper timing, an ACR recombinant gene expression cassette can be designed to be non-functional, then following Cas endonuclease expression and RNA guided cleavage, or after a sufficient time has passed for site-specific cleavage, converted into a functional expression cassette. To restore functionality by cleavage, a method like that described in PCT application publication number WO2017070032 may be utilized. In an embodiment, the translational open-reading frame (ORF) of the ACR protein of interest can be designed to be out of frame (for example but not limited to the deletion of a single base) (FIG. 9) where the ORF results in RNA transcript that contains a premature stop codon or encodes a non-sense protein. The resulting non-functional ORF can be then converted into a functional ORF by targeting the out of frame sequence for Cas endonuclease cleavage and cellular DSB repair (FIG. 9). Additionally, the gene encoding the out of frame ACR protein may be combined with other genes (for example but not limited to selective agents and marker genes (Miki, B. (2004) J Biotechnol. 107:193-232)) in a polycistron (separated by sequences encoding 'self-cleaving' 2A peptides (Szymczak, A. L. et al. (2004) Nature Biotech. 22:589-594) (FIG. 10). Then, following restoration of the ACR ORF, the other genes in the multicistronic expression cassette can also be converted into a functional state (FIG. 10). Thus, permitting simultaneous positive selection for functional ACR expression and Cas9 genome editing. Taken together, this approach results in an auto-regulatory feedback loop (ARFL) which through Cas endonuclease activity results in rapid inactivation of Cas endonuclease by ACR reducing the potential for off-target cleavage.

Example 7

In this example, methods to enhance the chromosomal DNA repair of Cas-generated double strand breaks (DSBs) with the homologous recombination (HR) DNA repair pathway using an anti-CRISPR protein are described. In some aspects, any Cas endonuclease may be used to generate double-strand breaks. In some aspects, a Type II Cas endonuclease may be used to generate double-strand breaks. In some aspects, a Cas9 endonuclease from any organism may be used to generate double-strand breaks. In some aspects, the Cas9 endonuclease is from S. pyogenes or S. thermophilus.

Cellular repair of Cas endonuclease induced DSBs utilizes the non-homologous end-joining (NHEJ) and the HR DNA repair pathways (Hsu, P. D. et al. (2014) Cell. 157: 1262-1278). NHEJ repair may result in the imprecise insertion or deletion (indel) of DNA base pairs (bps) at a chromosomal DNA target site and is useful for disrupting (knocking-out) gene expression. In contrast, HR-mediated repair offers a highly precise method to introduce desired changes into DNA using an exogenously supplied DNA repair template (Capecchi, M. R. (1989) Science. 244:1288-1292). The NHEJ pathway is typically the most prevalent DSB repair outcome making the recovery of HR-mediated alterations infrequent (Capecchi, M. R. (1989) Science. 244:1288-1292). To increase the frequency of HR repair, an anti-CRISPR (ACR) may be used to time Cas endonuclease cleavage activity with the part of the cell cycle where HR repair occurs, S (Synthesis) and G2 (Gap 2) phases (Heyer, W. D. et al. (2010) Annu. Rev. Genet. 44:113-139). To accomplish this, the ubiquitin-mediated proteolysis pathway may be leveraged. By fusing part or all of Cdt, a protein that is targeted for degradation by the $SCF^{Skp2}$ ubiquitination complex in the S and G2 cellular phases (Nishitani, H. et al. (2000) Nature. 404:625-628), to ACR, its expression can be limited to the G1 (Gap 1) phase. Thus, inactivating Cas endonuclease during G1 when HR repair is inactive and permitting Cas endonuclease re-activation during S and G2 when HR repair machinery is expressed and active (FIG.

11). Taken together, ACR may be used as a tool to modulate Cas endonuclease activity in a cell cycle-dependent manner resulting in enhanced HR repair. In some aspects, an ACR may be used to modulate Cas endonuclease activity during meiosis. In some aspects, an ACR may be used to modulate Cas endonuclease activity during mitosis. In some aspects, an ACR may be used to modulate Cas endonuclease activity during S phase or G2 phase.

Example 8

Methods for controlling the expression of a Cas endonuclease in a plant via spatial regulated expression, temporal regulated expression, or inducible expression of the ACR are contemplated. In some aspects, the ACR, the Cas endonuclease, or both is/are pre-integrated into the genome of at least one plant cell in the plant. In some aspects, ACR, the Cas endonuclease, or both is/are introduced as polynucleotides into at least one cell of the plant, or into a cell from which a whole plant or plant tissue may be derived. In some aspects, ACR, the Cas endonuclease, or both is/are introduced as polypeptides into at least one cell of the plant, or into a cell from which a whole plant or plant tissue may be derived.

In this example, methods to regulate the binding, nicking, and cleavage activity of a RNA guided CRISPR endonucleases in a tissue specific manner using an anti-CRISPR protein are described. In some aspects, any Cas endonuclease may be used. In some aspects, any Type II Cas endonuclease may be used. In some aspects, a Cas9 endonuclease from any organism may be used.

MicroRNAs (miRNAs) are small non-coding RNAs that provide a pleotropic cellular mechanism for modulating gene expression and key determinant for cellular differentiation (Baskerville, S. et al. (2005) RNA. 11: 241-247, Lagos-Quintana, M. et al. (2002) Curr. Biol. 12: 735-739, Chen, C. Z. et al. (2004) Science. 303: 83-86 and Lu, J. et al. (2005) Nature. 435: 834-838). They act to regulate gene expression post-transcriptionally by targeting transcribed RNAs for degradation (Lagos-Quintana, M. et al. (2001) Science. 294: 853-858). Additionally, they have been repurposed to regulate transgene expression in a tissue specific manner by placing their binding site(s) in the 3 prime untranslated region (UTR) of foreign genes (Brown, B. et al. (2006) Nat. Med. 12:585-591). To regulate the binding, nicking, and cleavage activity of a Cas9 protein in a tissue specific manner, a recombinant anti-CRISPR (ACR) encoding gene can be made into a substrate for cellular miRNA(s) regulation. By placing one or more miRNA binding sites in the 3' UTR of the ACR gene, its expression and consequential activity of Cas9 may be modulated as a function of tissue type, developmental stage, or growth condition. Cas9 will be active in the presence of miRNA translational repression and inactive in the absence of miRNA translation repression. As an alternative, miRNA binding sites can be also placed into the 3' UTR of the Cas9 gene to directly regulated its expression in a tissue specific manner. Moreover, miRNAs with different tissue specificities can be incorporated into the 3' UTRs of both the recombinant ACR and Cas9 expression constructs to provide additional layers of regulation.

We claim:

1. A method for modulating the activity of a Cas endonuclease with a target polynucleotide in a cell, comprising providing an anti-CRISPR (ACR) polypeptide having an amino acid sequence at least 90% identical to SEQ ID NO:8 to the cell, wherein the ACR polypeptide decreases the activity of the Cas endonuclease in the cell compared to a control cell comprising the Cas endonuclease but not comprising the ACR polypeptide.

2. The method of claim 1, wherein the Cas endonuclease activity is selected from the group consisting of target polynucleotide binding, target polynucleotide nicking, target polynucleotide double-strand-break creation, and target polynucleotide modification.

3. The method of claim 2, wherein said target polynucleotide modification is selected from the group consisting of insertion of at least one nucleotide, deletion of at least one nucleotide, substitution of at least one nucleotide, and chemical alteration of at least one nucleotide.

4. The method of claim 1, wherein the cell is selected from the group consisting of a plant cell, an animal cell, a mammalian cell, a microbial cell and a fungal cell.

* * * * *